US008680003B2

(12) United States Patent
Sydora et al.

(10) Patent No.: US 8,680,003 B2
(45) Date of Patent: Mar. 25, 2014

(54) PHOSPHINYL AMIDINE COMPOUNDS, METAL COMPLEXES, CATALYST SYSTEMS, AND THEIR USE TO OLIGOMERIZE OR POLYMERIZE OLEFINS

(75) Inventors: Orson L. Sydora, Houston, TX (US); Michael Carney, Eau Claire, WI (US); Brooke L. Small, Kingwood, TX (US); Jeffery C. Gee, Kingwood, TX (US); Steven Hutchison, Spring, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 13/519,825

(22) PCT Filed: Dec. 29, 2010

(86) PCT No.: PCT/US2010/062281
§ 371 (c)(1),
(2), (4) Date: Aug. 27, 2012

(87) PCT Pub. No.: WO2011/082192
PCT Pub. Date: Jul. 7, 2011

(65) Prior Publication Data
US 2012/0309965 A1      Dec. 6, 2012

Related U.S. Application Data

(60) Provisional application No. 61/291,459, filed on Dec. 31, 2009.

(51) Int. Cl.
*B01J 31/18* (2006.01)
*C07D 265/30* (2006.01)
*C07D 233/54* (2006.01)
*C07F 9/28* (2006.01)

(52) U.S. Cl.
USPC ............. 502/155; 544/64; 544/157; 548/109; 548/119; 556/20; 564/12; 585/527

(58) Field of Classification Search
USPC ............. 502/155; 544/64, 157; 548/109, 119; 556/20; 564/12; 585/527
See application file for complete search history.

(56) References Cited

FOREIGN PATENT DOCUMENTS

EP          0585683 A2      3/1994
WO       2011082192 A1      7/2011

OTHER PUBLICATIONS

Database Registry Chemical Abstracts Service, Columbus, Ohio, Accession No. RN 74141-00-7, Entered STN: Nov. 16, 1984.*
Benito-Garagorri, David, et al., "Achiral and Chiral Transition Metal Complexes with Modularly Designed Tridentate PNP Pincer-Type Ligands Based on N-Heterocyclic Diamines," Organometallics, 2006, vol. 25, pp. 1900-1913, American Chemical Society.
Benito-Garagorri, David, et al., "Iron(II) Complexes Bearing Tridentate PNP Pincer-Type Ligands as Catalysts for the Selective Formation of 3-Hydroxyacrylates from Aromatic Aldehydes and Ethyldiazoacetate," Organometallics, 2007, vol. 26, pp. 217-222, American Chemical Society.
Benito-Garagorri, David, et al., "Kinetically Controlled Formation of Octahedral trans-Dicarbonyl Iron(II) PNP Pincer Complexes: The Decisive Role of Spin-State Changes," Organometallics, 2010, vol. 29, pp. 4932-4342, American Chemical Society.
Benito-Garagorri, David, et al., "Striking Differences Between the Solution and Solid-State Reactivity of Iron PNP Pincer Complexes with Carbon Monoxide," Organometallics, 2009, vol. 28, pp. 6902-6914, American Chemical Society.
Dyer, Philip W., et al., "Rigid N-Phosphino Guanidine P,N Ligands and Their Use in Nickel-Catalyzed Ethylene Oligomerization," Organometallics, 2008, vol. 27, pp. 5082-5087, American Chemical Society.
Munchenberg, Jochen, et al., "N-(N', N', N'',N''-tetramethyl) guanidine-substituted phosphines as monodentate, bidentate or tridentate ligands in transition metal chemistry," Journal or Organometallic Chemistry, 1997, vol. 529, pp. 361-374, Elsevier Science S.A.
Yeh, Chun-Wei, et al., "Role of Ligand Conformation in the Structural Diversity of Divalent Complexes Containing Phosphinic Amide Ligand," Inorganic Chemistry Communications, vol. 14, 2011, pp. 1212-1216, Elsevier B.V.
Sun, Mingtai, et al., "Synthesis, structures and ethylene polymerization behavior of half-metallocene chromium(III) catalysts bearing salicylaldiminato ligands," XP 002625776, New Journal of Chemistry, 2010, vol. 34, pp. 2979-2987.
Negrebetskii, V.V., et al., "Phosphorotropic Tautomeric Migrations of Phosphorus(III)—Containing Groups in the N-C-N Triad of Amidines," Institute of Organic Chemistry, Academy of Sciences of the Ukrainian SSR, vol. 52, No. 1, pp. 40-49 (printed pp. 36-44), Jan. 1982, Plenum Publishing Corporation.
Baiget, Lise, et al., "N-Phosphino-amidines and -guanidines: synthesis, structure and P,N-chelate chemistry," Dalton Transactions, 2008, pp. 1043-1054, The Royal Society of Chemistry.
Braunstein, Pierre, et al., "Erratum to "Synthesis of nickel phenyl complexes with new chelating •²-P,N ligands derived from α-iminoazatriphenylphosphoranes"", Journal of Organometallic Chemistry, 1999, vol. 582, pp. 370-377, Elsevier Science S.A.
Braunstein, Pierre, et al., "Synthesis of nickel phenyl complexes with new chelating •²-P,N ligands derived from α-iminoazatriphenylphosphoranes," Journal of Organometallic Chemistry, 1997, vol. 529, pp. 387-393, Elsevier Science S.A.

(Continued)

*Primary Examiner* — Samantha Shterengarts
(74) *Attorney, Agent, or Firm* — Conley Rose, P.C.; Rodney B. Carroll; Lynda S. Jolly

(57) ABSTRACT

$N^2$-phosphinyl amidine compounds, $N^2$-phosphinyl amidinates, $N^2$-phosphinyl amidine metal salt complexes, $N^2$-phosphinyl amidinate metal salt complexes are described. Methods for making $N^2$-phosphinyl amidine compounds, $N^2$-phosphinyl amidinates, $N^2$-phosphinyl amidine metal salt complexes, and $N^2$-phosphinyl amidinate metal salt complexes are also disclosed. Catalyst systems utilizing the $N^2$-phosphinyl amidine metal salt complexes and $N^2$-phosphinyl amidinate metal salt complexes are also disclosed along with the use of the $N^2$-phosphinyl amidine compounds, $N^2$-phosphinyl amidinates, $N^2$-phosphinyl amidine metal salt complexes, and $N^2$-phosphinyl amidinate metal salt complexes for the oligomerization and/or polymerization of olefins.

31 Claims, 1 Drawing Sheet

(56) References Cited

OTHER PUBLICATIONS

Foreign communication from a corresponding application—International Search Report and Written Opinion, PCT/US2010/062281, Mar. 25, 2011, 14 pages.

Hartke, Klaus, et al., "Zur 1,3(N→N)- Wanderung N-heterosubstituierter N,N$^1$-Dimethylbenzamidine," Chem. Ber., 1980, vol. 113, pp. 1394-1405, Verlag Chemie.

McNaught, A.D., et al., "Compendium of Chemical Terminology," The Gold Book, International Union of Pure and Applied Chemistry, Second Edition, 1997, 1 page, http:www.chem.qmul.ac.uk/iupac/bibliog/gold.html.

"Acid-catalyzed rearrangements of phosphinoamidines," 1992, vol. 61, No. 7, pp. 1581-1589 plus 1 cover page, International Academic Publishing Co.

Negrebetskii, V.V., et al., "Phosphorotropic tautomeric migrations of trivalent phosphorus groups in the nitrogen-carbon-nitrogen triad of amidines," Inst. Org. Khim., XP 002625773, 1982, vol. 52, No. 1, 1 page.

Ostrowska, K., et al., "Amidines (imidamides) N-substituted by metals, halogens, oxygen, and other heteroatoms," Science of Synthesis, XP 002625772, 2005, vol. 22, pp. 489-563, 1 page.

"Periodic Table of Elements," Feb. 4, 1985, C&EN, p. 27.

Shalimov, A.A., et al., "N-Substituted N-Phosphinotrifluoroactetamides in the Staudinger Reaction," Russian Journal of General Chemistry, vol. 75, No. 9, 2005, pp. 1376-1378, Pleiades Publishing, Inc.

* cited by examiner

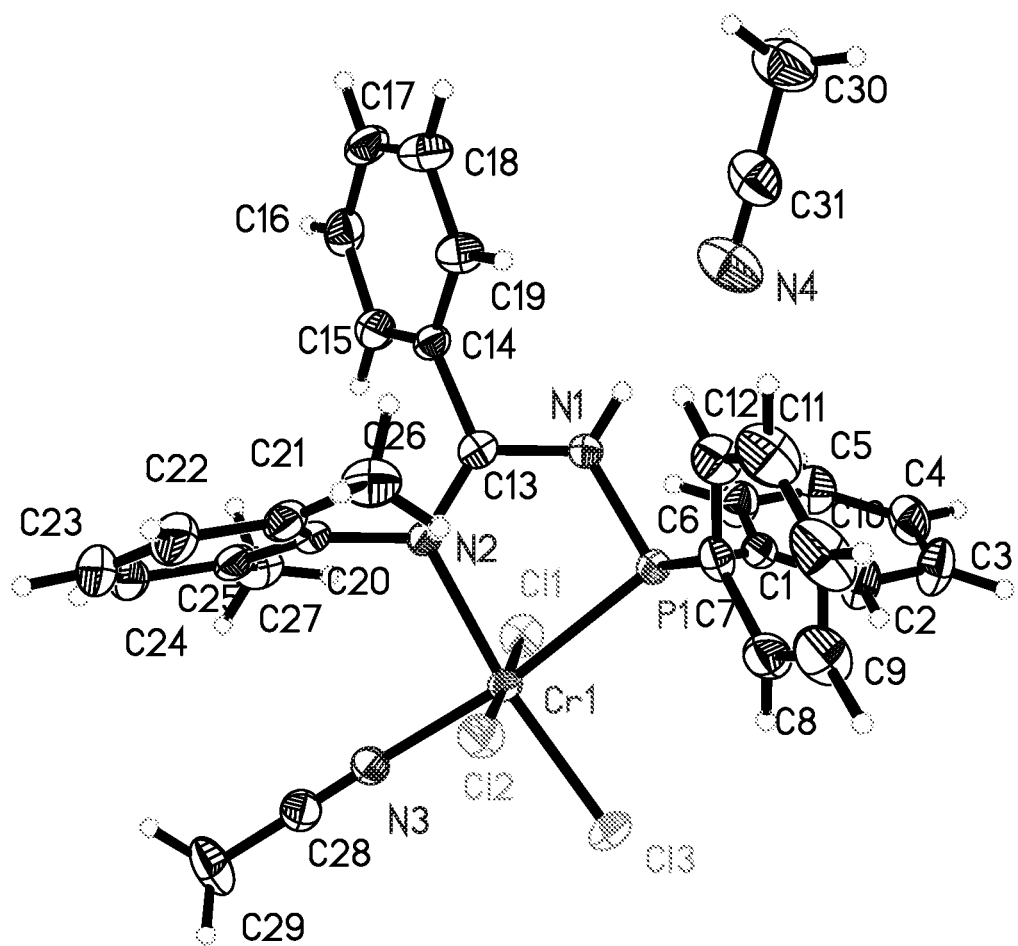

US 8,680,003 B2

PHOSPHINYL AMIDINE COMPOUNDS, METAL COMPLEXES, CATALYST SYSTEMS, AND THEIR USE TO OLIGOMERIZE OR POLYMERIZE OLEFINS

CROSS-REFERENCE TO RELATED APPLICATIONS

This application is a filing under 35 U.S.C. 371 of International Application No. PCT/US2010/062281 filed Dec. 29, 2010, entitled "Phosphinyl Amidine Compounds, Metal Complexes, Catalyst Systems, and Their Use to Oligomerize or Polymerize Olefins," claiming priority of U.S. Provisional Patent Application No. 61/291,459 filed Dec. 31, 2009, which applications are incorporated by reference herein in their entirety.

TECHNICAL FIELD OF THE INVENTION

This disclosure relates to $N^2$-phosphinyl amidine compounds and metal complexes of $N^2$-phosphinyl amidine compounds and their production. The disclosure also relates to methods of producing the $N^2$-phosphinyl amidine compounds and the metal complexes of $N^2$-phosphinyl amidine compounds. The disclosure further relates to catalyst systems utilizing the $N^2$-phosphinyl amidine compounds, metal complexes of $N^2$-phosphinyl amidine compounds, and their use in the oligomerization or polymerization of olefins.

BACKGROUND OF THE INVENTION

Olefins, also commonly known as alkenes, are important items of commerce. Their many applications include employment as intermediates in the manufacture of detergents, as precursors to more environmentally friendly refined oils, as monomers, and as precursors for many other types of products. An important subset of olefins are olefin oligomers, and one method of making olefin oligomers is via oligomerization of ethylene, which is a catalytic reaction involving various types of catalysts and/or catalyst systems. Examples of catalysts and catalyst systems used commercially in the oligomerization of olefins include alkylaluminum compounds, certain nickel-phosphine complexes, a titanium halide with a Lewis acid (e.g., diethyl aluminum chloride), and a selective 1-hexene catalyst system containing a chromium containing compound (e.g., a chromium carboxylate), a nitrogen containing ligand (e.g., a pyrrole), and a metal alkyl (e.g., alkyl aluminum compounds).

Several non-commercial olefin oligomerization catalyst systems are based upon metal complexes of pyridine bis-imines, metal complexes of α-diimine compounds having a metal complexing group, and selective trimerization and/or tetramerization catalyst system using a metal complex of a compound having a diphosphinylaminyl group. These catalyst systems typically use an alkyl aluminum compound (e.g., aluminoxane) to activate the metal complexes for olefin oligomerization.

Applications and demand for olefin oligomers (e.g., alpha olefins) continue to multiply, and competition to supply them correspondingly intensifies. Thus, additional novel and improved catalysts and methods for olefin oligomerization are desirable.

SUMMARY OF THE INVENTION

In an aspect, the present invention relates to a compound comprising one or more $N^2$-phosphinyl amidine groups. In an embodiment, the compound may comprise only one $N^2$-phosphinyl amidine group. In another embodiment, the compound may comprise only two $N^2$-phosphinyl amidine groups.

In an aspect, the present invention relates to a metal complex comprising a metal salt complexed to a compound having one or more $N^2$-phosphinyl amidine groups. In an embodiment, the metal complex may comprise a Group 4-10 metal salt complexed to a compound comprising one or more $N^2$-phosphinyl amidine groups. In some embodiments, the metal complex may comprise a Group 4-10 metal salt complexed to a compound comprises only one $N^2$-phosphinyl amidine group. In other embodiments, the metal complex may comprise a Group 4-10 metal salt complexed to a compound comprises only two $N^2$-phosphinyl amidine groups. In an embodiment, the metal salt may comprise chromium. In an embodiment, the metal salt may be a chromium halide or chromium β-diketonate.

In an aspect, the present invention relates to method of preparing a compound comprising one or more $N^2$-phosphinyl amidine groups. In an embodiment, the method for preparing a compound comprising one or more $N^2$-phosphinyl amidine groups comprise: a) contacting a metal amide with a nitrile; b) forming a metal amidinate; c) contacting a phosphine halide with the metal amidinate; and d) forming the compound comprising the $N^2$-phosphinyl amidine group. In some embodiments, the method for preparing an $N^2$-phosphinyl amidine compound may comprise: a) contacting an amine having a —$NH_2$ group and a compound capable of abstracting a proton from the —$NH_2$ group; b) forming a metal amide; c) contacting a metal amide and a nitrile; d) forming a metal amidinate; e) contacting the metal amidinate and a phosphine halide; and f) forming the $N^2$-phosphinyl amidine compound. In other embodiments, the method is a method for preparing an amidine compound having only one $N^2$ hydrogen atom and may comprise: a) contacting a metal amide and a nitrile; b) forming a first metal amidinate; c) contacting the first metal amidinate with a halogenated compound; d) forming an amidine compound having only one $N^2$ hydrogen atom; e) isolating the amidine compound having only one $N^2$ hydrogen atom; f) contacting the amidine compound having only one $N^2$ hydrogen atom with a compound capable of abstracting a proton from the amidine compound having only one $N^2$ hydrogen atom; g) forming a second metal amidinate; h) contacting the second metal amidinate and a phosphine halide; and i) forming the $N^2$-phosphinyl amidine compound. In other embodiments, the method is a method for preparing an amidine compound having only one $N^2$ hydrogen atom and may comprise: a) contacting a first amine and an acid halide; b) forming an amide; c) contacting the amide with phosphorus pentachloride; d) forming an N-substituted α-chloro imine; e) contacting the N-substituted α-chloro imine with a second amine; and f) forming the amidine compound having only one $N^2$ hydrogen atom.

In an aspect, the present invention relates to a method of preparing an $N^2$-phosphinyl amidine metal salt complex. In an embodiment, the method of preparing the $N^2$-phosphinyl amidine metal salt complex may comprise: a) contacting a metal salt with an $N^2$-phosphinyl amidine compound; and b) forming the $N^2$-phosphinyl amidine metal salt complex.

In an aspect, the present invention relates to a catalyst system comprising a metal salt complexed to a compound having one or more $N^2$-phosphinyl amidine groups and a metal alkyl. In another aspect, present invention relates to a catalyst system comprising a metal salt, a compound having one or more $N^2$-phosphinyl amidine groups, and a metal alkyl. In an embodiment, the catalyst system may comprise a metal salt complexed to a compound having only $N^2$-phosphinyl amidine groups. In some embodiments, the catalyst system may comprise a metal salt complexed to a compound having only two $N^2$-phosphinyl amidine groups. In an embodiment, the compound may comprise only one $N^2$-phosphinyl amidine groups. In some embodiments, the compound may comprise only one $N^2$-phosphinyl amidine group. In an embodiment, the metal salt of the metal complex or the catalyst system may comprise a Group 4-10 metal salt. In some embodiments, the metal salt of the metal complex or the catalyst system may comprise chromium. In other embodiments, the metal salt of the metal complex or the catalyst system may be a chromium halide or chromium β-diketonate.

In an aspect, the present invention relates to a method of olefin oligomerization or olefin polymerization. In an embodiment, the method of olefin oligomerization or olefin polymerization may comprise: contacting an olefin, a catalyst system comprising i) an $N^2$-phosphinyl amidine metal salt complex and ii) a metal alkyl, and optionally hydrogen; and b) forming an olefin oligomer product or olefin polymer product. In another embodiment, the method of olefin oligomerization or olefin polymerization may comprise: contacting an olefin, a catalyst system comprising i) an $N^2$-phosphinyl amidine compound, ii) a metal salt complex, and iii) a metal alkyl, and optionally hydrogen; and b) forming an olefin oligomer product or olefin polymer product. In a further embodiment, the method of olefin oligomerization or olefin polymerization may comprise: a) forming a catalyst system mixture comprising an $N^2$-phosphinyl amidine metal salt complex, a metal alkyl, and a first solvent; b) contacting the catalyst system mixture with an olefin, a second solvent, and optionally hydrogen; and c) forming an olefin oligomer product. In another embodiment, the method of olefin oligomerization or olefin polymerization may comprise: a) forming a composition comprising an $N^2$-phosphinyl amidine metal salt complex; b) forming a mixture comprising an olefin, a metal alkyl, and optionally hydrogen; c) contacting the composition of step a) and the mixture of step b); and d) forming an olefin oligomer product. In yet another embodiment, the method of olefin oligomerization or olefin polymerization may comprise: a) forming a mixture comprising an $N^2$-phosphinyl amidine compound, a metal salt, a metal alkyl, and a first solvent; b) contacting the mixture of step a) with an olefin, a second solvent, and optionally hydrogen; and c) forming an olefin oligomer product. In a further embodiment, the method of olefin oligomerization or olefin polymerization may comprise: a) forming a mixture comprising an $N^2$-phosphinyl amidine compound, a metal salt, and a first solvent; b) forming a mixture comprising an olefin, a metal alkyl, a second solvent, and optionally hydrogen; c) contacting the mixture formed in step a) and the mixture formed in step b); and d) forming an olefin oligomer product.

In an embodiment, the $N^2$-phosphinyl amidine compound or the $N^2$-phosphinyl amidine of the $N^2$-phosphinyl amidine metal salt complex utilized in the method of olefin oligomerization or olefin polymerization may comprise one or more $N^2$-phosphinyl amidine groups; alternatively, comprise only one $N^2$-phosphinyl amidine group; or alternatively, comprise only two $N^2$-phosphinyl amidine groups. In an embodiment, the metal salt or the metal salt of the $N^2$-phosphinyl amidine metal salt complex utilized in the method of olefin oligomerization or olefin polymerization may comprise a Group 4-10 metal salt; or alternatively, a chromium salt. In some embodiments, the metal salt or the metal salt of the $N^2$-phosphinyl amidine metal salt complex utilized in the method of olefin oligomerization or olefin polymerization may comprise a chromium halide or chromium β-diketonate. In an embodiment, the olefin utilized in the method of olefin oligomerization or olefin polymerization may comprise, or consist essentially of, $C_2$ to $C_{30}$ olefin; alternatively, $C_2$ to $C_{30}$ alpha olefin; alternatively, a $C_2$ to $C_{30}$ normal alpha olefin; alternatively, ethylene or propylene; or alternatively, ethylene. In an embodiment wherein the olefin is ethylene, the olefin oligomerization may be an ethylene trimerization and/or ethylene tetramerization process. In some embodiments, the olefin trimerization and/or olefin tetramerization process produces an ethylene oligomer product comprising a liquid product comprising at least 60 wt. % $C_6$ and $C_8$ olefins.

BRIEF DESCRIPTION OF THE FIGURES

FIG. 1 represents an X-ray of the $CrCl_3$ Complex B1 recrystallized from acetonitrile and consequently acetonitrile has displaced tetrahydrofuran in the complex.

DETAILED DESCRIPTION OF THE INVENTION

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the table are indicated using the numbering scheme indicated in the version of the periodic table of elements published in *Chemical and Engineering News,* 63(5), 27, 1985. In some instances a group of elements may be indicated using a common name assigned to the group; for example alkali earth metals (or alkali metals) for Group 1 elements, alkaline earth metals (or alkaline metals) for Group 2 elements, transition metals for Group 3-12 elements, and halogens for Group 17 elements.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter the composition or method to which the term is applied. For example, a feedstock consisting of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class which is utilized and it is possible to have different transitional terms or phrases utilized with different features within a claim. For example, a method can comprise several recited steps (and other non-recited steps) but utilize a catalyst system preparation consisting of specific or alternatively consist of specific steps and/or utilize a catalyst system comprising recited components and other non-recited components.

While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound unless otherwise specified.

For any particular compound disclosed herein, the general structure or name presented is also intended to encompass all structural isomers, conformational isomers, and stereoisomers that may arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethylpropane while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that may arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure that a substituent, ligand, or other chemical moiety may constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a group, for example, when referring to a substituted analog of a particular group, is intended to describe any non-hydrogen moiety that formally replaces a hydrogen in that group, and is intended to be non-limiting. A group or groups may also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

Unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms, and the like. Moreover, other identifiers or qualifying terms may be utilized to indicate the presence or absence of a particular substituent, a particular regiochemistry and/or stereochemistry, or the presence or absence of a branched underlying structure or backbone.

An amidine group is a group having the general structure

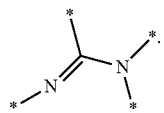

Within the amidine group the nitrogen participating in a double bond with the central carbon atom is referred to as the $N^1$ nitrogen and the nitrogen atom participating in a single bond with the central carbon atom is referred to as the $N^2$ nitrogen. Similarly, the groups attached to the $N^1$ and $N^2$ nitrogen atoms are referred to as the $N^1$ group and $N^2$ group respectively. An $N^2$-phosphinyl amidine group has the general structure

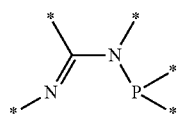

Within the $N^2$-phosphinyl amidine group the $N^1$ and $N^2$ nitrogen atoms and $N^1$ and $N^2$ groups have the same meaning as described for the amidine group. Consequently, an $N^2$-phosphinyl amidine group has the phosphinyl group is attached to the $N^2$ nitrogen atom. Within the amidine group and $N^2$-phosphinyl amidine group the carbon atom between the two nitrogen atoms is the central carbon atom and any substituent attached to it is referred to as the central carbon group. For the purpose of this disclosure and claims, a compound having a pyridine group with a 2-amine group (or its analogues—e.g., a pyrimidine ring, an imidazole ring, a compound having 2-aminopyridine group, etc. . . . ) or having a 2-phosphinylamine group is not considered to constitute an amidine group or $N^2$-phosphinyl amidine group, respectively.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. In one aspect, the hydrogen atom(s) removed to form the "organyl group," "organylene group," or "organic group" may be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C≡N), a carbamoyl group (—C(O)NH$_2$), an N-hydrocarbylcarbamoyl group (—C(O)NHR), or N,N'-dihydrocarbylcarbamoyl group (—C(O)NR$_2$), among other possibilities. In another aspect, the hydrogen atom(s) removed to form the "organyl group," "organylene group," or "organic group" may be attached to a carbon atom not belonging to, and remote from, a functional group, for example, —CH$_2$C(O)CH$_3$, —CH$_2$NR$_2$, and the like. An "organyl group," "organylene group," or "organic group" may be aliphatic, inclusive of being cyclic or acyclic, or may be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" may be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" definition includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the process described herein in which the material having an inert functional group takes part and/or does not complex with the metal compound of the metal complex. The term "does not complex with the metal compound" may include groups that could complex with a metal compound but in particular molecules described herein may not complex with a metal compound due to its positional relationship within a ligand. For example, while an ether group may complex with a metal compound, an ether group located at a para position of a substituted phenyl phosphinyl group may be an inert functional group because a single metal compound cannot complex with both the para ether group and the N$^2$-phosphinyl amidine group of the same metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g, alkoxy, and/or aroxy, among others), sulfidyl groups, and/or hydrocarbyl groups, among others.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or may be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane.

An "alkyl group," "alkylene group," and "alkane group" can be acyclic or cyclic groups, and/or may be linear or branched unless otherwise specified. Primary, secondary, and tertiary alkyl group are derived by removal of a hydrogen atom from a primary, secondary, tertiary carbon atom, respectively, of an alkane. The n-alkyl group may be derived by removal of a hydrogen atom from a terminal carbon atom of a linear alkane. The groups $RCH_2$ (R≠H), $R_2CH$ (R≠H), and $R_3C$ (R≠H) are primary, secondary, and tertiary alkyl groups, respectively.

A cycloalkane is a saturated cyclic hydrocarbon, with or without side chains, for example, cyclobutane. Unsaturated cyclic hydrocarbons having one or more endocyclic double or one triple bond are called cycloalkenes and cycloalkynes, respectively. Cycloalkenes and cycloalkynes having only one, only two, only three, etc. . . . endocyclic double or triple bonds, respectively, can be identified by use of the term "mono," "di," "tri,": etc. . . . within the name of the cycloalkene or cycloalkyne. Cycloalkenes and cycloalkynes can further identify the position of the endocyclic double or triple bonds.

A "cycloalkyl group" is a univalent group derived by removing a hydrogen atom from a ring carbon atom of a cycloalkane. For example, a 1-methylcyclopropyl group and a 2-methylcyclopropyl group are illustrated as follows.

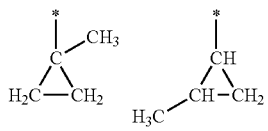

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane. It should be noted that according to the definitions provided herein, general cycloalkane groups (including cycloalkyl groups and cycloalkylene groups) include those having zero, one, or more than one hydrocarbyl substituent groups attached to a cycloalkane ring carbon atom (e.g. a methylcyclopropyl group) and is member of the group of hydrocarbon groups. However, when referring to a cycloalkane group having a specified number of cycloalkane ring carbon atoms (e.g. cyclopentane group or cyclohexane group, among others), the base name of the cycloalkane group having a defined number of cycloalkane ring carbon atoms refers to the unsubstituted cycloalkane group (including having no hydrocarbyl groups located on cycloalkane group ring carbon atom). Consequently, a substituted cycloalkane group having a specified number of ring carbon atoms (e.g. substituted cyclopentane or substituted cyclohexane, among others) refers to the respective group having one or more substituent groups (including halogens, hydrocarbyl groups, or hydrocarboxy groups, among other substituent groups) attached to a cycloalkane group ring carbon atom. When the substituted cycloalkane group having a defined number of cycloalkane ring carbon atoms is a member of the group of hydrocarbon groups (or a member of the general group of cycloalkane groups), each substituent of the substituted cycloalkane group having a defined number of cycloalkane ring carbon atoms is limited to hydrocarbyl substituent group. One can readily discern and select general groups, specific groups, and/or individual substituted cycloalkane group(s) having a specific number of ring carbons atoms which can be utilized as member of the hydrocarbon group (or a member of the general group of cycloalkane groups).

The term "olefin" whenever used in this specification and claims refers to compounds that have at least one carbon-carbon double bond that is not part of an aromatic ring or ring system. The term "olefin" includes aliphatic and aromatic, cyclic and cyclic, and/or linear and branched compounds having at least one carbon-carbon double bond that is not part of an aromatic ring or ring system unless specifically stated otherwise. The term "olefin," by itself, does not indicate the presence or absence of heteroatoms and/or the presence or absence of other carbon-carbon double bonds unless explicitly indicated. Olefins having only one, only two, only three, etc. . . . carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers a linear or branched hydrocarbon olefin that has one or more carbon-carbon double bonds. Alkenes having only one, only two, only three, etc. . . . such multiple bond can be identified by use of the term "mono," "di," "tri," etc. . . . within the name. For example, alkamonoenes, alkadienes, and alkatrienes refer to a linear or branched hydrocarbon olefins having only one carbon-carbon double bond (general formula $C_nH_{2n}$), only two carbon-carbon double bonds (general formula $C_nH_{2n-2}$), and only three carbon-carbon double bonds (general formula $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replace with a halogen atom.

An "alkenyl group" is a univalent group derived from an alkene by removal of a hydrogen atom from any carbon atom of the alkene. Thus, "alkenyl group" includes groups in which the hydrogen atom is formally removed from an $sp^2$ hybridized (olefinic) carbon atom and groups in which the hydrogen atom is formally removed from any other carbon atom. For example and unless otherwise specified, 1-propenyl (—CH═CHCH₃), 2-propenyl [(CH₃)C═CH₂], and 3-propenyl (—CH₂CH═CH₂) groups are all encompassed with the term "alkenyl group." Similarly, an "alkenylene group" refers to a group formed by formally removing two hydrogen atoms from an alkene, either two hydrogen atoms from one carbon atom or one hydrogen atom from two different carbon atoms. An "alkene group" refers to a generalized group formed by removing one or more hydrogen atoms (as necessary for the particular group) from an alkene. When the hydrogen atom is removed from a carbon atom participating in a carbon-carbon double bond, the regiochemistry of the carbon from which the hydrogen atom is removed, and regiochemistry of the carbon-carbon double bond may both be specified. Alkene groups can also have more than one carbon-carbon double bond. Alkene groups can also be further identified by the position of the carbon-carbon double bond.

The term "alkyne" whenever used in this specification and claims refers a linear or branched hydrocarbon olefin that has one or more carbon-carbon triple bonds. Alkynes having only one, only two, only three, etc. . . . such multiple bond can be identified by use of the term "mono," "di," "tri,": etc. . . . within the name. For example, alkamonoynes, alkadiynes, and alkatriynes refer to a linear or branched hydrocarbon olefins having only one carbon-carbon triple bond (general formula $C_nH_{2n-2}$), only two carbon-carbon triple bonds (general formula $C_nH_{2n-6}$), and only three carbon-carbon triple bonds (general formula $C_nH_{2n-10}$), respectively. Alkynes can be further identified by the position of the carbon-carbon triple bond(s). Other identifiers can be utilized to indicate the presence or absence of particular groups within an alkyne. For example, a haloalkyne refers to an alkyne having one or more hydrogen atoms replace with a halogen atom.

An "alkynyl group" is a univalent group derived from an alkyne by removal of a hydrogen atom from any carbon atom of the alkyne. Thus, "alkynyl group" includes groups in which the hydrogen atom is formally removed from an sp hybridized (acetylenic) carbon atom and groups in which the hydrogen atom is formally removed from any other carbon atom. For example and unless otherwise specified, 1-propynyl (—C≡CCH$_3$) and 3-propynyl (HC≡CCH$_2$—) groups are all encompassed with the term "alkynyl group." Similarly, an "alkynylene group" refers to a group formed by formally removing two hydrogen atoms from an alkyne, either two hydrogen atoms from one carbon atom if possible or one hydrogen atom from two different carbon atoms. An "alkyne group" refers to a generalized group formed by removing one or more hydrogen atoms (as necessary for the particular group) from an alkyne. Other identifiers may be utilized to indicate the presence or absence of particular groups within an alkyne group. Alkyne groups can also have more than one carbon carbon triple bond. Alkyne groups can also be further identified by the position of the carbon-carbon triple bond.

The term "alpha olefin" as used in this specification and claims refers to an olefin that has a carbon-carbon double bond between the first and second carbon atom of the longest contiguous chain of carbon atoms. The term "alpha olefin" includes linear and branched alpha olefins unless expressly stated otherwise. In the case of branched alpha olefins, a branch may be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of heteroatoms and/or the presence or absence of other carbon-carbon double bonds unless explicitly indicated. The terms "hydrocarbon alpha olefin" or "alpha olefin hydrocarbon" refer to alpha olefin compounds containing only hydrogen and carbon.

The term "linear alpha olefin" as used herein refers to a linear olefin having a carbon-carbon double bond between the first and second carbon atom. The term "linear alpha olefin" by itself does not indicate the presence or absence of heteroatoms and/or the presence or absence of other carbon-carbon double bonds, unless explicitly indicated. The terms "linear hydrocarbon alpha olefin" or "linear alpha olefin hydrocarbon" refers to linear alpha olefin compounds containing only hydrogen and carbon.

The term "normal alpha olefin" whenever used in this specification and claims refers to a linear hydrocarbon monoolefin having a carbon carbon double bond between the first and second carbon atom. It is noted that "normal alpha olefin" is not synonymous with "linear alpha olefin" as the term "linear alpha olefin" can include linear olefinic compounds having a double bond between the first and second carbon atoms and having heteroatoms and/or additional double bonds.

The term "consists essentially of normal alpha olefin(s)," or variations thereof, whenever used in this specification and claims refers to commercially available normal alpha olefin product(s). The commercially available normal alpha olefin product can contain non-normal alpha olefin impurities such as vinylidenes, internal olefins, branched alpha olefins, paraffins, and diolefins, among other impurities, which are not removed during the normal alpha olefin production process. One readily recognizes that the identity and quantity of the specific impurities present in the commercial normal alpha olefin product will depend upon the source of commercial normal alpha olefin product. Consequently, the term "consists essentially of normal alpha olefins" and its variants is not intended to limit the amount/quantity of the non-linear alpha olefin components any more stringently than the amounts/quantities present in a particular commercial normal alpha olefin product unless explicitly stated.

A "heterocyclic compound" is a cyclic compound having at least two different elements as ring member atoms. For example, heterocyclic compounds may comprise rings containing carbon and nitrogen (for example, tetrahydropyrrole), carbon and oxygen (for example, tetrahydrofuran), or carbon and sulfur (for example, tetrahydrothiophene), among others. Heterocyclic compounds and heterocyclic groups may be either aliphatic or aromatic.

A "heterocyclyl group" is a univalent group formed by removing a hydrogen atom from a heterocyclic ring or ring system carbon atom of a heterocyclic compound. By specifying that the hydrogen atom is removed from a heterocyclic ring or ring system carbon atom, a "heterocyclyl group" is distinguished from a "cycloheteryl group," in which a hydrogen atom is removed from a heterocyclic ring or ring system heteroatom. For example, a pyrrolidin-2-yl group illustrated below is one example of a "heterocyclyl group," and a pyrrolidin-1-yl group illustrated below is one example of a "cycloheteryl" group."

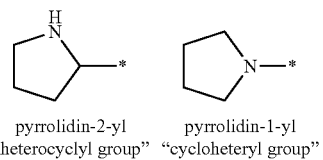

pyrrolidin-2-yl  pyrrolidin-1-yl
"heterocyclyl group"  "cycloheteryl group"

Similarly, a "heterocyclylene group" or more simply, a "heterocyclene group," refers to a group formed by removing two hydrogen atoms from a heterocyclic compound, at least one of which is from a heterocyclic ring or ring system carbon. Thus, in a "heterocyclylene group," at least one hydrogen is removed from a heterocyclic ring or ring system carbon atom, and the other hydrogen atom can be removed from any other carbon atom, including for example, the same heterocyclic ring or ring system carbon atom, a different heterocyclic ring or ring system ring carbon atom, or a non-ring carbon atom. A "heterocyclic group" refers to a generalized group formed by removing one or more hydrogen atoms (as necessary for the particular group and at least one of which is a heterocyclic ring carbon atom) from a heterocyclic compound. Generally, a heterocyclic compound may be aliphatic or aromatic unless otherwise specified.

A "cycloheteryl group" is a univalent group formed by removing a hydrogen atom from a heterocyclic ring or ring system heteroatom of a heterocyclic compound, as illustrated. By specifying that the hydrogen atom is removed from a heterocyclic ring or ring system heteroatom and not from a ring carbon atom, a "cycloheteryl group" is distinguished from a "heterocyclyl group" in which a hydrogen atom is removed from a heterocyclic ring or ring system carbon atom. Similarly, a "cycloheterylene group" refers to a group formed by removing two hydrogen atoms from an heterocyclic compound, at least one of which is removed from a heterocyclic ring or ring system heteroatom of the heterocyclic compound; the other hydrogen atom can be removed from any other atom, including for example, a heterocyclic ring or ring system ring carbon atom, another heterocyclic ring or ring system heteroatom, or a non-ring atom (carbon or heteroatom). A "cyclohetero group" refers to a generalized group formed by removing one or more hydrogen atoms (as necessary for the particular group and at least one of which is from a heterocyclic ring or ring system heteroatom) from a heterocyclic compound.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from the carbon atom of an aliphatic compound. Thus, an aliphatic compound is an acyclic or cyclic, saturated or unsaturated carbon compound, excluding aromatic compounds. That is, an aliphatic compound is a non-aromatic organic compound. Aliphatic compounds and therefore aliphatic groups may contain organic functional group(s) and/or atom(s) other than carbon and hydrogen.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group are generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon—the methylene group in diphenylmethane; oxygen—diphenyl ether; nitrogen—triphenyl amine; among others linking groups). As disclosed herein, the term "substituted" can be used to describe an aromatic group, arene, or heteroarene wherein a non-hydrogen moiety formally replaces a hydrogen in the compound, and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" may have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An arene is aromatic hydrocarbon, with or without side chains (e.g. benzene, toluene, or xylene, among others. An "aryl group" is a group derived from the formal removal of a hydrogen atom from an aromatic ring carbon of an arene. It should be noted that the arene may contain a single aromatic hydrocarbon ring (e.g., benzene, or toluene), contain fused aromatic rings (e.g., naphthalene or anthracene), and contain one or more isolated aromatic rings covalently linked via a bond (e.g., biphenyl) or non-aromatic hydrocarbon group(s) (e.g., diphenylmethane). One example of an "aryl group" is ortho-tolyl (o-tolyl), the structure of which is shown here.

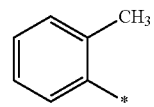 [SMILES: *c1ccccc1C]

Similarly, an "arylene group" refers to a group formed by removing two hydrogen atoms (at least one of which is from an aromatic ring carbon) from an arene. An "arene group" refers to a generalized group formed by removing one or more hydrogen atoms (as necessary for the particular group and at least one of which is an aromatic ring carbon) from an arene. However, if a group contains separate and distinct arene and heteroarene rings or ring systems (e.g. the phenyl and benzofuran moieties in 7-phenylbenzofuran) its classification depends upon the particular ring or ring system from which the hydrogen atom was removed, that is, an arene group if the removed hydrogen came from the aromatic hydrocarbon ring or ring system carbon atom (e.g. the 2 carbon atom in the phenyl group of 6-phenylbenzofuran and a heteroarene group if the removed hydrogen carbon came from a heteroaromatic ring or ring system carbon atom (e.g. the 2 or 7 carbon atom of the benzofuran group or 6-phenylbenzo-furan). It should be noted that according the definitions provided herein, general arene groups (including an aryl group and an areylene group) include those having zero, one, or more than one hydrocarbyl substituent groups located on an aromatic hydrocarbon ring or ring system carbon atom (e.g a toluene group or a xylene group, among others) and is a member of the group of hydrocarbon groups. However, a phenyl group (or phenylene group) and/or a naphthyl group (or naphthylene group) refer to the specific unsubstituted arene groups (including no hydrocarbyl group located on an aromatic hydrocarbon ring or ring system carbon atom). Consequently, a substituted phenyl group or substituted naphthyl group refers to the respective arene group having one or more substituent groups (including halogens, hydrocarbyl groups, or hydrocarboxy groups, among others) located on an aromatic hydrocarbon ring or ring system carbon atom. When the substituted phenyl group and/or substituted naphtyl group is a member of the group of hydrocarbon groups (or a member of the general group of arene groups), each substituent is limited to a hydrocarbyl substituent group. One having ordinary skill in the art can readily discern and select general phenyl and/or naphthyl groups, specific phenyl and/or naphthyl groups, and/or individual substituted phenyl or substituted naphthyl groups which can be utilized as a member of the group of hydrocarbon groups (or a member of the general group of arene groups).

A heteroarene is aromatic compound, with or without side chains, having a heteroatom within the aromatic ring or aromatic ring system (e.g. pyridene, indole, or benzofuran, among others). A "heteroaryl group" is a class of "heterocyclyl group" and is a univalent group formed by removing a hydrogen atom from a heteroaromatic ring or ring system carbon atom of a heteroarene compound. By specifying that the hydrogen atom is removed from a ring carbon atom, a "heteroaryl group" is distinguished from an "arylheteryl group," in which a hydrogen atom is removed from a heteroaromatic ring or ring system heteroatom. For example, an indol-2-yl group illustrated below is one example of a "heteroaryl group," and an indol-1-yl group illustrated below is one example of an "arylheteryl" group."

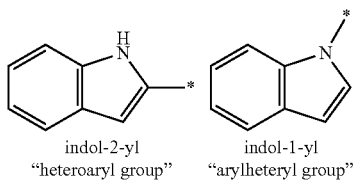

indol-2-yl
"heteroaryl group"

indol-1-yl
"arylheteryl group"

Similarly, a "heteroarylene group" refers to a group formed by removing two hydrogen atoms from a heteroarene compound, at least one of which is from a heteroarene ring or ring system carbon atom. Thus, in a "heteroarylene group," at least one hydrogen is removed from a heteroarene ring or ring system carbon atom, and the other hydrogen atom can be removed from any other carbon atom, including for example, a heteroarene ring or ring system carbon atom, or a non-heteroarene ring or ring system atom. A "heteroarene group" refers to a generalized group formed by removing one or more hydrogen atoms (as necessary for the particular group and at least one of which is a heteroarene ring or ring system carbon atom) from a heteroarene compound. If a hydrogen atom is removed from a heteroaromatic ring or ring system heteroatom and from a heteroaromatic ring or ring system carbon atom or an aromatic hydrocarbon ring or ring system carbon atom, the group is classified as an "arylheterylene group" or an "arylhetero group."

An "arylheteryl group" is a class of "cycloheteryl group" and is a univalent group formed by removing a hydrogen atom from a heteroaromatic ring or ring system heteroatom, as illustrated. By specifying that the hydrogen atom is removed from of a heteroaromatic ring or ring system heteroatom and not from a heteroaromatic ring or ring system carbon atom, an "arylheteryl group" is distinguished from a "heteroaryl group" in which a hydrogen atom is removed from a heteroaromatic ring or a ring system carbon atom. Similarly, an "arylheterylene group" refers to a group formed by removing two hydrogen atoms from a heteroaryl compound, at least one of which is removed from a heteroaromatic ring or ring system heteroatom of the heteroaryl compound; the other hydrogen atom can be removed from any other atom, including for example, a heteroaromatic ring or ring system carbon atom, another heteroaromatic ring or ring system heteroatom, or a non-ring atom (carbon or heteroatom) from a heteroaromatic compound. An "arylhetero group" refers to a generalized group formed by removing one or more hydrogen atoms (as necessary for the particular group and at least one of which is from a heteroaromatic ring or ring system) heteroatom from a heteroarene compound.

An "aralkyl group" is an aryl-substituted alkyl group having a free valance at a non-aromatic carbon atom (e.g. a benzyl group, or a 2-phenyleth-1yl group, among others). Similarly, an "aralkylene group" is an aryl-substituted alkylene group having two free valencies at a single non-aromatic carbon atom or a free valence at two non-aromatic carbon atoms while an "aralkane group" is a generalized is an aryl-substituted alkane group having one or more free valencies at a non-aromatic carbon atom(s). A "heteroaralkyl group" is a heteroaryl-substituted alkyl group having a free valence at a non-heteroaromatic ring or ring system carbon atom. Similarly a "heteroaralkylene group" is a heteroaryl-substituted alkylene group having two free valencies at a single non-heteroaromatic ring or ring system carbon atom or a free valence at two non-heteroaromatic ring or ring system carbon atoms while a "heteroaralkane group" is a generalized aryl-substituted alkane group having one or more free valencies at a non-heteroaromatic ring or ring system carbon atom(s). It should be noted that according the definitions provided herein, general aralkane groups include those having zero, one, or more than one hydrocarbyl substituent groups located on an aralkane aromatic hydrocarbon ring or ring system carbon atom and is a member of the group of hydrocarbon groups. However, specific aralkane groups specifying a particular aryl group (e.g. the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

A "halide" has its usual meaning; therefore, examples of halides include fluoride, chloride, bromide, and iodide.

An "organoheteryl group" is a univalent group containing carbon, which are thus organic, but which have their free valence at an atom other than carbon. Thus, organoheteryl and organyl groups are complementary and mutually exclusive. Organoheteryl groups can be cyclic or acyclic, and/or aliphatic or aromatic, and thus encompasses aliphatic "cycloheteryl groups" (e.g. pyrrolidin-1-yl or morpholin-1-yl, among others), aromatic "arylheteryl groups" (e.g. pyrrol-1-yl or indol-1-yl, among others), and acyclic groups (e.g. organylthio, trihydrocarbylsilyl, aryloxy, or alkoxy, among others). Similarly, an "organoheterylene group" is a divalent group containing carbon and at least one heteroatom having two free valencies, at least one of which is at a heteroatom. An "organohetero group" is a generalized group containing carbon and at least one heteroatom having one or more free valencies (as necessary for the particular group and at least one of which is at a heteroatom) from an organohetero compound.

An "oxygen group," also called an "oxygen-bonded group," is a chemical moiety having at least one free valence on an oxygen atom. Exemplary "oxygen groups" include, but are not limited to, hydroxy (—OH), —OR, —OC(O)R, —OSiR$_3$, —OPR$_2$, —OAlR$_2$, —OSiR$_2$, —OGeR$_3$, —OSnR$_3$, —OSO$_2$R, —OSO$_2$OR, —OBR$_2$, —OB(OR)$_2$, —OAlR$_2$, —OGaR$_2$, —OP(O)R$_2$, —OAs(O)R$_2$, —OAlR$_2$, and the like, including substituted analogs thereof. In an "oxygen group" having more than one free valency, the other free valencies may be on atom(s) other than oxygen, for example carbon, in accord with the rules of chemical structure and bonding.

A "sulfur group," also called a "sulfur-bonded group," is a chemical moiety having at least one free valence on a sulfur atom. Exemplary "sulfur group(s)" include, but are not limited to, —SR, —SCN, —S(O)R, —SO$_2$R, and the like, including substituted analogs thereof. In a "sulfur group" having more than one free valency, the other free valencies may be on atom(s) other than sulfur, for example carbon, in accord with the rules of chemical structure and bonding.

A "nitrogen group," also called a "nitrogen-bonded group," is a chemical moiety having at least one free valence on a nitrogen atom. Exemplary "nitrogen groups" include, but are not limited to, an aminyl group (—NH$_2$), an N-substituted aminyl group (—NRH), an N,N-disubstituted aminyl group (—NR$_2$), a hydrazido group (—NHNH$_2$), an N$^1$-substituted hydrazido group (—NRNH$_2$), an N$^2$-substituted hydrazido group (—NHNRH), an N$^2$,N$^2$-disubstituted hydrazido group (—NHNR$_2$), a nitro group (—NO$_2$), an azido group (—N$_3$), an amidyl group (—NHC(O)R), an N-substituted amido group (—NRC(O)R), and the like, including substituted analogs thereof. In a "nitrogen group" having more than one free valency, the other free valencies may be on any atom(s) in the group in accord with the rules of chemical structure and bonding, including atoms other than nitrogen, for example, carbon.

A "phosphorus group," also called a "phosphorus-bonded group," is a chemical moiety having at least one free valence on a phosphorus atom. Exemplary "phosphorous groups include, but are not limited to, —PR$_2$, —P(O)R$_2$, —P(OR)$_2$, —P(O)(OR)$_2$, —P(NR$_2$)$_2$, —P(O)(NR$_2$)$_2$, and the like, including substituted analogs thereof. In a "phosphorus group" having more than one free valency, the other free valencies may be on any atom(s) in the group in accord with the rules of chemical structure and bonding, including atoms other than phosphorus, for example, carbon.

For each of the specific groups in which the free valency is situated on a heteroatom (non-carbon atom), such as the "oxygen group," "sulfur group," "nitrogen group," "phosphorus group," can include a general "R" moiety. In each instance and unless other wise specified, R in a "oxygen group," "sulfur group," "nitrogen group," "phosphorus group," can be a $C_1$ to $C_{20}$ organyl group; alternatively, a $C_1$ to $C_{20}$ hydrocarbyl group; alternatively, a $C_1$ to $C_{20}$ alkyl group; alternatively, a $C_1$ to $C_{20}$ aliphatic group; alternatively, a $C_1$ to $C_{20}$ cycloalkyl group; alternatively, a $C_1$ to $C_{20}$ alkenyl group; alternatively, a $C_1$ to $C_{20}$ alkynyl group; alternatively, a $C_4$ to $C_{20}$ aromatic group; alternatively, $C_6$ to $C_{20}$ an aryl group; alternatively, a $C_3$ to $C_{20}$ heterocyclyl group; alternatively, a $C_3$ to $C_{20}$ cycloheteryl group; alternatively, a $C_3$ to $C_{20}$ heteroaryl group; alternatively, an $C_3$ to $C_{20}$ arylheteryl group; alternatively, an $C_1$ to $C_{20}$ organoheteryl group; alternatively, an $C_7$ to $C_{20}$ aralkyl group; or alternatively, a $C_5$ to $C_{20}$ heteroaralkyl group.

An "organoaluminum compound," is used to describe any compound that contains an aluminum-carbon bond. Thus, organoaluminum compounds include hydrocarbyl aluminum compounds such as trialkyl-, dialkyl-, or monoalkylaluminum compounds; hydrocarbyl alumoxane compounds, and aluminate compounds which contain an aluminum-organyl bond such as tetrakis(p-tolyl)aluminate salts.

Within this disclosure the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-subtituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be reference using comprising or some other alternative language. For example, a reference to a phenyl group comprising a substituent at the 4 position refers to a group having a non-hydrogen atom at the 4 position and hydrogen or any non-hydrogen group at the 2, 3, 5, and 6 positions.

The term "reactor effluent," and it derivatives (e.g. oligomerization reactor effluent) generally refers to all the material which exits the reactor. The term "reactor effluent," and its derivatives, can also be prefaced with other descriptors that limit the portion of the reactor effluent being referenced. For example, while the term "reactor effluent" would refer to all material exiting the reactor (e.g. product and solvent or diluent, among others), the term "olefin reactor effluent" refers to the effluent of the reactor which contains an olefin (i.e. carbon-carbon) double bond.

The term "oligomerization," and its derivatives, refers to processes which produce a mixture of products containing at least 70 weight percent products containing from 2 to 30 monomer units. Similarly, an "oligomer" is a product that contains from 2 to 30 monomer units while an "oligomerization product" includes all product made by the "oligomerization" process including the "oligomers" and products which are not "oligomers" (e.g. product which contain more than 30 monomer units). It should be noted that the monomer units in the "oligomer" or "oligomerization product" do not have to be the same. For example, an "oligomer" or "oligomerization product" of an "oligomerization" process using ethylene and propylene as monomers can contain both ethylene and/or propylene units.

The term "trimerization," and it derivatives, refers to a process which produces a mixture of products containing at least 70 weight percent products containing three and only three monomer units. A "trimer" is a product which contains three and only three monomer units while a "trimerization product" includes all products made by the trimerization process including trimer and product which are not trimer (e.g. dimers or tetramers). Generally, an olefin trimerization reduces number of olefinic bonds, i.e., carbon-carbon double bonds, by two when considering the number of olefin bonds in the monmer units and the number of olefin bonds in the trimer. It should be noted that the monomer units in the "trimer" or "trimerization product" do not have be the same. For example, a "trimer" of a "trimerization" process using ethylene and butene as monomers can contain ethylene and/or butene monomer units. That is to say the "trimer" will include $C_6$, $C_8$, $C_{10}$, and $C_{12}$ products. In another example, a "trimer"

of a "trimerization" process using ethylene as the monomer can contain ethylene monomer units. It should also be noted that a single molecule can contain two monomer units. For example, dienes such as 1,3-butadiene and 1,4-pentadiene have two monomer units within one molecule.

The term "tetramerization," and it derivatives, refers to a process which produces a mixture of products containing at least 70 weight percent products containing four and only four monomer units. A "tetramer" is a product which contains four and only four monomer units while a "tetramerization product" includes all products made by the tetramerization process including tetramer and product which are not tetramer (e.g. dimers or trimer). Generally, an olefin tetramerization reduces number of olefinic bonds, i.e., carbon-carbon double bonds, by three when considering the number of olefin bonds in the monmer units and the number of olefin bonds in the tetramer. It should be noted that the monomer units in the "tetramer" or "tetramerization product" do not have be the same. For example, a "tetramer" of a "tetramerization" process using ethylene and butene as monomers can contain ethylene and/or butene monomer units. In an example, a "tetramer" of a "tetramerization" process using ethylene as the monomer can contain ethylene monomer units. It should also be noted that a single molecule can contain two monomer units. For example, dienes such as 1,3-butadiene and 1,4-pentadiene have two monomer units within one molecule.

The term "trimerization and tetramerization," and it derivatives, refers to a process which produces a mixture of products containing at least 70 weight percent products containing three and/or four and only three and/or four monomer units. A "trimerization and tetramerization product" includes all products made by the "trimerization and tetramerization" process including trimer, tetramer, and product which are not tetramer (e.g. dimers). In an example, a "trimerization and tetramerization" process using ethylene as the monomer produces a mixture of products containing at least 70 weight percent hexene and/or octene.

The term or variation of the terms an "oligomerized product having X carbon atoms" and "$C_x$ oligomer product," wherein X can be any positive non-zero integer, refers to materials produced by monomer oligomerization which have X carbon atoms. Thus, the term oligomerized product having X carbon atoms excludes materials having X carbon atoms which were not produced by the olefin oligomerization (e.g. solvent). These terms can also include other descriptive words (e.g. olefin, liquid, and mixture, among others) without detracting from the essence of the term referring to materials having X carbon atoms, produced by monomer oligomerization, and fitting the additional descriptive terms.

Catalyst system activity is defined as grams of a product produced per gram of metal of the metal salt or the $N^2$-phosphinyl amidine metal salt complex utilized in the catalyst system over the first 30 minutes of an oligomerization or polymerization reaction beginning from the time when the complete catalyst system is contacted with the olefin. Catalyst system activity can be stated in terms of various products of an olefin oligomerization or polymerization. For example in an ethylene trimerization and tetramerization process utilizing a chromium based catalyst system, catalyst system activities which can be utilized include (g $C_6$)/(g Cr), (g $C_8$)/(g Cr), ($C_6$+$C_8$)/(g Cr), (g ethylene oligomer)/(g Cr), and (total product)/(g Cr), among other activities.

This disclosure encompasses $N^2$-phosphinyl amidine compounds, methods for making $N^2$-phosphinyl amidine compounds, metal salt complexes comprising $N^2$-phosphinyl amidine compounds, methods of making metal salt complexes comprising $N^2$-phosphinyl amidine compounds, catalyst systems comprising $N^2$-phosphinyl amidine compounds, methods of making catalyst systems comprising $N^2$-phosphinyl amidine compounds, and methods of oligomerizing olefins utilizing catalysts system comprising $N^2$-phosphinyl amidine compounds, among other aspects an embodiments. These aspects of this disclosure are further described herein. While these aspects may be disclosed under these headings, the heading does not limit the disclosure found therein. Additionally the various aspects and embodiments disclosed herein can be combined in any manner.

Generally, the $N^2$-phosphinyl amidine compounds encompassed by this disclosure have at least one $N^2$-phosphinyl amidine group. In an embodiment, the $N^2$-phosphinyl amidine compounds comprise only one $N^2$-phosphinyl amidine; or alternatively, comprise only two $N^2$-phosphinyl amidine groups.

In an aspect, the compounds encompassed by the present disclosure include an $N^2$-phosphinyl amidine compound. Generally, the $N^2$-phosphinyl amidine compounds encompassed by this disclosure comprise an $N^2$-phosphinyl amidine group; or alternatively, comprise two $N^2$-phosphinyl amidine groups. In an embodiment, the $N^2$-phosphinyl amidine compounds comprise only one $N^2$-phosphinyl amidine group; or alternatively, comprise only two $N^2$-phosphinyl amidine groups. In an embodiment, the compounds, regardless of the number of $N^2$-phosphinyl amidine groups, or structure, can be non-metallic (i.e., a non-metallic $N^2$-phosphinyl amidine compound or a non-metallic compound having an $N^2$-phosphinyl amidine group). In some embodiments, the amidine group of the $N^2$-phosphinyl amidine compounds is an acyclic amidine group (an amidine group wherein the two nitrogen atoms and the central carbon atom of the amine group are not contained in a ring).

In an aspect, the $N^2$-phosphinyl amidine compound may have Structure NP1, NP2, NP3, NP4, NP5, NP6, NP7, NP8, NP9, NP10, NP11, NP13, NP15, NP16, NP18, or NP20; alternatively, Structure NP1, NP2, NP3, NP4, or NP5; alternatively, NP6, NP7, NP8, NP9, or NP10; alternatively, NP11, NP13, or NP15; alternatively, NP16, NP18, or NP20; alternatively, Structure NP1; alternatively, Structure NP2; alternatively, Structure NP3; alternatively, Structure NP4; alternatively, Structure NP5; alternatively, NP6; alternatively, NP7; alternatively, NP8; alternatively, NP9; alternatively, NP10; alternatively, Structure NP11; alternatively, Structure NP13; alternatively, Structure NP15; alternatively, NP16; alternatively, NP 18; or alternatively, NP20.

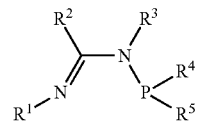

Structure NP1

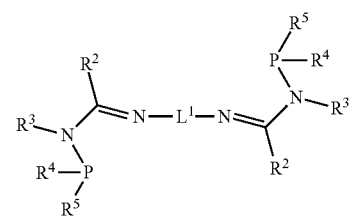

Structure NP2

Structure NP3

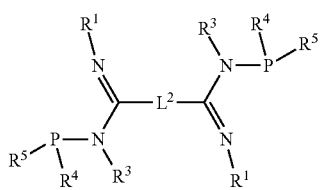

Structure NP4

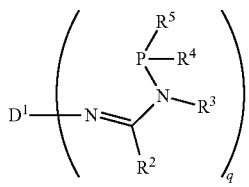

Structure NP5

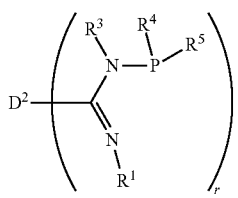

Structure NP6

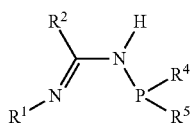

Structure NP7

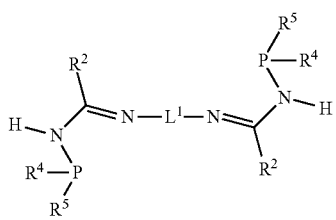

Structure NP8

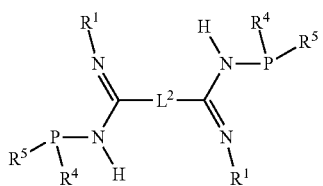

Structure NP9

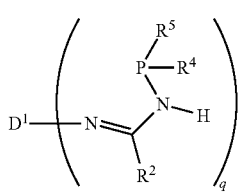

Structure NP10

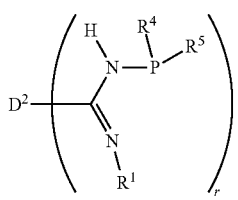

Structure NP11

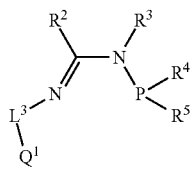

Structure NP13

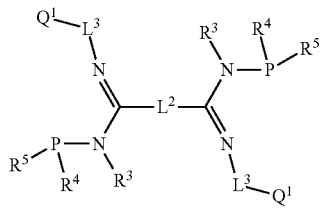

Structure NP15

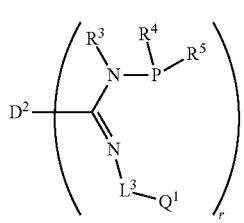

Structure NP16

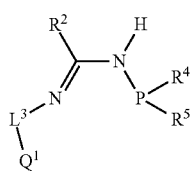

Structure NP18

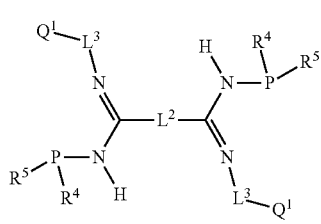

Structure NP20

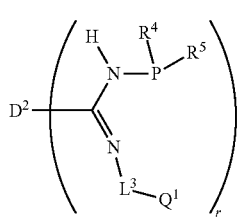

In an embodiment, the $N^2$-phosphinyl amidine compound comprising only one $N^2$-phosphinyl amidine group can be characterized by having the Structure NP1, NP6, NP11, or NP16; alternatively, Structure NP1 or NP6; alternatively, Structure NP11 or NP16; alternatively, Structure NP1 or NP11; or alternatively, Structure NP6 or NP16. In an embodiment, the $N^2$-phosphinyl amidine compound comprising only two $N^2$-phosphinyl amidine groups can be characterized by having Structure NP2, NP3, NP8, NP13, or NP18; alternatively, Structure NP2, NP3, or NP8; alternatively, Structure NP13, or NP18; alternatively, Structure NP2 or NP3; alternatively, Structure NP3 or NP13; or alternatively, Structure NP8 or NP18. In other embodiments, $N^2$-phosphinyl amidine compounds having at least one $N^2$-phosphinyl amidine group can be characterized by having the Structure NP4 NP5, NP9, NP10, NP15, or NP20; alternatively, Structure NP4, NP5, NP9, or NP10; alternatively, Structure NP15, or NP20; alternatively, Structure NP4 or NP5; alternatively, Structure NP9 or NP10; alternatively, Structure NP5 or NP15; or alternatively, Structure NP10 or NP20. $R^1$, $R^2$, $R^3$, $R^4$, $R^5$, $D^1$, $D^2$, $L^1$, $L^2$, $L^3$, $Q^1$, q, and r within $N^2$-phosphinyl amidine compound Structures NP1-NP10, NP11, NP13, NP15, NP16, NP18, and/or NP20 are independently described herein and can be utilized without limitation further describe the $N^2$-phosphinyl amidine compounds having Structures NP1-NP10, NP11, NP13, NP15, NP16, NP18, and/or NP20. In other embodiments, the $N^2$-phosphinyl amidine compounds can have any specific structure disclosed herein.

Generally, $R^1$ can be an organyl group; alternatively, an organyl group consisting essentially of inert functional groups; or alternatively, a hydrocarbyl group. In an embodiment, $R^1$ can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, $R^1$ can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In an embodiment, $R^1$ can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In yet other embodiments, $R^1$ can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group.

In an aspect, $R^1$ can be a $C_1$ to $C_{30}$ alkyl group, a $C_4$ to $C_{30}$ cycloalkyl group, a $C_4$ to $C_{30}$ substituted cycloalkyl group, a $C_3$ to $C_{30}$ aliphatic heterocyclic group, a $C_3$ to $C_{30}$ substituted aliphatic heterocyclic group, a $C_6$ to $C_{30}$ aryl group, a $C_6$ to $C_{30}$ substituted aryl group, a $C_3$ to $C_{30}$ heteroaryl group, or a $C_3$ to $C_{30}$ substituted heteroaryl group; alternatively, a $C_1$ to $C_{30}$ alkyl group, a $C_4$ to $C_{30}$ cycloalkyl group, a $C_4$ to $C_{30}$ substituted cycloalkyl group, a $C_6$ to $C_{30}$ aryl group, or a $C_6$ to $C_{30}$ substituted aryl group; alternatively, a $C_4$ to $C_{30}$ cycloalkyl group or a $C_4$ to $C_{30}$ substituted cycloalkyl group; alternatively, a $C_3$ to $C_{30}$ aliphatic heterocyclic group or a $C_3$ to $C_{30}$ substituted aliphatic heterocyclic group; alternatively, a $C_6$ to $C_{30}$ aryl group or a $C_6$ to $C_{30}$ substituted aryl group; alternatively, a $C_3$ to $C_{30}$ heteroaryl group or a $C_3$ to $C_{30}$ substituted heteroaryl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_3$ to $C_{30}$ aliphatic heterocyclic group; alternatively, a $C_3$ to $C_{30}$ substituted aliphatic heterocyclic group; alternatively, a $C_6$ to $C_{30}$ aryl group; alternatively, a $C_6$ to $C_{30}$ substituted aryl group; alternatively, a $C_3$ to $C_{30}$ heteroaryl group; or alternatively, a $C_3$ to $C_{30}$ substituted heteroaryl group. In an embodiment, $R^1$ can be a $C_1$ to $C_{15}$ alkyl group, a $C_4$ to $C_{20}$ cycloalkyl group, a $C_4$ to $C_{20}$ substituted cycloalkyl group, a $C_3$ to $C_{20}$ aliphatic heterocyclic group, a $C_3$ to $C_{20}$ substituted aliphatic heterocyclic group, a $C_6$ to $C_{20}$ aryl group, a $C_6$ to $C_{20}$ substituted aryl group, a $C_3$ to $C_{20}$ heteroaryl group, or a $C_3$ to $C_{20}$ substituted heteroaryl group; alternatively, a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group; alternatively, a $C_4$ to $C_{20}$ cycloalkyl group or a $C_4$ to $C_{20}$ substituted cycloalkyl group; alternatively, a $C_3$ to $C_{20}$ aliphatic heterocyclic group or a $C_3$ to $C_{20}$ substituted aliphatic heterocyclic group; alternatively, a $C_6$ to $C_{20}$ aryl group or a $C_6$ to $C_{20}$ substituted aryl group; alternatively, a $C_3$ to $C_{20}$ heteroaryl group or a $C_3$ to $C_{20}$ substituted heteroaryl group; alternatively, a $C_1$ to $C_{15}$ alkyl group; alternatively, a $C_4$ to $C_{20}$ cycloalkyl group; alternatively, a $C_4$ to $C_{20}$ substituted cycloalkyl group; alternatively, a $C_3$ to $C_{20}$ aliphatic heterocyclic group; alternatively, a $C_3$ to $C_{20}$ substituted aliphatic heterocyclic group; alternatively, a $C_6$ to $C_{20}$ aryl group; alternatively, a $C_6$ to $C_{20}$ substituted aryl group; alternatively, a $C_3$ to $C_{20}$ heteroaryl group; or alternatively, a $C_3$ to $C_{20}$ substituted heteroaryl group. In other embodiments, $R^1$ can be a $C_1$ to $C_{10}$ alkyl group, a $C_4$ to $C_{15}$ cycloalkyl group, a $C_4$ to $C_{15}$ substituted cycloalkyl group, a $C_3$ to $C_{15}$ aliphatic heterocyclic group, a $C_3$ to $C_{15}$ substituted aliphatic heterocyclic group, a $C_6$ to $C_{15}$ aryl group, a $C_6$ to $C_{15}$ substituted aryl group, a $C_3$ to $C_{15}$ heteroaryl group, or a $C_3$ to $C_{15}$ substituted heteroaryl group; alternatively, a $C_1$ to $C_{10}$ alkyl group, a $C_4$ to $C_{15}$ cycloalkyl group, a $C_4$ to $C_{15}$ substituted cycloalkyl group, a $C_6$ to $C_{15}$ aryl group, or a $C_6$ to $C_{15}$ substituted aryl group; alternatively, a $C_4$ to $C_{15}$ cycloalkyl group or a $C_4$ to $C_{15}$ substituted cycloalkyl group; alternatively, a $C_3$ to $C_{15}$ aliphatic heterocyclic group or a $C_3$ to $C_{15}$ substituted aliphatic heterocyclic group; alternatively, a $C_6$ to $C_{15}$ aryl group or a $C_6$ to $C_{15}$ substituted aryl group; alternatively, a $C_3$ to $C_{15}$ heteroaryl group or a $C_3$ to $C_{15}$ substituted heteroaryl group; alternatively, a $C_1$ to $C_{10}$ alkyl group; alternatively, a $C_4$ to $C_{15}$ cycloalkyl group; alternatively, a $C_4$ to $C_{15}$ substituted cycloalkyl group; alternatively, a $C_3$ to $C_{15}$ aliphatic heterocyclic group; alternatively, a $C_3$ to $C_{15}$ substituted aliphatic heterocyclic group; alternatively, a $C_6$ to $C_{15}$ aryl group; alternatively, a $C_6$ to $C_{15}$ substituted aryl group; alternatively, a $C_3$ to $C_{15}$ heteroaryl group; or alternatively, a $C_3$ to $C_{15}$ substituted heteroaryl group. In further embodiments, $R^1$ can be a $C_1$ to $C_5$ alkyl group.

In an embodiment, $R^1$ can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, or a nonadecyl group; or alternatively, a methyl group, an ethyl group, a propyl group, a butyl group, a pentyl group, a hexyl group, a heptyl group, an octyl group, a nonyl group, or a decyl group. In some embodiments, $R^1$ can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, an n-propyl group; alternatively, an iso-propyl group; alternatively, a tert-butyl group; or alternatively, a neopentyl group. In some embodiments, the alkyl groups which can be utilized as $R^1$ can be substituted. Each substituent of a substituted alkyl group independently can be a halogen or a hydrocarboxy group; alternatively, a halogen; or alternatively, a hydrocarboxy group. Halogens and hydrocarboxy groups that can be utilized as substituents are independently disclosed herein and can be utilized without limitation to further describe the substituted alkyl group which can be utilized as $R^1$.

In an embodiment, $R^1$ can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group.

In some embodiments, $R^1$ can be a cyclopentyl group, a substituted cyclopentyl group, a cyclohexyl group, or a substituted cyclohexyl group. In other embodiments, $R^1$ can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; or alternatively, a cyclooctyl group or a substituted cyclooctyl group. In further embodiments, $R^1$ can be a cyclopentyl group; alternatively, a substituted cyclopentyl group; a cyclohexyl group; or alternatively, a substituted cyclohexyl group. Substituents for the substituted cycloalkyl group are independently disclosed herein and can be utilized without limitation to further describe the substituted cycloalkyl group which can be utilized as $R^1$.

In an embodiment, each substituent for a substituted cycloalkyl group (general or specific) that can be utilized as $R^1$ independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, each substituent for a substituted cycloalkyl group (general or specific) that can be utilized as $R^1$ independently can be a halogen, an alkyl group, or an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Specific substituent halogens, hydrocarbyl groups, hydrocarboxy groups, alkyl group, and alkoxy groups are independently disclosed herein and can be utilized without limitation to further describe the substituents for a substituted cycloalkyl group (general or specific) that can be utilized as $R^1$.

In an aspect, $R^1$ can have Structure G1:

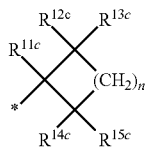

Structure G1 wherein the undesignated valency is attached to the $N^1$ nitrogen atom of the $N^2$-phosphinyl amidine group. Generally, $R^{11c}$, $R^{12c}$, $R^{13c}$, $R^{14c}$, and $R^{15c}$ can independently be hydrogen or a non-hydrogen substituent, and n can be an integer from 1 to 5. In an embodiment wherein $R^1$ has Structure G1, $R^{11c}$, $R^{13c}$, $R^{14c}$, and $R^{15c}$ can be hydrogen and $R^{12c}$ can be any non-hydrogen substituent disclosed herein; or alternatively, $R^{11c}$, $R^{13c}$, and $R^{15c}$ can be hydrogen and $R^{12c}$ and $R^{14c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively, 3. Substituents for the $R^1$ group having Structure G1 are independently disclosed herein and can be utilized without limitation to further describe the $R^1$ group having Structure G1.

In an embodiment, $R^{11c}$, $R^{12c}$, $R^{13c}$, $R^{14c}$, and $R^{15c}$ independently can be hydrogen, a halogen, a hydrocarbyl group, or a hydrocarboxy group; alternatively, hydrogen, a halogen, or a hydrocarbyl group; alternatively, hydrogen, a halogen, or a hydrocarboxy group; alternatively, hydrogen, a hydrocarbyl group, or a hydrocarboxy group; alternatively, hydrogen or a halogen; alternatively, hydrogen or a hydrocarbyl group; or alternatively, hydrogen or a hydrocarboxy group. In some embodiments, $R^{11c}$, $R^{12c}$, $R^{13c}$, $R^{14c}$, and $R^{15c}$ independently can be hydrogen, a halogen, and alkyl group, or an alkoxy group; alternatively, hydrogen, a halogen, or an alkyl group; alternatively, hydrogen, a halogen, and an alkoxy group; alternatively, hydrogen or a halogen; alternatively, hydrogen or an alkyl group; or alternatively, hydrogen or an alkoxy group. Specific substituent halogens, hydrocarbyl groups, hydrocarboxy groups, alkyl groups, and alkoxy groups are independently disclosed herein and can be utilized without limitation to further describe the $R^1$ group having Structure G1.

In an embodiment wherein $R^1$ has Structure G1, $R^{11c}$, $R^{13c}$, $R^{14c}$, and $R^{15c}$ can be hydrogen and $R^{12c}$ can be any non-hydrogen substituent indicated herein; or alternatively, $R^{11c}$, $R^{13c}$, and $R^{15c}$ can be hydrogen and $R^{12c}$ and $R^{14c}$ can be any non-hydrogen substituent indicated herein. In some embodiments, wherein $R^1$ has Structure G1, $R^{11c}$, $R^{13c}$, $R^{14c}$, and $R^{15c}$ can be hydrogen and $R^{12c}$ can be any alkyl group, alkoxy group, or halogen indicated herein; or alternatively, $R^{11c}$, $R^{13c}$, and $R^{15c}$ can be hydrogen and $R^{12c}$ and $R^{14c}$ can be any alkyl group, alkoxy group, or halogen indicated herein. In other embodiments, wherein $R^1$ has Structure G1, $R^{11c}$, $R^{13c}$, $R^{14c}$, and $R^{15c}$ can be hydrogen and $R^{12c}$ can be any alkyl group substituent indicated herein; or alternatively, $R^{11c}$, $R^{13c}$, and $R^{15c}$ can be hydrogen and $R^{12c}$ and $R^{14c}$ can be any alkyl group substituent indicated herein. In another embodiment wherein $R^1$ has Structure G1, $R^{11c}$, $R^{12c}$, $R^{13c}$, $R^{14c}$, and $R^{15c}$ can be hydrogen. In an embodiment, $R^{11c}$, $R^{12c}$, $R^{13c}$, $R^{14c}$, and $R^{15c}$ independently can be hydrogen, or an alkyl group; alternatively, $R^{11c}$, $R^{12c}$, and $R^{14c}$ can be hydrogen and $R^{13c}$ and $R^{15c}$ can be are alkyl groups; or alternatively, $R^{11c}$ can be hydrogen and $R^{12c}$, $R^{13c}$, $R^{14c}$, and $R^{15c}$ can be alkyl groups. Specific substituent halogens, hydrocarbyl groups, hydrocarboxy groups, alkyl group, and alkoxy groups are independently disclosed herein and can be utilized without limitation to further describe the $R^1$ group having Structure G1.

In an aspect, $R^1$ can be a phenyl group, a substituted phenyl group, a naphthyl group, or a substituted naphthyl group. In an embodiment, $R^1$ can be a phenyl group or a substituted phenyl group; alternatively, a naphthyl group or a substituted naphthyl group; alternatively, a phenyl group or a naphthyl group; or alternatively, a substituted phenyl group or a substituted naphthyl group. In some embodiments, $R^1$ can be a phenyl group; alternatively, a substituted phenyl group; alternatively, a naphthyl group; or alternatively, a substituted naphthyl group.

In an embodiment, the $R^1$ substituted phenyl group can be a 2-substituted phenyl group, a 3-substituted phenyl group, a 4-substituted phenyl group, a 2,4-disubstituted phenyl group, a 2,6-disubstituted phenyl group, 3,5-disubstituted phenyl group, or a 2,4,6-trisubstituted phenyl group. In other embodiments, the $R^1$ substituted phenyl group can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,6-disubstituted phenyl group or a 2,4,6-trisubstituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group.

In an embodiment, $R^1$ can be a naphth-1-yl group, a substituted naphth-1-yl group, a naphth-2-yl group, or a substituted naphth-2-yl group. In some embodiments, $R^1$ can be a naphth-1-yl group or a substituted naphth-1-yl group; alternatively, a naphth-2-yl group or a substituted naphth-2-yl group; alternatively, a naphth-1-yl group; alternatively, a substituted naphth-1-yl group; alternatively, a naphth-2-yl group; or alternatively, a substituted naphth-2-yl group. In other embodiments, $R^1$ can be a 2-substituted naphth-1-yl group, a 3-substituted naphth-1-yl group, a 4-substituted naphth-1-yl group, or a 8-substituted naphth-1-yl group; alternatively, a 2-substituted naphth-1-yl group; alternatively, a 3-substituted naphth-1-yl group; alternatively, a 4-substituted naphth-1-yl group; or alternatively, a 8-substituted naphth-1-yl group. In further embodiments, $R^1$ can be a 1-substituted naphth-2-yl group, a 3-substituted naphth-2-yl group, a 4-substituted naphth-2-yl group, or a 1,3-disubstituted naphth-2-yl group; alternatively, a 1-substituted naphth-2-yl group; alternatively, a 3-substituted naphth-2-yl group; alternatively, a 4-substituted naphth-2-yl group; or alternatively, a 1,3-disubstituted naphth-2-yl group. Substituents for the substituted phenyl or substituted naphthyl group that can be utilized as $R^1$ are independently disclosed herein. These substituents can be utilized without limitation to further describe the substituted phenyl groups or substituted naphthyl groups which can be utilized as $R^1$.

In an embodiment, each substituent for a substituted phenyl or substituted naphthyl $R^1$ group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, each substituents for the substituted phenyl or substituted naphthyl $R^1$ group independently can be a halogen, an alkyl group, or an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Specific substituent halogens, hydrocarbyl groups, hydrocarboxy groups, alkyl groups, and alkoxy groups are independently disclosed herein and can be utilized without limitation to further describe the substituents for the substituted phenyl or substituted naphthyl $R^1$ group.

In an aspect, the $R^1$ can have Structure G2:

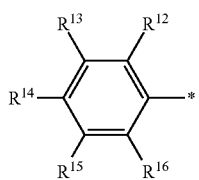

Structure G2 wherein the undesignated valency is attached to the $N^1$ nitrogen atom of the $N^2$-phosphinylamidine group. Generally, $R^{12}$, $R^{13}$, $R^{14}$, $R^{15}$, and $R^{16}$ independently can be hydrogen or a non-hydrogen substituent. In an embodiment where $R^1$ has Structure G2, $R^{12}$, $R^{13}$, $R^{14}$, $R^{15}$, and $R^{16}$ can be hydrogen, $R^{13}$, $R^{14}$, $R^{15}$, and $R^{16}$ can be hydrogen and $R^{12}$ can be a non-hydrogen substituent, $R^{12}$, $R^{14}$, $R^{15}$, and $R^{16}$ can be hydrogen and $R^{13}$ can be a non-hydrogen substituent, $R^{12}$, $R^{13}$, $R^{15}$, and $R^{16}$ can be hydrogen and $R^{14}$ can be a non-hydrogen substituent, $R^{13}$, $R^{15}$, and $R^{16}$ can be hydrogen and $R^{12}$ and $R^{14}$ can be non-hydrogen substituents, $R^{13}$, $R^{14}$, and $R^{15}$ can be hydrogen and $R^{12}$ and $R^{16}$ can be non-hydrogen substituents, $R^{12}$, $R^{14}$, and $R^{16}$ can be hydrogen and $R^{13}$ and $R^{15}$ can be non-hydrogen substituents, or $R^{13}$ and $R^{15}$ can be hydrogen and $R^{12}$, $R^{14}$, and $R^{16}$ can be non-hydrogen substituents. In some embodiments where $R^1$ has Structure G2, $R^{13}$, $R^{14}$, $R^{15}$, and $R^{16}$ can be hydrogen and $R^{12}$ can be a non-hydrogen substituent, $R^{12}$, $R^{13}$, $R^{15}$, and $R^{16}$ can be hydrogen and $R^{14}$ can be a non-hydrogen substituent, $R^{13}$, $R^{15}$, and $R^{16}$ can be hydrogen and $R^{12}$ and $R^{14}$ can be non-hydrogen substituents, $R^{13}$, $R^{14}$, and $R^{15}$ can be hydrogen and $R^{12}$ and $R^{16}$ can be non-hydrogen substituents, or $R^{13}$ and $R^{15}$ can be hydrogen and $R^{12}$, $R^{14}$, and $R^{16}$ can be non-hydrogen substituents; alternatively, $R^{13}$, $R^{14}$, $R^{15}$, and $R^{16}$ can be hydrogen and $R^{12}$ can be a non-hydrogen substituent, $R^{12}$, $R^{13}$, $R^{15}$, and $R^{16}$ can be hydrogen and $R^{14}$ can be a non-hydrogen substituent, $R^{13}$, $R^{15}$, and $R^{16}$ can be hydrogen and $R^{12}$ and $R^{14}$ can be non-hydrogen substituents, or $R^{13}$, $R^{14}$, and $R^{15}$ can be hydrogen and $R^{12}$ and $R^{16}$ can be non-hydrogen substituents; alternatively, $R^{12}$, $R^{14}$, $R^{15}$, and $R^{16}$ can be hydrogen and $R^{13}$ can be a non-hydrogen substituent, or $R^{12}$, $R^{14}$, $R^{15}$, and $R^{16}$ can be hydrogen and $R^{13}$ and $R^{15}$ can be non-hydrogen substituents; alternatively, $R^{13}$, $R^{14}$, and $R^{16}$ can be hydrogen and $R^{12}$ can be a non-hydrogen substituent, or $R^{12}$, $R^{13}$, $R^{14}$, and $R^{16}$ can be hydrogen and $R^{14}$ can be a non-hydrogen substituent; alternatively, $R^{13}$, $R^{15}$, and $R^{16}$ can be hydrogen and $R^{12}$ and $R^{14}$ can be non-hydrogen substituents, $R^{13}$, $R^{14}$, and $R^{15}$ can be hydrogen and $R^{12}$ and $R^{16}$ can be non-hydrogen substituents, or $R^{13}$ and $R^{15}$ can be hydrogen and $R^{12}$, $R^{14}$ and $R^{16}$ can be non-hydrogen substituents; or alternatively, $R^{13}$, $R^{15}$, and $R^{16}$ can be hydrogen and $R^{12}$ and $R^{14}$ can be non-hydrogen substituents, or $R^{13}$, $R^{14}$, and $R^{15}$ can be hydrogen and $R^{12}$ and $R^{16}$ can be non-hydrogen substituents. In other embodiments wherein $R^1$ has Structure G2, $R^{12}$, $R^{13}$, $R^{14}$, $R^{15}$, and $R^{16}$ can be hydrogen; alternatively, $R^{13}$ $R^{14}$, $R^{15}$, and $R^{16}$ can be hydrogen and $R^{12}$ can be a non-hydrogen substituent; alternatively, $R^{12}$, $R^{14}$, $R^{15}$, and $R^{16}$ can be hydrogen and $R^{13}$ can be a non-hydrogen substituent; alternatively, $R^{12}$, $R^{13}$, $R^{15}$, and $R^{16}$ can be hydrogen and $R^{14}$ can be a non-hydrogen substituent; alternatively, $R^{13}$, $R^{15}$, and $R^{16}$ can be hydrogen and $R^{12}$ and $R^{14}$ can be non-hydrogen substituents; alternatively, $R^{13}$, $R^{14}$, and $R^{15}$ can be hydrogen and $R^{12}$ and $R^{16}$ can be non-hydrogen substituents; alternatively, $R^{12}$, $R^{14}$, and $R^{16}$ can be hydrogen and $R^{13}$ and $R^{15}$ and can be non-hydrogen substituents; or alternatively, $R^{13}$ and $R^{15}$ can be hydrogen and $R^{12}$, $R^{14}$, and $R^{16}$ can be non-hydrogen substituents. Substituents for the $R^1$ group having Structure G2 are independently disclosed herein and can be utilized without limitation to further describe the $R^1$ group having Structure G2.

In an embodiment, the non-hydrogen substituents that can be utilized as $R^{12}$, $R^{13}$, $R^{14}$, $R^{15}$, and $R^{16}$ in the $R^1$ group having Structure G2 independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, the non-hydrogen substituents that can be utilized as $R^{12}$, $R^{13}$, $R^{14}$, $R^{15}$, and $R^{16}$ in the $R^1$ group having Structure G2 independently can be a halogen, an alkyl group, and an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Specific substituent halogens, hydrocarbyl groups, hydrocarboxy groups, alkyl group, and alkoxy groups are independently disclosed herein and can be utilized without limitation to further describe the $R^1$ group having Structure G2.

In an aspect, $R^1$ can be a pyridinyl group, a substituted pyridinyl group, a furyl group, a substituted furyl group, a thienyl group, or a substituted thienyl group. In an embodiment, $R^1$ can be a pyridinyl group or a substituted pyridinyl group; alternatively, a furyl group or a substituted furyl group; or alternatively, a thienyl group or a substituted thienyl group. In some embodiments, $R^1$ can be a pyridinyl group, a furyl group, or a thienyl group. In other embodiments, $R^1$ can be a pyridinyl group; alternatively, a substituted pyridinyl group; alternatively, a furyl group; alternatively, a substituted furyl group; alternatively, a thienyl group; or alternatively, a substituted thienyl group.

In an embodiment, the pyridinyl (or substituted pyridinyl) $R^1$ group can be a pyridin-2-yl group, a substituted pyridin-2-yl group, a pyridin-3-yl group, a substituted pyridin-3-yl group, a pyridin-4-yl group, or a substituted pyridin-4-yl group; alternatively, a pyridin-2-yl group, a pyridin-3-yl group, or a pyridin-4-yl group. In some embodiments, the pyridinyl (or substituted pyridinyl) $R^1$ group can be a pyridin-2-yl group or a substituted pyridin-2-yl group; alternatively, a pyridin-3-yl group or a substituted pyridin-3-yl group; alternatively, a pyridin-4-yl group or a substituted pyridin-4-yl group; alternatively, a pyridin-2-yl group; alternatively, a substituted pyridin-2-yl group; alternatively, a pyridin-3-yl group; alternatively, a substituted pyridin-3-yl group; alternatively, a pyridin-4-yl group; or alternatively, a substituted pyridin-4-yl group. In an embodiment, the substituted pyridinyl $R^1$ group can be a 2-substituted pyridin-3-yl group, a 4-substituted pyridin-3-yl group, a 5-substituted pyridin-3-yl group, a 6-substituted pyridin-3-yl group, a 2,4-disubstituted pyridin-3-yl group, a 2,6-disubstituted pyridin-3-yl group, or a 2,4,6-trisubstituted pyridin-3-yl group; alternatively, 2-substituted pyridin-3-yl group, a 4-substituted pyridin-3-yl group, or a 6-substituted pyridin-3-yl group; alternatively, a 2,4-disubstituted pyridin-3-yl group or a 2,6-disubstituted pyridin-3-yl group; alternatively, a 2-substituted pyridin-3-yl group; alternatively, a 4-substituted pyridin-3-yl group; alternatively, a 5-substituted pyridin-3-yl group; alternatively, a 6-substituted pyridin-3-yl group; alternatively, a 2,4-disubstituted pyridin-3-yl group; alternatively, a 2,6-disubstituted pyridin-3-yl group; or alternatively, a 2,4,6-trisubstituted pyridin-3-yl group. In an embodiment, the substituted pyridinyl $R^1$ group can be a 2-substituted pyridin-4-yl group, a 3-substituted pyridin-4-yl group, a 5-substituted pyridin-4-yl group, a 6-substituted pyridin-4-yl group, a 2,6-disubstituted pyridin-4-yl group, or a 3,5-disubstituted pyridin-4-yl group; alternatively, a 2-substituted pyridin-4-yl group or a 6-substituted pyridin-4-yl group; alternatively, a 3-substituted pyridin-4-yl group or a 5-substituted pyridin-4-yl group; alternatively, a 2-substituted pyridin-4-yl group; alternatively, a 3-substituted pyridin-4-yl group; alternatively, a 5-substituted pyridin-4-yl group; alternatively, a 6-substituted pyridin-4-yl group; alternatively, a 2,6-disubstituted pyridin-4-yl group; or alternatively, a 3,5-disubstituted pyridin-4-yl group. Substituents for the substituted pyridinyl groups are independently disclosed herein and can be utilized without limitation to further describe the substituted pyridinyl groups which can be utilized as $R^1$.

In an embodiment, the furyl (or substituted furyl) $R^1$ group can be a fur-2-yl group, a substituted fur-2-yl group, a fur-3-yl group, or a substituted fur-3-yl group; alternatively, a fur-2-yl or a fur-3-yl group. In some embodiments, the furyl (or substituted furyl) $R^1$ group can be a fur-2-yl group or a substituted fur-2-yl group; alternatively, a fur-3-yl group or a substituted fur-3-yl group; alternatively, a fur-2-yl group; alternatively, a substituted fur-2-yl group; alternatively, a fur-3-yl group; or alternatively, a substituted fur-3-yl group. In an embodiment, the substituted furyl $R^1$ group can be a 2-substituted fur-3-yl group, a 4-substituted fur-3-yl group, or a 2,4-disubstituted fur-3-yl group; alternatively, a 2-substituted fur-3-yl group; alternatively, a 4-substituted fur-3-yl group; or alternatively, a 2,4-disubstituted fur-3-yl group. Substituents for the substituted furyl groups are independently disclosed herein and can be utilized without limitation to further describe the substituted furyl groups which can be utilized as $R^1$.

In an embodiment, a thienyl (or substituted thienyl) $R^1$ group be a thien-2-yl group, a substituted thien-2-yl group, a thien-3-yl group, or a substituted thien-3-yl group; alternatively, a thien-2-yl group or a thien-3-yl group. In some embodiments, the thienyl (or substituted thienyl) $R^1$ group can be a thien-2-yl group or a substituted thien-2-yl group; alternatively, a thien-3-yl group or a substituted thien-3-yl group; alternatively, a thien-2-yl group; alternatively, a substituted thien-2-yl group; alternatively, a thien-3-yl group; or alternatively, a substituted thien-3-yl group. In an embodiment, the substituted thienyl $R^1$ group can be a 2-substituted thien-3-yl group, a 4-substituted thien-3-yl group, or a 2,4-disubstituted thien-3-yl group; alternatively, a 2-substituted thien-3-yl group; alternatively, a 4-substituted thien-3-yl group; or alternatively, a 2,4-disubstituted thien-3-yl group. Substituents for the substituted thienyl groups are independently disclosed herein and can be utilized without limitation to further describe the substituted thienyl groups which can be utilized as $R^1$.

In an aspect, $R^1$ can be a $C_1$ to $C_{30}$ organoheteryl group; alternatively, a $C_1$ to $C_{20}$ organoheteryl group; alternatively, a $C_1$ to $C_{15}$ organoheteryl group; alternatively, a $C_1$ to $C_{10}$ organoheteryl group; or alternatively, a $C_1$ to $C_5$ organoheteryl group. In an embodiment, $R^1$ can be a $C_4$ to $C_{30}$ cycloheteryl group; alternatively, a $C_4$ to $C_{20}$ cycloheteryl group; alternatively, a $C_4$ to $C_{15}$ cycloheteryl group; or alternatively, a $C_4$ to $C_{10}$ cycloheteryl group. In some embodiments, the cycloheteryl group which can be utilized as $R^1$ can be a substituted cycloheteryl group.

In some embodiments, $R^1$ can be a $C_1$ to $C_{30}$ hydrocarbyl aminyl group, a $C_2$ to $C_{30}$ dihydrocarbyl aminyl group, a $C_4$ to $C_{30}$ cycloaminyl group, or a $C_4$ to $C_{30}$ substituted cycloaminyl group; alternatively, a $C_1$ to $C_{30}$ hydrocarbyl aminyl group or a $C_2$ to $C_{30}$ dihydrocarbyl aminyl group; alternatively, a $C_4$ to $C_{30}$ cycloaminyl group or a $C_4$ to $C_{30}$ substituted cycloaminyl group; alternatively, a $C_2$ to $C_{30}$ dihydrocarbyl aminyl group or a $C_4$ to $C_{30}$ cycloaminyl group; alternatively, a $C_1$ to $C_{30}$ hydrocarbyl aminyl group; alternatively, a $C_2$ to $C_{30}$ dihydrocarbyl aminyl group; alternatively, a $C_4$ to $C_{30}$ cycloaminyl group; or alternatively, a $C_4$ to $C_{30}$ substituted cycloaminyl group. In other embodiments, $R^1$ can be a $C_1$ to $C_{20}$ hydrocarbyl aminyl group, a $C_2$ to $C_{20}$ dihydrocarbyl aminyl group, a $C_4$ to $C_{20}$ cycloaminyl group, or a $C_4$ to $C_{20}$ substituted cycloaminyl group; alternatively, a $C_1$ to $C_{20}$ hydrocarbyl aminyl group or a $C_2$ to $C_{20}$ dihydrocarbyl aminyl group; alternatively, a $C_4$ to $C_{20}$ cycloaminyl group or a $C_4$ to $C_{20}$ substituted cycloaminyl group; alternatively, a $C_2$ to $C_{20}$ dihydrocarbyl aminyl group or a $C_4$ to $C_{20}$ cycloaminyl group; alternatively, a $C_1$ to $C_{20}$ hydrocarbyl aminyl group; alternatively, a $C_2$ to $C_{20}$ dihydrocarbyl aminyl group; alternatively, a $C_4$ to $C_{20}$ cycloaminyl group; or alternatively, a $C_4$ to $C_{20}$ substituted cycloaminyl group. In yet other embodiments, $R^1$ can be a $C_1$ to $C_{10}$ hydrocarbyl aminyl group, a $C_2$ to $C_{15}$ dihydrocarbyl aminyl group, a $C_4$ to $C_{15}$ cycloaminyl group, or a $C_4$ to $C_{15}$ substituted cycloaminyl group; alternatively, a $C_1$ to $C_{10}$ hydrocarbyl aminyl group or a $C_2$ to $C_{15}$ dihydrocarbyl aminyl group; alternatively, a $C_4$ to $C_{15}$ cycloaminyl group or a $C_4$ to $C_{15}$ substituted cycloaminyl group; alternatively, a $C_2$ to $C_{15}$ dihydrocarbyl aminyl group or a $C_4$ to $C_{15}$ cycloaminyl group; alternatively, a $C_1$ to $C_{10}$ hydrocarbyl aminyl group; alternatively, a $C_2$ to $C_{15}$ dihydrocarbyl aminyl group; alternatively, a $C_4$ to $C_{15}$ cycloaminyl group; or alternatively, a $C_4$ to $C_{15}$ substituted cycloaminyl group. In further embodiments, $R^1$ can be a $C_1$ to $C_5$ hydrocarbyl aminyl group, a $C_2$ to $C_{10}$ dihydrocarbyl aminyl group, a $C_4$ to $C_{10}$ cycloaminyl group, or a $C_4$ to $C_{10}$ substituted cycloaminyl group; alternatively, a $C_1$ to $C_5$ hydrocarbyl aminyl group or a $C_2$ to $C_{10}$ dihydrocarbyl aminyl group; alternatively, a $C_4$ to $C_{10}$ cycloaminyl group or a $C_4$ to $C_{10}$ substituted cycloaminyl group; alternatively, a $C_2$ to $C_{10}$ dihydrocarbyl aminyl group or a $C_4$ to $C_{10}$ cycloaminyl group; alternatively, a $C_1$ to $C_5$ hydrocarbyl aminyl group; alternatively, a $C_2$ to $C_{10}$ dihydrocarbyl aminyl group; alternatively, a $C_4$ to $C_{10}$ cycloaminyl group; or alternatively, a $C_4$ to $C_{10}$ substituted cycloaminyl group.

In an embodiment, each hydrocarbyl group of a hydrocarbyl aminyl group or a dihydrocarbyl aminyl group can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In an embodiment, each hydrocarbyl group of a hydrocarbyl aminyl group or a dihydrocarbyl aminyl group can be an alkyl group, a cycloalkyl group, an aryl group, or an aralkyl group; alternatively, an alkyl group; alternatively, a cycloalkyl group; alternatively, an aryl group; or alternatively, or aralkyl group. Alkyl groups, cycloalkyl groups, aryl group, and aralkyl groups have been described herein a potential $R^1$, $R^2$, $R^3$, $R^4$, and $R^5$ groups (among other potential group) and these alkyl groups, cycloalkyl groups, aryl group, and aralkyl groups can be utilized without limitation to further describe the hydrocarbyl aminyl group and/ or a dihydrocarbyl aminyl group that can be utilized a $R^1$.

In an embodiment, $R^1$ can be a pyrrolidin-1-yl group, a substituted pyrrolidin-1-yl group, a piperidin-1-yl group, a substituted piperidin-1-yl group, a morphilin-1-yl group, a substituted morphilin-1-yl group, a pyrrol-1-yl group, or a substituted pyrrol-yl group. In some embodiments, $R^1$ can be a pyrrolidin-1-yl group, a substituted pyrrolidin-1-yl group, a piperidin-1-yl group, or a substituted piperidin-1-yl group; a pyrrolidin-1-yl group or a substituted pyrrolidin-1-yl group; alternatively, a piperidin-1-yl group or a substituted piperidin-1-yl group; alternatively, a morphilin-1-yl group or a substituted morphilin-1-yl group; alternatively, a pyrrol-1-yl group or a substituted pyrrol-yl group; alternatively, a pyrrolidin-1-yl group, a piperidin-1-yl group, a morphilin-1-yl group, or a pyrrol-1-yl group; alternatively, a pyrrolidin-1-yl group or a piperidin-1-yl group; alternatively, a pyrrolidin-1-yl group; alternatively, a substituted pyrrolidin-1-yl group; alternatively, a piperidin-1-yl group; alternatively, a substituted piperidin-1-yl group; alternatively, a morphilin-1-yl group; alternatively, a substituted morphilin-1-yl group; alternatively, a pyrrol-1-yl group; or alternatively, a substituted pyrrol-yl group. Generally, these specific cycloaminyl groups can have the same number of carbon atoms as the cycloaminyl and substituted cycloaminyl group described herein. Substituents for the substituted cycloaminyl group (general or specific) that can be utilized as $R^1$ are independently disclosed herein. These substituents can be utilized without limitation to further describe the substituted cycloaminyl groups (general or specific) which can be utilized as $R^1$.

In an embodiment, each substituent for a substituted pyridinyl, furyl, and/or thienyl group (general or specific) that can be utilized as $R^1$ independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, each substituent for a substituted pyridinyl, furyl, and/or thienyl group (general or specific) that can be utilized as $R^1$ independently can be a halogen, an alkyl group, or an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Specific substituent halogens, hydrocarbyl groups, hydrocarboxy groups, alkyl group, and alkoxy groups are independently disclosed herein and can be utilized without limitation to further describe the substituents for the substituted pyridinyl, furyl, and/or thienyl groups (general or specific) that can be utilized as $R^1$.

In an aspect, when the $N^1$ nitrogen atom of the $N^2$-phosphinyl amidine group is attached to an atom (carbon or a heteroatom) of a ring or ring system group (cycloalkane group, aliphatic heterocyclic group, cyclohetero group, aromatic group, arene group, heteroarene group, arylhetero group, or any other disclosed herein), the cyclic $R^1$ group can comprise at least one substituent at an atom adjacent to the atom attached to $N^1$ nitrogen atom of the $N^2$-phosphinyl amidine group. In an embodiment, when the $N^1$ nitrogen atom of the $N^2$-phosphinyl amidine group is attached to an atom (carbon or a heteroatom) of a ring or ring system group (cycloalkane group, aliphatic heterocyclic group, cyclohetero group, aromatic group, arene group, heteroarene group, or arylhetero group, or any other disclosed herein) the cyclic $R^1$ group can comprise at least one substituent at each atom adjacent to the atom attached to $N^1$ nitrogen atom of the $N^2$-phosphinyl amidine group. In another embodiment, when the $N^1$ nitrogen atom of the $N^2$-phosphinyl amidine group is attached to an atom (carbon or a heteroatom) of a ring or ring system group (cycloalkane group, aliphatic heterocyclic group, cyclohetero group, aromatic group, arene group, heteroarene group, or arylhetero group, or any other disclosed herein), the cyclic $R^1$ group can consist of one substituent at each atom adjacent to the atom attached to $N^1$ nitrogen atom of the $N^2$-phosphinyl amidine group. In other embodiments, when the $N^1$ nitrogen atom of the $N^2$-phosphinyl amidine group is attached to an atom (carbon or a heteroatom) of a ring or ring system group (cycloalkane group, aliphatic heterocyclic group, cyclohetero group, aromatic group, arene group, heteroarene group, or arylhetero group, or any other disclosed herein), the cyclic $R^1$ group can comprise only one substituent at an atom adjacent to the atom attached to $N^1$ nitrogen atom of the $N^2$-phosphinyl amidine group. In another embodiment, when the $N^1$ nitrogen atom of the $N^2$-phosphinyl amidine group is attached to an atom (carbon or a heteroatom) of a ring or ring system group (cycloalkane group, aliphatic heterocyclic group, cyclohetero group, aromatic group, arene group, heteroarene group, or arylhetero group, or any other disclosed herein), the cyclic $R^1$ group can comprise only one substituent at each atom adjacent to the atom attached to $N^1$ nitrogen atom of the $N^2$-phosphinyl amidine group. In yet another embodiment, when the $N^1$ nitrogen atom of the $N^2$-phosphinyl amidine group is attached to an atom (carbon or a heteroatom) of a ring or ring system group (cycloalkane group, aliphatic heterocyclic group, cyclohetero group, aromatic group, arene group, heteroarene group, or arylhetero group, or any other disclosed herein), the cyclic $R^1$ group can consist of only one substituent located at each atom adjacent to the atom attached to $N^1$ nitrogen atom of the $N^2$-phosphinyl amidine group.

In an embodiment, when the $N^1$ nitrogen atom of the $N^2$-phosphinyl amidine group is attached to a carbon atom of a cycloalkane or arene ring or ring system, the cyclic $R^1$ group can comprise at least one substituent located on a carbon atom adjacent to the carbon atom attached to $N^1$ nitrogen atom of the $N^2$-phosphinyl amidine group. In some embodiments, when the $N^1$ nitrogen atom of the $N^2$-phosphinyl amidine group is attached to a carbon atom of a cycloalkane or arene ring or ring system, the cyclic $R^1$ group can comprise at least one substituent located on each carbon atom adjacent to the carbon atom attached to $N^1$ nitrogen atom of the $N^2$-phosphinyl amidine group. In another embodiment, when the $N^1$ nitrogen atom of the $N^2$-phosphinyl amidine group is attached to a carbon atom of a cycloalkane or arene ring or ring system, the cyclic $R^1$ group can consist of one substituent located on each carbon atom adjacent to the carbon atom attached to $N^1$ nitrogen atom of the $N^2$-phosphinyl amidine group. In other embodiments, when the $N^1$ nitrogen atom of the $N^2$-phosphinyl amidine group is attached to a carbon atom of a cycloalkane or arene ring or ring system, the cyclic $R^1$ group can comprise only one substituent located on a carbon atom adjacent to the carbon atom attached to $N^1$ nitrogen atom of the $N^2$-phosphinyl amidine group. In another embodiment, when the $N^1$ nitrogen atom of the $N^2$-phosphinyl amidine group is attached to a carbon atom of a cycloalkane or arene ring or ring system, the cyclic $R^1$ group can comprise only one substituent located on each carbon atom adjacent to the carbon atom attached to $N^1$ nitrogen atom of the $N^2$-phosphinyl amidine group. In yet another embodiment, when the $N^1$ nitrogen atom of the $N^2$-phosphinyl amidine group is attached to a carbon atom of a cycloalkane or arene ring or ring system, the cyclic $R^1$ group can consist of only one substituent located on each carbon atom adjacent to the carbon atom attached to $N^1$ nitrogen atom of the $N^2$-phosphinyl amidine group.

The non-hydrogen substituents of any substituted $R^1$ group (general or specific) independently can be a hydrocarbyl group or an inert functional group. Non-limiting examples of inert functional group include halogens and hydrocarboxy groups. In an embodiment, each non-hydrogen substituent any substituted $R^1$ group (general or specific) independently can be a halide, a $C_1$ to $C_{10}$ hydrocarbyl group, or a $C_1$ to $C_{10}$ hydrocarboxy group; alternatively, a halide or a $C_1$ to $C_{10}$ hydrocarbyl group; alternatively, a halide or a $C_1$ to $C_{10}$ hydrocarboxy group; alternatively, a $C_1$ to $C_{10}$ hydrocarbyl group or a $C_1$ to $C_{10}$ hydrocarboxy group; alternatively, a halide; alternatively, a $C_1$ to $C_{10}$ hydrocarbyl group; or alternatively, a $C_1$ to $C_{10}$ hydrocarboxy group. In other embodiments, each non-hydrogen substituent any substituted $R^1$ group (general or specific) independently can be a halide, a $C_1$ to $C_5$ hydrocarbyl group, or a $C_1$ to $C_5$ hydrocarboxy group; alternatively, a halide or a $C_1$ to $C_5$ hydrocarbyl group; alternatively, a halide or a $C_1$ to $C_5$ hydrocarboxy group; alternatively, a $C_1$ to $C_5$ hydrocarbyl group or a $C_1$ to $C_5$ hydrocarboxy group; alternatively, a halide; alternatively, a $C_1$ to $C_5$ hydrocarbyl group; or alternatively, a $C_1$ to $C_5$ hydrocarboxy group.

In an embodiment, each halide substituent for any substituted $R^1$ group (general or specific) independently can be a fluoride, chloride, bromide, or iodide; alternatively, a fluoride or chloride. In some embodiments, each halide substituent any substituted $R^1$ group (general or specific) independently can be a fluoride; alternatively, a chloride; alternatively, a bromide; or alternatively, an iodide.

In an embodiment, each hydrocarbyl substituent for any substituted $R^1$ group (general or specific) independently can be an alkyl group, an aryl group, or an aralkyl group; alternatively, an alkyl group; alternatively, an aryl group; or alternatively, an aralkyl group. In an embodiment, each alkyl substituent for any substituted $R^1$ group (general or specific) independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, each aryl substituent for any substituted $R^1$ group (general or specific) independently can be a phenyl group, a tolyl group, a xylyl group, or a 2,4,6-trimethylphenyl group; alternatively, a phenyl group; alternatively, a tolyl group; alternatively, a xylyl group; or alternatively, a 2,4,6-trimethylphenyl group. In an embodiment, each aralkyl substituent for any substituted $R^1$ group (general or specific) independently can be a benzyl group or an ethylphenyl group (2-phenyleth-1-yl or 1-phenyleth-1-yl); alternatively, a benzyl group; alternatively, an ethylphenyl group; alternatively, a 2-phenyleth-1-yl group; or alternatively, a 1-phenyleth-1-yl group.

In an embodiment, each hydrocarboxy substituent for any substituted $R^1$ group (general or specific) independently can be an alkoxy group, an aryloxy group, or an aralkoxy group; alternatively, an alkoxy group; alternatively, an aryloxy group; or alternatively, an aralkoxy group. In an embodiment, each alkoxy substituent for any substituted $R^1$ group (general or specific) independently can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, each aroxy substituent for any substituted $R^1$ group (general or specific) independently can be a phenoxy group, a toloxy group, a xyloxy group, or a 2,4,6-trimethylphenoxy group; alternatively, a phenoxy group; alternatively, a toloxy group; alternatively, a xyloxy group; or alternatively, a 2,4,6-trimethylphenoxy group. In an embodiment, each aralkoxy substituent for any substituted $R^1$ group (general or specific) independently can be a benzoxy group.

In a non-limiting embodiment, $R^1$ can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group, or a 2,4,6-trialkylphenyl group; alternatively, a 2,4-dialkylphenyl group or a 2,6-dialkylphenyl group; alternatively, a 2,6-dialkylphenyl group, or a 2,4,6-trialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 3-alkylphenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. In another non-limiting embodiment, $R^1$ can be a napht-1-yl group, a naphth-2-yl group, a 2-alkylnaphth-1-yl group, a 1-alkylnaphth-2-yl group, a 3-alkylnapth-2-yl group, or a 1,3-dialkylnaphth-2-yl group; alternatively, a napht-1-yl group or a 2-alkylnaphth-1-yl group; alternatively, a naphth-2-yl group, a 1-alkylnaphth-2-yl group, a 3-alkylnapth-2-yl group, or a 1,3-dialkylnaphth-2-yl group; alternatively, a napht-1-yl group; alternatively, a naphth-2-yl group; alternatively, a 2-alkylnaphth-1-yl group; alternatively, a 1-alkylnaphth-2-yl group; alternatively, a 3-alkylnapth-2-yl group; or alternatively, a 1,3-dialkylnaphth-2-yl group. In other non-limiting embodiments, $R^1$ can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl group substituents are independently described herein and can be utilized, without limitation, to further describe the alkylphenyl, dialkylphenyl, trialkylphenyl, naphthyl, dialkylnaphthyl, alkylcyclohexyl, dialkylcyclohexyl, alkylcyclopentyl, or dialkylcyclopentyl groups that can be utilized $R^1$. Generally, the alkyl substituents of a dialkyl or trialkyl phenyl, naphthyl, cyclohexyl, or cyclopentyl group can be the same; or alternatively, the alkyl substituents of a dialkyl or trialkyl phenyl, naphthyl, cyclohexyl, or cyclopentyl group can be different.

In another non-limiting embodiment, $R^1$ can be a phenyl group, a 2-alkoxyphenyl group, a 3-alkoxyphenyl group, a 4-alkoxyphenyl group, or a 3,5-dialkoxyphenyl group; alternatively, a 2-alkoxyphenyl group or a 4-alkoxyphenyl group; alternatively, a 3-alkoxyphenyl group or a 3,5-dialkoxyphenyl group; alternatively, a 2-alkoxyphenyl group; alternatively, a 3-alkoxyphenyl group; alternatively, a 4-alkoxyphenyl group; alternatively, a 3,5-dialkoxyphenyl group. Alkoxy group substituents are independently described herein and can be utilized, without limitation, to further describe the alkoxyphenyl or dialkoxyphenyl groups that can be utilized $R^1$. Generally, the alkoxy substituents of a dialkoxyphenyl group can be the same; or alternatively, the alkoxy substituents of a dialkoxyphenyl group can be different.

In other non-limiting embodiments, $R^1$ can be a phenyl group, a 2-halophenyl group, a 3-halophenyl group, a 4-halophenyl group, a 2,6-dihalophenyl group, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenyl group; or alternatively, a 3,5-dihalophenyl group. Halides are independently described herein and can be utilized, without limitation, to further describe the halophenyl or dihalophenyl groups that can be utilized $R^1$. Generally, the halides of a dihalophenyl group can be the same; or alternatively, the halides of a dihalophenyl group can be different.

In a non-limiting embodiment, $R^1$ can be a 2-methylphenyl group, a 2-ethylphenyl group, a 2-n-propylphenyl group, a 2-isopropylphenyl group, a 2-tert-butylphenyl group, a 3-methylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, a 3,5-dimethyl group, or a 2,4,6-trimethylphenyl group; alternatively, a 2-methylphenyl group, a 2-ethylphenyl group, a 2-n-propylphenyl group, a 2-isopropylphenyl group, or a 2-tert-butylphenyl group; alternatively, a 2,6-dimethylphenyl group, a 2,6-diethylphenyl group, a 2,6-di-n-propylphenyl group, a 2,6-diisopropylphenyl group, a 2,6-di-tert-butylphenyl group, or a 2-isopropyl-6-methylphenyl group; alternatively, a 2-methylphenyl group; alternatively, a 2-ethylphenyl group; alternatively, a 2-n-propylphenyl group; alternatively, a 2-isopropylphenyl group; alternatively, a 2-tert-butylphenyl group; alternatively, a 3-methylphenyl group; alternatively, a 2,6-dimethylphenyl group; alternatively, a 2,6-diethylphenyl group; alternatively, a 2,6-di-n-propylphenyl group; alternatively, a 2,6-diisopropylphenyl group; alternatively, a 2,6-di-tert-butylphenyl group; alternatively, a 2-isopropyl-6-methylphenyl group; alternatively, a 3,5-dimethylphenyl group; or alternatively, a 2,4,6-trimethylphenyl group. In another non-limiting embodiment, $R^1$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group, a 2-ethylcyclohexyl group, a 2-isopropylcyclohexyl group, or a 2-tert-butylcyclohexyl group; alternatively, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group; alternatively, a 2-ethylcyclohexyl group; alternatively, a 2-isopropylcyclohexyl group; alternatively, a 2-tert-butylcyclohexyl group; alternatively, a 2,6-dimethylcyclohexyl group; alternatively, a 2,6-diethylcyclohexyl group; alternatively, a 2,6-diisopropylcyclohexyl group; or alternatively, a 2,6-di-tert-butylcyclohexyl group. In another non-limiting embodiment, $R^1$ can be a 2-methylnaphth-1-yl group, a 2-ethylnaphth-1-yl group, a 2-n-propylnaphth-1-yl group, a 2-isopropylnaphth-1-yl group, or a 2-tert-butylnaphth-1-yl group; alternatively, a 2-methylnaphth-1-yl group; alternatively, a 2-ethylnaphth-1-yl group; alternatively, a 2-n-propylnaphth-1-yl group; alternatively, a 2-isopropylnaphth-1-yl group; or alternatively, a 2-tert-butylnaphth-1-yl group.

In a non-limiting embodiment, $R^1$ can be a 3-methoxyphenyl group, a 3-ethoxyphenyl group, a 3-isopropoxyphenyl group, a 3-tert-butoxyphenyl group, a 4-methoxyphenyl group, a 4-ethoxyphenyl group, a 4-isopropoxyphenyl group, a 4-tert-butoxyphenyl group, a 3,5-dimethoxyphenyl group, a 3,5-diethoxyphenyl group, a 3,5-diisopropoxyphenyl group, or a 3,5-di-tert-butoxyphenyl group; alternatively, a 3-methoxyphenyl group, a 3-ethoxyphenyl group, a 3-isopropoxyphenyl group, or a 3-tert-butoxyphenyl group; alternatively, a 4-methoxyphenyl group, a 4-ethoxyphenyl group, a 4-isopropoxyphenyl group, or a 4-tert-butoxyphenyl group; or alternatively, a 3,5-dimethoxyphenyl group, a 3,5-diethoxyphenyl group, a 3,5-diisopropoxyphenyl group, or a 3,5-di-tert-butoxyphenyl group. In other non-limiting embodiments, $R^1$ can be a 3-methoxyphenyl group; alternatively, a 3-ethoxyphenyl group; alternatively, a 3-isopropoxyphenyl group;

alternatively, a 3-tert-butoxyphenyl group; alternatively, a 4-methoxyphenyl group; alternatively, a 4-ethoxyphenyl group; alternatively, a 4-isopropoxyphenyl group; alternatively, a 4-tert-butoxyphenyl group; alternatively, a 3,5-dimethoxyphenyl group; alternatively, a 3,5-diethoxyphenyl group; alternatively, a 3,5-diisopropoxyphenyl group; or alternatively, a 3,5-di-tert-butoxyphenyl group.

Generally, $R^2$ can be an organyl group, an organyl group consisting essentially of inert functional groups, or a hydrocarbyl group. In an embodiment, $R^2$ can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, $R^2$ can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In an embodiment, $R^2$ can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In yet other embodiments, $R^2$ can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group.

In an aspect, $R^2$ can be a $C_1$ to $C_{30}$ alkyl group, a $C_4$ to $C_{30}$ cycloalkyl group, a $C_4$ to $C_{30}$ substituted cycloalkyl group, a $C_3$ to $C_{30}$ aliphatic heterocyclic group, a $C_3$ to $C_{30}$ substituted aliphatic heterocyclic group, a $C_6$ to $C_{30}$ aryl group, a $C_6$ to $C_{30}$ substituted aryl group, a $C_7$ to $C_{30}$ aralkyl group, a $C_7$ to $C_{30}$ substituted aralkyl group, a $C_3$ to $C_{30}$ heteroaryl group, or a $C_3$ to $C_{30}$ substituted heteroaryl group; alternatively, a $C_1$ to $C_{30}$ alkyl group, a $C_4$ to $C_{30}$ cycloalkyl group, a $C_4$ to $C_{30}$ substituted cycloalkyl group, a $C_6$ to $C_{30}$ aryl group, a $C_6$ to $C_{30}$ substituted aryl group, a $C_7$ to $C_{30}$ aralkyl group, or a $C_7$ to $C_{30}$ substituted aralkyl group; alternatively, a $C_4$ to $C_{30}$ cycloalkyl group or a $C_4$ to $C_{30}$ substituted cycloalkyl group; alternatively, a $C_3$ to $C_{30}$ aliphatic heterocyclic group or a $C_3$ to $C_{30}$ substituted aliphatic heterocyclic group; alternatively, a $C_6$ to $C_{30}$ aryl group or a $C_6$ to $C_{30}$ substituted aryl group; alternatively, a $C_7$ to $C_{30}$ aralkyl group or a $C_7$ to $C_{30}$ substituted aralkyl group; alternatively, a $C_3$ to $C_{30}$ heteroaryl group or a $C_3$ to $C_{30}$ substituted heteroaryl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_3$ to $C_{30}$ aliphatic heterocyclic group; alternatively, a $C_3$ to $C_{30}$ substituted aliphatic heterocyclic group; alternatively, a $C_6$ to $C_{30}$ aryl group; alternatively, a $C_6$ to $C_{30}$ substituted aryl group; alternatively, a $C_7$ to $C_{30}$ aralkyl group; alternatively, a $C_7$ to $C_{30}$ substituted aralkyl group; alternatively, a $C_3$ to $C_{30}$ heteroaryl group; or alternatively, a $C_3$ to $C_{30}$ substituted heteroaryl group. In an embodiment, $R^2$ can be a $C_1$ to $C_{15}$ alkyl group, a $C_4$ to $C_{20}$ cycloalkyl group, a $C_4$ to $C_{20}$ substituted cycloalkyl group, a $C_3$ to $C_{20}$ aliphatic heterocyclic group, a $C_3$ to $C_{20}$ substituted aliphatic heterocyclic group, a $C_6$ to $C_{20}$ aryl group, a $C_6$ to $C_{20}$ substituted aryl group, a $C_7$ to $C_{20}$ aralkyl group, a $C_7$ to $C_{20}$ substituted aralkyl group, a $C_3$ to $C_{20}$ heteroaryl group, or a $C_3$ to $C_{20}$ substituted heteroaryl group; alternatively, a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, a $C_6$ to $C_{20}$ substituted aryl group, a $C_7$ to $C_{20}$ aralkyl group, or a $C_7$ to $C_{20}$ substituted aralkyl group; alternatively, a $C_4$ to $C_{20}$ cycloalkyl group or a $C_4$ to $C_{20}$ substituted cycloalkyl group; alternatively, a $C_3$ to $C_{20}$ aliphatic heterocyclic group or a $C_3$ to $C_{20}$ substituted aliphatic heterocyclic group; alternatively, a $C_6$ to $C_{20}$ aryl group or a $C_6$ to $C_{20}$ substituted aryl group; alternatively, a $C_7$ to $C_{20}$ aralkyl group or a $C_7$ to $C_{20}$ substituted aralkyl group; alternatively, a $C_3$ to $C_{20}$ heteroaryl group or a $C_3$ to $C_{20}$ substituted heteroaryl group; alternatively, a $C_1$ to $C_{15}$ alkyl group; alternatively, a $C_4$ to $C_{20}$ cycloalkyl group; alternatively, a $C_4$ to $C_{20}$ substituted cycloalkyl group; alternatively, a $C_3$ to $C_{20}$ aliphatic heterocyclic group; alternatively, a $C_3$ to $C_{20}$ substituted aliphatic heterocyclic group; alternatively, a $C_6$ to $C_{20}$ aryl group; alternatively, a $C_6$ to $C_{20}$ substituted aryl group; alternatively, a $C_7$ to $C_{20}$ aralkyl group; alternatively, a $C_7$ to $C_{20}$ substituted aralkyl group; alternatively, a $C_3$ to $C_{20}$ heteroaryl group; or alternatively, a $C_3$ to $C_{20}$ substituted heteroaryl group. In other embodiments, $R^2$ can be a $C_1$ to $C_{10}$ alkyl group, a $C_4$ to $C_{15}$ cycloalkyl group, a $C_4$ to $C_{15}$ substituted cycloalkyl group, a $C_3$ to $C_{15}$ aliphatic heterocyclic group, a $C_3$ to $C_{15}$ substituted aliphatic heterocyclic group, a $C_6$ to $C_{15}$ aryl group, a $C_6$ to $C_{15}$ substituted aryl group, a $C_7$ to $C_{15}$ aralkyl group, a $C_7$ to $C_{15}$ substituted aralkyl group, a $C_3$ to $C_{15}$ heteroaryl group, or a $C_3$ to $C_{15}$ substituted heteroaryl group; alternatively, a $C_1$ to $C_{10}$ alkyl group, a $C_4$ to $C_{15}$ cycloalkyl group, a $C_4$ to $C_{15}$ substituted cycloalkyl group, a $C_6$ to $C_{15}$ aryl group, a $C_6$ to $C_{15}$ substituted aryl group, a $C_7$ to $C_{15}$ aralkyl group, or a $C_7$ to $C_{15}$ substituted aralkyl group; alternatively, a $C_4$ to $C_{15}$ cycloalkyl group or a $C_4$ to $C_{15}$ substituted cycloalkyl group; alternatively, a $C_3$ to $C_{15}$ aliphatic heterocyclic group or a $C_3$ to $C_{15}$ substituted aliphatic heterocyclic group; alternatively, a $C_6$ to $C_{15}$ aryl group or a $C_6$ to $C_{15}$ substituted aryl group; alternatively, a $C_7$ to $C_{15}$ aralkyl group or a $C_7$ to $C_{15}$ substituted aralkyl group; alternatively, a $C_3$ to $C_{15}$ heteroaryl group or a $C_3$ to $C_{15}$ substituted heteroaryl group; alternatively, a $C_1$ to $C_{10}$ alkyl group; alternatively, a $C_4$ to $C_{15}$ cycloalkyl group; alternatively, a $C_4$ to $C_{15}$ substituted cycloalkyl group; alternatively, a $C_3$ to $C_{15}$ aliphatic heterocyclic group; alternatively, a $C_3$ to $C_{15}$ substituted aliphatic heterocyclic group; alternatively, a $C_6$ to $C_{15}$ aryl group; alternatively, a $C_6$ to $C_{15}$ substituted aryl group; alternatively, a $C_7$ to $C_{15}$ aralkyl group; alternatively, a $C_7$ to $C_{15}$ substituted aralkyl group; alternatively, a $C_3$ to $C_{15}$ heteroaryl group; or alternatively, a $C_3$ to $C_{15}$ substituted heteroaryl group. In further embodiments, $R^2$ can be a $C_1$ to $C_5$ alkyl group.

In an embodiment, $R^2$ can be a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, or a nonadecyl group; or alternatively, a methyl group, an ethyl group, a propyl group, a butyl group, a pentyl group, a hexyl group, a heptyl group, an octyl group, a nonyl group, or a decyl group. In some embodiments, $R^2$ can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, an n-propyl group; alternatively, an iso-propyl group; alternatively, a tert-butyl group; or alternatively, a neopentyl group. In some embodiments, the alkyl groups which can be utilized as $R^2$ can be substituted. Each substituent of a substituted alkyl group independently can be a halogen or a hydrocarboxy group; alternatively, a halogen; or alternatively, a hydrocarboxy group. Halogens and hydrocarboxy groups that can be utilized as substituents are independently disclosed herein (e.g. as substituents for substituted $R^1$ groups) and can be utilized without limitation to further describe the substituted alkyl group which can be utilized as $R^2$.

In an embodiment, $R^2$ can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, $R^2$ can be a cyclopentyl group, a substituted cyclopentyl group, a cyclohexyl group, or a substituted cyclohexyl group. In other embodiments, $R^2$ can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; or alternatively, a cyclooctyl group or a substituted cyclooctyl group. In further embodiments, $R^2$ can be a cyclopentyl group; alternatively, a substituted cyclopentyl group; a cyclohexyl group; or alternatively, a substituted cyclohexyl group.

In an embodiment, each substituent for a substituted cycloalkyl group (general or specific) that can be utilized as $R^2$ independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, each substituent for a substituted cycloalkyl group (general or specific) that can be utilized as $R^1$ independently can be a halogen, an alkyl group, or an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Halogens, hydrocarbyl groups, hydrocarboxy groups, alkyl group, and alkoxy groups that can be utilized as substituents are independently disclosed herein (e.g. as substituents for substituted $R^1$ groups) and can be utilized without limitation to further describe the substituents for a substituted cycloalkyl group (general or specific) that can be utilized as $R^2$.

In an aspect, $R^2$ may have Structure G3:

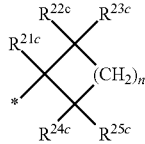

Structure G3 wherein, the undesignated valency is attached to the central carbon atom of the $N^2$-phosphinyl amidine group. Generally, $R^{21c}$, $R^{23c}$, $R^{24c}$, and $R^{25c}$ independently can be hydrogen or a non-hydrogen substituent, and n can be an integer from 1 to 5. In an embodiment wherein $R^2$ has Structure G3, $R^{21c}$, $R^{23c}$, $R^{24c}$, and $R^{25c}$ can be hydrogen and $R^{22c}$ can be any non-hydrogen substituent disclosed herein; or alternatively, $R^{21c}$, $R^{23c}$, and $R^{25c}$ can be hydrogen and $R^{22c}$ and $R^{24c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively, 3.

In an embodiment, $R^{21c}$, $R^{22c}$, $R^{23c}$, $R^{24c}$, and $R^{25c}$ independently can be hydrogen, a halogen, a hydrocarbyl group, or a hydrocarboxy group; alternatively, hydrogen, a halogen, or a hydrocarbyl group; alternatively, hydrogen, a halogen, or a hydrocarboxy group; alternatively, hydrogen, a hydrocarbyl group, or a hydrocarboxy group; alternatively, hydrogen or a halogen; alternatively, hydrogen or a hydrocarbyl group; or alternatively, hydrogen or a hydrocarboxy group. In some embodiments, $R^{21c}$, $R^{22c}$, $R^{23c}$, $R^{24c}$, and $R^{25c}$ independently can be hydrogen, a halogen, an alkyl group, or an alkoxy group; alternatively, hydrogen, a halogen, or an alkyl group; alternatively, hydrogen, a halogen, or an alkoxy group; alternatively, hydrogen, an alkyl group, or an alkoxy group; alternatively, hydrogen or a halogen; alternatively, hydrogen or an alkyl group; or alternatively, hydrogen or an alkoxy group. Halogens, hydrocarbyl groups, hydrocarboxy groups, alkyl group, and alkoxy groups that can be utilized as substituents are independently disclosed herein (e.g. as substituents for substituted $R^1$ groups) and can be utilized without limitation to further describe the $R^2$ group having Structure G3.

In an embodiment, $R^2$ can be a phenyl group or a substituted phenyl group. In some embodiments, $R^2$ can be a phenyl group; or alternatively, a substituted phenyl group. In an embodiment, the $R^2$ substituted phenyl group can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other embodiments, the $R^2$ substituted phenyl group can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,6-disubstituted phenyl group or a 2,4,6-trisubstituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group.

In an embodiment, each substituent for a substituted phenyl $R^2$ group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, each substituent for a substituted phenyl $R^2$ group independently can be a halogen, an alkyl group, or an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the substituents for the substituted phenyl $R^2$ group.

In an aspect, $R^2$ can have Structure G4:

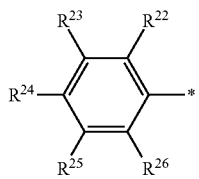

Structure G4 wherein the undesignated valency is attached to the $N^1$ nitrogen atom of the $N^2$-phosphinyl amidine group. Generally, $R^{22}$, $R^{23}$, $R^{24}$, $R^{25}$, and $R^{26}$ independently can be hydrogen or a non-hydrogen substituent. In an embodiment wherein $R^2$ has Structure G4, $R^{22}$, $R^{23}$, $R^{24}$, $R^{25}$, and $R^{26}$ can be hydrogen, $R^{23}$, $R^{24}$, $R^{25}$, and $R^{26}$ can be hydrogen and $R^{22}$ can be a non-hydrogen substituent, $R^{22}$, $R^{24}$, $R^{25}$, and $R^{26}$ can be hydrogen and $R^{23}$ can be a non-hydrogen substituent, $R^{22}$, $R^{23}$, $R^{25}$, and $R^{26}$ can be hydrogen and $R^{24}$ can be a non-hydrogen substituent, $R^{23}$, $R^{25}$, and $R^{26}$ can be hydrogen and $R^{22}$ and $R^{24}$ can be non-hydrogen substituents, $R^{23}$, $R^{24}$, and $R^{25}$ can be hydrogen and $R^{22}$ and $R^{26}$ can be non-hydrogen substituents, $R^{22}$, $R^{24}$, and $R^{26}$ can be hydrogen and $R^{23}$ and $R^{25}$ can be non-hydrogen substituents, or $R^{23}$ and $R^{25}$ can be hydrogen and $R^{22}$, $R^{24}$, and $R^{26}$ can be non-hydrogen substituents. In some embodiments wherein $R^2$ has Structure G4, $R^{23}$, $R^{24}$, $R^{25}$, and $R^{26}$ can be hydrogen and $R^{22}$ can be a non-hydrogen substituent, $R^{22}$, $R^{23}$, $R^{25}$, and $R^{26}$ can be hydrogen and $R^{24}$ can be a non-hydrogen substituent, $R^{23}$, $R^{25}$, and $R^{26}$ can be hydrogen and $R^{22}$ and $R^{24}$ can be non-hydrogen substituents, $R^{23}$, $R^{24}$, and $R^{25}$ can be hydrogen and $R^{22}$ and $R^{26}$ can be non-hydrogen substituents, or $R^{23}$ and $R^{25}$ can be hydrogen and $R^{22}$, $R^{24}$, and $R^{26}$ can be non-hydrogen substituents; alternatively, $R^{23}$, $R^{24}$, $R^{25}$, and $R^{26}$ can be hydrogen and $R^{22}$ can be a non-hydrogen substituent, $R^{22}$, $R^{23}$, $R^{25}$, and $R^{26}$ can be hydrogen and $R^{24}$ can be a non-hydrogen substituent, $R^{23}$, $R^{25}$, and $R^{26}$ can be hydrogen and $R^{22}$ and $R^{24}$ can be non-hydrogen substituents, or $R^{23}$, $R^{24}$, and $R^{25}$ can be hydrogen and $R^{22}$ and $R^{26}$ can be non-hydrogen substituents; alternatively, $R^{22}$, $R^{24}$, $R^{25}$, and $R^{26}$ can be hydrogen and $R^{23}$ can be a non-hydrogen substituent, or $R^{22}$, $R^{24}$, and $R^{26}$ can be hydrogen and $R^{23}$ and $R^{25}$ can be non-hydrogen substituents; alternatively, $R^{23}$, $R^{24}$, $R^{25}$, and $R^{26}$ can be hydrogen and $R^{22}$ can be a non-hydrogen substituent, or $R^{22}$, $R^{23}$, $R^{25}$, and $R^{26}$ can be hydrogen and $R^{24}$ can be a non-hydrogen substituent; alternatively, $R^{23}$, $R^{25}$, and $R^{26}$ can be hydrogen and $R^{22}$ and $R^{24}$ can be non-hydrogen substituents, $R^{23}$, $R^{24}$, and $R^{25}$ can be hydrogen and $R^{22}$ and $R^{26}$ can be non-hydrogen substituents, or $R^{23}$ and $R^{25}$ can be hydrogen and $R^{22}$, $R^{24}$, and $R^{26}$ can be non-hydrogen substituents. In other embodiments wherein $R^2$ has Structure G4, $R^{22}$, $R^{23}$, $R^{24}$, $R^{25}$, and $R^{26}$ can be hydrogen; alternatively, $R^{23}$, $R^{24}$, $R^{25}$, and $R^{26}$ can be hydrogen and $R^{22}$ can be a non-hydrogen substituent; alternatively, $R^{22}$, $R^{24}$, $R^{25}$, and $R^{26}$ can be hydrogen and $R^{23}$ can be a non-hydrogen substituent; alternatively, $R^{22}$, $R^{23}$, $R^{25}$, and $R^{26}$ can be hydrogen and $R^{24}$ can be a non-hydrogen substituent; alternatively, $R^{23}$, $R^{25}$, and $R^{26}$ can be hydrogen and $R^{22}$ and $R^{24}$ can be non-hydrogen substituents; alternatively, $R^{23}$, $R^{24}$, and $R^{25}$ can be hydrogen and $R^{22}$ and $R^{26}$ can be non-hydrogen substituents; alternatively, $R^{22}$, $R^{24}$, and $R^{26}$ can be hydrogen and $R^{23}$ and $R^{25}$ and can be non-hydrogen substituents; or alternatively, $R^{23}$ and $R^{25}$ can be hydrogen and $R^{22}$, $R^{24}$, and $R^{26}$ can be non-hydrogen substituents.

In an embodiment, the non-hydrogen substituents that can be utilized as $R^{22}$, $R^{23}$, $R^{24}$, $R^{25}$, and $R^{26}$ in the $R^2$ group having Structure G4 independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, the non-hydrogen substituents that can be utilized as $R^{22}$, $R^{23}$, $R^{24}$, $R^{25}$, and $R^{26}$ in the $R^2$ group having Structure G4 independently can be a halogen, an alkyl group, or an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the $R^2$ group having Structure G4.

In an aspect, $R^2$ can be a benzyl group, a substituted benzyl group, a 1-phenyleth-1-yl group, a substituted 1-phenyleth-1-yl, a 2-phenyleth-1-yl group, or a substituted 2-phenyleth-1-yl group. In an embodiment, $R^2$ can be a benzyl group, or a substituted benzyl group; alternatively, a 1-phenyleth-1-yl group or a substituted 1-phenyleth-1-yl; alternatively, a 2-phenyleth-1-yl group or a substituted 2-phenyleth-1-yl group; or alternatively, a benzyl group, a 1-phenyleth-1-yl group, or a 2-phenyleth-1-yl group. In some embodiments, $R^2$ can be a benzyl group; alternatively, a substituted benzyl group; alternatively, a 1-phenyleth-1-yl group; alternatively, a substituted 1-phenyleth-1-yl; alternatively, a 2-phenyleth-1-yl group; or alternatively, a substituted 2-phenyleth-1-yl group.

In an embodiment, each substituent for a substituted benzyl group, a 1-phenyleth-1-yl group, or a 2-phenyleth-1-yl group (general or specific) that can be utilized as $R^2$ independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, each substituent for a substituted benzyl group, 1-phenyleth-1-yl group, or a 2-phenyleth-1-yl group (general or specific) that can be utilized as $R^2$ independently can be halogen, an alkyl group, or an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the substituents for the substituted benzyl group, 1-phenyleth-1-yl group, or a 2-phenyleth-1-yl group (general or specific) that can be utilized as $R^2$.

In an aspect, $R^2$ can be a pyridinyl group, a substituted pyridinyl group, a furyl group, a substituted furyl group, a thienyl group, or a substituted thienyl group. In an embodiment, $R^2$ can be a pyridinyl group or a substituted pyridinyl group; alternatively, a furyl group or a substituted furyl group; or alternatively, a thienyl group or a substituted thienyl group.

In some embodiments, $R^2$ can be a pyridinyl group, a furyl group, or a thienyl group. In other embodiments, $R^2$ can be a pyridinyl group; alternatively, a substituted pyridinyl group; alternatively, a furyl group; alternatively, a substituted furyl group; alternatively, a thienyl group; or alternatively, a substituted thienyl group.

In an embodiment, the pyridinyl (or substituted pyridinyl) $R^2$ group can be a pyridin-2-yl group, a substituted pyridin-2-yl group, a pyridin-3-yl group, a substituted pyridin-3-yl group, a pyridin-4-yl group, or a substituted pyridin-4-yl group; alternatively, a pyridin-2-yl group, a pyridin-3-yl group, or a pyridin-4-yl group. In some embodiments, the pyridinyl (or substituted pyridinyl) $R^2$ group can be a pyridin-2-yl group or a substituted pyridin-2-yl group; alternatively, a pyridin-3-yl group or a substituted pyridin-3-yl group; alternatively, a pyridin-4-yl group or a substituted pyridin-4-yl group; alternatively, a pyridin-2-yl group; alternatively, a substituted pyridin-2-yl group; alternatively, a pyridin-3-yl group; alternatively, a substituted pyridin-3-yl group; alternatively, a pyridin-4-yl group; or alternatively, a substituted pyridin-4-yl group. In an embodiment, the substituted pyridinyl $R^2$ group can be a 2-substituted pyridin-3-yl group, a 4-substituted pyridin-3-yl group, a 5-substituted pyridin-3-yl group, a 6-substituted pyridin-3-yl group, a 2,4-disubstituted pyridin-3-yl group, a 2,6-disubstituted pyridin-3-yl group, or a 2,4,6-trisubstituted pyridin-3-yl group; alternatively, a 2-substituted pyridin-3-yl group, a 4-substituted pyridin-3-yl group, or a 6-substituted pyridin-3-yl group; alternatively, a 2,4-disubstituted pyridin-3-yl group or a 2,6-disubstituted pyridin-3-yl group; alternatively, a 2-substituted pyridin-3-yl group; alternatively, a 4-substituted pyridin-3-yl group; alternatively, a 5-substituted pyridin-3-yl group; alternatively, a 6-substituted pyridin-3-yl group; alternatively, a 2,4-disubstituted pyridin-3-yl group; alternatively, a 2,6-disubstituted pyridin-3-yl group; or alternatively, a 2,4,6-trisubstituted pyridin-3-yl group. In an embodiment, the substituted pyridinyl $R^2$ group can be a 2-substituted pyridin-4-yl group, a 3-substituted pyridin-4-yl group, a 5-substituted pyridin-4-yl group, a 6-substituted pyridin-4-yl group, a 2,6-disubstituted pyridin-4-yl group, or a 3,5-disubstituted pyridin-4-yl group; alternatively, a 2-substituted pyridin-4-yl group or a 6-substituted pyridin-4-yl group; alternatively, a 3-substituted pyridin-4-yl group or a 5-substituted pyridin-4-yl group; alternatively, a 2-substituted pyridin-4-yl group; alternatively, a 3-substituted pyridin-4-yl group; alternatively, a 5-substituted pyridin-4-yl group; alternatively, a 6-substituted pyridin-4-yl group; alternatively, a 2,6-disubstituted pyridin-4-yl group; or alternatively, a 3,5-disubstituted pyridin-4-yl group.

In an embodiment, the furyl (or substituted furyl) $R^2$ group can be a fur-2-yl group, a substituted fur-2-yl group, a fur-3-yl group, or a substituted fur-3-yl group; alternatively, a fur-2-yl or a fur-3-yl group. In some embodiments, the furyl (or substituted furyl) $R^2$ group can be a fur-2-yl group or a substituted fur-2-yl group; alternatively, a fur-3-yl group or a substituted fur-3-yl group; alternatively, a fur-2-yl group; alternatively, a substituted fur-2-yl group; alternatively, a fur-3-yl group; or alternatively, a substituted fur-3-yl group. In an embodiment, the substituted furyl $R^2$ group can be a 2-substituted fur-3-yl group, a 4-substituted fur-3-yl group, or a 2,4-disubstituted fur-3-yl group; alternatively, a 2-substituted fur-3-yl group; alternatively, a 4-substituted fur-3-yl group; or alternatively, a 2,4-disubstituted fur-3-yl group.

In an embodiment, the thienyl (or substituted thienyl) $R^2$ group can be a thien-2-yl group, a substituted thien-2-yl group, a thien-3-yl group, or a substituted thien-3-yl group; alternatively, a thien-2-yl group or a thien-3-yl group. In some embodiments, the thienyl (or substituted thienyl) $R^2$ group can be a thien-2-yl group or a substituted thien-2-yl group; alternatively, a thien-3-yl group or a substituted thien-3-yl group; alternatively, a thien-2-yl group; alternatively, a substituted thien-2-yl group; alternatively, a thien-3-yl group; or alternatively, a substituted thien-3-yl group. In an embodiment, the substituted thienyl $R^2$ group can be a 2-substituted thien-3-yl group, a 4-substituted thien-3-yl group, or a 2,4-disubstituted thien-3-yl group; alternatively, a 2-substituted thien-3-yl group; alternatively, a 4-substituted thien-3-yl group; or alternatively, a 2,4-disubstituted thien-3-yl group.

In an embodiment, each substituent for a substituted pyridinyl, furyl, or thienyl groups (general or specific) that can be utilized as $R^2$ independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, each substituent for a substituted pyridinyl, furyl, and/or or thienyl group (general or specific) that can be utilized as $R^2$ independently can be halogen, an alkyl group, or an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the substituents for the substituted pyridinyl, furyl, and/or thienyl groups (general or specific) that can be utilized as $R^2$.

General and specific non-hydrogen substituents of a substituted cycloalkyl group (general or specific), a substituted aliphatic heterocyclic group (general or specific), a substituted cycloheteryl group (general or specific), a substituted aromatic group (general or specific), a substituted aryl group (general or specific), a substituted aralkyl group (general or specific), a substituted heteroaryl group (general or specific), or a substituted arylheteryl group (general or specific) are disclosed herein. These general and specific non-hydrogen substituents can be utilized, without limitation, to further describe the substituted cycloalkyl groups (general or specific), substituted aliphatic heterocyclic groups (general or specific), substituted cycloheteryl groups (general or specific), substituted aromatic groups (general or specific), substituted aryl groups (general or specific), substituted heteroaryl groups (general or specific), substituted arylheteryl group (general or specific), or any other general or specific group which can be utilized as $R^2$.

In a non-limiting embodiment, $R^2$ can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group, or a 2,4,6-trialkylphenyl group; alternatively, a 2,4-dialkylphenyl group or a 2,6-dialkylphenyl group; alternatively, a 2,6-dialkylphenyl group, or a 2,4,6-trialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 3-alkylphenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. In another non-limiting embodiment, $R^2$ can be a phenyl group, a 2-alkoxyphenyl group, a 3-alkoxyphenyl group, a 4-alkoxyphenyl group, or 3,5-dialkoxyphenyl group; alternatively, a 2-alkoxyphenyl group or a 4-alkoxyphenyl group; alternatively, a 3-alkoxyphenyl group or 3,5-dialkoxyphenyl group; alternatively, a 2-alkoxyphenyl group; alternatively, 3-alkoxyphenyl group; alternatively, a 4-alkoxyphenyl group; alternatively, 3,5-dialkoxyphenyl group. In other non-limiting embodiments, $R^2$ can be a phenyl group, a 2-halophenyl group, a 3-halophenyl group, a 4-halophenyl group, a 2,6-dihalophenyl group, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenyl group; or alternatively, a 3,5-dihalophenyl group. Halides, alkyl group substituents, and alkoxy group substituents are independently described herein and can be utilized, without limitation, to further describe the alkylphenyl, dialkylphenyl, trialkylphenyl, alkoxyphenyl, dialkoxyphenyl, halophenyl, or dihalophenyl groups that can be utilized $R^2$. Generally, the halides, alkyl substituents, or alkoxy substituents of a dialkyl, trialkyl phenyl, dialkoxyphenyl, or dihalophenyl groups can be the same; or alternatively, the halo, alkyl substituents, or alkoxy substituents of alkylphenyl, dialkylphenyl, trialkylphenyl, dialkoxyphenyl, or dihalophenyl groups can be different.

In a non-limiting embodiment, $R^2$ can be a 2-methylphenyl group, a 2-ethylphenyl group, a 2-isopropylphenyl group, a 2-tert-butylphenyl group, a 4-methylphenyl group, a 4-ethylphenyl group, a 4-isopropylphenyl group, or a 4-tert-butylphenyl group; alternatively, a 2-methylphenyl group, a 2-ethylphenyl group, a 2-isopropylphenyl group, or a 2-tert-butylphenyl group; alternatively, a 4-methylphenyl group, a 4-ethylphenyl group, a 4-isopropylphenyl group, or a 4-tert-butylphenyl group; alternatively, a 2-methylphenyl group; alternatively, a 2-ethylphenyl group; alternatively, a 2-isopropylphenyl group; alternatively, a 2-tert-butylphenyl group; alternatively, a 4-methylphenyl group; alternatively, a 4-ethylphenyl group; alternatively, a 4-isopropylphenyl group; or alternatively, a 4-tert-butylphenyl group. In another non-limiting embodiment, $R^2$ can be a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; alternatively, a 4-methoxyphenyl group, a 4-ethoxyphenyl group, a 4-isopropoxyphenyl group, or a 4-tert-butoxyphenyl group; alternatively, a 2-methoxyphenyl group; alternatively, a 2-ethoxyphenyl group; alternatively, a 2-isopropoxyphenyl group; alternatively, a 2-tert-butoxyphenyl group; alternatively, a 4-methoxyphenyl group; alternatively, a 4-ethoxyphenyl group; alternatively, a 4-isopropoxyphenyl group; or alternatively, a 4-tert-butoxyphenyl group. In other non-limiting embodiments, $R^2$ can be a 2-fluorophenyl group, a 2-chlorophenyl group, a 3-fluorophenyl group, a 3-chlorophenyl group, a 4-fluorophenyl group, a 4-chlorophenyl group, a 3,5-difluorophenyl group, or a 3,5-dichlorophenyl group; alternatively, a 2-fluorophenyl group or a 2-chlorophenyl group; alternatively, a 3-fluorophenyl group or a 3-chlorophenyl group; alternatively, a 4-fluorophenyl group or a 4-chlorophenyl group; alternatively, a 3,5-difluorophenyl group or a 3,5-dichlorophenyl group; alternatively, a 3-fluorophenyl group, a 3-chlorophenyl group, a 3,5-difluorophenyl group or a 3,5-dichlorophenyl group; alternatively, a 3-fluorophenyl group or a 3,5-difluorophenyl group; alternatively, a 2-fluorophenyl group; alternatively, a 2-chlorophenyl group; alternatively, a 3-fluorophenyl group; alternatively, a 3-chlorophenyl group; alternatively, a 4-fluorophenyl group; alternatively, a 4-chlorophenyl; alternatively, a 3,5-difluorophenyl group; or alternatively, a 3,5-dichlorophenyl group.

In an aspect, $R^3$ can be hydrogen. In another aspect, $R^3$ can be an organyl group, an organyl group consisting essentially of inert functional groups, or a hydrocarbyl group. In an embodiment, $R^3$ can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, $R^3$ can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In an embodiment, $R^3$ can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In yet other embodiments, $R^3$ may be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group.

In an aspect, $R^3$ can be a $C_1$ to $C_{30}$ alkyl group, a $C_4$ to $C_{30}$ cycloalkyl group, a $C_4$ to $C_{30}$ substituted cycloalkyl group, a $C_3$ to $C_{30}$ aliphatic heterocyclic group, a $C_3$ to $C_{30}$ substituted aliphatic heterocyclic group, a $C_6$ to $C_{30}$ aryl group, a $C_6$ to $C_{30}$ substituted aryl group, a $C_3$ to $C_{30}$ heteroaryl group, or a $C_3$ to $C_{30}$ substituted heteroaryl group; alternatively, a $C_1$ to $C_{30}$ alkyl group, a $C_4$ to $C_{30}$ cycloalkyl group, a $C_4$ to $C_{30}$ substituted cycloalkyl group, a $C_6$ to $C_{30}$ aryl group, or a $C_6$ to $C_{30}$ substituted aryl group; alternatively, a $C_4$ to $C_{30}$ cycloalkyl group or a $C_4$ to $C_{30}$ substituted cycloalkyl group; alternatively, a $C_3$ to $C_{30}$ aliphatic heterocyclic group or a $C_3$ to $C_{30}$ substituted aliphatic heterocyclic group; alternatively, a $C_6$ to $C_{30}$ aryl group or a $C_6$ to $C_{30}$ substituted aryl group; alternatively, a $C_3$ to $C_{30}$ heteroaryl group or a $C_3$ to $C_{30}$ substituted heteroaryl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_3$ to $C_{30}$ aliphatic heterocyclic group; alternatively, a $C_3$ to $C_{30}$ substituted aliphatic heterocyclic group; alternatively, a $C_6$ to $C_{30}$ aryl group; alternatively, a $C_6$ to $C_{30}$ substituted aryl group; alternatively, a $C_3$ to $C_{30}$ heteroaryl group; or alternatively, a $C_3$ to $C_{30}$ substituted heteroaryl group. In an embodiment, $R^3$ can be a $C_1$ to $C_{15}$ alkyl group, a $C_4$ to $C_{20}$ cycloalkyl group, a $C_4$ to $C_{20}$ substituted cycloalkyl group, a $C_3$ to $C_{20}$ aliphatic heterocyclic group, a $C_3$ to $C_{20}$ substituted aliphatic heterocyclic group, a $C_6$ to $C_{20}$ aryl group, a $C_6$ to $C_{20}$ substituted aryl group, a $C_3$ to $C_{20}$ heteroaryl group, or a $C_3$ to $C_{20}$ substituted heteroaryl group; alternatively, a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group; alternatively, a $C_4$ to $C_{20}$ cycloalkyl group or a $C_4$ to $C_{20}$ substituted cycloalkyl group; alternatively, a $C_3$ to $C_{20}$ aliphatic heterocyclic group or a $C_3$ to $C_{20}$ substituted aliphatic heterocyclic group; alternatively, a $C_6$ to $C_{20}$ aryl group or a $C_6$ to $C_{20}$ substituted aryl group; alternatively, a $C_3$ to $C_{20}$ heteroaryl group or a $C_3$ to $C_{20}$ substituted heteroaryl group; alternatively, a $C_1$ to $C_{15}$ alkyl group; alternatively, a $C_4$ to $C_{20}$ cycloalkyl group; alternatively, a $C_4$ to $C_{20}$ substituted cycloalkyl group; alternatively, a $C_3$ to $C_{20}$ aliphatic heterocyclic group; alternatively, a $C_3$ to $C_{20}$ substituted aliphatic heterocyclic group; alternatively, a $C_6$ to $C_{20}$ aryl group; alternatively, a $C_6$ to $C_{20}$ substituted aryl group; alternatively, a $C_3$ to $C_{20}$ heteroaryl group; or alternatively, a $C_3$ to $C_{20}$ substituted heteroaryl group. In other embodiments, $R^3$ can be a $C_1$ to $C_{10}$ alkyl group, a $C_4$ to $C_{15}$ cycloalkyl group, a $C_4$ to $C_{15}$ substituted cycloalkyl group, a $C_3$ to $C_{15}$ aliphatic heterocyclic group, a $C_3$ to $C_{15}$ substituted aliphatic heterocyclic group, a $C_6$ to $C_{15}$ aryl group, a $C_6$ to $C_{15}$ substituted aryl group, a $C_3$ to $C_{15}$ heteroaryl group, or a $C_3$ to $C_{15}$ substituted heteroaryl group; alternatively, a $C_1$ to $C_{10}$ alkyl group, a $C_4$ to $C_{15}$ cycloalkyl group, a $C_4$ to $C_{15}$ substituted cycloalkyl group, a $C_6$ to $C_{15}$ aryl group, or a $C_6$ to $C_{15}$ substituted aryl group; alternatively, a $C_4$ to $C_{15}$ cycloalkyl group or a $C_4$ to $C_{15}$ substituted cycloalkyl group; alternatively, a $C_3$ to $C_{15}$ aliphatic heterocyclic group or a $C_3$ to $C_{15}$ substituted aliphatic heterocyclic group; alternatively, a $C_6$ to $C_{15}$ aryl group or a $C_6$ to $C_{15}$ substituted aryl group; alternatively, a $C_3$ to $C_{15}$ heteroaryl group or a $C_3$ to $C_{15}$ substituted heteroaryl group; alternatively, a $C_1$ to $C_{10}$ alkyl group; alternatively, a $C_4$ to $C_{15}$ cycloalkyl group; alternatively, a $C_4$ to $C_{15}$ substituted cycloalkyl group; alternatively, a $C_3$ to $C_{15}$ aliphatic heterocyclic group; alternatively, a $C_3$ to $C_{15}$ substituted aliphatic heterocyclic group; alternatively, a $C_6$ to $C_{15}$ aryl group; alternatively, a $C_6$ to $C_{15}$ substituted aryl group; alternatively, a $C_3$ to $C_{15}$ heteroaryl group; or alternatively, a $C_3$ to $C_{15}$ substituted heteroaryl group. In further embodiments, $R^3$ can be a $C_1$ to $C_5$ alkyl group In an embodiment, $R^3$ can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, or a nonadecyl group; or alternatively, a methyl group, an ethyl group, a propyl group, a butyl group, a pentyl group, a hexyl group, a heptyl group, an octyl group, a nonyl group, or a decyl group. In some embodiments, $R^3$ can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, an n-propyl group; alternatively, an iso-propyl group; alternatively, a tert-butyl group; or alternatively, a neopentyl group. In some embodiments, the alkyl groups which can be utilized as $R^3$ can be substituted. Each substituent of a substituted alkyl group independently can be a halogen or a hydrocarboxy group; alternatively, a halogen; or alternatively, a hydrocarboxy group. Halogens and hydrocarboxy groups that can be utilized as substituents are independently disclosed herein (e.g. as substituents for substituted $R^1$ groups) and can be utilized without limitation to further describe the substituted alkyl group which can be utilized as $R^3$.

In an embodiment, $R^3$ can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, $R^3$ can be a cyclopentyl group, a substituted cyclopentyl group, a cyclohexyl group, or a substituted cyclohexyl group. In other embodiments, $R^3$ can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; or alternatively, a cyclooctyl group or a substituted cyclooctyl group. In further embodiments, $R^3$ can be a cyclopentyl group; alternatively, a substituted cyclopentyl group; a cyclohexyl group; or alternatively, a substituted cyclohexyl group.

In an embodiment, each substituent for a substituted cycloalkyl group (general or specific) that can be utilized as $R^3$ independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, each substituent for a substituted cycloalkyl group (general or specific) that can be utilized as $R^3$ independently can be a halogen, an alkyl group, or an alkoxy group; alternatively, an alkyl group or an alkoxy group; alternatively, a halogen or an alkyl group; alternatively, a halogen or an alkoxy group; alternatively, a halogen; alternatively, an alkyl group; or alternatively, an alkoxy group. Halogens, hydrocarbyl groups, hydrocarboxy groups, alkyl group, and alkoxy groups that can be utilized as substituents are independently disclosed herein (e.g. as substituents for substituted $R^1$ groups) and can be utilized without limitation to further describe the substituents for a substituted cycloalkyl group (general or specific) that can be utilized as $R^3$.

In an aspect, $R^3$ can have Structure G5:

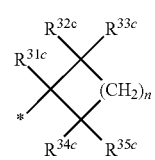

Structure G5 wherein, the undesignated valency is attached to the $N^2$ nitrogen atom of the $N^2$-phosphinyl amidine group. Generally, $R^{31c}$, $R^{32c}$, $R^{33c}$, $R^{34c}$, and $R^{35c}$ independently can be hydrogen or a non-hydrogen substituent, and n can be an integer from 1 to 5. In an embodiment wherein $R^3$ has Structure G5, $R^{31c}$, $R^{33c}$, $R^{34c}$, and $R^{35c}$ can be hydrogen and $R^{32c}$ can be any non-hydrogen substituent disclosed herein; or alternatively, $R^{31c}$, $R^{33c}$, and $R^{35c}$ can be hydrogen and $R^{32c}$ and $R^{34c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively, 3.

In an embodiment, $R^{31c}$, $R^{32c}$, $R^{33c}$, $R^{34c}$, and $R^{35c}$ independently can be hydrogen, a halogen, a hydrocarbyl group, or a hydrocarboxy group; alternatively, hydrogen, a halogen, or a hydrocarbyl group; alternatively, hydrogen, a halogen, or a hydrocarboxy group; alternatively, hydrogen, a hydrocarbyl group, or a hydrocarboxy group; alternatively, hydrogen or a halogen; alternatively, hydrogen or a hydrocarbyl group; or alternatively, hydrogen or a hydrocarboxy group. In some embodiments, $R^{31c}$, $R^{32c}$, $R^{33c}$, $R^{34c}$, and $R^{35c}$ independently can be hydrogen, a halogen, an alkyl group, or an alkoxy group; alternatively, hydrogen, a halogen, or an alkyl group; alternatively, hydrogen, a halogen, or an alkoxy group; alternatively, an alkyl group or an alkoxy group; alternatively, hydrogen or a halogen; alternatively, hydrogen or an alkyl group; or alternatively, hydrogen or an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the $R^3$ group having Structure G5.

In an embodiment, $R^3$ can be a phenyl group or a substituted phenyl group. In some embodiments, $R^3$ can be a phenyl group; or alternatively, a substituted phenyl group. In an embodiment, the $R^3$ substituted phenyl group can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other embodiments, the $R^3$ substituted phenyl group can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,6-disubstituted phenyl group or a 2,4,6-trisubstituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group.

In an embodiment, each substituent for a substituted phenyl $R^3$ group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, each substituent for a substituted phenyl $R^3$ group independently can be a halogen, an alkyl group, or an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the substituents for the substituted phenyl $R^3$ group.

In an aspect, $R^3$ can have Structure G6:

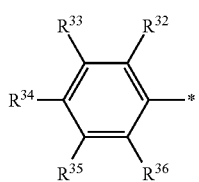

Structure G6 wherein the undesignated valency is attached to the $N^1$ nitrogen atom of the $N^2$-phosphinylamidine group. Generally, $R^{32}$, $R^{33}$, $R^{34}$, $R^{35}$, and $R^{36}$ independently can be hydrogen or a non-hydrogen substituent. In an embodiment wherein $R^3$ has Structure G6, $R^{32}$, $R^{33}$, $R^{34}$, $R^{35}$, and $R^{36}$ can be hydrogen, $R^{33}$, $R^{34}$, $R^{35}$, and $R^{36}$ can be hydrogen and $R^{32}$ can be a non-hydrogen substituent, $R^{32}$, $R^{34}$, $R^{35}$, and $R^{36}$ can be hydrogen and $R^{33}$ can be a non-hydrogen substituent, $R^{32}$, $R^{33}$, $R^{35}$, and $R^{36}$ can be hydrogen and $R^{34}$ can be a non-hydrogen substituent, $R^{33}$, $R^{35}$, and $R^{36}$ can be hydrogen and $R^{32}$ and $R^{34}$ can be non-hydrogen substituents, $R^{33}$, $R^{34}$, and $R^{35}$ can be hydrogen and $R^{32}$ and $R^{36}$ can be non-hydrogen substituents, $R^{32}$, $R^{34}$, and $R^{36}$ can be hydrogen and $R^{33}$ and $R^{35}$ can be non-hydrogen substituents, or $R^{33}$ and $R^{35}$ can be hydrogen and $R^{32}$, $R^{34}$, and $R^{36}$ can be non-hydrogen substituents. In some embodiments wherein $R^3$ has Structure G6, $R^{33}$, $R^{34}$, $R^{35}$, and $R^{36}$ can be hydrogen and $R^{32}$ can be a non-hydrogen substituent, $R^{32}$, $R^{33}$, $R^{35}$, and $R^{36}$ can be hydrogen and $R^{34}$ can be a non-hydrogen substituent, $R^{33}$, $R^{35}$, and $R^{36}$ can be hydrogen and $R^{32}$ and $R^{34}$ can be non-hydrogen substituents, $R^{33}$, $R^{34}$, and $R^{35}$ can be hydrogen and $R^{32}$ and $R^{36}$ can be non-hydrogen substituents, or $R^{33}$ and $R^{35}$ can be hydrogen and $R^{32}$, $R^{34}$, and $R^{36}$ can be non-hydrogen substituents; alternatively, $R^{33}$, $R^{34}$, $R^{35}$, and $R^{36}$ can be hydrogen and $R^{32}$ can be a non-hydrogen substituent, $R^{32}$, $R^{33}$, $R^{35}$, and $R^{36}$ can be hydrogen and $R^{34}$ can be a non-hydrogen substituent, $R^{33}$, $R^{35}$, and $R^{36}$ can be hydrogen and $R^{32}$ and $R^{34}$ can be non-hydrogen substituents, or $R^{33}$, $R^{34}$, and $R^{35}$ can be hydrogen and $R^{32}$ and $R^{36}$ can be non-hydrogen substituents; alternatively, $R^{32}$, $R^{34}$, $R^{35}$, and $R^{36}$ can be hydrogen and $R^{33}$ can be a non-hydrogen substituent, or $R^{32}$, $R^{34}$, and $R^{36}$ can be hydrogen and $R^{33}$ and $R^{35}$ can be non-hydrogen substituents; alternatively, $R^{33}$, $R^{34}$, $R^{35}$, and $R^{36}$ can be hydrogen and $R^{32}$ can be a non-hydrogen substituent, or $R^{32}$, $R^{33}$, $R^{35}$, and $R^{36}$ can be hydrogen and $R^{34}$ can be a non-hydrogen substituent; alternatively, $R^{33}$, $R^{35}$, and $R^{36}$ can be hydrogen and $R^{32}$ and $R^{34}$ can be non-hydrogen substituents, $R^{33}$, $R^{34}$, and $R^{35}$ can be hydrogen and $R^{32}$ and $R^{36}$ can be non-hydrogen substituents, or $R^{33}$ and $R^{35}$ can be hydrogen and $R^{32}$, $R^{34}$, and $R^{36}$ can be non-hydrogen substituents; or alternatively, $R^{33}$, $R^{35}$, and $R^{36}$ can be hydrogen and $R^{32}$, $R^{34}$, and $R^{36}$ can be non-hydrogen substituents, or $R^{33}$, $R^{34}$, and $R^{35}$ can be hydrogen and $R^{32}$ and $R^{36}$ can be non-hydrogen substituents. In other embodiments wherein $R^3$ has Structure G6, $R^{32}$, $R^{33}$, $R^{34}$, $R^{35}$, and $R^{36}$ can be hydrogen; alternatively, $R^{33}$, $R^{34}$, $R^{35}$, and $R^{36}$ can be hydrogen and $R^{32}$ can be a non-hydrogen substituent; alternatively, $R^{32}$, $R^{34}$, $R^{35}$, and $R^{36}$ can be hydrogen and $R^{33}$ can be a non-hydrogen substituent; alternatively, $R^{32}$, $R^{33}$, $R^{35}$, and $R^{36}$ can be hydrogen and $R^{34}$ can be a non-hydrogen substituent; alternatively, $R^{33}$, $R^{35}$, and $R^{36}$ can be hydrogen and $R^{32}$ and $R^{34}$ can be non-hydrogen substituents; alternatively, $R^{33}$, $R^{34}$, and $R^{35}$ can be hydrogen and $R^{32}$ and $R^{36}$ can be non-hydrogen substituents; alternatively, $R^{32}$, $R^{34}$, and $R^{36}$ can be hydrogen and $R^{33}$ and $R^{35}$ and can be non-hydrogen substituents; or alternatively, $R^{33}$ and $R^{35}$ can be hydrogen and $R^{32}$, $R^{34}$, and $R^{36}$ can be non-hydrogen substituents.

In an embodiment, the non-hydrogen substituents that can be utilized as $R^{32}$, $R^{33}$, $R^{34}$, $R^{35}$, and $R^{36}$ in the $R^3$ group having Structure G6 independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, the non-hydrogen substituents that can be utilized as $R^{32}$, $R^{33}$, $R^{34}$, $R^{35}$, and $R^{36}$ in the $R^3$ group having Structure G6 independently can be a halogen, an alkyl group, or an alkoxy group; alternatively, halogen, or an alkyl group; alternatively, a halogen or an alkoxy group; alternatively, an alkyl group or an alkoxy group; alternatively, a halogen; alternatively, an alkyl group; or alternatively, or an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the $R^3$ group having Structure G6.

In an aspect, $R^3$ can be a pyridinyl group, a substituted pyridinyl group, a furyl group, a substituted furyl group, a thienyl group, or a substituted thienyl group. In an embodiment, $R^3$ can be a pyridinyl group or a substituted pyridinyl group; alternatively, a furyl group or a substituted furyl group; or alternatively, a thienyl group or a substituted thienyl group. In some embodiments, $R^3$ can be a pyridinyl group, a furyl group, or a thienyl group. In other embodiments, $R^3$ can be a pyridinyl group; alternatively, a substituted pyridinyl group; alternatively, a furyl group; alternatively, a substituted furyl group; alternatively, a thienyl group; or alternatively, a substituted thienyl group.

In an embodiment, the pyridinyl (or substituted pyridinyl) $R^3$ group can be a pyridin-2-yl group, a substituted pyridin-2-yl group, a pyridin-3-yl group, a substituted pyridin-3-yl group, a pyridin-4-yl group, or a substituted pyridin-4-yl group; alternatively, a pyridin-2-yl group, a pyridin-3-yl group, or a pyridin-4-yl group. In some embodiments, the pyridinyl (or substituted pyridinyl) $R^3$ group can be a pyridin-2-yl group or a substituted pyridin-2-yl group; alternatively, a pyridin-3-yl group or a substituted pyridin-3-yl group; alternatively, a pyridin-4-yl group or a substituted pyridin-4-yl group; alternatively, a pyridin-2-yl group; alternatively, a substituted pyridin-2-yl group; alternatively, a pyridin-3-yl group; alternatively, a substituted pyridin-3-yl group; alternatively, a pyridin-4-yl group; or alternatively, a substituted pyridin-4-yl group. In an embodiment, the substituted pyridinyl $R^3$ group can be a 2-substituted pyridin-3-yl group, a 4-substituted pyridin-3-yl group, a 5-substituted pyridin-3-yl group, a 6-substituted pyridin-3-yl group, a 2,4-disubstituted pyridin-3-yl group, a 2,6-disubstituted pyridin-3-yl group, or a 2,4,6-trisubstituted pyridin-3-yl group; alternatively, a 2-substituted pyridin-3-yl group, a 4-substituted pyridin-3-yl group, or a 6-substituted pyridin-3-yl group; alternatively, a 2,4-disubstituted pyridin-3-yl group or a 2,6-disubstituted pyridin-3-yl group; alternatively, a 2-substituted pyridin-3-yl group; alternatively, a 4-substituted pyridin-3-yl group; alternatively, a 5-substituted pyridin-3-yl group; alternatively, a 6-substituted pyridin-3-yl group; alternatively, a 2,4-disubstituted pyridin-3-yl group; alternatively, a 2,6-disubstituted pyridin-3-yl group; or alternatively, a 2,4,6-trisubstituted pyridin-3-yl group. In an embodiment, the substituted pyridinyl $R^3$ group can be a 2-substituted pyridin-4-yl group, a 3-substituted pyridin-4-yl group, a 5-substituted pyridin-4-yl group, a 6-substituted pyridin-4-yl group, a 2,6-disubstituted pyridin-4-yl group, or a 3,5-disubstituted pyridin-4-yl group; alternatively, a 2-substituted pyridin-4-yl group or a 6-substituted pyridin-4-yl group; alternatively, a 3-substituted pyridin-4-yl group or a 5-substituted pyridin-4-yl group; alternatively, a 2-substituted pyridin-4-yl group; alternatively, a 3-substituted pyridin-4-yl group; alternatively, a 5-substituted pyridin-4-yl group; alternatively, a 6-substituted pyridin-4-yl group; alternatively, a 2,6-disubstituted pyridin-4-yl group; or alternatively, a 3,5-disubstituted pyridin-4-yl group.

In an embodiment, the furyl (or substituted furyl) $R^3$ group can be a fur-2-yl group, a substituted fur-2-yl group, a fur-3-yl group, or a substituted fur-3-yl group; alternatively, a fur-2-yl group or a fur-3-yl group. In some embodiments, the furyl (or substituted furyl) $R^3$ group can be a fur-2-yl group or a substituted fur-2-yl group; alternatively, a fur-3-yl group or a substituted fur-3-yl group; alternatively, a fur-2-yl group; alternatively, a substituted fur-2-yl group; alternatively, a fur-3-yl group; or alternatively, a substituted fur-3-yl group. In an embodiment, the substituted furyl $R^3$ group can be a 2-substituted fur-3-yl group, a 4-substituted fur-3-yl group, or a 2,4-disubstituted fur-3-yl group; alternatively, a 2-substituted fur-3-yl group; alternatively, a 4-substituted fur-3-yl group; or alternatively, a 2,4-disubstituted fur-3-yl group.

In an embodiment, the thienyl (or substituted thienyl) $R^3$ group can be a thien-2-yl group, a substituted thien-2-yl group, a thien-3-yl group, or a substituted thien-3-yl group; alternatively, a thien-2-yl group or a thien-3-yl group. In some embodiments, thienyl (or substituted thienyl) $R^3$ group can be a thien-2-yl group or a substituted thien-2-yl group; alternatively, a thien-3-yl group or a substituted thien-3-yl group; alternatively, a thien-2-yl group; alternatively, a substituted thien-2-yl group; alternatively, a thien-3-yl group; or alternatively, a substituted thien-3-yl group. In an embodiment, the substituted thienyl $R^3$ group can be a 2-substituted thien-3-yl group, a 4-substituted thien-3-yl group, or a 2,4-disubstituted thien-3-yl group; alternatively, a 2-substituted thien-3-yl group; alternatively, a 4-substituted thien-3-yl group; or alternatively, a 2,4-disubstituted thien-3-yl group.

In an embodiment, each substituent for a substituted pyridinyl, furyl, and/or thienyl groups (general or specific) that can be utilized as $R^3$ independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, each substituent for a substituted pyridinyl, furyl, and/or thienyl groups (general or specific) that can be utilized as $R^3$ independently can be a halogen, an alkyl group, or an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the substituents for the substituted pyridinyl, furyl, and/or thienyl groups (general or specific) that can be utilized as $R^3$.

General and specific non-hydrogen substituents of a substituted cycloalkyl group (general or specific), a substituted aliphatic heterocyclic group (general or specific), a substituted cycloheteryl group (general or specific), a substituted aromatic group (general or specific), a substituted aryl group (general or specific), a substituted heteroaryl group (general or specific), or a substituted arylheteryl group (general or specific) are disclosed herein. These general and specific non-hydrogen substituents can be utilized, without limitation, to further describe the substituted cycloalkyl groups (general or specific), substituted aliphatic heterocyclic groups (general or specific), substituted cycloheteryl groups (general or specific), substituted aromatic groups (general or specific), substituted aryl groups (general or specific), substituted heteroaryl groups (general or specific), substituted arylheteryl group (general or specific), or any other general or specific group which can be utilized as $R^3$.

In a non-limiting embodiment, $R^3$ can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group, or a 2,4,6-trialkylphenyl group; alternatively, a 2,4-dialkylphenyl group or a 2,6-dialkylphenyl group; alternatively, a 2,6-dialkylphenyl group, or a 2,4,6-trialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 3-alkylphenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. In another non-limiting embodiment, $R^3$ can be a phenyl group, a 2-alkoxyphenyl group, a 3-alkoxyphenyl group, a 4-alkoxyphenyl group, or a 3,5-dialkoxyphenyl group; alternatively, a 2-alkoxyphenyl group or a 4-alkoxyphenyl group; alternatively, a 3-alkoxyphenyl group or 3,5-dialkoxyphenyl group; alternatively, a 2-alkoxyphenyl group; alternatively, a 3-alkoxyphenyl group; alternatively, a 4-alkoxyphenyl group; alternatively, a 3,5-dialkoxyphenyl group. In other non-limiting embodiments, $R^1$ can be a phenyl group, a 2-halophenyl group, a 3-halophenyl group, a 4-halophenyl group, a 2,6-dihalophenyl group, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenyl group; or alternatively, a 3,5-dihalophenyl group. Halogens, alkyl groups, and alkoxy groups are independently described herein (e.g. as substituents for substituted $R^1$ groups) and can be utilized, without limitation, to further describe the alkylphenyl, dialkylphenyl, trialkylphenyl, alkoxyphenyl, dialkoxyphenyl, halophenyl, or dihalophenyl groups that can be utilized $R^3$. Generally, the halides, alkyl substituents, or alkoxy substituents of a dialkyl, trialkyl phenyl, dialkoxyphenyl, or dihalophenyl group can be the same; or alternatively, the halo, alkyl substituents, or alkoxy substituents of alkylphenyl, dialkylphenyl, trialkylphenyl, dialkoxyphenyl, or dihalophenyl groups can be different.

In a non-limiting embodiment, $R^3$ can be a 2-methylphenyl group, a 2-ethylphenyl group, a 2-isopropylphenyl group, a 2-tert-butylphenyl group, a 4-methylphenyl group, a 4-ethylphenyl group, a 4-isopropylphenyl group, a 4-tert-butylphenyl group, a 2,6-dimethylphenyl group, a 2,6-diethylphenyl group, a 2,6-diisopropylphenyl group, or a 2,6-di-tert-butylphenyl group; alternatively, a 2-methylphenyl group, a 2-ethylphenyl group, a 2-isopropylphenyl group, or a 2-tert-butylphenyl group, a 4-methylphenyl group, a 4-ethylphenyl group, a 4-isopropylphenyl group, or a 4-tert-butylphenyl group; alternatively, a 2-methylphenyl group, a 2-ethylphenyl group, a 2-isopropylphenyl group, or a 2-tert-butylphenyl group; alternatively, a 4-methylphenyl group, a 4-ethylphenyl group, a 4-isopropylphenyl group, or a 4-tert-butylphenyl group; or alternatively, a 2,6-dimethylphenyl group, a 2,6-diethylphenyl group, a 2,6-di-n-propylphenyl group, or a 2,6-di-tert-butylphenyl group. In another non-limiting embodiment, $R^3$ can be a 2-methylphenyl group; alternatively, a 2-ethylphenyl group; alternatively, a 2-isopropylphenyl group; alternatively, a 2-tert-butylphenyl group; alternatively, a 4-methylphenyl group; alternatively, a 4-ethylphenyl group; alternatively, a 4-isopropylphenyl group; or alternatively, a 4-tert-butylphenyl group.

In an aspect, $R^4$ and/or $R^5$ independently can be an organyl group, an organyl group consisting essentially of inert functional groups, or a hydrocarbyl group. In an embodiment, $R^4$ and/or $R^5$ independently can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, $R^4$ and/or $R^5$ independently can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In an embodiment, $R^4$ and/or $R^5$ independently can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group In yet other embodiments, $R^4$ and $R^5$ can be independently selected from a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group. In an aspect, $R^4$ and $R^5$ can be joined to form a ring (regardless of particular type of group—organyl, organyl consisting of inert functional groups, hydrocarbyl, or any species within) containing the phosphorus atom of the $N^2$-phosphinyl amidine group.

In another aspect, $R^4$ and/or $R^5$ independently can be a $C_1$ to $C_{30}$ alkyl group, a $C_4$ to $C_{30}$ cycloalkyl group, a $C_4$ to $C_{30}$ substituted cycloalkyl group, a $C_3$ to $C_{30}$ aliphatic heterocyclic group, a $C_3$ to $C_{30}$ substituted aliphatic heterocyclic group, a $C_6$ to $C_{30}$ aryl group, a $C_6$ to $C_{30}$ substituted aryl group, a $C_3$ to $C_{30}$ heteroaryl group, or a $C_3$ to $C_{30}$ substituted heteroaryl group; alternatively, a $C_1$ to $C_{30}$ alkyl group, a $C_4$ to $C_{30}$ cycloalkyl group, a $C_4$ to $C_{30}$ substituted cycloalkyl group, a $C_6$ to $C_{30}$ aryl group, or a $C_6$ to $C_{30}$ substituted aryl group; alternatively, a $C_4$ to $C_{30}$ cycloalkyl group or a $C_4$ to $C_{30}$ substituted cycloalkyl group; alternatively, a $C_3$ to $C_{30}$ aliphatic heterocyclic group or a $C_3$ to $C_{30}$ substituted aliphatic heterocyclic group; alternatively, a $C_6$ to $C_{30}$ aryl group or a $C_6$ to $C_{30}$ substituted aryl group; alternatively, a $C_3$ to $C_{30}$ heteroaryl group or a $C_3$ to $C_{30}$ substituted heteroaryl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_3$ to $C_{30}$ aliphatic heterocyclic group; alternatively, a $C_3$ to $C_{30}$ substituted aliphatic heterocyclic group; alternatively, a $C_6$ to $C_{30}$ aryl group; alternatively, a $C_6$ to $C_{30}$ substituted aryl group; alternatively, a $C_3$ to $C_{30}$ heteroaryl group; or alternatively, a $C_3$ to $C_{30}$ substituted heteroaryl group. In an embodiment, $R^4$ and $R^5$ independently can be a $C_1$ to $C_{15}$ alkyl group, a $C_4$ to $C_{20}$ cycloalkyl group, a $C_4$ to $C_{20}$ substituted cycloalkyl group, a $C_3$ to $C_{20}$ aliphatic heterocyclic group, a $C_3$ to $C_{20}$ substituted aliphatic heterocyclic group, a $C_6$ to $C_{20}$ aryl group, a $C_6$ to $C_{20}$ substituted aryl group, a $C_3$ to $C_{20}$ heteroaryl group, or a $C_3$ to $C_{20}$ substituted heteroaryl group; alternatively, a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group; alternatively, a $C_4$ to $C_{20}$ cycloalkyl group or a $C_4$ to $C_{20}$ substituted cycloalkyl group; alternatively, a $C_3$ to $C_{20}$ aliphatic heterocyclic group or a $C_3$ to $C_{20}$ substituted aliphatic heterocyclic group; alternatively, a $C_6$ to $C_{20}$ aryl group or a $C_6$ to $C_{20}$ substituted aryl group;

alternatively, a $C_3$ to $C_{20}$ heteroaryl group or a $C_3$ to $C_{20}$ substituted heteroaryl group; alternatively, a $C_1$ to $C_{15}$ alkyl group; alternatively, a $C_4$ to $C_{20}$ cycloalkyl group; alternatively, a $C_4$ to $C_{20}$ substituted cycloalkyl group; alternatively, a $C_3$ to $C_{20}$ aliphatic heterocyclic group; alternatively, a $C_3$ to $C_{20}$ substituted aliphatic heterocyclic group; alternatively, a $C_6$ to $C_{20}$ aryl group; alternatively, a $C_6$ to $C_{20}$ substituted aryl group; alternatively, a $C_3$ to $C_{20}$ heteroaryl group; or alternatively, a $C_3$ to $C_{20}$ substituted heteroaryl group. In other embodiments, $R^4$ and $R^5$ independently can be a $C_1$ to $C_{10}$ alkyl group, a $C_4$ to $C_{15}$ cycloalkyl group, a $C_4$ to $C_{15}$ substituted cycloalkyl group, a $C_3$ to $C_{15}$ aliphatic heterocyclic group, a $C_3$ to $C_{15}$ substituted aliphatic heterocyclic group, a $C_6$ to $C_{15}$ aryl group, a $C_6$ to $C_{15}$ substituted aryl group, a $C_3$ to $C_{15}$ heteroaryl group, or a $C_3$ to $C_{15}$ substituted heteroaryl group; alternatively, a $C_1$ to $C_{10}$ alkyl group, a $C_4$ to $C_{15}$ cycloalkyl group, a $C_4$ to $C_{15}$ substituted cycloalkyl group, a $C_6$ to $C_{15}$ aryl group, or a $C_6$ to $C_{15}$ substituted aryl group; alternatively, a $C_4$ to $C_{15}$ cycloalkyl group or a $C_4$ to $C_{15}$ substituted cycloalkyl group; alternatively, a $C_3$ to $C_{15}$ aliphatic heterocyclic group or a $C_3$ to $C_{15}$ substituted aliphatic heterocyclic group; alternatively, a $C_6$ to $C_{15}$ aryl group or a $C_6$ to $C_{15}$ substituted aryl group; alternatively, a $C_3$ to $C_{15}$ heteroaryl group or a $C_3$ to $C_{15}$ substituted heteroaryl group; alternatively, a $C_1$ to $C_{10}$ alkyl group; alternatively, a $C_4$ to $C_{15}$ cycloalkyl group; alternatively, a $C_4$ to $C_{15}$ substituted cycloalkyl group; alternatively, a $C_3$ to $C_{15}$ aliphatic heterocyclic group; alternatively, a $C_3$ to $C_{15}$ substituted aliphatic heterocyclic group; alternatively, a $C_6$ to $C_{15}$ aryl group; alternatively, a $C_6$ to $C_{15}$ substituted aryl group; alternatively, a $C_3$ to $C_{15}$ heteroaryl group; or alternatively, a $C_3$ to $C_{15}$ substituted heteroaryl group. In further embodiments, $R^4$ and $R^5$ independently can be $C_1$ to $C_5$ alkyl group.

In a further aspect, $R^4$ and/or $R^5$ independently can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, or a nonadecyl group; or alternatively, a methyl group, an ethyl group, a propyl group, a butyl group, a pentyl group, a hexyl group, a heptyl group, an octyl group, a nonyl group, or a decyl group. In some embodiments, $R^4$ and $R^5$ independently can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, an n-propyl group; alternatively, an iso-propyl group; alternatively, a tert-butyl group; or alternatively, a neopentyl group. In some embodiments, the alkyl groups which can be utilized as $R^4$ and/or $R^5$ can be substituted. Each substituent of a substituted alkyl group independently can be a halogen or a hydrocarboxy group; alternatively, a halogen; or alternatively, a hydrocarboxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the substituted alkyl group which can be utilized as $R^4$ and/or $R^5$.

In a further aspect, $R^4$ and/or $R^5$ independently can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, $R^4$ and $R^5$ independently can be a cyclopentyl group, a substituted cyclopentyl group, a cyclohexyl group, or a substituted cyclohexyl group. In other embodiments, $R^4$ and $R^5$ may be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; or alternatively, a cyclooctyl group or a substituted cyclooctyl group. In further embodiments, $R^4$ and $R^5$ independently can be a cyclopentyl group; alternatively, a substituted cyclopentyl group; a cyclohexyl group; or alternatively, a substituted cyclohexyl group.

In an embodiment, each substituent for a substituted cycloalkyl group (general or specific) that can be utilized as $R^4$ and/or $R^5$ independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, each substituent for a substituted cycloalkyl group (general or specific) that can be utilized as $R^4$ and/or $R^5$ independently can be a halogen, an alkyl group, or an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the substituents for a substituted cycloalkyl group (general or specific) that can be utilized as $R^4$ and/or $R^5$.

In an aspect, $R^4$ can have Structure G7:

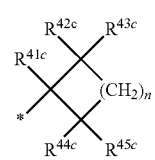

Structure G7 wherein, the undesignated valency is attached to the phosphorus atom of the $N^2$-phosphinylamidine group. Generally, $R^{41c}$, $R^{42c}$, $R^{43c}$, $R^{44c}$, and $R^{45c}$ independently can be hydrogen or a non-hydrogen substituent, and n can be an integer from 1 to 5. In an embodiment wherein $R^4$ has Structure G7, $R^{41c}$, $R^{43c}$, $R^{44c}$, and $R^{45c}$ can be hydrogen and $R^{32c}$ can be any non-hydrogen substituent disclosed herein; or alternatively, $R^{41c}$, $R^{43c}$, and $R^{45c}$ can be hydrogen and $R^{42c}$ and $R^{44c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively, 3.

In an embodiment, $R^{41c}$, $R^{42c}$, $R^{43c}$, $R^{44c}$, and $R^{45c}$ independently can be hydrogen, a halogen, a hydrocarbyl group, or a hydrocarboxy group; alternatively, hydrogen, a halogen, or a hydrocarbyl group; alternatively, hydrogen, a halogen, or a hydrocarboxy group; alternatively, a hydrocarbyl group or a hydrocarboxy group; alternatively, hydrogen or a halogen; alternatively, hydrogen or a hydrocarbyl group; or alternatively, hydrogen or a hydrocarboxy group. In some embodiments, $R^{41c}$, $R^{42c}$, $R^{43c}$, $R^{44c}$, and $R^{45c}$ independently can be hydrogen, a halogen, an alkyl group, or an alkoxy group; alternatively, hydrogen, a halogen, or an alkyl group; alternatively, hydrogen, a halogen, an alkyl group, or an alkoxy group; alternatively, hydrogen, an alkyl group, or an alkoxy group; alternatively, hydrogen or a halogen; alternatively, hydrogen or an alkyl group; or alternatively, hydrogen or an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the $R^4$ group having Structure G7.

In an aspect, $R^5$ can have Structure G8:

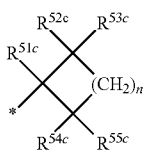

Structure G8 wherein, the undesignated valency is attached to the phosphorus atom of the $N^2$-phosphinylamidine group. Generally, $R^{51c}$, $R^{52c}$, $R^{53c}$, $R^{54c}$, and $R^{55c}$ independently can be hydrogen or a non-hydrogen substituent, and n may be an integer from 1 to 5. In an embodiment wherein $R^5$ has Structure G8, $R^{51c}$, $R^{53c}$, $R^{54c}$, and $R^{55c}$ can be hydrogen and $R^{32c}$ can be any non-hydrogen substituent disclosed herein; or alternatively, $R^{51c}$, $R^{53c}$, and $R^{55c}$ can be hydrogen and $R^{52c}$ and $R^{54c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively, 3.

In an embodiment, $R^{51c}$, $R^{52c}$, $R^{53c}$, $R^{54c}$, and $R^{55c}$ independently can be hydrogen, a halogen, a hydrocarbyl group, or a hydrocarboxy group; alternatively, hydrogen, a halogen, or a hydrocarbyl group; alternatively, hydrogen, a halogen, or a hydrocarboxy group; alternatively, a hydrocarbyl group or a hydrocarboxy group; alternatively, hydrogen or a halogen; alternatively, hydrogen or a hydrocarbyl group; or alternatively, hydrogen or a hydrocarboxy group. In some embodiments, $R^{51c}$, $R^{52c}$, $R^{53c}$, $R^{54c}$, and $R^{55c}$ independently can be hydrogen, a halogen, an alkyl group, or an alkoxy group; alternatively, hydrogen, a halogen, or an alkyl group; alternatively, hydrogen, a halogen, or an alkoxy group; alternatively, hydrogen, an alkyl group, or an alkoxy group; alternatively, hydrogen or a halogen; alternatively, hydrogen or an alkyl group; or alternatively, hydrogen or an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the $R^5$ group having Structure G8.

In an aspect, $R^4$ and/or $R^5$ independently can be a phenyl group, a substituted phenyl group, a naphthyl group, or a substituted naphthyl group. In an embodiment, $R^4$ and $R^5$ independently can be a phenyl group or a substituted phenyl group; alternatively, a naphthyl group or a substituted naphthyl group; alternatively, a phenyl group or a naphthyl group; or alternatively, a substituted phenyl group or a substituted naphthyl group. In some embodiments, $R^4$ and/or $R^5$ independently can be a phenyl group; alternatively, a substituted phenyl group; alternatively, a naphthyl group; or alternatively, a substituted naphthyl group.

In an embodiment, the $R^4$ and/or $R^5$ substituted phenyl group can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other embodiments, the $R^4$ and/or $R^5$ substituted phenyl group can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,6-disubstituted phenyl group or a 2,4,6-trisubstituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group.

In an embodiment, $R^4$ and/or $R^5$ independently can be a naphth-1-yl group, a substituted naphth-1-yl group, a naphth-2-yl group, or a substituted naphth-2-yl group. In some embodiments, $R^4$ and/or $R^5$ independently can be a naphth-1-yl group or a substituted naphth-1-yl group; alternatively, a naphth-2-yl group or a substituted naphth-2-yl group; alternatively, a naphth-1-yl group; alternatively, a substituted naphth-1-yl group; alternatively, a naphth-2-yl group; or alternatively, a substituted naphth-2-yl group. In other embodiments, $R^4$ and/or $R^5$ independently can be a 2-substituted naphth-1-yl group, a 3-substituted naphth-1-yl group, a 4-substituted naphth-1-yl group, or a 8-substituted naphth-1-yl group; alternatively, a 2-substituted naphth-1-yl group; alternatively, a 3-substituted naphth-1-yl group; alternatively, a 4-substituted naphth-1-yl group; or alternatively, a 8-substituted naphth-1-yl group. In further embodiments, $R^4$ and/or $R^5$ independently can be a 1-substituted naphth-2-yl group, a 3-substituted naphth-2-yl group, a 4-substituted naphth-2-yl group, or a 1,3-disubstituted naphth-2-yl group; alternatively, a 1-substituted naphth-2-yl group; alternatively, a 3-substituted naphth-2-yl group; alternatively, a 4-substituted naphth-2-yl group; alternatively, a 1,3-disubstituted naphth-2-yl group.

In an embodiment, each substituent for a substituted phenyl or substituted naphthyl $R^4$ and/or $R^5$ group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, each substituent for a substituted phenyl or substituted naphthyl $R^4$ and/or $R^5$ group independently can be a halogen, an alkyl group, or an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the substituents for the substituted phenyl or substituted naphthyl $R^4$ and/or $R^5$ group.

In an aspect, $R^4$ have Structure G9:

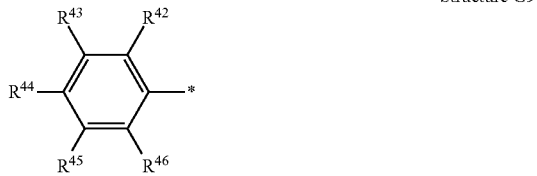

Structure G9 wherein the undesignated valency is attached to the phosphorus atom of the $N^2$-phosphinyl amidine group. Generally, $R^{42}$, $R^{43}$, $R^{44}$, $R^{45}$, $R^{46}$ can independently be hydrogen or a non-hydrogen substituent. In an embodiment wherein $R^4$ has Structure G9, $R^{42}$, $R^{43}$, $R^{44}$, $R^{45}$, and $R^{46}$ can be hydrogen, $R^{43}$, $R^{44}$, $R^{45}$, and $R^{46}$ can be hydrogen and $R^{42}$ can be a non-hydrogen substituent, $R^{42}$, $R^{44}$, $R^{45}$, and $R^{46}$ can be hydrogen and $R^{43}$ can be a non-hydrogen substituent, $R^{42}$, $R^{43}$, $R^{45}$, and $R^{46}$ can be hydrogen and $R^{44}$ can be a non-hydrogen substituent, $R^{43}$, $R^{45}$, and $R^{46}$ can be hydrogen and $R^{42}$ and $R^{44}$ can be non-hydrogen substituents, $R^{43}$, $R^{44}$, and $R^{45}$ can be hydrogen and $R^{42}$ and $R^{46}$ can be non-hydrogen substituents, $R^{42}$, $R^{44}$, and $R^{46}$ can be hydrogen and $R^{43}$ and $R^{45}$ can be non-hydrogen substituents, or $R^{43}$ and $R^{45}$ can be hydrogen and $R^{42}$, $R^{44}$, and $R^{46}$ can be non-hydrogen substituents. In some embodiments wherein $R^4$ has Structure G9, $R^{43}$, $R^{44}$, $R^{45}$, and $R^{46}$ can be hydrogen and $R^{42}$ can be a non-hydrogen substituent, $R^{42}$, $R^{43}$, $R^{45}$, and $R^{46}$ can be hydrogen and $R^{44}$ can be a non-hydrogen substituent, $R^{43}$, $R^{45}$, and $R^{46}$ can be hydrogen and $R^{42}$ and $R^{44}$ can be non-hydrogen substituents, $R^{43}$, $R^{44}$, and $R^{45}$ can be hydrogen and $R^{42}$ and $R^{46}$ can be non-hydrogen substituents, or $R^{43}$ and $R^{45}$ can be hydrogen and $R^{42}$, $R^{44}$, and $R^{46}$ can be non-hydrogen substituents; alternatively, $R^{43}$, $R^{44}$, $R^{45}$, and $R^{46}$ can be hydrogen and $R^{42}$ can be a non-hydrogen substituent, $R^{42}$, $R^{43}$, $R^{45}$, and $R^{46}$ can be hydrogen and $R^{44}$ can be a non-hydrogen substituent, $R^{43}$, $R^{45}$, and $R^{46}$ can be hydrogen and $R^{42}$ and $R^{44}$ can be non-hydrogen substituents, or $R^{43}$, $R^{44}$, and $R^{45}$ can be hydrogen and $R^{42}$ and $R^{46}$ can be non-hydrogen substituents; alternatively, $R^{43}$, $R^{44}$, $R^{45}$, and $R^{46}$ can be hydrogen and $R^{42}$ can be a non-hydrogen substituent, or $R^{42}$, $R^{43}$, $R^{45}$, and $R^{46}$ can be hydrogen and $R^{44}$ can be a non-hydrogen substituent; alternatively, $R^{43}$, $R^{45}$, and $R^{46}$ can be hydrogen and $R^{42}$ and $R^{44}$ can be non-hydrogen substituents, $R^{43}$, $R^{44}$, and $R^{45}$ can be hydrogen and $R^{42}$ and $R^{46}$ can be non-hydrogen substituents, or $R^{43}$ and $R^{45}$ can be hydrogen and $R^{42}$, $R^{44}$, and $R^{46}$ can be non-hydrogen substituents; or alternatively, $R^{43}$, $R^{45}$, and $R^{46}$ can be hydrogen and $R^{42}$ and $R^{44}$ can be non-hydrogen substituents, or $R^{43}$, $R^{44}$, and $R^{45}$ can be hydrogen and $R^{42}$ and $R^{46}$ can be non-hydrogen substituents. In other embodiments wherein $R^4$ has Structure G9, $R^{42}$, $R^{43}$, $R^{44}$, $R^{45}$, and $R^{46}$ can be hydrogen; alternatively, $R^{43}$, $R^{44}$, $R^{45}$, and $R^{46}$ can be hydrogen and $R^{42}$ can be a non-hydrogen substituent; alternatively, $R^{42}$, $R^{44}$, $R^{45}$, and $R^{46}$ can be hydrogen and $R^{43}$ can be a non-hydrogen substituent; alternatively, $R^{42}$, $R^{43}$, $R^{45}$, and $R^{46}$ can be hydrogen and $R^{44}$ can be a non-hydrogen substituent; alternatively, $R^{43}$, $R^{45}$, and $R^{46}$ can be hydrogen and $R^{42}$ and $R^{44}$ can be non-hydrogen substituents; alternatively, $R^{43}$, $R^{44}$, and $R^{45}$ can be hydrogen and $R^{42}$ and $R^{46}$ can be non-hydrogen substituents; alternatively, $R^{42}$, $R^{44}$, and $R^{46}$ can be hydrogen and $R^{43}$ and $R^{45}$ can be non-hydrogen substituents; or alternatively, $R^{43}$ and $R^{45}$ can be hydrogen and $R^{42}$, $R^{44}$, and $R^{46}$ can be non-hydrogen substituents.

In an embodiment, the non-hydrogen substituents that can be utilized as $R^{42}$, $R^{43}$, $R^{44}$, $R^{45}$, and $R^{46}$ in the $R^1$ group having Structure G9 independently can be a halogen, a hydrocarbyl group, or a hydrocarboxy group; alternatively, a halogen, or a hydrocarbyl group; alternatively, halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, the non-hydrogen substituents that can be utilized as $R^{42}$, $R^{43}$, $R^{44}$, $R^{45}$, and $R^{46}$ in the $R^1$ group having Structure G9 independently can be a halogen, an alkyl group, or an alkoxy group; alternatively, a halogen, or an alkyl group; alternatively, a halogen or an alkoxy group; alternatively, an alkyl group or an alkoxy group; alternatively, a halogen; alternatively, an alkyl group; or alternatively, an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the $R^4$ group having Structure G9.

In an aspect, $R^5$ can have Structure G10:

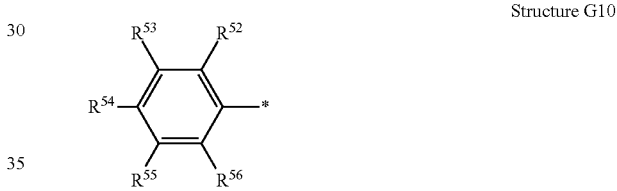

Structure G10 wherein the undesignated valency is attached to the phosphorus atom of the $N^2$-phosphinyl amidine group. Generally, $R^{52}$, $R^{53}$, $R^{54}$, $R^{55}$, and $R^{56}$ independently can be hydrogen or a non-hydrogen substituent. In an embodiment wherein $R^5$ has Structure G10, $R^{52}$, $R^{53}$, $R^{54}$, $R^{55}$, and $R^{56}$ can be hydrogen, $R^{53}$, $R^{54}$, $R^{55}$, and $R^{56}$ can be hydrogen and $R^{52}$ can be a non-hydrogen substituent, $R^{52}$, $R^{54}$, $R^{55}$, and $R^{56}$ can be hydrogen and $R^{53}$ can be a non-hydrogen substituent, $R^{52}$, $R^{53}$, $R^{55}$, and $R^{56}$ can be hydrogen and $R^{54}$ can be a non-hydrogen substituent, $R^{53}$, $R^{55}$, and $R^{56}$ can be hydrogen and $R^{52}$ and $R^{54}$ can be non-hydrogen substituents, $R^{53}$, $R^{54}$, and $R^{55}$ can be hydrogen and $R^{52}$ and $R^{56}$ can be non-hydrogen substituents, $R^{52}$, $R^{54}$, and $R^{56}$ can be hydrogen and $R^{53}$ and $R^{55}$ can be non-hydrogen substituents, or $R^{53}$ and $R^{55}$ can be hydrogen and $R^{52}$, $R^{54}$, and $R^{56}$ can be non-hydrogen substituents. In some embodiments wherein $R^5$ has Structure G10, $R^{53}$, $R^{54}$, $R^{55}$, and $R^{56}$ can be hydrogen and $R^{52}$ can be a non-hydrogen substituent, $R^{52}$, $R^{53}$, $R^{55}$, and $R^{56}$ can be hydrogen and $R^{54}$ can be a non-hydrogen substituent, $R^{53}$, $R^{55}$, and $R^{56}$ can be hydrogen and $R^{52}$ and $R^{54}$ can be non-hydrogen substituents, $R^{53}$, $R^{54}$, and $R^{55}$ can be hydrogen and $R^{52}$ and $R^{56}$ can be non-hydrogen substituents, or $R^{53}$ and $R^{55}$ can be hydrogen and $R^{52}$, $R^{54}$, and $R^{56}$ can be non-hydrogen substituents; alternatively, $R^{53}$, $R^{54}$, $R^{55}$, and $R^{56}$ can be hydrogen and $R^{52}$ can be a non-hydrogen substituent, $R^{52}$, $R^{53}$, $R^{55}$, and $R^{56}$ can be hydrogen and $R^{54}$ can be a non-hydrogen substituent, $R^{53}$, $R^{55}$, and $R^{56}$ can be hydrogen and $R^{52}$ and $R^{54}$ can be non-hydrogen substituents, or $R^{53}$, $R^{54}$, and $R^{55}$ can be hydrogen and $R^{52}$ and $R^{56}$ can be non-hydrogen substituents; alternatively, $R^{52}$, $R^{54}$, $R^{55}$, and $R^{56}$ can be hydrogen and $R^{53}$ can be a non-hydrogen substituent, or $R^{52}$, $R^{54}$, and $R^{56}$ can be hydrogen and $R^{53}$ and $R^{55}$ can be non-hydrogen substituents; alternatively, $R^{53}$, $R^{54}$, $R^{55}$, and $R^{56}$ can be hydrogen and $R^{52}$ can be a non-hydrogen substituent, or $R^{52}$, $R^{53}$, $R^{55}$, and $R^{56}$ can be hydrogen and $R^{54}$ can be a non-hydrogen substituent; alternatively, $R^{53}$, $R^{55}$, and $R^{56}$ can be hydrogen and $R^{52}$ and $R^{54}$ can be non-hydrogen substituents, $R^{53}$, $R^{54}$, and $R^{55}$ can be hydrogen and $R^{52}$ and $R^{56}$ can be non-hydrogen substituents, or $R^{53}$ and $R^{55}$ can be hydrogen and $R^{52}$, $R^{54}$, and $R^{56}$ can be non-hydrogen substituents; or alternatively, $R^{53}$, $R^{55}$, and $R^{56}$ can be hydrogen and $R^{52}$ and $R^{54}$ can be non-hydrogen substituents, or $R^{53}$, $R^{54}$, and $R^{55}$ can be hydrogen and $R^{52}$ and $R^{56}$ can be non-hydrogen substituents. In other embodiments wherein $R^5$ has Structure G10, $R^{52}$, $R^{53}$, $R^{54}$, $R^{55}$, and $R^{56}$ can be hydrogen; alternatively, $R^{53}$, $R^{54}$, $R^{55}$, and $R^{56}$ can be hydrogen and $R^{52}$ can be a non-hydrogen substituent; alternatively, $R^{52}$, $R^{54}$, $R^{55}$, and $R^{56}$ can be hydrogen and $R^{53}$ can be a non-hydrogen substituent; alternatively, $R^{52}$, $R^{53}$, $R^{55}$, and $R^{56}$ can be hydrogen and $R^{54}$ can be a non-hydrogen substituent; alternatively, $R^{53}$, $R^{55}$, and $R^{56}$ can be hydrogen and $R^{52}$ and $R^{54}$ can be non-hydrogen substituents; alternatively, $R^{53}$, $R^{54}$, and $R^{55}$ can be hydrogen and $R^{52}$ and $R^{56}$ can be non-hydrogen substituents; alternatively, $R^{52}$, $R^{54}$, and $R^{56}$ can be hydrogen and $R^{53}$ and $R^{55}$ and can be non-hydrogen substituents; or alternatively, $R^{53}$ and $R^{55}$ can be hydrogen and $R^{52}$, $R^{54}$, and $R^{56}$ can be non-hydrogen substituents.

In an embodiment, the non-hydrogen substituents that can be utilized as $R^{52}$, $R^{53}$, $R^{54}$, $R^{55}$, and $R^{56}$ in the $R^5$ group having Structure G2 independently can be a halogen, a hydrocarbyl group, or a hydrocarboxy group; alternatively, a halogen or a hydrocarbyl group; alternatively, a halogen, or a hydrocarboxy group; alternatively, a hydrocarbyl group or a hydrocarboxy group; alternatively, a halogen; alternatively, a hydrocarbyl group; or alternatively, a hydrocarboxy group. In some embodiments, the non-hydrogen substituents that can be utilized as $R^{52}$, $R^{53}$, $R^{54}$, $R^{55}$, and $R^{56}$ in the $R^5$ group having Structure G2 independently can be a halogen, an alkyl group, or an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the $R^5$ group having Structure G10.

In an aspect, $R^4$ and $R^5$ independently can be a pyridinyl group, a substituted pyridinyl group, a furyl group, a substituted furyl group, a thienyl group, or a substituted thienyl group. In an embodiment, $R^4$ and $R^5$ independently can be a pyridinyl group or a substituted pyridinyl group; alternatively, a furyl group or a substituted furyl group; or alternatively, a thienyl group or a substituted thienyl group. In some embodiments, $R^4$ and $R^5$ independently can be a pyridinyl group, a furyl group, or a thienyl group. In other embodiments, $R^4$ and $R^5$ can be a pyridinyl group; alternatively, a substituted pyridinyl group; alternatively, a furyl group; alternatively, a substituted furyl group; alternatively, a thienyl group; or alternatively, a substituted thienyl group.

In an embodiment, the pyridinyl (or substituted pyridinyl) $R^4$ and/or $R^5$ group independently can be a pyridin-2-yl group, a substituted pyridin-2-yl group, a pyridin-3-yl group, a substituted pyridin-3-yl group, a pyridin-4-yl group, or a substituted pyridin-4-yl group; alternatively, a pyridin-2-yl group, a pyridin-3-yl group, or a pyridin-4-yl group. In some embodiments, the pyridinyl (or substituted pyridinyl) $R^4$ and/or $R^5$ group independently can be a pyridin-2-yl group or a substituted pyridin-2-yl group; alternatively, a pyridin-3-yl group or a substituted pyridin-3-yl group; alternatively, a pyridin-4-yl group or a substituted pyridin-4-yl group; alternatively, a pyridin-2-yl group; alternatively, a substituted pyridin-2-yl group; alternatively, a pyridin-3-yl group; alternatively, a substituted pyridin-3-yl group; alternatively, a pyridin-4-yl group; or alternatively, a substituted pyridin-4-yl group. In an embodiment, the substituted pyridinyl $R^4$ and/or $R^5$ group independently can be a 2-substituted pyridin-3-yl group, a 4-substituted pyridin-3-yl group, a 5-substituted pyridin-3-yl group, a 6-substituted pyridin-3-yl group, a 2,4-disubstituted pyridin-3-yl group, a 2,6-disubstituted pyridin-3-yl group, or a 2,4,6-trisubstituted pyridin-3-yl group; alternatively, 2-substituted pyridin-3-yl group, a 4-substituted pyridin-3-yl group, or a 6-substituted pyridin-3-yl group; alternatively, a 2,4-disubstituted pyridin-3-yl group or a 2,6-disubstituted pyridin-3-yl group; alternatively, a 2-substituted pyridin-3-yl group; alternatively, a 4-substituted pyridin-3-yl group; alternatively, a 5-substituted pyridin-3-yl group; alternatively, a 6-substituted pyridin-3-yl group; alternatively, a 2,4-disubstituted pyridin-3-yl group; alternatively, a 2,6-disubstituted pyridin-3-yl group; or alternatively, a 2,4,6-trisubstituted pyridin-3-yl group. In an embodiment, the substituted pyridinyl $R^4$ and/or $R^5$ group independently can be a 2-substituted pyridin-4-yl group, a 3-substituted pyridin-4-yl group, a 5-substituted pyridin-4-yl group, a 6-substituted pyridin-4-yl group, a 2,6-disubstituted pyridin-4-yl group, or a 3,5-disubstituted pyridin-4-yl group; alternatively, 2-substituted pyridin-4-yl group or a 6-substituted pyridin-4-yl group; alternatively, a 3-substituted pyridin-4-yl group or a 5-substituted pyridin-4-yl group; alternatively, a 2-substituted pyridin-4-yl group; alternatively, a 3-substituted pyridin-4-yl group; alternatively, a 5-substituted pyridin-4-yl group; alternatively, a 6-substituted pyridin-4-yl group; alternatively, a 2,6-disubstituted pyridin-4-yl group; or alternatively, a 3,5-disubstituted pyridin-4-yl group.

In an embodiment, each furyl (or substituted furyl) $R^4$ and/or $R^5$ group can be independently selected from a fur-2-yl group, a substituted fur-2-yl group, a fur-3-yl group, or a substituted fur-3-yl group; alternatively, a fur-2-yl or a fur-3-yl group. In some embodiments, the furyl (or substituted furyl) $R^4$ and/or $R^5$ group can be independently selected from a fur-2-yl group or a substituted fur-2-yl group; alternatively, a fur-3-yl group or a substituted fur-3-yl group; alternatively, a fur-2-yl group; alternatively, a substituted fur-2-yl group; alternatively, a fur-3-yl group; or alternatively, a substituted fur-3-yl group. In an embodiment, the substituted furyl $R^4$ and/or $R^5$ group can be a 2-substituted fur-3-yl group, a 4-substituted fur-3-yl group, or a 2,4-disubstituted fur-3-yl group; alternatively, a 2-substituted fur-3-yl group; alternatively, a 4-substituted fur-3-yl group; or alternatively, a 2,4-disubstituted fur-3-yl group.

In an embodiment, the thienyl (or substituted thienyl) $R^4$ and/or $R^5$ group can be independently selected from a thien-2-yl group, a substituted thien-2-yl group, a thien-3-yl group, or a substituted thien-3-yl group; alternatively, a thien-2-yl group or a thien-3-yl group. In some embodiments, the thienyl (or substituted thienyl) $R^4$ and/or $R^5$ group can be independently selected from a thien-2-yl group or a substituted thien-2-yl group; alternatively, a thien-3-yl group or a substituted thien-3-yl group; alternatively, a thien-2-yl group; alternatively, a substituted thien-2-yl group; alternatively, a thien-3-yl group; or alternatively, a substituted thien-3-yl group. In an embodiment, the substituted thienyl $R^4$ and/or $R^5$ group can be a 2-substituted thien-3-yl group, a 4-substituted thien- 3-yl group, or a 2,4-disubstituted thien-3-yl group; alternatively, a 2-substituted thien-3-yl group; alternatively, a 4-substituted thien-3-yl group; or alternatively, a 2,4-disubstituted thien-3-yl group.

In an embodiment, substituent for a substituted pyridinyl, furyl, and/or thienyl group (general or specific) that can be utilized as $R^4$ and/or $R^5$ independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, each substituent for a substituted pyridinyl, furyl, and/or thienyl groups (general or specific) that can be utilized as $R^4$ and/or $R^5$ independently can be a halogen, an alkyl group, or an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the substituents for the substituted pyridinyl, furyl, and/or thienyl groups (general or specific) can be utilized as $R^4$ and/or $R^5$.

General and specific non-hydrogen substituents of a substituted cycloalkyl group (general or specific), a substituted aliphatic heterocyclic group (general or specific), a substituted cycloheteryl group (general or specific), a substituted aromatic group (general or specific), a substituted aryl group (general or specific), a substituted heteroaryl group (general or specific), or a substituted arylheteryl group (general or specific) are disclosed herein. These general and specific non-hydrogen substituents can be utilized, without limitation, to further describe the substituted cycloalkyl groups (general or specific), substituted aliphatic heterocyclic groups (general or specific), substituted cycloheteryl groups (general or specific), substituted aromatic groups (general or specific), substituted aryl groups (general or specific), substituted heteroaryl groups (general or specific), substituted arylheteryl group (general or specific), or any other general or specific group which can be utilized as $R^4$ and/or $R^5$.

In an aspect, when $R^4$ and $R^5$ are joined to form a cyclic group including the phosphorus atom of the $N^2$-phosphinyl amidine group, the phosphinyl group can be a phosphol-1-yl group, a substituted phosphol-1-yl group, a 2,3-dihydrophosphol-1-yl group, a substituted 2,3-dihydrophosphol-1-yl group, a 3,5-dihydrophosphol-1-yl group, a substituted 3,5-dihydrophosphol-1-yl group, a phospholan-1-yl group, a substituted phospholan-1-yl group, a 1,2-dihydrophosphinin-1-yl group, a substituted, 1,2-dihydro-phosphinin-1-yl group, a 1,4-dihydrophosphinin-1-yl group, a substituted 1,4-dihydrophosphinin-1-yl group, a 1,2,3,4-tetrahydrophosphinin-1-yl group, a substituted 1,2,3,4-tetrahydrophosphinin-1-yl group, a 1,2,3,6-tetrahydrophosphinin-1-yl group, a substituted 1,2,3,6-tetrahydrophosphinin-1-yl group, a phosphinan-1-yl group, or a substituted phosphinan-1-yl group. In some embodiments, when $R^4$ and $R^5$ are joined to form a cyclic group including the phosphorus atom of the $N^2$-phosphinylamidine group, the phosphinyl group can be a phosphol-1-yl group or a substituted phosphol-1-yl group; alternatively, a 2,3-dihydrophosphol-1-yl group or a substituted 2,3-dihydrophosphol-1-yl group; alternatively, a 3,5-dihydrophosphol-1-yl group or a substituted 3,5-dihydrophosphol-1-yl group; alternatively, a phospholan-1-yl group or a substituted phospholan-1-yl group; alternatively, a 1,2-dihydro-phosphinin-1-yl group or a substituted, 1,2-dihydrophosphinin-1-yl group; alternatively, a 1,4-dihydro-phosphinin-1-yl group or a substituted 1,4-dihydrophosphinin-1-yl group; alternatively, a 1,2,3,4-tetra-hydrophosphinin-1-yl group or a substituted 1,2,3,4-tetrahydrophosphinin-1-yl group; alternatively, a 1,2,3,6-tetrahydrophosphinin-1-yl group or a substituted 1,2,3,6-tetrahydrophosphinin-1-yl group; or alternatively, a phosphinan-1-yl group or a substituted phosphinan-1-yl group. In some embodiments, when $R^4$ and $R^5$ are joined to form a cyclic group including the phosphorus atom of the $N^2$-phosphinyl amidine group, the phosphinyl group can be a phosphol-1-yl group, a 2,3-dihydrophosphol-1-yl group, a 3,5-dihydrophosphol-1-yl group, a phospholan-1-yl group, a 1,2-dihydrophosphinin-1-yl group, a 1,4-dihydrophosphinin-1-yl group, a 1,2,3,4-tetrahydrophosphinin-1-yl group, a 1,2,3,6-tetrahydrophosphinin-1-yl group, or a phosphinan-1-yl group. In other embodiments, when $R^4$ and $R^5$ are joined to form a cyclic group including the phosphorus atom of the $N^2$-phosphinylamidine group, the phosphinyl group can be a substituted phosphol-1-yl group, a substituted 2,3-dihydrophosphol-1-yl group, a substituted 3,5-dihydrophosphol-1-yl group, a substituted phospholan-1-yl group, a substituted, 1,2-dihydrophosphinin-1-yl group, a substituted 1,4-dihydro-phosphinin-1-yl group, a substituted 1,2,3,4-tetrahydrophosphinin-1-yl group, a substituted 1,2,3,6-tetra-hydrophosphinin-1-yl group, or a substituted phosphinan-1-yl group. In yet other embodiments, a phospholan-1-yl group, a substituted phospholan-1-yl group, a phosphinan-1-yl group, or a substituted phosphinan-1-yl group; alternatively, a phospholan-1-yl group or a phosphinan-1-yl group; or alternatively, a substituted phospholan-1-yl group or a substituted phosphinan-1-yl group. In further embodiments, when $R^4$ and $R^5$ are joined to form a cyclic group including the phosphorus atom of the $N^2$-phosphinyl amidine group, the phosphinyl group can be a phosphol-1-yl group; alternatively, a substituted phosphol-1-yl group; alternatively, a 2,3-dihydrophosphol-1-yl group; alternatively, a substituted 2,3-dihydrophosphol-1-yl group; alternatively, a 3,5-dihydrophosphol-1-yl group; alternatively, a substituted 3,5-dihydrophosphol-1-yl group; alternatively, a phospholan-1-yl group; alternatively, a substituted phospholan-1-yl group; alternatively, a 1,2-dihydrophosphinin-1-yl group; alternatively, a substituted, 1,2-dihydrophosphinin-1-yl group; alternatively, a 1,4-dihydrophosphinin-1-yl group; alternatively, a substituted 1,4-dihydrophosphinin-1-yl group; alternatively, a 1,2,3,4-tetrahydro-phosphinin-1-yl group; alternatively, a substituted 1,2,3,4-tetrahydrophosphinin-1-yl group; alternatively, a 1,2,3,6-tetrahydrophosphinin-1-yl group; alternatively, a substituted 1,2,3,6-tetrahydrophosphinin-1-yl group; alternatively, a phosphinan-1-yl group; or alternatively, a substituted phosphinan-1-yl group.

In an embodiment, when $R^4$ and $R^5$ are joined to form a cyclic group including the phosphorus atom of the $N^2$-phosphinyl amidine group, the cyclic group including the phosphorus atom can comprise at least one substituent on a carbon atom adjacent to the phosphorus atom attached to the $N^2$ nitrogen atom of the $N^2$-phosphinyl amidine group. In some embodiments, when $R^4$ and $R^5$ are joined to form a cyclic group including the phosphorus atom of the $N^2$-phosphinylamidine group, the cyclic group including the phosphorus atom can comprise at least one substituent on each carbon atom adjacent to the phosphorus atom attached to the $N^2$ nitrogen atom of the $N^2$-phosphinyl amidine group. In other embodiments, when $R^4$ and $R^5$ are joined to form a cyclic group including the phosphorus atom of the $N^2$-phosphinyl amidine group, the cyclic group including the phosphorus atom can comprise, or consist of, only one substituent on a carbon atom adjacent to the phosphorus atom attached to the $N^2$ nitrogen atom of the $N^2$-phosphinyl amidine group. In yet other embodiments, when $R^4$ and $R^5$ are joined to form a cyclic group including the phosphorus atom of the $N^2$-phosphinyl amidine group, the cyclic group including the phosphorus atom can comprise, or consist of, only one substituent on each carbon atom adjacent to the phosphorus atom attached to the $N^2$ nitrogen atom of the $N^2$-phosphinyl amidine group.

In an embodiment, each substituent for a cyclic group including the phosphorus atom of the $N^2$-phosphinyl amidine group independently can be a halogen, a hydrocarbyl group, a hydrocarboxy group; alternatively, a halogen, a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In some embodiments, each substituent for a substituted cycloalkyl group which can be utilized for the cyclic group including the phosphorus atom of the $N^2$-phosphinyl amidine group independently can be a halogen, an alkyl group, and an alkoxy group; alternatively, a halogen and an alkyl group; alternatively, a halogen or an alkoxy group; alternatively, an alkyl group or an alkoxy group; alternatively, a halogen; alternatively, an alkyl group; or alternatively, an alkoxy group. Halogens, hydrocarbyl groups, hydrocarboxy groups, alkyl groups, and alkoxy groups that can be utilized as substituents are independently disclosed herein (e.g. as substituents for substituted $R^1$ groups) and can be utilized without limitation to further describe the substituents for the cyclic group including the phosphorus atom of the $N^2$-phosphinyl amidine group.

In an embodiment, $R^4$ and/or $R^5$ independently can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group, or a 2,4,6-trialkylphenyl group; alternatively, a 2,4-dialkylphenyl group or a 2,6-dialkylphenyl group; alternatively, a 2,6-dialkylphenyl group, or a 2,4,6-trialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 3-alkylphenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. In another non-limiting embodiment, $R^4$ and/or $R^5$ independently can be a napht-1-yl group, a 2-naphth-2-yl group, a 2-alkylnaphth-1-yl group, a 1-alkylnaphth-2-yl group, a 3-alkylnapth-2-yl group, or a 1,3-dialkylnaphth-2-yl group; alternatively, a napht-1-yl group or a 2-alkylnaphth-1-yl group; alternatively, a naphth-2-yl group, a 1-alkylnaphth-2-yl group, a 3-alkylnapth-2-yl group, or a 1,3-dialkyl-naphth-2-yl group; alternatively, a napht-1-yl group; alternatively, a 2-naphth-2-yl group; alternatively, a 2-alkylnaphth-1-yl group; alternatively, a 1-alkylnaphth-2-yl group; alternatively, a 3-alkylnapth-2-yl group; or alternatively, a 1,3-dialkylnapth-2-yl group. In other non-limiting embodiments, $R^4$ and/or $R^5$ independently can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, cyclopentyl group; alternatively, a 2-alkylcyclopentyl group; or alternatively, a 2,5-dialkylcyclopentyl group. Alkyl group substituents are independently described herein and can be utilized, without limitation, to further describe the alkylphenyl, dialkylphenyl, trialkylphenyl, naphthyl, dialkylnaphthyl, alkylcyclohexyl, dialkylcyclohexyl, alkylcyclopentyl, or dialkylcyclopentyl groups that can be utilized $R^4$ and/or $R^5$. Generally, the alkyl substituents of a dialkyl or trialkyl phenyl, naphthyl, cyclohexyl, or cyclopentyl group can be the same; or alternatively, the alkyl substituents of a dialkyl or trialkyl phenyl, naphthyl, cyclohexyl, or cyclopentyl group can be different.

In another non-limiting embodiment, $R^4$ and/or $R^5$ independently can be a phenyl group, a 2-alkoxyphenyl group, a 3-alkoxyphenyl group, a 4-alkoxyphenyl group, or 3,5-dialkoxyphenyl group; alternatively, a 2-alkoxyphenyl group or a 4-alkoxyphenyl group; alternatively, a 3-alkoxyphenyl group or 3,5-dialkoxyphenyl group; alternatively, a 2-alkoxyphenyl group; alternatively, a 3-alkoxyphenyl group; alternatively, a 4-alkoxyphenyl group; alternatively, a 3,5-dialkoxyphenyl group. Alkoxy group substituents are independently described herein and may be utilized, without limitation, to further describe the alkoxyphenyl or dialkoxyphenyl groups that can be utilized $R^4$ and/or $R^5$. Generally, the alkoxy substituents of a dialkoxyphenyl groups can be the same; or alternatively, the alkoxy substituents of a dialkoxyphenyl group can be different.

In other non-limiting embodiments, $R^4$ and/or $R^5$ independently can be a phenyl group, a 2-halophenyl group, a 3-halophenyl group, a 4-halophenyl group, a 2,6-dihalophenyl group, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenyl group; or alternatively, a 3,5-dihalophenyl group. Halides are independently described herein and may be utilized, without limitation, to further describe the halophenyl or dihalophenyl groups that can be utilized $R^4$ and/or $R^5$. Generally, the halides of a dihalophenyl group can be the same; or alternatively, the halides of a dihalophenyl group can be different.

In a non-limiting embodiment, $R^4$ and/or $R^5$ independently can be a 2-methylphenyl group, a 2-ethylphenyl group, a 2-isopropylphenyl group, a 2-tert-butylphenyl group, a 3-methylphenyl group, a 2,6-dimethylphenyl group, a 2,6-diethylphenyl group, a 2,6-diisopropylphenyl group, a 2,6-di-tert-butylphenyl group, a 3,5-dimethyl group, or a 2,4,6-trimethylphenyl group; alternatively, a 2-methylphenyl group, a 2-ethylphenyl group, a 2-isopropylphenyl group, or a 2-tert-butylphenyl group; alternatively, a 2,6-dimethylphenyl group, a 2,6-diethylphenyl group, a 2,6-diisopropylphenyl group, or a 2,6-di-tert-butylphenyl group; alternatively, 2-methylphenyl group; alternatively, a 2-ethylphenyl group; alternatively, a 2-isopropylphenyl group; alternatively, a 2-tert-butylphenyl group; alternatively, a 3-methylphenyl group; alternatively, a 2,6-dimethylphenyl group; alternatively, a 2,6-diethylphenyl group; alternatively, a 2,6-diisopropylphenyl group; alternatively, a 2,6-di-tert-butylphenyl group; alternatively, a 3,5-dimethyl group; or alternatively, a 2,4,6-trimethylphenyl group. In another non-limiting embodiment, $R^4$ and/or $R^5$ independently can be cyclohexyl group, a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group, a 2-ethylcyclohexyl group, a 2-isopropylcyclohexyl group, or a 2-tert-butylcyclohexyl group; alternatively, a 2,6-dimethylcyclohexyl group, a 2,6-diethylcyclohexyl group, a 2,6-diisopropylcyclohexyl group, or a 2,6-di-tert-butylcyclohexyl group; alternatively, a cyclohexyl group; alternatively, a 2-methylcyclohexyl group; alternatively, a 2-ethylcyclohexyl group; alternatively, a 2-isopropylcyclohexyl group; alternatively, a 2-tert-butyl-cyclohexyl group; alternatively, a 2,6-dimethylcyclohexyl group; alternatively, a 2,6-diethylcyclohexyl group; alternatively, a 2,6-diisopropylcyclohexyl group; or alternatively, a 2,6-di-tert-butylcyclohexyl group. In another non-limiting embodiment, $R^4$ and/or $R^5$ independently can be a 2-methylnaphth-1-yl group, a 2-ethylnaphth-1-yl group, a 2-n-propylnaphth-1-yl group, a 2-isopropylnaphth-1-yl group, or a 2-tert-butylnaphth-1-yl group; alternatively, a 2-methylnaphth-1-yl group; alternatively, a 2-ethyl-naphth-1-yl group; alternatively, a 2-n-propylnaphth-1-yl group; alternatively, a 2-isopropylnaphth-1-yl group; or alternatively, a 2-tert-butylnaphth-1-yl group.

In a non-limiting embodiment, $R^4$ and/or $R^5$ independently can be a 2-methoxyphenyl group, a 2-ethoxyphenyl group, a 2-isopropoxyphenyl group, a 2-tert-butoxyphenyl group, a 3-methoxyphenyl group, a 3-ethoxyphenyl group, a 3-isopropoxyphenyl group, a 3-tert-butoxyphenyl group, a 4-methoxyphenyl group, a 4-ethoxyphenyl group, a 4-isopropoxyphenyl group, a 4-tert-butoxyphenyl group, a 2,4-dimethoxyphenyl group, a 2,4-diethoxyphenyl group, a 2,4-diisopropoxyphenyl group, a 2,4-di-tert-butoxyphenyl group, a 3,5-dimethoxyphenyl group, a 3,5-diethoxyphenyl group, a 3,5-diisopropoxyphenyl group, a 3,5-di-tert-butoxyphenyl group, a 2,6-dimethoxyphenyl group, a 2,6-diethoxyphenyl group, a 2,6-diisopropoxyphenyl group, a 2,6-di-tert-butoxyphenyl group, or a 2,4,6-trimethoxyphenyl group; alternatively, a 2-methoxyphenyl group, a 2-ethoxyphenyl group, a 2-isopropoxyphenyl group, or a 2-tert-butoxyphenyl group; alternatively, a 3-methoxyphenyl group, a 3-ethoxyphenyl group, a 3-isopropoxyphenyl group, or a 3-tert-butoxyphenyl group; alternatively, a 4-methoxyphenyl group, a 4-ethoxyphenyl group, a 4-isopropoxyphenyl group, or a 4-tert-butoxyphenyl group; alternatively, a 2,4-dimethoxyphenyl group, a 2,4-diethoxyphenyl group, a 2,4-diisopropoxyphenyl group, or a 2,4-di-tert-butoxyphenyl group; alternatively, a 3,5-dimethoxyphenyl group, a 3,5-diethoxyphenyl group, a 3,5-diisopropoxyphenyl group, or a 3,5-di-tert-butoxyphenyl group; or alternatively, a 2,6-dimethoxyphenyl group, a 2,6-diethoxyphenyl group, a 2,6-diisopropoxyphenyl group, or a 2,6-di-tert-butoxyphenyl group. In other non-limiting embodiments, $R^4$ and/or $R^5$ independently can be a 2-methoxyphenyl group; alternatively, a 2-ethoxyphenyl group; alternatively, a 2-isopropoxyphenyl group; alternatively, a 2-tert-butoxyphenyl group; alternatively, a 3-methoxyphenyl group; alternatively, a 3-ethoxyphenyl group; alternatively, a 3-isopropoxyphenyl group; alternatively, a 3-tert-butoxyphenyl group; alternatively, a 4-methoxyphenyl group; alternatively, a 4-ethoxyphenyl group; alternatively, a 4-isopropoxyphenyl group; alternatively, a 4-tert-butoxyphenyl group; alternatively, a 2,4-dimethoxyphenyl group; alternatively, a 2,4-diethoxyphenyl group; alternatively, a 2,4-diisopropoxyphenyl group; alternatively, a 2,4-di-tert-butoxyphenyl group; alternatively, a 3,5-dimethoxyphenyl group; alternatively, a 3,5-diethoxyphenyl group; alternatively, a 3,5-diisopropoxyphenyl group; alternatively, a 3,5-di-tert-butoxyphenyl group; alternatively, a 2,6-dimethoxyphenyl group; alternatively, a 2,6-diethoxyphenyl group; alternatively, a 2,6-diisopropoxyphenyl group; alternatively, a 2,6-di-tert-butoxyphenyl group; or alternatively, a 2,4,6-trimethoxyphenyl group.

In another non-limiting embodiment, $R^4$ and/or $R^5$ independently can be a 2-fluorophenyl group, a 2-chlorophenyl group, a 3-fluorophenyl group, a 3-chlorophenyl group, a 4-fluorophenyl group, a 4-chlorophenyl group, a 3,5-difluorophenyl group, or a 3,5-dichlorophenyl group; alternatively, a 2-fluorophenyl group or a 2-chlorophenyl group; alternatively, a 3-fluorophenyl group or a 3-chlorophenyl group; alternatively, a 4-fluorophenyl group or a 4-chlorophenyl group; alternatively, a 3,5-difluorophenyl group or a 3,5-dichlorophenyl group; alternatively, a 3-fluorophenyl group, a 3-chlorophenyl group, a 3,5-difluorophenyl group or a 3,5-dichlorophenyl group; or alternatively, a 3-fluorophenyl group or a 3,5-difluorophenyl group. In another non-limiting embodiments, $R^4$ and/or $R^5$ independently can be a 2-fluorophenyl group; alternatively, a 2-chlorophenyl group; alternatively, a 3-fluorophenyl group; alternatively, a 3-chlorophenyl group; alternatively, a 4-fluorophenyl group; alternatively, a 4-chlorophenyl; alternatively, a 3,5-difluorophenyl group; or alternatively, a 3,5-dichlorophenyl group.

Generally, the $R^4$ and/or $R^5$ groups of the phosphinyl group independently can be any $R^4$ or $R^5$ group described herein and utilized in any combination to further describe the phosphinyl group of any $N^2$-phosphinyl amidine compound described herein. In an embodiment, $R^4$ and $R^5$ can be the same. In other embodiments $R^4$ and $R^5$ can be different.

In an aspect, the phosphinyl group of the $N^2$-phosphinyl amidine compound can be a diphenylphosphinyl group, a dialkylphosphinyl group, a bis(mono-halo substituted phenyl)phosphinyl group, a bis(mono-alkyl substituted phenyl) phosphinyl group, or a bis(mono-alkoxy substituted phenyl)-phosphinyl group; alternatively, a diphenylphosphinyl group; alternatively, a dialkylphosphinyl group; alternatively, a bis(mono-halo substituted phenyl)phosphinyl group; alternatively, a bis(mono-alkyl substituted phenyl)phosphinyl group; alternatively, a bis(mono-alkoxy substituted phenyl) phosphinyl group. In another aspect, the phosphinyl group of the $N^2$-phosphinyl amidine compound can be an (alkyl)(phenyl)phosphinyl group, a (mono-halo substituted phenyl)(phenyl)phosphinyl group, a (mono-alkyl substituted phenyl)(phenyl)phosphinyl group, a (mono-alkoxy substituted phenyl)(phenyl)-phosphinyl group, a (mono-alkyl substituted phenyl)(mono-halo substituted phenyl) phosphinyl group, or a (mono-alkyl substituted phenyl)(mono-alkoxy substituted phenyl) phosphinyl group; alternatively, an (alkyl)(phenyl)phosphinyl group; alternatively, a (mono-halo substituted phenyl)(phenyl)phosphinyl group; alternatively, a (mono-alkyl substituted phenyl)(phenyl)phosphinyl group; alternatively, a (mono-alkoxy substituted phenyl)(phenyl) phosphinyl group; alternatively, a (mono-alkyl substituted phenyl)-(mono-halo substituted phenyl) phosphinyl group; or alternatively, a (mono-alkyl substituted phenyl)-(mono-alkoxy substituted phenyl) phosphinyl group. In another aspect, the phosphinyl group of the $N^2$-phosphinyl amidine compound can be a bis(dihalo substituted phenyl)phosphinyl group, a bis(dialkyl substituted phenyl)phosphinyl group, a bis(dialkoxy substituted phenyl)phosphinyl group, a bis(trialkyl-phenyl)phosphinyl group, or a bis(trialkoxyphenyl) phosphinyl group; alternatively, bis(dihalo substituted phenyl)phosphinyl group; alternatively, a bis(dialkyl substituted phenyl)phosphinyl group; alternatively, a bis(dialkoxy substituted phenyl)phosphinyl group; alternatively, a bis(trialkylphenyl)phosphinyl group; or alternatively, a bis(trialkoxyphenyl)phosphinyl group. Halogens, alkyl groups, and alkoxy groups are independently described herein (e.g. as substituents for substituted R¹ groups) and can be utilized, without limitation to further describe the phosphinyl group which can be utilized in the N²-phosphinyl amidine compound.

In a non-limiting aspect, the phosphinyl group of the N²-phosphinyl amidine compound can be a dimethylphosphinyl group, a diethylphosphinyl group, a diisopropylphosphinyl group, a di-tert-butylphosphinyl group, or a di-neopentylphosphinyl group. In a non-limiting embodiment, the phosphinyl group of the N²-phosphinyl amidine compound can be a dimethylphosphinyl group; alternatively, a diethyl phosphinyl group; alternatively, a diisopropylphosphinyl group; alternatively, a di-tert-butyl-phosphinyl group; or alternatively, a di-neo-pentylphosphinyl group.

In a non-limiting aspect, the phosphinyl group of the N²-phosphinyl amidine compound can be a (methyl)(phenyl)phosphinyl group, a (ethyl)(phenyl)phosphinyl group, a (isopropyl)(phenyl)phosphinyl group, a (tert-butyl)(phenyl)phosphinyl group, or a (neo-pentyl)(phenyl)phosphinyl group. In an embodiment, the phosphinyl group of the N²-phosphinyl amidine compound can be a (methyl)(phenyl)-phosphinyl group; alternatively, a (ethyl)(phenyl) phosphinyl group; alternatively, a (isopropyl)(phenyl)phosphinyl group; alternatively, a (tert-butyl)(phenyl)phosphinyl group; or alternatively, a (neo-pentyl)(phenyl)phosphinyl group.

In some non-limiting embodiments, the phosphinyl group of the N²-phosphinyl amidine compound can be a dicyclopentyl phosphinyl group, a dicyclohexyl phosphinyl group; alternatively, a dicyclopentylphosphinyl group; or alternatively, a dicyclohexylphosphinyl group.

In yet another non non-limiting aspect, the phosphinyl group of the N²-phosphinyl amidine compound can be a bis(2-fluorophenyl)phosphinyl group, a bis(2-chlorophenyl)phosphinyl group, a bis(3-fluorophenyl)phosphinyl group, a bis(3-chlorophenyl)phosphinyl group, a bis(4-fluorophenyl)-phosphinyl group, or a bis(4-chlorophenyl)phosphinyl group. In some non-limiting embodiments, the phosphinyl group of the N²-phosphinyl amidine compound can be a bis(2-fluorophenyl)phosphinyl group, a bis(3-fluorophenyl)phosphinyl group, or a bis(4-fluorophenyl)phosphinyl group; or alternatively, a bis(2-chlorophenyl)phosphinyl group, a bis(3-chlorophenyl)phosphinyl group, or a bis(4-chlorophenyl)-phosphinyl group. In other non-limiting embodiments, the phosphinyl group of the N²-phosphinyl amidine compound can be a bis(2-fluorophenyl)phosphinyl group; alternatively, a bis(2-chlorophenyl)-phosphinyl group; alternatively, a bis(3-fluorophenyl)phosphinyl group; alternatively, a bis(3-chloro-phenyl)phosphinyl group; alternatively, a bis(4-fluorophenyl)phosphinyl group; or alternatively, a bis(4-chlorophenyl)phosphinyl group.

In yet another non-limiting aspect, the phosphinyl group of the N²-phosphinyl amidine compound can be a (2-fluorophenyl)(phenyl)phosphinyl group, a (2-chlorophenyl)(phenyl)phosphinyl group, a (3-fluorophenyl)(phenyl)phosphinyl group, a (3-chlorophenyl)(phenyl)phosphinyl group, a (4-fluorophenyl)(phenyl)phosphinyl group, or a (4-chlorophenyl)(phenyl)phosphinyl group. In some non-limiting embodiments, the phosphinyl group of the N²-phosphinyl amidine compound can be a (2-fluorophenyl)(phenyl)phosphinyl group, a (3-fluorophenyl)(phenyl)phosphinyl group, or a (4-fluoro-phenyl)(phenyl)phosphinyl group; or alternatively, a (2-chlorophenyl)(phenyl)phosphinyl group, a (3-chlorophenyl)(phenyl)phosphinyl group, or a (4-chlorophenyl)(phenyl)phosphinyl group. In other non-limiting embodiments, the phosphinyl group of the N²-phosphinyl amidine compound can be a (2-fluorophenyl)(phenyl)phosphinyl group; alternatively, a (2-chlorophenyl)(phenyl)phosphinyl group; alternatively, a (3-fluorophenyl)(phenyl)phosphinyl group; alternatively, a (3-chlorophenyl)(phenyl)phosphinyl group; alternatively, a (4-fluorophenyl)(phenyl)phosphinyl group; or alternatively, a (4-chlorophenyl)(phenyl)phosphinyl group.

In yet another non non-limiting aspect, the phosphinyl group of the N²-phosphinyl amidine compound can be a diphenylphosphinyl group, a bis(2-methylphenyl)phosphinyl group, a bis(2-ethyl-phenyl)phosphinyl group, a bis(2-isopropylphenyl)phosphinyl group, a bis(2-tert-butylphenyl)phosphinyl group, a bis(3-methylphenyl)phosphinyl group, a bis(3-ethylphenyl)phosphinyl group, bis(3-isopropyl-phenyl)phosphinyl group, a bis(3-tert-butylphenyl)phosphinyl group, a diphenylphosphinyl group, a bis(4-methylphenyl) phosphinyl group, a bis(4-ethylphenyl)phosphinyl group, a bis(4-isopropylphenyl)-phosphinyl group, or a bis(4-tert-butylphenyl)phosphinyl group. In a non-limiting embodiment, the phosphinyl group of the N²-phosphinyl amidine compound can be a bis(2-methylphenyl)phosphinyl group, a bis (2-ethylphenyl)phosphinyl group, a bis(2-isopropylphenyl) phosphinyl group, or a bis(2-tert-butylphenyl)phosphinyl group; alternatively, a diphenylphosphinyl group, a bis(3-methyl-phenyl)phosphinyl group, a bis(3-ethylphenyl)phosphinyl group, a bis(3-isopropylphenyl)phosphinyl group, or a bis(3-tert-butylphenyl)phosphinyl group; or alternatively, a diphenylphosphinyl group, a bis(4-methylphenyl)phosphinyl group, a bis(4-ethylphenyl)phosphinyl group, a bis(4-isopropyl-phenyl)phosphinyl group, or a bis(4-tert-butylphenyl) phosphinyl group. In other non-limiting embodiments, the phosphinyl group of the N²-phosphinyl amidine compound can be a diphenyl-phosphinyl group; alternatively, a bis(2-methylphenyl)phosphinyl group; alternatively, a bis(2-ethylphenyl)phosphinyl group; alternatively, a bis(2-isopropylphenyl)phosphinyl group; alternatively, a bis(2-tert-butylphenyl)phosphinyl group; alternatively, a bis(3-methylphenyl)phosphinyl group; alternatively, a bis(3-ethylphenyl)phosphinyl group; alternatively, a bis(3-isopropylphenyl)phosphinyl group; alternatively, a bis(3-tert-butylphenyl)phosphinyl group; alternatively, a diphenylphosphinyl group; alternatively, a bis(4-methylphenyl)phosphinyl group; alternatively, a bis(4-ethylphenyl)-phosphinyl group; alternatively, a bis(4-isopropylphenyl)phosphinyl group; or alternatively, a bis(4-tert-butylphenyl) phosphinyl group.

In yet another non non-limiting aspect, the phosphinyl group of the N²-phosphinyl amidine compound can be a diphenylphosphinyl group, a (2-methylphenyl)(phenyl)phosphinyl group, a (2-ethyl-phenyl)(phenyl)phosphinyl group, a (2-isopropylphenyl)(phenyl)phosphinyl group, a (2-tert-butyl-phenyl)(phenyl)phosphinyl group, a (3-methylphenyl)(phenyl)phosphinyl group, a (3-ethylphenyl)-(phenyl)phosphinyl group, (3-isopropylphenyl)(phenyl)phosphinyl group, a (3-tert-butylphenyl)(phenyl)-phosphinyl group, a diphenylphosphinyl group, a (4-methylphenyl)(phenyl)phosphinyl group, a (4-ethyl-phenyl)(phenyl)phosphinyl group, a (4-isopropylphenyl)(phenyl)phosphinyl group, or a (4-tert-butylphenyl)(phenyl)phosphinyl group. In a non-limiting embodiment, the phosphinyl group of the N²-phosphinyl amidine compound can be a (2-methylphenyl)(phenyl)phosphinyl group, a (2-ethyl-phenyl)(phenyl)phosphinyl group, (2-isopropylphenyl)(phenyl)phosphinyl group, or a (2-tert-butylphenyl)(phenyl)phosphinyl group; alternatively, a diphenylphosphinyl group, a (3-methylphenyl)-(phenyl) phosphinyl group, a (3-ethylphenyl)(phenyl)phosphinyl group, a (3-isopropylphenyl)(phenyl)-phosphinyl group, or a (3-tert-butylphenyl)(phenyl)phosphinyl group; or alternatively, a diphenyl-phosphinyl group, a (4-methylphenyl)(phenyl)phosphinyl group, a (4-ethylphenyl)(phenyl)phosphinyl group, a (4-isopropylphenyl)(phenyl)phosphinyl group, or a (4-tert-butylphenyl)(phenyl)phosphinyl group. In other non-limiting embodiments, the phosphinyl group of the $N^2$-phosphinyl amidine compound can be a diphenylphosphinyl group; alternatively, a (2-methylphenyl)(phenyl)phosphinyl group; alternatively, a (2-ethylphenyl)(phenyl)phosphinyl group; alternatively, a (2-isopropylphenyl)-(phenyl)phosphinyl group; alternatively, a (2-tert-butylphenyl)(phenyl)phosphinyl group; alternatively, a (3-methylphenyl)(phenyl)phosphinyl group; alternatively, a (3-ethylphenyl)(phenyl) phosphinyl group; alternatively, a (3-isopropylphenyl) (phenyl)phosphinyl group; alternatively, a (3-tert-butylphenyl)-(phenyl)phosphinyl group; alternatively, a diphenylphosphinyl group; alternatively, a (4-methylphenyl)-(phenyl)phosphinyl group; alternatively, a (4-ethylphenyl)(phenyl)phosphinyl group, (4-isopropyl-phenyl)(phenyl) phosphinyl group; or alternatively, a (4-tert-butylphenyl) (phenyl)phosphinyl group.

In yet another non non-limiting aspect, the phosphinyl group of the $N^2$-phosphinyl amidine compound can be a diphenylphosphinyl group, a bis(2-methoxyphenyl)phosphinyl group, a bis(2-ethoxy-phenyl)phosphinyl group, a bis(2-isopropoxyphenyl)phosphinyl group, a bis(2-tert-butoxyphenyl)-phosphinyl group, a bis(3-methoxyphenyl)phosphinyl group, a bis(3-ethoxyphenyl)phosphinyl group, a bis(3-isopropoxyphenyl)phosphinyl group, a bis(3-tert-butoxyphenyl)phosphinyl group, a diphenoxy-phosphinyl group, a bis (4-methoxyphenyl)phosphinyl group, a bis(4-ethoxyphenyl) phosphinyl group, bis(4-isopropoxyphenyl)phosphinyl group, or a bis(4-tert-butoxyphenyl)phosphinyl group. In a non-limiting embodiment, the phosphinyl group of the $N^2$-phosphinyl amidine compound can be a bis(2-methoxyphenyl)phosphinyl group, a bis(2-ethoxyphenyl)phosphinyl group, a bis(2-isopropoxy-phenyl)phosphinyl group, or a bis (2-tert-butoxyphenyl)phosphinyl group; alternatively, a diphenoxy-phosphinyl group, a bis(3-methoxyphenyl)phosphinyl group, a bis(3-ethoxyphenyl)phosphinyl group, a bis (3-isopropoxyphenyl)phosphinyl group, or a bis(3-tert-butoxyphenyl)phosphinyl group; or alternatively, a diphenoxyphosphinyl group, a bis(4-methoxyphenyl)phosphinyl group, a bis(4-ethoxy-phenyl)phosphinyl group, a bis (4-isopropoxyphenyl)phosphinyl group, or a bis(4-tert-butoxyphenyl)-phosphinyl group. In other non-limiting embodiments, the phosphinyl group of the $N^2$-phosphinyl amidine compound can be a diphenylphosphinyl group; alternatively, a bis(2-methoxyphenyl)phosphinyl group; alternatively, a bis(2-ethoxyphenyl)phosphinyl group; alternatively, a bis(2-isopropoxyphenyl)-phosphinyl group; alternatively, a bis(2-tert-butoxyphenyl)phosphinyl group; alternatively, a bis(3-methoxyphenyl)phosphinyl group; alternatively, a bis (3-ethoxyphenyl)phosphinyl group; alternatively, a bis(3-isopropoxyphenyl)phosphinyl group; alternatively, a bis(3-tert-butoxyphenyl)-phosphinyl group; alternatively, a diphenoxyphosphinyl group; alternatively, a bis(4-methoxyphenyl)-phosphinyl group; alternatively, a bis(4-ethoxyphenyl)phosphinyl group; alternatively, a bis(4-isopropoxyphenyl)phosphinyl group; or alternatively, a bis(4-tert-butoxyphenyl)phosphinyl group.

In yet another non non-limiting aspect, the phosphinyl group of the $N^2$-phosphinyl amidine compound can be a diphenylphosphinyl group, a (2-methoxyphenyl)(phenyl) phosphinyl group, a (2-ethoxyphenyl)(phenyl)phosphinyl group, a (2-isopropoxyphenyl)(phenyl)phosphinyl group, a (2-tert-butoxyphenyl)(phenyl)phosphinyl group, a (3-methoxyphenyl)(phenyl)phosphinyl group, a (3-ethoxyphenyl) (phenyl)phosphinyl group, a (3-isopropoxyphenyl)(phenyl) phosphinyl group, a (3-tert-butoxyphenyl)(phenyl) phosphinyl group, a diphenoxyphosphinyl group, a (4-methoxyphenyl)-(phenyl)phosphinyl group, a (4-ethoxyphenyl)(phenyl)phosphinyl group, a (4-isopropoxyphenyl)-(phenyl)phosphinyl group, or a (4-tert-butoxyphenyl)(phenyl)phosphinyl group. In a non-limiting embodiment, the phosphinyl group of the $N^2$-phosphinyl amidine compound can be a (2-methoxy-phenyl)(phenyl)phosphinyl group, a (2-ethoxyphenyl)(phenyl)phosphinyl group, (2-isopropoxyphenyl)-(phenyl)phosphinyl group, or a (2-tert-butoxyphenyl)(phenyl)phosphinyl group; alternatively, a diphenoxyphosphinyl group, a (3-methoxyphenyl)(phenyl) phosphinyl group, a (3-ethoxyphenyl)-(phenyl)phosphinyl group, a (3-isopropoxyphenyl)(phenyl)phosphinyl group, or a (3-tert-butoxyphenyl)-(phenyl)phosphinyl group; or alternatively, a diphenoxyphosphinyl group, a (4-methoxyphenyl) (phenyl)-phosphinyl group, a (4-ethoxyphenyl)(phenyl) phosphinyl group, (4-isopropoxyphenyl)(phenyl)-phosphinyl group, or a (4-tert-butoxyphenyl)(phenyl) phosphinyl group. In other non-limiting embodiments, the phosphinyl group of the $N^2$-phosphinyl amidine compound can be a diphenyl-phosphinyl group; alternatively, a (2-methoxyphenyl)(phenyl)phosphinyl group; alternatively, a (2-ethoxyphenyl)(phenyl)phosphinyl group; alternatively, a (2-isopropoxyphenyl)(phenyl)phosphinyl group; alternatively, a (2-tert-butoxyphenyl)(phenyl)phosphinyl group; alternatively, a (3-methoxy-phenyl)(phenyl)phosphinyl group; alternatively, a (3-ethoxyphenyl)(phenyl)phosphinyl group; alternatively, a (3-isopropoxyphenyl)(phenyl)phosphinyl group; alternatively, a (3-tert-butoxyphenyl)-(phenyl) phosphinyl group; alternatively, a diphenoxyphosphinyl group; alternatively, a (4-methoxy-phenyl)(phenyl)phosphinyl group; alternatively, a (4-ethoxyphenyl)(phenyl)phosphinyl group, (4-isopropoxyphenyl)(phenyl)phosphinyl group; or alternatively, a (4-tert-butoxyphenyl)(phenyl)-phosphinyl group.

Generally, $D^1$ can be a q valent organic group; alternatively, a q valent an organic group consisting essentially of inert functional groups; or alternatively, a q valent hydrocarbon group. In an aspect, $D^1$ can be a q valent $C_1$ to $C_{30}$ organic group; alternatively, a q valent $C_1$ to $C_{20}$ organic group; alternatively, a q valent $C_1$ to $C_{15}$ organic group; alternatively, a q valent $C_1$ to $C_{10}$ organic group; or alternatively, a q valent $C_1$ to $C_5$ organic group. In another aspect, $D^1$ can be a q valent $C_1$ to $C_{30}$ organic group consisting essentially of inert functional groups; alternatively, a q valent $C_1$ to $C_{20}$ organic group consisting essentially of inert functional groups; alternatively, a q valent $C_1$ to $C_{15}$ organic group consisting essentially of inert functional groups; alternatively, a q valent $C_1$ to $C_{10}$ organic group consisting essentially of inert functional groups; or alternatively, a q valent $C_1$ to $C_5$ organic group consisting essentially of inert functional groups. In yet another aspect, $D^1$ can be a q valent $C_1$ to $C_{30}$ hydrocarbyl group; alternatively, a q valent $C_1$ to $C_{20}$ hydrocarbyl group; alternatively, a q valent $C_1$ to $C_{15}$ hydrocarbyl group; alternatively, a q valent $C_1$ to $C_{10}$ hydrocarbyl group; or alternatively, a q valent $C_1$ to $C_5$ hydrocarbyl group. In yet other aspects, $D^1$ can be a q valent $C_3$ to $C_{30}$ aromatic group; alternatively, a q valent $C_3$ to $C_{20}$ aromatic group; alternatively, a q valent $C_3$ to $C_{15}$ aromatic group; or alternatively, a q valent $C_3$ to $C_{10}$ aromatic group.

In an aspect, q can be an integer greater than zero. In some embodiments, q can be an integer from 1 to 5; alternatively, an integer from 1 to 4; or alternatively, 2 or 3. In other embodiments, q can be 1; alternatively, 2; alternatively, 3; alternatively, 4; or alternatively, 5.

In an aspect, $L^1$ can be a $C_1$ to $C_{30}$ organylene group; alternatively, a $C_1$ to $C_{20}$ organylene group; alternatively, a $C_1$ to $C_{15}$ organylene group; alternatively, a $C_1$ to $C_{10}$ organylene group; or alternatively, a $C_1$ to $C_5$ organylene group. In another aspect, $L^1$ can be a $C_1$ to $C_{30}$ organylene group consisting essentially of inert functional groups; alternatively, a $C_1$ to $C_{20}$ organylene group consisting essentially of inert functional groups; alternatively, a $C_1$ to $C_{15}$ organylene group consisting essentially of inert functional groups; alternatively, a $C_1$ to $C_{10}$ organylene group; or alternatively, a $C_1$ to $C_5$ organylene group consisting essentially of inert functional groups. In yet another aspect, $L^1$ can be a $C_1$ to $C_{30}$ hydrocarbylene group; alternatively, a $C_1$ to $C_{20}$ hydrocarbylene group; alternatively, a $C_1$ to $C_{15}$ hydrocarbylene group; alternatively, a $C_1$ to $C_{10}$ hydrocarbylene group; or alternatively, a $C_1$ to $C_5$ hydrocarbylene group. In yet other aspects, $L^1$ can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group.

In an aspect, $L^1$ can be a $C_1$ to $C_{30}$ alkylene group, a $C_4$ to $C_{30}$ cycloalkylene group, a $C_4$ to $C_{30}$ substituted cycloalkylene group, a $C_3$ to $C_{30}$ aliphatic heterocyclylene group, a $C_3$ to $C_{30}$ substituted aliphatic heterocyclylene group, a $C_6$ to $C_{30}$ arylene group, a $C_6$ to $C_{30}$ substituted arylene group, a $C_3$ to $C_{30}$ heteroarylene group, or a $C_3$ to $C_{30}$ substituted heteroarylene group; alternatively, a $C_1$ to $C_{30}$ alkylene group, a $C_4$ to $C_{30}$ cycloalkylene group, a $C_4$ to $C_{30}$ substituted cycloalkylene group, a $C_6$ to $C_{30}$ arylene group, or a $C_6$ to $C_{30}$ substituted arylene group; alternatively, a $C_4$ to $C_{30}$ cycloalkylene group or a $C_4$ to $C_{30}$ substituted cycloalkylene group; alternatively, a $C_3$ to $C_{30}$ aliphatic heterocyclylene group or a $C_3$ to $C_{30}$ substituted aliphatic heterocyclylene group; alternatively, a $C_6$ to $C_{30}$ arylene group or a $C_6$ to $C_{30}$ substituted arylene group; alternatively, a $C_3$ to $C_{30}$ heteroarylene group or a $C_3$ to $C_{30}$ substituted heteroarylene group; alternatively, a $C_1$ to $C_{30}$ alkylene group; alternatively, a $C_4$ to $C_{30}$ cycloalkylene group; alternatively, a $C_4$ to $C_{30}$ substituted cycloalkylene group; alternatively, a $C_3$ to $C_{30}$ aliphatic heterocyclylene group; alternatively, a $C_3$ to $C_{30}$ substituted aliphatic heterocyclylene group; alternatively, a $C_6$ to $C_{30}$ arylene group; alternatively, a $C_6$ to $C_{30}$ substituted arylene group; alternatively, a $C_3$ to $C_{30}$ heteroarylene group; or alternatively, a $C_3$ to $C_{30}$ substituted heteroarylene group. In an embodiment, $L^1$ can be a $C_1$ to $C_{15}$ alkylene group, a $C_4$ to $C_{20}$ cycloalkylene group, a $C_4$ to $C_{20}$ substituted cycloalkylene group, a $C_3$ to $C_{20}$ aliphatic heterocyclylene group, a $C_3$ to $C_{20}$ substituted aliphatic heterocyclylene group, a $C_6$ to $C_{20}$ arylene group, a $C_6$ to $C_{20}$ substituted arylene group, a $C_3$ to $C_{20}$ heteroarylene group, or a $C_3$ to $C_{20}$ substituted heteroarylene group; alternatively, a $C_1$ to $C_{15}$ alkylene group, a $C_4$ to $C_{20}$ cycloalkylene group, a $C_4$ to $C_{20}$ substituted cycloalkylene group, a $C_6$ to $C_{20}$ arylene group, or a $C_6$ to $C_{20}$ substituted arylene group; alternatively, a $C_4$ to $C_{20}$ cycloalkylene group or a $C_4$ to $C_{20}$ substituted cycloalkylene group; alternatively, a $C_3$ to $C_{20}$ aliphatic heterocyclylene group or a $C_3$ to $C_{20}$ substituted aliphatic heterocyclylene group; alternatively, a $C_6$ to $C_{20}$ arylene group or a $C_6$ to $C_{20}$ substituted arylene group; alternatively, a $C_3$ to $C_{20}$ heteroarylene group or a $C_3$ to $C_{20}$ substituted heteroarylene group; alternatively, a $C_1$ to $C_{15}$ alkylene group; alternatively, a $C_4$ to $C_{20}$ cycloalkylene group; alternatively, a $C_4$ to $C_{20}$ substituted cycloalkylene group; alternatively, a $C_3$ to $C_{20}$ aliphatic heterocyclylene group; alternatively, a $C_3$ to $C_{20}$ substituted aliphatic heterocyclylene group; alternatively, a $C_6$ to $C_{20}$ arylene group; alternatively, a $C_6$ to $C_{20}$ substituted arylene group; alternatively, a $C_3$ to $C_{20}$ heteroarylene group; or alternatively, a $C_3$ to $C_{20}$ substituted heteroarylene group.

In other embodiments, $L^1$ be a $C_1$ to $C_{10}$ alkylene group, a $C_4$ to $C_{15}$ cycloalkylene group, a $C_4$ to $C_{15}$ substituted cycloalkylene group, a $C_3$ to $C_{15}$ aliphatic heterocyclylene group, a $C_3$ to $C_{15}$ substituted aliphatic heterocyclylene group, a $C_6$ to $C_{15}$ arylene group, a $C_6$ to $C_{15}$ substituted arylene group, a $C_3$ to $C_{15}$ heteroarylene group, or a $C_3$ to $C_{15}$ substituted heteroarylene group; alternatively, a $C_1$ to $C_{10}$ alkylene group, a $C_4$ to $C_{15}$ cycloalkylene group, a $C_4$ to $C_{15}$ substituted cycloalkylene group, a $C_6$ to $C_{15}$ arylene group, or a $C_6$ to $C_{15}$ substituted arylene group; alternatively, a $C_4$ to $C_{15}$ cycloalkylene group or a $C_4$ to $C_{15}$ substituted cycloalkylene group; alternatively, a $C_3$ to $C_{15}$ aliphatic heterocyclylene group or a $C_3$ to $C_{15}$ substituted aliphatic heterocyclylene group; alternatively, a $C_6$ to $C_{15}$ arylene group or a $C_6$ to $C_{15}$ substituted arylene group; alternatively, a $C_3$ to $C_{15}$ heteroarylene group or a $C_3$ to $C_{15}$ substituted heteroarylene group; alternatively, a $C_1$ to $C_{10}$ alkylene group; alternatively, a $C_4$ to $C_{15}$ cycloalkylene group; alternatively, a $C_4$ to $C_{15}$ substituted cycloalkylene group; alternatively, a $C_3$ to $C_{15}$ aliphatic heterocyclylene group; alternatively, a $C_3$ to $C_{15}$ substituted aliphatic heterocyclylene group; alternatively, a $C_6$ to $C_{15}$ arylene group; alternatively, a $C_6$ to $C_{15}$ substituted arylene group; alternatively, a $C_3$ to $C_{15}$ heteroarylene group; or alternatively, a $C_3$ to $C_{15}$ substituted heteroarylene group. In further embodiments, $L^1$ can be a $C_1$ to $C_5$ alkylene group.

In an embodiment, $L^1$ can be a methylene group, an ethylene group, a propylene group, a butylene group, a pentylene group, a hexylene group, a heptylene group, an octylene group, a nonylene group, a decylene group, a undecylene group, a dodecylene group, a tridecylene group, a tetradecylene group, a pentadecylene group, a hexadecylene group, a heptadecylene group, an octadecylene group, or a nonadecylene group; or alternatively, a methylene group, an ethylene group, a propylene group, a butylene group, a pentylene group, a hexylene group, a heptylene group, an octylene group, a nonylene group, a decylene group. In some embodiments, $L^1$ can be a methylene group, an ethylene group, a propylene group, a butylene group, or a pentylene group. In other embodiments, $L^1$ can be a methylene group; alternatively, an ethylene group; alternatively, a propylene group; alternatively, a butylene group; alternatively, a pentylene group; alternatively, a hexylene group; alternatively, a heptylene group; alternatively, an octylene group; alternatively, a nonylene group; alternatively, a decylene group; alternatively, a undecylene group; alternatively, a dodecylene group; alternatively, a tridecylene group; alternatively, a tetradecylene group; alternatively, a pentadecylene group; alternatively, a hexadecylene group; alternatively, a heptadecylene group; alternatively, an octadecylene group; or alternatively, a nonadecylene group. In some embodiments, $L^1$ can be a eth-1,2-ylene group, a prop-1,3-ylene group, a but-1,4-ylene group, a but-2,3-ylene group, a pent-1,5-ylene group, a 2,2-dimethylprop-1,3-ylene group, a hex-1,6-ylene group, or a 2,3-dimethylbut-2,3-ylene group; alternatively, a eth-1,2-ylene group, a prop-1,3-ylene group, a but-1,4-ylene group, a pent-1,5-ylene group, or a hex-1,6-ylene group; alternatively, a eth-1,2-ylene group; alternatively, a prop-1,3-ylene group; alternatively, a but-1,4-ylene group; alternatively, a but-2,3-ylene group; alternatively, a pent-1,5-ylene group; alternatively, a 2,2-dimethylprop-1,3-ylene group; alternatively, a hex-1,6-ylene group; or alternatively, a 2,3-dimethyl-but-2,3-ylene group. In some embodiments, the alkylene groups which can be utilized as $L^1$ can be substituted. Each substituent of a substituted alkylene group independently can be a halogen or a hydrocarboxy group; alternatively, a halogen; or alternatively, a hydrocarboxy group. Halogens and hydrocarboxy groups that can be utilized as substituents are independently disclosed herein (e.g. as substituents for substituted $R^1$ groups) and can be utilized without limitation to further describe the substituted alkylene group which can be utilized as $L^1$.

In an aspect, $L^1$ can have the formula —$CR^{1a}R^{2a}(CH_2)_t CR^{3a}R^{4a}$— wherein each $R^{1a}$, $R^{2a}$, $R^{3a}$, and $R^{4a}$ independently can be a hydrogen, a halogen, a $C_1$ to $C_5$ alkyl group, or a $C_1$ to $C_5$ alkoxy group and t can be zero or an integer ranging from 1 to 28. In an embodiment, $R^{1a}$, $R^{2a}$, $R^{3a}$, and $R^{4a}$ independently can be hydrogen, a halogen, and a $C_1$ to $C_5$ alkyl group; alternatively, hydrogen, a halogen, or a $C_1$ to $C_5$ alkoxy group; alternatively, hydrogen, a $C_1$ to $C_5$ alkyl group, or a $C_1$ to $C_5$ alkoxy group; alternatively, hydrogen or a halogen; alternatively, hydrogen or a $C_1$ to $C_5$ alkyl group; alternatively, hydrogen or a $C_1$ to $C_5$ alkoxy group; alternatively, hydrogen; or alternatively, a $C_1$ to $C_5$ alkyl group. In an embodiment, t can be an integer ranging from 1 to 18; alternatively, 1 to 13; alternatively, 1 to 8; or alternatively, 1 to 3. In other embodiments, t can be zero. Halogens, $C_1$ to $C_5$ alkyl groups, and $C_1$ to $C_s$ alkoxy groups that can be utilized as substitutents are independently described herein and can be utilized, without limitation, to further describe $L^1$ having the formula —$CR^{1a}R^{2a}(CH_2)_tCR^{3a}R^{4a}$—. In another aspect, $L^1$ may have the formula —$(CH_2)_s$— wherein s can be an integer ranging from 1 to 30. In an embodiment, s can be an integer ranging from 1 to 20; alternatively, 1 to 15; alternatively, 1 to 10; or alternatively, 1 to 5.

In an aspect, $L^1$ can be any $L^1$ group described herein (or $D^1$ can be any $D^1$ group described herein) wherein one or more carbon atoms of $L^1$ attached to the $N^1$ nitrogen atom of the $N^2$-phosphinyl amidine group (one or more carbon atoms of $D^1$ attached to the $N^1$ nitrogen atom of the $N^2$-phosphinyl amidine group) can be a tertiary carbon atom or a quaternary carbon atom; alternatively, a tertiary carbon atom; or alternatively, a quaternary carbon atom. In an embodiment, each carbon atom of $L^1$ attached to the $N^1$ nitrogen atom of the $N^2$-phosphinyl amidine group (or each carbon atom of $D^1$ attached to the $N^1$ nitrogen atom of the $N^2$-phosphinyl amidine group) can be a tertiary carbon atom or a quaternary carbon atom; alternatively, a tertiary carbon atom; or alternatively, a quaternary carbon atom.

In an embodiment, $L^1$ can be a cyclobutylene group, a substituted cyclobutylene group, a cyclopentylene group, a substituted cyclopentylene group, a cyclohexylene group, a substituted cyclohexylene group, a cycloheptylene group, a substituted cycloheptylene group, a cyclooctylene group, or a substituted cyclooctylene group. In some embodiments, $L^1$ can be a cyclopentylene group, a substituted cyclopentylene group, a cyclohexylene group, a substituted cyclohexylene group. In other embodiments, $L^1$ can be a cyclobutylene group or a substituted cyclobutylene group; alternatively, a cyclopentylene group or a substituted cyclopentylene group; alternatively, a cyclohexylene group or a substituted cyclohexylene group; alternatively, a cycloheptylene group or a substituted cycloheptylene group; or alternatively, a cyclooctylene group, or a substituted cyclooctylene group. In further embodiments, $L^1$ can be a cyclopentylene group; alternatively, a substituted cyclopentylene group; a cyclohexylene group; or alternatively, a substituted cyclohexylene group.

In an embodiment, $L^1$ can be a cyclopent-1,3-ylene group, a substituted cyclopent-1,3-ylene group, a cyclohex-1,3-ylene group, a substituted cyclohex-1,3-ylene group, a cyclohex-1,4-ylene group, or a substituted cyclohex-1,4-ylene group; alternatively, a cyclopent-1,3-ylene group, a cyclohex-1,3-ylene group, or a cyclohex-1,4-ylene group. In some embodiments, $L^1$ can be a cyclopent-1,3-ylene group or a substituted cyclopent-1,3-ylene group; alternatively, a cyclohex-1,3-ylene group, a substituted cyclohex-1,3-ylene group, a cyclohex-1,4-ylene group, or a substituted cyclohex-1,4-ylene group; alternatively, a cyclohex-1,3-ylene group or a substituted cyclohex-1,3-ylene group; alternatively, a cyclohex-1,4-ylene group or a substituted cyclohex-1,4-ylene group; alternatively, a cyclopent-1,3-ylene group, a cyclohex-1,3-ylene group, or a cyclohex-1,4-ylene group; or alternatively, a substituted cyclopent-1,3-ylene group, a substituted cyclohex-1,3-ylene group, or a substituted cyclohex-1,4-ylene group. In other embodiments, $L^1$ can be a cyclopent-1,3-ylene group; alternatively, a substituted cyclopent-1,3-ylene group; alternatively, a cyclohex-1,3-ylene group; alternatively, a substituted cyclohex-1,3-ylene group; alternatively, a cyclohex-1,4-ylene group; or alternatively, a substituted cyclohex-1,4-ylene group.

In a non-limiting embodiment, $L^1$ can be a 2-substituted cyclopen-1,3-ylene group, a 4,5-disubstituted cyclopen-1,3-ylene group, a 2,5-disubstituted cyclopen-1,3-ylene group, or a 2,4,5-trisubstituted cyclopen-1,3-ylene group. In some embodiments, $L^1$ can be a 2-substituted cyclopen-1,3-ylene group; alternatively, a 4,5-disubstituted cyclopen-1,3-ylene group; alternatively, a 2,5-disubstituted cyclopen-1,3-ylene group; alternatively, a 2,4,5-trisubstituted cyclopen-1,3-ylene group. In another non-limiting embodiment, $L^1$ can be a 2,6-disubstituted cyclohex-1,4-ylene group, a 2,3-disubstituted cyclohex-1,4-ylene group, a 2,5-disubstituted cyclohex-1,4-ylene group, or a 2,3,5,6-tetrasubstituted cyclohex-1,4-ylene group. In some embodiments, $L^1$ can be a 2,6-disubstituted cyclohex-1,4-ylene group or a 2,5-disubstituted cyclohex-1,4-ylene group; alternatively, a 2,6-disubstituted cyclohex-1,4-ylene group; alternatively, a 2,3-disubstituted cyclohex-1,4-ylene group; alternatively, a 2,5-disubstituted cyclohex-1,4-ylene group; or alternatively, a 2,3,5,6-tetrasubstituted cyclohex-1,4-ylene group. In yet another non-limiting embodiment, $L^1$ can be a 2-substituted cyclohex-1,3-ylene group, a 2,4-disubstituted cyclohex-1,3-ylene group, a 4,6-disubstituted cyclohex-1,3-ylene group, or a 2,4,6-trisubstituted cyclohex-1,3-ylene group. In a further non-limiting embodiment, $L^1$ can be a 2-substituted cyclohex-1,3-ylene group; alternatively, a 2,4-disubstituted cyclohex-1,3-ylene group; alternatively, a 4,6-disubstituted cyclohex-1,3-ylene group; or alternatively, a 2,4,6-trisubstituted cyclohex-1,3-ylene group.

In an aspect, $L^1$ can be a bicyclylene group, a substituted bicyclylene group, a bis(cyclylene)methane group, a substituted bis(cyclylene)methane group, a bis(cyclylene)ethane group, or a substituted bis(cyclylene)ethane group; alternatively, a bicyclylene group, a bis(cyclylene)methane group, or a bis(cyclylene)ethane group; or alternatively, a substituted bicyclylene group, a substituted bis(cyclylene)methane group, or a substituted bis(cyclylene)ethane group. In an embodiment, $L^1$ can be a bicyclylene group or a substituted bicyclylene group; alternatively, a bis(cyclylene)methane group or a substituted bis(cyclylene)methane group; or alternatively, a bis(cyclylene)ethane group or a substituted bis(cyclylene)ethane group. In some embodiments, $L^1$ can be a bicyclylene group; alternatively, a substituted bicyclylene group; alternatively, a bis(cyclylene)methane group; alternatively, a substituted bis(cyclylene)methane group; alternatively, a bis(cyclylene)ethane group; or alternatively, a substituted bis(cyclylene)ethane group. Generally, any bis(cyclylene)ethane group disclosed herein (substituted or unsubstituted) can be a bis-1,1-(cyclylene)ethane group or a bis-1,2-(cyclylene)ethane group; alternatively, a bis-1,1-(cyclylene)ethane group; or alternatively, a bis-1,2-(cyclylene)ethane group.

In an aspect, $L^1$ can be a bicyclohexylene group, a substituted bicyclohexylene group, a bis(cyclohexylene)methane group, a substituted bis(cyclohexylene)methane group, a bis(cyclohexylene)ethane group, or a substituted bis(cyclohexylene)ethane group; alternatively, a bicyclohexylene group, a bis(cyclohexylene)methane group, or a bis(cyclohexylene)ethane group; or alternatively, a substituted bicyclohexylene group, a substituted bis(cyclohexylene)methane group, or a substituted bis(cyclohexylene)ethane group. In an embodiment, $L^1$ can be a bicyclohexylene group or a substituted bicyclohexylene group; alternatively, a bis(cyclohexylene)methane group or a substituted bis(cyclohexylene)methane group; or alternatively, a bis(cyclohexylene)ethane group or a substituted bis(cyclohexylene)ethane group. In some embodiments, $L^1$ can be a bicyclohexylene group; alternatively, a substituted bicyclohexylene group; alternatively, a bis(cyclohexylene)methane group; alternatively, a substituted bis(cyclohexylene)methane group; alternatively, a bis(cyclohexylene)ethane group; or alternatively, a substituted bis(cyclohexylene)ethane group. Generally, any bis(cyclohexylene)ethane group disclosed herein (substituted or unsubstituted) can be a bis-1,1-(cyclohexylene)ethane group or a bis-1,2-(cyclohexylene)ethane group; alternatively, a bis-1,1-(cyclohexylene)ethane group; or alternatively, a bis-1,2-(cyclohexylene)ethane group.

In an embodiment, $L^1$ can be a bicyclohex-4,4'-ylene group, a 3,3'-disubstituted bicyclohex-4,4'-ylene group, a 3,3',5,5'-tetrasubstitutedbicyclohex-4,4'-ylene group, a bis(cyclohex-4-ylene) group, a bis(3-substituted cyclohex-4-ylene)methane group, a bis(3,5-disubstituted cyclohex-4-ylene)methane group, a bis-1,2-(cyclohex-4-ylene)ethane group, a bis-1,2-(3-substituted cyclohex-4-ylene)ethane group, a bis-1,2-(3,5-disubstituted cyclohex-4-ylene)ethane group. In some embodiments, $L^1$ can be a bicyclohex-4,4'-ylene group, 3,3'-disubstituted bicyclohex-4,4'-ylene group or a 3,3',5,5'-tetrasubstitutedbicyclohex-4,4'-ylene group; alternatively, a bis(cyclohex-4-ylene)methane group, a bis(3-substituted cyclohex-4-ylene)methane group or a bis(3,5-disubstituted cyclohex-4-ylene)methane group; alternatively, a bis-1,2-(cyclohex-4-ylene)ethane group, a bis-1,2-(3-substituted cyclohex-4-ylene)ethane group or a bis-1,2-(3,5-disubstituted cyclohex-4-ylene)ethane group. In other embodiments, $L^1$ can be a bicyclohex-4,4'-ylene group; alternatively, a 3,3'-disubstituted bicyclohex-4,4'-ylene group; alternatively, a 3,3',5,5'-tetrasubstitutedbicyclohex-4,4'-ylene group; alternatively, a bis(cyclohex-4-ylene)methane group; alternatively, a bis(3-substituted cyclohex-4-ylene)methane group; alternatively, a bis(3,5-disubstituted cyclohex-4-ylene)methane group; alternatively, a bis-1,2-(cyclohex-4-ylene)ethane group; alternatively, a bis-1,2-(3-substituted cyclohex-4-ylene)ethane group; or alternatively, a bis-1,2-(3,5-disubstituted cyclohex-4-ylene)ethane group.

In an aspect, $L^1$ can be a phenylene group or a substituted phenylene group. In an embodiment, $L^1$ can be a phenylene group; or alternatively, a substituted phenylene group. In some embodiments, $L^1$ can be a phen-1,2-ylene group or a substituted phen-1,2-ylene group; alternatively, a phen-1,2-ylene group; or alternatively, a substituted phen-1,2-ylene group. In other embodiments, $L^1$ can be a phen-1,3-ylene group or a substituted phen-1,3-ylene group; alternatively, a phen-1,3-ylene group; or alternatively, a substituted phen-1,3-ylene group. In yet other embodiments, $L^1$ can be a phen-1,4-ylene group or a substituted phen-1,4-ylene group; alternatively, a phen-1,4-ylene group; or alternatively, a substituted phen-1,4-ylene group. In further embodiments, $L^1$ can be a phen-1,2-ylene group, a phen-1,3-ylene group, or a phen-1,4-ylene group; alternatively, a phen-1,3-ylene group or a phen-1,4-ylene group. In other embodiments, $L^1$ can be a substituted phen-1,2-ylene group, a substituted phen-1,3-ylene group, or a substituted phen-1,4-ylene group; alternatively, a substituted phen-1,3-ylene group or a substituted phen-1,4-ylene group.

In a non-limiting embodiment, $L^1$ can be a 2,6-disubstituted phen-1,4-ylene group, a 2,3-disubstituted phen-1,4-ylene group, a 2,5-disubstituted phen-1,4-ylene group, or a 2,3,5,6-tetrasubstituted phen-1,4-ylene group. In some embodiments, $L^1$ can be a 2,6-disubstituted phen-1,4-ylene group or a 2,5-disubstituted phen-1,4-ylene group; alternatively, a 2,6-disubstituted phen-1,4-ylene group; alternatively, a 2,3-disubstituted phen-1,4-ylene group; alternatively, a 2,5-disubstituted phen-1,4-ylene group; or alternatively, a 2,3,5,6-tetrasubstituted phen-1,4-ylene group. In yet another non-limiting embodiment, $L^1$ can be a 2-substituted phen-1,3-ylene group, a 2,4-disubstituted phen-1,3-ylene group, a 4,6-disubstituted phen-1,3-ylene group, or a 2,4,6-trisubstituted phen-1,3-ylene group. In a further non-limiting embodiment, $L^1$ can be a 2-substituted phen-1,3-ylene group; alternatively, a 2,4-disubstituted phen-1,3-ylene group; alternatively, a 4,6-disubstituted phen-1,3-ylene group; or alternatively, a 2,4,6-trisubstituted phen-1,3-ylene group.

In an aspect, $L^1$ can be a naphthylene group or a substituted naphthylene group. In an embodiment, $L^1$ can be a naphthylene group; or alternatively, a substituted naphthylene group. In some embodiments, $L^1$ can be a naphth-1,3-ylene group, a substituted naphth-1,3-ylene group, a naphth-1,4-ylene group, a substituted naphth-1,4-ylene group, a naphth-1,5-ylene group, a substituted naphth-1,5-ylene group, a naphth-1,6-ylene group, a substituted naphth-1,6-ylene group, a naphth-1,7-ylene group, a substituted naphth-1,7-ylene group, a naphth-1,8-ylene group, or a substituted naphth-1,8-ylene group. In other embodiments, $L^1$ can be a naphth-1,3-ylene group or a substituted naphth-1,3-ylene group; alternatively, a naphth-1,4-ylene group or a substituted naphth-1,4-ylene group; alternatively, a naphth-1,5-ylene group or a substituted naphth-1,5-ylene group; alternatively, a naphth-1,6-ylene group or a substituted naphth-1,6-ylene group; alternatively, a naphth-1,7-ylene group or a substituted naphth-1,7-ylene group; or alternatively, a naphth-1,8-ylene group or a substituted naphth-1,8-ylene group. In yet other embodiments, $L^1$ can be a naphth-1,3-ylene group; alternatively, a substituted naphth-1,3-ylene group; alternatively, a naphth-1,4-ylene group; alternatively, a substituted naphth-1,4-ylene group; alternatively, a naphth-1,5-ylene group; alternatively, a substituted naphth-1,5-ylene group; alternatively, a naphth-1,6-ylene group; alternatively, a substituted naphth-1,6-ylene group; alternatively, a naphth-1,7-ylene group; alternatively, a substituted naphth-1,7-ylene group; alternatively, a naphth-1,8-ylene group; or alternatively, a substituted naphth-1,8-ylene group.

In an aspect, $L^1$ can be a biphenylene group, a substituted biphenylene group, a bis(phenylene)methane group, a substituted bis(phenylene)methane group, a bis(phenylene)ethane group, or a substituted bis(phenylene)ethane group; alternatively, a biphenylene group, a bis(phenylene)methane group, or a bis(phenylene)ethane group; or alternatively, a substituted biphenylene group, a substituted bis(phenylene)methane group, or a substituted bis(phenylene)ethane group. In an embodiment, $L^1$ can be a biphenylene group or a substituted biphenylene group; alternatively, bis(phenylene)methane group or a substituted bis(phenylene)methane group; or alternatively, a bis(phenylene)ethane group or a substituted bis(phenylene)ethane group. In some embodiments, $L^1$ can be a biphenylene group; alternatively, a substituted biphenylene group; alternatively, a bis(phenylene)methane group; alternatively, a substituted bis(phenylene)methane group; alternatively, a bis(phenylene)ethane group; or alternatively, a substituted bis(phenylene)ethane group. Generally, any bis(phenylene)ethane group disclosed herein (substituted or unsubstituted) can be a bis-1,1-(phenylene)ethane group or a bis-1,2-(phenylene)ethane group; alternatively, a bis-1,1-(phenylene)ethane group; or alternatively, a bis-1,2-(phenylene)ethane group.

In an embodiment, $L^1$ can be a biphen-2-ylene group, a substituted biphen-2-ylene group, a biphen-3-ylene group, a substituted biphen-3-ylene group, a biphen-4-ylene group, or a substituted biphen-4-ylene group; or alternatively, a biphen-3-ylene group, a substituted biphen-3-ylene group, a biphen-4-ylene group, or a substituted biphen-4-ylene group. In some embodiments, $L^1$ can be a biphen-2-ylene group or a substituted biphen-2-ylene group; alternatively, a biphen-3-ylene group or a substituted biphen-3-ylene group; or alternatively, a biphen-4-ylene group or a substituted biphen-4-ylene group. In other embodiments, $L^1$ can be a biphen-2-ylene group; alternatively, a substituted biphen-2-ylene group; alternatively, a biphen-3-ylene group; alternatively, a substituted biphen-3-ylene group; alternatively, biphen-4-ylene group; or alternatively, a substituted biphen-4-ylene group.

In an embodiment, $L^1$ can be a bis(phen-2-ylene)methane group, a substituted bis(phen-2-ylene)methane group, a bis(phen-3-ylene)methane group, a substituted bis(phen-3-ylene)methane group, a bis(phen-4-ylene)methane group, or a substituted bis(phen-4-ylene)methane group; or alternatively, a bis(phen-3-ylene)methane group, a substituted bis(phen-3-ylene)methane group, a bis(phen-4-ylene)methane group, or a substituted bis(phen-4-ylene)methane group. In some embodiments, $L^1$ can be a bis(phen-2-ylene)methane group or a substituted bis(phen-2-ylene)methane group; alternatively, a bis(phen-3-ylene)methane group or a substituted bis(phen-3-ylene)methane group; or alternatively, a bis(phen-4-ylene)methane group or a substituted bis(phen-4-ylene)methane group. In other embodiments, $L^1$ can be a bis(phen-2-ylene)methane group; alternatively, a substituted bis(phen-2-ylene)methane group; alternatively, a bis(phen-3-ylene)methane group; alternatively, a substituted bis(phen-3-ylene)methane group; alternatively, a bis(phen-4-ylene)methane group; or alternatively, a substituted bis(phen-4-ylene)methane group.

In an embodiment, $L^1$ can be a bis(phen-2-ylene)ethane group, a substituted bis(phen-2-ylene)ethane group, a bis(phen-3-ylene)ethane group, a substituted bis(phen-3-ylene)ethane group, a bis(phen-4-ylene)ethane group, or a substituted bis(phen-4-ylene)ethane group; or alternatively, a bis(phen-3-ylene)ethane group, a substituted bis(phen-3-ylene)ethane group, a bis(phen-4-ylene)ethane group, or a substituted bis(phen-4-ylene)ethane group. In some embodiments, $L^1$ can be a bis(phen-2-ylene)ethane group or a substituted bis(phen-2-ylene)ethane group; alternatively, a bis(phen-3-ylene)ethane group or a substituted bis(phen-3-ylene)ethane group; or alternatively, a bis(phen-4-ylene)ethane group or a substituted bis(phen-4-ylene)ethane group. In other embodiments, $L^1$ can be a bis(phen-2-ylene)ethane group; alternatively, a substituted bis(phen-2-ylene)ethane group; alternatively, a bis(phen-3-ylene)ethane group; alternatively, a substituted bis(phen-3-ylene)ethane group; alternatively, a bis(phen-4-ylene)ethane group; or alternatively, a substituted bis(phen-4-ylene)ethane group. Generally, any bis(phenylene)ethane group disclosed herein (substituted or unsubstituted) may be a bis-1,1-(phenylene)ethane group or a bis-1,2-(phenylene)ethane group; alternatively, a bis-1,1-(phenylene)ethane group; or alternatively, a bis-1,2-(phenylene)ethane group.

In an embodiment, $L^1$ can be a 3,3'-disubstituted biphen-4,4'-ylene group, a 3,3',5,5'-tetrasubstitutedbiphen-4,4'-ylene group, a bis(3-substituted phen-4-ylene)methane group, a bis(3,5-disubstituted phen-4-ylene)methane group, a bis-1,2-(3-substituted phen-4-ylene)ethane group, a bis-1,2-(3,5-disubstituted phen-4-ylene)ethane group. In some embodiments, $L^1$ can be a 3,3'-disubstituted biphen-4,4'-ylene group or a 3,3',5,5'-tetrasubstitutedbiphen-4,4'-ylene group; alternatively, a bis(3-substituted phen-4-ylene)methane group or a bis(3,5-disubstituted phen-4-ylene)methane group; alternatively, a bis-1,2-(3-substituted phen-4-ylene)ethane group or a bis-1,2-(3,5-disubstituted phen-4-ylene)ethane group. In other embodiments, $L^1$ can be a 3,3'-disubstituted biphen-4,4'-ylene group; alternatively, 3,3',5,5'-tetrasubstitutedbiphen-4,4'-ylene group; alternatively, a bis(3-substituted phen-4-ylene)methane group; alternatively, a bis(3,5-disubstituted phen-4-ylene)methane group; alternatively, a bis-1,2-(3-substituted phen-4-ylene)ethane group; or alternatively, a bis-1,2-(3,5-disubstituted phen-4-ylene)ethane group.

In an embodiment, $L^1$ can be a di(methylene)cycloalkane group or a substituted di(methylene)cycloalkane group; alternatively, a di(methylene)cycloalkane group. The cycloalkane group of the di(methylene)cycloalkane group can be cyclobutane group, a substituted cyclobutane group, a cyclopentane group, a substituted cyclopentane group, a cyclohexane group, a substituted cyclohexane group, a cycloheptane group, a substituted cycloheptane group, a cyclooctane group, or a substituted cyclooctane group; alternatively, a cyclopentane group, a substituted cyclopentane group, a cyclohexane group, or a substituted cyclohexane group; alternatively, a cyclobutane group or a substituted cyclobutane group; alternatively, a cyclopentane group or a substituted cyclopentane group; alternatively, a cyclohexane group or a substituted cyclohexane group; alternatively, a cycloheptane group or a substituted cycloheptane group; or alternatively, a cyclooctane group, or a substituted cyclooctane group. In some embodiments, the cycloalkane group of the di(methylene)cycloalkane group can be cyclobutane group, a cyclopentane group, a cyclohexane group, a cycloheptane group or a cyclooctane group; or alternatively, a cyclopentane group or a cyclohexane group. In other embodiments, the cycloalkane group of the di(methylene)cycloalkane group can be cyclopentane group; alternatively, a substituted cyclopentane group; a cyclohexane group; or alternatively, a substituted cyclohexane group.

In an embodiment, $L^1$ can be a 1,3-di(methylene)cyclopentane group, a substituted 1,3-di(methylene)cyclopentane group, a 1,3-di(methylene)cyclohexane group, a substituted 1,3-di(methylene)cyclohexane group, a 1,4-di(methylene)cyclohexane group, or a substituted 1,4-di(methylene)cyclohexane group; alternatively, 1,3-di(methylene)cyclopentane group, a 1,3-di(methylene)cyclohexane group, or a 1,4-di(methylene)cyclohexane group. In some embodiments, $L^1$ can be a 1,3-di(methylene)cyclopentane group or a substituted 1,3-di(methylene)cyclopentane group; alternatively, a 1,3-di(methylene)cyclohexane group, a substituted 1,3-di(methylene)cyclohexane group, a 1,4-di(methylene)cyclohexane group, or a substituted 1,4-di(methylene)cyclohexane group; alternatively, a 1,3-di(methylene)cyclohexane group or a substituted 1,3-di(methylene)cyclohexane group; alternatively, a 1,4-di(methylene)cyclohexane group or a substituted 1,4-di(methylene)cyclohexane group; alternatively, 1,3-di(methylene)cyclopentane group; alternatively, a 1,3-di(methylene)cyclohexane group; or alternatively, a 1,4-di(methylene)cyclohexane group.

In an aspect, $L^1$ can be a di(methylene)benzene group or a substituted di(methylene)benzene group; alternatively, a di(methylene) benzene group. In an embodiment, $L^1$ can be a 1,2-di(methylene)benzene group, a substituted 1,2-di(methylene)benzene group, a 1,3-di(methylene)benzene group, a substituted 1,3-di(methylene)benzene group, a 1,4-di(methylene)benzene group, or a substituted 1,4-di(methylene)benzene group; alternatively, a 1,2-di(methylene)benzene group, a 1,3-di(methylene)benzene group, or a 1,4-di(methylene) benzene group. In some embodiments, $L^1$ can be a 1,2-di(methylene)benzene group or a substituted 1,2-di(methylene) benzene group; alternatively, a 1,3-di(methylene)benzene group or a substituted 1,3-di(methylene)benzene group; alternatively, a 1,4-di(methylene)benzene group or a substituted 1,4-di(methylene)benzene group; alternatively, a 1,2-di(methylene)benzene group; alternatively, a 1,3-di(methylene)benzene group; or alternatively, a 1,4-di(methylene)benzene group.

In an embodiment, each substituent for any substituted $L^1$ group (general or specific) independently can be a halogen, a hydrocarbyl group, or a hydrocarboxy group; alternatively, a halogen or a hydrocarbyl group; alternatively, a hydrocarbyl group or a hydrocarboxy group; alternatively, a halogen; alternatively, a hydrocarbyl group; or alternatively, a hydrocarboxy group. In some embodiments, each substituent for any substituted $L^1$ group (general or specific) independently can be a halogen, an alkyl group, or an alkoxy group; alternatively, a halogen or an alkyl group; alternatively, an alkyl group or an alkoxy group; alternatively, a halogen; alternatively, an alkyl group; or alternatively, alkoxy group. Halogens, hydrocarbyl groups, hydrocarboxy groups, alkyl group, and alkoxy groups that can be utilized as substituents are independently disclosed herein (e.g. as substituents for substituted $R^1$ groups) and can be utilized without limitation to further describe a substituted $L^1$ group.

In an aspect, $L^1$ can have any Structure in Table 1. In an embodiment, $L^1$ can have Structure 1L, 2L, 3L, 4L, 5L, 6L, or 7L; or alternatively, 8L, 9L, 10L, 11L, 12L, 13L, or 14L. In some embodiments, $L^1$ can have Structure 1L, 2L, or 3L; alternatively, Structure 4L, 5L, 6L, or 7L; alternatively, Structure 8L, 9L, or 10L; or alternatively, Structure 11L, 12L, 13L, or 14L. In other embodiments, $L^1$ can have Structure 2L or 3L; alternatively, Structure 9L or 10L; alternatively, Structure 4L or 5L; alternatively, Structure 6L or 7L; or alternatively, Structure 11L or 12L; or alternatively, Structure 13L or 14L. In further embodiments, $L^1$ can have Structure 1L; alternatively, Structure 2L; alternatively, Structure 3L; alternatively, Structure 4L; alternatively, Structure 5L; alternatively, Structure 6L; alternatively, Structure 7L; alternatively, Structure 8L; alternatively, Structure 9L; alternatively, Structure 10L; alternatively, Structure 11L; alternatively, Structure 12L; alternatively, Structure 13L; or alternatively, Structure 14L.

TABLE 1

Linking groups, $L^1$ or $L^2$ for $N^2$-phosphinyl amidine compounds having Structure NP2, NP3, NP4, or NP5.

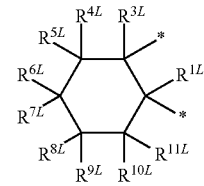

Structure 1L

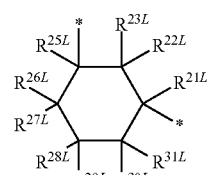

Structure 2L

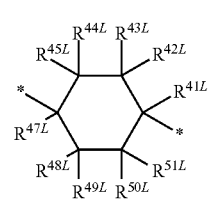

Structure 3L

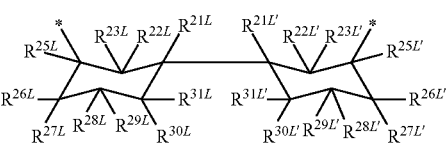

Structure 4L

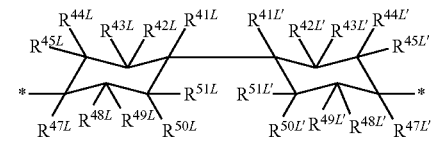

Structure 5L

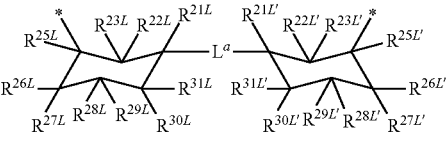

Structure 6L

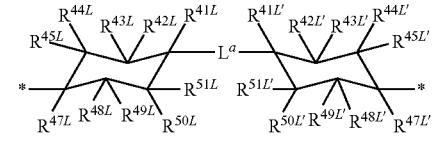

Structure 7L

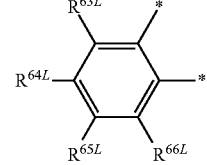

Structure 8L

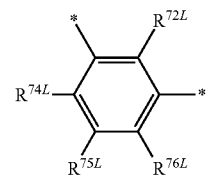

Structure 9L

TABLE 1-continued

Linking groups, $L^1$ or $L^2$ for $N^2$-phosphinyl amidine compounds having Structure NP2, NP3, NP4, or NP5.

[Structure 10L: benzene ring with substituents $R^{83L}$, $R^{82L}$, $R^{85L}$, $R^{86L}$ and two attachment points]

[Structure 11L: biphenyl with substituents $R^{72L}$, $R^{72L'}$, $R^{74L}$, $R^{74L'}$, $R^{75L}$, $R^{76L}$, $R^{76L'}$, $R^{75L'}$]

[Structure 12L: biphenyl with substituents $R^{83L}$, $R^{82L}$, $R^{82L'}$, $R^{83L'}$, $R^{85L}$, $R^{86L}$, $R^{86L'}$, $R^{85L'}$]

[Structure 13L: two benzene rings linked by $L^a$, with substituents $R^{72L}$, $R^{72L'}$, $R^{74L}$, $R^{74L'}$, $R^{75L}$, $R^{76L}$, $R^{76L'}$, $R^{75L'}$]

[Structure 14L: two benzene rings linked by $L^a$, with substituents $R^{83L}$, $R^{82L}$, $R^{82L'}$, $R^{83L'}$, $R^{85L}$, $R^{86L}$, $R^{86L'}$, $R^{85L'}$]

In an embodiment, $L^a$ within $L^1$ Structures 6L, 7L, 13L, or 14L can be —$(CR^L R^L)_m$— where each $R^L$ independently can be hydrogen, a methyl group, an ethyl group, a propyl group, an isopropyl group, or a butyl group and m can be an integer from 1 to 5. In an embodiment, $L^a$ within $L^1$ Structures 6L, 7L, 13L, or 14L can be —$CR^L R^L (CH_2)_n CR^L R^L$— where each $R^L$ independently can be hydrogen, a methyl group, an ethyl group, a propyl group, an isopropyl group, or a butyl group and n can be an integer from 0 to 3. In some embodiments, each $R^L$ independently can be hydrogen or a methyl group; alternatively, hydrogen. In other embodiments, $L^a$ can be a methylene group (—$CH_2$—), an ethylene group (—$CH_2 CH_2$—), a propylene group (—$CH_2 CH_2 CH_2$—), a —$CH(CH_3)CH_2$— group, —$C(CH_3)_2$— group, or a butylene group (—$CH_2 CH_2 CH_2 CH_2$—). In some non-limiting embodiments, $L^a$ can be a methylene group (—$CH_2$—), an ethylene group (—$CH_2 CH_2$—) or a —$CH(CH_3)CH_2$— group; or alternatively, an ethylene group (—$CH_2 CH_2$—), or a —$CH(CH_3)CH_2$— group. In yet other embodiments, $L^a$ can be a methylene group; alternatively, an ethylene group; alternatively, a propylene group; alternatively, a —$CH(CH_3)CH_2$— group; or alternatively, —$C(CH_3)_2$— group.

Generally, within $L^1$ Structures 1L, 2L, 3L, 4L, 5L, 6L, 7L, 8L, 9L, 10L, 11L, 12L, 13L, or 14L, $R^{1L}$-$R^{11L}$, $R^{21L}$-$R^{31L}$, $R^{21L'}$-$R^{31L'}$, $R^{41L}$-$R^{51L}$, $R^{41L'}$-$R^{51L'}$, $R^{62L}$-$R^{66L}$, $R^{72L}$-$R^{76L}$, $R^{72L'}$-$R^{76L'}$, $R^{82L}$-$R^{86L}$, $R^{82L'}$-$R^{86L'}$ (when present in a indicated structure) independently can be hydrogen, a halogen, a hydrocarbyl group, or a hydrocarboxy group; alternatively, hydrogen, a halogen, or a hydrocarbyl group; alternatively, hydrogen, a halogen, or a hydrocarboxy group; alternatively, hydrogen, a hydrocarbyl group, or a hydrocarboxy group; alternatively, hydrogen or a halogen; alternatively, hydrogen or hydrocarbyl group; or alternatively, hydrogen or a hydrocarboxy group. In an embodiment, $R^{1L}$-$R^{11L}$, $R^{21L}$-$R^{31L}$, $R^{21L'}$-$R^{31L'}$, $R^{41L}$-$R^{51L}$, $R^{41L'}$-$R^{51L'}$, $R^{62L}$-$R^{66L}$, $R^{72L}$-$R^{76L}$, $R^{72L'}$-$R^{76L'}$, $R^{82L}$-$R^{86L}$, $R^{82L'}$-$R^{86L'}$, when present in any 1L-14L structure, independently can be hydrogen, a halogen, an alkyl group, or an alkoxy group; alternatively, hydrogen, a halogen, and an alkyl group; alternatively, hydrogen, a halogen, or an alkoxy group; alternatively, hydrogen, an alkyl group, or an alkoxy group; alternatively, hydrogen or a halogen; alternatively, hydrogen or an alkyl group; or alternatively, hydrogen or an alkoxy group. Halogens, hydrocarbyl groups, hydrocarboxy groups, alkyl group, and alkoxy groups that can be utilized as substituents are independently disclosed herein (e.g. as substituents for substituted $R^1$ groups) and can be utilized without limitation to further describe $L^1$ having any 1L-14L structure.

In an aspect, $L^1$ can have a formula (or structure) wherein one or more carbon atom attached to the $N^1$ nitrogen atom of the $N^2$-phosphinyl amidine group can be a tertiary carbon atom or a quaternary carbon atom; a tertiary carbon atom; or alternatively, a quaternary carbon atom. In an embodiment, $L^1$ can have a formula (or structure) wherein each carbon atom attached to an $N^1$ nitrogen atom of the $N^2$-phosphinyl amidine group can be a tertiary carbon atom or a quaternary carbon atom; alternatively, a tertiary carbon atom; or alternatively, a quaternary carbon atom.

In an embodiment, when an $N^1$ nitrogen atom of the $N^2$-phosphinyl amidine group is attached to a ring atom of a $L^1$ group (e.g., cycloalkylene, arylene, dicycloalkylene, dicycloalkylenemethylene, diarylene, diarylenemethylene, a $L^1$ having Structure 1L-14L, or any other $L^1$ group disclosed herein), the $L^1$ group can comprise at least one substituent located on a carbon atom adjacent to the ring carbon atom attached to $N^1$ nitrogen atom of the $N^2$-phosphinyl amidine group; or alternatively, the $L^1$ group can comprise at least one substituent at each carbon atom adjacent to the ring carbon atom attached to $N^1$ nitrogen atom of the $N^2$-phosphinyl amidine group. In some embodiments, when the $N^1$ nitrogen atom of the $N^2$-phosphinyl amidine group is attached to a ring atom of a $L^1$ group (e.g., cycloalkylene, arylene, dicycloalkylene, dicycloalkylenemethylene, diarylene, diarylenemethylene, a $L^1$ having Structure 1L-14L, or any other $L^1$ group disclosed herein), the $L^1$ group can consist of one substituent located on a carbon atom adjacent to the ring carbon atom attached to $N^1$ nitrogen atom of the $N^2$-phosphinyl amidine group. In some embodiments, when the $N^1$ nitrogen atom of the $N^2$-phosphinyl amidine group is attached to a ring atom of a $L^1$ group (e.g., cycloalkylene, arylene, dicycloalkylene, dicycloalkylenemethylene, diarylene, diarylenemethylene, a $L^1$ having Structure 1L-14L, or any other $L^1$ group disclosed herein), the $L^1$ group can comprise only one substituent located on carbon atom adjacent to the ring carbon atom attached to $N^1$ nitrogen atom of the $N^2$-phosphinyl amidine group; or alternatively, the $L^1$ group can comprise, or consist of, only one substituent located on each carbon atom adjacent to the ring carbon atom attached to $N^1$ nitrogen atom of the $N^2$-phosphinyl amidine group.

In a non-limiting embodiment, $L^1$ can be a phen-1,4-ylene group, a 2,6-dimethylphen-1,4-ylene group, a 2,6-diethylphen-1,4-ylene group, a 2,6-diisopropyl phen-1,4-ylene group, a 2,6-di-tert-butylphen-1,4-ylene group, a 2,5-dimethylphen-1,4-ylene group, a 2,5-diethylphen-1,4-ylene group, a 2,5-diisopropylphen-1,4-ylene group, a 2,5-di-tert-butylphen-1,4-ylene group, or a 2,3,5,6-tetramethylphen-1,4-ylene group. In other non-limiting embodiments, $L^1$ can be a phen-1,4-ylene group, a 2,6-dimethylphen-1,4-ylene group, a 2,6-diethylphen-1,4-ylene group, a 2,6-diisopropyl phen-1,4-ylene group, or a 2,6-di-tert-butylphen-1,4-ylene group; or alternatively, a 2,5-dimethylphen-1,4-ylene group, a 2,5-diethylphen-1,4-ylene group, a 2,5-diisopropylphen-1,4-ylene group, or a 2,5-di-tert-butylphen-1,4-ylene group. In yet further non-limiting embodiments, $L^1$ can be a phen-1,4-ylene group; alternatively, a 2,6-dimethylphen-1,4-ylene group; alternatively, a 2,6-diethylphen-1,4-ylene group; alternatively, a 2,6-diisopropyl phen-1,4-ylene group; alternatively, a 2,6-di-tert-butylphen-1,4-ylene group; alternatively, a 2,5-dimethylphen-1,4-ylene group; alternatively, a 2,5-diethylphen-1,4-ylene group; alternatively, a 2,5-diisopropylphen-1,4-ylene group; alternatively, a 2,5-di-tert-butylphen-1,4-ylene group; or alternatively, a 2,3,5,6-tetramethylphen-1,4-ylene group.

In a non-limiting embodiment, $L^1$ can be a 3,3'-dimethylbiphen-4,4'-ylene group, 3,3'-diethylbiphen-4,4'-ylene group, a 3,3'-diisopropylbiphen-4,4'-ylene group, a 3,3'-di-tert-butylbiphen-4,4'-ylene group, a 3,3',5,5'-tetramethylbiphen-4,4'-ylene group, 3,3',5,5'-tetraethylbiphen-4,4'-ylene group, a 3,3',5,5'-tetraisopropylbiphen-4,4'-ylene group, or a 3,3',5,5'-tetra-tert-butylbiphen-4,4'-ylene group. In some embodiments, $L^1$ can be a 3,3'-dimethylbiphen-4,4'-ylene group, 3,3'-diethylbiphen-4,4'-ylene group, a 3,3'-diisopropylbiphen-4,4'-ylene group, or a 3,3'-di-tert-butylbiphen-4,4'-ylene group; or alternatively, a 3,3',5,5'-tetramethylbiphen-4,4'-ylene group, 3,3',5,5'-tetraethylbiphen-4,4'-ylene group, a 3,3',5,5'-tetraisopropylbiphen-4,4'-ylene group, or a 3,3',5,5'-tetra-tert-butylbiphen-4,4'-ylene group. In other embodiments, $L^1$ can be a 3,3'-dimethylbiphen-4,4'-ylene group; alternatively, 3,3'-diethylbiphen-4,4'-ylene group; alternatively, a 3,3'-diisopropylbiphen-4,4'-ylene group; alternatively, a 3,3'-di-tert-butylbiphen-4,4'-ylene group; alternatively, a 3,3',5,5'-tetramethylbiphen-4,4'-ylene group; alternatively, 3,3',5,5'-tetraethylbiphen-4,4'-ylene group; alternatively, a 3,3',5,5'-tetraisopropylbiphen-4,4'-ylene group; or alternatively, a 3,3',5,5'-tetra-tert-butylbiphen-4,4'-ylene group.

In a non-limiting embodiment, $L^1$ can be a bis(3-methylphen-4-ylene)methane group, a bis(3-ethylphen-4-ylene)methane group, a bis(3-isopropyphen-4-ylene)methane group, a bis(3-tert-butylphen-4-ylene)methane group, a bis(3,5-dimethylphen-4-ylene)methane group, a bis(3,5-diethylphen-4-ylene)methane group, a bis(3,5-diisopropyphen-4-ylene)methane group, or a bis(3,5-di-tert-butylphen-4-ylene)methane group. In some embodiments, $L^1$ can be a bis(3-methylphen-4-ylene)methane group, a bis(3-ethylphen-4-ylene)methane group, a bis(3-isopropyphen-4-ylene)methane group, a bis(3-tert-butylphen-4-ylene)methane group; or alternatively, a bis(3,5-dimethylphen-4-ylene)methane group, a bis(3,5-diethylphen-4-ylene)methane group, a bis(3,5-diisopropyphen-4-ylene)methane group, or a bis(3,5-di-tert-butylphen-4-ylene)methane group. In other embodiments, $L^1$ can be a bis(3-methylphen-4-ylene)methane group; alternatively, a bis(3-ethylphen-4-ylene)methane group; alternatively, a bis(3-isopropyphen-4-ylene)methane group; alternatively, a bis(3-tert-butylphen-4-ylene)methane group; alternatively, a bis(3,5-dimethylphen-4-ylene)methane group; alternatively, a bis(3,5-diethylphen-4-ylene)methane group; alternatively, a bis(3,5-diisopropyphen-4-ylene)methane group; or alternatively, a bis(3,5-di-tert-butylphen-4-ylene)methane group.

In a non-limiting embodiment, $L^1$ can be a bis(3-methylphen-4-ylene)ethane group, a bis(3-ethylphen-4-ylene)ethane group, a bis(3-isopropylphen-4-ylene)ethane group, a bis(3-tert-butylphen-4-ylene)ethane group a bis(3,5-dimethylphen-4-ylene)ethane group, a bis(3,5-diethylphen-4-ylene)ethane group, a bis(3,5-diisopropylphen-4-ylene)ethane group, or a bis(3,5-di-tert-butylphen-4-ylene)ethane group. In some embodiments, $L^1$ can be a bis(3-methylphen-4-ylene)ethane group, a bis(3-ethylphen-4-ylene)ethane group, a bis(3-isopropylphen-4-ylene)ethane group, a bis(3-tert-butylphen-4-ylene)ethane group; or alternatively, a bis(3,5-dimethylphen-4-ylene)ethane group, a bis(3,5-diethylphen-4-ylene)ethane group, a bis(3,5-diisopropylphen-4-ylene)ethane group, or a bis(3,5-di-tert-butylphen-4-ylene)ethane group. In other embodiments, $L^1$ can be a bis(3-methylphen-4-ylene)ethane group; alternatively, a bis(3-ethylphen-4-ylene)ethane group; alternatively, a bis(3-isopropylphen-4-ylene)ethane group; alternatively, a bis(3-tert-butylphen-4-ylene)ethane group; alternatively, a bis(3,5-dimethylphen-4-ylene)ethane group; alternatively, a bis(3,5-diethylphen-4-ylene)ethane group; alternatively, a bis(3,5-diisopropylphen-4-ylene)ethane group; or alternatively, a bis(3,5-di-tert-butylphen-4-ylene)ethane group.

Generally, $D^2$ can be an r valent organic group; alternatively, an an r valent organic group consisting essentially of inert functional groups; or alternatively, an r valent hydrocarbon group. In an aspect, $D^2$ can be an r valent $C_1$ to $C_{30}$ organic group; alternatively, an r valent $C_1$ to $C_{20}$ organic group; alternatively, an r valent $C_1$ to $C_{15}$ organic group; alternatively, an r valent $C_1$ to $C_{10}$ organic group; or alternatively, an r valent $C_1$ to $C_5$ organic group. In another aspect, $D^2$ can be an r valent $C_1$ to $C_{30}$ organic group consisting essentially of inert functional groups; alternatively, an r valent $C_1$ to $C_{20}$ organic group consisting essentially of inert functional groups; alternatively, an r valent $C_1$ to $C_{15}$ organic group consisting essentially of inert functional groups; alternatively, an r valent $C_1$ to $C_{10}$ organic group consisting essentially of inert functional groups; or alternatively, an r valent $C_1$ to $C_5$ organic group consisting essentially of inert functional groups. In yet another aspect, $D^2$ can be an r valent $C_1$ to $C_{30}$ hydrocarbyl group; alternatively, an r valent $C_1$ to $C_{20}$ hydrocarbyl group; alternatively, an r valent $C_1$ to $C_{15}$ hydrocarbyl group; alternatively, an r valent $C_1$ to $C_{10}$ hydrocarbyl group; or alternatively, an r valent $C_1$ to $C_5$ hydrocarbyl group. In yet other embodiments, $D^2$ can be an r valent $C_3$ to $C_{30}$ aromatic group; alternatively, an r valent $C_3$ to $C_{20}$ aromatic group; alternatively, an r valent $C_3$ to $C_{15}$ aromatic group; or alternatively, an r valent $C_3$ to $C_{10}$ aromatic group.

In an aspect, r can be an integer greater than zero. In some embodiments, r can be an integer from 1 to 5; alternatively, an integer from 1 to 4; or alternatively, 2 or 3. In other embodiments, r can be 1; alternatively, 2; alternatively, 3; alternatively, 4; or alternatively, 5.

In an aspect, $L^2$ can be a $C_1$ to $C_{30}$ organylene group; alternatively, a $C_1$ to $C_{20}$ organylene group; alternatively, a $C_1$ to $C_{15}$ organylene group; alternatively, a $C_1$ to $C_{10}$ organylene group; or alternatively, a $C_1$ to $C_5$ organylene group. In another aspect, $L^2$ can be a $C_1$ to $C_{30}$ organylene group consisting essentially of inert functional groups; alternatively, a $C_1$ to $C_{20}$ organylene group consisting essentially of inert functional groups; alternatively, a $C_1$ to $C_{15}$ organylene group consisting essentially of inert functional groups; alternatively, a $C_1$ to $C_{10}$ organylene group; or alternatively, a $C_1$ to $C_5$ organylene group consisting essentially of inert functional groups. In yet another aspect, $L^2$ can be a $C_1$ to $C_{30}$ hydrocarbylene group; alternatively, a $C_1$ to $C_{20}$ hydrocarbylene group; alternatively, a $C_1$ to $C_{15}$ hydrocarbylene group; alternatively, a $C_1$ to $C_{10}$ hydrocarbylene group; or alternatively, a $C_1$ to $C_5$ hydrocarbylene group. In yet other embodiments, $L^2$ can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group.

In an aspect, $L^2$ can be a $C_1$ to $C_{30}$ alkylene group, a $C_4$ to $C_{30}$ cycloalkylene group, a $C_4$ to $C_{30}$ substituted cycloalkylene group, a $C_3$ to $C_{30}$ aliphatic heterocyclylene group, a $C_3$ to $C_{30}$ substituted aliphatic heterocyclylene group, a $C_6$ to $C_{30}$ arylene group, a $C_6$ to $C_{30}$ substituted arylene group, a $C_3$ to $C_{30}$ heteroarylene group, or a $C_3$ to $C_{30}$ substituted heteroarylene group; alternatively, a $C_1$ to $C_{30}$ alkylene group, a $C_4$ to $C_{30}$ cycloalkylene group, a $C_4$ to $C_{30}$ substituted cycloalkylene group, a $C_6$ to $C_{30}$ arylene group, or a $C_6$ to $C_{30}$ substituted arylene group; alternatively, a $C_4$ to $C_{30}$ cycloalkylene group or a $C_4$ to $C_{30}$ substituted cycloalkylene group; alternatively, a $C_3$ to $C_{30}$ aliphatic heterocyclylene group or a $C_3$ to $C_{30}$ substituted aliphatic heterocyclylene group; alternatively, a $C_6$ to $C_{30}$ arylene group or a $C_6$ to $C_{30}$ substituted arylene group; alternatively, a $C_3$ to $C_{30}$ heteroarylene group or a $C_3$ to $C_{30}$ substituted heteroarylene group; alternatively, a $C_1$ to $C_{30}$ alkylene group; alternatively, a $C_4$ to $C_{30}$ cycloalkylene group; alternatively, a $C_4$ to $C_{30}$ substituted cycloalkylene group; alternatively, a $C_3$ to $C_{30}$ aliphatic heterocyclylene group; alternatively, a $C_3$ to $C_{30}$ substituted aliphatic heterocyclylene group; alternatively, a $C_6$ to $C_{30}$ arylene group; alternatively, a $C_6$ to $C_{30}$ substituted arylene group; alternatively, a $C_3$ to $C_{30}$ heteroarylene group; or alternatively, a $C_3$ to $C_{30}$ substituted heteroarylene group. In an embodiment, $L^2$ can be a $C_1$ to $C_{15}$ alkylene group, a $C_4$ to $C_{20}$ cycloalkylene group, a $C_4$ to $C_{20}$ substituted cycloalkylene group, a $C_3$ to $C_{20}$ aliphatic heterocyclylene group, a $C_3$ to $C_{20}$ substituted aliphatic heterocyclylene group, a $C_6$ to $C_{20}$ arylene group, a $C_6$ to $C_{20}$ substituted arylene group, a $C_3$ to $C_{20}$ heteroarylene group, or a $C_3$ to $C_{20}$ substituted heteroarylene group; alternatively, a $C_1$ to $C_{15}$ alkylene group, a $C_4$ to $C_{20}$ cycloalkylene group, a $C_4$ to $C_{20}$ substituted cycloalkylene group, a $C_6$ to $C_{20}$ arylene group, or a $C_6$ to $C_{20}$ substituted arylene group; alternatively, a $C_4$ to $C_{20}$ cycloalkylene group or a $C_4$ to $C_{20}$ substituted cycloalkylene group; alternatively, a $C_3$ to $C_{20}$ aliphatic heterocyclylene group or a $C_3$ to $C_{20}$ substituted aliphatic heterocyclylene group; alternatively, a $C_6$ to $C_{20}$ arylene group or a $C_6$ to $C_{20}$ substituted arylene group; alternatively, a $C_3$ to $C_{20}$ heteroarylene group or a $C_3$ to $C_{20}$ substituted heteroarylene group; alternatively, a $C_1$ to $C_{15}$ alkylene group; alternatively, a $C_4$ to $C_{20}$ cycloalkylene group; alternatively, a $C_4$ to $C_{20}$ substituted cycloalkylene group; alternatively, a $C_3$ to $C_{20}$ aliphatic heterocyclylene group; alternatively, a $C_3$ to $C_{20}$ substituted aliphatic heterocyclylene group; alternatively, a $C_6$ to $C_{20}$ arylene group; alternatively, a $C_6$ to $C_{20}$ substituted arylene group; alternatively, a $C_3$ to $C_{20}$ heteroarylene group; or alternatively, a $C_3$ to $C_{20}$ substituted heteroarylene group. In other embodiments, $L^2$ can be a $C_1$ to $C_{10}$ alkylene group, a $C_4$ to $C_{15}$ cycloalkylene group, a $C_4$ to $C_{15}$ substituted cycloalkylene group, a $C_3$ to $C_{15}$ aliphatic heterocyclylene group, a $C_3$ to $C_{15}$ substituted aliphatic heterocyclylene group, a $C_6$ to $C_{15}$ arylene group, a $C_6$ to $C_{15}$ substituted arylene group, a $C_3$ to $C_{15}$ heteroarylene group, or a $C_3$ to $C_{15}$ substituted heteroarylene group; alternatively, a $C_1$ to $C_{10}$ alkylene group, a $C_4$ to $C_{15}$ cycloalkylene group, a $C_4$ to $C_{15}$ substituted cycloalkylene group, a $C_6$ to $C_{15}$ arylene group, or a $C_6$ to $C_{15}$ substituted arylene group; alternatively, a $C_4$ to $C_{15}$ cycloalkylene group or a $C_4$ to $C_{15}$ substituted cycloalkylene group; alternatively, a $C_3$ to $C_{15}$ aliphatic heterocyclylene group or a $C_3$ to $C_{15}$ substituted aliphatic heterocyclylene group; alternatively, a $C_6$ to $C_{15}$ arylene group or a $C_6$ to $C_{15}$ substituted arylene group; alternatively, a $C_3$ to $C_{15}$ heteroarylene group; or alternatively, a $C_3$ to $C_{15}$ substituted heteroarylene group. In further embodiments, $L^2$ can be a $C_1$ to $C_5$ alkylene group.

In an embodiment, $L^2$ be a bond, a methylene group, an ethylene group, a propylene group, a butylene group, a pentylene group, a hexylene group, a heptylene group, an octylene group, a nonylene group, a decylene group, a undecylene group, a dodecylene group, a tridecylene group, a tetradecylene group, a pentadecylene group, a hexadecylene group, a heptadecylene group, an octadecylene group, or a nonadecylene group; or alternatively, a methylene group, an ethylene group, a propylene group, a butylene group, a pentylene group, a hexylene group, a heptylene group, an octylene group, a nonylene group, a decylene group. In some embodiments, $L^2$ can be a methylene group, an ethylene group, a propylene group, a butylene group, or a pentylene group. In other embodiments, $L^2$ can be a bond; alternatively, a methylene group; alternatively, an ethylene group; alternatively, a propylene group; alternatively, a butylene group; alternatively, a pentylene group; alternatively, a hexylene group; alternatively, a heptylene group; alternatively, an octylene group; alternatively, a nonylene group; alternatively, a decylene group; alternatively, a undecylene group; alternatively, a dodecylene group; alternatively, a tridecylene group; alternatively, a tetradecylene group; alternatively, a pentadecylene group; alternatively, a hexadecylene group; alternatively, a heptadecylene group; alternatively, an octadecylene group; or alternatively, a nonadecylene group. In some embodiments, $L^2$ can be a bond, a methylene group, an eth-1,2-ylene group, a prop-1,3-ylene group, a but-1,4-ylene group, a but-2,3-ylene group, a pent-1,5-ylene group, a 2,2-dimethylprop-1,3-ylene group, a hex-1,6-ylene group, or a 2,3-dimethylbut-2,3-ylene group; alternatively, an eth-1,2-ylene group, a prop-1,3-ylene group, a but-1,4-ylene group, a pent-1,5-ylene group, or a hex-1,6-ylene group; alternatively, a bond; alternatively, a methylene group; alternatively, an eth-1,2-ylene group; alternatively, a prop-1,3-ylene group; alternatively, a but-1,4-ylene group; alternatively, a but-2,3-ylene group; alternatively, a pent-1,5-ylene group; alternatively, a 2,2-dimethylprop-1,3-ylene group; alternatively, a hex-1,6-ylene group; or alternatively, a 2,3-dimethylbut-2,3-ylene group. In some embodiments, the alkylene groups which can be utilized as $L^2$ can be substituted. Each substituent of a substituted alkylene group independently can be a halogen or a hydrocarboxy group; alternatively, a halogen; or alternatively, a hydrocarboxy group. Halogens and hydrocarboxy groups that can be utilized as substituents are independently disclosed herein (e.g. as substituents for substituted $R^1$ groups) and can be utilized without limitation to further describe the substituted alkylene group which can be utilized as $L^2$.

In an aspect, $L^2$ can have the formula $-CR^{1a}R^{2a}(CH_2)_t$ $CR^{3a}R^{4a}-$ wherein each $R^{1a}$, $R^{2a}$, $R^{3a}$, and $R^{4a}$ independently can be hydrogen, a halogen, a $C_1$ to $C_5$ alkyl group, or a $C_1$ to $C_5$ alkoxy group and t can be zero or an integer ranging from 1 to 28. In an embodiment, $R^{1a}$, $R^{2a}$, $R^{3a}$, $R^{4a}$ independently can be hydrogen, a halogen, or a $C_1$ to $C_5$ alkyl group; alternatively, hydrogen, a halogen, or a $C_1$ to $C_5$ alkoxy group; alternatively, hydrogen, a $C_1$ to $C_5$ alkyl group, or a $C_1$ to $C_5$ alkoxy group; alternatively, hydrogen or a halogen; alternatively, hydrogen or a $C_1$ to $C_5$ alkyl group; alternatively, hydrogen or a $C_1$ to $C_5$ alkoxy group; alternatively, hydrogen; or alternatively, a $C_1$ to $C_5$ alkyl group. In an embodiment, t can be an integer ranging from 1 to 18; alternatively, 1 to 13; alternatively, 1 to 8; or alternatively, 1 to 3. In other embodiments, t can be zero. Halogens, $C_1$ to $C_5$ alkyl groups, and $C_1$ to $C_s$ alkoxy groups that can be utilized as substituents are independently described herein and can be utilized, without limitation, to further describe $L^2$ having the formula —$CR^{1a}R^{2a}(CH_2)_t CR^{3a}R^{4a}$—. In another aspect, $L^2$ may have the formula —$(CH_2)_s$— wherein s can be an integer ranging from 1 to 30. In an embodiment, s can be an integer ranging from 1 to 20; alternatively, 1 to 15; alternatively, 1 to 10; or alternatively, 1 to 5.

In an embodiment, $L^2$ can be a cyclobutylene group, a substituted cyclobutylene group, a cyclopentylene group, a substituted cyclopentylene group, a cyclohexylene group, a substituted cyclohexylene group, a cycloheptylene group, a substituted cycloheptylene group, a cyclooctylene group, or a substituted cyclooctylene group. In some embodiments, a $L^2$ can be a cyclopentylene group, a substituted cyclopentylene group, a cyclohexylene group, a substituted cyclohexylene group. In other embodiments, $L^2$ can be a cyclobutylene group or a substituted cyclobutylene group; alternatively, a cyclopentylene group or a substituted cyclopentylene group; alternatively, a cyclohexylene group or a substituted cyclohexylene group; alternatively, a cycloheptylene group or a substituted cycloheptylene group; or alternatively, a cyclooctylene group, or a substituted cyclooctylene group. In further embodiments, $L^2$ can be a cyclopentylene group; alternatively, a substituted cyclopentylene group; a cyclohexylene group; or alternatively, a substituted cyclohexylene group.

In an embodiment, $L^2$ can be a cyclopent-1,3-ylene group, a substituted cyclopent-1,3-ylene group, a cyclohex-1,3-ylene group, a substituted cyclohex-1,3-ylene group, a cyclohex-1,4-ylene group, or a substituted cyclohex-1,4-ylene group; alternatively, cyclopent-1,3-ylene group, a cyclohex-1,3-ylene group, or a cyclohex-1,4-ylene group. In some embodiments, $L^2$ can be a cyclopent-1,3-ylene group, or a substituted cyclopent-1,3-ylene group; alternatively, acyclohex-1,3-ylene group, a substituted cyclohex-1,3-ylene group, a cyclohex-1,4-ylene group, or a substituted cyclohex-1,4-ylene group; alternatively, a cyclohex-1,3-ylene group or a substituted cyclohex-1,3-ylene group; alternatively, a cyclohex-1,4-ylene group or a substituted cyclohex-1,4-ylene group; alternatively, a cyclopent-1,3-ylene group, a cyclohex-1,3-ylene group, or a cyclohex-1,4-ylene group; or alternatively, a substituted cyclopent-1,3-ylene group, a substituted cyclohex-1,3-ylene group, or a substituted cyclohex-1,4-ylene group. In other embodiments, $L^1$ can be a cyclopent-1,3-ylene group; alternatively, a substituted cyclopent-1,3-ylene group; alternatively, a cyclohex-1,3-ylene group; alternatively, a substituted cyclohex-1,3-ylene group; alternatively, a cyclohex-1,4-ylene group; or alternatively, a substituted cyclohex-1,4-ylene group.

In an aspect, $L^2$ can be a bicyclylene group, a substituted bicyclylene group, a bis(cyclylene)methane group, a substituted bis(cyclylene)methane group, a bis(cyclylene)ethane group, or a substituted bis(cyclylene)ethane group; alternatively, a bicyclylene group, a bis(cyclylene)methane group, or a bis(cyclylene)ethane group; or alternatively, a substituted bicyclylene group, a substituted bis(cyclylene)methane group, or a substituted bis(cyclylene)ethane group. In an embodiment, $L^2$ can be a bicyclylene group or a substituted bicyclylene group; alternatively, a bis(cyclylene)methane group or a substituted bis(cyclylene)methane group; or alternatively, a bis(cyclylene)ethane group or a substituted bis(cyclylene)ethane group. In some embodiments, $L^2$ can be a bicyclylene group; alternatively, a substituted bicyclylene group; alternatively, a bis(cyclylene)methane group; alternatively, a substituted bis(cyclylene)methane group; alternatively, a bis(cyclylene)ethane group; or alternatively, a substituted bis(cyclylene)ethane group. Generally, any bis(cyclylene)ethane group disclosed herein (substituted or unsubstituted) can be a bis-1,1-(cyclylene)ethane group or a bis-1,2-(cyclylene)ethane group; alternatively, a bis-1,1-(cyclylene)ethane group; or alternatively, a bis-1,2-(cyclylene)ethane group.

In an aspect, $L^2$ can be a bicyclohexylene group, a substituted bicyclohexylene group, a bis(cyclohexylene)methane group, a substituted bis(cyclohexylene)methane group, a bis(cyclohexylene)ethane group, or a substituted bis(cyclohexylene)ethane group; alternatively, a bicyclohexylene group, a bis(cyclohexylene)methane group, or a bis(cyclohexylene)ethane group; or alternatively, a substituted bicyclohexylene group, a substituted bis(cyclohexylene)methane group, or a substituted bis(cyclohexylene)ethane group. In an embodiment, $L^2$ can be a bicyclohexylene group or a substituted bicyclohexylene group; alternatively, a bis(cyclohexylene)methane group or a substituted bis(cyclohexylene)methane group; or alternatively, a bis(cyclohexylene)ethane group or a substituted bis(cyclohexylene)ethane group. In some embodiments, $L^2$ can be a bicyclohexylene group; alternatively, a substituted bicyclohexylene group; alternatively, a bis(cyclohexylene)methane group; alternatively, a substituted bis(cyclohexylene)methane group; alternatively, a bis(cyclohexylene)ethane group; or alternatively, a substituted bis(cyclohexylene)ethane group. Generally, any bis(cyclohexylene)ethane group disclosed herein (substituted or unsubstituted) can be a bis-1,1-(cyclohexylene)ethane group or a bis-1,2-(cyclohexylene)ethane group; alternatively, a bis-1,1-(cyclohexylene)ethane group; or alternatively, a bis-1,2-(cyclohexylene)ethane group.

In an embodiment, $L^2$ can be a bicyclohex-4,4'-ylene group, a 3,3'-disubstituted bicyclohex-4,4'-ylene group, a 3,3',5,5'-tetrasubstitutedbicyclohex-4,4'-ylene group, a bis(cyclohex-4-ylene) group, a bis(3-substituted cyclohex-4-ylene)methane group, a bis(3,5-disubstituted cyclohex-4-ylene)methane group, a bis-1,2-(cyclohex-4-ylene)ethane group, a bis-1,2-(3-substituted cyclohex-4-ylene)ethane group, or a bis-1,2-(3,5-disubstituted cyclohex-4-ylene)ethane group. In some embodiments, $L^2$ can be a bicyclohex-4,4'-ylene group, 3,3'-disubstituted bicyclohex-4,4'-ylene group or a 3,3',5,5'-tetrasubstitutedbicyclohex-4,4'-ylene group; alternatively, a bis(cyclohex-4-ylene)methane group, a bis(3-substituted cyclohex-4-ylene)methane group or a bis(3,5-disubstituted cyclohex-4-ylene)methane group; or alternatively, a bis-1,2-(cyclohex-4-ylene)ethane group, a bis-1,2-(3-substituted cyclohex-4-ylene)ethane group or a bis-1,2-(3,5-disubstituted cyclohex-4-ylene)ethane group. In other embodiments, $L^2$ can be a bicyclohex-4,4'-ylene group; alternatively, a 3,3'-disubstituted bicyclohex-4,4'-ylene group; alternatively, a 3,3',5,5'-tetrasubstitutedbicyclohex-4,4'-ylene group; alternatively, a bis(cyclohex-4-ylene)methane group; alternatively, a bis(3-substituted cyclohex-4-ylene)methane group; alternatively, a bis(3,5-disubstituted cyclohex-4-ylene)methane group; alternatively, a bis-1,2-(cyclohex-4-ylene)ethane group; alternatively, a bis-1,2-(3-substituted cyclohex-4-ylene)ethane group; or alternatively, a bis-1,2-(3,5-disubstituted cyclohex-4-ylene)ethane group.

In an embodiment, $L^2$ can be a di(methylene)cycloalkane group or a substituted di(methylene)cycloalkane group; or alternatively, a di(methylene)cycloalkane group. The cycloalkane group of the di(methylene)cycloalkane group can be cyclobutane group, a substituted cyclobutane group, a cyclopentane group, a substituted cyclopentane group, a cyclohexane group, a substituted cyclohexane group, a cycloheptane group, a substituted cycloheptane group, a cyclooctane group, or a substituted cyclooctane group; alternatively, a cyclopentane group, a substituted cyclopentane group, a cyclohexane group, or a substituted cyclohexane group; alternatively, a cyclobutane group or a substituted cyclobutane group; alternatively, a cyclopentane group or a substituted cyclopentane group; alternatively, a cyclohexane group or a substituted cyclohexane group; alternatively, a cycloheptane group or a substituted cycloheptane group; or alternatively, a cyclooctane group, or a substituted cyclooctane group. In some embodiments, the cycloalkane group of the di(methylene)cycloalkane group can be cyclobutane group, a cyclopentane group, a cyclohexane group, a cycloheptane group, or a cyclooctane group; or alternatively, a cyclopentane group or a cyclohexane group. In other embodiments, the cycloalkane group of the di(methylene)cycloalkane group can be cyclopentane group; alternatively, a substituted cyclopentane group; a cyclohexane group; or alternatively, a substituted cyclohexane group.

In an embodiment, $L^2$ can be a 1,3-di(methylene)cyclopentane group, a substituted 1,3-di(methylene)cyclopentane group, a 1,3-di(methylene)cyclohexane group, a substituted 1,3-di(methylene)cyclohexane group, a 1,4-di(methylene)cyclohexane group, or a substituted 1,4-di(methylene)cyclohexane group; or alternatively, a 1,3-di(methylene)cyclopentane group, a 1,3-di(methylene)cyclohexane group, or a 1,4-di(methylene)cyclohexane group. In some embodiments, $L^2$ can be a 1,3-di(methylene)cyclopentane group, a substituted 1,3-di(methylene)cyclopentane group; alternatively, a 1,3-di(methylene)cyclohexane group, a substituted 1,3-di(methylene)cyclohexane group, a 1,4-di(methylene)cyclohexane group, or a substituted 1,4-di(methylene)cyclohexane group; alternatively, a 1,3-di(methylene)cyclohexane group, a substituted 1,3-di(methylene)cyclohexane group; alternatively, a 1,4-di(methylene)cyclohexane group, or a substituted 1,4-di(methylene)cyclohexane group; alternatively, 1,3-di(methylene)cyclopentane group; alternatively, a 1,3-di(methylene)cyclohexane group; or alternatively, a 1,4-di(methylene)cyclohexane group.

In an aspect, $L^2$ can be a phenylene group or a substituted phenylene group. In an embodiment, $L^2$ can be a phenylene group; or alternatively, a substituted phenylene group. In some embodiments, $L^2$ can be a phen-1,2-ylene group or a substituted phen-1,2-ylene group; alternatively, a phen-1,2-ylene group; or alternatively, a substituted phen-1,2-ylene group. In other embodiments, $L^2$ can be a phen-1,3-ylene group or a substituted phen-1,3-ylene group; alternatively, a phen-1,3-ylene group; or alternatively, a substituted phen-1,3-ylene group. In yet other embodiments, $L^2$ can be a phen-1,4-ylene group or a substituted phen-1,4-ylene group; alternatively, a phen-1,4-ylene group; or alternatively, a substituted phen-1,4-ylene group. In further embodiments, $L^2$ can be a phen-1,2-ylene group, a phen-1,3-ylene group, or a phen-1,4-ylene group; alternatively, a phen-1,3-ylene group or a phen-1,4-ylene group. In other embodiments, $L^2$ can be a substituted phen-1,2-ylene group, a substituted phen-1,3-ylene group, or a substituted phen-1,4-ylene group; alternatively, a substituted phen-1,3-ylene group, or a substituted phen-1,4-ylene group.

In an aspect, $L^2$ can be a naphthylene group or a substituted naphthylene group. In an embodiment, $L^2$ can be a naphthylene group; or alternatively, a substituted naphthylene group. In some embodiments, $L^2$ can be a naphth-1,3-ylene group, a substituted naphth-1,3-ylene group, a naphth-1,4-ylene group, a substituted naphth-1,4-ylene group, a naphth-1,5-ylene group, a substituted naphth-1,5-ylene group, a naphth-1,6-ylene group, a substituted naphth-1,6-ylene group, a naphth-1,7-ylene group, a substituted naphth-1,7-ylene group, a naphth-1,8-ylene group, or a substituted naphth-1,8-ylene group. In other embodiments, $L^2$ can be a naphth-1,3-ylene group or a substituted naphth-1,3-ylene group; alternatively, a naphth-1,4-ylene group or a substituted naphth-1,4-ylene group; alternatively, a naphth-1,5-ylene group or a substituted naphth-1,5-ylene group; alternatively, a naphth-1,6-ylene group or a substituted naphth-1,6-ylene group; alternatively, a naphth-1,7-ylene group or a substituted naphth-1,7-ylene group; or alternatively, a naphth-1,8-ylene group or a substituted naphth-1,8-ylene group. In yet other embodiments, $L^2$ can be a naphth-1,3-ylene group; alternatively, a substituted naphth-1,3-ylene group; alternatively, a naphth-1,4-ylene group; alternatively, a substituted naphth-1,4-ylene group; alternatively, a naphth-1,5-ylene group; alternatively, a substituted naphth-1,5-ylene group; alternatively, a naphth-1,6-ylene group; alternatively, a substituted naphth-1,6-ylene group; alternatively, a naphth-1,7-ylene group; alternatively, a substituted naphth-1,7-ylene group; alternatively, a naphth-1,8-ylene group; or alternatively, a substituted naphth-1,8-ylene group.

In an aspect, $L^2$ can be a biphenylene group, a substituted biphenylene group, a bis(phenylene)methane group, a substituted bis(phenylene)methane group, a bis(phenylene)ethane group, or a substituted bis(phenylene)ethane group; or alternatively, a biphenylene group, a bis(phenylene)methane group, or a bis(phenylene)ethane group; or alternatively, a substituted biphenylene group, a substituted bis(phenylene)methane group, or a substituted bis(phenylene)ethane group. In an embodiment, $L^2$ can be a biphenylene group or a substituted biphenylene group; alternatively, bis(phenylene)methane group or a substituted bis(phenylene)methane group; or alternatively, a bis(phenylene)ethane group or a substituted bis(phenylene)ethane group. In some embodiments, $L^2$ can be a biphenylene group; alternatively, a substituted biphenylene group; alternatively, a bis(phenylene)methane group; alternatively, a substituted bis(phenylene)methane group; alternatively, a bis(phenylene)ethane group; or alternatively, a substituted bis(phenylene)ethane group. Generally, any bis(phenylene)ethane group disclosed herein (substituted or unsubstituted) can be a bis-1,1-(phenylene)ethane group or a bis-1,2-(phenylene)ethane group; alternatively, a bis-1,1-(phenylene)ethane group; or alternatively, a bis-1,2-(phenylene)ethane group.

In an embodiment, $L^2$ can be a biphen-3-ylene group, a substituted biphen-3-ylene group, a biphen-4-ylene group, or a substituted biphen-4-ylene group. In some embodiments, $L^2$ can be a biphen-3-ylene group or a substituted biphen-3-ylene group; or alternatively, a biphen-4-ylene group or a substituted biphen-4-ylene group. In other embodiments, $L^1$ can be a biphen-3-ylene group; alternatively, a substituted biphen-3-ylene group; alternatively, a biphen-4-ylene group; or alternatively, a substituted biphen-4-ylene group.

In an embodiment, $L^2$ can be a bis(phen-3-ylene)methane group, a substituted bis(phen-3-ylene)methane group, a bis(phen-4-ylene)methane group, or a substituted bis(phen-4-ylene)methane group. In some embodiments, $L^2$ can be a bis(phen-3-ylene)methane group or a substituted bis(phen-3-ylene)methane group; or alternatively, a bis(phen-4-ylene)

methane group or a substituted bis(phen-4-ylene)methane group. In other embodiments, $L^2$ can be a bis(phen-3-ylene) methane group; alternatively, a substituted bis(phen-3-ylene) methane group; alternatively, a bis(phen-4-ylene)methane group; or alternatively, a substituted bis(phen-4-ylene)methane group.

In an embodiment, $L^2$ can be a bis(phen-3-ylene)ethane group, a substituted bis(phen-3-ylene)ethane group, a bis (phen-4-ylene)ethane group, or a substituted bis(phen-4-ylene)ethane group. In some embodiments, $L^2$ can be a bis (phen-3-ylene)ethane group or a substituted bis(phen-3-ylene)ethane group; or alternatively, a bis(phen-4-ylene) ethane group or a substituted bis(phen-4-ylene)ethane group. In other embodiments, $L^2$ can be a bis(phen-3-ylene)ethane group; alternatively, a substituted bis(phen-3-ylene)ethane group; alternatively, bis(phen-4-ylene)ethane group; or alternatively, a substituted bis(phen-4-ylene)ethane group. Generally, any bis(phenylene)ethane group disclosed herein (substituted or unsubstituted) may be a bis-1,1-(phenylene)ethane group or a bis-1,2-(phenylene)ethane group; alternatively, a bis-1,1-(phenylene)ethane group; or alternatively, a bis-1,2-(phenylene)ethane group.

In an aspect, $L^2$ can be a di(methylene)benzene group, or a substituted di(methylene)benzene group; alternatively, a di(methylene) benzene group. In an embodiment, $L^2$ can be a 1,2-di(methylene)benzene group, a substituted 1,2-di(methylene)benzene group, a 1,3-di(methylene)benzene group, a substituted 1,3-di(methylene)benzene group, a 1,4-di(methylene)benzene group, or a substituted 1,4-di(methylene)benzene group; alternatively, a 1,2-di(methylene)benzene group, a 1,3-di(methylene)benzene group, or a 1,4-di(methylene) benzene group. In some embodiments, $L^2$ can be a 1,2-di (methylene)benzene group or a substituted 1,2-di(methylene) benzene group; alternatively, a 1,3-di(methylene)benzene group or a substituted 1,3-di(methylene)benzene group; alternatively, a 1,4-di(methylene)benzene group or a substituted 1,4-di(methylene)benzene group; alternatively, a 1,2-di (methylene)benzene group; alternatively, a 1,3-di(methylene)benzene group; or alternatively, a 1,4-di(methylene) benzene group.

In an embodiment, each substituent for any substituted $L^2$ group (general or specific) independently can be a halogen, a hydrocarbyl group, or a hydrocarboxy group; alternatively, a halogen or a hydrocarbyl group; alternatively, a hydrocarbyl group or a hydrocarboxy group; alternatively, a halogen; alternatively, a hydrocarbyl group; or alternatively, a hydrocarboxy group. In some embodiments, each substituent for any substituted $L^2$ group (general or specific) independently can be a halogen, an alkyl group, or an alkoxy group; alternatively, a halogen or an alkyl group; alternatively, an alkyl group or an alkoxy group; alternatively, a halogen; alternatively, an alkyl group; or alternatively, an alkoxy group. Halogens, hydrocarbyl groups, hydrocarboxy groups, alkyl group, and alkoxy groups that can be utilized as substituents are independently disclosed herein (e.g. as substituents for substituted $R^1$ groups) and can be utilized without limitation to further describe a substituted $L^2$ group.

In an embodiment, $L^2$ can have any Structure in Table 1. In an embodiment, $L^2$ can have Structure 1L, 2L, 3L, 4L, 5L, 6L, or 7L; or alternatively, 8L, 9L, 10L, 11L, 12L, 13L, or 14L. In some embodiments, $L^2$ can have Structure 1L, 2L, or 3L; alternatively, 4L, 5L, 6L, or 7L; alternatively, 8L, 9L, or 10L; or alternatively, 11L, 12L, 13L, or 14L. In other embodiments, $L^2$ can have Structure 2L or 3L; alternatively, 9L, or 10L; alternatively, 4L or 5L; alternatively, 6L or 7L; or alternatively, 11L or 12L; or alternatively, 13L or 14L. In further embodiments, $L^2$ can have Structure 1L; alternatively, 2L; alternatively, 3L; alternatively, 4L; alternatively, 5L; alternatively, 6L; alternatively, 7L; alternatively, 8L; alternatively, 9L; alternatively, 10L; alternatively, 11L; alternatively, 12L; alternatively, 13L; or alternatively, 14L. Generally, $L^2$ may have any embodiment of Structures 1L-14L described herein. Generally, $L^2$ can have any aspect or embodiment of the Structures of Table 1 described for $L^1$.

In an aspect, the $N^2$-phosphinyl amidine compound can comprise an $N^2$-phosphinyl amidine group and a metal salt complexing group. In another aspect, the $N^2$-phosphinyl amidine compound can comprise an $N^2$-phosphinyl amidine group, a metal salt complexing group, and a linking group linking the metal salt complexing group to the $N^2$-phosphinyl amidine group. In yet another aspect, the $N^2$-phosphinyl amidine compound can comprise an $N^2$-phosphinyl amidine group, a metal salt complexing group, and a linking group linking the metal salt complexing group to the $N^1$ nitrogen atom of the $N^2$-phosphinyl amidine group. Generally, the $N^2$-phosphinyl amidine group and the metal salt complexing group are independent elements of the $N^2$-phosphinyl amidine compound comprising an $N^2$-phosphinyl amidine group and a metal salt complexing group. Consequently, the $N^2$-phosphinyl amidine compound comprising an $N^2$-phosphinyl amidine group and a metal salt complexing group can be described using any combination of the aspects and embodiments of the $N^2$-phosphinyl amidine group described herein and the metal salt complexing group described herein. Additionally, the $N^2$ phosphinyl amidine group, the metal salt complexing group, and the linking group linking the metal salt complexing group to the $N^2$-phosphinyl amidine group (or the linking group linking the metal salt complexing group to the $N^1$ nitrogen atom of the $N^2$-phosphinyl amidine group) are independent elements of the $N^2$-phosphinyl amidine compound comprising an $N^2$-phosphinyl amidine group, a metal salt complexing group, and a linking group liking the metal salt complexing group to the $N^2$-phosphinyl amidine group. Thus, the $N^2$-phosphinyl amidine compound comprising an $N^2$-phosphinyl amidine group, a metal salt complexing group, and a linking group linking the metal salt complexing group to the $N^2$-phosphinyl amidine group (or the linking group linking the metal salt complexing group to the $N^1$ nitrogen atom of the $N^2$-phosphinyl amidine group) can be described using any combination of the aspects and embodiments of the $N^2$-phosphinyl amidine group described herein, the metal salt complexing group described herein, and linking group described herein.

In embodiments, the $N^2$-phosphinyl amidine compound comprising an $N^2$-phosphinyl amidine group, a metal salt complexing group, and a linking group linking the metal salt complexing group to the $N^2$-phosphinyl amidine group can have Structure NP11, Structure NP13, Structure NP15, Structure NP16, Structure NP18, or Structure NP20; alternatively, Structure NP11, Structure NP13, or Structure NP15; alternatively, Structure NP16, Structure NP18, or Structure NP20; alternatively, Structure NP11; alternatively, Structure NP13; alternatively, Structure NP15; alternatively, Structure NP16; alternatively, Structure NP18; or alternatively, Structure NP20. $R^2$, $R^3$, $R^4$, $R^5$, $L^2$, D, and r are independently described as features of the $N^2$-phosphinyl amidine compounds described herein and can be utilized without limitation to describe $R^2$, $R^3$, $R^4$, $R^5$, $L^2$, D, and r in the $N^2$-phosphinyl amidine compounds having Structure NP11, Structure NP13, Structure NP15, Structure NP16, Structure NP18, and/or Structure NP20.

The metal salt complexing group, $Q^1$, can be any group comprising a heteroatom capable of complexing with the metal salt. The linking group, $L^3$, can be any group capable of linking the metal salt complexing group to the $N^2$-phosphinyl amidine group. In some embodiments, the linking group includes all atoms between the $N^1$ nitrogen atom of the $N^2$-phosphinyl amidine group, and the metal salt complexing group. If the metal salt complexing group is acyclic, the linking group includes all atoms between an atom of the $N^2$-phosphinyl amidine group and the heteroatom of metal complexing group; or alternatively, between the $N^1$ nitrogen atom of the $N^2$-phosphinyl amidine group and the heteroatom of the metal salt complexing functional group. For example, in $N^1$-(2-(dimethylamino)ethyl)-$N^2$-(diphenylphosphino) the linking group is —$CH_2CH_2$— and the metal salt complexing group is the N,N-dimethylaminyl group, and in $N^1$-(2-(phenylthio)phenyl)-$N^2$-(diisopropylphosphino) the linking group is the phenyl-1,2-ene group and the metal salt complexing group is the phenylthio group. However, if the heteroatom of the metal salt complexing group is contained within a ring or a ring system, the linking group includes all the atoms between an atom of the $N^2$-phosphinyl amidine group and the first atom of the ring or ring system containing the heteroatom of metal complexing group; or alternatively, between the $N^1$ nitrogen atom of the $N^2$-phosphinyl amidine group and the first atom of the ring or ring system containing the heteroatom of metal complexing group. For example, in $N^1$-(2-(morpholin-1-yl)ethyl)-$N^2$-(diisopropylphosphino) the linking group is —$CH_2CH_2$— and the metal salt complexing group is the morpholin-1-yl group and in $N^1$-(thiazol-2-yl)-$N^2$-(diphenylphosphino) the linking group is a bond and the metal salt complexing group is the thiazol-2-yl group.

The metal salt complexing group, $Q^1$, can be any group comprising a heteroatom capable of complexing with the metal salt. In embodiments, the metal salt complexing group can be a $C_1$ to $C_{30}$ group comprising a heteroatom; alternatively, a $C_1$ to $C_{20}$ group comprising a heteroatom; alternatively, a $C_1$ to $C_{15}$ group comprising a heteroatom; alternatively, a $C_1$ to $C_{10}$ group comprising a heteroatom; or alternatively, a $C_1$ to $C_5$ group comprising a heteroatom. In some embodiments, the metal salt complexing heteroatom of the metal salt complexing group can be oxygen, sulfur, nitrogen, or phosphorus. In other embodiments, the metal salt complexing heteroatom of the metal salt complexing group can be oxygen or sulfur. In yet other embodiments, the metal salt complexing heteroatom of the metal salt complexing group can be nitrogen, or phosphorus. In further embodiments, the metal salt complexing heteroatom of the metal salt complexing group can be oxygen; alternatively, sulfur; alternatively, nitrogen; or alternatively, phosphorus. Optionally, the metal salt complexing group can contain additional heteroatoms which do not complex the metal salt in an $N^2$-phosphinyl amidine metal salt complex such as inert heteroatoms (e.g. halides, or silicon) and/or additional metal salt complexing heteroatom(s) which do not complex with the metal salt (e.g. because of the position in the non-complexing metal complexing group within the $N^2$-phosphinyl amidine compound).

In an embodiment, the metal salt complexing group can be a dihydrocarbyl aminyl group, a dihydrocarbyl phosphinyl group, a hydrocarbyl etheryl group, or a hydrocarbyl sulfidyl group. In some embodiments, the metal salt complexing group can be a dihydrocarbyl aminyl group; alternatively, a dihydrocarbyl phosphinyl group; alternatively, a hydrocarbyl etheryl group; or alternatively, a hydrocarbyl sulfidyl group. In an embodiment, each hydrocarbyl group of the dihydrocarbyl aminyl group, the dihydrocarbyl phosphinyl group, the hydrocarbyl etheryl group, or a hydrocarbyl sulfidyl group utilized as a metal salt complexing group can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In some embodiments, each hydrocarbyl group of the dihydrocarbyl aminyl group, the dihydrocarbyl phosphinyl group, the hydrocarbyl etheryl group, or a hydrocarbyl sulfidyl group utilized as a metal salt complexing group can be an alkyl group, an cycloalkyl group, an aryl group, or an aralkyl group; alternatively, an alkyl group; alternatively, an cycloalkyl group; alternatively, an aryl group; or alternatively, an aralkyl group. Alkyl groups, cycloalkyl groups, aryl groups, and aralkyl groups are independently disclosed herein and may be utilized without limitation to further describe the metal salt complexing group.

In some embodiments, the metal complexing group can be dialkyl aminyl group, a dicycloalkyl aminyl group, a di(substituted cycloalkyl) aminyl group), an N-(alkyl)-N-(cycloalkyl) aminyl group, an N-(alkyl)-N-(substituted cycloalkyl) aminyl group, an N-(cycloalkyl)-N-(substituted cycloalkyl) aminyl group, a diaryl aminyl group, a di(substituted aryl) aminyl group, an N-aryl-N-(substituted aryl) aminyl group, an N-alkyl-N-aryl aminyl group, an N-alkyl-N-(substituted aryl) aminyl group, a dialkyl phosphinyl group, a dicycloalkyl phosphinyl group, a di(substituted cycloalkyl) phosphinyl group), an N-(alkyl)-N-(cycloalkyl) phosphinyl group, an N-(alkyl)-N-(substituted cycloalkyl) phosphinyl group, an N-(cycloalkyl)-N-(substituted cycloalkyl) phosphinyl group, a diaryl phosphinyl group, a di(substituted aryl) phosphinyl group, a P-aryl-P-(substituted aryl) phosphinyl group, a P-alkyl-P-aryl phosphinyl group, a P-alkyl-P-(substituted aryl) phosphinyl group, an alkyl etheryl group, an aryl etheryl group, a substituted aryl etheryl group, an alkyl sulfidyl group, an aryl sulfidyl group, a substituted aryl sulfidyl group, a furanyl group, a substituted furanyl group, a thienyl group, a substituted thienyl group, a tetrahydrofuranyl group, a substituted tetrahydrofuranyl group, a thiophanyl group, a substituted thiophanyl group, a pyridinyl group, a substituted pyridinyl group, a morphilinyl group, a substituted morphilinyl group, a pyranyl group, a substituted pyranyl group, a tetrahydropyranyl group, a substituted tetrahydropyranyl group, a quinolinyl group, a substituted quinolinyl group, a pyrrolyl group, a substituted pyrrolyl group, a pyrrolidinyl group, a substituted pyrrolidinyl group, a piperidinyl group, or a substituted piperidinyl group. In embodiments, the metal salt complexing group can be a dialkyl aminyl group, a dicycloalkyl aminyl group, a diaryl aminyl group, a dialkyl phosphinyl group, a dicycloalkyl phosphinyl group, a diaryl phosphinyl group, an alkyl etheryl group, an aryl etheryl group, an alkyl sulfidyl group, an aryl sulfidyl group, a furanyl group, a thienyl group, a tetrahydrofuranyl group, a thiophanyl group, a pyridinyl group, a morphilinyl group, a pyranyl group, a tetrahydropyranyl group, a quinolinyl group, a pyrrolyl group, a pyrrolidinyl group, or a piperidinyl group. In some embodiments, the metal salt complexing group can be a dialkyl aminyl group, a dicycloalkyl aminyl group, a di(substituted cycloalkyl) aminyl group, a diaryl aminyl group, a di(substituted aryl) aminyl group, a dialkyl phosphinyl group, a dicycloalkyl phosphinyl group, a di(substituted cycloalkyl) phosphinyl group, a diaryl phosphinyl group, a di(substituted aryl) phosphinyl group, an alkyl etheryl group, an aryl etheryl group, a substituted aryl etheryl group, an alkyl sulfidyl group, an aryl sulfidyl group, a substituted aryl sulfidyl group, a pyridinyl group, a substituted pyridinyl group, a morphilinyl group, or a substituted morphilinyl group; alternatively, a dialkyl aminyl group, a diaryl aminyl group, a dialkyl phosphinyl group, a diaryl phosphinyl group, an alkyl etheryl group, an aryl etheryl group, an alkyl sulfidyl group, an aryl sulfidyl group, a pyridinyl group, or a morphilinyl group;

alternatively, a dialkyl aminyl group, a dicycloalkyl aminyl group, a di(substituted cycloalkyl) aminyl group, a diaryl aminyl group, a di(substituted aryl) aminyl group, a dialkyl phosphinyl group, a dicycloalkyl phosphinyl group, a di(substituted cycloalkyl) phosphinyl group, a diaryl phosphinyl group, or a di(substituted aryl) phosphinyl group; alternatively, a dialkyl aminyl group, a diaryl aminyl group, a dialkyl phosphinyl group, a diaryl phosphinyl group; or alternatively, a diaryl aminyl group, a di(substituted aryl) aminyl group, or an N-aryl-N-(substituted aryl) aminyl group a diaryl phosphinyl group, a di(substituted aryl) phosphinyl group, or an P-aryl-P-(substituted aryl) phosphinyl group; alternatively, a diaryl aminyl group, a di(substituted aryl) phosphinyl group, or an N-aryl-N-(substituted aryl) aminyl group a diaryl phosphinyl group, a di(substituted aryl) phosphinyl group, or an P-aryl-P-(substituted aryl) phosphinyl group, an aryl sulfidyl group, a substituted aryl sulfidyl group, a pyridinyl group, or a substituted pyridinyl group; or alternatively, a diaryl aminyl group, a diaryl phosphinyl group, an aryl sulfidyl group, or a pyridinyl group. In other embodiments, the metal salt complexing group can be a dialkyl aminyl group or a dialkyl phosphinyl group; alternatively, a diaryl aminyl group or a diaryl phosphinyl group; alternatively, a di(substituted aryl) aminyl group or a di(substituted aryl) phosphinyl group; alternatively, a 2-pyridinyl group or a substituted 2-pyridinyl group; alternatively, an alkyl etheryl group, a phenyl etheryl group, a substituted aryl etheryl group, an alkyl sulfidyl group, an aryl sulfidyl group, or a substituted sulfidyl group; alternatively, an alkyl etheryl group or an alkyl sulfidyl group; alternatively, an aryl etheryl group, a substituted aryl etheryl group, an aryl sulfidyl group, or a substituted sulfidyl group; alternatively, an aryl etheryl group or a substituted aryl etheryl group; alternatively, an aryl sulfidyl group, or a substituted aryl sulfidyl group; alternatively, an aryl sulfidyl group or a substituted aryl sulfidyl group; alternatively, a furanyl group, a substituted furanyl group, a thienyl group or a substituted thienyl group; alternatively, a 1-morphilinyl group or a substituted 1-morphilinyl group; alternatively, a 2-morphilinyl group or a substituted 2-morphilinyl group; alternatively, a 2-pyranyl group or a substituted 2-pyranyl group; alternatively, a 2-tetrahydropyranyl group, a substituted 2-tetrahydropyranyl group; alternatively, a 1-piperidinyl group, or a substituted 1-piperidinyl group; alternatively, a 1-pyrrolidinyl group, a substituted 1-pyrrolidinyl group; alternatively, a 2-pyrrolidinyl group, a substituted 2-pyrrolidinyl group; alternatively, a 2-piperidinyl group, or a substituted 2-piperidinyl group; alternatively, a 2-quinolinyl group or a substituted 2-quiolinyl group; alternatively, a 1-pyrrolyl group or a substituted 1-pyrrolyl group; alternatively, a 2-pyrrolyl group or a substituted 2-pyrrolyl group; alternatively, a 2-tetrahydrofuranyl group or a substituted 2-tetrahydrofuranyl group; or alternatively, a 2-thiophanyl group or a substituted 2-thiophanyl group. In yet other embodiments, the metal salt complexing group can be a diaryl aminyl group; alternatively, a di(substituted aryl) aminyl group; alternatively, a diaryl phosphinyl group; or alternatively, a di(substituted aryl) phosphinyl group. Alkyl groups, cycloalkyl groups, aryl groups, and aralkyl groups, and substituent groups which can be utilized for substituted metal complexing groups are independently disclosed herein and can be utilized without limitation to further describe the metal salt complexing group.

In any aspect or embodiment disclosed herein, each alkyl group attached to the heteroatom of a metal salt complexing group independently can be a $C_1$ to $C_{30}$ alkyl group; alternatively, a $C_1$ to $C_{20}$ alkyl group; alternatively, a $C_1$ to $C_{10}$ alkyl group; or alternatively, a $C_1$ to $C_5$ alkyl group. In any aspect or embodiment disclosed herein, each cycloalkyl group attached to the heteroatom of a metal salt complexing group independently can be a $C_4$ to $C_{30}$ cycloalkyl group; alternatively, a $C_4$ to $C_{20}$ cycloalkyl group; alternatively, a $C_4$ to $C_{15}$ cycloalkyl group; or alternatively, a $C_4$ to $C_{10}$ cycloalkyl group. In any aspect or embodiment disclosed herein, each substituted cycloalkyl group attached to the heteroatom of a metal salt complexing group independently can be a $C_4$ to $C_{30}$ substituted cycloalkyl group; alternatively, a $C_4$ to $C_{20}$ substituted cycloalkyl group; alternatively, a $C_4$ to $C_{15}$ substituted cycloalkyl group; or alternatively, a $C_4$ to $C_{10}$ substituted cycloalkyl group. In any aspect or embodiment disclosed herein, each aryl group attached to the heteroatom of a metal salt complexing group independently can be a $C_6$ to $C_{30}$ aryl group; alternatively, a $C_6$ to $C_{20}$ aryl group; alternatively, a $C_6$ to $C_{15}$ aryl group; or alternatively, a $C_6$ to $C_{10}$ aryl group. In any aspect or embodiment disclosed herein, each substituted aryl group attached to the heteroatom of a metal salt complexing group independently can be a $C_6$ to $C_{30}$ substituted aryl group; alternatively, a $C_6$ to $C_{20}$ substituted aryl group; alternatively, a $C_6$ to $C_{15}$ substituted aryl group; or alternatively, a $C_6$ to $C_{10}$ substituted aryl group. In any aspect or embodiment disclosed herein, each aralkyl group attached to the heteroatom of a metal salt complexing group independently can be a $C_7$ to $C_{30}$ aralkyl group; alternatively, a $C_7$ to $C_{20}$ aralkyl group; alternatively, a $C_7$ to $C_{15}$ aralkyl group; or alternatively, a $C_7$ to $C_{10}$ aralkyl group. In any aspect or embodiment disclosed herein, each substituted aryl group attached to the heteroatom of a metal complexing group independently can be a $C_7$ to $C_{30}$ substituted aralkyl group; alternatively, a $C_7$ to $C_{20}$ substituted aralkyl group; alternatively, a $C_7$ to $C_{15}$ aralkyl group; or alternatively, $C_7$ to $C_{10}$ substituted aralkyl group. Each substituent of a general cycloalkyl group, general aryl group, and/or general aralkyl group can be a halogen or a hydrocarboxy group; alternatively, a halogen; or alternatively, a hydrocarboxy group. Substituent halogens, substituent hydrocarbyl groups, and substituent hydrocarboxy groups are independently disclosed herein (e.g. as non-hydrogen substituents of $R^1$ groups in the $N^2$-phosphinyl amidine compound, among other places). These substituent halogens, substituent hydrocarbyl groups, and substituent hydrocarboxy can be utilized without limitation to further describe the metal salt complexing group.

In an embodiment, the metal salt complexing group ($Q^1$) of any $N^2$-phosphinyl amidine compound having a metal salt complexing group ($Q^1$) can have a metal complexing group structure provided in Table 2.

TABLE 2

Example Metal Salt Complexing Groups, $Q^1$.

| | |
|---|---|
| —OR$^{q1}$ | Structure Q1 |
| —SR$^{q2}$ | Structure Q2 |
| —NR$^{q3}$R$^{q4}$ | Structure Q3 |
| —PR$^{q5}$R$^{q6}$ | Structure Q4 |
| 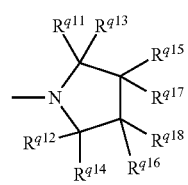 | Structure Q5 |

TABLE 2-continued

Example Metal Salt Complexing Groups, $Q^1$.

Structure Q6

Structure Q7

Structure Q8

Structure Q9

Structure Q10

Structure Q11

Structure Q12

Structure Q13

Structure Q14

TABLE 2-continued

Example Metal Salt Complexing Groups, $Q^1$.

Structure Q15

Structure Q16

Structure Q17

Structure Q18

Structure Q19

Structure Q20

Structure Q21

TABLE 2-continued

Example Metal Salt Complexing Groups, $Q^1$.

Structure Q22

[Structure showing a phosphorus atom bonded to two biphenyl groups with substituents $R^{q71}$, $R^{q72}$, $R^{q73}$, $R^{q74}$, $R^{q75}$, $R^{q76}$, $R^{q77}$, $R^{q78}$, $R^{q79}$, $R^{q70}$]

In some embodiments, the metal salt complexing group can have Structure Q1, Structure Q2, Structure Q3, Structure Q4, Structure Q5, Structure Q6, Structure Q7, Structure Q8, Structure Q9, Structure Q10, Structure Q11, Structure Q12, Structure 13, Structure Q16, Structure Q17, Structure Q18, Structure Q19, or Structure Q20. In other embodiments, the metal salt complexing group can have Structure Q1, Structure Q2, Structure Q3, or Structure Q4; alternatively, Structure Q1 or Structure Q2; alternatively, Structure Q3 or Structure Q4; alternatively, Structure Q5 or Structure Q6; alternatively, Structure Q7 or Structure Q10; alternatively, Structure Q8 or Structure Q9; alternatively, Structure Q11 or Structure Q12; alternatively, Structure Q11 or Structure Q13; alternatively, Structure Q19 or Structure Q20; alternatively, Structure Q1; alternatively, Structure Q2; alternatively, Structure Q3; alternatively, Structure Q4; alternatively, Structure Q5; alternatively, Structure Q6; alternatively, Structure Q7; alternatively, Structure Q8; alternatively, Structure Q9; alternatively, Structure Q10; alternatively, Structure Q11; alternatively, Structure Q12; alternatively, Structure 13; alternatively, Structure Q16; alternatively, Structure Q17; alternatively, Structure Q18; alternatively, Structure Q19; or alternatively, Structure Q20. In further embodiments, the metal salt complexing group can have Structure Q14, Structure Q15, Structure Q21, or Structure Q22; alternatively, Structure Q14 or Structure Q15; alternatively, Structure Q21 or Structure Q22; alternatively, Structure Q14; alternatively, Structure Q15; alternatively, Structure Q21; or alternatively, Structure Q22.

In an aspect, $R^{q1}$, $R^{q2}$, $R^{q3}$, $R^{q4}$, $R^{q5}$, and $R^{q6}$ within Structure Q1, Structure Q2, Structure Q3, and/or Structure Q4 can be a $C_1$ to $C_{20}$ organyl group consisting essentially of inert functional groups; alternatively, a $C_1$ to $C_{20}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In another aspect, $R^{q1}$, $R^{q2}$, $R^{q3}$, $R^{q4}$, $R^{q5}$, and $R^{q6}$ within Structure Q1, Structure Q2, Structure Q3, and/or Structure Q4 can be a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group.

In an embodiment, $R^{q1}$, $R^{q2}$, $R^{q3}$, $R^{q4}$, $R^{q5}$, and $R^{q6}$ within Structure Q1, Structure Q2, Structure Q3, and/or Structure Q4 independently can be a $C_1$ to $C_{20}$ alkyl group, a $C_1$ to $C_{20}$ substituted alkyl group, a $C_4$ to $C_{20}$ cycloalkyl group, a $C_4$ to $C_{20}$ substituted cycloalkyl group, a $C_6$ to $C_{20}$ aryl group, a $C_6$ to $C_{20}$ substituted aryl group, a $C_7$ to $C_{20}$ aralkyl group, or a $C_7$ to $C_{20}$ substituted aralkyl group; alternatively, a $C_1$ to $C_{20}$ alkyl group, a $C_4$ to $C_{20}$ cycloalkyl group, a $C_6$ to $C_{20}$ aryl group, or a $C_7$ to $C_{20}$ aralkyl group; alternatively, a $C_1$ to $C_{20}$ alkyl group or a $C_1$ to $C_{20}$ substituted alkyl group; alternatively, a $C_4$ to $C_{20}$ cycloalkyl group or a $C_4$ to $C_{20}$ substituted cycloalkyl group; alternatively, a $C_6$ to $C_{20}$ aryl group or a $C_6$ to $C_{20}$ substituted aryl group; alternatively, a $C_7$ to $C_{20}$ aralkyl group or a $C_7$ to $C_{20}$ substituted aralkyl group; alternatively, a $C_1$ to $C_{20}$ alkyl group; alternatively, a $C_1$ to $C_{20}$ substituted alkyl group; alternatively, a $C_4$ to $C_{20}$ cycloalkyl group; alternatively, a $C_4$ to $C_{20}$ substituted cycloalkyl group; alternatively, a $C_6$ to $C_{20}$ aryl group; alternatively, a $C_6$ to $C_{20}$ substituted aryl group; alternatively, a $C_7$ to $C_{20}$ aralkyl group; or alternatively, a $C_7$ to $C_{20}$ substituted aralkyl group. In some embodiments, $R^{q1}$, $R^{q2}$, $R^{q3}$, $R^{q4}$, $R^{q5}$, and $R^{q6}$ within Structure Q1, Structure Q2, Structure Q3, and/or Structure Q4 independently can be a $C_1$ to $C_{10}$ alkyl group, a $C_1$ to $C_{10}$ substituted alkyl group, a $C_4$ to $C_{15}$ cycloalkyl group, a $C_4$ to $C_{15}$ substituted cycloalkyl group, a $C_6$ to $C_{15}$ aryl group, a $C_6$ to $C_{15}$ substituted aryl group, a $C_7$ to $C_{15}$ aralkyl group, or a $C_7$ to $C_{15}$ substituted aralkyl group; alternatively, a $C_1$ to $C_{10}$ alkyl group, a $C_4$ to $C_{15}$ cycloalkyl group, a $C_6$ to $C_{15}$ aryl group, or a $C_7$ to $C_{15}$ aralkyl group; alternatively, a $C_1$ to $C_{10}$ alkyl group or a $C_1$ to $C_{10}$ substituted alkyl group; alternatively, a $C_4$ to $C_{15}$ cycloalkyl group or a $C_4$ to $C_{15}$ substituted cycloalkyl group; alternatively, a $C_6$ to $C_{15}$ aryl group or a $C_6$ to $C_{15}$ substituted aryl group; alternatively, a $C_7$ to $C_{15}$ aralkyl group or a $C_7$ to $C_{15}$ substituted aralkyl group; alternatively, a $C_1$ to $C_{10}$ alkyl group; alternatively, a $C_1$ to $C_{10}$ substituted alkyl group; alternatively, a $C_4$ to $C_{15}$ cycloalkyl group; alternatively, a $C_4$ to $C_{15}$ substituted cycloalkyl group; alternatively, a $C_6$ to $C_{15}$ aryl group; alternatively, a $C_6$ to $C_{15}$ substituted aryl group; alternatively, a $C_7$ to $C_{15}$ aralkyl group; or alternatively, a $C_7$ to $C_{15}$ substituted aralkyl group. In some embodiments, $R^{q1}$, $R^{q2}$, $R^{q3}$, $R^{q4}$, $R^{q5}$, and $R^{q6}$ within Structure Q1, Structure Q2, Structure Q3, and/or Structure Q4 independently can be a $C_1$ to $C_5$ alkyl group, a $C_1$ to $C_5$ substituted alkyl group, a $C_4$ to $C_{10}$ cycloalkyl group, a $C_4$ to $C_{10}$ substituted cycloalkyl group, a $C_6$ to $C_{10}$ aryl group, a $C_6$ to $C_{10}$ substituted aryl group, a $C_7$ to $C_{10}$ aralkyl group, or a $C_7$ to $C_{10}$ substituted aralkyl group; alternatively, a $C_1$ to $C_5$ alkyl group, a $C_4$ to $C_{10}$ cycloalkyl group, a $C_6$ to $C_{10}$ aryl group, or a $C_7$ to $C_{10}$ aralkyl group; alternatively, a $C_1$ to $C_5$ alkyl group or a $C_1$ to $C_{10}$ substituted alkyl group; alternatively, a $C_4$ to $C_{10}$ cycloalkyl group or a $C_4$ to $C_{10}$ substituted cycloalkyl group; alternatively, a $C_6$ to $C_{10}$ aryl group or a $C_6$ to $C_{10}$ substituted aryl group; alternatively, a $C_7$ to $C_{10}$ aralkyl group or a $C_7$ to $C_{10}$ substituted aralkyl group; alternatively, a $C_1$ to $C_5$ alkyl group; alternatively, a $C_1$ to $C_s$ substituted alkyl group; alternatively, a $C_4$ to $C_{10}$ cycloalkyl group; alternatively, a $C_4$ to $C_{10}$ substituted cycloalkyl group; alternatively, a $C_6$ to $C_{10}$ aryl group; alternatively, a $C_6$ to $C_{10}$ substituted aryl group; alternatively, a $C_7$ to $C_{10}$ aralkyl group; or alternatively, a $C_7$ to $C_{10}$ substituted aralkyl group.

In an embodiment, each group attached to the heteroatom of a metal salt complexing group or $R^{q1}$, $R^{q2}$, $R^{q3}$, $R^{q4}$, $R^{q5}$, and/or $R^{q6}$ of the metal complexing group having Structures Q1, Q2, Q3, and/or Q4 independently can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, or a nonadecyl group; or alternatively, a methyl group, an ethyl group, a propyl group, a butyl group, a pentyl group, a hexyl group, a heptyl group, an octyl group, a nonyl group, or a decyl group. In some embodiments, each group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4 independently can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, an n-propyl group; alternatively, an iso-propyl group; alternatively, a tert-butyl group; or alternatively, a neopentyl group. Independently, these alkyl group which can be attached to the heteroatom of the metal complexing group can be a primary alkyl group, a secondary hydrocarbyl group, or a tertiary alkyl group; alternatively, a primary alkyl group; alternatively, a secondary alkyl group; or alternatively, a tertiary alkyl group. In some embodiments, the alkyl groups which can be utilized as $R^{q1}$, $R^{q2}$, $R^{q3}$, $R^{q4}$, $R^{q5}$, and/or $R^{q6}$ of the metal salt complexing group having Structures Q1, Q2, Q3, and/or Q4 can be substituted. Each substituent of a substituted alkyl group independently can be a halogen or a hydrocarboxy group; alternatively, a halogen; or alternatively, a hydrocarboxy group. Substituent halogens and substituent hydrocarboxy groups are independently disclosed herein (e.g. as non-hydrogen substituents of $R^1$ groups in the $N^2$-phosphinyl amidine compound, among other places). These substituent halogens and substituent hydrocarboxy groups can be utilized without limitation to further describe a substituted alkyl group which can be utilized as $R^{q1}$, $R^{q2}$, $R^{q3}$, $R^{q4}$, $R^{q5}$, and/or $R^{q6}$.

In an embodiment, each group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4 independently can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, each cycloalkyl group attached to the heteroatom of a metal salt complexing group can be a cyclopentyl group, a substituted cyclopentyl group, a cyclohexyl group, or a substituted cyclohexyl group. In other embodiments, each group attached to the heteroatom of a metal salt complexing group or $R^{q1}$, $R^{q2}$, $R^{q3}$, $R^{q4}$, $R^{q5}$, and/or $R^{q6}$ of the metal complexing group having Structures Q1, Q2, Q3, and/or Q4 independently can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; or alternatively, a cyclooctyl group, or a substituted cyclooctyl group. In further embodiments, each group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4 independently can be a cyclopentyl group; alternatively, a substituted cyclopentyl group; a cyclohexyl group; or alternatively, a substituted cyclohexyl group. Each substituent of a cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a halogen; alternatively, a hydrocarbyl group; or alternatively, a hydrocarboxy group. Substituent halogens, substituent hydrocarbyl groups, and substituent hydrocarboxy groups are independently disclosed herein (e.g. as non-hydrogen substituents of $R^1$ groups in the $N^2$-phosphinyl amidine compound, among other places). These substituent halogens, substituent hydrocarbyl groups, and substituent hydrocarboxy can be utilized without limitation to further describe a substituted cycloalkyl group (general or specific) which can be utilized as a group attached to the heteroatom of a metal complexing group or utilized $R^{q1}$, $R^{q2}$, $R^{q3}$, $R^{q4}$, $R^{q5}$, and/or $R^{q6}$ of the metal complexing group having Structures Q1, Q2, Q3, and/or Q4.

In other non-limiting embodiments, each group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4 independently can be a cyclohexyl group, a 2-alkylcyclohexyl group, or a 2,6-dialkylcyclohexyl group; alternatively, cyclopentyl group, a 2-alkylcyclopentyl group, or a 2,5-dialkylcyclopentyl group; alternatively, cyclohexyl group; alternatively, a 2-alkylcyclohexyl group; alternatively, a 2,6-dialkylcyclohexyl group; alternatively, cyclopentyl group; alternatively, a 2-alkylcyclopentyl group; or alternatively, or 2,5-dialkylcyclopentyl group. Alkyl substituent groups are independently described herein (e.g. as alkyl substituents of $R^1$ groups in the $N^2$-phosphinyl amidine compound, among other places). These alkyl substituent groups can be utilized, without limitation, to further describe an alkylcyclohexyl, dialkylcyclohexyl, alkylcyclopentyl, and/or dialkylcyclopentyl group which can be utilized as a group attached to the heteroatom of a metal salt complexing group or utilized as $R^{q1}$, $R^{q2}$, $R^{q3}$, $R^{q4}$, $R^{q5}$, and/or $R^{q6}$ of the metal salt complexing group having Structures Q1, Q2, Q3, and/or Q4. Generally, the alkyl substituents of a disubstituted cyclohexyl or cyclopentyl group can be the same; or alternatively, the alkyl substituents of a dialkyl cyclohexyl or cyclopentyl group can be different.

In a non-limiting embodiment, each group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4 independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In a non-limiting embodiment, each group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4 independently can be, a 2-methylcyclohexyl group, a 2-ethylcyclohexyl group, a 2-isopropylcyclohexyl group, or a 2-tert-butylcyclohexyl group; alternatively, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group; alternatively, a 2-ethylcyclohexyl group; alternatively, a 2-isopropylcyclohexyl group; alternatively, a 2-tert-butylcyclohexyl group; alternatively, a 2,6-dimethylcyclohexyl group; alternatively, a 2,6-diethylcyclohexyl group; alternatively, a 2,6-diisopropylcyclohexyl group; or alternatively, or 2,6-di-tert-butylcyclohexyl group.

In an embodiment, each group attached to the heteroatom of a metal salt complexing group or $R^{q1}$, $R^{q2}$, $R^{q3}$, $R^{q4}$, $R^{q5}$, and/or $R^{q6}$ of the metal complexing salt group having Structures Q1, Q2, Q3, and/or Q4 independently can be a phenyl group, a substituted phenyl group, a naphthyl group, or a substituted naphthyl group; alternatively, a phenyl group or a substituted phenyl group; alternatively, a naphthyl group or a substituted naphthyl group; alternatively, a phenyl group or a naphthyl group; alternatively, a phenyl group; alternatively, a substituted phenyl group; alternatively, a naphthyl group; or alternatively, a substituted naphthyl group. In an embodiment, each group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3 and/or Q4 independently can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other embodiments, each group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4 independently can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Each substituent of a substituted phenyl group (general or specific) or a substituted naphthyl group (general of specific) independently can be a halogen, a hydrocarbyl group, or a hydrocarboxy group; alternatively, a halogen or a hydrocarbyl group; alternatively, a halogen or a hydrocarboxy group; alternatively, a halogen; alternatively, a hydrocarbyl group; or alternatively, a hydrocarboxy group. Substituent halogens, substituent hydrocarbyl groups, and substituent hydrocarboxy groups are independently disclosed herein (e.g. as non-hydrogen substituents of $R^1$ groups in the $N^2$-phosphinyl amidine compound, among other places). These substituent halogens, substituent hydrocarbyl groups, and substituent hydrocarboxy can be utilized without limitation to further describe a substituted phenyl group (general or specific) or a substituted naphthyl group (general or specific) which can be utilized as a group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4.

In a non-limiting embodiment, each group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4 independently can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 3-alkylphenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. Alkyl substituent groups are independently described herein (e.g. as alkyl substituents of $R^1$ groups in the $N^2$-phosphinyl amidine compound, among other places). These alkyl substituent groups can be utilized, without limitation, to further describe an alkylphenyl, dialkylphenyl, and/or trialkylphenyl groups which can be utilized as a group attached to the heteroatom of a metal salt complexing group or utilized as $R^{q1}$, $R^{q2}$, $R^{q3}$, $R^{q4}$, $R^{q5}$, and/or $R^{q6}$ of the metal salt complexing group having Structures Q1, Q2, Q3, and/or Q4. Generally, the alkyl substituents of the dialkylphenyl groups or trialkyl groups can be the same; or alternatively, the alkyl substituents of a dialkylphenyl group can be different.

In some non-limiting embodiments, each group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4 independently can be a phenyl group, a 2-alkoxyphenyl group, a 3-alkoxyphenyl group, a 4-alkoxyphenyl group, or 3,5-dialkoxyphenyl group; alternatively, a 2-alkoxyphenyl group or a 4-alkoxyphenyl group; alternatively, a 3-alkoxyphenyl group or a 3,5-dialkoxyphenyl group; alternatively, a 2-alkoxyphenyl group; alternatively, a 3-alkoxyphenyl group; alternatively, a 4-alkoxyphenyl group; alternatively, a 3,5-dialkoxyphenyl group. Alkoxy group substituents are independently described herein (e.g. as alkoxy substituents of $R^1$ groups in the $N^2$-phosphinyl amidine compound, among other places). These alkoxy substituents can be utilized, without limitation, to further describe the alkoxyphenyl group(s) and/or dialkoxyphenyl group(s) which can be utilized as a group attached to the heteroatom of a metal salt complexing group or utilized as $R^{q1}$, $R^{q2}$, $R^{q3}$, $R^{q4}$, $R^{q5}$, and/or $R^{q6}$ of the metal salt complexing group having Structures Q1, Q2, Q3, and/or Q4. Generally, the alkoxy substituents of a dialkoxyphenyl groups can be the same; or alternatively, the alkoxy substituents of a dialkoxyphenyl group can be different.

In other non-limiting embodiments, each group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4 independently can be a phenyl group, a 2-halophenyl group, a 3-halophenyl group, a 4-halophenyl group, a 2,6-dihalophenyl group, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenyl group; or alternatively, a 3,5-dihalophenyl group. Halide substituents are independently described herein (e.g. as halide substituents of $R^1$ groups in the $N^2$-phosphinyl amidine compound, among other places). These halide substituents can be utilized, without limitation, to further describe a halophenyl group and/or a dihalophenyl group which can be utilized as a group attached to the heteroatom of a metal complexing group or utilized $R^{q1}$, $R^{q2}$, $R^{q3}$, $R^{q4}$, $R^{q5}$, and/or $R^{q6}$ of the metal complexing group having Structures Q1, Q2, Q3, and/or Q4. Generally, the halides of a dihalophenyl group can be the same; or alternatively, the halides of a dihalophenyl group can be different.

In a non-limiting embodiment, each group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4 independently can be a phenyl group, a 2-methylphenyl group, a 2-ethylphenyl group, a 2-n-propylphenyl group, a 2-isopropylphenyl group, a 2-tert-butylphenyl group, a 3-methylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, a 3,5-dimethyl group, or a 2,4,6-trimethylphenyl group; alternatively, a 2-methylphenyl group, a 2-ethylphenyl group, a 2-n-propylphenyl group, a 2-isopropylphenyl group, or a 2-tert-butylphenyl group; alternatively, a 2,6-dimethylphenyl group, a 2,6-diethylphenyl group, a 2,6-di-n-propylphenyl group, a 2,6-diisopropylphenyl group, a 2,6-di-tert-butylphenyl group, or a 2-isopropyl-6-methylphenyl group; alternatively, a 2-methylphenyl group; alternatively, a 2-ethylphenyl group; alternatively, a 2-n-propylphenyl group; alternatively, a 2-isopropylphenyl group; alternatively, a 2-tert-butylphenyl group; alternatively, a 3-methylphenyl group; alternatively, a 2,6-dimethylphenyl group; alternatively, a 2,6-diethylphenyl group; alternatively, a 2,6-di-n-propylphenyl group; alternatively, a 2,6-diisopropylphenyl group; alternatively, a 2,6-di-tert-butylphenyl group; alternatively, a 2-isopropyl-6-methylphenyl group; alternatively, a 3,5-dimethylphenyl group; or alternatively, a 2,4,6-trimethylphenyl group. In some non-limiting embodiments, each group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4 independently can be a phenyl group, a 3-methoxyphenyl group, a 3-ethoxyphenyl group, a 3-isopropoxypheny group, a 3-tert-butoxyphenyl group, a 4-methoxyphenyl group, a 4-ethoxyphenyl group, a 4-isopropoxyphenyl group, a 4-tert-butoxyphenyl group, a 3,5-dimethoxyphenyl group, a 3,5-diethoxyphenyl group, a 3,5-diisopropoxyphenyl group, or a 3,5-di-tert-butoxyphenyl group; alternatively, 3-methoxyphenyl group, a 3-ethoxyphenyl group, a 3-isopropoxyphenyl group, or a 3-tert-butoxyphenyl group; alternatively, a 4-methoxyphenyl group, a 4-ethoxyphenyl group, a 4-isopropoxyphenyl group, or a 4-tert-butoxyphenyl group; or alternatively, a 3,5-dimethoxyphenyl group, a 3,5-diethoxyphenyl group, a 3,5-diisopropoxyphenyl group, or a 3,5-di-tert-butoxyphenyl group. In other non-limiting embodiments, each group attached to the heteroatom of a metal complexing group or $R^{q1}$, $R^{q2}$, $R^{q3}$, $R^{q4}$, $R^{q5}$, and/or $R^{q6}$ of the metal complexing group having Structures Q1, Q2, Q3, and/or Q4 independently can be a 3-methoxyphenyl group; alternatively, a 3-ethoxyphenyl group; alternatively, a 3-isopropoxyphenyl group; alternatively, a 3-tert-butoxyphenyl group; alternatively, a 4-methoxyphenyl group; alternatively, a 4-ethoxyphenyl group; alternatively, a 4-isopropoxyphenyl group; alternatively, a 4-tert-butoxyphenyl group; alternatively, a 3,5-dimethoxyphenyl group; alternatively, a 3,5-diethoxyphenyl group; alternatively, a 3,5-diisopropoxyphenyl group; or alternatively, a 3,5-di-tert-butoxyphenyl group.

In an embodiment, each group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4 independently can be a benzyl group, a substituted benzyl group, a 2-phenylethyl group, or a 1-phenylethyl group. In some embodiments, each group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4 independently can be a benzyl group or a substituted benzyl group; alternatively, a benzyl group; alternatively, a substituted benzyl group; alternatively, a 2-phenylethyl group; or alternatively, a 1-phenylethyl group. Each substituent of a substituted benzyl group (general or specific) independently can be a halogen, a hydrocarbyl group, or a hydrocarboxy group; alternatively, a halogen or a hydrocarbyl group; alternatively, a halogen or a hydrocarboxy group; alternatively, a halogen; alternatively, a hydrocarbyl group; or alternatively, a hydrocarboxy group. Substituent halogens, substituent hydrocarbyl groups, and substituent hydrocarboxy groups are independently disclosed herein (e.g. as non-hydrogen substituents of $R^1$ groups in the $N^2$-phosphinyl amidine compound, among other places). These substituent can be utilized without limitation to further describe a substituted benzyl group (general or specific) which can be utilized as a group attached to the heteroatom of a metal salt complexing group or $R^{q1}$, $R^{q2}$, $R^{q3}$, $R^{q4}$, $R^{q5}$, and/or $R^{q6}$ of the metal salt complexing group having Structures Q1, Q2, Q3, and/or Q4.

In an aspect, $R^{q21}$ of the metal salt complexing groups having Structure Q8, Structure Q9, or Structure Q10 can be a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In some embodiments, $R^{q21}$ of the metal salt complexing groups having Structure Q8, Structure Q9, or Structure Q10 can be a $C_1$ to $C_{20}$ alkyl group, a $C_4$ to $C_{20}$ cycloalkyl group, a $C_6$ to $C_{20}$ aryl group, or a $C_7$ to $C_{20}$ aralkyl group; alternatively, a $C_1$ to $C_{20}$ alkyl group; alternatively, a $C_4$ to $C_{20}$ cycloalkyl group; alternatively, a $C_6$ to $C_{20}$ aryl group; or alternatively, a $C_7$ to $C_{20}$ aralkyl group. In some embodiments, $R^{q21}$ of the metal salt complexing groups having Structure Q8, Structure Q9, or Structure Q10 can be a $C_1$ to $C_{10}$ alkyl group, a $C_4$ to $C_{15}$ cycloalkyl group, a $C_6$ to $C_{15}$ aryl group, or a $C_7$ to $C_{15}$ aralkyl group; alternatively, a $C_1$ to $C_{10}$ alkyl group; alternatively, a $C_4$ to $C_{15}$ cycloalkyl group; alternatively, a $C_6$ to $C_{15}$ aryl group; or alternatively, a $C_7$ to $C_{15}$ aralkyl group. In other embodiments, $R^{q21}$ of the metal salt complexing groups having Structure Q8, Structure Q9, or Structure Q10 can be a $C_1$ to $C_5$ alkyl group, a $C_4$ to $C_{10}$ cycloalkyl group, a $C_6$ to $C_{10}$ aryl group, or a $C_7$ to $C_{10}$ aralkyl group; alternatively, a $C_1$ to $C_5$ alkyl group; alternatively, a $C_4$ to $C_{10}$ cycloalkyl group; alternatively, a $C_6$ to $C_{10}$ aryl group; or alternatively, a $C_7$ to $C_{10}$ aralkyl group. General and specific alkyl groups, cycloalkyl groups, aryl group, and aralkyl groups have been described herein as groups which can be utilized as a group attached to the heteroatom of a metal salt complexing group or as $R^{q1}$, $R^{q2}$, $R^{q3}$, $R^{q4}$, $R^{q5}$, and/or $R^{q6}$ of the metal salt complexing group having Structures Q1, Q2, Q3, and/or Q4. These general and specific alkyl groups, cycloalkyl groups, aryl group, and aralkyl groups can be utilized, without limitation, as $R^{q21}$ of the metal salt complexing groups having Structure Q8, Structure Q9, or Structure Q10.

In an aspect, each $R^{q11}$, $R^{q12}$, $R^{q13}$, $R^{q14}$, $R^{q15}$, $R^{q16}$, $R^{q17}$, $R^{q18}$, $R^{q19}$, $R^{q20}$, $R^{q31}$, $R^{q32}$, $R^{q33}$, $R^{q34}$, $R^{q35}$, $R^{q41}$, $R^{q42}$, $R^{q43}$, $R^{q44}$, $R^{q45}$, $R^{q51}$, $R^{q52}$, $R^{q53}$, $R^{q54}$, $R^{q61}$, $R^{q62}$, $R^{q63}$, $R^{q71}$, $R^{q72}$, $R^{q73}$, $R^{q74}$, $R^{q75}$, $R^{q76}$, $R^{q77}$, $R^{q78}$, $R^{q79}$, and/or $R^{q80}$ of Structures Q5-Q22 independently can be a hydrogen or a non-hydrogen substituent group. Each $R^{q11}$-$R^{q20}$, $R^{q31}$-$R^{q35}$, $R^{q41}$-$R^{q45}$, $R^{q51}$-$R^{q54}$, $R^{q61}$-$R^{q63}$, and/or $R^{q71}$-$R^{q80}$ non-hydrogen, a substituent utilized in the metal salt complexing groups having Structures Q5-Q22 can be a halogen, a hydrocarbyl group, or a hydrocarboxy group; alternatively, a halogen or a hydrocarbyl group; alternatively, a halogen or a hydrocarboxy group; alternatively, a halogen; alternatively, a hydrocarbyl group; or alternatively, a hydrocarboxy group. Substituent halogens, substituent hydrocarbyl groups, and substituent hydrocarboxy groups are independently disclosed herein (e.g. as non-hydrogen substituents $R^1$ in the $N^2$-phosphinyl amidine compound, among other places). These substituent halogens, substituent hydrocarbyl groups, and substituent hydrocarboxy can be utilized without limitation to further describe a $R^{q11}$-$R^{q20}$, $R^{q31}$-$R^{q35}$, $R^{q41}$-$R^{q45}$, $R^{q51}$-$R^{q54}$, $R^{q61}$-$R^{q63}$, and/or $R^{q71}$-$R^{q80}$ non-hydrogen substituent utilized in the metal complexing groups having Structures Q5-Q22.

The linking group ($L^3$) linking the metal salt complexing group to the $N^2$-phosphinyl amidine group or linking the metal salt complexing group to the $N^1$ nitrogen atom of the $N^2$-phosphinyl amidine group can be a bond or an organyl group; alternatively, a bond or an organyl group consisting of inert functional groups; or alternatively, a bond or a hydrocarbyl group. In other embodiments, the linking group can be a bond; alternatively, an organyl group; alternatively, an organyl group consisting of inert functional groups; or alternatively, a hydrocarbyl group. In any aspect or embodiment disclosed herein, the organyl linking group linking the metal salt complexing group to the $N^2$-phosphinyl amidine group or linking the metal salt complexing group to the $N^1$ nitrogen atom of the $N^2$-phosphinyl amidine group can be a $C_1$ to $C_{10}$ organyl group; or alternatively, a $C_1$ to $C_5$ organyl group. In any aspect or embodiment disclosed herein, the organyl consisting of inert functional groups linking the metal salt complexing group to the $N^2$-phosphinyl amidine group or linking the metal salt complexing group to the $N^1$ nitrogen atom of the $N^2$-phosphinyl amidine group can be a $C_1$ to $C_{10}$ organyl group consisting of inert functional groups; or alternatively, a $C_1$ to $C_5$ organyl group consisting of inert functional groups. In any aspect or embodiment disclosed herein, the hydrocarbyl linking group linking the metal salt complexing group to the $N^2$-phosphinyl amidine group or linking the metal salt complexing group to the $N^1$ nitrogen atom of the $N^2$-phosphinyl amidine group can be a $C_1$ to $C_{10}$ hydrocarbyl group; or alternatively, a $C_1$ to $C_5$ hydrocarbyl group.

In some embodiments, the linking group linking the metal salt complexing group to the $N^2$-phosphinyl amidine group or linking the metal salt complexing group to the $N^1$ nitrogen atom of the $N^2$-phosphinyl amidine group can be —$(CR^{1m}R^{1m'})_m$— where each $R^{1m}$ and $R^{1m'}$ independently can be hydrogen, a methyl group, an ethyl group, an n-propyl group, an isopropyl group, or an n-butyl group and m can be an integer from 1 to 5. In other embodiments, the linking group can be a methylene group (—$CH_2$—), an eth-1,2-ylene group (—$CH_2CH_2$—), a prop-1,3-ylene group (—$CH_2CH_2CH_2$—), a 1-methyleth-1,2-ylene group (—$CH(CH_3)CH_2$—), dimethylmethylene group (—$C(CH_3)_2$—), a but-1,4-ylene group (—$CH_2CH_2CH_2CH_2$—), or a phen-1,2-ylene group. In some non-limiting embodiments, the linking group linking the metal salt complexing group to the $N^2$-phosphinyl amidine group or linking the metal salt complexing group to the $N^1$ nitrogen atom of the $N^2$-phosphinyl amidine group can be a methylene group (—$CH_2$—), an eth-1,2-ylene group (—$CH_2CH_2$—), a prop-1,3-ylene group (—$CH_2CH_2CH_2$—), or a phen-1,2-ylene group; alternatively, a methylene group (—$CH_2$—), an eth-1,2-ylene group (—$CH_2CH_2$—), or a phen-1,2-ylene group; alternatively, an ethylene group (—$CH_2CH_2$—) or a propylene group (—$CH_2CH_2CH_2$—); alternatively, an eth-1,2-ylene group (—$CH_2CH_2$—) or a phen-1,2-ylene group; alternatively, a methylene group (—$CH_2$—); alternatively, an eth-1,2-ylene group (—$CH_2CH_2$—); alternatively, a prop-1,3-ylene group (—$CH_2CH_2CH_2$—); or alternatively, a phen-1,2-ylene group.

In some embodiments, the linking group can have any structure indicated in Table 3. Within the structures of Table 3, the undesignated valancies are the points of attachment for the $N^2$-phosphinyl amidine group (or the $N^1$ nitrogen atom of the $N^2$-phosphinyl amidine group) and the metal salt complexing group; each $R^{2m}$ and/or $R^{2m'}$ can independently be hydrogen, a methyl group, or an ethyl group; and m can be an integer ranging from 1 to 5. In further embodiments, m can be an integer ranging from 1 to 3; alternatively, m can be 2 or 3; alternatively, m can be 1; alternatively, m can be 2; or alternatively, m can be 3.

TABLE 3

Example Linking Groups

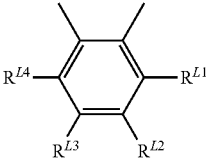

| | |
|---|---|
| —$(CR^{2m}R^{2m'})_m$— | Structure 1QL |
| —$(CH_2)_m$— | Structure 2QL |
| —$(CH_2)$— | Structure 3QL |
| —$(CH_2CH_2)$— | Structure 4QL |
| | Structure 5QL |

In some embodiments, the linking group can have Structure 1QL, Structure 2QL, Structure 3QL, Structure 4QL or Structure 5QL. In some embodiments, the linking group can have Structure 4QL or Structure 5QL. In other embodiments, the linking group can have Structure 2QL; alternatively, Structure 3QL; alternatively, Structure 4QL; or alternatively, Structure 5QL.

Generally, when an $N^2$-phosphinyl amidine compound contains a metal salt complexing group and linking group, the metal salt complexing group and linking group are independent elements of an $N^2$-phosphinyl amidine compound. Consequently, the $N^2$-phosphinyl amidine compound can be described as having any combination of a metal salt complexing group described herein and a linking group described herein. In a non-limiting embodiment, when the heteroatom of the metal complexing is not contained in a ring or a ring system, the linking group linking the metal salt complexing group to the $N^2$-phosphinyl amidine group or linking the metal salt complexing group to the $N^1$ nitrogen atom of the $N^2$-phosphinyl amidine group can be a methylene group (—$CH_2$—), an eth-1,2-ylene group (—$CH_2CH_2$—), a prop-1,3-ylene group (—$CH_2CH_2CH_2$—), or a phen-1,2-ylene group; alternatively, an ethylene group (—$CH_2CH_2$—), or a propylene group (—$CH_2CH_2CH_2$—); alternatively, an eth-1,2-ylene group (—$CH_2CH_2$—) or a phen-1,2-ylene group; alternatively, a methylene group (—$CH_2$—); alternatively, an eth-1,2-ylene group (—$CH_2CH_2$—); alternatively, a prop-1,3-ylene group (—$CH_2CH_2CH_2$—); or alternatively, a phen-1,2-ylene group. In another non-limiting embodiment, when the heteroatom of the metal salt complexing group is contained within a ring, the linking group linking the metal salt complexing group to the $N^2$-phosphinyl amidine group or linking the metal salt complexing group to the $N^1$ nitrogen atom of the $N^2$-phosphinyl amidine group can be a bond or a methylene group; alternatively, a bond; or alternatively, a methylene group.

In an aspect, this disclosure provides for an $N^2$-phosphinyl amidine metal salt complex. Generally, the $N^2$-phosphinyl amidine metal salt complex can comprise a metal salt complexed to an $N^2$-phosphinyl amidine compound. In some embodiments, the $N^2$-phosphinyl amidine metal salt complex can further comprise a neutral ligand, Q. $N^2$-phosphinyl amidine compounds are generally described herein and can be utilized, without limitation, to further describe the $N^2$-phosphinyl amidine metal salt complex comprising a metal salt complexed to an $N^2$-phosphinyl amidine compound. In an embodiment, the $N^2$-phosphinyl amidine metal salt complex can have Structure MC1, MC2, MC3, MC4, MC5, MC6, MC7, MC8, MC9, MC10, MC11, MC13, MC15, MC16, MC18, or MC20; alternatively, Structure MC1, MC2, MC3, MC4, or MC5; alternatively, MC6, MC7, MC8, MC9, or MC10; alternatively, MC11, MC13, or MC15; alternatively, MC16, MC18, or MC20; alternatively, Structure MC1; alternatively, Structure MC2; alternatively, Structure MC3; alternatively, Structure MC4; alternatively, Structure MC5; alternatively, MC6; alternatively, MC7; alternatively, MC8; alternatively, MC9; alternatively, MC10; alternatively, Structure MC11; alternatively, Structure MC13; alternatively, Structure MC15; alternatively, MC16; alternatively, MC18; or alternatively, MC20. In an embodiment, the $N^2$-phosphinyl amidine metal salt complex comprising only one $N^2$-phosphinyl amidine group complexed to metal salt can be characterized by having the Structure MC1, MC6, MC11, or MC16; alternatively, Structure MC1 or MC6; alternatively, Structure MC11 or MC16; alternatively, Structure MC1 or MC11; or alternatively, Structure MC6 or MC16. In an embodiment, the $N^2$-phosphinyl amidine metal salt complex comprising only two $N^2$-phosphinyl amidine groups complexed to a metal salt can be characterized by having Structure MC2, MC3, MC8, MC13, or MC18; alternatively, Structure MC2, MC3, or MC8; alternatively, Structure MC13, or MC18; alternatively, Structure MC2 or MC3; alternatively, Structure MC3 or MC13; or alternatively, Structure MC8 or MC18. In other embodiments, $N^2$-phosphinyl amidine metal salt complex compounds having at least one $N^2$-phosphinyl amidine group complexed to a metal salt can be characterized by having the Structure MC4, MC5, MC9, MC10, MC15, or MC20; alternatively, Structure MC4, MC5, MC9, or MC10; alternatively, Structure MC15, or MC20; alternatively, Structure MC4 or MC5; alternatively, Structure MC9 or MC10; alternatively, Structure MC5 or MC15; or alternatively, Structure MC10 or MC20.

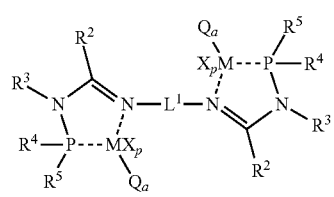

Structure MC1

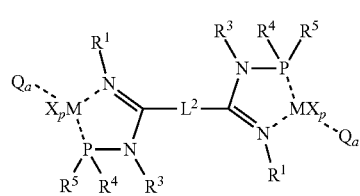

Structure MC2

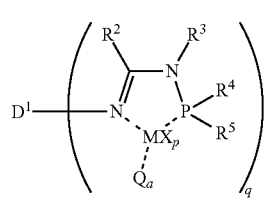

Structure MC3

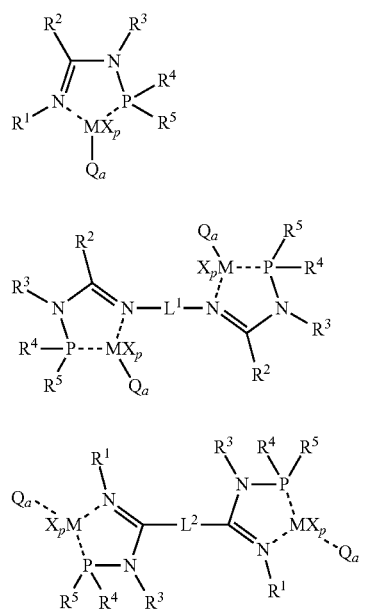

Structure MC4

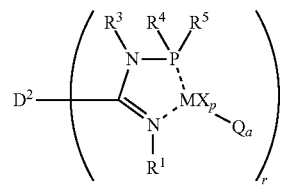

Structure MC5

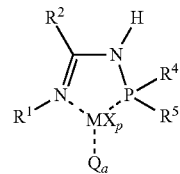

Structure MC6

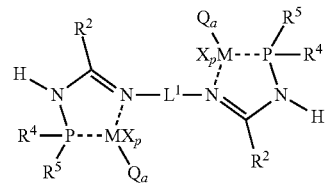

Structure MC7

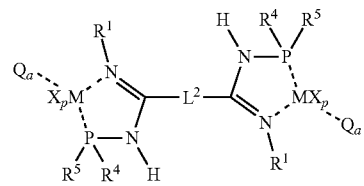

Structure MC8

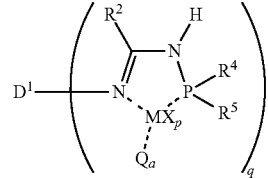

Structure MC9

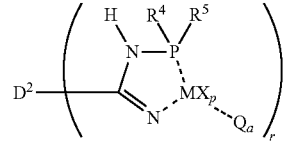

Structure MC10

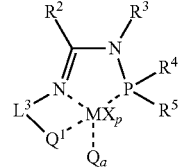

Structure MC11

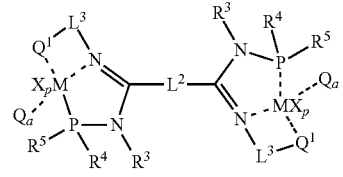

Structure MC13

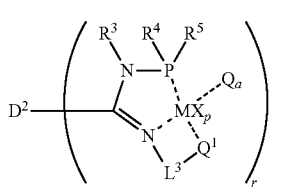
Structure MC15

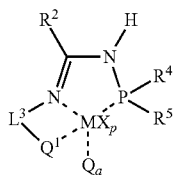
Structure MC16

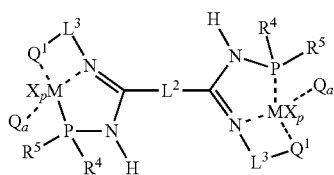
Structure MC18

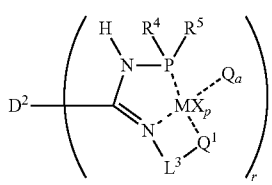
Structure MC20

$R^1, R^2, R^3, R^4, R^5, D^1, D^2, L^1, L^2, L^3, Q^1$, q, r, M, X, Q, p, and a within the $N^2$-phosphinyl amidine metal salt complex Structures MC1-MC10, MC11, MC13, MC15, MC16, MC18, and/or MC20 are independently described herein and these description can be utilized in any combination to further describe the $N^2$-phosphinyl amidine metal salt complexes of this disclosure. Generally, $MX_p$ or $MX_pQ_a$ represents the metal salt of the metal complex, Q represents a neutral ligand, and a represents the number of neutral ligands in the $N^2$-phosphinyl amidine metal salt complex. The $N^2$-phosphinyl amidine compound features $R^1, R^2, R^3, R^4, R^5, D^1, D^2, L^1, L^2, L^3, Q^1$, q, and r are described for $N^2$-phosphinyl amidine compounds having Structures Structures NP1-NP10, NP11, NP13, NP15, NP16, NP18, and/or NP20 can be utilized without limitation to describe the $N^2$-phosphinyl amidine metal salt complexes having Structures Structures MC1-MC10, MC11, MC13, MC15, MC16, MC18, and/or MC20.

Generally, the metal salt, $MX_p$ or $MX_pQ_a$, of the $N^2$-phosphinyl amidine metal salt complex comprising a metal salt complexed to an $N^2$-phosphinyl amidine compound can comprise a cationic metal, M, and a monoanionic ligand, X. In some embodiments, the metal salt can further comprises a neutral ligand which may or may not be present in the $N^2$-phosphinyl amidine metal salt complex comprising a metal salt complexed to an $N^2$-phosphinyl amidine compound.

Generally, the metal atom of the metal salt, $MX_p$ or $MX_pQ_a$ can be any metal atom. In an aspect, the metal atom of the metal salt can be a transition metal. In an embodiment, suitable metal salts can comprise, or consist essentially of, a Group 3-12 transition metal; alternatively, a Group 4-10 transition metal; alternatively, a Group 6-9 transition metal; alternatively, a Group 7-8 transition metal; alternatively, a Group 4 transition metal; alternatively, a Group 5 transition metal alternatively, a Group 6 transition metal; alternatively, a Group 7 transition metal; alternatively, a Group 8 transition metal; alternatively, a Group 9 transition metal; or alternatively, a Group 10 transition metal. In some embodiments, the metal salt can comprise titanium, zirconium, hafnium, vanadium, niobium, tantalum, chromium, molybdenum, tungsten, manganese, iron, cobalt, nickel, palladium, platinum, copper, or zinc. In other embodiments, the metal salt can comprise titanium, zirconium, vanadium, chromium, molybdenum, tungsten, iron, cobalt, nickel, palladium, or platinum; alternatively, chromium, iron, cobalt, or nickel; alternatively, titanium, zirconium or hafnium; alternatively, vanadium or niobium; alternatively, chromium, molybdenum or tungsten; alternatively, iron or cobalt; or alternatively, nickel, palladium, platinum, copper, or zinc. In other embodiments, the metal salt can comprise titanium; alternatively, zirconium; alternatively, hafnium; alternatively, vanadium; alternatively, niobium; alternatively, tantalum; alternatively, chromium; alternatively, molybdenum; alternatively, tungsten; alternatively, manganese; alternatively, iron; alternatively, cobalt; alternatively, nickel; alternatively, palladium; alternatively, platinum; alternatively, copper; or alternatively, zinc.

Generally, the metal atom of the transition metal salt, $MX_p$ or $MX_pQ_a$ can have any positive oxidation state available to the metal atom. In an embodiment, the transition metal can have an oxidation state of from +2 to +6; alternatively, from +2 to +4; or alternatively, from +2 to +3. In some embodiments, the metal atom of the transition metal salt, $MX_p$ or $MX_pQ_a$ can have an oxidation state or +1; alternatively, +2; alternatively, +3; or alternatively, +4.

The anion X, of the transition metal salt can be any monoanion. In an embodiment, the monoanion, X, can be a halide, a carboxylate, a β-diketonate, a hydrcarboxide, a nitrate, or a chlorate. In some embodiments, the monoanion, X, can be a halide, a carboxylate, a β-diketonate, or a hydrocarboxide. In any aspect or embodiment, the hydrocarboxide can be an aloxide, an aryloxide, or an aralkoxide. Generally, hydrocarboxide (and subdivisions of hydrocarboxide) are the anion analogues of the hydrocarboxy group. In other embodiments, the monoanion, X, can be a halide, a carboxylate, a β-diketonate, or an alkoxide; or alternatively, a halide or a β-diketonate. In other embodiments, the monoanion X can be a halide; alternatively, a carboxylate; alternatively, a β-diketonate; alternatively, a hydrocarboxide; alternatively, an alkoxide; or alternatively, an aryloxide. Generally, the number, p, of monoanions, X, can equal the oxidation state of the metal atom. In an embodiment, the number, p, of monoanions, X, can be from 2 to 6; alternatively, from 2 to 4; alternatively, from 2 to 3; alternatively, 1; alternatively, 2; alternatively, 3; or alternatively, 4.

Generally, each halide monoanion independently can be fluorine, chlorine, bromine, or iodine; or alternatively, chlorine, bromine, or iodine. In an embodiment, each halide monoanion can be chlorine; alternatively, bromine; or alternatively, iodine.

Generally, the carboxylate, a β-diketonate, hydrocarboxide (also alkoxide, aryloxide, or aralkoxide) can be any $C_1$ to $C_{20}$ carboxylate, a β-diketonate, hydrocarboxide (also alkoxide, aryloxide or aralkoxide); or alternatively, any $C_1$ to $C_{10}$ carboxylate, a β-diketonate, hydrocarboxide (also alkoxide, aryloxide, or aralkoxide). In some embodiments, the anion, X, can be a $C_1$ to $C_{20}$ carboxylate; alternatively, a $C_1$ to $C_{20}$ carboxylate; alternatively, a $C_1$ to $C_{20}$ β-diketonate; alternatively, a $C_1$ to $C_{10}$ β-diketonate; alternatively, a $C_1$ to $C_{20}$ hydrocarboxide; alternatively, a $C_1$ to $C_{10}$ hydrocarboxide; alternatively, a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide.

In an aspect, each carboxylate monoanion independently can be acetate, a propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, or an octadecanoate; or alternatively, a pentanoate, a hexanoate, a heptanoate, a octanoate, a nonanoate, a decanoate, a undecanoate, or a dodecanoate. In an embodiment, each carboxylate monoanion independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, laurate (n-dodecanoate), or stearate (n-octadecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some embodiments, the carboxylate anion can be triflate (trifluoroacetate).

In an aspect, each β-diketonate independently can be acetylacetonate (alternatively, 2,4-pentanedionate), hexafluoroacetylacetone (alternatively, 1,1,1,5,5,5-hexafluoro-2,4-pentanediuonate, or benzoylacetonate); alternatively, acetylacetonate; alternatively, hexafluoroacetylacetone; or alternatively, benzoylacetonate. In an aspect, each alkoxide monoanion independently can be methoxide, ethoxide, a propoxide, or a butoxide. In an embodiment, each alkoxide monoanion independently can be methoxide, ethoxide, isopropoxide, or tert-butoxide; alternatively, methoxide; alternatively, an ethoxide; alternatively, an iso-propoxide; or alternatively, a tert-butoxide. In an aspect, the aryloxide can be phenoxide.

Generally, neutral ligand of the transition metal salt or the $N^2$-phosphinyl amidine metal salt complex comprising a transition metal salt complexed to an $N^2$-phosphinyl amidine compound, if present, independently can be any neutral ligand that forms an isolatable compound of the metal salt or $N^2$-phosphinyl amidine metal salt complex comprising a transition metal salt complexed to an $N^2$-phosphinyl amidine compound. In an aspect, each neutral ligand independently can be a nitrile or an ether. In an embodiment, the neutral ligand can be a nitrile; or alternatively, an ether. The number of neutral ligands, a, of the metal salt or $N^2$-phosphinyl amidine metal salt complex comprising transition metal salt complexed to an $N^2$-phosphinyl amidine compound can be any number that forms an isolatable metal salt or $N^2$-phosphinyl amidine metal salt complex comprising a transition metal salt complexed to an $N^2$-phosphinyl amidine compound. In an aspect, the number of neutral ligands can be from 0 to 6; alternatively, 0 to 3; alternatively, 0; alternatively, 1; alternatively, 2; alternatively, 3; or alternatively, 4. It should be noted that the neutral ligand of the $N^2$-phosphinyl amidine metal salt complex comprising a transition metal salt complexed to an $N^2$-phosphinyl amidine compound does not have to be the same, if present, as the neutral ligand of the transition metal salt used to form the $N^2$-phosphinyl amidine metal salt complex. Additionally, a metal salt not having a neutral ligan can be utilized to prepare an $N^2$-phosphinyl amidine metal salt complex comprising a transition metal salt complexed to an $N^2$-phosphinyl amidine compound having a neutral ligand.

Generally, each neutral nitrile ligand independently can be a $C_2$ to $C_{20}$ nitrile; or alternatively, a $C_2$ to $C_{10}$ nitrile. In an embodiment, each neutral nitrile ligand independently can be a $C_2$-$C_{20}$ aliphatic nitrile, a $C_7$-$C_{20}$ aromatic nitrile, a $C_8$-$C_{20}$ aralkane nitrile, or any combination thereof; alternatively, a $C_2$-$C_{20}$ aliphatic nitrile; alternatively, a $C_7$-$C_{20}$ aromatic nitrile; or alternatively, a $C_8$-$C_{20}$ aralkane nitrile. In some embodiments, each neutral nitrile ligand independently can be a $C_2$-$C_{10}$ aliphatic nitrile, a $C_7$-$C_{10}$ aromatic nitrile, a $C_8$-$C_{10}$ aralkane nitrile, or any combination thereof; alternatively, a $C_1$-$C_{10}$ aliphatic nitrile; alternatively, a $C_7$-$C_{10}$ aromatic nitrile; or alternatively, a $C_8$-$C_{10}$ aralkane nitrile.

In an embodiment, each aliphatic nitrile independently can be acetonitrile, propionitrile, a butyronitrile, or any combination thereof; alternatively, acetonitrile; alternatively, propionitrile; alternatively, or a butyronitrile. In an embodiment, each aromatic nitrile independently can be benzonitrile, 2-methylbenzonitrile, 3-methylbenzonitrile, 4-methylbenzonitrile, 2-ethylbenzonitrile, 3-ethylbenzonitrile, 4-ethylbenzonitrile, or any combination thereof; alternatively, benzonitrile; alternatively, 2-methylbenzonitrile; alternatively, 3-methylbenzonitrile; alternatively, 4-methylbenzonitrile; alternatively, 2-ethylbenzonitrile; alternatively, 3-ethylbenzonitrile; or alternatively, 4-ethylbenzonitrile.

Generally, each neutral ether ligand independently can be a $C_2$ to $C_{40}$ ether; alternatively, a $C_2$ to $C_{30}$ ether; or alternatively, a $C_2$ to $C_{20}$ ether. In an embodiment, neutral ligand independently can be a $C_2$ to $C_{40}$ aliphatic acyclic ether, a $C_3$ to $C_{40}$ aliphatic cyclic ether, a $C_4$ to $C_{40}$ aromatic cyclic ether, or a $C_{12}$ to $C_{40}$ diaryl ether; alternatively, a $C_2$ to $C_{40}$ aliphatic acyclic ether; alternatively, a $C_3$ to $C_{40}$ aliphatic cyclic ether; alternatively, a $C_4$ to $C_{40}$ aromatic cyclic ether; or alternatively, a $C_{12}$ to $C_{40}$ diaryl ether. In some embodiments, each neutral ligand independently can be a $C_2$ to $C_{30}$ aliphatic acyclic ether, a $C_3$ to $C_{30}$ aliphatic cyclic ether, a $C_4$ to $C_{30}$ aromatic cyclic ether, or a $C_{12}$ to $C_{30}$ diaryl ether; alternatively, a $C_2$ to $C_{30}$ aliphatic acyclic ether; alternatively, a $C_3$ to $C_{30}$ aliphatic cyclic ether; alternatively, a $C_4$ to $C_{30}$ aromatic cyclic ether; or alternatively, a $C_{12}$ to $C_{30}$ diaryl ether. In other embodiments, each neutral ligand independently can be a $C_2$ to $C_{20}$ aliphatic acyclic ether, a $C_3$ to $C_{20}$ aliphatic cyclic ether, a $C_4$ to $C_{20}$ aromatic cyclic ether, or a $C_{12}$ to $C_{20}$ diaryl ether; alternatively, a $C_2$ to $C_{20}$ aliphatic acyclic ether; alternatively, a $C_3$ to $C_{20}$ aliphatic cyclic ether; alternatively, a $C_4$ to $C_{20}$ aromatic cyclic ether; or alternatively, a $C_{12}$ to $C_{20}$ diaryl ether.

In an embodiment, the aliphatic acyclic ether can be dimethyl ether, diethyl ether, a dipropyl ether, a dibutyl ether, methyl ethyl ether, a methyl propyl ether, a methyl butyl ether, or any combination thereof. In some embodiments, the aliphatic acyclic ether can be dimethyl ether; alternatively, diethyl ether; alternatively, a dipropyl ether; alternatively, a dibutyl ether; alternatively, methyl ethyl ether; alternatively, a methyl propyl ether; or alternatively, a methyl butyl ether.

In an embodiment, the aliphatic cyclic ether can be tetrahydrofuran, a substituted tetrahydrofuran, a dihydrofuran, a substituted dihydrofuran, 1,3-dioxolane, a substituted 1,3-dioxolane, tetrahydropyran, a substituted tetrahydropyran, a dihydropyran, a substituted dihydropyran, pyran, a substituted pyran, a dioxane, or a substituted dioxane; alternatively, tetrahydrofuran or a substituted tetrahydrofuran; alternatively, a dihydrofuran or a substituted dihydrofuran; alternatively, 1,3-dioxolane or a substituted 1,3-dioxolane; alternatively, tetrahydropyran or a substituted tetrahydropyran; alternatively, a dihydropyran or a substituted dihydropyran; alternatively, pyran or a substituted pyran; or alternatively, a dioxane or a substituted dioxane. In some embodiments, the aliphatic cyclic ether can be tetrahydrofuran, tetrahydropyran, or dioxane, or any combination thereof; alternatively, tetrahydrofuran; alternatively, tetrahydropyran; or alternatively, dioxane.

In an embodiment, the aromatic cyclic ether can be furan, a substituted furan, benzofuran, a substituted benzofuran, isobenzofuran, a substituted isobenzofuran, dibenzofuran, a substituted dibenzofuran, or any combination thereof; alternatively, furan or a substituted furan; alternatively, benzofuran or a substituted benzofuran; alternatively, isobenzofuran or a substituted isobenzofuran; or alternatively, a dibenzofuran or a substituted dibenzofuran. In some embodiments, the aromatic cyclic ether can be furan, benzofuran, isobenzofuran, dibenzofuran, or any combination thereof; alternatively, furan; alternatively, benzofuran; alternatively, isobenzofuran; or alternatively, dibenzofuran.

In an embodiment, the diaryl ether can be diphenyl ether, a substituted diphenyl ether, ditolyl ether, a substituted ditolyl ether, or any combination thereof; alternatively, diphenyl ether or a substituted diphenyl ether; or alternatively, ditolyl ether or a substituted ditolyl ether. In some embodiments, the diaryl ether can be diphenyl ether or ditolyl ether; alternatively, diphenyl ether; or ditolyl ether.

Generally, each substituent of any subtituted neutral ligand, Q, described herein independently can be a halide and a $C_1$ to $C_{10}$ hydrocarbyl group; alternatively, a halide and a $C_1$ to $C_6$ hydrocarbyl group; alternatively, a halide; alternatively, a $C_1$ to $C_{10}$ hydrocarbyl group; or alternatively, a $C_1$ to $C_6$ hydrocarbyl group. In an embodiment, each substituent of any subtituted neutral ligand, Q, described herein independently can be a halide and a $C_1$ to $C_{10}$ alkyl group; alternatively, a halide and a $C_1$ to $C_6$ alkyl; alternatively, a halide; alternatively, a $C_1$ to $C_{10}$ alkyl group; or alternatively, a $C_1$ to $C_6$ alkyl group. Generally, each halide substituent independently can be independently a fluoride, chloride, bromide, or iodide; alternatively, fluoride; alternatively, chloride; alternatively, bromide; or alternatively, iodide. Generally, each hydrocarbyl substituent independently can be a methyl group, an ethyl group a propyl group, a butyl group, a pentyl group, a cyclopentyl group, a hexyl group, a cyclohexyl group, or a phenyl group; alternatively, a cyclopentyl group; a cyclohexyl group; or alternatively, a phenyl group. Generally, each alkyl substituents independently can be a methyl group, an ethyl group a propyl group, a butyl group, or pentyl group; alternatively, a methyl group, an ethyl group, an iso-propyl group, a tert-butyl group, or a neo-pentyl group; alternatively, a methyl group; alternatively, an ethyl group; alternatively, an iso-propyl group; alternatively, a tert-butyl group; or alternatively, a neo-pentyl group.

The features of the transition metal salts have been independently described herein and may be utilized in any combination to describe the transition metal salt of the $N^2$-phosphinyl amidine metal salt complex comprising a transition metal salt complexed to an $N^2$-phosphinyl amidine compound.

In a non-limiting embodiment, the transition metal salts which can be utilized include chromium(II) halides, chromium(III) halides, chromium(II) carboxylates, chromium (III) carboxylates, chromium(II) β-diketonates, chromium (III) β-diketonates, chromium(II) halide (THF) complexes, chromium(III) halide (THF) complexes, iron(II) halides, iron (III) halides, iron(II) carboxylates, iron(III) carboxylates, iron(II) β-diketonates, iron(III) β-diketonates, cobalt(II) halides, cobalt(III) halides, cobalt(II) carboxylates, cobalt (III) carboxylates, cobalt(II) β-diketonates, cobalt(III) β-diketonates, nickel(II) halides, nickel(II) carboxylates, nickel(II) β-diketonates, palladium(II) halides, palladium(II) carboxylates, palladium(II) β-diketonates, platinum(II) halides, platinum(IV) halides, platinum(II) carboxylates, or platinum(IV) carboxylates. In some non-limiting embodiments, the transition metal salt can be a chromium(II) halide, a chromium(III) halide, a chromium (II) carboxylate, a chromium(III) carboxylate, a chromium(II) β-diketonate, a chromium(III) β-diketonate, a chromium(II) halide (THF) complex, or a chromium(III) halide (THF) complex; alternatively, an iron(II) halide, an iron(III) halide, an iron(II) carboxylate, an iron(III) carboxylate, an iron(II) β-diketonate, or an iron (III) β-diketonate; alternatively, a cobalt(II) halide, a cobalt (III) halide, a cobalt(II) carboxylate, a cobalt(III) carboxylate, a cobalt(II) β-diketonate, or a cobalt(III) β-diketonate; alternatively, a nickel(II) halide, a nickel(II) carboxylate, or a nickel(II) β-diketonate; alternatively, a palladium(II) halide, a palladium(II) carboxylate, or a palladium(II) β-diketonate; or alternatively, a platinum(II) halide, a platinum(IV) halide, a platinum(II) carboxylate, or a platinum(IV) carboxylate. In some embodiments, the transition metal salt can be a chromium(III) halide, a chromium(III) carboxylate, a chromium (III) β-diketonate, a chromium(III) halide (THF) complex; alternatively, an iron(III) halide, an iron(III) carboxylate, or an iron(III) β-diketonate; or alternatively, a cobalt(III) halide, a cobalt(III) carboxylate, or a cobalt(III) β-diketonate. In other embodiments, the transition metal salt can be a be a chromium(II) halide; alternatively, a chromium(III) halide; alternatively, a chromium (II) carboxylate; alternatively, a chromium(III) carboxylate; alternatively, a chromium(II) β-diketonate; alternatively, a chromium(III) β-diketonate; alternatively, a chromium(II) halide (THF) complex; alternatively, a chromium(III) halide (THF) complex; alternatively, an iron(II) halide; alternatively, an iron(III) halide; alternatively, an iron(II) carboxylate; alternatively, an iron(III) carboxylate; alternatively, an iron(II) β-diketonate; alternatively, an iron(III) β-diketonate; alternatively, a cobalt(II) halide; alternatively, a cobalt(III) halide; alternatively, a cobalt(II) carboxylate; alternatively, a cobalt(III) carboxylate; alternatively, a cobalt(II) β-diketonate; alternatively, a cobalt(III) β-diketonate; alternatively, a nickel(II) halide; alternatively, a nickel(II) carboxylate; alternatively, a nickel(II) β-diketonate; alternatively, a palladium(II) halide; alternatively, a palladium(II) carboxylate; alternatively, a palladium(II) β-diketonate; alternatively, a platinum(II) halide; alternatively, a platinum(IV) halide; alternatively, a platinum(II) carboxylate; or alternatively, a platinum(IV) carboxylate.

In some non-limiting embodiments, transition metal salts which can be utilized include chromium(II) chloride, chromium(III) chloride, chromium(II) fluoride, chromium(III) fluoride, chromium(II) bromide, chromium(III) bromide, chromium(II) iodide, chromium(III) iodide, chromium(III) chloride (THF) complex, chromium(II) acetate, chromium (III) acetate, chromium(II) 2-ethylhexanoate, chromium(III) 2-ethylhexanoate, chromium(II) triflate, chromium(III) triflate, chromium(III) nitrate, chromium(III) acetylacetonate, chromium(III) hexafluoracetylacetonate, chromium(III) benzoylacetonate, iron(II) chloride, iron(III) chloride, iron(II) fluoride, iron(III) fluoride, iron(II) bromide, iron(III) bromide, iron(II) iodide, iron(III) iodide, iron(II) acetate, iron (III) acetate, iron(II) acetylacetonate, iron(III) acetylacetonate, iron(II) 2-ethylhexanoate, iron(III) 2-ethylhexanoate, iron(II) triflate, iron(III) triflate, iron(III) nitrate, cobalt(II) chloride, cobalt(III) chloride, cobalt(II) fluoride, cobalt(III) fluoride, cobalt(II) bromide, cobalt(III) bromide, cobalt(II) iodide, cobalt(III) iodide, cobalt(II) acetate, cobalt(III) acetate, cobalt(II) acetylacetonate, cobalt(III) acetylacetonate, cobalt(II) 2-ethylhexanoate, cobalt(III) 2-ethylhexanoate, cobalt(II) triflate, cobalt(III) triflate, cobalt(III) nitrate, nickel(II) chloride, nickel(II) fluoride, nickel(II) bromide, nickel(II) iodide, nickel(II) acetate, nickel(II) 2-ethylhexanoate, nickel(II) triflate, nickel(II) nitrate, nickel(II) acetylacetonate, nickel(II) benzoylacetonate, nickel(II)

hexafluoracetylacetonate, palladium(II) chloride, palladium(II) fluoride, palladium(II) bromide, palladium(II) iodide, palladium(II) acetate, palladium(II) acetylacetonate, palladium(II) nitrate, platinum(II) chloride, platinum(II) bromide, platinum(II) iodide, or platinum(IV) chloride. In other embodiments, the transition metal salt can be chromium(II) chloride, chromium(III) chloride, chromium(II) fluoride, chromium(III) fluoride, chromium(II) bromide, chromium (III) bromide, chromium(II) iodide, chromium(III) iodide, chromium(III) chloride (THF) complex, chromium(II) acetate, chromium(III) acetate, chromium(II) 2-ethylhexanoate, chromium(III) 2-ethylhexanoate chromium(II) triflate, chromium(III) triflate, chromium(III) nitrate, chromium(III) acetylacetonate, chromium(III) hexafluoracetylacetonate, or chromium(III) benzoylacetonate; alternatively, iron(II) chloride, iron(III) chloride, iron (II) fluoride, iron(III) fluoride, iron(II) bromide, iron(III) bromide, iron(II) iodide, iron(III) iodide, iron(II) acetate, iron (III) acetate, iron(II) acetylacetonate, iron(III) acetylacetonate, iron(II) 2-ethylhexanoate, iron(III) 2-ethylhexanoate, iron(II) triflate, iron(III) triflate, or iron(III) nitrate; alternatively, cobalt(II) chloride, cobalt(III) chloride, cobalt(II) fluoride, cobalt(III) fluoride, cobalt(II) bromide, cobalt(III) bromide, cobalt(II) iodide, cobalt(III) iodide, cobalt(II) acetate, cobalt(III) acetate, cobalt(II) acetylacetonate, cobalt(III) acetylacetonate, cobalt(II) 2-ethylhexanoate, cobalt(III) 2-ethylhexanoate, cobalt(II) triflate, cobalt(III) triflate, or cobalt(III) nitrate; alternatively, nickel(II) chloride, nickel(II) fluoride, nickel(II) bromide, nickel(II) iodide, nickel(II) acetate, nickel(II) 2-ethylhexanoate, nickel(II) triflate, nickel(II) nitrate, nickel(II) acetylacetonate, nickel(II) benzoylacetonate, or nickel(II) hexafluoracetylacetonate; alternatively, palladium(II) chloride, palladium(II) fluoride, palladium(II) bromide, palladium(II) iodide, palladium(II) acetate, palladium(II) acetylacetonate, or palladium(II) nitrate; or alternatively, platinum(II) chloride, platinum(II) bromide, platinum(II) iodide, or platinum(IV) chloride. In yet other embodiments, the transition metal salt can be chromium (III) chloride, chromium(III) fluoride, chromium(III) bromide, chromium(III) iodide, chromium(III) chloride (THF) complex, chromium(III) acetate, chromium(III) 2-ethylhexanoate, chromium(III) triflate, chromium(III) nitrate, chromium(III) acetylacetonate, chromium(III) hexafluoracetylacetonate, or chromium(III) benzoylacetonate; or alternatively, iron(III) chloride, iron(III) fluoride, iron(III) bromide, iron(III) iodide, iron(III) acetate, iron(III) acetylacetonate, iron(III) 2-ethylhexanoate, iron(III) triflate, or iron (III) nitrate. In further embodiments, the transition metal salt can be chromium(III) chloride, chromium(III) chloride (THF) complex, or chromium(III) acetylacetonate; or alternatively, iron(III) chloride, or iron(III) acetylacetonate.

In some non-limiting embodiments, transition metal salts which can be utilized include chromium(II) chloride; alternatively, chromium(III) chloride; alternatively, chromium(II) fluoride; alternatively, chromium(III) fluoride; alternatively, chromium(II) bromide; alternatively, chromium(III) bromide; alternatively, chromium(II) iodide; alternatively, chromium(III) iodide; alternatively, chromium(III) chloride (THF) complex; alternatively, chromium(II) acetate; alternatively, chromium(III) acetate; alternatively, chromium(II) 2-ethylhexanoate; alternatively, chromium(III) 2-ethylhexanoate; alternatively, chromium(II) triflate; alternatively, chromium(III) triflate; alternatively, chromium(III) nitrate; alternatively, chromium(III) acetylacetonate; alternatively, chromium(III) hexafluoracetylacetonate; alternatively, chromium(III) benzoylacetonate; alternatively, iron(II) chloride; alternatively, iron(III) chloride; alternatively, iron(II) fluoride; alternatively, iron(III) fluoride; alternatively, iron(II) bromide; alternatively, iron(III) bromide; alternatively, iron (II) iodide; alternatively, iron(III) iodide; alternatively, iron (II) acetate; alternatively, iron(III) acetate; alternatively, iron (II) acetylacetonate; alternatively, iron(III) acetylacetonate; alternatively, iron(II) 2-ethylhexanoate; alternatively, iron (III) 2-ethylhexanoate; alternatively, iron(II) triflate; alternatively, iron(III) triflate; alternatively, iron(III) nitrate; alternatively, cobalt(II) chloride; alternatively, cobalt(III) chloride; alternatively, cobalt(II) fluoride; alternatively, cobalt(III) fluoride; alternatively, cobalt(II) bromide; alternatively, cobalt(III) bromide; alternatively, cobalt(II) iodide; alternatively, cobalt(III) iodide; alternatively, cobalt(II) acetate; alternatively, cobalt(III) acetate; alternatively, cobalt(II) acetylacetonate; alternatively, cobalt(III) acetylacetonate; alternatively, cobalt(II) 2-ethylhexanoate; alternatively, cobalt(III) 2-ethylhexanoate; alternatively, cobalt(II) triflate; alternatively, cobalt(III) triflate; alternatively, cobalt(III) nitrate; alternatively, nickel(II) chloride; alternatively, nickel (II) fluoride; alternatively, nickel(II) bromide; alternatively, nickel(II) iodide; alternatively, nickel(II) acetate; alternatively, nickel(II) 2-ethylhexanoate; alternatively, nickel(II) triflate; alternatively, nickel(II) nitrate; alternatively, nickel (II) acetylacetonate; alternatively, nickel(II) benzoylacetonate; alternatively, nickel(II) hexafluoracetylacetonate; alternatively, palladium(II) chloride; alternatively, palladium(II) fluoride; alternatively, palladium(II) bromide; alternatively, palladium(II) iodide; alternatively, palladium(II) acetate; alternatively, palladium(II) acetylacetonate; alternatively, palladium(II) nitrate; alternatively, platinum(II) chloride; alternatively, platinum(II) bromide; alternatively, platinum (II) iodide; or alternatively, platinum(IV) chloride.

It should be appreciated, that a given $N^2$-phosphinyl amidine metal salt complex can have one or more neutral ligands even when the metal salt utilized to produce the $N^2$-phosphinyl amidine metal salt complex did not have any neutral ligands.

In an aspect, the present disclosure relates to catalyst systems comprising an $N^2$-phosphinyl amidine compound and a metal salt; alternatively, an $N^2$-phosphinyl amidine metal salt complex. In an embodiment, the catalyst system can comprise, or consist essentially of, an $N^2$-phosphinyl amidine metal salt complex and a metal alkyl; or alternatively, an $N^2$-phosphinyl amidine metal salt complex and an aluminoxane. In another aspect, the catalyst system can comprise, or consist essentially of, an $N^2$-phosphinyl amidine compound, a metal salt, and a metal alkyl; or alternatively, an $N^2$-phosphinyl amidine compound, a metal salt, and an aluminoxane. The $N^2$-phosphinyl amidine metal salt complex, metal salt, $N^2$-phosphinyl amidine compound, metal alky, and aluminoxane which can be utilized in various aspects and/or embodiments of the catalyst system are independently described herein and can be utilized in any combination and without limitation to describe various catalyst systems of this disclosure.

The $N^2$-phosphinyl amidine metal salt complex(es) and metal alkyls which can be utilized in various catalyst systems of this disclosure can comprise a metal salt complexed to an $N^2$-phosphinyl amidine compound. The $N^2$-phosphinyl amidine metal salt complexes, metal salts, and $N^2$-phosphinyl amidine compounds are independently described herein and can be utilized without limitation to describe an $N^2$-phosphinyl amidine metal salt complex which can be utilized in various catalyst systems of this disclosure.

Generally, the metal alkyl compound which can be utilized in the catalyst system of this disclosure can be any heteroleptic or homoleptic metal alkyl compound. In an embodiment, the metal alkyl can comprise, consist essentially of, or consist of, a non-halide metal alkyl, a metal alkyl halide, or any combination thereof; alternatively, a non-halide metal alkyl; or alternatively, a metal alkyl halide.

In an embodiment, the metal of the metal alkyl can comprise, consist essentially of, or consist of, a group 1, 2, 11, 12, 13, or 14 metal; or alternatively, a group 13 or 14 metal; or alternatively, a group 13 metal. In some embodiments, the metal of the metal alkyl (non-halide metal alkyl or metal alkyl halide) can be lithium, sodium, potassium, rubidium, cesium, beryllium, magnesium, calcium, strontium, barium, zinc, cadmium, boron, aluminum, or tin; alternatively, lithium, sodium, potassium, magnesium, calcium, zinc, boron, aluminum, or tin; alternatively, lithium, sodium, or potassium; alternatively, magnesium, calcium; alternatively, lithium; alternatively, sodium; alternatively, potassium; alternatively, magnesium; alternatively, calcium; alternatively, zinc; alternatively, boron; alternatively, aluminum; or alternatively, tin. In some embodiments, the metal alkyl (non-halide metal alkyl or metal alkyl halide) can comprise, consist essentially of, or consist of, a lithium alkyl, a sodium alkyl, a magnesium alkyl, a boron alkyl, a zinc alkyl, or an aluminum alkyl. In some embodiments, the metal alkyl (non-halide metal alkyl or metal alkyl halide) can comprise, consist essentially of, or consist of, an aluminum alkyl.

In an embodiment, the aluminum alkyl can be a trialkylaluminum, an alkylaluminum halide, an alkylaluminum alkoxide, an aluminoxane, or any combination thereof. In some embodiments, the aluminum alkyl can be a trialkylaluminum, an alkylaluminum halide, an aluminoxane, or any combination thereof; or alternatively, a trialkylaluminum, an aluminoxane, or any combination thereof. In other embodiments, the aluminum alkyl can be a trialkylaluminum; alternatively, an alkylaluminum halide; alternatively, an alkylaluminum alkoxide; or alternatively, an aluminoxane.

In a non-limiting embodiment, the aluminoxane can have a repeating unit characterized by the

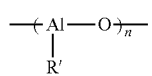

Formula I wherein $R^1$ is a linear or branched alkyl group. Alkyl groups for metal alkyls have been independently described herein and can be utilized without limitation to further describe the aluminoxanes having Formula I. Generally, n of Formula I is greater than 1; or alternatively, greater than 2. In an embodiment, n can range from 2 to 15; or alternatively, range from 3 to 10.

In an aspect, each halide of any metal alkyl halide disclosed herein can independently be fluoride, chloride, bromide, or iodide; alternatively, chloride, bromide, or iodide. In an embodiment, each halide of any metal alkyl halide disclosed herein can be fluoride; alternatively, chloride; alternatively, bromide; or alternatively, iodide.

In an aspect, each alkyl group of any metal alkyl disclosed herein (non-halide metal alkyl or metal alkyl halide) independently can be a $C_1$ to $C_{20}$ alkyl group; alternatively, a $C_1$ to $C_{10}$ alkyl group; or alternatively, a $C_1$ to $C_6$ alkyl group. In an embodiment, each alkyl group(s) independently can be a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some embodiments, alkyl group independently can be a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, alkoxide group of any metal alkyl alkoxide disclosed herein independently can be a $C_1$ to $C_{20}$ alkoxy group; alternatively, a $C_1$ to $C_{10}$ alkoxy group; or alternatively, a $C_1$ to $C_6$ alkoxy group. In an embodiment, each alkoxide group of any metal alkyl alkoxide disclosed herein independently can be a methoxy group, an ethoxy group, a propoxy group, a butoxy group, a pentoxy group, a hexoxy group, a heptoxy group, or an octoxy group; alternatively, a methoxy group, a ethoxy group, a butoxy group, a hexoxy group, or an octoxy group. In some embodiments, each alkoxide group of any metal alkyl alkoxide disclosed herein independently can be a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting embodiment, useful metal alkyls can include methyl lithium, n-butyl lithium, sec-butyl lithium, tert-butyl lithium, diethyl magnesium, di-n-butylmagnesium, ethylmagnesium chloride, n-butylmagnesium chloride, and diethyl zinc.

In a non-limiting embodiment, useful trialkylaluminum compounds can include trimethylaluminum, triethylaluminum, tripropylaluminum, tributylaluminum, trihexylaluminum, trioctylaluminum, or mixtures thereof. In some non-limiting embodiments, trialkylaluminum compounds can include trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting embodiments, useful trialkylaluminum compounds can include trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting embodiment, useful alkylaluminum halides can include diethylaluminum chloride, diethylaluminum bromide, ethylaluminum dichloride, ethylaluminum sesquichloride, and mixtures thereof. In some non-limiting embodiments, useful alkylaluminum halides can include diethylaluminum chloride, ethylaluminum dichloride, ethylaluminum sesquichloride, and mixtures thereof. In other non-limiting embodiments, useful alkylaluminum halides can include diethylaluminum chloride; alternatively, diethylaluminum bromide; alternatively, ethylaluminum dichloride; or alternatively, ethylaluminum sesquichloride.

In a non-limiting embodiment, useful aluminoxanes can include methylaluminoxane (MAO), ethylaluminoxane, modified methylaluminoxane (MMAO), n-propylaluminoxane, iso-propyl-aluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or mixtures thereof; In some non-limiting embodiments, useful aluminoxanes can include methylaluminoxane (MAO), modified methylaluminoxane (MMAO), isobutyl aluminoxane, t-butyl aluminoxane, or mixtures thereof. In other non-limiting embodiments, useful aluminoxanes can include methylaluminoxane (MAO); alternatively, ethylaluminoxane; alternatively, modified methylaluminoxane (MMAO); alternatively, n-propylaluminoxane; alternatively, iso-propylaluminoxane; alternatively, n-butylaluminoxane; alternatively, sec-butylaluminoxane; alternatively, iso-butylaluminoxane; alternatively, t-butyl aluminoxane; alternatively, 1-pentylaluminoxane; alternatively, 2-pentylaluminoxane; alternatively, 3-pentylaluminoxane; alternatively, iso-pentylaluminoxane; or alternatively, neopentylaluminoxane.

In an aspect, the metal alkyl and $N^2$-phosphinyl amidine metal salt complex may be combined in any ratio that forms an active catalyst system. In an embodiment, the metal of the metal alkyl to the metal of the $N^2$-phosphinyl amidine metal salt complex molar ratio can be greater than or equal to 5:1; alternatively, greater than or equal to 10:1; alternatively, greater than or equal to 25:1; alternatively, greater than or equal to 50:1; or alternatively, greater than or equal to 100:1. In some embodiments, the metal of the metal alkyl to the metal of the $N^2$-phosphinyl amidine metal salt complex molar ratio can range from 5:1 to 100,000:1; alternatively, range from 10:1 to 50,000:1; alternatively, range from 25:1 to 10,000:1; alternatively, range from 50:1 to 5,000:1; or alternatively, range from 100:1 to 2,500:1. When a metal alkyl having a specific metal and an $N^2$-phosphinyl amidine metal salt complex having a specific metal is utilized the metal of the metal alkyl to the metal of the $N^2$-phosphinyl amidine metal salt complex molar ratio can be stated as a specific metal of the metal alkyl to specific metal of the $N^2$-phosphinyl amidine metal salt complex molar ratio. For example, when the metal alkyl is an alkylaluminum compound (e.g. trialkylaluminum, alkylaluminum halide, alkylaluminum alkoxide, and/or aluminoxane) and the $N^2$-phosphinyl amidine metal salt complex is an $N^2$-phosphinyl amidine chromium salt complex, the metal of the metal alkyl to metal of the metal salt can be an aluminum to chromium molar ratio. In some non-limiting embodiments, the aluminum to chromium molar ratio can be greater than or equal to 5:1; alternatively, greater than or equal to 10:1; alternatively, greater than or equal to 25:1; alternatively, greater than or equal to 50:1; alternatively, greater than or equal to 100:1; alternatively, range from 5:1 to 100,000:1; alternatively, range from 10:1 to 50,000:1; alternatively, range from 25:1 to 10,000:1; alternatively, range from 50:1 to 5,000:1; or alternatively, range from 100:1 to 2,500:1.

In another aspect, the metal alkyl, metal salt, and $N^2$-phosphinyl amidine compound can be combined in any ratio that forms an active catalyst system. Generally the ratio of the components of the catalyst system comprising, consisting essentially of, or consisting of a metal alkyl, metal salt, and $N^2$-phosphinyl amidine compound can be provided as a molar ratio of the metal of the metal alkyl to metal of the metal salt and an equivalent ratio of the $N^2$-phosphinyl amidine compound to metal salt.

In an embodiment, the metal of the metal alkyl to the metal of the metal salt molar ratio can be greater than or equal to 5:1; alternatively, greater than or equal to 10:1; alternatively, greater than or equal to 25:1; alternatively, greater than or equal to 50:1; alternatively, greater than or equal to 100:1. In some embodiments, the metal of the metal alkyl to the metal of the metal salt molar ratio can range from 5:1 to 100,000:1; alternatively, ranges from 10:1 to 50,000:1; alternatively, ranges from 25:1 to 10,000:1; alternatively, ranges from 50:1 to 5,000:1; or alternatively, ranges from 100:1 to 2,500:1. When a metal alkyl having a specific metal and a metal salt having a specific metal is utilized the metal of the metal alkyl to the metal of the metal salt molar ratio can be stated as a specific metal of the metal alkyl to specific metal of the metal salt molar ratio. For example, when the metal alkyl is an alkylaluminum compound (e.g. trialkylaluminum, alkylaluminum halide, alkylaluminum alkoxide, and/or aluminoxane) and the metal salt is a chromium salt, the metal of the metal alkyl to metal of the metal salt can be an aluminum to chromium molar ratio. In some non-limiting embodiments, the aluminum to chromium molar ratio can be greater than or equal to 5:1; alternatively, greater than or equal to 10:1; alternatively, greater than or equal to 25:1; alternatively, greater than or equal to 50:1; alternatively, greater than or equal to 100:1; alternatively, range from 5:1 to 100,000:1; alternatively, range from 10:1 to 50,000:1; alternatively, range from 25:1 to 10,000:1; alternatively, range from 50:1 to 5,000:1; or alternatively, range from 100:1 to 2,500:1

In an embodiment, the $N^2$-phosphinyl amidine compound to metal salt equivalent ratio can be greater than or equal to 0.8:1; alternatively, greater than or equal to 0.9:1; or alternatively, greater than or equal to 0.95:1; or alternatively, greater than or equal to 0.98:1. In some embodiments, the $N^2$-phosphinyl amidine compound to metal salt equivalent ratio can be range from 0.8:1 to 5:1; alternatively, range from 0.9:1 to 4:1; or alternatively, range from 0.95:1 to 3:1; or alternatively, range from 0.98:1 to 2.5:1. In other embodiments, the $N^2$-phosphinyl amidine compound to metal salt equivalent ratio can be about 1:1.

In an aspect, this disclosure relates to a method of preparing an $N^2$-phosphinyl amidine compound and/or an $N^2$-phosphinyl amidine metal salt complex. $N^2$-phosphinyl amidine compounds and $N^2$-phosphinyl amidine metal salt complexes are generally described herein and methods of preparing them can be generally applied to any $N^2$-phosphinyl amidine compound and/or $N^2$-phosphinyl amidine metal salt complex described herein.

In an aspect, this disclosure relates to a method of preparing an $N^2$-phosphinyl amidine compound. Generally, the method of preparing an $N^2$-phosphinyl amidine compound can comprise: a) contacting a phosphine halide with a metal amidinate, and b) forming the $N^2$-phosphinyl amidinate. Generally, the $N^2$-phosphinyl amidine compound can be formed under conditions capable of forming an $N^2$-phosphinyl amidine group. In some embodiments, the $N^2$-phosphinyl amidine compound can be isolated; alternatively, purified; or alternatively, isolated and purified. In an embodiment, the $N^2$-phosphinyl amidine compound can have any Structure described herein.

Generally, the metal amidinate utilized in the method of preparing the $N^2$-phosphinyl amidine compound can have Structure MAM1, MAM2, MAM3, MAM4, MAM5, MAM6, MAM7, MAM8, MAM9, MAM10, MAM11, MAM13, MAM15, MAM16, MAM18, or MAM20; alternatively, Structure MAM1, MAM2, MAM3, MAM4, or MAM5; alternatively, Structure MAM6, MAM7, MAM8, MAM9, or MAM10; alternatively, Structure MAM11, MAM13, or MAM15; alternatively, Structure MAM16, MAM18, or MAM20; alternatively, Structure MAM1; alternatively, Structure MAM2; alternatively, Structure MAM3; alternatively, Structure MAM4; alternatively, Structure MAM5; alternatively, Structure MAM11; alternatively, MAM6; alternatively, MAM7; alternatively, MAM8; alternatively, MAM9; alternatively, MAM10; alternatively, Structure MAM13; alternatively Structure MAM15; alternatively, MAM16; alternatively, MAM18; or alternatively, MAM20. In an embodiment, the $N^2$-phosphinyl amidine metal salt complex comprising only one $N^2$-phosphinyl amidine group complexed to a metal salt can be characterized by having the Structure MAM1, MAM6, MAM11, or MAM16; alternatively, Structure MAM1 or MAM6; alternatively, Structure MAM11 or MAM16; alternatively, Structure MAM1 or MAM11; or alternatively, Structure MAM6 or MAM16. In an embodiment, the $N^2$-phosphinyl amidine metal salt complex comprising only two $N^2$-phosphinyl amidine groups complexed to a metal salt can be characterized by having Structure MAM2, MAM3, MAM8, MAM13, or MAM18; alternatively, Structure MAM2, MAM3, or MAM8; alternatively, Structure MAM13, or MAM18; alternatively, Structure MAM2 or MAM3; alternatively, Structure MAM3 or MAM13; or alternatively, Structure MAM8 or MAM18. In other embodiments, $N^2$-phosphinyl amidine metal salt complex compounds having at least one $N^2$-phosphinyl amidine group complexed to a metal salt can be characterized by having the Structure MAM4, MAM5, MAM9, MAM10, MAM15, or MAM20; alternatively, Structure MAM4, MAM5, MAM9, or MAM10; alternatively, Structure MAM15, or MAM20; alternatively, Structure MAM4 or MAM5; alternatively, Structure MAM9 or MAM10; alternatively, Structure MAM5 or MAM15; or alternatively, Structure MAM10 or MAM20.

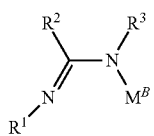

Structure MAM1

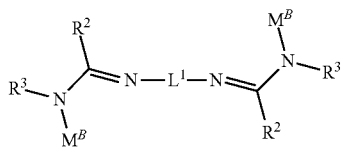

Structure MAM2

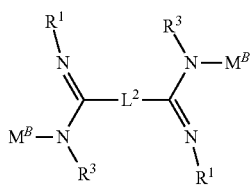

Struture MAM3

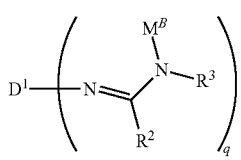

Structure MAM4

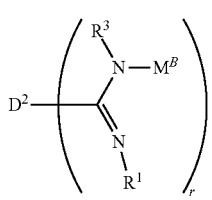

Structure MAM5

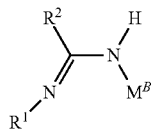

Structure MAM6

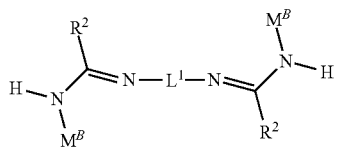

Structure MAM7

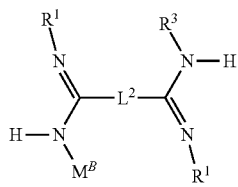

Structure MAM8

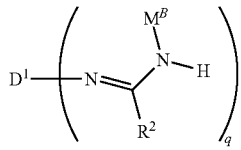

Structure MAM9

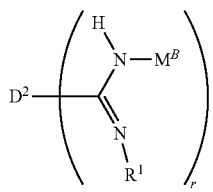

Structure MAM10

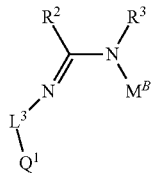

Structure MAM11

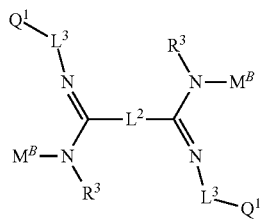

Structure MAM13

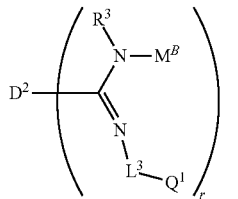

Structure MAM15

-continued

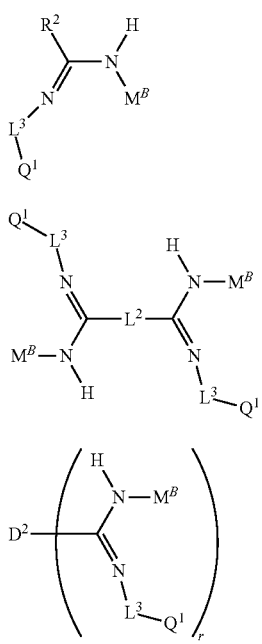

Structure MAM16

Structure MAM18

Structure MAM20

Generally, the metal amidinate structures prefaced with the designation MAM correspond with the N2-phosphinyl amidine structures prefaced with the designation NP having the same number designation. R1, R2, R3, D1, D2, $L^1$, $L^2$, $L^3$, $Q^1$, q, and r within metal amidine Structures MAM1-MAM10, MAM11, MAM13, MAM15, MAM16, MAM18, and/or MAM20 are independently described as features of the N2-phosphinyl amidine compound Structures NP1-NP10, NP11, NP13, NP15, NP16, NP18, and/or NP20. Since metal amidine Structures MAM1-MAM10, MAM11, MAM13, MAM15, MAM16, MAM18, and/or MAM20 are utilized to prepare embodiments of N2-phosphinyl amidine compounds having Structures NP1-NP10, NP11, NP13, NP15, NP16, NP18, and/or NP20, the $R^1$, $R^2$, $R^3$, D1, D2, $L^1$, $L^2$, $L^3$, $Q^1$, q, and r descriptions for the N2-phosphinyl amidine compounds may be utilized without limitation to further describe metal amidine Structures MAM1-MAM10, MAM11, MAM13, MAM15, MAM16, MAM18, and/or MAM20.

In an embodiment, the phosphine halide utilized in the method to prepare the $N^2$-phosphinyl amidine compound can have the Structure PH1.

Structure PH1

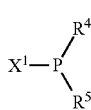

$R^4$ and $R^5$ of the phosphine halide having Structure PH1 correspond to $R^4$ and $R^5$ of the embodiments of the $N^2$-phosphinyl amidine compounds Structures NP1-NP10, NP11, NP13, NP15, NP16, NP18, and/or NP20. Since the phosphine halide having Structure PH1 is utilized to prepare embodiments of $N^2$-phosphinyl amidine compounds having Structures NP1-NP10, NP11, NP13, NP15, NP16, NP18, and/or NP20, the $R^4$ and $R^5$ descriptions for the $N^2$-phosphinyl amidine compounds can be utilized without limitation to further describe the phosphine halide having Structures PH1. In an embodiment, $X^1$ of the phosphine halide can be fluoro, chloro, bromo, or iodo; alternatively, fluoro; alternatively, chloro; alternatively, bromo; or alternatively, iodo. Phosphine halides are disclosed herein and can be utilized, without limitation, to further describe the method to prepare the $N^2$-phosphinyl amidine compound.

Generally, the phosphine halide and the metal amidinate can be combined at a phosphine halide to metal amidinate equivalent ratio of at least 0.9:1. In some embodiments, the phosphine halide and the metal amidinate can be combined at a phosphine halide to metal amidinate equivalent ratio of at least 0.95:1; alternatively, of at least 0.975:1; or alternatively, of at least 0.99:1. In some embodiments, the phosphine halide and the metal amidinate can be combined at a phosphine halide to metal amidinate equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the phosphine halide and the metal amidinate can be combined at a phosphine halide to metal amidinate equivalent ratio of about 1:1.

In an embodiment, the conditions capable of forming an $N^2$-phosphinyl amidine can include a reaction temperature of at least 0° C.; alternatively, of at least 5° C.; alternatively, of at least 10° C.; or alternatively, of at least 15° C. In some embodiments, the conditions capable of forming an $N^2$-phosphinyl amidine can include a reaction temperature ranging from 0° C. to 60° C.; alternatively, ranging from 5° C. to 50° C.; alternatively, ranging from 10° C. to 45° C.; or alternatively, ranging from 15° C. to 40° C. In an embodiment, the conditions capable of forming an $N^2$-phosphinyl amidine can include a reaction time of at least 5 minutes; alternatively, of at least 10 minutes; alternatively, of at least 15 minutes; or alternatively, of at least 20 minutes. In some embodiments, the conditions capable of forming an $N^2$-phosphinyl amidine can include a reaction time ranging from 5 minutes to 6 hours; alternatively, ranging from 10 minutes to 5 hours; alternatively, ranging from 15 minutes to 4.5 hours; or alternatively, ranging from 20 minutes to 4 hours.

In an embodiment, the phosphine halide and the metal amidinate can be contacted in an aprotic solvent. In some embodiments, the phosphine halide and the metal amidinate can be contacted in a polar aprotic solvent. Aprotic solvents which can be utilized include hydrocarbon solvents and ether solvents. Polar aprotic solvents which can be utilized include ether solvents. Solvents are generally disclosed herein and any general or specific aprotic solvent and/or polar aprotic solvent described herein can be utilized to further describe the method of preparing an $N^2$-phosphinyl amidine compound comprising contacting a phosphine halide with a metal amidinate and forming the $N^2$-phosphinyl amidinate.

In an embodiment, the $N^2$-phosphinyl amidine compound can be utilized without further isolation or purification. In some embodiments, the $N^2$-phosphinyl amidine compound can be isolated; or alternatively, isolated and purified. In an embodiment, wherein the $N^2$-phosphinyl amidine compound can be prepared in a solvent (aprotic or polar aprotic), the method to prepare the $N^2$-phosphinyl amidine compound can include a step of isolating the $N^2$-phosphinyl amidine compound by evaporating the solvent. In an embodiment wherein the $N^2$-phosphinyl amidine compound can prepared in a solvent (aprotic or polar aprotic), the method to prepare the $N^2$-phosphinyl amidine compound can include the step of isolating the $N^2$-phosphinyl amidine compound by filtering the solution to remove particulate materials and/or byproducts of the reaction and evaporating the solvent. In embodiments, the method to prepare the $N^2$-phosphinyl amidine compound can include a purification step wherein the $N^2$-phosphinyl amidine compound can be purified by dissolving the $N^2$-phosphinyl amidine compound in a solvent and filtering the solution to remove particulate materials and/or byproducts of the reaction. The solvent utilized to purify the $N^2$-phosphinyl amidine compound can be the same solvent utilized to form the $N^2$-phosphinyl amidine compound or it can be different than the solvent utilized to form the $N^2$-phosphinyl amidine compound. In some embodiments, the method to prepare the $N^2$-phosphinyl amidine compound can include a purification step of washing the $N^2$-phosphinyl amidine compound with a solvent. In other embodiments, the method to prepare the $N^2$-phosphinyl amidine compound can include a purification step of recrystallizing the $N^2$-phosphinyl amidine compound.

Generally, the evaporation of the solvent can be performed using any suitable method. In some embodiments, the solvent can be evaporated at ambient temperature (15-35° C.—no applied external heat source). In other embodiments, the solvent can be evaporated with gentle heating (e.g., at a temperature ranging from 25° C. to 50° C.). In further embodiments, the solvent can be evaporated at ambient temperature under reduced pressure. In yet other embodiments, the solvent can be evaporated with gentle heating under reduced pressure.

In an aspect, the metal amidinate utilized in the method to prepare the $N^2$-phosphinyl amidine can be formed by a) contacting an amidine compound (non-metallic) having an $N^2$ hydrogen atom with a metallic compound capable of abstracting the hydrogen atom from the amidine compound; and b) forming the metal amidinate. Generally, the metal amidinate can be formed under conditions capable of forming a metal amidinate. In some embodiments, the metal amidinate can be isolated; alternatively, purified; or alternatively, isolated and purified.

In an embodiment, the amidine compound (non-metallic) can have Structure AM1, AM2, AM3, AM4, AM5, AM6, AM7, AM8, AM9, AM10, AM11, AM13, AM15, AM16, AM18, or AM20; alternatively, Structure AM1, AM2, AM3, AM4, or AM5; alternatively, AM6, AM7, AM8, AM9, or AM10; alternatively, AM11, AM13, or AM15; alternatively, AM16, AM18, or AM20; alternatively, Structure AM1; alternatively, Structure AM2; alternatively, Structure AM3; alternatively, Structure AM4; alternatively, Structure AM5; alternatively, Structure AM11; alternatively, Structure AM6; alternatively, Structure AM7; alternatively, Structure AM8; alternatively, Structure AM9; alternatively, Structure AM10; alternatively, Structure AM11; alternatively, Structure AM13; alternatively, Structure AM15; alternatively, AM16; alternatively, AM18; or alternatively, AM20. In an embodiment, the amidine compound (non-metallic) comprising only one $N^2$-phosphinyl amidine group complexed to a metal salt can be characterized by having the Structure AM1, AM6, AM11, or AM16; alternatively, Structure AM1 or AM6; alternatively, Structure AM11 or AM16; alternatively, Structure AM1 or AM11; or alternatively, Structure AM6 or AM16. In an embodiment, the amidine compound (non-metallic) comprising only two $N^2$-phosphinyl amidine groups complexed to a metal salt can be characterized by having Structure AM2, AM3, AM8, AM13, or AM18; alternatively, Structure AM2, AM3, or AM8; alternatively, Structure AM13, or AM18; alternatively, Structure AM2 or AM3; alternatively, Structure AM3 or AM13; or alternatively, Structure AM8 or AM18. In other embodiments, the amidine compound (non-metallic) having at least one $N^2$-phosphinyl amidine group complexed to a metal salt can be characterized by having the Structure AM4, AM5, AM9, AM10, AM15, or AM20; alternatively, Structure AM4, AM5, AM9, or AM10; alternatively, Structure AM15, or AM20; alternatively, Structure AM4 or AM5; alternatively, Structure AM9 or AM10; alternatively, Structure AM5 or AM15; alternatively, Structure AM10 or AM20. In some embodiments, the amidine compounds may have only one $N^2$ hydrogen atom (i.e., $R^3$ is a non-hydrogen group in the amidine compounds). In other embodiments, the amidine may have two $N^2$ hydrogen atoms (i.e., $R^3$ is a non-hydrogen group in the amidine compounds).

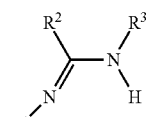

Structure AM1

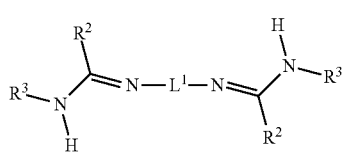

Structure AM2

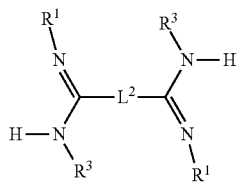

Structure AM3

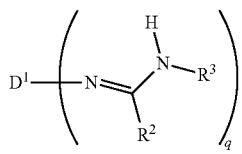

Structure AM4

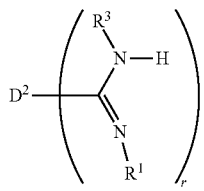

Structure AM5

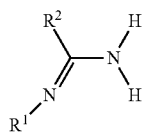

Structure AM6

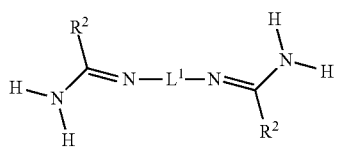

Structure AM7

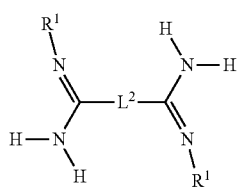

Structure AM8

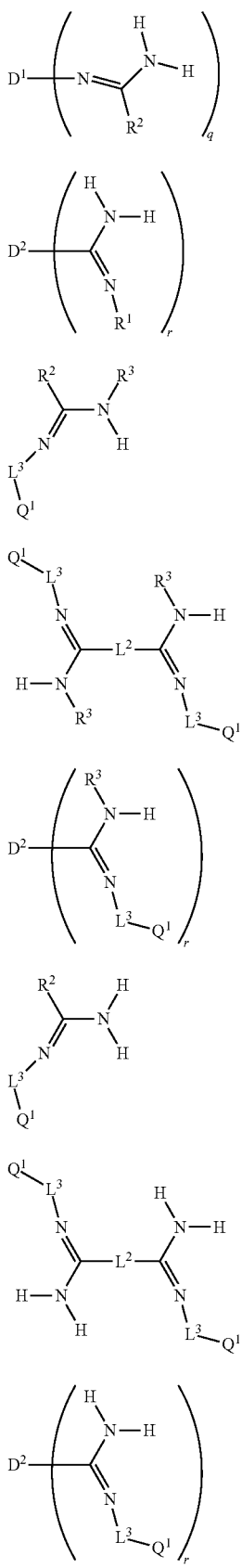

Structure AM9

Structure AM10

Structure AM11

Structure AM13

Structure AM15

Structure AM16

Structure AM18

Structure AM20

Generally, the amidine structure prefaced with AM corresponds to the metal amidinate structure prefaced with MAM having the same number designation. However, it should be noted that methods described herein provide for the conversion of amidine compounds having Structures AM6-AM10, AM16, AM18, and/or AM20 (wherein $R^3$ is hydrogen) into amidine compounds having Structures AM1-AM5, AM11, AM13, and/or AM15 (wherein $R^3$ is not hydrogen), respectively. $R^1$, $R^2$, $R^3$, $D^1$, $D^2$, $L^1$, $L^2$, $L^3$, $Q^1$, q, and r within amidine compound Structures AM1-AM10, AM11, AM13, AM15, AM16, AM18, and/or AM20 are independently described as features of the N2-phosphinyl amidine compound Structures NP1-NP10, NP11, NP13, NP15, NP16, NP18, and/or NP20. Since amidine Structures AM1-AM10, AM11, AM13, AM15, AM16, AM18, and/or AM20 can be utilized to prepare embodiments of N2-phosphinyl amidine compounds having Structures NP1-NP10, NP11, NP13, NP15, NP16, NP18, and/or NP20, the $R^1$, $R^2$, $R^3$, $D^1$, $D^2$, $L^1$, $L^2$, $L^3$, $Q^1$, q, and r descriptions for the N2-phosphinyl amidine compounds can be utilized without limitation to further describe the amidine Structures AM1-AM10, AM11, AM13, AM15, AM16, AM18, and/or AM20.

In an embodiment, the metal compound capable of abstracting the proton from the amidine compound (non-metallic) can be a metal hydride or a metal alkyl; alternatively, a metal hydride; or alternatively, a metal alkyl. In an embodiment the metal hydride can be sodium hydride, calcium hydride, lithium aluminum hydride or sodium borohydride; alternatively, sodium hydride or calcium hydride; alternatively, lithium aluminum hydride or sodium borohydride; alternatively, sodium hydride; alternatively, calcium hydride; alternatively, lithium aluminum hydride; or alternatively, sodium borohydride. Metal alkyl compounds are described herein and can be utilized, without limitation, as the metal alkyl for abstracting the proton from the amidine compound (non-metallic). Particularly useful metal alkyls for abstracting the proton from the amidine compound (non-metallic) can be Group 1 metal hydrides or Group 1 metal alkyls; alternatively, Group 1 metal hydrides; or alternatively, Group 1 metal alkyls. In an embodiment, the metal alkyl can be a lithium alkyl, a sodium alkyl, or a potassium alkyl; alternatively, a lithium alkyl or a sodium alkyl; alternatively, a lithium alkyl; alternatively, a sodium alkyl; or alternatively, a potassium alkyl. Alkyl groups for the metal alkyl are described herein and can be utilized without limitation to further describe the metal alkyls which can be contacted with the amidine compound. In some exemplary embodiments, the metal alkyl can be methyl lithium, n-butyl lithium, sec-butyl lithium, or tert-butyl lithium; alternatively, methyl lithium; alternatively, n-butyl lithium; alternatively, sec-butyl lithium; or alternatively, tert-butyl lithium.

Generally, the amidine compound (non-metallic) and the metal compound can be combined in an amidine compound to metal compound equivalent ratio of at least 0.9:1. In an embodiment, the amidine compound (non-metallic) and the metal compound can be combined in an amidine compound to metal compound equivalent ratio of at least 0.95:1; alternatively, of at least 0.975:1; or alternatively, of at least 0.99:1. In some embodiments, the amidine compound (non-metallic) and the metal compound can be combined in an amidine compound and metal compound equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the amidine compound (non-metallic) and the metal compound can be combined in an amidine compound to metal compound equivalent ratio of about 1:1.

In an embodiment, the conditions capable of forming the metal amidinate can include a temperature of at least −45° C.; alternatively, of at least −30° C.; alternatively, of at least −25° C.; or alternatively, of at least −20° C. In some embodiments, the reaction conditions capable of forming a metal amidinate can include a temperature ranging from −45° C. to 60° C.; alternatively, ranging from −30° C. to 50° C.; alternatively, ranging from −25° C. to 45° C.; or alternatively, ranging from −20° C. to 40° C.

In some embodiments, the conditions capable of forming the metal amidinate can include an initial metal compound and amidine compound contact temperature and a second temperature to form the metal amidinate. It should be noted the when the conditions capable of forming the metal amidinate is described as occurring at two temperatures (one for the contact of the metal compound and the amidine compound and one for the formation of the metal amidinate) that this description does not exclude the prospect that metal amidinate can be formed at the contact temperature. The description just relates that, in some embodiments, the metal amidinate formation may proceed better when the initial contact between the metal compound and amidine compound is performed at one temperature and the formation of the metal amidinate is completed at a second different temperature.

In an embodiment, the metal compound and amidine compound can be contacted at a temperature ranging from −45° C. to 20° C.; alternatively, ranging from −30° C. to 15° C.; alternatively, ranging from −25° C. to 45° C.; or alternatively, ranging from −20° C. to 40° C. In an embodiment, the metal amidinate can be formed at a temperature ranging from 0° C. to 20° C.; alternatively, ranging from 5° C. to 15° C.; alternatively, ranging from 10° C. to 45° C.; or alternatively, ranging from 15° C. to 40° C.

In an embodiment, the conditions capable of forming the metal amidinate can include a metal amidinate formation time of at least 5 minutes; alternatively, of at least 10 minutes; alternatively, of at least 15 minutes; or alternatively, of at least 20 minutes. In some embodiments, the conditions capable of forming the metal amidinate can include a metal amidinate formation time ranging from 5 minutes to 6 hours; alternatively, ranging from 10 minutes to 5 hours; alternatively, ranging from 15 minutes to 4.5 hours; or alternatively, ranging from 20 minutes to 4 hours.

In an embodiment, the metal compound and the amidine compound (non-metallic) can be contacted in an aprotic solvent. In some embodiments, the metal compound and the amidine compound (non-metallic) can be contacted in a polar aprotic solvent. Aprotic solvents which can be utilized include hydrocarbon solvents and ether solvents. Polar aprotic solvents which can be utilized include ether solvents. Solvents are generally disclosed herein and any general or specific aprotic solvent and/or polar aprotic solvent described herein can be utilized to further describe the method of preparing the metal amidinate by contacting a metal compound and an amidine compound and forming a metal amidinate.

In an embodiment, the metal amidinate can be utilized without further isolation or purification. In some embodiments, the metal amidinate can be isolated; alternatively, purified; or alternatively, isolated and purified. In an embodiment, the method to prepare the metal amidinate can include a step of isolating the metal amidinate by filtering the metal amidate from the solution. In some embodiments, the method to prepare the metal amidinate can include a step of purifying the metal amidinate by washing the metal amidinate with a solvent. Generally, the washing solvent can be an aprotic solvent. In other embodiments, the washing solvent can be a polar aprotic solvent. In other embodiments, the washing solvent can be a non-polar aprotic solvent.

In an aspect, the metal amidinate which can be utilized to prepare the $N^2$-phosphinyl amidine can be prepared by a method comprising: a) contacting a metal amide and a nitrile; and b) forming the metal amidinate. Generally, the metal amidinate can be formed under conditions capable of forming a metal amidinate. In some embodiments, the metal amidinate can be isolated; alternatively, purified; or alternatively, isolated and purified. It should be noted that this method prepares a metal amidinate having a $N^2$ hydrogen atom (i.e., $R^3$ is hydrogen). Other methods for preparing metal amidinates having a non-hydrogen $R^3$ group are disclosed herein.

In an embodiment, the metal amide has Structures MA1, MA2, MA3, or MA4; alternatively, MA1; alternatively, MA2; alternatively, MA3; or alternatively, MA4.

$$R^1\text{—NHM}^A \quad \text{Structure MA1}$$

$$M^A\text{HN—L}^1\text{—NHM}^A \quad \text{Structure MA2}$$

$$D^1\text{—(NHM}^A)_q \quad \text{Structure MA3}$$

$$Q^1\text{—L}^3\text{—NHM}^A \quad \text{Structure MA4}$$

In an embodiment, the nitrile may have Structure $N^1$, $N^2$, or $N^3$; alternatively, N1; alternatively, N2; or alternatively, N3.

$$R^2\text{—C}\equiv\text{N} \quad \text{Structure N1}$$

$$N\equiv\text{C—L}^2\text{—C}\equiv\text{N} \quad \text{Structure N2}$$

$$D^2\text{—(C}\equiv\text{N)}_r \quad \text{Structure N3}$$

Generally, utilizing the present disclosure, one can readily recognize the metal amide structure and the nitrile structure necessary to produce a particular metal amidinate. For example, a metal amidinate having Structure AM6 can be prepared from the metal amide having Structure MA1 and the nitrile having Structure $N^1$, a metal amidinate having Structure AM7 can be prepared from the metal amide having Structure MA2 and the nitrile having Structure $N^1$, a metal amidinate having Structure AM8 can be prepared from the metal amide having Structure MA1 and the nitrile having Structure N2, a metal amidinate having Structure AM9 can be prepared from the metal amide having Structure MA3 and the nitrile having Structure $N^1$, a metal amidinate having Structure AM10 can be prepared from the metal amide having Structure MA1 and the nitrile having Structure N3, a metal amidinate having Structure AM16 can be prepared from the metal amide having Structure MA4 and the nitrile having Structure $N^1$, a metal amidinate having Structure AM18 can be prepared from the metal amide having Structure MA4 and the nitrile having Structure N2, and a metal amidinate having Structure AM20 can be prepared from the metal amide having Structure MA4 and the nitrile having Structure N3. $R^1$, $R^2$, $R^3$, $R^4$, $R^5$, $D^1$, $D^2$, $L^1$, $L^2$, $L^3$, $Q^1$, q, and r within metal amide Structures MA1-MA4 and nitrile Structures N1-N3 are independently described as features of the N2-phosphinyl amidine compounds Structures NP1-NP10, NP11, NP13, NP15, NP16, NP18, and/or NP20. Since the metal amides having Structures MA1-MA4 and the nitriles having Structures N1-N3 are utilized to ultimately prepare embodiments of N2-phosphinyl amidine compounds having Structures NP1-NP10, NP11, NP13, NP15, NP16, NP18, and/or NP20, the $R^1, R^2, R^3, R^4, R^5, D^1, D^2, L^1, L^2, L^3, Q^1$, q, and r descriptions for the N2-phosphinyl amidine compounds can be utilized without limitation to further describe the metal amides having Structures MA1-MA4 and the nitriles having Structures N1-N3. General and specific metal amides (or the amines from which they are derived) and nitriles are provided herein and can be utilized without limitation to further describe the method of preparing the herein disclosed metal amidinates.

Generally, the nitrile and the metal amide can be combined in a nitrile to metal amide equivalent ratio of at least 0.9:1. In an embodiment, the nitrile and the metal amide can be combined in a nitrile to metal amide equivalent ratio of at least 0.95:1; alternatively, of at least 0.975:1; or alternatively, of at least 0.99:1. In some embodiments, the nitrile and the metal amide can be combined in a nitrile to metal amide equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the nitrile and the metal amide can be combined in a metal amide to nitrile equivalent ratio of about 1:1.

In an embodiment, the conditions capable of forming the metal amidinate can include a reaction temperature of at least 10° C.; alternatively, of at least 15° C.; alternatively, of at least 20° C.; or alternatively, of at least 25° C. In some embodiments, the conditions capable of forming the metal amidinate can include a reaction temperature ranging from 10° C. to 100° C.; alternatively, ranging from 15° C. to 90° C.; alternatively, ranging from 20° C. to 85° C.; or alternatively, ranging from 25° C. to 80° C. In an embodiment, the conditions capable of forming the metal amidinate can include a reaction time of at least 15 minutes; alternatively, of at least 30 minutes; alternatively, of at least 45 minutes; or alternatively, of at least 1 hour. In some embodiments, the conditions capable of forming the metal amidinate can include a reaction time ranging from 15 minutes to 36 hours; alternatively, ranging from 30 minutes to 30 hours; alternatively, ranging from 45 minutes to 24 hours; or alternatively, ranging from 1 hour to 18 hours.

In an embodiment, the nitrile and the metal amide can be contacted in an aprotic solvent. In some embodiments, the nitrile and the metal amide can be contacted in a polar aprotic solvent. Aprotic solvents which can be utilized include hydrocarbon solvents and ether solvents. Polar aprotic solvents which may be utilized include ether solvents. Solvents are generally disclosed herein and any general or specific aprotic solvent and/or polar aprotic solvent described herein can be utilized to further describe the method of preparing the metal amidinate by contacting a nitrile and a metal amide and forming the metal amidinate.

In an embodiment, the metal amidinate can be utilized without further isolation or purification. In some embodiments, the metal amidinate can be isolated; alternatively, purified; or alternatively, isolated and purified. In an embodiment, the method to prepare the metal amidinate can include a step of isolating the metal amidinate by filtering the metal amidate from the solution. In some embodiments, the method to prepare the metal amidinate can include a step of purifying the metal amidinate washing the metal amidinate with a solvent. Generally, the washing solvent can be an aprotic solvent. In other embodiments, the washing solvent can be a polar aprotic solvent. In other embodiments, the washing solvent can be a non-polar aprotic solvent.

In an aspect, the amidine compound which can be utilized to form the $N^2$-phosphinyl amidine compound can be prepared by a method comprising: a) contacting a metal amide and a nitrile; b) forming the metal amidinate; and c) neutralizing the formed metal amidinate with a protic compound to form a non-metal amidine compound. Steps a) and b) of this method are the same as the method of preparing a metal amidinate comprising contacting a metal amide and a nitrile and forming the metal amidinate. As such, embodiments relating to the steps of contacting a metal amide and a nitrile and forming the metal amidinate described herein can be utilized without limitation to further describe the method of making an amidinate compound comprising; a) contacting a metal amide and a nitrile; b) forming the metal amidinate; and c) neutralizing the formed metal amidinate. In some embodiments, the non-metal amidine compound can be isolated; alternatively, purified; or alternatively, isolated and purified.

In an embodiment, the protic compound can be any compound capable of providing a proton to neutralize the metal amidinate. In some embodiments, the protic compound can be Brønsted acid. In other embodiments, the protic compound can be water, a mineral acid, a carboxylic acid, an alcohol, or an amine hydrohalide; alternatively, water; alternatively, a mineral acid; alternatively, a carboxylic acid; alternatively, an alcohol; or alternatively, an amine hydrohalide. In an embodiment, the mineral acid can be hydrochloric acid, hydrobromic acid, sulfuric acid, nitric acid, phosphoric acid, or boric acid; alternatively, hydrochloric acid; alternatively, sulfuric acid; alternatively, nitric acid; alternatively, phosphoric acid; or alternatively, boric acid. In an embodiment, the carboxylic acid can be a $C_1$ to $C_5$ carboxylic acid. In some embodiments, the carboxylic acid can be formic acid, acetic acid, propionic acid, or butyric acid; alternatively, formic acid or acetic acid; alternatively, formic acid; alternatively, acetic acid; alternatively, propionic acid; or alternatively, butyric acid. In an embodiment, the alcohol can be a $C_1$ to $C_{10}$ alcohol; or alternatively, a $C_1$ to $C_5$ alcohol. In some embodiments, the alcohol can be methanol, ethanol, propanol, butanol, or pentanol; alternatively, methanol, ethanol, n-propanol, iso-propanol, n-butanol, or tert-butanol; alternatively, methanol; alternatively, ethanol; alternatively, n-propanol; alternatively, iso-propanol; alternatively, n-butanol; or alternatively, or tert-butanol. In an embodiment, the amine hydrohalide can be a $C_1$ to $C_{15}$ hydrohalide. In some embodiments, the amine hydrohalide may be a methylamine hydrohalide, dimethylamine hydrohalide, trimethylamine hydrohalide, ethylamine hydrohalide, diethylamine hydrohalide, or triethylamine hydrohalide, or triethanolamine hydrohalide; alternatively, methylamine hydrohalide; alternatively, dimethylamine hydrohalide; alternatively, trimethylamine hydrohalide; alternatively, ethylamine hydrohalide; alternatively, diethylamine hydrohalide; alternatively, triethylamine hydrohalide; alternatively, ethanolamine hydrohalide; alternatively, diethanolamine hydrohalide; or alternatively, triethanolamine hydrochloride. In some embodiments, the amine hydrohalide can be an amine hydrochloride, hydrobromide, or hydroiodide; or alternatively, hydrochloride. In some embodiments, the amine hydrohalide can be methylamine hydrochloride, methylamine hydrobromide, dimethylamine hydrochloride, dimethylamine hydrobromide, trimethylamine hydrochloride, trimethylamine hydrobromide, ethylamine hydrochloride, ethylamine hydrobromide, diethylamine hydrochloride, diethylamine hydrobromide, triethylamine hydrochloride, triethylamine hydrobromide, ethanolamine hydrochloride, ethanolamine hydrobromide, diethanolamine hydrochloride, diethanolamine hydrobromide, triethanolamine hydrochloride, triethanolamine hydrobromide; alternatively, methylamine hydrochloride, dimethylamine hydrochloride, trimethylamine hydrochloride, ethylamine hydrochloride, diethylamine hydrochloride, triethylamine hydrochloride, ethanolamine hydrochloride, diethanolamine hydrochloride, or triethanolamine hydrochloride; alternatively, methylamine hydrochloride; alternatively, dimethylamine hydrochloride; alternatively, trimethylamine hydrochloride; alternatively, ethylamine hydrochloride; alternatively, diethylamine hydrochloride; alternatively, triethylamine hydrochloride; alternatively, ethanolamine hydrochloride; alternatively, diethanolamine hydrochloride; or alternatively, triethanolamine hydrochloride.

In an embodiment, the non-metal amidine compound can be utilized without further isolation or purification. In some embodiments, the non-metal amidine compound can be isolated; alternatively, purified; or alternatively, isolated and purified. In an embodiment, wherein the amidine compound can be prepared in a solvent (aprotic or polar aprotic), the method to prepare the amidine compound can include a step of isolating the amidine compound by evaporating the solvent. In an embodiment wherein the non-metal amidine compound can be prepared in a solvent (aprotic or polar aprotic), the method to prepare the non-metal amidine compound can include the step of isolating the amidine compound by filtering the solution to remove particulate materials and/or byproducts of the reaction and evaporating the solvent. In embodiments, the method to prepare the non-metal amidine compound can include a purification step wherein the non-metal amidine compound can be purified by dissolving the non-metal amidine compound in a solvent and filtering the solution to remove particulate materials and/or byproducts of the reaction. The solvent utilized to purify the non-metal amidine compound can be the same solvent utilized to form the non-metal amidine compound or it may be different than the solvent utilized to form the non-metal amidine compound. In some embodiments, the method to prepare the non-metal amidine compound may include a purification step wherein the non-metal amidine compound can be purified by washing with a solvent. In other embodiments, the method to prepare the non-metal amidine compound can include a purification step of recrystallizing the amidine compound.

Generally, the evaporation of the solvent can be performed using any suitable method. In some embodiments, the solvent can be evaporated at ambient temperature (15-35° C.—no applied external heat source). In other embodiments, the solvent can be evaporated with gentle heating (e.g., at a temperature ranging from 25° C. to 50° C.). In further embodiments, the solvent can be evaporated at ambient temperature under reduced pressure. In yet other embodiments, the solvent can be evaporated with gentle heating under reduced pressure.

In an aspect the metal amides, which are utilized in the preparation of some of the metal amidinates and amidine compound described herein, can be prepared by a method comprising: a) contacting an amine having an —NH$_2$ group and a compound capable of abstracting the proton from the amine —NH$_2$ group; and b) forming the metal amide. Generally, the metal amide can be formed under conditions capable of forming a metal amide. In some embodiments, the metal amide may be isolated; alternatively, purified; or alternatively, isolated and purified.

In an embodiment, the amine may have Structures A1, A2, A3, or A4; alternatively, A1; alternatively, A2; alternatively, A3; or alternatively, A4. Generally, utilizing the present disclosure, one can readily recognize the metal amine structure and the nitrile structure necessary to produce a particular metal amidinate. For example, the amine having Structure A1 can utilized when $R^1$—NH$_2$  Structure A1

H$_2$N—L$^1$—NH$_2$  Structure A2

D$^1$—(NH$_2$)$_q$  Structure A3

Q$^1$—L$^3$—NH$_2$  Structure MA4 preparing a metal amidinate having Structure MAM6, MAM8, or MAM10 and/or an amidine compound having Structure AM6, AM8, or AM10, the amine having Structure A2 is utilized when preparing a metal amidinate having Structure MAM7 and/or an amidine compound having Structure AM7, the amine having Structure A3 is utilized when preparing a metal amidinate having Structure MAM9 and/or an amidine compound having Structure AM9, an the amine having Structure A4 is utilized when preparing a metal amidinate having Structure MAM16. MAM18, or MAM20 and/or an amidine compound having Structure AM16, AM18, or AM20. However, it should be noted that the methods described herein provide for the conversion amidine compounds having Structures AM6-10, AM16, AM18, and/or AM20 (wherein $R^3$ is hydrogen) or metal amidinates having Structures MAM6-MAM10, MAM16, MAM18, and/or MAM20 (wherein $R^3$ is hydrogen) into amidine compounds having Structures NP1-NP5, NP11, NP13, and/or NP15 (wherein $R^3$ is not hydrogen). $R^1$, $D^1$, $L^1$, $L^3$, $Q^1$, and q within amine Structures A1-A4 are independently described as features of the $N^2$-phosphinyl amidine compounds Structures NP1-NP10, NP11, NP13, NP15, NP16, NP18, and/or NP20. Since amine Structures A1-A4 are ultimately utilized to prepare embodiments of $N^2$-phosphinyl amidine compounds having Structures NP1-NP10, NP11, NP13, NP15, NP16, NP18, and/or NP20, the $R^1$, $D^1$, $L^1$, $L^3$, $Q^1$, and q, descriptions for the $N^2$-phosphinyl amidine compounds may be utilized without limitation to further describe the amine Structures A1-A4 Amines are disclosed herein and may be utilized, without limitation, to further describe the method to prepare the amidine compound.

In an embodiment, the metal compound capable of abstracting the proton from an amine having an —NH2 group can be a metal hydride or a metal alkyl. Generally, metal hydrides and metal alkyls capable of abstracting the proton from an amine having an —NH2 group can be the same as those capable of abstracting the proton from the amidine compound (described herein). Consequently, the metal hydrides and metal alkyls describe herein as capable of capable of abstracting the proton from the amidine compound can be utilized, without limitation, to further describe the method preparing the metal amide.

Generally, the amine and the metal compound can be combined in an amine to metal compound equivalent ratio of at least 0.9:1. In an embodiment, the amine and the metal compound can be combined in an amine to metal compound equivalent ratio of at least 0.95:1; alternatively, of at least 0.975:1; or alternatively, of at least 0.99:1. In some embodiments, the amine and the metal compound can be combined in an amine and metal compound equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the amine and the metal compound can be combined in an amine to metal compound equivalent ratio of about 1:1.

In an embodiment, the conditions capable of forming the metal amide can include a temperature of at least −45° C.; alternatively, of at least −30° C.; alternatively, of at least −25° C.; or alternatively, of at least −20° C. In some embodiments, the reaction conditions capable of forming a metal amide can include a temperature ranging from −45° C. to 60° C.; alternatively, ranging from −30° C. to 50° C.; alternatively, ranging from −25° C. to 45° C.; or alternatively, ranging from −20° C. to 40° C.

In some embodiments, the conditions capable of forming the metal amide can include an initial metal compound and amine contact temperature and a second temperature to form the metal amide. It should be noted the when the conditions capable of forming the metal amide is described as occurring at two temperatures (one for the contact of the metal compound and the amine and one for the formation of the metal amide) that this description does not exclude the prospect that metal amide can be formed at the contact temperature. The description just relates that, in some embodiments, the formation can proceed better when the initial contact between the metal compound and amine is performed at one temperature and the formation of the metal amide is completed at a second different temperature.

In an embodiment, the metal compound and amine can be contacted at a temperature ranging from −45° C. to 20° C.; alternatively, ranging from −30° C. to 15° C.; alternatively, ranging from −25° C. to 45° C.; or alternatively, ranging from −20° C. to 40° C. In an embodiment, the metal amide can be formed at a temperature ranging from 0° C. to 20° C.; alternatively, ranging from 5° C. to 15° C.; alternatively, ranging from 10° C. to 45° C.; or alternatively, ranging from 15° C. to 40° C.

In an embodiment, the conditions capable of forming the metal amide can include a metal amide formation time of at least 5 minutes; alternatively, of at least 10 minutes; alternatively, of at least 15 minutes; or alternatively, of at least 20 minutes. In some embodiments, the conditions capable of forming the metal amide can include a metal amide formation time ranging from 5 minutes to 6 hours; alternatively, ranging from 10 minutes to 5 hours; alternatively, ranging from 15 minutes to 4.5 hours; or alternatively, ranging from 20 minutes to 4 hours.

In an embodiment, the metal compound and the amine can be contacted in an aprotic solvent. In some embodiments, the metal compound and the amine can be contacted in a polar aprotic solvent. Aprotic solvents which can be utilized include hydrocarbon solvents and ether solvents. Polar aprotic solvents which can be utilized include ether solvents. Solvents are generally disclosed herein and any general or specific aprotic solvent and/or polar aprotic solvent described herein can be utilized to further describe the method of preparing the metal amide by contacting a metal compound and an amine compound and forming a metal amide.

In an embodiment, the metal amide can be utilized without further isolation or purification. In some embodiments, the metal amide can be isolated; alternatively, purified; or alternatively, isolated and purified. In an embodiment, the method can include a step of isolating the metal amide by filtering the metal amide from the solution. In some embodiments, the method can include a step of purifying the metal amide by washing the metal amide with a solvent. Generally, the washing solvent is an aprotic solvent. In other embodiments, the washing solvent can be polar aprotic solvent. In other embodiments, the washing solvent can be a non-polar aprotic solvent.

Generally, methods of preparing an amidine compound utilizing metal amides and nitriles produce amidine compounds having two $N^2$ hydrogens (e.g., amidine compounds having Structure AM6-AM10, AM16, AM18, and/or AM20) which can then be utilized to prepare an $N^2$-phosphinyl amidine compound having an $N^2$ hydrogen atom (e.g. $N^2$-phosphinyl amidine compounds having Structures NP6-NP10, NP16, NP18, and/or NP20, respectively) utilizing methods described herein. However, in some instances it may be desirable to have $N^2$-phosphinyl amidine compounds having a non-hydrogen $N^2$ group; e.g., $N^2$-phosphinyl amidine compounds having Structures NP1-NP5, NP11, NP13, and/or NP15 wherein $R^3$ is a non-hydrogen group. Some methods of preparing the $N^2$-phosphinyl amidine compounds having a non-hydrogen $N^2$ group include: a) alkylating an $N^2$-phosphinyl amidine compound having an $N^2$ hydrogen atom (e.g., $N^2$-phosphinyl amidine compounds having Structure NP6-NP10, NP16, NP18, and/or NP20), b) alkylating a metal amidinate (e.g., an amidinate having Structure MAM6-MAM10, MAM16, MAM18, and /MAM20) to produce an amidine compound having Structures AM1-AM5, AM11, AM13, AM15 wherein $R^3$ is an non-hydrogen group and converting the amidine compound to an $N^2$-phosphinyl amidine compound (e.g., $N^2$-phosphinyl amidine compounds having Structure NP1-NP5, NP11, NP13, and/or NP15) utilizing methods described herein, and c) preparing an amidine compound having only one $N^2$ hydrogen atom by contacting an N-substituted α-chloro imine with an amine and converting the amidine compound to an $N^2$-phosphinyl amidine compound (e.g., $N^2$-phosphinyl amidine compounds having Structure NP1-NP5, NP11, NP13, and/or NP15) utilizing methods described herein.

In an aspect, a method of preparing an $N^2$-phosphinyl amidine compound can comprise: a) contacting an $N^2$-phosphinyl amidine compound having an $N^2$ hydrogen and a metallic compound capable of abstracting a proton from the $N^2$-phosphinyl amidine compound; b) forming a metal $N^2$-phosphinyl amidinate; c) contacting a halogenated compound with the formed metal $N^2$-phosphinyl amidinate and d) forming the $N^2$-phosphinyl amidine compound. Generally, the $N^2$-phosphinyl metal amidinate can be formed under conditions capable of forming a metal amidinate. In an embodiment, the metal $N^2$-phosphinyl amidinate can be isolated; alternatively, purified; or alternatively, isolated and purified. Generally, the $N^2$-phosphinyl amidine compound can be formed under conditions capable of forming an $N^2$-phosphinyl amidine compound. In an embodiment, the $N^2$-phosphinyl amidine compound can be isolated; alternatively, purified; or alternatively, isolated and purified.

In an embodiment, the amidine compound having an $N^2$ hydrogen can have Structure NP6, NP7, NP8, NP9, NP10, NP16, NP18, or NP20; alternatively, NP6, NP7, NP8, NP9, or NP10; alternatively, NP16, NP18, or NP20; alternatively, NP6 or NP16; alternatively, NP8 or NP18; alternatively, NP10 or NP20; alternatively, NP6; alternatively, NP7; alternatively, NP8; alternatively, NP9; alternatively, NP10; alternatively, NP16; alternatively, NP18; or alternatively, NP20. $R^1$, $R^2$, $D^1$, $D^2$, $L^1$, $L^2$, $L^3$, $Q^1$, q, and r within amidine compounds having an $N^2$ hydrogen having Structures NP6-NP10, NP16, NP18, and/or NP20 are independently described as features of the $N^2$-phosphinyl amidine compound Structures NP1-NP10, NP11, NP13, NP15, NP16, NP18, and/or NP20. Since $N^2$-phosphinyl amidine compound Structures NP6-NP10, NP16, NP18, and/or NP20 are utilized to prepare the $N^2$-phosphinyl amidine compounds having Structures NP1-NP5, NP11, NP13, and NP15 (respectively), the $R^1$, $R^2$, $D^1$, $D^2$, $L^1$, $L^2$, $L^3$, $Q^1$, q, and r descriptions for the $N^2$-phosphinyl amidine compounds having Structures NP1-NP10, NP11, NP13, NP15, NP16, NP18, and/or NP20 can be utilized without limitation to further describe the $N^2$-phosphinyl amidine compounds having Structures NP6-NP10, NP16, NP18, and/or NP20.

In an embodiment, the metal compound capable of abstracting a proton from the $N^2$-phosphinyl amidine compound can be a metal hydride or a metal alkyl. Generally, metal hydrides and metal alkyls capable of abstracting the proton from the $N^2$-phosphinyl amidine compound are the same as those capable of abstracting the proton from the amidine compound. Consequently, the metal hydrides and metal alkyls described herein as capable of abstracting the proton from the amidine compound can be utilized, without limitation, to further describe the method preparing the $N^2$-phosphinyl amidine compound.

Generally, the $N^2$-phosphinyl amidine compound and the metal compound can be combined in an amidine to metal compound equivalent ratio of at least 0.9:1. In an embodiment, the $N^2$-phosphinyl amidine compound and the metal compound can be combined in an amidine to metal compound equivalent ratio of at least 0.95:1; alternatively, of at least 0.975:1; or alternatively, of at least 0.99:1. In some embodiments, the $N^2$-phosphinyl amidine compound and the metal compound can be combined in an amidine and metal compound equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the $N^2$-phosphinyl amidine compound and the metal compound can be combined in an amidine to metal compound equivalent ratio of about 1:1.

In an embodiment, the conditions capable of forming the metal $N^2$-phosphinyl amidinate can include a temperature of at least −45° C.; alternatively, of at least −30° C.; alternatively, of at least −25° C.; or alternatively, of at least −20° C. In some embodiments, the reaction conditions capable of forming a metal $N^2$-phosphinyl amidinate can include a temperature ranging from −45° C. to 60° C.; alternatively, ranging from −30° C. to 50° C.; alternatively, ranging from −25° C. to 45° C.; or alternatively, ranging from −20° C. to 40° C.

In some embodiments, the conditions capable of forming the metal $N^2$-phosphinyl amidinate can include an initial metal compound and amidine contact temperature and a second temperature to form the metal $N^2$-phosphinyl amidinate. It should be noted that when the conditions capable of forming the metal $N^2$-phosphinyl amidinate is described as occurring at two temperatures (one for the contact of the metal compound and the amidine and one for the formation of the metal $N^2$-phosphinyl amidinate) that this description does not exclude the prospect that the metal $N^2$-phosphinyl amidinate can be formed at the contact temperature. The description just relates that, in some embodiments, the formation can proceed better when the initial contact between the metal compound and amidine is performed at one temperature and the formation of the metal $N^2$-phosphinyl amidinate is completed at a second different temperature.

In an embodiment, the metal compound and amidine can be contacted at a temperature ranging from −45° C. to 20° C.; alternatively, ranging from −30° C. to 15° C.; alternatively, ranging from −25° C. to 45° C.; or alternatively, ranging from −20° C. to 40° C. In an embodiment, the metal $N^2$-phosphinyl amidinate can be formed at a temperature ranging from 0° C. to 20° C.; alternatively, ranging from 5° C. to 15° C.; alternatively, ranging from 10° C. to 45° C.; or alternatively, ranging from 15° C. to 40° C.

In an embodiment, the conditions capable of forming the metal $N^2$-phosphinyl amidinate can include a metal $N^2$-phosphinyl amidinate formation time of at least 5 minutes; alternatively, of at least 10 minutes; alternatively, of at least 15 minutes; or alternatively, of at least 20 minutes. In some embodiments, the conditions capable of forming the metal $N^2$-phosphinyl amidinate can include a metal $N^2$-phosphinyl amidinate formation time ranging from 5 minutes to 6 hours; alternatively, ranging from 10 minutes to 5 hours; alternatively, ranging from 15 minutes to 4.5 hours; or alternatively, ranging from 20 minutes to 4 hours.

In an embodiment, the metal compound and the $N^2$-phosphinyl amidine can be contacted in an aprotic solvent. In some embodiments, the metal compound and the $N^2$-phosphinyl amidine can be contacted in a polar aprotic solvent. Aprotic solvents which can be utilized include hydrocarbon solvents and ether solvents. Polar aprotic solvents which can be utilized include ether solvents. Solvents are generally disclosed herein and any general or specific aprotic solvent and/or polar aprotic solvent described herein can be utilized to further describe the method of preparing the metal $N^2$-phosphinyl amidinate by contacting a metal compound and an $N^2$-phosphinyl amidine compound and forming a metal $N^2$-phosphinyl amidinate.

In an embodiment, the metal $N^2$-phosphinyl amidinate can be utilized without further isolation or purification. In some embodiments, the metal $N^2$-phosphinyl amidinate can be isolated; alternatively, purified; or alternatively, isolated and purified. In an embodiment, the method can include a step of isolating the metal $N^2$-phosphinyl amidinate by filtering the metal $N^2$-phosphinyl amidinate from the solution. In some embodiments, the method can include a step of purifying the metal $N^2$-phosphinyl amidinate by washing the metal $N^2$-phosphinyl amidinate with a solvent. Generally, the washing solvent is an aprotic solvent. In other embodiments, the washing solvent can be polar aprotic solvent. In other embodiments, the washing solvent can be a non-polar aprotic solvent.

In an embodiment, the halogenated compound can have Structure HC1.

$X^2R^3$            Structure HC1

$X^2$ of Structure HC1 represents a halide. In an embodiment, $X^2$ of the halogenated compound can be fluoride, chloride, bromide, or iodide; alternatively, fluoride; alternatively, chloride; alternatively, bromide; or alternatively, iodide. $R^3$ within halogenated compound Structure HC1 is independently described as a feature of the $N^2$-phosphinyl amidine compound Structures NP1-NP10, NP11, NP13, NP15, NP16, NP18, and/or NP20. Since halogenated compound HC1 is utilized to prepare embodiments of $N^2$-phosphinyl amidine compounds having Structures NP1-NP5, NP11, NP13, and/or NP15, the $R^3$ description for the $N^2$-phosphinyl amidine compounds can be utilized without limitation to further describe halogenated compounds having Structure HC1. Halogenated compounds are disclosed herein and can be utilized, without limitation, to further describe the method to prepare the $N^2$-phosphinyl amidine compound.

Generally, the halogenated compound and the metal $N^2$-phosphinyl amidinate can be combined in a halogenated compound to metal $N^2$-phosphinyl amidate equivalent ratio of at least 0.9:1. In some embodiments, the halogenated compound and the metal $N^2$-phosphinyl amidinate can be combined in a halogenated compound to metal $N^2$-phosphinyl amidate equivalent ratio of at least 0.95:1; alternatively, at least 0.975:1; or alternatively, at least 0.99:1. In some embodiments, the halogenated compound and the metal $N^2$-phosphinyl amidinate can be combined in a halogenated compound to metal $N^2$-phosphinyl amidate equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the halogenated compound and the metal $N^2$-phosphinyl amidinate can be combined in a halogenated compound to metal $N^2$-phosphinyl amidate equivalent ratio of about 1:1.

In an embodiment, the conditions capable of forming an $N^2$-phosphinyl amidine compound can include a reaction temperature of at least 0° C.; alternatively, of at least 5° C.; alternatively, of at least 10° C.; or alternatively, of at least 15° C. In some embodiments, the conditions capable of forming an $N^2$-phosphinyl amidine compound can include a reaction temperature ranging from 0° C. to 60° C.; alternatively, ranging from 5° C. to 50° C.; alternatively, ranging from 10° C. to 45° C.; or alternatively, ranging from 15° C. to 40° C. In an embodiment, the conditions capable of forming an N2-phosphinyl amidine compound can include a reaction time of at least 5 minutes; alternatively, of at least 10 minutes; alternatively, of at least 15 minutes; or alternatively, of at least 20 minutes. In some embodiments, the conditions capable of forming an $N^2$-phosphinyl amidine compound can include a reaction time ranging from 5 minutes to 6 hours; alternatively, ranging from 10 minutes to 5 hours; alternatively, ranging from 15 minutes to 4.5 hours; or alternatively, ranging from 20 minutes to 4 hours.

In an embodiment, the halogenated compound and the metal $N^2$-phosphinyl amidinate can be contacted in an aprotic solvent. In some embodiments, the halogenated compound and the metal $N^2$-phosphinyl amidinate can be contacted in a polar aprotic solvent. Aprotic solvents which can be utilized include hydrocarbon solvents and ether solvents. Polar aprotic solvents which can be utilized include ether solvents. Solvents are generally disclosed herein and any general or specific aprotic solvent and/or polar aprotic solvent described herein can be utilized to further describe the method of preparing an $N^2$-phosphinyl amidine compound comprising contacting a halogenated compound with a metal $N^2$-phosphinyl amidinate and forming the $N^2$-phosphinyl amidinate.

In an embodiment, the $N^2$-phosphinyl amidine compound can be utilized without further isolation or purification. In some embodiments, the $N^2$-phosphinyl amidine compound can be isolated; alternatively, purified; or alternatively, isolated and purified. In an embodiment, wherein the $N^2$-phosphinyl amidine compound can be prepared in a solvent (aprotic or polar aprotic), the method to prepare the $N^2$-phosphinyl amidine compound can include a step of isolating the $N^2$-phosphinyl amidine compound by evaporating the solvent. In an embodiment wherein the $N^2$-phosphinyl amidine compound can be prepared in a solvent (aprotic or polar aprotic), the method to prepare the $N^2$-phosphinyl amidine compound can include the step of isolating the $N^2$-phosphinyl amidine compound by filtering the solution to remove particulate materials and/or byproducts of the reaction and evaporating the solvent. In embodiments, the method to prepare the $N^2$-phosphinyl amidine compound can include a purification step wherein the $N^2$-phosphinyl amidine compound can purified by dissolving the $N^2$-phosphinyl amidine compound in a solvent and filtering the solution to remove particulate materials and/or byproducts of the reaction. The solvent utilized to purify the $N^2$-phosphinyl amidine compound can be the same as the solvent utilized to form the $N^2$-phosphinyl amidine compound or it can be different than the solvent utilized to form the $N^2$-phosphinyl amidine compound. In some embodiments, the method to prepare the $N^2$-phosphinyl amidine compound can include a purification step of purifying the $N^2$-phosphinyl amidine compound by washing the $N^2$-phosphinyl amidine compound with a solvent. In other embodiments, the method to prepare the $N^2$-phosphinyl amidine compound can include a purification step wherein the $N^2$-phosphinyl amidine compound is recrystallized.

Generally, the evaporation of the solvent can be performed using any suitable method. In some embodiments, the solvent can be evaporated at ambient temperature (15-35° C.—no applied external heat source). In other embodiments, the solvent can be evaporated with gentle heating (e.g., at a temperature ranging from 25° C. to 50° C.). In further embodiments, the solvent can be evaporated at ambient temperature under reduced pressure. In yet other embodiments, the solvent can be evaporated with gentle heating under reduced pressure.

In an aspect, a method of preparing an $N^2$-phosphinyl amidine compound can comprise: a) contacting an $N^2$-phosphinyl amidine compound having an $N^2$ hydrogen and a metallic compound capable of abstracting the proton from the $N^2$-phosphinyl amidine compound; b) forming a metal $N^2$-phosphinyl amidinate; c) contacting a halogenated compound with the formed metal $N^2$-phosphinyl amidinate and d) forming the $N^2$-phosphinyl amidine compound. Generally, the metal amidinate can be formed under conditions capable of forming a metal amidinate. In an embodiment, the metal $N^2$-phosphinyl amidinate can be isolated; alternatively, purified; or alternatively, isolated and purified. Generally, the $N^2$-phosphinyl amidine compound can be formed under conditions capable of forming an $N^2$-phosphinyl amidine compound. In an embodiment, the $N^2$-phosphinyl amidine compound can be isolated; alternatively, purified; or alternatively, isolated and purified.

In an embodiment, the amidine compound having an $N^2$ hydrogen can have Structure NP6, NP7, NP8, NP9, NP10, NP16, NP18 or NP20; alternatively, NP6; alternatively, NP7; alternatively, NP8; alternatively, NP9; alternatively, NP10; alternatively, NP16; alternatively, NP18; or alternatively, NP20. $R^1$, $R^2$, $D^1$, $D^2$, $L^1$, $L^2$, $L^3$, $Q^1$, q, and r within amidine compounds having an $N^2$ hydrogen having Structures NP6-NP10, NP16, NP18, and NP20 are independently described as features of the $N^2$-phosphinyl amidine compound Structures NP1-NP5. Since $N^2$-phosphinyl amidine compound Structures AM1-AM10, AM16, AM18 and AM20 are utilized to prepare the $N^2$-phosphinyl amidine compounds having Structures NP1-NP10, NP16, NP18, and NP20 the $R^1$, $R^2$, $D^1$, $D^2$, $L^1$, $L^2$, $L^3$, $Q^1$, q, and r descriptions for the $N^2$-phosphinyl amidine compounds having Structures NP1-NP5 can be utilized without limitation to further describe the $N^2$-phosphinyl amidine compounds having Structures NP6-NP10, NP16, NP18, and NP20 alternatively, Structure NP6; alternatively, Structure NP7; alternatively, Structure NP8; alternatively, NP9; alternatively, Structure NP10; alternatively, Structure NP16; alternatively, Structure NP18; or alternatively, Structure NP20.

In an embodiment, the metal compound capable of abstracting the proton from the $N^2$-phosphinyl amidine compound can be a metal hydride or a metal alkyl. Generally, metal hydrides and metal alkyls capable of abstracting the proton from the $N^2$-phosphinyl amidine compound are the same as those capable of abstracting the proton from the amidine compound. Consequently, the metal hydrides and metal alkyls described herein as capable of abstracting the proton from the amidine compound can be utilized, without limitation, to further describe the method preparing the $N^2$-phosphinyl amidine compound.

Generally, the $N^2$-phosphinyl amidine compound and the metal compound can be combined in an amidine to metal compound equivalent ratio of at least 0.9:1. In an embodiment, the $N^2$-phosphinyl amidine compound and the metal compound can be combined in an amidine to metal compound equivalent ratio of at least 0.95:1; alternatively, of at least 0.975:1; or alternatively, of at least 0.99:1. In some embodiments, the $N^2$-phosphinyl amidine compound and the metal compound can be combined in an amidine and metal compound equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the $N^2$-phosphinyl amidine compound and the metal compound can be combined in an amidine to metal compound equivalent ratio of about 1:1.

In an embodiment, the conditions capable of forming the metal $N^2$-phosphinyl amidinate can include a temperature of at least $-45°$ C.; alternatively, of at least $-30°$ C.; alternatively, of at least $-25°$ C.; or alternatively, of at least $-20°$ C. In some embodiments, the reaction conditions capable of forming a metal $N^2$-phosphinyl amidinate can include a temperature ranging from $-45°$ C. to $60°$ C.; alternatively, ranging from $-30°$ C. to $50°$ C.; alternatively, ranging from $-25°$ C. to $45°$ C.; or alternatively, ranging from $-20°$ C. to $40°$ C.

In some embodiments, the conditions capable of forming the metal $N^2$-phosphinyl amidinate can include an initial metal compound and amidine contact temperature and a second temperature to form the metal $N^2$-phosphinyl amidinate. It should be noted the when the conditions capable of forming the metal $N^2$-phosphinyl amidinate is described as occurring at two temperatures (one for the contact of the metal compound and the amidine and one for the formation of the metal $N^2$-phosphinyl amidinate) that this description does not exclude the prospect that metal $N^2$-phosphinyl amidinate can be formed at the contact temperature. The description just relates that, in some embodiments, the formation proceed better when the initial contact between the metal compound and amidine is performed at one temperature and the formation of the metal $N^2$-phosphinyl amidinate is completed at a second different temperature.

In an embodiment, the metal compound and amidine can be contacted at a temperature ranging from $-45°$ C. to $20°$ C.; alternatively, ranging from $-30°$ C. to $15°$ C.; alternatively, ranging from $-25°$ C. to $45°$ C.; or alternatively, ranging from $-20°$ C. to $40°$ C. In an embodiment, metal N2-phosphinyl amidinate is formed at a temperature ranging from $0°$ C. to $20°$ C.; alternatively, ranging from $5°$ C. to $15°$ C.; alternatively, ranging from $10°$ C. to $45°$ C.; or alternatively, ranging from $15°$ C. to $40°$ C.

In an embodiment, the conditions capable of forming the metal $N^2$-phosphinyl amidinate can include a metal $N^2$-phosphinyl amidinate formation time of at least 5 minutes; alternatively, of at least 10 minutes; alternatively, of at least 15 minutes; or alternatively, of at least 20 minutes. In some embodiments, the conditions capable of forming the metal $N^2$-phosphinyl amidinate can include a metal $N^2$-phosphinyl amidinate formation time ranging from 5 minutes to 6 hours; alternatively, ranging from 10 minutes to 5 hours; alternatively, ranging from 15 minutes to 4.5 hours; or alternatively, ranging from 20 minutes to 4 hours.

In an embodiment, the metal compound and the $N^2$-phosphinyl amidine can be contacted in an aprotic solvent. In some embodiments, the metal compound and the $N^2$-phosphinyl amidine can be contacted in a polar aprotic solvent. Aprotic solvents which may be utilized include hydrocarbon solvents and ether solvents. Polar aprotic solvents which may be utilized include ether solvents. Solvents are generally disclosed herein and any general or specific aprotic solvent and/or polar aprotic solvent described herein can be utilized to further describe the method of preparing the metal $N^2$-phosphinyl amidinate by contacting a metal compound and an $N^2$-phosphinyl amidine compound and forming a metal $N^2$-phosphinyl amidinate.

In an embodiment, the metal $N^2$-phosphinyl amidinate can be utilized without further isolation or purification. In some embodiments, the metal $N^2$-phosphinyl amidinate can be isolated; alternatively, purified; or alternatively, isolated and purified. In an embodiment, the method can include a step of isolating the metal $N^2$-phosphinyl amidinate by filtering the metal $N^2$-phosphinyl amidinate from the solution. In some embodiments, the method can include a step of purifying the metal $N^2$-phosphinyl amidinate by washing the metal $N^2$-phosphinyl amidinate with a solvent. Generally, the washing solvent is an aprotic solvent. In other embodiments, the washing solvent can be polar aprotic solvent. In other embodiments, the washing solvent can be a non-polar aprotic solvent.

In an embodiment, the halogenated compound can have Structure HC1.

$$X^2R^3 \qquad \text{Structure HC1}$$

$X^2$ of Structure HC1 represents a halide. In an embodiment, $X^2$ of the halogenated compound can be fluoride, chloride, bromide, or iodide; alternatively, fluoride; alternatively, chloride; alternatively, bromide; or alternatively, iodide. $R^3$ within halogenated compound Structure HC1 is independently described as a feature of the $N^2$-phosphinyl amidine compound Structures NP1-NP5. Since halogenated compound HC1 is utilized to prepare embodiments of $N^2$-phosphinyl amidine compounds having Structures NP1-NP5, the $R^3$ description for the $N^2$-phosphinyl amidine compounds can be utilized without limitation to further describe the halogenated compound having Structure HC1. Halogenated compounds are disclosed herein and can be utilized, without limitation, to further describe the method to prepare the $N^2$-phosphinyl amidine compound.

Generally, the halogenated compound and the metal $N^2$-phosphinyl amidinate can be combined in a halogenated compound to metal $N^2$-phosphinyl amidate equivalent ratio of at least 0.9:1. In some embodiments, the halogenated compound and the metal $N^2$-phosphinyl amidinate can be combined in a halogenated compound to metal $N^2$-phosphinyl amidate equivalent ratio of at least 0.95:1; alternatively, of at least 0.975:1; or alternatively, of at least 0.99:1. In some embodiments, the halogenated compound and the metal $N^2$-phosphinyl amidinate can be combined in a halogenated compound to metal $N^2$-phosphinyl amidate equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the halogenated compound and the metal $N^2$-phosphinyl amidinate can be combined in a halogenated compound to metal $N^2$-phosphinyl amidate equivalent ratio of about 1:1.

In an embodiment, the conditions capable of forming an $N^2$-phosphinyl amidine compound can include a reaction temperature of at least $0°$ C.; alternatively, of at least $5°$ C.; alternatively, of at least $10°$ C.; or alternatively, of at least $15°$ C. In some embodiments, the conditions capable of forming an $N^2$-phosphinyl amidine compound can include a reaction temperature ranging from $0°$ C. to $60°$ C.; alternatively, ranging from $5°$ C. to $50°$ C.; alternatively, ranging from $10°$ C. to $45°$ C.; or alternatively, ranging from $15°$ C. to $40°$ C. In an embodiment, the conditions capable of forming an $N^2$-phosphinyl amidine compound can include a reaction time of at least 5 minutes; alternatively, of at least 10 minutes; alternatively, of at least 15 minutes; or alternatively, of at least 20 minutes. In some embodiments, the conditions capable of forming an $N^2$-phosphinyl amidine compound can include a reaction time ranging from 5 minutes to 6 hours; alternatively, ranging from 10 minutes to 5 hours; alternatively, ranging from 15 minutes to 4.5 hours; or alternatively, ranging from 20 minutes to 4 hours.

In an embodiment, the halogenated compound and the metal $N^2$-phosphinyl amidinate can be contacted in an aprotic solvent. In some embodiments, the halogenated compound and the metal $N^2$-phosphinyl amidinate can be contacted in a polar aprotic solvent. Aprotic solvents which can be utilized include hydrocarbon solvents and ether solvents. Polar aprotic solvents which can be utilized include ether solvents. Solvents are generally disclosed herein and any general or specific aprotic solvent and/or polar aprotic solvent described herein can be utilized to further describe the method of preparing an $N^2$-phosphinyl amidine compound comprising contacting a halogenated compound with a metal $N^2$-phosphinyl amidinate and forming the $N^2$-phosphinyl amidinate.

In an embodiment, the $N^2$-phosphinyl amidine compound can be utilized without further isolation or purification. In some embodiments, the $N^2$-phosphinyl amidine compound can be isolated; alternatively, purified; or alternatively, isolated and purified. In an embodiment, wherein the $N^2$-phosphinyl amidine compound is prepared in a solvent (aprotic or polar aprotic), the method to prepare the $N^2$-phosphinyl amidine compound can include a step of isolating the $N^2$-phosphinyl amidine compound by evaporating the solvent. In an embodiment wherein the $N^2$-phosphinyl amidine compound is prepared in a solvent (aprotic or polar aprotic), the method to prepare the $N^2$-phosphinyl amidine compound can include the step of isolating the $N^2$-phosphinyl amidine compound by filtering the solution to remove particulate materials and/or byproducts of the reaction and evaporating the solvent. In embodiments, the method to prepare the $N^2$-phosphinyl amidine compound can include a purification step wherein the $N^2$-phosphinyl amidine compound is purified by dissolving the $N^2$-phosphinyl amidine compound in a solvent and filtering the solution to remove particulate materials and/or byproducts of the reaction. The solvent utilized to purify the $N^2$-phosphinyl amidine compound can be the same a solvent utilized to form the $N^2$-phosphinyl amidine compound or it can be different than the solvent utilized to form the $N^2$-phosphinyl amidine compound. In some embodiments, the method to prepare the $N^2$-phosphinyl amidine compound can include a purification step of purifying the $N^2$-phosphinyl amidine compound by washing the $N^2$-phosphinyl amidine compound with a solvent. In other embodiments, the method to prepare the $N^2$-phosphinyl amidine compound can include a purification step wherein the $N^2$-phosphinyl amidine compound is recrystallized.

Generally, the evaporation of the solvent can be performed using any suitable method. In some embodiments, the solvent can be evaporated at ambient temperature (15-35° C.—no applied external heat source). In other embodiments, the solvent can be evaporated with gentle heating (e.g. at a temperature ranging from 25° C. to 50° C.). In further embodiments, the solvent can be evaporated at ambient temperature under reduced pressure. In yet other embodiments, the solvent can be evaporated with gentle heating under reduced pressure.

In an aspect, a method to prepare an amidine compound having only one $N^2$ hydrogen atom can comprise: a) contacting a metal amidinate and a halogenated compound; and b) forming the amidine compound having only one $N^2$ hydrogen atom. Methods of preparing a metal amidinate are disclosed herein and can be utilized, without limitation, to further describe the method to prepare an amidine compound having only one $N^2$ hydrogen atom. Generally, an amidine compound having only one $N^2$ hydrogen atom can be formed under conditions capable of forming an amidine compound having only one $N^2$ hydrogen atom. In an embodiment, the amidine compound having only one $N^2$ hydrogen atom can be isolated; alternatively, purified; or alternatively, isolated and purified.

In an embodiment, the metal amidinate can have Structure MAM6, MAM7, MAM8, MAM9, MAM10; MAM16; MAM18, or MAM20; alternatively, MAM6; alternatively, MAM7; alternatively, MAM8; alternatively, MAM9; alternatively, MAM10; alternatively, MAM16; alternatively, MAM18 or alternatively, MAM20. $R^1$, $R^2$, $D^1$, $D^2$, $L^1$, $L^2$, $L^3$, $Q^1$, q, and r within metal amidine Structures MAM6-MAM10, MAM16, MAM18 and MAM20 are independently described as features of the $N^2$-phosphinyl amidine compound Structures NP1-NP5. Since metal amidine Structures MAM6-MAM10 MAM16, MAM18, and MAM20 are utilized to prepare embodiments of $N^2$-phosphinyl amidine compounds having Structures NP6-NP10, NP16 and NP18, the $R^1$, $R^2$, $D^1$, $D^2$, $L^1$, $L^2$, $L^3$, $Q^1$, q, and r descriptions for the $N^2$-phosphinyl amidine compounds can be utilized without limitation to further describe metal amidine Structures MAM6-MAM10, MAM16, MAM18, and MAM20.

The halogenated compound has been described herein as a component for reacting with an $N^2$-phosphinyl amidinate. Generally, the halogenated compounds useful for reacting with an $N^2$-phosphinyl amidinate are the same as those which can be utilized for reacting with a metal amidinate. Consequently, the halogenated compounds describe herein as a potential reactant with an $N^2$-phosphinyl amidinate can be utilized, without limitation, to further describe halogenated compound which can be contacted with the metal amidinate.

Generally, the halogenated compound and the metal amidinate can be combined in a halogenated compound to metal amidate equivalent ratio of at least 0.9:1. In some embodiments, the halogenated compound and the metal amidinate can be combined in a halogenated compound to metal amidate equivalent ratio of at least 0.95:1; alternatively, of at least 0.975:1; or alternatively, of at least 0.99:1. In some embodiments, the halogenated compound and the metal amidinate can be combined in a halogenated compound to metal amidate equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the halogenated compound and the metal amidinate can be combined in a halogenated compound to metal $N^2$-phosphinyl amidate equivalent ratio of about 1:1.

In an embodiment, the conditions capable of forming the amidine compound having only one $N^2$ hydrogen atom can include a reaction temperature of at least 0° C.; alternatively, of at least 5° C.; alternatively, of at least 10° C.; or alternatively, of at least 15° C. In some embodiments, the conditions capable of forming the amidine compound having only one $N^2$ hydrogen atom can include a reaction temperature ranging from 0° C. to 60° C.; alternatively, ranging from 5° C. to 50° C.; alternatively, ranging from 10° C. to 45° C.; or alternatively, ranging from 15° C. to 40° C. In an embodiment, the conditions capable of forming the amidine compound having only one $N^2$ hydrogen atom can include a reaction time of at least 5 minutes; alternatively, of at least 10 minutes; alternatively, of at least 15 minutes; or alternatively, of at least 20 minutes. In some embodiments, the conditions capable of forming the amidine compound having only one $N^2$ hydrogen atom can include a reaction time ranging from 5 minutes to 6 hours; alternatively, ranging from 10 minutes to 5 hours;

alternatively, ranging from 15 minutes to 4.5 hours; or alternatively, ranging from 20 minutes to 4 hours.

In an embodiment, the halogenated compound and the metal amidinate can be contacted in an aprotic solvent. In some embodiments, the halogenated compound and the metal amidinate can be contacted in a polar aprotic solvent. Aprotic solvents which can be utilized include hydrocarbon solvents and ether solvents. Polar aprotic solvents which can be utilized include ether solvents. Solvents are generally disclosed herein and any general or specific aprotic solvent and/or polar aprotic solvent described herein can be utilized to further describe the method of preparing the amidine compound having only one $N^2$ hydrogen atom comprising contacting a halogenated compound with a metal amidinate and forming the amidine compound having only one $N^2$ hydrogen atom.

In an embodiment, the amidine compound having only one $N^2$ hydrogen atom can be utilized without further isolation or purification. In some embodiments, the amidine compound having only one $N^2$ hydrogen atom can be isolated; or alternatively, isolated and purified. In an embodiment, wherein the amidine compound having only one $N^2$ hydrogen atom can be prepared in a solvent (aprotic or polar aprotic), the method to prepare the $N^2$-phosphinyl amidine compound can include a step of isolating the amidine compound having only one $N^2$ hydrogen atom by evaporating the solvent. In an embodiment wherein the amidine compound having only one $N^2$ hydrogen atom can be prepared in a solvent (aprotic or polar aprotic), the method to prepare the amidine compound having only one $N^2$ hydrogen atom can include the step of isolating the amidine compound having only one $N^2$ hydrogen atom by filtering the solution to remove particulate materials and/or byproducts of the reaction and evaporating the solvent. In some embodiments, the method to prepare the amidine compound having only one $N^2$ hydrogen atom can include a purification step wherein the amidine compound having only one $N^2$ hydrogen atom can be purified by dissolving the amidine compound having only one $N^2$ hydrogen atom in a solvent and filtering the solution to remove particulate materials and/or byproducts of the reaction. The solvent utilized to purify the amidine compound having only one $N^2$ hydrogen atom can be the same as the solvent utilized to form the $N^2$-phosphinyl amidine compound or it can be different than the solvent utilized to form the amidine compound having only one $N^2$ hydrogen atom. In some embodiments, the method to prepare the amidine compound having only one hydrogen atom can include a step of purifying the amidine compound having only one hydrogen atom by washing the amidine compound having only one hydrogen atom with a solvent. In other embodiments, the method to prepare the amidine compound having only one hydrogen atom can include a step of purifying the amidine compound having only one hydrogen atom by recrystallization.

Generally, the evaporation of the solvent can be performed using any suitable method. In some embodiments, the solvent can be evaporated at ambient temperature (15-35° C.—no applied external heat source). In other embodiments, the solvent can be evaporated with gentle heating (e.g. at a temperature ranging from 25° C. to 50° C.). In further embodiments, the solvent can be evaporated at ambient temperature under reduced pressure. In yet other embodiments, the solvent can be evaporated with gentle heating under reduced pressure.

Generally, the methods for forming the metal amide, the amidine compound, the metal amidinate, and the $N^2$-phosphinyl amidine compound can combined in various embodiments to provide a method of forming an $N^2$-phosphinyl amidine compound having only one $N^2$ hydrogen atom utilizing amines, nitriles, compounds capable of abstracting a proton from the —$NH_2$ group, alkylating compounds, and phosphine halides. In a non-limiting embodiment, the method of preparing an $N^2$-phosphinyl amidine compound can comprise, or consist essentially of, or consist of: a) contacting the metal amide and a nitrile; b) forming a first metal amidinate; c) contacting the first metal amidinate with a halogenated compound; d) forming an amidine compound having only one $N^2$ hydrogen atom; e) isolating the amidine compound having only one $N^2$ hydrogen atom; f) contacting the amidine compound having only one $N^2$ hydrogen atom with a compound capable of abstracting a proton from the amidine compound having only one $N^2$ hydrogen atom; g) forming a second metal amidinate; j) contacting the second metal amidinate and a phosphine halide; and h) forming the $N^2$-phosphinyl amidine compound. In an embodiment, the metal amidinate formed in step b) is contacted with the halogenated compound without forming a non-metal amidine compound. In other embodiments, the first metal amidinate formed in step b) is neutralized with a protic compound to form a non-metal amidine compound which can then be isolated and optionally purified and then utilized to reform the first amidinate by contacting the non-metal amidine compound with a metal alkyl. In a further non-limiting embodiment, the method of preparing an $N^2$-phosphinyl amidine compound can comprise: a) contacting an amine having a —$NH_2$ group and a compound capable of abstracting a proton from the —$NH_2$ group; b) forming a metal amide; c) contacting the metal amide and a nitrile; d) forming a first metal amidinate; e) contacting the first metal amidinate with a halogenated compound; f) forming an amidine compound having only one $N^2$ hydrogen atom; g) isolating the amidine compound having only one $N^2$ hydrogen atom; h) contacting the amidine compound having only one $N^2$ hydrogen atom with a compound capable of abstracting a proton from the amidine compound having only one $N^2$ hydrogen atom; i) forming a second metal amidinate; j) contacting the second metal amidinate and a phosphine halide; and k) forming the $N^2$-phosphinyl amidine compound. In an embodiment, the metal amidinate formed in step d) is contacted with the halogenated compound without forming a non-metal amidine compound. In other embodiments, the first metal amidinate formed in step d) is neutralized with a protic compound to form a non-metal amidine compound which can then be isolated and optionally purified and then utilized to reform the first amidinate by contacting the non-metal amidine compound with a metal alkyl. These methods can contain steps other than those recited in the methods of preparing metal amides described herein, methods of preparing metal amidinates described herein, methods of preparing amidine compounds described herein, methods of alkylating amidine compound (or metal amidinates) described herein, and methods of preparing $N^2$-phosphinyl amidine compounds described herein which can be utilized to further describe these methods. Additional features of each of these steps (e.g. reagent ratios, formation conditions, among other considerations) are described herein and can be utilized to further describe the methods.

Generally, the methods for forming the metal amide, the amidine compound, the metal amidinate, and the $N^2$-phosphinyl amidine compound can combined in various methods to provide a method to form an $N^2$-phosphinyl amidine compound utilizing amines, nitriles, compounds capable of abstracting a proton from the —$NH_2$ group, and phosphine halides. In a non-limiting embodiment, a method of preparing an $N^2$-phosphinyl amidine compound can comprise a) contacting a metal amide and a nitrile; b) forming a metal amidinate; c) contacting the metal amidinate (formed in step b) and a phosphine halide; and d) forming the $N^2$-phosphinyl amidine compound. In an embodiment, the metal amidinate formed in step b) is contacted with the phosphine halide without forming a non-metal amidine compound. In another exemplary embodiment, a method of preparing an $N^2$-phosphinyl amidine compound can comprise a) contacting an amine having a $-NH_2$ group and a compound capable of abstracting a proton from the $-NH_2$ group; b) forming a metal amide; c) contacting the metal amide and a nitrile; d) forming a metal amidinate; e) contacting the metal amidinate (formed in step d) and a phosphine halide; and f) forming the $N^2$-phosphinyl amidine compound. In an embodiment, the metal amidinate formed in step d) is contacted with the phosphine halide without forming a non-metal amidine compound.

In another non-limiting embodiment, a method of preparing an $N^2$-phosphinyl amidine compound can comprise: a) contacting a metal amide and a nitrile; b) forming a first metal amidinate; c) neutralizing the first metal amidinate with a protic compound to form an amidine compound having an $N^2$ hydrogen atom; d) contacting the amidine compound having an $N^2$ hydrogen atom with a metallic compound capable of abstracting the hydrogen atom from the amidine compound; e) forming a second metal amidinate; f) contacting the second metal amidinate and a phosphine halide; and f) forming the $N^2$-phosphinyl amidine compound. In a further embodiment, a method of preparing an $N^2$-phosphinyl amidine compound can comprise: a) contacting an amine having a $-NH_2$ group and a compound capable of abstracting a proton from the $-NH_2$ group; b) forming a metal amide; c) contacting the metal amide and a nitrile; d) forming a first metal amidinate; e) neutralizing the first metal amidinate with a protic compound to form an amidine compound having an $N^2$ hydrogen atom; f) contacting the amidine compound having an $N^2$ hydrogen atom with a metallic compound capable of abstracting the hydrogen atom from the amidine compound; g) forming a second metal amidinate; h) contacting the second metal amidinate and a phosphine halide; and i) forming the $N^2$-phosphinyl amidine compound. These methods can contain steps other than those recited in the methods of preparing metal amides described herein, methods of preparing metal amidinates described herein, methods of preparing amidine compounds described herein, and methods of preparing $N^2$-phosphinyl amidine compounds described herein and can be utilized to further describe these methods. Additional features of each of these steps (e.g. reagent ratios, formation conditions, among other considerations) are described herein and can be utilized to further describe the methods.

In an embodiment, step a) can comprise contacting an amine having a $-NH_2$ group and a compound capable of abstracting a proton from the $-NH_2$ group and forming a metal amide. In an embodiment, the compound capable of abstracting a proton from the $-NH_2$ group can be a metal alkyl. In some embodiments, the compound capable of abstracting a proton from the $-NH_2$ group can be an alkyl lithium and the metal amide formed is a lithium amide. Metal alkyl and alkyl lithium compounds are independently disclosed herein and can be utilized without limitation to further describe the methods. In an embodiment, the step of contacting a metal amide and a nitrile can also be a step of contacting a metal amide and a nitrile under conditions suitable to form a metal amidinate. It should be appreciated that other methods of preparing $N^2$-phosphinyl amidine compounds can be provided using the steps described herein and that these steps can be carried out in any order compatible with one or more user and/or process desired goals. In an embodiment, the method of preparing an $N^2$-phosphinyl amidine compound is carried out in the order described herein. For example, the method of preparing an $N^2$-phosphinyl amidine compound can comprise formation of a metal amide by contacting of an amine group and a first metal alkyl under conditions suitable for the formation of a metal amide. The metal amide can subsequently be contacted with a nitrile to form an intermediate which can be quenched by contacting the intermediate with a proton source to form a quenched intermediate. The quenched intermediate can be isolated; alternatively, purified; or alternatively, isolated and purified. The isolated and/or purified intermediate can be reacted with second metal alkyl to produce a metal amidinate which is subsequently contacted with a phosphine halide under conditions suitable for the formation of an $N^2$-phosphinyl amidine compound. In an embodiment, the first metal alkyl and the second metal alkyl can be the same. In an embodiment, the first metal alkyl and the second metal alkyl can be different.

In an embodiment, the method of preparing an $N^2$-phosphinyl amidine compound can comprise formation of a metal amide by contacting of an amine group and a metal alkyl under conditions suitable for the formation of a metal amide. The metal amide can subsequently be contacted with a nitrile to form an intermediate which can subsequently contacted with a phosphine halide under conditions suitable for the formation of an $N^2$-phosphinyl amidine compound. In such embodiments, formation of the $N^2$-phosphinyl amidine compound can occur in the absence of a quenched intermediate. In such embodiments, formation of the $N^2$-phosphinyl amidine compound can occur in the absence of a second metal alkyl. Other embodiments of preparing the amidine compounds utilizing steps of this disclosure will be apparent to those of ordinary skill in the art by reading the present disclosure.

In an embodiment, the method of preparing an amidine compound having only one $N^2$ hydrogen atom can comprise: a) contacting a first amine and an acid halide; b) forming an amide; c) contacting the amide with phosphorus pentachloride; d) forming an N-substituted α-chloro imine; e) contacting the N-substituted α-chloro imine with a second amine; and f) forming the amidine compound having only one $N^2$ hydrogen atom. In an embodiment, the amide can be formed under conditions capable of forming an amide. In some embodiments, the amide can be isolated; alternatively, purified; alternatively, isolated and purified. In an embodiment, the N-substituted α-chloro imine can be formed under conditions capable of forming an N-substituted α-chloro imine. In an embodiment, the N-substituted α-chloro imine can be isolated; alternatively, purified; or alternatively, isolated and purified. In an embodiment, the amidine compound having only one $N^2$ hydrogen atom can be isolated; alternatively, purified; or alternatively, isolated and purified. In an embodiment, the amidine compound having only one $N^2$ hydrogen atom can be formed under conditions capable of forming an amidine compound having only one $N^2$ hydrogen atom.

In an embodiment, the first amine can have Structure A1, A2, A3, or A4; alternatively, Structure A1; alternatively, Structure A2; alternatively, A3; or alternatively, Structure A4. Generally, utilizing the present disclosure, one can readily recognize the amine structure necessary to produce a particular amidine compound or $N^2$-phosphinyl amidine compound. For example, the amine having Structure A1 can be utilized when preparing an amidine compound having Structure AM1, AM3, or AM5 and/or an $N^2$-phosphinyl amidine compound having Structure NP1, NP3, or NP5, the amine having Structure A2 can be utilized when preparing an amidine compound having Structure AM2 and/or an $N^2$-phosphinyl amidine compound having Structure NP2, the amine having Structure A3 can utilized when preparing an amidine compound having Structure AM4 and/or an $N^2$-phosphinyl amidine compound having Structure AM4, the amine having Structure A4 can be utilized when preparing an amidine compound having Structure AM11, AM13, or AM15 and/or an $N^2$-phosphinyl amidine compound having Structure NP11, NP13, or NP15 Amines having Structure A1, A2, A3, and A4 are describe herein and can be utilized without limitation to further describe the method of preparing an amidine compound having only one $N^2$ hydrogen atom.

In an embodiment, the acid halide can have Structure AC1, AC2, or AC3; alternatively, AC1; alternatively, AC2; or alternatively, AC3. Generally, utilizing the present disclosure, one can readily recognize the acid halide structure necessary to produce a particular amidine compound or $N^2$-phosphinyl amidine compound. For example, the acid halide having Structure AC1 can be

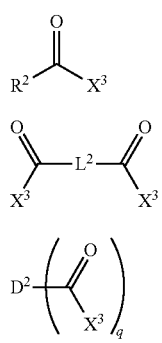

utilized when preparing an amidine compound having Structure AM1, AM2, AM4, AM11, AM12, or AM14 and/or an $N^2$-phosphinyl amidine compound having Structure NP1, NP2, NP4, NP11, NP12, or NP12, the acid halide having Structure AC2 can be utilized when preparing an amidine having Structure AM3 or AM13 and/or an $N^2$-phosphinyl amidine compound having Structure NP3, or NP13, and the acid halide having Structure AC3 can be utilized when preparing an amidine compound having Structure AM5 or AM15 and/or an $N^2$-phosphinyl amidine compound having Structure NP5 or NP15. $R^2$, $D^2$, $L^2$, and q within acid halide Structures AC1-AC3 are independently described as features of the $N^2$-phosphinyl amidine compound having Structures NP1-NP10, NP11, NP13, NP15, NP16, NP18, and NP20. Since acid halide Structures AC1-AC3 are utilized to prepare embodiments of $N^2$-phosphinyl amidine compounds having Structures NP1-NP5, NP11, NP13, and NP15, the $R^2$, $D^2$, $L^2$, and q descriptions for the $N^2$-phosphinyl amidine compounds can be utilized without limitation to further describe acid halide Structures AC1-AC3. In an embodiment, $X^3$ of acid halide Structures AC1-AC3 represents a halide. In an embodiment, $X^3$ of the acid halide can be fluoride, chloride, bromide, or iodide; alternatively, fluoride; alternatively, chloride; alternatively, bromide; or alternatively, iodide.

In an embodiment, the formed amide can have Structure AD1, AD2, AD3, AD4, or AD5; alternatively, AD1; alternatively, AD2; alternatively, AD3; alternatively, AD4; or alternatively, AD5.

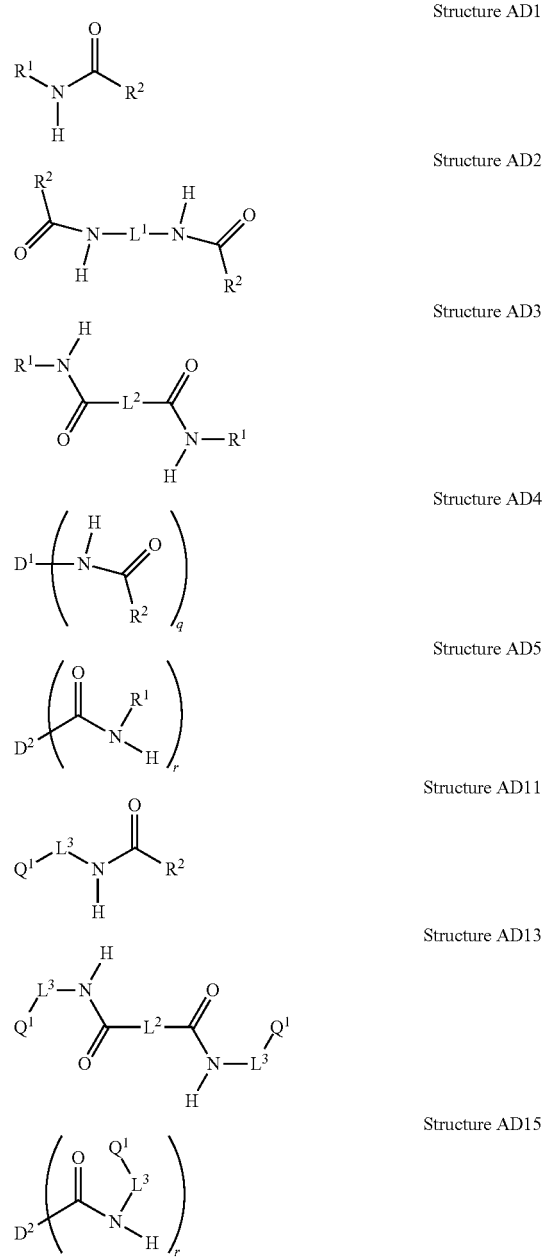

Generally, utilizing the present disclosure, one can readily recognize the acid halide structure necessary to produce a particular amide. For example, the acid halide having Structure AC1 can be utilized when preparing the amide having Structure AD1, AD2, AD4, or AD11, the acid halide having Structure AC2 can be utilized when preparing the amide having Structure AD3 or AD13, and the acid halide having Structure AC3 can be utilized when preparing an amidine compound having Structure AD5 or AD15. Generally utilizing the present disclosure, one can readily recognize the amine structure necessary to produce a particular amide. For example, the amine having Structure A1 can be utilized when preparing the amide having Structure AD1, AD3, or AD5, the amine having Structure A2 can be utilized when preparing the amide having Structure AD2, the amine having Structure A3 can be utilized when preparing the amide having Structure AD4, and the amine having Structure A4 can be utilized when preparing the amide having Structure AD11, AD13, or AD15. $R^1, R^2, D^1, D^2, L^1, L^2, L^3, Q^1$, q, and r within amide Structures AD1-AD5, AD11, AD13, and/or AD15 are independently described as features of the $N^2$-phosphinyl amidine compound Structures NP1-NP10, NP11, NP13, NP15, NP16, NP18, and/or NP20. Since the amide having Structures AD1-AD5, AD11, AD13, and/or AD15 are utilized to prepare embodiments of $N^2$-phosphinyl amidine compounds having Structures NP1-NP10, NP11, NP13, NP15, NP16, NP18, and/or NP20, the $R^1$, $R^2$, $D^1$, $D^2$, $L^1$, $L^2$, $L^3$, $Q^1$, q, and r descriptions for the $N^2$-phosphinyl amidine compounds can be utilized without limitation to further describe the amide having Structures AD1-AD5, AD11, AD13, and/or AD15.

Generally, the acid halide and the first amine can be combined in an acid halide to first amine equivalent ratio of at least 0.9:1. In some embodiments, the acid halide and the first amine can be combined in an acid halide to first amine equivalent ratio of at least 0.95:1; alternatively, of at least 0.975:1; or alternatively, of at least 0.99:1. In some embodiments, the acid halide and the first amine can be combined in an acid halide to first amine equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the acid halide and the first amine can be combined in an acid halide to first amine equivalent ratio of about 1:1.

In some embodiments, the step of contacting the first amine and the acid halide further comprises contacting the first amine and the acid halide with a compound capable of forming a hydrogen halide salt (i.e. can be a step of contacting a first amine, an acid halide, and a compound capable of forming a hydrogen halide salt). In an embodiment, the compound capable of forming a hydrogen halide salt is an amine. In some embodiments, the amine utilized to form a hydrogen halide salt can have the formula $(R^4)_3N$. In an embodiment, each $R^4$ independently can be a $C_1$ to $C_{10}$ hydrocarbyl group; alternatively, a $C_1$ to $C_5$ hydrocarbyl group; alternatively, a $C_1$ to $C_{10}$ alkyl group; or alternatively, a $C_1$ to $C_5$ alkyl group. Hydrocarbyl and alkyl groups are independently described herein (for example as substitutent groups for substituent $R^1$ groups, among other places) and can be utilized without limitation to further describe the amine having the formula $(R^4)_3N$. In some embodiments, the amine utilized as the compound capable of forming a hydrogen halide salt can be trimethylamine or triethylamine; alternatively, trimethylamine; or alternatively, triethylamine.

Generally, the compound capable of forming a hydrogen halide salt, when used, can be utilized at a compound capable of forming a hydrogen halide salt to first amine equivalent ratio of at least 1:1. In an embodiment, the compound capable of forming a hydrogen halide salt, when used, can be utilized at a compound capable of forming a hydrogen halide salt to first amine equivalent ratio of at least 1.025:1; alternatively, of at least 1.05:1; or alternatively, of at least 1.075:1. In some embodiments, the compound capable of forming a hydrogen halide salt, when used, can be utilized at a compound capable of forming a hydrogen halide salt to first amine equivalent ratio ranging from 1:1 to 2:1; alternatively, ranging from 1.025:1 to 1.50:1; alternatively, ranging from 1.05:1 to 1.5:1; or alternatively, ranging from 1.075:1 to 1.25:1.

In an embodiment, the conditions capable of forming the metal amidinate can include a temperature of at least −25° C.; alternatively, of at least −20° C.; alternatively, of at least −25° C.; or alternatively, of at least −10° C. In some embodiments, the reaction conditions capable of forming a metal amidinate can include a temperature ranging from −25° C. to 100° C.; alternatively, ranging from −20° C. to 90° C.; alternatively, ranging from −15° C. to 85° C.; or alternatively, ranging from −10° C. to 80° C.

In some embodiments, the conditions capable of forming the amide can include an initial first amine and acid halide contact temperature and a second temperature to form the amide. It should be noted the when the conditions capable of forming the amide is described as occurring at two temperatures (one for the contact of the first amine and the acid halide and one for the formation of the amide) that this description does not exclude the prospect that the amide may be formed at the contact temperature. The description just relates that, in some embodiments, the formation may proceed better when the initial contact between the first amine and acid halide is performed at one temperature and the formation of the amide is completed at a second different temperature.

In an embodiment, the first amine and acid halide can be contacted at a temperature ranging from −25° C. to 40° C.; alternatively, ranging from −20° C. to 35° C.; alternatively, ranging from −15° C. to 30° C.; or alternatively, ranging from −10° C. to 25° C. In an embodiment, the amide can be formed at a temperature ranging from 10° C. to 100° C.; alternatively, ranging from 15° C. to 90° C.; alternatively, ranging from 20° C. to 85° C.; or alternatively, ranging from 25° C. to 80° C. In an embodiment, the conditions capable of forming the amide can include a reaction time of at least 15 minutes; alternatively, of at least 30 minutes; alternatively, of at least 45 minutes; or alternatively, of at least 1 hour. In some embodiments, the conditions capable of forming the amide can include a reaction time ranging from 15 minutes to 36 hours; alternatively, ranging from 30 minutes to 30 hours; alternatively, ranging from 45 minutes to 24 hours; or alternatively, ranging from 1 hour to 18 hours.

In an embodiment, the first amine and the acid halide can be contacted in an aprotic solvent. In some embodiments, the first amine and the acid halide can be contacted in a polar aprotic solvent. Aprotic solvents which can be utilized include hydrocarbon, halogenated hydrocarbon solvents, and ether solvents. Solvents are generally disclosed herein and any general or specific aprotic solvent and/or polar aprotic solvent described herein can be utilized to further describe the method of preparing an amide.

In an embodiment, the amide can be utilized without further isolation or purification. In some embodiments, the amide can be isolated; alternatively, purified; or alternatively, isolated and purified. In an embodiment, the method can include a step of isolating the amide by evaporating the solvent in which the amide is formed, treating the amide with water, and separating the amide by filtration. In some embodiments, the method can include a step of isolating the amide by contacting the composition comprising the amide and the solvent in which the amide was formed with water, separating the aqueous portion from the solvent in which the amide was formed, and evaporating the solvent in which the amide was formed. In embodiments, the method to prepare the amide can include a purification step wherein the amide is purified by dissolving the amide in a solvent and filtering the solution to remove particulate materials and/or byproducts of the reaction. The solvent utilized to purify the amide can be the same as the solvent utilized to form the amide or it can be different than the solvent utilized to form amide. In some embodiments, the method can include a purification step wherein the amide is purified by washing the amide with a solvent. In other embodiments, the method to prepare the amide can include a purification step wherein the amide is recrystallized.

Generally, the evaporation of the solvent can be performed using any suitable method. In some embodiments, the solvent can be evaporated at ambient temperature (15-35° C.—no applied external heat source). In other embodiments, the solvent can be evaporated with gentle heating (e.g. at a temperature ranging from 25° C. to 50° C.). In further embodiments, the solvent can be evaporated at ambient temperature under reduced pressure. In yet other embodiments, the solvent can be evaporated with gentle heating under reduced pressure.

In some embodiments, the N-substituted α-chloro imine can have Structure CI1, CI2, CI3, CI4, CI5, CI11, CI13, or CI5; alternatively, Structure CI1, CI2, CI3, CI4, or CI5; alternatively, Structure CI11, CI13, or CI5; alternatively, Structure CI1 or CI11; alternatively, Structure CI3 or CI13; alternatively, Structure CI5 or CI15; alternatively, Structure CI1; alternatively, Structure CI2; alternatively, Structure CI3; alternatively, Structure CI4; alternatively, CI5; alternatively, Structure CI11; alternatively, Structure CI13; or alternatively, Structure CI5.

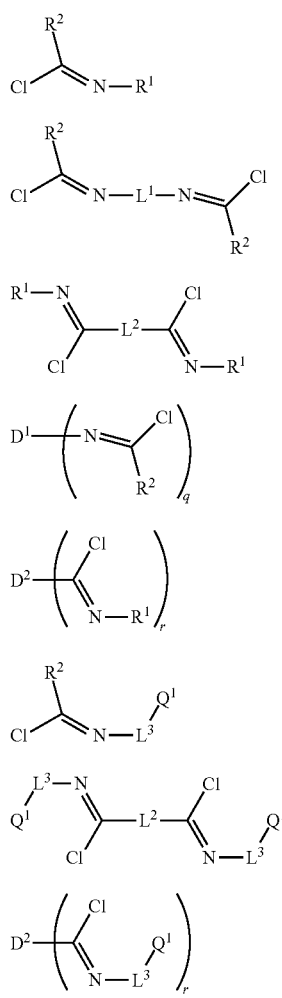

Structure CI1
Structure CI2
Structure CI2
Structure CI4
Structure CI5
Structure CI11
Structure CI13
Structure CI15

Generally, utilizing the present disclosure, one can readily recognize the amide structure necessary to produce a particular α-chloro imine. For example, the amide having Structure AD1 can be utilized when preparing an N-substituted α-chloro imine having Structure CI1, the amide having Structure AD2 can be utilized when preparing an N-substituted α-chloro imine having Structure CI2, the amide having Structure AD3 can be utilized when preparing an N-substituted α-chloro imine having Structure CI3, the amide having Structure AD4 can be utilized when preparing an N-substituted α-chloro imine having Structure CI4, the amide having Structure AD5 can be utilized when preparing an N-substituted α-chloro imine having Structure CI5, the amide having Structure AD11 can be utilized when preparing an N-substituted α-chloro imine having Structure CI11, the amide having Structure AD13 can be utilized when preparing an N-substituted α-chloro imine having Structure CI13, and the amide having Structure AD15 can be utilized when preparing an N-substituted α-chloro imine having Structure CI15. $R^1$, $R^2$, $D^1$, $D^2$, $L^1$, $L^2$, $L^3$, $Q^1$, q, and r within N-substituted α-chloro imine Structures CI1-CI5, CI11, CI13, and CI15 are independently described as features of the $N^2$-phosphinyl amidine compound Structures NP1-NP10, NP11, NP13, NP15, NP16, NP18, and/or NP20. Since N-substituted α-chloro imine Structures CI1-CI5 can be utilized to prepare embodiments of $N^2$-phosphinyl amidine compounds having Structures NP1-NP10, NP11, NP13, NP15, NP16, NP18, and/or NP20, the $R^1$, $R^2$, $D^1$, $D^2$, $L^1$, $L^2$, $L^3$, $Q^1$, q, and r descriptions for the $N^2$-phosphinyl amidine compounds can be utilized without limitation to further describe the N-substituted α-chloro imine Structures CI1-CI5, CI11, CI13, and CI15.

Generally, phosphorus pentachloride and the amide can be contacted in a phosphorus pentachloride to amide group molar ratio of at least 1:1. In an embodiment, phosphorus pentachloride and the amide can be contacted in a phosphorus pentachloride to amide group molar ratio of at least 1.025:1; alternatively, of at least 1.05:1; or alternatively, of at least 1.075:1. In some embodiments, phosphorus pentachloride and the amide can be contacted in a phosphorus pentachloride to amide group molar ratio ranging from 1:1 to 1.5:1; alternatively, ranging from 1.025:1 to 1.30:1; alternatively, ranging from 1.05:1 to 1.25:1; or alternatively, ranging from 1.075:1 to 1.20:1.

In an embodiment, the conditions capable of forming the N-substituted α-chloro imine can include a temperature of at least 0° C.; alternatively, of at least 5° C.; alternatively, of at least 10° C.; or alternatively, of at least 15° C. In some embodiments, the reaction conditions capable of forming the N-substituted α-chloro imine can include a temperature ranging from 0° C. to 160° C.; alternatively, ranging from 5° C. to 150° C.; alternatively, ranging from 10° C. to 140° C.; or alternatively, ranging from 15° C. to 130° C.

In some embodiments, the conditions capable of forming the N-substituted α-chloro imine can include an initial phosphorus and amide contact temperature and a second temperature to form the N-substituted α-chloro imine. It should be noted the when the conditions capable of forming the N-substituted α-chloro imine is described as occurring at two temperatures (one for the contact of the initial phosphorus and amide and one for the formation of the amide) that this description does not exclude the prospect that the N-substituted α-chloro imine may be formed at the contact temperature. The description just relates that, in some embodiments, the N-substituted α-chloro imine formation may proceed better when the initial contact between the initial phosphorus and amide is performed at one temperature and the formation of the N-substituted α-chloro imine is completed at a second different temperature.

In an embodiment, the first amine and acid halide can be contacted at a temperature ranging from 0° C. to 60° C.; alternatively, ranging from 5° C. to 50° C.; alternatively, ranging from 10° C. to 45° C.; or alternatively, ranging from 15° C. to 40° C. In an embodiment, the amide can be formed at a temperature ranging from 20° C. to 160° C.; alternatively, ranging from 30° C. to 150° C.; alternatively, ranging from 35° C. to 140° C.; or alternatively, ranging from 40° C. to 130° C. In an embodiment, the conditions capable of forming the amide can include a reaction time of at 5 minutes; alternatively, of at least 10 minutes; alternatively, of at least 15 minutes; or alternatively, of at least 20 minutes. In some embodiments, the conditions capable of forming the N-substituted α-chloro imine can include a reaction time ranging from 5 minutes to 6 hours; alternatively, ranging from 10 minutes to 5 hours; alternatively, ranging from 15 minutes to 4.5 hours; or alternatively, ranging from 20 minutes to 4 hours.

In an embodiment, the phosphorus pentachloride and the amide can be contacted in an aprotic solvent. In some embodiments, the phosphorus pentachloride and the amide can be contacted in a polar aprotic solvent. Aprotic solvents which can be utilized include hydrocarbon solvents, halogenated hydrocarbon solvents, ether solvents, and any combination thereof; alternatively, hydrocarbon solvents; alternatively, halogenated hydrocarbon solvents; or alternatively, ether solvents. Solvents are generally disclosed herein and any general or specific aprotic solvent and/or polar aprotic solvent described herein can be utilized to further describe the method of preparing an N-substituted α-chloro imine.

In an embodiment, the N-substituted α-chloro imine can be utilized without further isolation or purification. In some embodiments, the amide can be isolated; alternatively, purified; or alternatively, isolated and purified. In an embodiment, the method can include a step of isolating the N-substituted α-chloro imine by evaporating the solvent in which the N-substituted α-chloro imine is formed. In some embodiments, the method can include a step of isolating the N-substituted α-chloro imine by filtering the solution to remove particulate materials and/or byproducts of the reaction and evaporating the solvent. In some embodiments, the method can include a purification step wherein the N-substituted α-chloro imine is purified by dissolving the N-substituted α-chloro imine in a solvent and filtering the solution to remove particulate materials and/or byproducts of the reaction. The solvent utilized to purify the N-substituted α-chloro imine can be the same as the solvent utilized to form the N-substituted α-chloro imine or it can be different than the solvent utilized to form amide. In some embodiments, the method can include a step of purifying the N-substituted α-chloro imine by washing the N-substituted α-chloro imine with a solvent. In some embodiments, the method can include a step of purifying the N-substituted α-chloro imine by distillation. In other embodiments, the method can include a step of purifying the N-substituted α-chloro imine by recrystallization.

Generally, the evaporation of the solvent can be performed using any suitable method. In some embodiments, the solvent can be evaporated at ambient temperature (15-35° C.—no applied external heat source). In other embodiments, the solvent can be evaporated with gentle heating (e.g. at a temperature ranging from 25° C. to 50° C.). In further embodiments, the solvent can be evaporated at ambient temperature under reduced pressure. In yet other embodiments, the solvent can be evaporated with gentle heating under reduced pressure. Generally, the distillation of the N-substituted α-chloro imine can be performed using any suitable method. In some embodiments, the N-substituted α-chloro imine can be distilled at ambient pressure. In other embodiments, the N-substituted α-chloro imine can be distilled under reduced pressure.

The N-substituted α-chloro imine then can be contacted with a second amine. In an embodiment, the second amine can have the Structure A5. $R^3$ within amine

$R^3$—$NH_2$   Structure A5

Structure A5 is independently described as a feature of the $N^2$-phosphinyl amidine compounds Structures NP1-NP10, NP11, NP13, NP15, NP16, NP18, and/or NP20. Since amine Structure A5 is utilized to prepare embodiments of $N^2$-phosphinyl amidine compounds having Structures NP1-NP10, NP11, NP13, NP15, NP16, NP18, and/or NP20 the $R^3$ description for the $N^2$-phosphinyl amidine compounds can be utilized without limitation to further describe the amine Structure A5. In an embodiment, the second amine can be the same as the first amine. In another embodiment, the second amine is different from the first amine Amines having Structure A5 are described herein and can be utilized without limitation to further describe the method of preparing the amidine compound having only one $N^2$ hydrogen atom.

Generally, the second amine and N-substituted α-chloro imine can be contacted in a second amine to N-substituted α-chloro imine equivalent ratio of at least 0.9:1. In some embodiments, the second amine and N-substituted α-chloro imine can be contacted in a second amine to N-substituted α-chloro imine equivalent ratio of at least 0.95:1; alternatively, of at least 0.975:1; or alternatively, of at least 0.99:1. In some embodiments, the second amine and N-substituted α-chloro imine can be contacted in a second amine to N-substituted α-chloro imine equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the second amine and N-substituted α-chloro imine can be contacted in a second amine to N-substituted α-chloro imine equivalent ratio of about 1:1.

In an embodiment, the conditions capable of forming the amidine compound having only one $N^2$ hydrogen atom can include a temperature of at least 0° C.; alternatively, of at least 5° C.; alternatively, of at least 10° C.; or alternatively, of at least 15° C. In some embodiments, the reaction conditions capable of forming the amidine compound having only one $N^2$ hydrogen atom includes a temperature ranging from 0° C. to 160° C.; alternatively, ranging from 5° C. to 150° C.; alternatively, ranging from 10° C. to 140° C.; or alternatively, ranging from 15° C. to 130° C.

In some embodiments, the conditions capable of forming the amidine compound having only one $N^2$ hydrogen atom can include a second amine and N-substituted α-chloro imine contact temperature and a second temperature to form the amidine compound having only one $N^2$ hydrogen atom. It should be noted the when the conditions capable of forming the amidine compound having only one $N^2$ hydrogen atom is described as occurring at two temperatures (one for the contact of the second amine and N-substituted α-chloro imine and one for the formation of the amidine compound having only one $N^2$ hydrogen atom) that this description does not exclude the prospect that the amidine compound having only one $N^2$ hydrogen atom may be formed at the contact temperature. The description just relates that, in some embodiments, the amidine compound having only one $N^2$ hydrogen atom formation may precede better when the initial contact between the second amine and N-substituted α-chloro imine is performed at one temperature and the formation of the amidine compound having only one $N^2$ hydrogen atom is completed at a second different temperature.

In an embodiment, the second amine and N-substituted α-chloro imine can be contacted at a temperature ranging from 0° C. to 60° C.; alternatively, ranging from 5° C. to 50° C.; alternatively, ranging from 10° C. to 45° C.; or alternatively, ranging from 15° C. to 40° C. In an embodiment, amidine compound having only one $N^2$ hydrogen atom can be formed at a temperature ranging from 40° C. to 160° C.; alternatively, ranging from 50° C. to 150° C.; alternatively, ranging from 55° C. to 140° C.; or alternatively, ranging from 60° C. to 130° C. In an embodiment, the conditions capable of forming the amidine compound having only one $N^2$ hydrogen atom can include a reaction time of at 15 minutes; alternatively, of at least 30 minutes; alternatively, of at least 45 minutes; or alternatively, of at least 1 hour. In some embodiments, the conditions capable of forming the amidine compound having only one $N^2$ hydrogen atom can include a reaction time ranging from 15 minutes to 36 hours; alternatively, ranging from 30 minutes to 30 hours; alternatively, ranging from 45 minutes to 24 hours; or alternatively, ranging from 1 hour to 18 hours.

In an embodiment, the second amine and N-substituted α-chloro imine can be contacted in an aprotic solvent. In some embodiments, the second amine and N-substituted α-chloro imine can be contacted in a polar aprotic solvent. Aprotic solvents which can be utilized include hydrocarbon, halogenated hydrocarbon, ethers, and any combination thereof; alternatively, hydrocarbons, halogenated hydrocarbons, and any combination thereof; alternatively, hydrocarbons; alternatively, halogenated hydrocarbons; or alternatively, ethers. Solvents are generally disclosed herein and any general or specific aprotic solvent and/or polar aprotic solvent described herein can be utilized to further describe the method of preparing the amidine compound having only one $N^2$ hydrogen atom.

In an embodiment, the formed amidine compound having only one $N^2$ hydrogen atom can be a hydrogen chloride salt of the amidine compound having only one $N^2$ hydrogen atom. When the formed amidine compound having only one $N^2$ hydrogen atom is a hydrogen chloride salt of the amidine compound having only one $N^2$ hydrogen atom, the method of preparing the amidine compound having only one $N^2$ hydrogen atom further comprises a step of neutralizing the hydrogen chloride salt to release a non-ionic amidine compound having only one $N^2$ hydrogen atom (e.g. an amidine compound having Structures AM1-AM5, AM11, AM13, and/or AM 15 wherein $R^3$ is a non-hydrogen group). In an embodiment, the hydrogen chloride salt of the amidine compound having only one $N^2$ hydrogen atom is neutralized by contacting the hydrogen chloride salt of the amidine compound having only one $N^2$ hydrogen atom with an aqueous solution of a Group 1 or Group 2 metal hydroxide: alternatively, a Group 1 metal hydroxide; alternatively, a group 2 metal hydroxide. In an embodiment, the Group 1 metal hydroxide of the aqueous solution of a Group 1 metal hydroxide can be lithium hydroxide, sodium hydroxide, potassium hydroxide, rubidium hydroxide, or any combination thereof; alternatively, sodium hydroxide, potassium hydroxide, or any combination thereof; alternatively, lithium hydroxide; alternatively, sodium hydroxide; or alternatively, potassium hydroxide.

In an embodiment, the Group 1 or Group 2 metal hydroxide can be added before the hydrogen chloride salt of the amidine compound having only one $N^2$ hydrogen atom is separated from the solvent utilized to produce the hydrogen chloride salt of the amidine compound having only one $N^2$ hydrogen atom. In this scenario, the aqueous Group 1 or Group 2 metal hydroxide can be mixed with the solution comprising the hydrogen chloride salt of the amidine compound having only one $N^2$ hydrogen atom and solvent. The aqueous layer and organic layer (comprising the non-ionic amidine compound having only one $N^2$ hydrogen atom and solvent) can then be separated. In some embodiments, an additional solvent is contacted with the mixture to facilitate the separation of the non-ionic amidine compound having only one $N^2$ hydrogen atom from the aqueous layer. Solvents are generally disclosed herein and any general or specific aprotic solvent and/or polar aprotic solvent described herein can be utilized to further describe neutralizing the hydrogen chloride salt of the amidine compound having only one $N^2$ hydrogen atom.

Generally, the evaporation of the solvent can be performed using any suitable method. In some embodiments, the solvent can be evaporated at ambient temperature (15-35° C.—no applied external heat source). In other embodiments, the solvent can be evaporated with gentle heating (e.g. at a temperature ranging from 25° C. to 50° C.). In further embodiments, the solvent can be evaporated at ambient temperature under reduced pressure. In yet other embodiments, the solvent can be evaporated with gentle heating under reduced pressure.

In an embodiment, the non-ionic amidine compound having only one $N^2$ hydrogen atom can be utilized without further purification. In some embodiments, the non-ionic amidine compound having only one $N^2$ hydrogen atom can be purified. In an embodiment, the method can include a purification step of dissolving the non-ionic amidine compound having only one $N^2$ hydrogen atom in a solvent and filtering the solution to remove particulate materials and/or byproducts of the reaction. Solvents are generally disclosed herein and can be utilized without limitation as the solvent for washing the non-ionic amidine compound having only one $N^2$ hydrogen atom. In some embodiments, the method can include a step of purifying the non-ionic amidine compound having only one $N^2$ hydrogen atom by washing non-ionic amidine compound having only one $N^2$ hydrogen atom with a solvent. In other embodiments, the method can include a step of purifying the non-ionic amidine compound having only one $N^2$ hydrogen atom by recrystallization.

In an aspect, the steps for preparing the intermediate compounds in the preparation of the $N^2$-phosphinyl amidine compound (the steps of preparing amidine compounds—e.g. amidine compounds having Structures AM1-AM11, AM13, AM 15, AM 16, AM18, and AM20—from nitriles, amines, compounds capable of abstracting protons, halogenated compounds, acid chlorides, and/or phosphorus pentachloride) can be included in the process for producing the $N^2$-phosphinyl amidine compounds of this disclosure. These intermediate steps are disclosed herein and may be combined in an appropriate fashion to describe a method of preparing the $N^2$-phosphinyl amidine compound. When the steps are combined, appropriate step identifiers (e.g. 1), 2), etc. . . . , a), b), etc. . . . , or i), ii), etc. . . . ) and compound/solvent identifiers (e.g. first, second, etc. . . . ) can be added to indicate individual and/or different steps/compounds/solvents utilized within the preparation of the amidine compound without detracting from the general disclosure.

Generally, the methods for forming the amide, the N-substituted α-chloro imine, the amidine compound, the metal amidinate, and the $N^2$-phosphinyl amidine compound can combined in various embodiments to provide a method to form an $N^2$-phosphinyl amidine compound having only one $N^2$ hydrogen atom utilizing amines, acid halides, compounds capable of abstracting a proton from the —NH$_2$ group, and phosphine halides. In a non-limiting embodiment, a method of preparing an $N^2$-phosphinyl amidine compound can comprise: a) contacting a first amine and an acid halide; b) forming an amide c) contacting the amide with phosphorus pentachloride; d) forming an N-substituted α-chloro imine; e) contacting the N-substituted α-chloro imine with a second amine; f) forming an amidine compound having only one $N^2$ hydrogen atom; g) isolating the amidine compound having only one $N^2$ hydrogen atom; h) contacting the amidine compound having only one $N^2$ hydrogen atom with a compound capable of abstracting a proton from the amidine compound having only one $N^2$ hydrogen atom; i) forming a metal amidinate; j) contacting the metal amidinate and a phosphine halide; and k) forming the $N^2$-phosphinyl amidine compound. These methods can contain steps other than those recited in the methods of preparing the amide described herein, methods of preparing the N-substituted α-chloro imine described herein, methods of preparing amidine compounds described herein, methods of preparing the metal amidinate described herein, and methods of preparing $N^2$-phosphinyl amidine compounds described herein which can be utilized to further describe these methods. Additional features of each of these steps (e.g. reagent ratios, formation conditions, among other considerations) are described herein and may be utilized to further describe the methods.

In an aspect, this disclosure relates to a method of preparing an $N^2$-phosphinyl amidine metal salt complex. Generally, the method of preparing the $N^2$-phosphinyl amidine metal salt complex can comprise: a) contacting a metal salt with an $N^2$-phosphinyl amidine compound; and b) forming the $N^2$-phosphinyl amidine metal salt complex. Generally, the $N^2$-phosphinyl amidine metal salt complex can be formed under conditions capable of forming an $N^2$-phosphinyl amidine metal salt complex. In some embodiments, the $N^2$-phosphinyl amidine metal salt complex can be isolated; alternatively, purified; or alternatively, isolated and purified.

$N^2$-phosphinyl amidine compounds are disclosed herein and can be utilized without limitation to further describe the method of preparing an $N^2$-phosphinyl amidine metal salt complex. Metal salts are disclosed herein and can be utilized without limitation to further describe the method of preparing an $N^2$-phosphinyl amidine metal salt complex.

Generally, the metal salt and the $N^2$-phosphinyl amidine compound can be contacted at a metal salt to $N^2$-phosphinyl amidine compound equivalent ratio of at least 0.9:1. In some embodiments, the metal salt and the $N^2$-phosphinyl amidine compound can be contacted at a metal salt to $N^2$-phosphinyl amidine compound equivalent ratio of at least 0.95:1; alternatively, of at least 0.975:1; or alternatively, of at least 0.99:1. In some embodiments, the metal salt and the $N^2$-phosphinyl amidine compound can be contacted at a metal salt to $N^2$-phosphinyl amidine compound equivalent ratio ranging from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In other embodiments, the metal salt and the $N^2$-phosphinyl amidine compound can be contacted at a metal salt to $N^2$-phosphinyl amidine compound equivalent ratio of about 1:1.

In an embodiment, the conditions capable of forming an $N^2$-phosphinyl amidine metal salt complex can include a contact temperature of at least 0° C.; alternatively, of at least 5° C.; alternatively, of at least 10° C.; or alternatively, of at least 15° C. In some embodiments, the conditions capable of forming the $N^2$-phosphinyl amidine metal salt complex can include a contact temperature ranging from 0° C. to 60° C.; alternatively, ranging from 5° C. to 50° C.; alternatively, ranging from 10° C. to 45° C.; or alternatively, ranging from 15° C. to 40° C. In an embodiment, the conditions capable of forming the $N^2$-phosphinyl amidine metal salt complex can include a contact time of at least 15 minutes; alternatively, of at least 30 minutes; alternatively, of at least 45 minutes; or alternatively, of at least 1 hour. In some embodiments, the conditions capable of forming the $N^2$-phosphinyl amidine metal salt complex can include a contact time ranging from 15 minutes to 36 hours; alternatively, ranging from 30 minutes to 30 hours; alternatively, ranging from 45 minutes to 24 hours; or alternatively, ranging from 1 hour to 18 hours.

In an embodiment, the metal salt and the $N^2$-phosphinyl amidine compound can be contacted in a solvent. In some embodiments, the metal salt and the $N^2$-phosphinyl amidine compound can be contacted in a polar solvent. In some embodiments, the solvent is the same as the neutral ligand, Q, within some embodiments of the $N^2$-phosphinyl amidine metal salt complex. Solvents (general and specific) are generally disclosed herein and can be utilized, without limitation, to further describe the method of preparing the $N^2$-phosphinyl amidine metal salt complex.

In an embodiment, the $N^2$-phosphinyl amidine metal salt complex can be utilized without further isolation or purification. In some embodiments, the $N^2$-phosphinyl amidine metal salt complex can be isolated; alternatively, purified; or alternatively, isolated and purified. In an embodiment, wherein the $N^2$-phosphinyl amidine metal salt complex is prepared in a solvent, the method to prepare the $N^2$-phosphinyl amidine metal salt complex can include a step of isolating the $N^2$-phosphinyl amidine metal salt complex by evaporating the solvent. In an embodiment wherein the $N^2$-phosphinyl amidine metal salt complex is prepared in a solvent, the method to prepare the $N^2$-phosphinyl amidine metal salt complex can include the step of isolating the $N^2$-phosphinyl amidine metal salt complex by filtering the solution to remove particulate materials and/or byproducts of the reaction and evaporating the solvent. In embodiments, the method to prepare the $N^2$-phosphinyl amidine metal salt complex can include a purification step wherein the $N^2$-phosphinyl amidine compound is purified by dissolving the $N^2$-phosphinyl amidine metal salt complex in a solvent and filtering the solution to remove particulate materials and/or byproducts of the reaction. The solvent utilized to purify the $N^2$-phosphinyl amidine metal salt complex can be the same a solvent utilized to form the $N^2$-phosphinyl amidine metal salt complex or it can be different than the solvent utilized to form the $N^2$-phosphinyl amidine metal salt complex. In some embodiments, the method of preparing the $N^2$-phosphinyl amidine metal salt complex can include a purification step of isolating the $N^2$-phosphinyl amidine metal salt complex by washing the $N^2$-phosphinyl amidine metal salt complex with a solvent. In other embodiments, the method of preparing the $N^2$-phosphinyl amidine metal salt complex can include a purification step of recrystallizing the $N^2$-phosphinyl amidine metal salt complex.

Generally, the evaporation of the solvent can be performed using any suitable method. In some embodiments, the solvent can be evaporated at ambient temperature (15-35° C.—no applied external heat source). In other embodiments, the solvent can be evaporated with gentle heating (e.g. at a temperature ranging from 25° C. to 50° C.). In further embodiments, the solvent can be evaporated at ambient temperature under reduced pressure. In yet other embodiments, the solvent can be evaporated with gentle heating under reduced pressure.

It has been unexpectedly discovered that the time between the isolation and/or purification of the $N^2$-phosphinyl amidine metal salt complex and the formation of the oligomerization catalyst system can have an impact on aspects of the oligomerization. Firstly, it has been observed that increasing the time between the isolation and/or purification of the $N^2$-phosphinyl amidine metal salt complex and the formation of the oligomerization catalyst system can increase the catalytic activity and/or increase the productivity of the catalyst system. Secondly, it has been observed that increasing the time between the isolation and/or purification of the $N^2$-phosphinyl amidine metal salt complex and the formation of the oligomerization catalyst system can increase the percentage of polymer produced by the oligomerization catalyst system. Without being limited by theory, it is believed that these effects result from the disassociation of (or alternatively, evaporation of) neutral ligand, Q, from the $N^2$-phosphinyl amidine metal salt complex and/or from the crystal lattice of the $N^2$-phosphinyl amidine metal salt complex.

Controlling the time between the isolation and/or purification of the $N^2$-phosphinyl amidine metal salt complex and the formation of the oligomerization catalyst system can improve the olefin oligomerization process. For instance, one can increase the activity and/or productivity of the catalyst system by increasing the time between the isolation and/or purification of the $N^2$-phosphinyl amidine metal salt complex and formation of the oligomerization catalyst system. Increasing the activity and/or the productivity of the catalyst system can provide increased olefin oligomer product per unit of catalyst system.

However, it may not be possible to increase the time between the isolation and/or purification of the $N^2$-phosphinyl amidine metal salt complex and formation of the oligomerization catalyst system indiscriminately. As noted herein, increasing the time between the isolation and/or purification of the $N^2$-phosphinyl amidine metal salt complex and the formation of the oligomerization catalyst system can increase the percentage of polymer produced by the oligomerization catalyst system. If the polymer production of the catalyst system utilizing the $N^2$-phosphinyl amidine metal salt complex increases too much, polymer production can adversely impact the oligomerization process. For example, polymer could adhere to the oligomerization reactor walls or cooling apparatus and cause fouling which can necessitate a reactor shut down to remove the polymer. Consequently, there can be a need to balance increases in catalyst system activity and/or productivity against increased polymer production.

It has also been discovered that at least some of the effects of increasing the time between the isolation and/or purification of the $N^2$-phosphinyl amidine metal salt complex and the formation of the oligomerization catalyst system can be reversed by adding a neutral ligand to the $N^2$-phosphinyl amidine metal salt complex. The ability to reverse some of the effects of increasing the time between the isolation and/or purification of the $N^2$-phosphinyl amidine metal salt complex and the formation of the oligomerization catalyst system can reduce potentially negative effects. Non-limiting examples of negative effects of increasing the time between the isolation and/or purification of the $N^2$-phosphinyl amidine metal salt complex and the formation of the oligomerization catalyst system can include 1) prohibiting the ability to use an $N^2$-phosphinyl amidine metal salt complex by increasing the time between the isolation and/or purification of the $N^2$-phosphinyl amidine metal salt complex and the formation of the oligomerization catalyst system to a point wherein the formed catalyst system produces an undesirable quantity of polymer and 2) reducing the need to minimize the time between preparing the $N^2$-phosphinyl amidine metal salt complex and the preparation of the catalyst system utilizing the $N^2$-phosphinyl amidine metal salt complex.

However, it has also been discovered that too much neutral ligand associated with the $N^2$-phosphinyl amidine metal salt complex can significantly reduce or eliminate the catalyst system olefin oligomer productivity. Consequently, it can be necessary to take precautions to control the amount of neutral ligand provided to the $N^2$-phosphinyl amidine metal salt complex. Generally, addition of the neutral ligand to the $N^2$-phosphinyl amidine metal salt complex can be accomplished by any suitable method. For example, the $N^2$-phosphinyl amidine metal salt complex can be recrystallized from a solution containing a neutral ligand or the $N^2$-phosphinyl amidine metal salt complex can be placed in a solvent containing a neutral ligand. Excess neutral ligand can be removed from the $N^2$-phosphinyl amidine metal salt complex by allowing the solvent to evaporate or by increasing the time between the treatment of the $N^2$-phosphinyl amidine metal salt complex with the neutral ligand and the formation of the oligomerization catalyst system.

In an embodiment the isolated and/or purified $N^2$-phosphinyl amidine metal salt complex can be utilized in an olefin oligomerization process. In an embodiment, the olefin oligomerization process can comprise: a) forming a composition comprising an $N^2$-phosphinyl amidine metal salt complex; b) forming a mixture comprising an olefin and a metal alkyl; c) contacting the composition of step a) and the mixture of step b); and d) forming an olefin oligomer product. In an embodiment, the olefin oligomerization process can comprise: a) forming a composition comprising an $N^2$-phosphinyl amidine metal salt complex; b) forming a mixture comprising an olefin, a metal alkyl, and hydrogen; c) contacting the composition of step a) and the mixture of step b); and d) forming an olefin oligomer product. In some embodiments, the mixture comprising the olefin and the metal alkyl can also comprise hydrogen. In some embodiments the composition comprising the $N^2$-phosphinyl amidine metal salt complex also can comprise a solvent (e.g., a first solvent). In some embodiments, the mixture comprising an olefin, a metal alkyl, and optionally hydrogen, also can comprise a solvent (e.g., a second solvent). In an embodiment, the solvents used in the composition comprising the $N^2$-phosphinyl amidine metal salt complex and the mixture comprising the olefin and the metal alkyl (and optionally hydrogen) can be the same; or can be different. The $N^2$-phosphinyl amidine metal salt complex, metal alkyl, olefin, solvents, and features of the olefin oligomer are independently described herein and can be utilized, without limitation to further describe the olefin oligomerization process. In some embodiments, the metal alkyl can comprise an aluminoxane. Ratios for the metal of the $N^2$-phosphinyl amidine metal salt complex to the metal of the metal alkyl are provided herein and can be utilized without limitation to further describe the olefin oligomerization process.

In an aspect, any method of producing a catalyst system disclosed herein or any method of oligomerizing or polymerizing an olefin can further comprise a step of aging the $N^2$-phosphinyl amidine metal salt complex. In another aspect, any method of producing a catalyst system disclosed herein or any method of oligomerizing or polymerizing an olefin can further comprise a step of treating the $N^2$-phosphinyl amidine metal salt complex with a neutral ligand; or alternatively, 1) treating the $N^2$-phosphinyl amidine metal salt complex with a neutral ligand and 2) allowing the treated $N^2$-phosphinyl amidine metal salt complex to age. In another aspect, any method of producing a catalyst system disclosed herein or any method of oligomerizing or polymerizing an olefin can further comprise a step of treating an aged $N^2$-phosphinyl amidine metal salt complex with a neutral ligand; or alternatively, 1) treating the $N^2$-phosphinyl amidine metal salt complex with a neutral ligand and 2) allowing the treated $N^2$-phosphinyl amidine metal salt complex to age.

In an aspect, the activity of any olefin oligomerization method described herein (using any catalyst system described herein comprising any $N^2$-phosphinyl amidine metal salt complex described herein) can be controlled by aging the $N^2$-phosphinyl amidine metal salt complex. In an aspect, the activity of any olefin oligomerization method described herein (using any catalyst system as described herein comprising any $N^2$-phosphinyl amidine metal salt complex described herein) can be controlled by treating the $N^2$-phosphinyl amidine metal salt complex with a neutral ligand; or alternatively, 1) treating the $N^2$-phosphinyl amidine metal salt complex with a neutral ligand and 2) allowing the treated $N^2$-phosphinyl amidine metal salt complex to age. In an aspect, the activity of any olefin oligomerization method described herein (using any catalyst system described herein comprising any $N^2$-phosphinyl amidine metal salt complex described herein) can be controlled by treating an aged N2-phosphinyl amidine metal salt complex with a neutral ligand; or alternatively, 1) treating the $N^2$-phosphinyl amidine metal salt complex with a neutral ligand and 2) allowing the treated $N^2$-phosphinyl amidine metal salt complex to age.

The catalytic activity of any catalyst system described herein comprising any $N^2$-phosphinyl amidine metal salt complex described herein in an olefin oligomerization process can be defined as the grams of olefin oligomer product (or liquid olefin oligomer product, or any other defined portion of the olefin oligomerization product) produced per gram of metal of the metal salt in the $N^2$-phosphinyl amidine metal salt complex utilized. In an embodiment, the catalyst system activity of any catalyst system described herein comprising any $N^2$-phosphinyl amidine metal salt complex described herein can be increased by utilizing an aged $N^2$-phosphinyl amidine metal salt complex. This activity increase can be described as a percentage increase in the catalyst system activity and can be related to the activity of the catalyst system prepared using a fresh $N^2$-phosphinyl amidine metal salt complex, $a_0$. Generally, a fresh $N^2$-phosphinyl amidine metal salt complex is one which has been utilized to prepare an oligomerization catalyst system within 14 days of its isolation and/or purification. It should be noted, a fresh $N^2$-phosphinyl amidine metal salt complex does not contain excess neutral ligand which can give an inactive olefin oligomerization catalyst system (i.e. a catalyst system that produces less than 550 grams oligomer per gram metal of metal salt in the $N^2$-phosphinyl amidine metal salt complex). The activity of the catalyst system based upon an aged $N^2$-phosphinyl amidine metal salt complex can be denoted $a_x$.

In an embodiment, the $N^2$-phosphinyl amidine metal salt complex can be aged for up to 24 months; alternatively, up to 18 months; alternatively, up to 15 months; alternatively, up to 12 months; alternatively, up to 11 months; alternatively, up to 10 months; alternatively, up to 9 months; alternatively, up to 8 months; alternatively, up to 7 months; or alternatively, up to 6 months. In an embodiment, aging the $N^2$-phosphinyl amidine metal salt complex (for any time period described herein) can increase the activity of any catalyst system described herein utilizing any $N^2$-phosphinyl amidine metal salt complex described herein at least 10%; alternatively, by at least 20%; alternatively, by at least 30%; alternatively, by at least 40%; or alternatively, at least 50%. In some embodiments, aging the $N^2$-phosphinyl amidine metal salt complex (for any time period described herein) can increase the activity of any catalyst system described herein utilizing any $N^2$-phosphinyl amidine metal salt complex described herein from 10 to 1500%; alternatively, from 20% to 1000%; alternatively, from 30 to 750%; alternatively, from 40 to 600%; or alternatively, from 50 to 500%.

In an embodiment, aging the $N^2$-phosphinyl amidine metal salt complex (for any time period described herein) for any catalyst system described herein utilizing any $N^2$-phosphinyl amidine metal salt complex described herein can provide a catalyst system which can produce any defined percentage of polymer described herein. In an embodiment, aging the $N^2$-phosphinyl amidine metal salt complex (for any time period described herein) for any catalyst system described herein utilizing any $N^2$-phosphinyl amidine metal salt complex described herein can provide a catalyst system can provide a catalyst system which can produce less than 5 weight percent polymer; alternatively, equal to or less than 2 weight % polymer; alternatively, equal to or less than 1.5 alternatively, equal to or less than 1 weight % polymer; alternatively, equal to or less than 0.75 alternatively, equal to or less than 2 weight % polymer; alternatively, equal to or less than 0.5 weight % polymer; alternatively, equal to or less than 0.4 weight % polymer; alternatively, equal to or less than 0.3 weight % polymer; alternatively, equal to or less than 0.2 weight % polymer; or, alternatively, equal to or less than 0.1 weight % polymer. Generally, the basis for weight percent polymer is based upon all products of the olefin oligomerization (excluding unreacted monomer, catalyst system components, solvent, and other non-olefin oligomerization products).

In some embodiments, any catalyst system described herein utilizing an aged $N^2$-phosphinyl amidine metal salt complex can have a combination of any increased activity described herein and any amount of polymer described herein. The catalyst system described herein utilizing an aged $N^2$-phosphinyl amidine metal salt complex can further be described utilizing, individually or in any combination, any other catalyst system feature or olefin oligomerization product feature described herein.

In an embodiment, a calibration curve can be produced depicting catalytic activity and or polymer product of any catalyst system described herein comprising any $N^2$-phosphinyl amidine metal salt complex described herein in response to aging the phosphinyl amidine metal salt complex. In some embodiments, a calibration curve (for catalyst activity and/or polymer production) can be depicted as a function of the period of $N^2$-phosphinyl amidine metal salt complex age in order to derive a predictive equation. The calibration curve or predictive equation relating catalyst system activity and/or polymer production in response to $N^2$-phosphinyl amidine metal salt complex age can be utilized to adjust one or more user and/or process parameters based upon the interpolation or extrapolation the calibration curve and/or the predictive equation. It is contemplated that in some aspects, the extent to which $a_x$ increases with respect to $a_0$ can fall outside the instantly disclosed ranges and can be larger than would be expected based on the presently disclosed values depending on the conditions under which the $N^2$-phosphinyl amidine metal salt complex is aged. For example, the $N^2$-phosphinyl amidine metal salt complex can be subjected to aging for time periods that are 5 to 10 times longer than those presently recited or under conditions of elevated temperature and/or reduced pressure. The effects of aging the $N^2$-phosphinyl amidine metal salt complex under such conditions can be subject to the herein mentioned analysis to provide predictive information that can lead one to conditions under which aging the $N^2$-phosphinyl amidine metal salt complex can increase catalyst system activity using an aged $N^2$-phosphinyl amidine metal salt complexes outside of the recited numerical ranges. It is contemplated that given the benefits of this disclosure and using routine experimentation one having ordinary skill in the art can modify the methodologies disclosed herein to alter the catalytic system activity using an aged $N^2$-phosphinyl amidine metal salt complexes to a desired value or range. Such modifications fall within the scope of this disclosure.

In an embodiment, contacting of the $N^2$-phosphinyl amidine metal salt complex (aged or otherwise) with a neutral ligand can be carried out using any suitable molar ratio of neutral ligand to $N^2$-phosphinyl amidine metal salt. In an embodiment, the molar ratio neutral ligand to $N^2$-phosphinyl amidine metal salt complex can be at least 0.2:1; alternatively, at least 0.3:1; alternatively, at least 0.4:1; or alternatively, at least 0.5:1. In an embodiment, the molar ratio neutral ligand to $N^2$-phosphinyl amidine metal salt complex can be from 0.2:1 to 10,000:1; alternatively, 0.3:1 to 8,000:1; alternatively, from 0.4:1 to 6,000:1; or alternatively, from 0.5:1 to 5,000:1. In an embodiment, the contact of the $N^2$-phosphinyl amidine metal salt complex can occur in a solvent consisting essentially of the neutral ligand; or alternatively, in a solvent comprising, or consisting essentially of, the neutral ligand and a non-complexing solvent.

When the $N^2$-phosphinyl amidine metal salt complex is contacted with a solvent consisting essentially of the neutral ligand, the molar ratio of neutral ligand to $N^2$-phosphinyl amidine metal salt can be any molar ratio of neutral ligand to $N^2$-phosphinyl amidine metal salt disclosed herein. In other embodiments wherein the $N^2$-phosphinyl amidine metal salt complex is contacted with a solvent consisting essentially of the neutral ligand, the molar ratio of neutral ligand to $N^2$-phosphinyl amidine metal salt can be any molar ratio of neutral ligand to $N^2$-phosphinyl amidine metal salt can be at least 5:1; alternatively, at least 7.5:1; alternatively, at least 10:1; alternatively, at least 10:1; alternatively, at least 15:1; alternatively, 5:1; alternatively, range from 7.5:1 to 10,000:1; alternatively, range from 10:1 to 8,000:1; alternatively, range from 10:1 to 6,000:1; or alternatively, range from 15:1 to 5,000:1.

When the $N^2$-phosphinyl amidine metal salt complex is contacted with a solvent comprising, or consisting essentially of, the neutral ligand and a non-complexing solvent, the molar ratio of neutral ligand to $N^2$-phosphinyl amidine metal salt can be any molar ratio of neutral ligand to $N^2$-phosphinyl amidine metal salt disclosed herein. In other embodiments wherein the $N^2$-phosphinyl amidine metal salt complex is contacted with a solvent comprising, or consisting essentially of, the neutral ligand and a non-complexing solvent, the molar ratio of neutral ligand to $N^2$-phosphinyl amidine metal salt can be less than or equal to 500:1; less than or equal to 300:1; less than or equal to 200:1; alternatively, less than or equal to 100:1; alternatively, range from 0.2:1 to 500:1; alternatively, range from 0.3:1 to 300:1; alternatively, range from 0.4:1 to 200:1; or alternatively, from 0.5:1 to 100:1. In some embodiments, wherein the $N^2$-phosphinyl amidine metal salt complex is contacted with a solvent comprising, or consisting essentially of, the neutral ligand and a non-complexing solvent, the volumetric ratio of neutral ligand to non-complexing solvent can range from 1:1 to 10,000:1; alternatively, range from 5:1 to 8,000:1; alternatively, range from 7.5:1 to 6,000:1; or alternatively, range from 10:1 to 5,000:1.

In an embodiment, the neutral ligand can be any neutral ligand disclosed herein. In some embodiments, the neutral ligand utilized to treat the $N^2$-phosphinyl amidine metal salt complex can be the same as the neutral ligand of the $N^2$-phosphinyl amidine metal salt complex; or alternatively, the neutral ligand utilized to treat the $N^2$-phosphinyl amidine metal salt complex can be different from the neutral ligand of the $N^2$-phosphinyl amidine metal salt complex. In an embodiment, the non-complexing solvent utilized in an embodiment comprising, or consisting essentially of, a neutral ligand and a non-complexing solvent can be a hydrocarbon or a halogenated hydrocarbon; alternatively, a hydrocarbon or a halogenated hydrocarbon. Hydrocarbon and halogenated hydrocarbon solvents (general and specific) are disclosed herein and can be utilized, without limitation, to further describe any aspect and/or embodiment utilizing a solvent comprising, or consisting essentially of, a neutral ligand and a non-complexing solvent.

In an embodiment, the $N^2$-phosphinyl amidine metal salt complex can be aged (whether or not it has been treated with a neutral ligand) utilizing any suitable methodology. In some embodiments, the $N^2$-phosphinyl amidine metal salt complex can be aged (whether or not it has been treated with a neutral ligand) at ambient temperature (15-35° C.—no applied external heat source); or alternatively, at ambient temperature under an inert atmosphere. In other embodiments, the $N^2$-phosphinyl amidine metal salt complex can be aged (whether or not it has been treated with a neutral ligand) with gentle heating (e.g., at a temperature ranging from 25° C. to 50° C.); alternatively, under reduced pressure; alternatively, ambient temperature under reduced pressure; or alternatively, with gentle heating under reduced pressure.

In an embodiment, the aged $N^2$-phosphinyl amidine metal salt complex, the neutral ligand treated $N^2$-phosphinyl amidine metal salt complex, or the neutral ligand treated and aged $N^2$-phosphinyl amidine metal salt complex can be utilized in a catalyst system, utilized in a process to prepare a catalyst, and/or a method to oligomerize (or polymerize) an olefin. Generally, the steps of aging the $N^2$-phosphinyl amidine metal salt complex, the steps of treating the $N^2$-phosphinyl amidine metal salt complex with a neutral ligand, and/or treating the $N^2$-phosphinyl amidine metal salt complex with a neutral ligand and aging the neutral ligand treated the $N^2$-phosphinyl amidine metal salt complex can be utilized, without limitation, to further describe the catalyst system, the method of preparing the catalyst system, and/or the method to oligomerize (or polymerize) an olefin.

In an aspect, the step(s) for preparing the $N^2$-phosphinyl amidine compound can be incorporated into the preparation of the $N^2$-phosphinyl amidine metal salt complex. When the steps are combined, appropriate step identifiers (e.g. 1), 2), etc. . . . , a), b), etc. . . . , or i), ii), etc. . . . ) and compound/solvent identifiers (e.g. first, second, etc. . . . ) can be added to indicate individual and/or different steps/compounds/solvents utilized within the preparation of the amidine compound without detracting from the general disclosure.

In an aspect, the present disclosure relates to an olefin oligomerization process; or alternatively, an olefin polymerization process. Within this disclosure, olefin oligomerization relates to processes which produce products of which at least 80 weight percent contain from 1 to 20 monomer units. Within this disclosure, olefin polymerization relates to process(es) which produces products of which at least 80 weight percent contain greater than 20 monomer units.

In an embodiment, the olefin oligomerization process can comprise: a) contacting an olefin and a catalyst system; and b) forming an olefin oligomer product. In some embodiments, the olefin oligomerization process can comprise, a) contacting an olefin, hydrogen, and a catalyst system; and b) forming an olefin oligomer product. In an embodiment, the olefin polymerization process can comprise: a) contacting an olefin and a catalyst system; and b) forming an olefin polymer product. In some embodiments, the olefin polymerization process can comprise a) contacting an olefin, hydrogen, and a catalyst system and b) forming an olefin polymer product. The catalyst system, olefin, and features of the olefin oligomer or olefin polymer product are independently described herein and can be utilized, without limitation to further describe the olefin oligomerization or olefin polymerization process. In an embodiment, the catalyst system can be prepared in a first solvent. In an embodiment, the olefin, catalyst system, and optionally hydrogen, can be contacted in a second solvent. Generally, a solvent in which the catalyst system can be prepared and the solvent in which the olefin and catalyst system can be contacted can be the same; or alternatively, can be different.

In an embodiment, the olefin oligomerization process can comprise: a) forming a catalyst system mixture comprising an $N^2$-phosphinyl amidine metal salt complex and a metal alkyl; b) contacting the catalyst system mixture with an olefin; and c) forming an olefin oligomer product. In an embodiment, the olefin polymerization process can comprise: a) forming a catalyst system mixture comprising an $N^2$-phosphinyl amidine metal salt complex and a metal alkyl; b) contacting the catalyst system mixture with an olefin; and c) forming an olefin oligomer product. In some embodiments, the step of contacting the catalyst system mixture with the olefin can be a step of contacting the catalyst system mixture with an olefin and hydrogen. In some embodiments, the catalyst system mixture can further comprise a solvent (e.g. a first solvent). In some embodiments, the catalyst system mixture and olefin can be contacted in a solvent (e.g. a second solvent when the catalyst system is prepared in a solvent). In an embodiment, the olefin oligomerization process can comprise: a) forming a catalyst system mixture comprising, or consisting essentially of, an $N^2$-phosphinyl amidine metal salt complex, a metal alkyl, and a first solvent; b) contacting the catalyst system mixture with an olefin and a second solvent; and c) forming an olefin oligomer product. In an embodiment, the olefin polymerization process can comprise: a) forming a catalyst system mixture comprising, or consisting essentially of, an $N^2$-phosphinyl amidine metal salt complex, a metal alkyl, and a first solvent; b) contacting the catalyst system mixture with an olefin and a second solvent; and c) forming an olefin oligomer product. In some embodiments, the step of contacting the catalyst system mixture with the olefin and the second solvent can be a step of contacting the catalyst system mixture with an olefin, a second solvent, and hydrogen. The $N^2$-phosphinyl amidine metal salt complex, metal alkyl, olefin, solvents, and features of the olefin oligomer or olefin polymer product are independently described herein (among other catalyst system and olefin oligomerization or polymerization features) and can be utilized, without limitation to further describe the olefin oligomerization or olefin polymerization process. In some embodiments, the first and second solvent can be the same; or alternatively, the first and second solvent can be different. In some embodiments, the metal alkyl can comprise, or consist essentially of, an aluminoxane. Ratios for the metal of the $N^2$-phosphinyl amidine metal salt complex to the metal of the metal alkyl are independently provided herein (among other catalyst system and olefin oligomerization or polymerization features) and can be utilized without limitation to further describe the olefin oligomerization or olefin polymerization process.

In an embodiment, the olefin oligomerization process can comprise: a) forming a composition comprising an $N^2$-phosphinyl amidine metal salt complex; b) forming a mixture comprising an olefin and a metal alkyl; c) contacting the composition of step a) and the mixture of step b); and d) forming an olefin oligomer product. In an embodiment, the olefin polymerization process can comprise: a) forming a composition comprising a the $N^2$-phosphinyl amidine metal salt complex; b) forming a mixture comprising an olefin and a metal alkyl; c) contacting the composition of step a) and the mixture of step b); and d) forming an olefin polymer product. In some embodiments, the mixture comprising the olefin and the metal alkyl can further comprise hydrogen. In some embodiments the composition comprising the $N^2$-phosphinyl amidine metal salt complex can further comprise a solvent (e.g. a first solvent). In some embodiments, the mixture comprising an olefin, a metal alkyl, and optionally hydrogen, can further comprise a solvent (e.g. a second solvent). In an embodiment, the olefin oligomerization process can comprise: a) forming a composition comprising, or consisting essentially of, an $N^2$-phosphinyl amidine metal salt complex and a first solvent; b) forming a mixture comprising an olefin, a metal alkyl, hydrogen, and a second solvent; c) contacting the composition of step a) and the mixture of step b); and d) forming an olefin oligomer product. In an embodiment, the olefin polymerization process can comprise: a) forming a composition comprising, or consisting essentially of, a the $N^2$-phosphinyl amidine metal salt complex and a first solvent; b) forming a mixture comprising an olefin, a metal alkyl, hydrogen, and a second solvent; c) contacting the composition of step a) and the mixture of step b); and d) forming an olefin polymer product. In an embodiment, the solvents used in the composition comprising the $N^2$-phosphinyl amidine metal salt complex and the mixture comprising the olefin and the metal alkyl (and optionally hydrogen) can be the same; or alternatively, can be different. The $N^2$-phosphinyl amidine metal salt complex, metal alkyl, olefin, solvents, and features of the olefin oligomer or olefin polymer product (among other catalyst system and olefin oligomerization or polymerization features) are independently described herein and can be utilized, without limitation to further describe the olefin oligomerization or olefin polymerization process. In some embodiments, the metal alkyl can comprise an aluminoxane. Ratios for the metal of the $N^2$-phosphinyl amidine metal salt complex to the metal of the metal alkyl are independently provided herein (among other catalyst system and olefin oligomerization or polymerization features) and can be utilized without limitation to further describe the olefin oligomerization or olefin polymerization process.

In an embodiment, the olefin oligomerization process can comprise: a) forming a catalyst system mixture comprising an $N^2$-phosphinyl amidine compound, a metal salt, and a metal alkyl; b) contacting the catalyst system mixture with an olefin; and c) forming an olefin oligomer product. In an embodiment, the olefin polymerization process can comprise: a) forming a catalyst system mixture comprising an $N^2$-phosphinyl amidine compound, a metal salt, and a metal alkyl; b) contacting the catalyst system mixture with an olefin; and c) forming an olefin oligomer product. In some embodiments, the step of contacting the catalyst system mixture with the olefin can be a step of contacting the catalyst system mixture with an olefin and hydrogen. In some embodiments, the catalyst system mixture can further comprise a solvent (e.g. a first solvent). In some embodiments, the catalyst system mixture and olefin can be contacted in a solvent (e.g. a second solvent when the catalyst system is prepared in a solvent). In an embodiment, the olefin oligomerization process can comprise: a) forming a catalyst system mixture comprising, or consisting essentially of, an $N^2$-phosphinyl amidine compound, a metal salt, a metal alkyl, and a first solvent; b) contacting the catalyst system mixture with an olefin and a second solvent; and c) forming an olefin oligomer product. In an embodiment, the olefin polymerization process can comprise: a) forming a catalyst system mixture comprising, or consisting essentially of an $N^2$-phosphinyl amidine compound, a metal salt, a metal alkyl, and a first solvent; b) contacting the catalyst system mixture with an olefin and a second solvent; and c) forming an olefin polymer product. In some embodiments, the step of contacting the catalyst system mixture with the olefin and the second solvent can be a step of contacting the catalyst system mixture with an olefin, a second solvent, and hydrogen. In some embodiments, the first and second solvent can be the same; or alternatively, the first and second can be different. The $N^2$-phosphinyl amidine compound, metal salt, metal alkyl, olefin, solvents, and features of the olefin oligomer or olefin polymer product are independently described herein (among other catalyst system and olefin oligomerization or polymerization features) and can be utilized, without limitation to further describe the olefin oligomerization or olefin polymerization process. In some embodiments, the first and second solvent can be the same; or alternatively, the first and second solvent can be different. In some embodiments, the metal alkyl can comprise, or consist essentially of, an aluminoxane. The $N^2$-phosphinyl amidine compound, metal salt, metal alkyl, olefin, solvents, and features of the olefin oligomer or olefin polymer product are independently described herein (among other catalyst system and olefin oligomerization or polymerization features) and can be utilized, without limitation to further describe the olefin oligomerization or olefin polymerization process. Ratios for the $N^2$-phosphinyl amidine compound to metal salt and ratios for the metal of the metal alkyl to metal of the metal salt are independently provided herein (among other catalyst system and olefin oligomerization or polymerization features) and can be utilized without limitation to further describe the olefin oligomerization or olefin polymerization process.

In an embodiment, the olefin oligomerization process can comprise: a) forming a composition comprising an $N^2$-phosphinyl amidine compound and a metal salt; b) forming a mixture comprising an olefin and a metal alkyl; c) contacting the composition formed in step a) and the mixture formed in step b); and d) forming an olefin oligomer product. In an embodiment, the olefin polymerization process can comprise: a) forming a mixture comprising an $N^2$-phosphinyl amidine compound and a metal salt; b) forming a mixture comprising an olefin and a metal alkyl; c) contacting the composition formed in step a) and the mixture formed in step b); and d) forming an olefin polymer product. In some embodiments, the mixture comprising an olefin and a metal alkyl can further comprise hydrogen. In some embodiments, the composition of step a) can further comprise a solvent (e.g. a first solvent). In some embodiments, the mixture of step b) can further comprise a solvent (e.g. a second solvent when the catalyst system is prepared in a solvent). In an embodiment, the olefin oligomerization process can comprise: a) forming a composition comprising, or consisting essentially of, an $N^2$-phosphinyl amidine compound, a metal salt, and a first solvent; b) forming a mixture comprising an olefin, a metal alkyl, and a second solvent; c) contacting the composition formed in step a) and the mixture formed in step b); and d) forming an olefin oligomer product. In an embodiment, the olefin polymerization process can comprise: a) forming a composition comprising, or consisting essentially of, an $N^2$-phosphinyl amidine compound, a metal salt, and a first solvent; b) forming a mixture comprising an olefin, a metal alkyl, and a second solvent; c) contacting the composition formed in step a) and the mixture formed in step b); and d) forming an olefin polymer product. In some embodiments, the first and second solvent can be the same; or alternatively, the first and second solvent can be different. The $N^2$-phosphinyl amidine compound, metal salt, metal alkyl, olefin, solvents, and features of the olefin oligomer or olefin polymer product (among other catalyst system and olefin oligomerization or polymerization features) are independently described herein and can be utilized, without limitation to further describe the olefin oligomerization or olefin polymerization process. In some embodiments, the metal alkyl can comprise an aluminoxane. Ratios for the $N^2$-phosphinyl amidine compound to metal salt and ratios for the metal of the metal alkyl to metal of the metal salt are independently provided herein (among other catalyst system and olefin oligomerization or polymerization features) and can be utilized without limitation to further describe the olefin oligomerization or olefin polymerization process.

In an embodiment, a solvent utilized with the catalyst system, a mixture comprising an $N^2$-phosphinyl amidine metal salt complex, a mixture comprising an $N^2$-phosphinyl amidine metal salt complex and a metal alkyl, a composition comprising an $N^2$-phosphinyl amidine compound and a metal salt, or a composition comprising an $N^2$-phosphinyl amidine compound, a metal salt, and a metal alkyl can be a hydrocarbon solvent, a halogenated hydrocarbon solvent, or any combination thereof; alternatively, a hydrocarbon solvent; or alternatively, a halogenated hydrocarbon solvent. In some embodiments, a solvent utilized with a mixture comprising an $N^2$-phosphinyl amidine metal salt complex, a mixture comprising an $N^2$-phosphinyl amidine metal salt complex and a metal alkyl, a composition comprising an $N^2$-phosphinyl amidine compound and a metal salt, or a composition comprising an $N^2$-phosphinyl amidine compound, a metal salt, and a metal alkyl can be an aliphatic hydrocarbon solvent, a halogenated aliphatic hydrocarbon solvent, an aromatic hydrocarbon solvent, a halogenated aromatic solvent, or any combination thereof; alternatively, an aliphatic hydrocarbon solvent, a halogenated aliphatic hydrocarbon solvent, or any combination thereof; alternatively, an aromatic hydrocarbon solvent, a halogenated aromatic solvent, or any combination thereof; alternatively, an aliphatic hydrocarbon solvent; alternatively, a halogenated aliphatic hydrocarbon solvent; alternatively, an aromatic hydrocarbon solvent; or alternatively, a halogenated aromatic solvent. General and specific hydrocarbon solvents, halogenated hydrocarbon solvents, aliphatic hydrocarbon solvents, halogenated aliphatic hydrocarbon solvents, aromatic hydrocarbon solvents, and halogenated aromatic solvents are described herein and can be utilized without limitation to further describe the olefin oligomerization or olefin polymerization process(es) described herein.

In an embodiment, a solvent utilized in any mixture including the olefin or utilized to form the olefin product or polymer product can be hydrocarbon solvent, a halogenated hydrocarbon solvent, or any combination thereof; alternatively, a hydrocarbon solvent; or alternatively, a halogenated hydrocarbon solvent. In some embodiments, a solvent utilized in any mixture including the olefin or utilized to form the olefin product or polymer product can be an aliphatic hydrocarbon solvent, a halogenated aliphatic hydrocarbon solvent, an aromatic hydrocarbon solvent, a halogenated aromatic solvent, or any combination thereof; alternatively, an aliphatic hydrocarbon solvent, a halogenated aliphatic hydrocarbon solvent, or any combination thereof; alternatively, an aromatic hydrocarbon solvent, a halogenated aromatic solvent, or any combination thereof; alternatively, an aliphatic hydrocarbon solvent; alternatively, a halogenated aliphatic hydrocarbon solvent; alternatively, an aromatic hydrocarbon solvent; or alternatively, a halogenated aromatic solvent. General and specific hydrocarbon solvents, halogenated hydrocarbon solvents, aliphatic hydrocarbon solvents, halogenated aliphatic hydrocarbon solvents, aromatic hydrocarbon solvents, and halogenated aromatic solvents are described herein and can be utilized without limitation to further describe the olefin oligomerization or olefin polymerization process described herein.

In some embodiments, the solvent utilized with the catalyst system, a mixture comprising an $N^2$-phosphinyl amidine metal salt complex, a mixture comprising an $N^2$-phosphinyl amidine metal salt complex and a metal alkyl, a composition comprising an $N^2$-phosphinyl amidine compound and a metal salt, or a composition comprising an $N^2$-phosphinyl amidine compound, a metal salt, and a metal alkyl and the solvent utilized in any mixture including the olefin or utilized to form the olefin oligomer product or olefin polymer product can be the same; or alternatively, can be different. In an embodiment, the solvent utilized with the catalyst system, a mixture comprising an $N^2$-phosphinyl amidine metal salt complex, a mixture comprising an $N^2$-phosphinyl amidine metal salt complex and a metal alkyl, a composition comprising an $N^2$-phosphinyl amidine compound and a metal salt, or a composition comprising an $N^2$-phosphinyl amidine compound, a metal salt, and a metal alkyl and the solvent utilized in any mixture including the olefin or utilized to form the olefin product or product has a boiling point which allows for its easy separation (e.g. by distillation) from the olefin oligomer product or olefin polymer product.

Generally, the olefin which can be oligomerized or polymerized can comprise, or consist essentially of, a $C_2$ to $C_{30}$ olefin; alternatively, a $C_2$ to $C_{16}$ olefin; or alternatively, a $C_2$ to $C_{10}$ olefin. In an embodiment, the olefin can be an alpha olefin; alternatively, a linear alpha olefin; or alternatively, a normal alpha olefin. In an embodiment, the olefin can comprise, or consist essentially of, ethylene, propylene, or a combination thereof; alternatively, ethylene; or alternatively, propylene. When the olefin consists essentially of ethylene, the olefin oligomerization process can be an ethylene oligomerization process or an ethylene polymerization process.

In an aspect, the olefin oligomerization process can be an olefin trimerization process; alternatively, an olefin tetramerization process; or alternatively, an olefin trimerization and tetramerization process. When the olefin is ethylene, the olefin oligomerization process can be an ethylene trimerization process; alternatively, an ethylene tetramerization process; or alternatively, an ethylene trimerization and tetramerization process. When the process is an ethylene trimerization process, the olefin product can comprise hexene; or alternatively, can comprise 1-hexene. When the process is an ethylene tetramerization process, the olefin product can comprise octene; or alternatively, can comprise 1-octene. When the process is an ethylene trimerization and tetramerization process, the olefin product can comprise hexene and octene; or can comprise 1-hexene and 1-octene.

Unless otherwise specified, the terms contacted, combined, and "in the presence of" refer to any addition sequence, order, or concentration for contacting or combining two or more components of the oligomerization process. Combining or contacting of oligomerization components, according to the various methods described herein can occur in one or more contact zones under suitable contact conditions such as temperature, pressure, contact time, flow rates, etc. . . . The contact zone can be disposed in a vessel (e.g. a storage tank, tote, container, mixing vessel, reactor, etc.), a length of pipe (e.g. a tee, inlet, injection port, or header for combining component feed lines into a common line), or any other suitable apparatus for bringing the components into contact. The processes can be carried out in a batch or continuous process as is suitable for a given embodiment.

In an embodiment, the olefin oligomerization or olefin polymerization can be a continuous process carried out in one or more reactors. In some embodiments, the continuous olefin oligomerization or olefin polymerization reactor can comprise a loop reactor, a tubular reactor, a continuous stirred tank reactor (CSTR), or combinations thereof. In other embodiments, the continuous olefin oligomerization or olefin polymerization reactor can be a loop reactor; alternatively, a tubular reactor; or alternatively, a continuous stirred tank reactor (CSTR). In other embodiments, the continuous olefin oligomerization or olefin polymerization reactor can be employed in the form of different types of continuous reactors in combination, and in various arrangements.

In an embodiment, the olefin product or polymer product can be formed under suitable oligomerization or polymerization reaction conditions such as reaction temperatures, reaction pressure, and/or reaction times. Reaction temperatures, reaction pressure, and/or reaction times can be impacted by a number of factors such as the metal complex stability, metal complex activity, cocatalyst identity, cocatalyst activity, desired product distribution, and/or desired product purity among other factors.

Generally, the olefin oligomerization or olefin polymerization can be performed using any $N^2$-phosphinyl amidine compound, metal salt, or $N^2$-phosphinyl amidine metal complex concentration that forms the desired olefin product or olefin polymer. In an embodiment, the concentration of the $N^2$-phosphinyl amidine compound, metal salt, or $N^2$-phosphinyl amidine metal complex can be at least $1 \times 10^{-6}$ equivalents/liter; alternatively, at least $1 \times 10^{-5}$ equivalents/liter; or alternatively, at least $5 \times 10^{-4}$ equivalents/liter. In other embodiments, the concentration of the diphosphino aminyl complexed metal compound can range from $1 \times 10^{-6}$ equivalents/liter to 1 equivalents/liter; alternatively, range from $1 \times 10^{-5}$ equivalents/liter to $5 \times 10^{-1}$ equivalents/liter; or alternatively, range from $5 \times 10^4$ equivalents/liter to $1 \times 10^{-1}$ equivalents/liter.

Generally, the olefin oligomerization or olefin polymerization reaction pressure can be any pressure that facilitates the oligomerization or polymerization of the olefin. In an embodiment, the reaction pressure of the olefin oligomerization or olefin polymerization process can be any reaction pressure required to produce the desired olefin product or polymer product. In some embodiments, the olefin oligomerization or olefin polymerization pressure can be greater than or equal to 0 psig (0 KPa); alternatively, greater than or equal to 50 psig (344 KPa); alternatively, greater than or equal to 100 psig (689 KPa); or alternatively, greater than or equal to 150 psig (1.0 MPa). In other embodiments, the olefin oligomerization or olefin polymerization pressure can range from 0 psig (0 KPa) to 5,000 psig (34.5 MPa); alternatively, 50 psig (344 KPa) to 4,000 psig (27.6 MPa); alternatively, 100 psig (689 KPa) to 3,000 psig (20.9 MPa); or alternatively, 150 psig (1.0 MPa) to 2,000 psig (13.8 MPa). In embodiments wherein the monomer is a gas (e.g. ethylene), the olefin oligomerization or olefin polymerization pressure can be carried out under a monomer gas pressure. When the olefin oligomerization or olefin polymerization pressure produces an ethylene oligomer or polyethylene, the reaction pressure can be the monomer ethylene pressure. In some embodiments, the ethylene pressure can be greater than or equal to 0 psig (0 KPa); alternatively, greater than or equal to 50 psig (344 KPa); alternatively, greater than or equal to 100 psig (689 KPa); or alternatively, greater than or equal to 150 psig (1.0 MPa). In other embodiments, the ethylene pressure can range from 0 psig (0 KPa) to 5,000 psig (34.5 MPa); alternatively, 50 psig (344 KPa) to 4,000 psig (27.6 MPa); alternatively, 100 psig (689 KPa) to 3,000 psig (20.9 MPa); or alternatively, 150 psig (1.0 MPa) to 2,000 psig (13.8 MPa). In some cases when ethylene is the monomer, inert gases can form a portion of the total reaction pressure. In the cases where inert gases form a portion of the reaction pressure, the previously stated ethylene pressures can be the applicable ethylene partial pressures of the polymerization or oligomerization reaction. In the situation where the monomer provides all or a portion of the olefin oligomerization or olefin polymerization pressure, the reaction system pressure can decrease as the gaseous monomer is consumed. In this situation, additional gaseous monomer and/or inert gas can be added to maintain a desired olefin oligomerization or olefin polymerization pressure. In some embodiments, additional gaseous monomer can be added to the olefin oligomerization or olefin polymerization pressure at a set rate (e.g. for a continuous flow reactor), or at different rates (e.g. to maintain a set system pressure in a batch reactor). In other embodiments, the olefin oligomerization or olefin polymerization pressure can be allowed to decrease without adding any additional gaseous monomer and/or inert gas.

In embodiments wherein hydrogen is utilized, hydrogen can be added in any amount that produces the desired effect. In some embodiments, the hydrogen partial pressure can be greater than or equal to 1 psig (kPa); alternatively, greater than or equal to 5 psig (34 kPa); alternatively, greater than or equal to 10 psig (69 kPa); or alternatively, greater than or equal to 15 psig (100 kPa). In other embodiments, the hydrogen partial pressure can range from 1 psig (6.9 kPa) to 500 psig (3.5 MPa); alternatively, 5 psig (34 kPa) to 400 psig (2.8 MPa); alternatively, 10 psig (69 kPa) to 300 psig (2.1 MPa); or alternatively, 15 psig (100 kPa) to 200 psig (1.4 MPa).

In an embodiment, a condition to form an olefin product or polymer product can include an oligomerization temperature or polymerization temperature. Generally, the oligomerization temperature or polymerization temperature can be any temperature which forms the desired olefin product or polymer product. In an embodiment, the oligomerization temperature or polymerization temperature can be at least 0° C.; alternatively, at least 10° C.; alternatively, at least 20° C.; or alternatively, at least 30° C. In some embodiments, the oligomerization temperature or polymerization temperature can range from 0° C. to 200° C.; alternatively, range from 10° C. to 160° C.; alternatively, ranges from 20° C. to 140° C.; or alternatively, ranges from 30° C. to 120° C.

In an embodiment, a condition to form an olefin product or polymer product can include an oligomerization time or polymerization time. Generally, the oligomerization time or polymerization time can be any time that produces the desired quantity of olefin product or polymer product; or alternatively, provide a desired catalyst system productivity; or alternatively, provide a desired conversion of monomer. In some embodiments, the oligomerization time or polymerization time can range from 1 minute to 5 hours; alternatively, ranges from 5 minutes to 2.5 hours; alternatively, ranges from 10 minutes to 2 hours; or alternatively, ranges from 15 minutes to 1.5 hours. In an embodiment, the olefin oligomerization can have a single pass olefin conversion of ethylene of at least 30 wt. % percent; alternatively, at least 35 wt. % percent; alternatively, at least 40 wt. % percent; or alternatively, at least 45 wt. % percent. When the olefin is ethylene, the olefin conversion is ethylene conversion.

In an embodiment, the olefin oligomerization process produces an olefin product comprising an olefin trimer, an olefin tetramer, or mixtures thereof. In some embodiments, when the olefin is ethylene the olefin oligomerization is an ethylene oligomerization process. In some embodiments, the olefin oligomerization produces an alpha olefin product having at least four carbon atoms. In an embodiment, the ethylene oligomerization process produces an olefin product comprising an ethylene trimer (e.g. hexene, or alternatively, 1-hexene), an ethylene tetramer (e.g. octene, or alternatively, 1-octene), or a combination thereof; alternatively, hexene; alternatively, octene; alternatively, hexene and octene. In other embodiments, the ethylene oligomerization produces an olefin product comprising 1-hexene, 1-octene, or a combination thereof; alternatively, 1-hexene; alternatively, 1-octene; alternatively, 1-hexene and 1-octene. In an embodiment, when the olefin is ethylene and the process produces an alpha olefin (e.g. 1-hexene, 1-octene, or a combination thereof) the olefin oligomerization process can be an alpha olefin production process.

In an embodiment, the ethylene oligomerization process can produce an olefin product comprising a liquid product comprising at least 60 wt. % $C_6$ and $C_s$ olefins. In some embodiments, the olefin product comprises a liquid product comprising at least 70 wt. % $C_6$ and $C_s$ olefins; alternatively, at least 75 wt. % $C_6$ and $C_s$ olefins; alternatively, at least 80 wt. % $C_6$ and $C_s$ olefins; alternatively, at least 85 wt. % $C_6$ and $C_s$ olefins; or alternatively, at least 90 wt. % $C_6$ and $C_s$ olefins. In other embodiments, the ethylene oligomerization process can produce an olefin product comprising a liquid product having from 60 to 99.9 wt. % of $C_6$ and $C_s$ olefins; alternatively, from 70 to 99.8 wt. % $C_6$ and $C_s$ olefins; alternatively, from 75 to 99.7 wt. % $C_6$ and $C_s$ olefins; or alternatively, from 80 to 99.6 wt. % $C_6$ and $C_s$ olefins. Throughout this application, a liquid product refers to the olefin oligomer product having from 4 to 18 carbon atoms.

In an embodiment, the ethylene oligomerization process can produce an olefin product comprising a liquid product comprising at least 60 wt. % $C_6$ olefins. In some embodiments, the olefin product can comprise a liquid product comprising at least 70 wt. % $C_6$ olefins; alternatively, at least 75 wt. % $C_6$ olefins; alternatively, at least 80 wt. % $C_6$ olefins; alternatively, at least 85 wt. % $C_6$ olefins; or alternatively, at least 90 wt. % $C_6$ olefins. In other embodiments, the ethylene oligomerization process can produce an olefin product comprising a liquid product having from 60 to 99.9 wt. % of $C_6$ olefins; alternatively, from 70 to 99.8 wt. % $C_6$ olefins; alternatively, from 75 to 99.7 wt. % $C_6$ olefins; or alternatively, from 80 to 99.6 wt. % $C_6$ olefins; or alternatively, 85 to 99.6 wt. % $C_6$ olefins.

In an embodiment, the $C_6$ olefin product produced by the ethylene oligomerization process can comprise at least 85 wt. % 1-hexene. In some embodiments, the $C_6$ olefin product produced by the ethylene oligomerization process can comprise at least 87.5 wt. % 1-hexene; alternatively, at least 90 wt % 1-hexene; alternatively, at least 92.5 wt. % 1-hexene; alternatively, at least 95 wt. percent 1-hexene; alternatively, at least 97 weight percent 1-hexene; or alternatively, at least 98 weight percent 1-hexene. In other embodiments, the $C_6$ olefin product produced by the ethylene oligomerization process can comprise from 85 to 99.9 wt % 1-hexene; alternatively, from 87.5 to 99.9 wt % 1-hexene; alternatively, from 90 to 99.9 wt % 1-hexene; alternatively, from 92.5 to 99.9 wt % 1-hexene; alternatively, from 95 to 99.9 wt. % 1-hexene; alternatively, from 97 to 99.9 wt. % 1-hexene; or alternatively, from 98 to 99.9 wt. % 1-hexene.

In an embodiment, the $C_s$ olefin product produced by the ethylene oligomerization process can comprise at least 85 wt. % 1-octene. In some embodiments, the $C_s$ olefin product produced by the ethylene oligomerization process can comprise at least 87.5 wt. % 1-octene; alternatively, at least 90 wt % 1-octene; alternatively, at least 92.5 wt. % 1-octene; alternatively, at least 95 wt. percent 1-octene; alternatively, at least 97 weight percent 1-octene; or alternatively, at least 98 weight percent 1-octene. In other embodiments, the $C_s$ olefin product produced by the ethylene oligomerization process can comprise from 85 to 99.9 wt % 1-octene; alternatively, from 87.5 to 99.9 wt % 1-octene; alternatively, from 90 to 99.9 wt % 1-octene; alternatively, from 92.5 to 99.9 wt % 1-octene; alternatively, from 95 to 99.9 wt. % 1-octene; alternatively, from 97 to 99.9 wt. % 1-octene; or alternatively, from 98 to 99.9 wt. % 1-octene.

It has been discovered that, in some aspects and/or embodiments, aging the catalyst system before contacting the catalyst system with the olefin to be oligomerized and/or polymerized can improve aspects of the olefin oligomerization and/or olefin polymerization process. Firstly, it has been observed that aging the catalyst system can increase the productivity of the catalyst system. Secondly, in olefin oligomerization, it has been observed that aging the catalyst system can decrease the amount of polymer produced in an olefin oligomerization process. In some olefin oligomerization aspects and/or embodiments, aging the catalyst system can increase the productivity of the catalyst system; alternatively, can decrease the amount of polymer produced in the olefin oligomerization; or alternatively, can increase the productivity of the catalyst system and decrease the amount of polymer produced in the olefin oligomerization.

The catalyst system aging impacts can be utilized to provide positive benefits to olefin oligomerization and/or olefin polymerization processes. For example, increasing the activity and/or the productivity of the catalyst system can provide increased olefin oligomer product per unit of catalyst system among other benefits. Additionally, the decrease in polymer produced in an olefin oligomerization upon aging the catalyst system can reduce polymer which could adhere to the oligomerization reactor walls or cooling apparatus. The reduction in polymer produced in the olefin oligomerization process can reduce the need to shut down a reactor to remove the polymer which can cause fouling.

In any aspect or embodiment wherein an $N^2$-phosphinyl amidine compound, a metal salt, and a metal alkyl are contacted prior to contacting the olefin, the mixture comprising the $N^2$-phosphinyl amidine compound, the metal salt, and the metal alkyl can be allowed to age for a period of time prior to contacting the mixture comprising the $N^2$-phosphinyl amidine compound, a metal salt, and a metal alkyl with a mixture comprising the olefin. In some embodiments, a mixture comprising an $N^2$-phosphinyl amidine compound, a metal salt, and a metal alkyl can further comprise a solvent.

In any aspect or embodiment wherein an $N^2$-phosphinyl amidine metal salt complex and a metal alkyl are contacted prior to contacting the olefin, the mixture comprising the $N^2$-phosphinyl amidine metal salt complex and the metal alkyl can be allowed to age for a period of time prior to contacting the mixture comprising the $N^2$-phosphinyl amidine metal salt complex and the metal alkyl with a mixture comprising the olefin. In some embodiments, a mixture comprising an $N^2$-phosphinyl amidine metal salt complex and a metal alkyl can further comprise a solvent.

In a non-limiting embodiment, the olefin oligomerization process can comprise: a) preparing a catalyst system; b) allowing the catalyst system to age for a period of time; c) contacting the aged catalyst system with an olefin; and d) forming an olefin oligomer product. In some non-limiting embodiments, the olefin oligomerization process can comprise, a) preparing a catalyst system; b) allowing the catalyst system to age for a period of time; c) contacting the aged catalyst system with an olefin and hydrogen; and d) forming an olefin oligomer product. The catalyst system, olefin, and other features of the olefin oligomerization and olefin polymer product are independently described herein and can be utilized, without limitation to further describe the olefin oligomerization process. In some embodiments, the catalyst system can be prepared in a first solvent. In an embodiment, the olefin, aged catalyst system, and optionally hydrogen, can be contacted in a second solvent. Generally, a solvent in which the catalyst system can be prepared and the solvent in which the olefin and aged catalyst system can be contacted can be the same; or alternatively, can be different. The catalyst system, features of aging the catalyst system, features of the olefin oligomer, and features of the impacts of aging the catalysts system, among other features, are independently described herein and can be utilized, without limitation to further describe the olefin oligomerization process. In some embodiments, the first and second solvent can be the same; or alternatively, the first and second solvent can be different.

In a non-limiting embodiment, the olefin oligomerization process can comprise: a) forming a catalyst system mixture comprising an $N^2$-phosphinyl amidine metal salt complex and metal alkyl; b) aging the catalyst system mixture; c) contacting the aged catalyst system mixture with an olefin; and c) forming an olefin oligomer product. In another non-limiting embodiment, the olefin oligomerization process can comprise: a) forming a catalyst system mixture comprising an $N^2$-phosphinyl amidine compound, a metal salt, and a metal alkyl; b) aging the catalyst system mixture; c) contacting the aged catalyst system mixture with an olefin; and c) forming an olefin oligomer product. In some embodiments the catalyst system mixture can further comprise a solvent (e.g. a first solvent). In some embodiments, the catalyst system mixture and the olefin can be contacted in a solvent (e.g. a second solvent). In yet another non-limiting embodiment, the olefin oligomerization process can comprise: a) forming a catalyst system mixture comprising (or consisting essentially of) an $N^2$-phosphinyl amidine metal salt complex, a metal alkyl, and a first solvent; b) aging the catalyst system mixture; c) contacting the aged catalyst system mixture with an olefin and a second solvent; and c) forming an olefin oligomer product. In a further non-limiting embodiment, the olefin oligomerization process can comprise: a) forming a catalyst system mixture comprising (or consisting essentially of) an $N^2$-phosphinyl amidine compound, a metal salt, a metal alkyl, and a first solvent; b) aging the catalyst system mixture; c) contacting the aged catalyst system mixture with an olefin and a second solvent; and d) forming an olefin oligomer product.

In some embodiments, the step of contacting the aged catalyst system mixture with the olefin (and optionally a solvent—e.g. second solvent) can be a step of contacting the aged catalyst system mixture with an olefin and hydrogen. The $N^2$-phosphinyl amidine compound, metal salt, the metal salt $N^2$-phosphinyl amidine metal salt complex, the metal alkyl, the olefin, solvents, features of aging the catalyst system, features of the olefin oligomer, and features of the impacts of aging the catalysts system, among other features, are independently described herein and can be utilized, without limitation to further describe the olefin oligomerization. In some embodiments, the first and second solvent can be the same; or alternatively, the first and second solvent can be different. In some embodiments, the metal alkyl can comprise an aluminoxane. Ratios for the $N^2$-phosphinyl amidine compound to metal salt and ratios for the metal of the metal alkyl to metal of the metal salt or the metal of the $N^2$-phosphinyl amidine metal salt complex, among other features, are independently described herein and can be utilized without limitation to further describe the olefin oligomerization or olefin polymerization process.

In an embodiment, the catalyst system can be aged for up 14 days; alternatively, up to 10 days; alternatively, up to 8 days; alternatively, up to 6 days; alternatively, up to 4 days; alternatively, up to 3 days; alternatively, up to 48 hours; alternatively, up to 36 hours; alternatively, up to 24 hours; alternatively, up to 18 hours; alternatively, up to 10 hours; alternatively, up to 8 hours; alternatively, up to 6 hours;

alternatively, up to 4 hours; or alternatively, up to 3 hours. In an embodiment, the catalyst system can be aged for at least 15 minutes; alternatively, at least 20 minutes; or alternatively, at least 30 minutes. In an embodiment, the catalyst system can be aged for a time ranging from any catalyst system aging minimum time disclosed herein to any catalyst system aging maximum time disclosed herein. In some non-limiting embodiments, the catalyst system can be aged for from 15 minutes to 14 days; alternatively, from 15 minutes to 10 days; alternatively, from 15 minutes to 8 days; alternatively, from 15 minutes to 6 days; alternatively, from 20 minutes to 4 days; alternatively, from 20 minutes to 3 days; alternatively, from 30 minutes to 48 hours; alternatively, from 30 minutes to 36 hours; alternatively, from 30 minutes to 24 hours; alternatively, from 30 minutes to 18 hours; alternatively, from 30 minutes to 10 hours; alternatively, from 30 minutes to 8 hours; alternatively, from 30 minutes to 6 hours; alternatively, from 30 minutes to 4 hours; or alternatively, from 30 minutes to 3 hours.

In an embodiment, any catalyst system described herein can be aged at ambient temperature (15° C.-35° C.—no external heat source). In other embodiments, any catalyst system described herein can be aged at a temperature from 25° C. to 100° C.; alternatively, from 30° C. to 80° C.; or alternatively, from 35° C. to 60° C. In some embodiments, any catalyst system described herein can be aged under an inert atmosphere. Generally, one can recognize that the temperature at which the catalyst system is aged can have an impact upon the time necessary to achieve an increase in catalyst system activity and/or reduction in catalyst system polymer production. In any aspect or embodiment, the catalyst system can be aged at a combination of any catalyst system aging time described herein and any aging catalyst system aging temperature described herein.

The catalytic activity of any olefin oligomerization or polymerization catalyst system described herein comprising any $N^2$-phosphinyl amidine metal salt complex or comprising any $N^2$-phosphinyl amidine compound described herein and any metal salt described herein can be defined as the grams of product produced per gram of metal of the metal salt in the $N^2$-phosphinyl amidine metal salt complex utilized and is measured over 30 minutes beginning from when complete catalyst system is contacted with the olefin. In an embodiment, any aged catalyst system described herein (using any aging time period described herein and/or any aging temperature described herein) can increase the olefin oligomerization or olefin polymerization activity of the catalyst system by at least 10%; alternatively, at least 20%; alternatively, at least 30%; alternatively, at least 40%; or alternatively, at least 50%. In some embodiments, any aged catalyst system described herein (using any aging time period described herein and/or any aging temperature described herein) can increase the olefin oligomerization or olefin polymerization activity of the catalyst system from 10 to 1000%; alternatively, from 20 to 800%; alternatively, from 30 to 600%; alternatively, from 40 to 500%; or alternatively, from 50 to 400%. Generally, the increase in the olefin oligomerization or olefin polymerization catalyst system activity as a result of aging the catalyst system is determined by comparing the activity of the aged catalyst system to the activity of a catalyst system that has been aged for less than 12 minutes.

In an embodiment, any aged catalyst system described herein (using any aging time period described herein and/or any aging temperature described herein) can provide a catalyst system which can produce a reduction in the percentage of polymer produced described herein. In some embodiments, aging of any catalyst system described herein can reduce (using any aging time period described herein and/or any aging temperature described herein) the amount of polymer produced in an olefin oligomerization process by at least 5%; alternatively, 7.5%; alternatively, 10%; alternatively, 12.5%; or alternatively, at least 15%. In some embodiments, aging of any catalyst system described herein (for any time period described herein) can reduce the amount of polymer produced in an olefin oligomerization by at least 20%; alternatively, at least 25%; alternatively, at least 30%; or alternatively, at least 35%. Generally, the decrease in the catalyst system polymer production as a result of aging can be determined by comparing the polymer production of the aged catalyst system to the polymer production of a catalyst system that has been aged for less than 12 minutes.

In an embodiment, aging any olefin oligomerization catalyst system described herein can have a combination of any increase in activity described herein and any reduction in the amount of polymer produced described herein.

In an embodiment, a calibration curve can be produced depicting the catalyst system activity and/or polymer production of any aged catalyst system described herein in response to one or more catalyst system aging variables (e.g. time, temperature, or time and temperature). In some embodiments the calibration curve can be depicted graphically as a function of a catalyst system aging variable(s) (e.g. time, temperature, or time and temperature); or alternatively, the calibration curve can be depicted as a predictive equation of a catalyst system aging variable(s) (e.g. time, temperature, or time and temperature). The graphical representation and/or predictive equation relating catalyst system activity and/or polymer production in response catalyst aging can be utilized to adjust one or more user and/or process parameters based upon the interpolation or extrapolation of the graphical representation or predictive equation. It is contemplated that in some aspects, the extent to which the catalyst system activity increases and/or the extent to which there is a decrease in polymer production with respect to catalyst system aging can fall outside the instantly disclosed ranges and can be larger than would be expected based on the presently disclosed values depending on conditions under which the catalyst system is aged. For example, the catalyst system can be subjected to aging for time periods that are longer than those presently recited and/or at temperatures greater than those presently recited. The effects of aging the catalyst system under such conditions can be subject to the herein mentioned analysis to provide predictive information that can lead one to conditions under which catalyst system aging increases the catalyst system activity and/or reduces the polymer production in the olefin oligomerization to within some user and/or process desired range of values. It is contemplated that given the benefits of this disclosure and using routine experimentation one having ordinary skill in the art can modify the methodologies disclosed herein to alter the catalytic system activity of a disclosed catalyst system and/or reduce the amount of polymer produced in an olefin oligomerization process to a desired value or range. Such modifications fall within the scope of this disclosure.

It has also been discovered that when the metal alkyl is an alumoxane (also referred to as an aluminoxane), aging the alumoxane can improve aspects of the olefin oligomerization. For example, it has been observed that aging the alumoxane prior to its contact with the other components of the catalyst system can decrease the amount of polymer produced in the olefin oligomerization process. In some embodiments, any process for preparing the catalyst system described herein and/or any olefin oligomerization process described herein can include a step (or steps) for aging an alumoxane.

In an embodiment, the alumoxane can be aged at ambient temperature (15° C.-35° C.—no external heat source) for at least 2 months; at least 4 months; at least 6 months; or at least 8 months. In some embodiments, the alumoxane can be aged at ambient temperature (15° C.-35° C.—no external heat source) from 2 months to 4 years; from 4 months to 3 years; from 6 months to 2.5 years; or from 8 months to 2 years. In some embodiments, the alumoxane can be aged under an inert atmosphere.

The aging of the alumoxane can be performed at elevated temperature. It has been discovered that the aging of the alumoxane at elevated temperature can reduce the time needed to achieve the benefits observed when the aged alumoxane is utilized in an olefin oligomerization catalyst system. In an embodiment, the alumoxane can be aged at a temperature from 30° C. to 100° C.; from 35° C. to 90° C.; from 40° C. to 80° C.; or 45° C. to 70° C. In an embodiment, the alumoxane can be aged at any elevated temperature disclosed herein for at least 12 hours; at least 18 hours; at least 24 hours; or at least 36 hours. In an embodiment, the alumoxane can be aged at any elevated temperature disclosed herein for up to 1 year; up to 9 months; up to 6 months; or up to 3 months. In some embodiments, the alumoxane can be aged under an inert atmosphere. In an embodiment, the alumoxane can be aged for a time ranging from any alumoxane aging minimum time disclosed herein to any alumoxane aging maximum time disclosed herein. In some embodiments, the alumoxane can be aged at any elevated temperature disclosed herein and any alumoxane aging time disclosed herein.

In an embodiment, any aging of the alumoxane described herein can provide any reduction in the percentage of polymer produced by the olefin oligomerization described herein. In some embodiments, any aging of the alumoxane described herein can reduce the amount of polymer produced in an olefin oligomerization process by at least 20%; at least 40%; at least 60%; at least 70%; at least 75%; at least 80%; or at least 85%.

In an embodiment, a calibration curve can be produced depicting the polymer production of any catalyst system described herein utilizing an aged alumoxane in response to one or more alumoxane aging variables (e.g. time, temperature, or time and temperature). In some embodiments the alumoxane aging calibration curve can be depicted graphically as a function of an alumoxane aging variable(s) (e.g. time, temperature, or time and temperature); alternatively, the calibration curve can be depicted as a predictive equation of an alumoxane aging variable(s) (e.g. time, temperature, or time and temperature). The graphical representation and/or predictive equation relating catalyst system polymer production in response to alumoxane aging can be utilized to adjust one or more user and/or process parameters based upon the interpolation or extrapolation of the graphical representation or predictive equation. It is contemplated that in some aspects, the extent to which the polymer production of the catalyst system decreases with respect to alumoxane aging can fall outside the instantly disclosed ranges and can be larger than would be expected based on the presently disclosed values depending on the conditions under which alumoxane is aged. For example, the catalyst system can be subjected to aging for time periods that are longer than those presently recited and/or at temperatures greater than those presently recited. The effects of alumoxane aging under such conditions can be subject to the herein mentioned analysis to provide predictive information that can lead to conditions under which alumoxane aging can reduce the polymer production of the catalyst system in the olefin oligomerization. It is contemplated that given the benefits of this disclosure and using routine experimentation one having ordinary skill in the art can modify the methodologies disclosed herein to alter a reduction in the amount of polymer produced in an olefin oligomerization. Such modifications fall within the scope of this disclosure.

Within this disclosure, amines can be used to ultimately prepare the $N^2$-phosphinyl amidine compounds and/or the $N^2$-phosphinyl amidine metal salt complexes utilized in various aspects of this disclosure. In various embodiments, amines which can be utilized have Structure A1-A5; alternatively, A1; alternatively, A2; alternatively, A3; alternatively, A4; or alternatively, A5.

$$R^1—NH_2 \quad \text{Structure A1}$$

$$H_2N—L^1—NH_2 \quad \text{Structure A2}$$

$$D^1\text{—}(NH_2)_q \quad \text{Structure A3}$$

$$Q^1—L^3—NH_2 \quad \text{Structure A4}$$

$$R^3—NH_2 \quad \text{Structure A5}$$

$R^1$, $R^3$, $D^1$, $L^1$, $L^3$, $Q^1$, and q within amine Structures A1-A5 are independently described as features of the $N^2$-phosinyl amidine compounds Structures NP1-NP10, NP11, NP13, NP15, NP16, NP18, and/or NP20. Since amines having Structures A1-A4 are ultimately utilized to prepare embodiments of $N^2$-phospinyl amidine compounds having Structures NP1-NP10, NP11, NP13, NP15, NP16, NP18, and/or NP20, the $R^1$, $R^3$, $D^1$, $L^1$, $L^3$, $Q^1$, and q descriptions for the $N^2$-phospinyl amidine compounds can be utilized without limitation to further describe the amine Structures A1-A5.

In an aspect, the amine having Structure A1 or Structure A5 can be methylamine, ethylamine, a propylamine, a butylamine, a pentylamine, a hexylamine, a heptylamine, an octylamine, a nonylamine, a decylamine, a undecylamine, a dodecylamine, a tridecylamine, a tetradecylamine, a pentadecylamine, a hexadecylamine, a heptadecylamine, an octadecylamine, or a nonadecylamine; or alternatively, methylamine, ethylamine, a propylamine, a butylamine, a pentylamine, a hexylamine, a heptylamine, an octylamine, a nonylamine, or a decylamine. In some embodiments, the amine having Structure A1 or Structure A5 can be methylamine, ethylamine, n-propylamine, iso-propylamine, butylamine, iso-butylamine, sec-butylamine, tert-butylamine, n-pentylamine, iso-pentylamine, sec-pentylamine, or neopentylamine; alternatively, methylamine, ethylamine, iso-propylamine, tert-butylamine, or neopentylamine; alternatively, methylamine; alternatively, ethylamine; alternatively, n-propylamine; alternatively, iso-propylamine; alternatively, tert-butylamine; or alternatively, neopentylamine.

In other aspects, the amine having Structure A1 or Structure A5 can be cyclobutylamine, a substituted cyclobutylamine, cyclopentylamine, a substituted cyclopentylamine, cyclohexylamine, a substituted cyclohexylamine, cycloheptylamine, a substituted cycloheptylamine, cyclooctylamine, or a substituted cyclooctylamine. In an embodiment the amine having Structure A1 or Structure A5 can be cyclopentylamine, a substituted cyclopentylamine, cyclohexylamine, or a substituted cyclohexylamine. In other embodiments, the amine having Structure A1 or Structure A5 can be cyclobutylamine or a substituted cyclobutylamine; alternatively, a cyclopentylamine or a substituted cyclopentylamine; alternatively, a cyclohexylamine or a substituted cyclohexylamine;

alternatively, a cycloheptylamine or a substituted cycloheptylamine; or alternatively, a cyclooctylamine, or a substituted cyclooctylamine. In further embodiments, the amine having Structure A1 or Structure A5 can be cyclopentylamine; alternatively, a substituted cyclopentylamine; a cyclohexylamine; or alternatively, a substituted cyclohexylamine. Substituents and substituents patterns for the $R^1$ and $R^3$ cycloalkyl groups are described herein and can be utilized without limitation to further describe the substituted cycloalkylamines which can be utilized as the amine having Structure A1 or Structure A5 in aspects and/or embodiments described herein.

In an aspect, the amine having Structure A1 can have Structure A6. In an aspect, the amine having Structure A5 can have Structure A7.

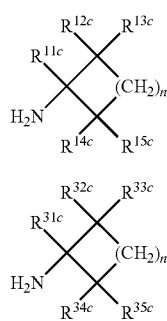

Structure A6

Structure A7

The $R^{11c}$, $R^{12c}$, $R^{13c}$, $R^{14c}$, and $R^{15c}$ substituents, substituent patterns, and n for the $R^1$ group having Structure G1 are described herein and can be utilized without limitation to describe the amine having Structure A6 which can be utilized in the various aspects and embodiments described herein. The $R^{31c}$, $R^{32c}$, $R^{33c}$, $R^{34c}$, and $R^{35c}$ substituents, substituent patterns, and n for the $R^3$ group having Structure G5 are described herein and can be utilized without limitation to describe the amine having Structure A7 which can be utilized in the various aspects and/or embodiments described herein.

In an aspect, the amine having Structure A1 or Structure A5 can be aniline, a substituted aniline, a naphthylamine, or a substituted naphthylamine. In an embodiment, $R^1$ can be aniline or a substituted aniline; alternatively, a naphthylamine or a substituted naphthylamine; alternatively, an aniline or a naphthylamine; or alternatively, a substituted aniline or a substituted naphthylamine. Substituents and substituents patterns for $R^1$ and $R^3$ are described herein and can be utilized without limitation to further describe the substituted anilines and substituted naphthylamines which can be utilized in aspects and/or embodiments described herein.

In an embodiment, the amine having Structure A1 or Structure A5 can be a 2-substituted aniline, a 3-substituted aniline, a 4-substituted aniline, a 2,4-disubstituted aniline, a 2,6-disubstituted aniline, 3,5-disubstituted aniline, or a 2,4,6-trisubstituted aniline. In other embodiments, the $R^1$ substituted aniline can be a 2-substituted aniline, a 4-substituted aniline, a 2,4-disubstituted aniline, or a 2,6-disubstituted aniline; alternatively, a 3-substituted aniline or a 3,5-disubstituted aniline; alternatively, a 2-substituted aniline or a 4-substituted aniline; alternatively, a 2,4-disubstituted aniline or a 2,6-disubstituted aniline; alternatively, a 2-substituted aniline; alternatively, a 3-substituted aniline; alternatively, a 4-substituted aniline; alternatively, a 2,4-disubstituted aniline; alternatively, a 2,6-disubstituted aniline; alternatively, 3,5-disubstituted aniline; or alternatively, a 2,4,6-trisubstituted aniline. Substituents for the $R^1$ and $R^3$ phenyl groups are generally disclosed herein and can be utilized without limitation to further describe the substituted anilines which can be utilized in the various aspects and/or embodiments described herein.

In an embodiment, the amine having Structure A1 or Structure A5 can be 1-naphthylamine, a substituted 1-naphthylamine, 2-naphthylamine, or a substituted 2-naphthylamine. In some embodiments, the amine having Structure A1 or Structure A5 can be 1-naphthylamine or a substituted 1-naphthylamine; alternatively, 2-naphthylamine or a substituted 2-naphthylamine; alternatively, 1-naphthylamine; alternatively, a substituted 1-naphthylamine; alternatively, 2-naphthylamine; or alternatively, a substituted 2-naphthylamine. In other embodiments, the amine having Structure A1 or Structure A4 can be a 2-substituted 1-naphthylamine, a 3-substituted 1-naphthylamine, a 4-substituted 1-naphthylamine, or a 8-substituted 1-naphthylamine; alternatively, a 2-substituted 1-naphthylamine; alternatively, a 3-substituted 1-naphthylamine; alternatively, a 4-substituted 1-naphthylamine; or alternatively, a 8-substituted 1-naphthylamine. In further embodiments, the amine having Structure A1 or Structure A5 can be a 1-substituted 2-naphthylamine, a 3-substituted 2-naphthylamine, or a 4-substituted 2-naphthylamine, or a 1,3-disubstituted 2-naphthylamine; alternatively, a 1-substituted 2-naphthylamine; alternatively, a 3-substituted 2-naphthylamine; alternatively, a 4-substituted 2-naphthylamine; alternatively, or a 1,3-disubstituted 2-naphthylamine. Substituents for the $R^1$ and $R^3$ naphthyl groups are generally disclosed herein and can be utilized without limitation to further describe the substituted naphthylamines which can be utilized in the various aspects and/or embodiments described herein.

In an aspect, the amine having Structure A1 can have Structure A8. In an aspect, the amine having Structure A5 can have Structure A9.

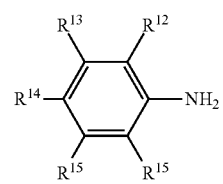

Structure A8

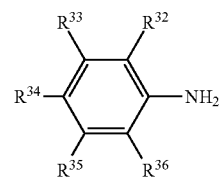

Structure A9

The $R^{12}$, $R^{13}$, $R^{14}$, $R^{15}$, and $R^{16}$ substituents and substituent patterns for the $R^1$ group having Structure G2 are described herein and can be utilized without limitation to describe the amine having Structure A8 which can be utilized in the various aspects and embodiments described herein. The $R^{32}$, $R^{33}$, $R^{34}$, $R^{35}$, and $R^{36}$ substituents and substituent patterns for the $R^3$ group having Structure G6 are described herein and can be utilized without limitation to describe the amine having Structure A9 which can be utilized in the various aspects and/or embodiments described herein.

In an aspect, the amine having Structure A1 or Structure A5 can be an aminopyridine, a substituted aminopyridine, an aminofuran, a substituted aminofuran, an aminothiophene, or a substituted aminothiophene. In an embodiment, the amine having Structure A1 or Structure A5 can be an amino-pyridine or a substituted aminopyridine; alternatively, an aminofuran or a substituted aminofuran; or alternatively, an aminothiophene, or a substituted aminothiophene. In some embodiments, the amine having Structure A1 or Structure A5 can be an aminopyridine, an aminofuran, or an aminothiophene. In other embodiments, the amine having Structure A1 or Structure A5 can be an aminopyridine; alternatively, a substituted aminopyridine; alternatively, an aminofuran; alternatively, a substituted aminofuran; alternatively, an aminothiophene; or alternatively, a substituted aminothiophene.

In an embodiment, the amine having Structure A1 or Structure A5 can be 2-aminopyridine, a substituted 2-aminopyridine, 3-aminopyridine, a substituted 3-aminopyridine, 4-aminopyridine, or a substituted 4-aminopyridine; alternatively, 2-aminopyridine, 3-aminopyridine, or 4-aminopyridine. In some embodiments, the amine having Structure A1 or Structure A5 can be 2-aminopyridine or a substituted 2-aminopyridine; alternatively, 3-aminopyridine or a substituted pyridin-3-yl group; alternatively, 4-aminopyridine or a substituted pyridin-4-yl group; alternatively, 2-aminopyridine; alternatively, a substituted 2-aminopyridine; alternatively, 3-aminopyridine; alternatively, a substituted pyridin-3-yl group; alternatively, 4-aminopyridine; or alternatively, a substituted pyridin-4-yl group. In an embodiment, the amine having Structure A1 or Structure A5 can be a 2-substituted 3-aminopyridine, a 4-substituted 3-aminopyridine, a 5-substituted 3-aminopyridine, a 6-substituted 3-aminopyridine, a 2,4-disubstituted 3-aminopyridine, a 2,6-disubstituted 3-aminopyridine, or a 2,4,6-trisubstituted 3-amino-pyridine; alternatively, 2-substituted 3-aminopyridine, a 4-substituted 3-aminopyridine, a 6-substituted 3-aminopyridine; alternatively, a 2,4-disubstituted 3-aminopyridine or a 2,6-disubstituted 3-aminopyridine; alternatively, a 2-substituted 3-aminopyridine; alternatively, a 4-substituted 3-aminopyridine; alternatively, a 5-substituted 3-aminopyridine; alternatively, a 6-substituted 3-aminopyridine; alternatively, a 2,4-disubstituted 3-aminopyridine; alternatively, a 2,6-disubstituted 3-aminopyridine; or alternatively, a 2,4,6-trisubstituted 3-aminopyridine. In an embodiment, the amine having Structure A1 or Structure A5 can be a 2-substituted 4-aminopyridine, a 3-substituted 4-aminopyridine, a 5-substituted 4-aminopyridine, a 6-substituted 4-aminopyridine, a 2,6-disubstituted 4-aminopyridine, or a 3,5-disubstituted 4-aminopyridine; alternatively, 2-substituted 4-aminopyridine, a 6-substituted 4-amino-pyridine; alternatively, a 3-substituted 4-aminopyridine or a 5-substituted 4-aminopyridine; alternatively, a 2-substituted 4-aminopyridine; alternatively, a 3-substituted 4-aminopyridine; alternatively, a 5-substituted 4-aminopyridine; alternatively, a 6-substituted 4-aminopyridine; alternatively, a 2,6-disubstituted 4-aminopyridine; or alternatively, a 3,5-disubstituted 4-aminopyridine. Substituents for the $R^1$ and $R^3$ pyridinyl groups are generally disclosed herein and can be utilized without limitation to further describe the substituted aminopyridines which can be utilized in the various aspects and/or embodiments described herein.

In an embodiment, the amine having Structure A1 or Structure A5 can be 2-aminofuran, a substituted 2-aminofuran, 3-aminofuran, or a substituted 3-aminofuran; alternatively, fur-2-yl or 3-amino-furan. In some embodiments, the amine having Structure A1 or Structure A5 can be 2-aminofuran or a substituted 2-aminofuran; alternatively, 3-aminofuran, or a substituted 3-aminofuran; alternatively, 2-aminofuran; alternatively, a substituted 2-aminofuran; alternatively, 3-aminofuran; or alternatively, a substituted 3-aminofuran. In an embodiment, the amine having Structure A1 or Structure A5 can be a 2-substituted 3-aminofuran, a 4-substituted 3-aminofuran, or a 2,4-disubstituted 3-aminofuran; alternatively, a 2-substituted 3-aminofuran; alternatively, a 4-substituted 3-aminofuran; or alternatively, a 2,4-disubstituted 3-aminofuran. Substituents for the $R^1$ and $R^3$ furan groups are generally disclosed herein and can be utilized without limitation to further describe the substituted aminofurans which can be utilized in the various aspects and/or embodiments described herein.

In an embodiment, the amine having Structure A1 or Structure A5 can be 2-aminothiophene, a substituted 2-aminothiophene, 3-aminothiophene, or a substituted 3-aminothiophene; alternatively, 2-aminothiophene or 3-aminothiophene. In some embodiments, the amine having Structure A1 or Structure A5 can be 2-aminothiophene or a substituted thien-2-yl group; alternatively, 3-aminothiophene or a substituted thien-3-yl group; alternatively, 2-aminothiophene; alternatively, a substituted thien-2-yl group; alternatively, 3-aminothiophene; or alternatively, a substituted 3-aminothiophene. In an embodiment, the amine having Structure A1 or Structure A5 can be a 2-substituted 3-aminothiophene, a 4-substituted 3-aminothiophene, or a 2,4-disubstituted 3-aminothiophene; alternatively, a 2-substituted 3-amino-thiophene; alternatively, a 4-substituted 3-aminothiophene; or alternatively, a 2,4-disubstituted 3-aminothiophene. Substituents for the $R^1$ and $R^3$ thienyl groups are generally disclosed herein and can be utilized without limitation to further describe the substituted aminothiophenes which can be utilized in the various aspects and/or embodiments described herein.

In a non-limiting embodiment, the amine having Structure A1 or Structure A5 can be aniline, a 2-alkylaniline, a 3-alkylaniline, a 4-alkylaniline, a 2,4-dialkylaniline a 2,6-dialkylaniline, a 3,5-dialkyl-aniline, or a 2,4,6-trialkylaniline; alternatively, a 2-alkylaniline, a 4-alkylaniline, a 2,4-dialkylaniline, a 2,6-dialkylaniline, or a 2,4,6-trialkylaniline; alternatively, a 2-alkylaniline or a 4-alkylaniline; alternatively, a 2,4-dialkylaniline a 2,6-dialkylaniline; alternatively, a 3-alkylaniline or a 3,5-dialkyl-aniline; alternatively, a 2-alkylaniline or a 2,6-dialkylaniline; alternatively, a 2-alkylaniline; alternatively, a 3-alkylaniline; alternatively, a 4-alkylaniline; alternatively, a 2,4-dialkylaniline; alternatively, a 2,6-dialkylaniline; alternatively, a 3,5-dialkylaniline; or alternatively, a 2,4,6-trialkylaniline. In another non-limiting embodiment, the amine having Structure A1 or Structure A5 can be a 1-aminonaphthylene, a 2-aminonaphthylene, a 2-alkylnaphth-1-yl group, a 1-alkyl-2-aminonaphthylene, a 3-alkylnapth-2-yl group, or a 1,3-dialkyl-2-aminonaphthylene; alternatively, a 1-aminonaphthylene or a 2-alkyl-1-amino-naphthylene; alternatively, a 2-aminonaphthylene, a 1-alkyl-2-aminonaphthylene, a 3-alkylamin-napthylene, or a 1,3-dialkyl-2-aminonaphthylene; alternatively, 1-aminonaphthylene; alternatively, a 2-aminonaphthylene; alternatively, a 2-alkyl-1-aminonaphthylene; alternatively, a 1-alkyl-2-amino-naphthylene; alternatively, a 3-alkyl-2-aminonapthylene; or alternatively, a 1,3-dialkyl-2-amino-naphthylene. In other non-limiting embodiments, the amine having Structure A1 or Structure A5 can be a cyclohexylamine, a 2-alkylcyclohexylamine, or a 2,6-dialkylcyclohexylamine; alternatively, cyclopentyl-amine, a 2-alkylcyclopentylamine, or a 2,5-dialkylcyclopentylamine; alternatively, cyclohexylamine; alternatively, a 2-alkylcyclohexylamine; alternatively, a 2,6-dialkylcyclohexylamine; alternatively, cyclopentylamine; alternatively, a 2-alkylcyclopentylamine; or alternatively, 2,5-dialkylcyclopentyl-amine. Alkyl group substituents are independently described herein and can be utilized, without limitation, to further describe the alkylanilines, dialkylanilines, trialkylanilines, alkylaminonaphthylenes, dialkylaminonaphthylenes, alkylcyclohexylamines, dialkylcyclohexylamines, alkylcyclopentylamines, or dialkylcyclopentylamine which can be utilized in the various aspects and/or embodiments described herein. Generally, the alkyl substituents of a dialkyl or trialkyl anilines, aminonaphthylenes, cyclohexylamines, or cyclopentylamines can be the same; or alternatively, can be different.

In another non-limiting embodiment, the amine having Structure A1 or Structure A5 can be aniline, a 2-alkoxyaniline, a 3-alkoxyaniline, a 4-alkoxyaniline, or a 3,5-dialkoxyaniline; alternatively, a 2-alkoxyaniline or a 4-alkoxyaniline; alternatively, a 3-alkoxyaniline or 3,5-dialkoxyaniline; alternatively, a 2-alkoxyaniline; alternatively, a 3-alkoxyaniline; alternatively, a 4-alkoxyaniline; alternatively, a 3,5-dialkoxyaniline. Alkoxy group substituents are independently described herein and can be utilized, without limitation, to further describe the alkoxyanilines or dialkoxyanilines which can be utilized in the various aspects and/or embodiments described herein. Generally, the alkoxy substitutents of a dialkoxyaniline can be the same; or alternatively, can be different.

In other non-limiting embodiments, the amine having Structure A1 or Structure A5 can be aniline, a 2-haloaniline, a 3-haloaniline, a 4-haloaniline, a 2,6-dihalophenyl group, or a 3,5-dialkylaniline; alternatively, a 2-haloaniline, a 4-haloaniline, or a 2,6-dihaloaniline; alternatively, a 2-haloaniline or a 4-haloaniline; alternatively, a 3-haloaniline or a 3,5-dihaloaniline; alternatively, a 2-haloaniline; alternatively, a 3-haloaniline; alternatively, a 4-haloaniline; alternatively, a 2,6-dihaloaniline; or alternatively, a 3,5-dialkylaniline. Halides are independently described herein and can be utilized, without limitation, to further describe the haloanilines or dihaloanilines which can be utilized in the various aspects and/or embodiments described herein. Generally, the halides of a dihaloaniline can be the same; or alternatively, can be different.

In a non-limiting embodiment, the amine having Structure A1 or Structure A5 can be 2-methylaniline, 2-ethylaniline, 2-n-propylaniline, 2-isopropylaniline, 2-tert-butylaniline, 3-methylaniline, 2,6-dimethylaniline, 2,6-diethylaniline, 2,6-di-n-propylaniline, 2,6-diisopropylaniline, 2,6-di-tert-butylaniline, 2-isopropyl-6-methylaniline, or 2,4,6-trimethylaniline; alternatively, 2-methylaniline, 2-ethylaniline, 2-n-propylaniline, 2-isopropylaniline, or 2-tert-butylaniline; alternatively, 2,6-dimethyl-aniline, 2,6-diethylaniline, 2,6-di-n-propylaniline, 2,6-diisopropylaniline, 2,6-di-tert-butylaniline, or 2-isopropyl-6-methylaniline; alternatively, 2-methylaniline; alternatively, 2-ethylaniline; alternatively, 2-n-propylaniline; alternatively, 2-isopropylaniline; alternatively, 2-tert-butylaniline; alternatively, 3-methyl-aniline; alternatively, 2,6-dimethylaniline; alternatively, 2,6-diethylaniline; alternatively, 2,6-di-n-propylaniline; alternatively, 2,6-diisopropylaniline; alternatively, 2,6-di-tert-butylaniline; alternatively, 2-isopropyl-6-methylaniline; alternatively, 3,5-dimethylaniline; or alternatively, 2,4,6-trimethylaniline. In another non-limiting embodiment, the amine having Structure A1 or Structure A5 can be 2-methyl-cyclohexylamine, 2-ethylcyclohexylamine, 2-isopropylcyclohexylamine, 2-tert-butylcyclohexylamine, 2,6-dimethylcyclohexylamine, 2,6-diethylcyclohexylamine, 2,6-diisopropylcyclohexylamine, or 2,6-di-tert-butylcyclohexylamine; alternatively, 2-methylcyclohexylamine, 2-ethylcyclohexylamine, 2-isopropylcyclohexylamine, or 2-tert-butylcyclohexylamine; alternatively, 2,6-dimethylcyclohexylamine, 2,6-diethylcyclohexylamine, 2,6-diisopropylcyclohexylamine, or 2,6-di-tert-butylcyclohexylamine; alternatively, 2-methylcyclohexylamine; alternatively, 2-ethylcyclohexylamine; alternatively, 2-isopropylcyclohexylamine; alternatively, 2-tert-butylcyclohexylamine; alternatively, 2,6-dimethyl-cyclohexylamine; alternatively, 2,6-diethylcyclohexylamine; alternatively, 2,6-diisopropylcyclohexyl-amine; or alternatively, or 2,6-di-tert-butylcyclohexylamine. In another non-limiting embodiment, the amine having Structure A1 or Structure A5 can be 2-methyl-1-aminonaphthylene, 2-ethyl-1-amino-naphthylene group, 2-n-propyl-1-aminonaphthylene, 2-isopropyl-1-aminoenaphthylene group, or 2-tert-butyl-1-aminonaphthylene group; alternatively, 2-methyl-1-aminonaphthylene group; alternatively, 2-ethyl-1-aminonaphthylene group; alternatively, 2-n-propyl-1-aminonaphthylene group; alternatively, 2-isopropyl-1-naphthylene group; or alternatively, 2-tert-butyl-1-amononaphthylene group.

In a non-limiting embodiment, the amine having Structure A1 or Structure A5 can be a 3-methoxyaniline, 3-ethoxyaniline, 3-isoprooxyaniline, 3-tert-butoxyaniline, 4-methoxyaniline, 4-ethoxyaniline, 4-isopropoxyaniline, 4-tert-butoxyaniline, 3,5-dimethoxyaniline, 3,5-diethoxyaniline, 3,5-diisopropoxyaniline, or 3,5-di-tert-butoxyaniline; alternatively, 3-methoxyaniline, 3-ethoxyaniline, 3-isopropoxyaniline, or 3-tert-butoxyaniline; alternatively, 4-methoxyaniline, 4-ethoxyaniline, 4-isopropoxyaniline, or 4-tert-butoxyaniline; or alternatively, 3,5-dimethoxyaniline, 3,5-diethoxyaniline, 3,5-diisopropoxyaniline, or 3,5-di-tert-butoxyaniline. In other non-limiting embodiments, the amine having Structure A1 or Structure A5 can be 3-methoxyaniline; alternatively, 3-ethoxyaniline; alternatively, 3-isopropoxyaniline; alternatively, 3-tert-butoxyaniline; alternatively, 4-methoxyaniline; alternatively, 4-ethoxyaniline; alternatively, 4-isopropoxyaniline; alternatively, 4-tert-butoxyaniline; alternatively, 3,5-dimethoxyaniline; alternatively, 3,5-diethoxyaniline; alternatively, 3,5-diisopropoxyaniline; or alternatively, 3,5-di-tert-butoxyaniline.

In an aspect, the amine having Structure A1 can be a hydrocarbyl hydrazine or an N,N-dihydrocarbyl hydrazine; alternatively, a hydrocarbyl hydrazine; or alternatively, an N,N-dihydrocarbyl hydrazine. Hydrocarbyl groups for $R^1$, hydrocarbylaminyl groups and dihydrocarbylaminyl groups have been described herein and these can be utilized, without limitation to further describe the N-hydrocarbyl hydrazines and N,N-dihydrocarbyl hydrazines which can be utilized as the amine having Structure A1 in the various aspects and/or embodiments described herein. In some non-limiting embodiments, the amine having Structure A1 can be methyl hydrazine, ethyl hydrazine, ispropyl hydrazine, tert-butyl hydrazine, neopentyl hydrazine, N,N-dimethyl hydrazine, N,N-diethyl hydrazine, N,N-diispropyl hydrazine, N,N-di-tert-butyl hydrazine, or N,N-dineopentyl hydrazine; alternatively, methyl hydrazine, ethyl hydrazine, ispropyl hydrazine, tert-butyl hydrazine, or neopentyl hydrazine; alternatively, N,N-dimethyl hydrazine, N,N-diethyl hydrazine, N,N-diispropyl hydrazine, N,N-ditert-butyl hydrazine, or N,N-dineopentyl hydrazine; alternatively, methyl hydrazine; alternatively, ethyl hydrazine; alternatively, isopropyl hydrazine; alternatively, tert-butyl hydrazine; alternatively, neopentyl hydrazine; alternatively, dimethyl hydrazine; alternatively, N,N-diethyl hydrazine; alternatively, N,N-diisopropyl hydrazine; alternatively, N,N-ditert-butyl hydrazine; or alternatively, N,N-dineopentyl hydrazine. In other non-limiting embodiments, the amine having Structure A1 can be cyclopentylhydrazine, cyclohexylhydrazine, N,N-dicyclopentylhydrazine, N,N-dicyclohexylhydrazine; alternatively, cyclopentylhydrazine or cyclohexylhydrazine; alternatively, N,N-dicyclopentylhydrazine or N,N-dicyclohexylhydrazine;

alternatively, cyclopentylhydrazine; alternatively, cyclohexylhydrazine; alternatively, N,N-dicyclopentylhydrazine; or alternatively, N,N-dicyclohexylhydrazine. In other non-limiting embodiments, the amine having Structure A1 can be phenylhydrazine, a substituted phenyl phenylhydrazine, N,N-diphenylhydrazine, or a substituted phenyl N,N-diphenylhydrazine; alternatively, phenylhydrazine, or a substituted phenyl phenylhydrazine; alternatively, N,N-diphenylhydrazine or a substituted phenyl N,N-diphenylhydrazine; alternatively, phenylhydrazine or N,N-diphenylhydrazine; alternatively, phenylhydrazine; alternatively, a substituted phenyl phenylhydrazine; alternatively, N,N-diphenylhydrazine; or alternatively, a substituted phenyl N,N-diphenylhydrazine. Substituents and substituent patterns for substituted phenylaminyl groups and diphenylaminyl groups are generally disclosed herein and can be utilized without limitation to further describe the substituted phenyl phenylhydrazines and substituted phenyl N,N-diphenylhydrazines which can be utilized as the amine having Structure A1 in the various aspects and/or embodiments described herein.

In an aspect, the amine having Structure A1 can be a 1-aminylcycloamine or a cycloamine substituted 1-aminylcycloamine; alternatively, a 1-aminylcycloamine; or alternatively, a cycloamine substituted 1-aminylcycloamine. Cycloaminyl groups and substituted cycloaminyl groups have been described herein and these can be utilized, without limitation to further describe the N,N-dihydrocarbyl hydrazine which can be utilized as the amine having Structures A2 in the various aspects and/or embodiments described herein. In some non-limiting embodiments, the amine having Structure A1 can be 1-aminopyrrolidine, a substituted pyrrolidine 1-aminopyrrolidine, 1-aminopiperidine, or a substituted piperidine 1-aminopiperidine; alternatively, 1-aminopyrrolidine or a substituted pyrrolidine 1-aminopyrrolidine; alternatively, 1-aminopiperidine or a substituted piperidine 1-aminopiperidine; alternatively, 1-aminopyrrolidine; alternatively, a substituted pyrrolidine 1-aminopyrrolidine; alternatively, 1-aminopiperidine; or alternatively, a substituted piperidine 1-aminopiperidine. Substituents and substituent patterns for substituted cycloaminyl groups are generally disclosed herein and can be utilized without limitation to further describe the cycloaminyl substituted 1-aminocycloamines which can be utilized as the amine having Structure A1 in the various aspects and/or embodiments described herein.

In an aspect, $L^1$ of the amine having Structure A2 can be any $L^1$ described herein. $L^1$ is described herein as a feature of the $N^2$-phosphinyl amidine metal salt complexes utilized in various aspects of this disclosure. Since the amines having structure A2 can be utilized to prepare embodiments of the $N^2$-phospinyl amidine compounds having Structure NP2 or Structure NP7, the aspect and embodiments of $L^1$ can utilized without limitation to further describe the amines having Structures A2.

In an aspect, the amine having Structure A2 can be a diaminomethane, a diaminoethane, a diaminopropane, a diaminobutane, a diaminopentane, a diaminohexane, a diaminoheptane, a diamino-octane, a diaminononane, a diaminodecane, a diaminoundecane, a diaminododecane, a diaminotridecane, a diaminotetradecane, a diaminopentadecane, a diaminohexadecane, a diaminoheptadecane, a diamino-octadecane, or a diaminononadecane; or alternatively, a diaminomethane, a diaminoethane, a diamino-propane, a diaminobutane, a diaminopentane, a diaminohexane, a diaminoheptane, a diaminooctane, a diaminononane, or a diaminodecane. In some embodiments, the amine having Structure A2 can be a diaminomethane, a diaminoethane, a diaminopropane, a diaminobutane, or a diaminopentane. In other embodiments, the amine having Structure A2 can be a diaminomethane; alternatively, a diaminoethane; alternatively, a diaminopropane; alternatively, a diaminobutane; alternatively, a diaminopentane; alternatively, a diaminohexane; alternatively, a diaminoheptane; alternatively, a diaminooctane; alternatively, a diaminononane; alternatively, a diaminodecane; alternatively, a diaminoundecane; alternatively, a diaminododecane; alternatively, a diaminotridecane; alternatively, a diaminotetradecane; alternatively, a diaminopentadecane; alternatively, a diaminohexadecane; alternatively, a diamino-heptadecane; alternatively, a diaminooctadecane; or alternatively, a diaminononadecane. In some embodiments, the amine having Structure A2 can be 1,2-diaminoethane, 1,3-diaminopropane, 1,4-diaminobutane, 2,3-diaminobutane, 1,5-diaminopentane, 1,3-diamino-2,2-dimethylpropane, 1,6-diaminohexane, or 2,3-diamino-2,3-dimethylbutane; alternatively, 1,2-diaminoethane, 1,3-diamino-propane, 1,4-diaminobutane, 1,5-diaminopentane, or 1,6-diaminohexane; alternatively, 1,2-diaminoethane; alternatively, 1,3-diaminopropane; alternatively, 1,4-diaminobutane; alternatively, 2,3-diaminobutane; alternatively, 1,5-diaminopentane; alternatively, 1,3-diamino-2,2-dimethylpropane; alternatively, 1,6-diaminohexane; or alternatively, 2,3-diamino-2,3-dimethylbutane.

In an aspect, the amine having Structure A2 can have the formula $H_2N$—$CR^{1a}R^{2a}(CH_2)_tCR^{3a}R^{4a}$—$C\equiv NH_2$. $R^{1a}$, $R^{2a}$, $R^{3a}$, $R^{4a}$, and t are described herein as embodiments of an $L^1$ group having structure —$CR^{1a}R^{2a}(CH_2)_tCR^{3a}R^{4a}$—. The descriptions of $R^{1a}$, $R^{2a}$, $R^{3a}$, $R^{4a}$, and t can be utilized without limitation to further describe the amines having the formula $H_2N$—$CR^{1a}R^{2a}(CH_2)_tCR^{3a}R^{4a}$—$NH_2$ which can be utilized in the various aspects and/or embodiments described herein.

In an embodiment, the amine having Structure A2 can be a diaminocyclobutane, a substituted diaminocyclobutane, a diaminocyclopentane, a substituted diaminocyclopentane, a diaminocyclohexane, a substituted diaminocyclohexane, a diaminocycloheptane, a substituted diaminocycloheptane, a diaminocyclooctane, or a substituted diaminocyclooctane. In some embodiments, the amine having Structure A2 can be a diaminocyclopentane, a substituted diaminocyclopentane, a diaminocyclohexane, a substituted diaminocyclohexane. In other embodiments, the amine having Structure A2 can be a diaminocyclobutane or a substituted diaminocyclobutane; alternatively, a diaminocyclopentane or a substituted diaminocyclopentane; alternatively, a diaminocyclohexane or a substituted diamino-cyclohexane; alternatively, a diaminocycloheptane or a substituted diaminocycloheptane; or alternatively, a diaminocyclooctane, or a substituted diaminocyclooctane. In further embodiments, the amine having Structure A2 can be a diaminocyclopentane; alternatively, a substituted diaminocyclopentane; a diaminocyclohexane; or alternatively, a substituted diaminocyclohexane.

In an embodiment, the amine having Structure A2 can be 1,3-diaminocyclopentane, a substituted 1,3-diaminocyclopentane, 1,3-diaminocyclohexane, a substituted 1,3-diaminocyclohexane, 1,4-diaminocyclohexane, or a substituted 1,4-diaminocyclohexane; alternatively, 1,3-diamino-cyclopentane, 1,3-diaminocyclohexane, or 1,4-diaminocyclohexane. In some embodiments, the amine having Structure A2 can be 1,3-diaminocyclopentane or a substituted 1,3-diaminocyclopentane; alternatively, 1,3-diaminocyclohexane, a substituted 1,3-diaminocyclohexane, 1,3-diaminocyclohexane, or a substituted 1,4-diaminocyclohexane; alternatively, 1,3-diaminocyclohexane or a substituted 1,3-diaminocyclohexane; alternatively, 1,4-diaminocyclohexane or a substituted 1,4-diaminocyclohexane; alternatively, 1,3-cyclopentane; alternatively, 1,3-diaminocyclohexane; or alternatively, 1,4-diaminocyclohexane.

In a non-limiting embodiment, the amine having Structure A2 can be a 2-disubstituted 1,3-diaminocyclopenane group, a 4,5-disubstituted 1,3-diaminocyclopenane group, a 2,5-disubstituted 1,3-diaminocyclopenane group, or a 2,4,5-trisubstituted 1,3-diaminocyclopenane group. In some embodiments, the amine having Structure A2 can be a 2-disubstituted 1,3-diaminocyclopenane group; alternatively, a 4,5-disubstituted 1,3-diaminocyclopenane group; alternatively, a 2,5-disubstituted 1,3-diaminocyclopenane group; alternatively, or a 2,4,5-trisubstituted 1,3-diaminocyclopenane group. In another non-limiting embodiment, the amine having Structure A2 can be a 2,6-disubstituted 1,4-diamino-cyclohexane group, a 2,3-disubstituted 1,4-diaminocyclohexane group, a 2,5-disubstituted 1,4-diamino-cyclohexane group, or a 2,3,5,6-tetrasubstituted 1,4-diaminocyclohexane group. In some embodiments, the amine having Structure A2 can be a 2,6-disubstituted 1,4-diaminocyclohexane group or a 2,5-disubstituted 1,4-diaminocyclohexane group; alternatively, a 2,6-disubstituted 1,4-diaminocyclohexane group; alternatively, a 2,3-disubstituted 1,4-diaminocyclohexane group; alternatively, a 2,5-disubstituted 1,4-diaminocyclohexane group; or alternatively, a 2,3,5,6-tetrasubstituted 1,4-diaminocyclohexane group.

$L^1$ substituents and substituent patterns for substituted $L^1$ cycloalkane groups are generally disclosed herein and can be utilized without limitation to further describe the substituted diamino-cycloalkanes which can be utilized as the amine having Structure A2 in the various aspects and/or embodiments described herein.

In an aspect, the amine having Structure A2 can be a bi(aminocyclyl), a substituted bi(amino-cyclyl), a bis(aminocyclyl)methane, a substituted bis(aminocyclyl)methane, a bis(aminocyclyl)ethane, or a substituted bis(aminocyclyl)ethane; or alternatively, a bis(aminocyclyl), a bis(aminocyclyl)methane, or a bis(aminocyclyl)ethane. In an embodiment, the amine having Structure A2 can be a bi(aminocyclyl) or a substituted bi(aminocyclyl); alternatively, a bis(aminocyclyl)methane or a substituted bis(aminocyclyl)-methane; or alternatively, a bis(aminocyclyl)ethane or a substituted bis(aminocyclyl)ethane. In some embodiments, the amine having Structure A2 can be a bi(aminocyclyl); alternatively, a substituted bi(aminocyclyl); alternatively, a bis(aminocyclyl) methane; alternatively, a substituted bis(aminocyclyl)-methane; alternatively, a bis(aminocyclyl)ethane; or alternatively, a substituted bis(aminocylyl)ethane. In an aspect, the amine having Structure A2 can be a bi(aminocyclohexyl), a substituted bi(amino-cyclohexyl), a bis(aminocyclohexyl)methane, a substituted bis(aminocyclohexyl)methane, a bis(amino-cyclohexyl)ethane, or a substituted bis(aminocyclohexyl)ethane; or alternatively, a bi(aminocyclohexyl), a bis(aminocyclohexyl)methane, or a bis(aminocyclohexyl)ethane. In an embodiment, the amine having Structure A2 can be a bi(aminocyclohexyl) or a substituted bi(aminocyclohexyl); alternatively, a bis(aminocyclohexyl)methane or a substituted bis(aminocyclohexyl)methane; or alternatively, a bis(aminocyclohexyl)ethane or a substituted bis(aminocyclohexyl)ethane. In some embodiments, the amine having Structure A2 can be a bi(aminocyclohexyl); alternatively, a substituted bi(amino-cyclohexyl); alternatively, a bis(aminocyclohexyl)methane; alternatively, a substituted bis(amino-cyclohexyl)methane; alternatively, a bis(aminocyclohexyl)ethane; or alternatively, a substituted bis(aminocyclohexyl)ethane. $L^1$ substituents and substituent patterns for substituted $L^1$ bicyclylene groups, bis(cyclylene) methane groups, and bis(cyclylene)ethane groups are generally disclosed herein and can be utilized without limitation to further describe the substituted bi(aminocyclyl)s, substituted bis(aminocyclyl)methanes, and substituted bis(aminocyclyl) ethanes which can be utilized as the amine having structure A2 in the various aspects and/or embodiments described herein.

In an embodiment, the amine having Structure A2 can be a 4,4'-bicyclohexyldiamine, a 3,3'-disubstituted-4,4'-bicyclohexyldiamine, a 3,3',5,5'-tetrasubstituted-4,4'-bicyclohexyldiamine, bis(4-aminocyclohexyl)methane, a bis(3-substituted-4-aminocyclohexyl)methane, a bis(3,5-disubstituted-4-aminocyclohexyl)methane, bis-1,2-(4-aminocyclohexyl) ethane, a bis-1,2-(3-substituted-4-amino-cyclohexyl)ethane, or a bis-1,2-(3,5-disubstituted-4-aminocyclohexyl)ethane. In some embodiments, the amine having Structure A2 can be a 4,4'-bicyclohexyldiamine, a 3,3'-disubstituted-4,4'-bicyclohexyl-diamine, a 3,3',5,5'-tetrasubstituted-4,4'-bicyclohexyldiamine; alternatively, a bis(4-aminocyclohexyl)-methane, a bis(3-substituted-4-aminocyclohexyl)methane or a bis(3,5-disubstituted-4-aminocyclohexyl)-methane; alternatively, a bis-1,2-(4-aminocyclohexyl)ethane, a bis-1,2-(3-substituted-4-amino-cyclohexyl)ethane or a bis-1,2-(3,5-disubstituted-4-aminocyclohexyl)ethane. In other embodiments, the amine having Structure A2 can be a 4,4'-bicyclohexyldiamine; alternatively, a 3,3'-disubstituted-4,4'-bicyclohexyldiamine; alternatively, a 3,3',5,5'-tetrasubstituted-4,4'-bicyclohexyldiamine; alternatively, a bis(4-aminocyclohexyl)methane; alternatively, a bis(3-substituted-4-aminocyclohexyl)methane; alternatively, a bis(3,5-disubstituted-4-aminocyclohexyl)methane; alternatively, a bis-1,2-(4-amino-cyclohexyl)ethane; alternatively, a bis-1,2-(3-substituted-4-aminocyclohexyl)ethane; or alternatively, a bis-1,2-(3,5-disubstituted-4-aminocyclohexyl)ethane. Generally, any bis (aminocyclohexyl)ethane disclosed herein (substituted or unsubstituted) can be a bis-1,1-(aminocyclohexyl)ethane or a bis-1,2-(aminocyclohexyl)ethane group; alternatively, a bis-1,1-(aminocyclohexyl)ethane; or alternatively, a bis-1,2-(aminocyclohexyl)ethane. Substituents for the substituted $L^1$ bicyclohex-4,4'-ylene groups, bis(cyclohex-4-ylene)methane groups, and a bis-1,2-(cyclohex-4-ylene)ethane groups are generally disclosed herein and can be utilized without limitation to further describe the substituted 4,4'-bicyclohexyldiamines, substituted bis(4-aminocyclohexyl)methanes, and substituted bis-1,2-(4-amino-cyclohexyl)ethanes which can be utilized as the amine having structure A2 in the various aspects and/or embodiments described herein.

In an aspect, the amine having Structure A2 can be a diaminobenzene or a substituted diaminobenzene. In an embodiment, the amine having Structure A2 can be a diaminobenzene; or alternatively, a substituted diaminobenzene. In some embodiments, the amine having Structure A2 can be 1,2-diaminobenzene or a substituted 1,2-diaminobenzene; alternatively, a 1,2-diaminobenzene; or alternatively, a substituted 1,2-diaminobenzene. In other embodiments, the amine having Structure A2 can be a 1,3-diaminobenzene or a substituted 1,3-diaminobenzene; alternatively, a 1,3-diaminobenzene; or alternatively, a substituted 1,3-diaminobenzene. In yet other embodiments, the amine having Structure A2 can be a 1,4-diaminobenzene or a substituted 1,4-diaminobenzene; alternatively, a 1,4-diamino-benzene; or alternatively, a substituted 1,4-diaminobenzene. In further embodiments, the amine having Structure A2 can be a 1,2-diaminobenzene, a 1,3-diaminobenzene, or a 1,4-diaminobenzene; alternatively, a 1,3-diaminobenzene, or a 1,4-diaminobenzene. In other embodiments, the amine having Structure A2 can be a substituted 1,2-diaminobenzene, a substituted 1,3-diaminobenzene, or a substituted 1,4-diaminobenzene; alternatively, a substituted 1,3-diaminobenzene, or a substituted 1,4-diamino-benzene. In a non-limiting embodiment, the amine having Structure A2 can be a 2,6-disubstituted 1,4-diaminobenzene, a 2,3-disubstituted 1,4-diaminobenzene, a 2,5-disubstituted 1,4-diaminobenzene, or a 2,3,5,6-tetrasubstituted 1,4-diaminobenzene. In some embodiments, the amine having Structure A2 can be a 2,6-disubstituted 1,4-diaminobenzene or a 2,5-disubstituted 1,4-diaminobenzene; alternatively, a 2,6-disubstituted 1,4-diaminobenzene; alternatively, a 2,3-disubstituted 1,4-diaminobenzene; alternatively, a 2,5-disubstituted 1,4-diaminobenzene; or alternatively, a 2,3,5,6-tetrasubstituted 1,4-diaminobenzene. $L^1$ substituents and substituent patterns for substituted $L^1$ phenylene groups are generally disclosed herein and can be utilized without limitation to further describe the substituted diaminobenzenes which can be utilized as the amine having structure A2 in the various aspects and/or embodiments described herein.

In an aspect, the amine having Structure A2 can be a diaminonaphthalene or a substituted diaminonaphthalene. In an embodiment, the amine having Structure A2 can be a diaminonaphthalene; or alternatively, a substituted diaminonaphthalene. In some embodiments, the amine having Structure A2 can be 1,3-diaminonaphthalene, a substituted 1,3-diaminonaphthalene, 1,4-diaminonaphthalene, a substituted 1,4-diaminonaphthalene, 1,5-diaminonaphthalene, a substituted 1,5-diaminonaphthalene, 1,6-diaminonaphthalene, a substituted 1,6-diaminonaphthalene, 1,7-diaminonaphthalene, a substituted 1,7-diaminonaphthalene, 1,8-diaminonaphthalene, or a substituted 1,8-diaminonaphthalene. In other embodiments, the amine having Structure A2 can be 1,3-diaminonaphthalene or a substituted 1,3-diaminonaphthalene; alternatively, 1,4-diaminonaphthalene or a substituted 1,4-diaminonaphthalene; alternatively, 1,5-diaminonaphthalene or a substituted 1,5-diaminonaphthalene; alternatively, 1,6-diaminonaphthalene or a substituted 1,6-diaminonaphthalene; alternatively, 1,7-diaminonaphthalene or a substituted 1,7-diaminonaphthalene; or alternatively, 1,8-diaminonaphthalene or a substituted 1,8-diaminonaphthalene. In yet other embodiments, the amine having Structure A2 can be 1,3-diamino-naphthalene; alternatively, a substituted 1,3-diaminonaphthalene; alternatively, 1,4-diaminonaphthalene; alternatively, a substituted 1,4-diaminonaphthalene; alternatively, 1,5-diaminonaphthalene; alternatively, a substituted 1,5-diaminonaphthalene; alternatively, 1,6-diaminonaphthalene; alternatively, a substituted 1,6-diaminonaphthalene; alternatively, 1,7-diaminonaphthalene; alternatively, a substituted 1,7-diamino-naphthalene; alternatively, 1,8-diaminonaphthalene; or alternatively, a substituted 1,8-diamino-naphthalene. $L^1$ substituents and substituent patterns for substituted $L^1$ naphthylene groups are generally disclosed herein and can be utilized without limitation to further describe the substituted diamino-naphthalenes which can be utilized as the amine having structure A2 in the various aspects and/or embodiments described herein.

In an aspect, the amine having Structure A2 can be a bianiline, a substituted bianiline, a bis(aminophenyl)methane group, a substituted bis(aminophenyl)methane group, a bis(aminophenyl)-ethane group, or a substituted bis(aminophenyl)ethane group; or alternatively, a bianiline, a bis(aminophenyl)methane group, or a bis(aminophenyl)ethane group. In an embodiment, the amine having Structure A2 can be a bianiline or a substituted bianiline; alternatively, a bis(aminophenyl)-methane group or a substituted bis(aminophenyl)-methane group; or alternatively, a bis(aminophenyl)-ethane group or a substituted bis(aminophenyl)ethane group. In some embodiments, the amine having Structure A2 can be a bianiline; alternatively, a substituted bianiline; alternatively, a bis(aminophenyl)-methane group; alternatively, a substituted bis(aminophenyl)methane group; alternatively, a bis(amino-phenyl)ethane group; or alternatively, a substituted bis(aminophenyl)ethane group.

In an embodiment, the amine having Structure A2 can be 2,2'-bianiline, a substituted 2,2'-bianiline, 3,3'-bianiline, a substituted 3,3'-bianiline, 4,4'-bianiline, or a substituted 4,4'-bianiline; or alternatively, 3,3'-bianiline, a substituted 3,3'-bianiline, 4,4'-bianiline, or a substituted 4,4'-bianiline. In some embodiments, the amine having Structure A2 can be 2,2'-bianiline or a substituted 2,2'-bianiline; alternatively, 3,3'-bianiline or a substituted 3,3'-bianiline; or alternatively, 4,4'-bianiline or a substituted 4,4'-bianiline. In other embodiments, the amine having Structure A2 can be 2,2'-bianiline; alternatively, a substituted 2,2'-bianiline; alternatively, 3,3'-bianiline; alternatively, a substituted 3,3'-bianiline; alternatively, 4,4'-bianiline; or alternatively, a substituted 4,4'-bianiline.

In an embodiment, the amine having Structure A2 can be bis(2-aminophenyl)methane, a substituted bis(2-aminophenyl)methane, bis(3-aminophenyl)methane, a substituted bis(3-aminophenyl)-methane, bis(4-aminophenyl)methane, or a substituted bis(4-aminophenyl)methane; or alternatively, bis(3-aminophenyl)methane, a substituted bis(3-aminophenyl)methane, bis(4-aminophenyl)methane, or a substituted bis(4-aminophenyl)methane. In some embodiments, the amine having Structure A2 can be bis(2-aminophenyl)methane or a substituted bis(2-aminophenyl)methane; alternatively, bis(3-amino-phenyl)methane or a substituted bis(3-aminophenyl)methane; or alternatively, bis(4-aminophenyl)-methane or a substituted bis(4-aminophenyl)methane. In other embodiments, the amine having Structure A2 can be bis(2-aminophenyl)methane; alternatively, a substituted bis(2-aminophenyl)methane; alternatively, bis(3-aminophenyl)methane; alternatively, a substituted bis(3-aminophenyl)methane; alternatively, bis(4-aminophenyl)methane; or alternatively, a substituted bis(4-aminophenyl)methane.

In an embodiment, the amine having Structure A2 can be bis(2-aminophenyl)ethane, a substituted bis(2-aminophenyl)ethane, bis(3-aminophenyl)ethane, or a substituted bis(3-aminophenyl)-ethane, bis(4-aminophenyl)ethane, or a substituted bis(4-aminophenyl)ethane; or alternatively, bis(3-aminophenyl)ethane, a substituted bis(3-aminophenyl)ethane, bis(4-aminophenyl)ethane, or a substituted bis(4-aminophenyl)ethane. In some embodiments, the amine having Structure A2 can be bis(2-amino-phenyl)ethane or a substituted bis(2-aminophenyl)ethane; alternatively, bis(3-aminophenyl)ethane or a substituted bis(3-aminophenyl)ethane; or alternatively, bis(4-aminophenyl)ethane or a substituted bis(4-aminophenyl)ethane. In other embodiments, the amine having Structure A2 can be bis(2-aminophenyl)-ethane; alternatively, a substituted bis(2-aminophenyl)ethane; alternatively, bis(3-aminophenyl)ethane; alternatively, a substituted bis(3-aminophenyl)ethane; alternatively, bis(4-aminophenyl)ethane; or alternatively, a substituted bis(4-aminophenyl)ethane. Generally, any bis(aminophenyl)ethane disclosed herein (substituted or unsubstituted) can be a bis-1,1-(aminophenyl)ethane or a bis-1,2-(aminophenyl)ethane group; alternatively, a bis-1,1-(aminophenyl)ethane; or alternatively, a bis-1,2-(aminophenyl)ethane.

In an embodiment, the amine having Structure A2 can be a 3,3'-disubstituted-4,4'-bianiline, a 3,3',5,5'-tetrasubstituted-4,4'-bianiline, a bis(3-substituted-4-aminophenyl)methane, a bis(3,5-disubstituted-4-aminophenyl)methane, a bis-1,2-(3-substituted-4-aminophenyl)ethane, a bis-1,2-(3,5-disubstituted-4-aminophenyl)ethane. In some embodiments, the amine having Structure A2 can be a 3,3'-disubstituted 4,4'-bianiline or a 3,3',5,5'-tetrasubstituted-4,4'-bianiline; alternatively, a bis(3-substituted-4-aminophenyl)methane or a bis(3,5-disubstituted-4-aminophenyl)methane; alternatively, a bis-1,2-(3-substituted-4-aminophenyl)ethane or a bis-1,2-(3,5-disubstituted-4-aminophenyl)ethane. In other embodiments, the amine having Structure A2 can be a 3,3'-disubstituted-4,4'-bianiline; alternatively, 3,3',5,5'-tetrasubstituted-4,4'-bianiline; alternatively, a bis(3-substituted-4-aminophenyl)methane; alternatively, a bis(3,5-disubstituted-4-aminophenyl)methane; alternatively, a bis-1,2-(3-substituted-4-aminophenyl)ethane; or alternatively, a bis-1,2-(3,5-disubstituted-4-aminophenyl)ethane.

$L^1$ substituents and substituent patterns for general and specific substituted $L^1$ biphenylene groups, bis(phenylene)methane groups, and bis(phenylene)ethane groups are generally disclosed herein and can be utilized without limitation to further describe the general and specific substituted bianilines, substituted bis(aminophenyl)methanes, and substituted bis(aminophenyl)ethanes which can be utilized as the amine having structure A2 in the various aspects and/or embodiments described herein.

In an embodiment, the amine having Structure A2 can be a di(aminomethyl)cycloalkane or a substituted di(aminomethyl)cycloalkane; alternatively, a di(aminomethyl)cycloalkane. The cycloalkane group of the di(aminomethyl)cycloalkane can be cyclobutane group, a substituted cyclobutane group, a cyclopentane group, a substituted cyclopentane group, a cyclohexane group, a substituted cyclohexane group, a cycloheptane group, a substituted cycloheptane group, a cyclooctane group, or a substituted cyclooctane group; alternatively, a cyclopentane group, a substituted cyclopentane group, a cyclohexane group, or a substituted cyclohexane group; alternatively, a cyclobutane group or a substituted cyclobutane group; alternatively, a cyclopentane group or a substituted cyclopentane group; alternatively, a cyclohexane group or a substituted cyclohexane group; alternatively, a cycloheptane group or a substituted cycloheptane group; or alternatively, a cyclooctane group, or a substituted cyclooctane group. In some embodiments, the cycloalkane group of the di(aminomethyl)cycloalkane can be a cyclobutane group, a cyclopentane group, a cyclohexane group, a cycloheptane group, or a cyclooctane group; or alternatively, a cyclopentane group or a cyclohexane group. In other embodiments, the cycloalkane group of the di(aminomethyl)cycloalkane can be cyclopentane group; alternatively, a substituted cyclopentane group; a cyclohexane group; or alternatively, a substituted cyclohexane group.

In an embodiment, the amine having Structure A2 can be 1,3-di(aminomethyl)cyclopentane, a substituted 1,3-di(aminomethyl)cyclopentane, 1,3-di(aminomethyl)cyclohexane, a substituted 1,3-di(aminomethyl)cyclohexane, 1,4-di(aminomethyl)cyclohexane, or a substituted 1,4-di(amino-methyl)cyclohexane; alternatively, 1,3-di(aminomethyl)cyclopentane, 1,3-di(aminomethyl)cyclohexane, or 1,4-di(aminomethyl)cyclohexane. In some embodiments, the amine having Structure A2 can be 1,3-di(aminomethyl)cyclopentane or a substituted 1,3-di(aminomethyl)cyclopentane; alternatively, 1,3-di(aminomethyl)cyclohexane or a substituted 1,3-di(aminomethyl)cyclohexane, 1,4-di(amino-methyl)cyclohexane, or a substituted 1,4-di(aminomethyl)cyclohexane; alternatively, 1,3-di(amino-methyl)cyclohexane or a substituted 1,3-di(aminomethyl)cyclohexane; alternatively, 1,4-di(amino-methyl)cyclohexane or a substituted 1,4-di(aminomethyl)cyclohexane; alternatively, 1,3-di(aminomethyl)cyclopentane; alternatively, a 1,3-di(aminomethyl)cyclohexane; or alternatively, a 1,4-di(aminomethyl)cyclohexane.

In an aspect, the amine having Structure A2 can be a di(aminomethyl)benzene, or a substituted di(aminomethyl)benzene; alternatively, a di(aminomethyl)benzene. In an embodiment, $L^1$ can be a 1,2-di(aminomethyl)benzene, a substituted 1,2-di(aminomethyl)benzene, a 1,3-di(aminomethyl)benzene, a substituted 1,3-di(aminomethyl)benzene, a 1,4-di(aminomethyl)benzene, or a substituted 1,4-di(aminomethyl)benzene; alternatively, a 1,2-di(aminomethyl)benzene, a 1,3-di(aminomethyl)benzene, or a 1,4-di(aminomethyl)benzene. In some embodiments, the amine having Structure A2 can be a 1,2-di(aminomethyl)benzene or a substituted 1,2-di(aminomethyl)benzene; alternatively, a 1,3-di(amino-methyl)benzene or a substituted 1,3-di(aminomethyl)benzene; alternatively, a 1,4-di(aminomethyl)-benzene or a substituted 1,4-di(aminomethyl)benzene; alternatively, a 1,2-di(aminomethyl)benzene; alternatively, a 1,3-di(aminomethyl)benzene; or alternatively, a 1,4-di(aminomethyl)benzene.

$L^1$ substituents for the general and specific substituted di(methylene)cycloalkane groups and di(methylene)benzene groups are generally disclosed herein and can be utilized without limitation to further describe the general and specific substituted di(aminomethyl)cycloalkanes and substituted di(aminomethyl)benzenes which can be utilized as the amine having structure A2 in the various aspects and/or embodiments described herein.

In an aspect, the amine having Structure A2 can have Structure A10, A11, A12, A13, A14, A15, A16, A17, A18, A19, A20, A21, A22, or A23. In some embodiments, the amine having Structure A2 can have Structure A10, A11, or A12; alternatively, A13, A14, A15, or A16; alternatively, A17, A18, or A19; or alternatively, A20, A21, A22, or A23. In other embodiments, the amine having Structure A2 can have Structure A11 or A12; alternatively, A13 or A14; alternatively, A15 or A16; alternatively, A18 or A19; alternatively, A20 or A21; or alternatively, A22 or A23. In further embodiments, the amine having Structure A2 can have alternatively, A10; alternatively, A11; alternatively, A12; alternatively, A13; alternatively, A14; alternatively, A15; alternatively, A16; alternatively, A17; alternatively, A18; alternatively, A19; alternatively, A20; alternatively, A21; alternatively, A22; or alternatively, A23.

TABLE 2

Diamines which can be utilized as the amine having Structure A2.

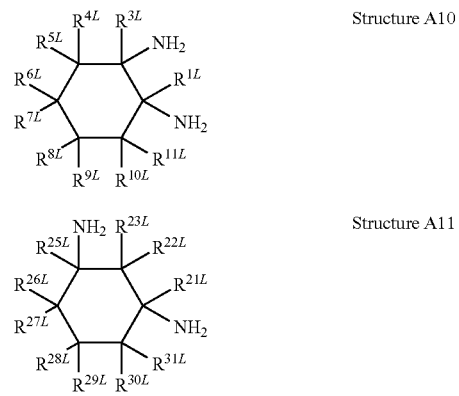

TABLE 2-continued

Diamines which can be utilized as the amine having Structure A2.

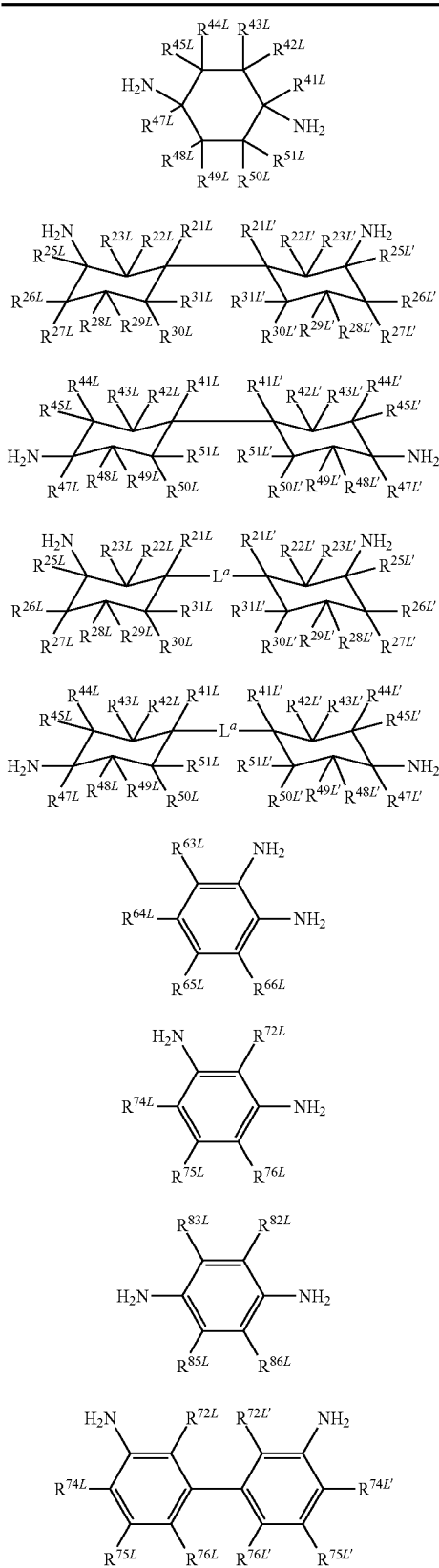

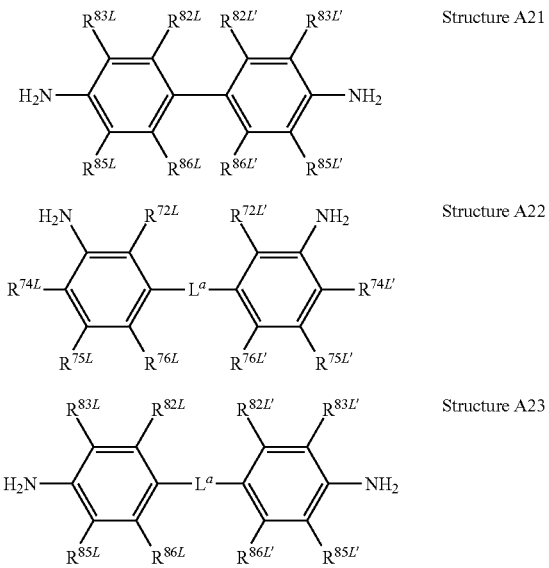

Aspects and embodiments for $R^{1L}$-$R^{11L}$, $R^{21L}$-$R^{31L}$, $R^{21L'}$-$R^{31L'}$, $R^{41L}$-$R^{51L}$, $R^{41L'}$-$R^{51'}$, $R^{62L}$-$R^{66L}$, $R^{72L}$-$R^{76L}$, $R^{72L'}$-$R^{76L'}$, $R^{82L}$-$R^{86L}$, $R^{82L'}$-$R^{86L'}$, and $L^a$, are herein described for the linking group having Structures 1L-14L. These aspects and embodiment can be utilized without limitation to describe the amine having Structures A9-A22 which can be utilized in the various aspects and/or embodiments described herein.

In a non-limiting embodiment, the amine having Structure A2 can be 1,4-diaminobenzene, 2,6-dimethyl-1,4-diaminobenzene, 2,6-diethyl-1,4-diaminobenzene, 2,6-diisopropyl 1,4-diaminobenzene, 2,6-di-tert-butyl-1,4-diaminobenzene, 2,5-dimethyl-1,4-diaminobenzene, 2,5-diethyl-1,4-diaminobenzene, 2,5-diisopropyl-1,4-diaminobenzene, 2,5-di-tert-butyl-1,4-diaminobenzene, or 2,3,5,6-tetramethyl-1,4-diaminobenzene. In other non-limiting embodiments, the amine having Structure A2 can be 1,4-diaminobenzene, 2,6-dimethyl-1,4-diaminobenzene, 2,6-diethyl-1,4-diaminobenzene, 2,6-diisopropyl 1,4-diaminobenzene, or 2,6-di-tert-butyl-1,4-diaminobenzene; alternatively, 2,5-dimethyl-1,4-diaminobenzene, 2,5-diethyl-1,4-diaminobenzene, 2,5-diisopropyl-1,4-diaminobenzene, or 2,5-di-tert-butyl-1,4-diaminobenzene. In yet further non-limiting embodiments, the amine having Structure A2 can be 1,4-diaminobenzene; alternatively, 2,6-dimethyl-1,4-diaminobenzene; alternatively, 2,6-diethyl-1,4-diaminobenzene; alternatively, 2,6-diisopropyl 1,4-diaminobenzene; alternatively, 2,6-di-tert-butyl-1,4-diaminobenzene; alternatively, 2,5-dimethyl-1,4-diaminobenzene; alternatively, 2,5-diethyl-1,4-diaminobenzene; alternatively, 2,5-diisopropyl-1,4-diaminobenzene; alternatively, 2,5-di-tert-butyl-1,4-diaminobenzene; or alternatively, 2,3,5,6-tetramethyl-1,4-diaminobenzene.

In a non-limiting embodiment, the amine having Structure A2 can be 3,3'-dimethyl-4,4'-bianiline, 3,3'-diethyl-4,4'-bianiline, 3,3'-diisopropyl-4,4'-bianiline, 3,3'-di-tert-butyl-4,4'-bianiline, 3,3',5,5'-tetramethyl-4,4'-bianiline, 3,3',5,5'-tetraethyl-4,4'-bianiline, 3,3',5,5'-tetraisopropyl-4,4'-bianiline, or 3,3',5,5'-tetra-tert-butyl-4,4'-bianiline. In some embodiments, the amine having Structure A2 can be 3,3'-dimethyl-4,4'-bianiline, 3,3'-diethyl-4,4'-bianiline, 3,3'-diisopropyl-4, 4'-bianiline, or 3,3'-di-tert-butyl-4,4'-bianiline; alternatively, 3,3',5,5'-tetramethyl-4,4'-bianiline, 3,3',5,5'-tetraethyl-4,4'-bianiline, 3,3',5,5'-tetraisopropyl-4,4'-bianiline, or 3,3',5,5'-tetra-tert-butyl-4,4'-bianiline. In other embodiments, the amine having Structure A2 can be 3,3'-dimethyl-4,4'-bianiline; alternatively, 3,3'-diethyl-4,4'-bianiline; alternatively, 3,3'-diisopropyl-4,4'-bianiline; alternatively, 3,3'-di-tert-butyl-4,4'-bianiline; alternatively, 3,3',5,5'-tetramethyl-4,4'-bianiline; alternatively, 3,3',5,5'-tetraethyl-4,4'-bianiline; alternatively, 3,3',5,5'-tetraisopropyl-4,4'-bianiline; or alternatively, 3,3',5,5'-tetra-tert-butyl-4,4'-bianiline.

In a non-limiting embodiment, the amine having Structure A2 can be bis(3-methyl-4-aminophenyl)methane, bis(3-ethyl-4-aminophenyl)methane, bis(3-isopropy-4-aminophenyl)methane, bis(3-tert-butyl-4-aminophenyl)methane bis(3,5-dimethyl-4-aminophenyl)methane, bis(3,5-diethyl-4-aminophenyl)methane, bis(3,5-diisopropy-4-aminophenyl)methane, or bis(3,5-di-tert-butyl-4-amino-phenyl)methane. In some embodiments, the amine having Structure A2 can be bis(3-methyl-4-amino-phenyl)methane, bis(3-ethyl-4-aminophenyl)methane, bis(3-isopropy-4-aminophenyl)methane, bis(3-tert-butyl-4-aminophenyl)methane; alternatively, bis(3,5-dimethyl-4-aminophenyl)methane, bis(3,5-diethyl-4-aminophenyl)methane, bis(3,5-diisopropy-4-aminophenyl)methane, or bis(3,5-di-tert-butyl-4-amino-phenyl)methane. In other embodiments, the amine having Structure A2 can be bis(3-methyl-4-amino-phenyl)methane; alternatively, bis(3-ethyl-4-aminophenyl)methane; alternatively, bis(3-isopropy-4-aminophenyl)methane; alternatively, bis(3-tert-butyl-4-aminophenyl)methane; alternatively, bis(3,5-dimethyl-4-aminophenyl)methane; alternatively, bis(3,5-diethyl-4-aminophenyl)methane; alternatively, bis(3,5-diisopropy-4-aminophenyl)methane; or alternatively, bis(3,5-di-tert-butyl-4-aminophenyl)-methane.

In a non-limiting embodiment, the amine having Structure A2 can be bis(3-methyl-4-amino-phenyl)ethane, bis(3-ethyl-4-aminophenyl)ethane, bis(3-isopropy-4-aminophenyl)ethane, bis(3-tert-butyl-4-aminophenyl)ethane bis(3,5-dimethyl-4-aminophenyl)ethane, bis(3,5-diethyl-4-aminophenyl)ethane, bis(3,5-diisopropy-4-aminophenyl)ethane, or bis(3,5-di-tert-butyl-4-aminophenyl)ethane. In some embodiments, the amine having Structure A2 can be bis(3-methyl-4-aminophenyl)ethane, bis(3-ethyl-4-aminophenyl)ethane, bis(3-isopropy-4-aminophenyl)ethane, bis(3-tert-butyl-4-aminophenyl)ethane; alternatively, bis(3,5-dimethyl-4-aminophenyl)ethane, bis(3,5-diethyl-4-aminophenyl)ethane, bis(3,5-diisopropyl-4-aminophenyl)ethane, or bis(3,5-di-tert-butyl-4-aminophenyl)ethane. In other embodiments, the amine having Structure A2 can be bis(3-methyl-4-aminophenyl)ethane; alternatively, bis(3-ethyl-4-aminophenyl)ethane; alternatively, bis(3-isopropy-4-aminophenyl)ethane; alternatively, bis(3-tert-butyl-4-aminophenyl)ethane; alternatively, bis(3,5-dimethyl-4-aminophenyl)ethane; alternatively, bis(3,5-diethyl-4-aminophenyl)ethane; alternatively, bis(3,5-diisopropy-4-aminophenyl)-ethane; or alternatively, bis(3,5-di-tert-butyl-4-aminophenyl)ethane. Generally, these substituted bis(aminophenyl)ethanes can be bis-1,1-(aminophenyl)ethane or bis-1,2-(aminophenyl)ethane group; alternatively, bis-1,1-(aminophenyl)ethane; or alternatively, bis-1,2-(aminophenyl)ethane.

In an aspect, the amine having Structure A2 can have a structure wherein one or more of the carbon atoms attached to the nitrogen atom of the —NH$_2$ group can be a tertiary carbon atom or a quaternary carbon atom; alternatively, a tertiary carbon atom; or alternatively, a quaternary carbon atom. In an embodiment, the amine having Structure A2 can have a structure wherein each carbon atom attached to a nitrogen atom of the —NH$_2$ group can be a tertiary carbon atom or a quaternary carbon atom; alternatively, a tertiary carbon atom; or alternatively, a quaternary carbon atom.

In an embodiment, when a nitrogen atom of the amine group is attached to a ring atom (e.g. aminocycloalkane, aromatic amine, aminoarene, diamiocycloalkane, diaminoarene, bi(aminocyclyl), bis(aminocycloalkyl)methane, bis(aminocycloalkyl)ethane, bi(aminoanline), bis(aminophenyl)methane, bis(aminophenyl)ethane, or an amine having Structure A10-A23, among others), the amine can comprise at least one substituent located on a carbon atom adjacent to the ring carbon atom attached to the nitrogen atom of the amine group; or alternatively, the amine can comprise at least one substituent at each carbon atom adjacent to the ring carbon atom attached to the nitrogen atom of the amine group. In some embodiments, when the nitrogen atom of the amine group is attached to a ring atom(e.g. aminocycloalkane, aromatic amine, aminoarene, diamiocycloalkane, diaminoarene, bi(aminocyclyl), bis(aminocycloalkyl)methane, bis(aminocycloalkyl)ethane, bi(aminoanline), bis(aminophenyl)methane, bis(aminophenyl)ethane, or an amine having Structure A10-A23, among others), the amine can consist of one substituent located on a carbon atom adjacent to the ring carbon atom attached to the nitrogen atom of the amine group. In some embodiments, when the nitrogen atom of the amine group is attached to a ring atom (e.g. aminocycloalkane, aromatic amine, aminoarene, diamio-cycloalkane, diaminoarene, bi(aminocyclyl), bis(aminocycloalkyl)methane, bis(aminocycloalkyl)ethane, bi(aminoanline), bis(aminophenyl)methane, bis(aminophenyl)ethane, or an amine having Structure A10-A23, among others), the amine can comprise only one substituent located on the carbon atom adjacent to the ring carbon atom attached to the nitrogen atom of the amine group; or alternatively, the amine can comprise only one substituent located on each carbon atom adjacent to the ring carbon atom attached to the nitrogen atom of the amine group. In yet other embodiments, when the nitrogen atom of the amine is attached to a ring atom (e.g. aminocycloalkane, aromatic amine, aminoarene, diamiocycloalkane, diaminoarene, bi(aminocyclyl), bis(aminocycloalkyl)methane, bis(aminocycloalkyl)ethane, bi(amino-anline), bis(aminophenyl)methane, bis(aminophenyl)ethane, or an amine having Structure A10-A23, among others), the amine can consist of only one substituent located on a carbon atom adjacent to the ring carbon atom attached to the nitrogen atom of the amine group.

In an aspect, the amine having Structure A3 can be 1-(2-aminoethyl)pyrrolidine, 1-(2-amino-ethyl)morpholine, 1-(2-aminoethyl)piperidine, 2-(2-aminoethyl)piperidine, 2-(2-aminoethyl)pyrrolidine, N,N-dimethylethylenediamine, N,N-diethylethylenediamine, N,N-diphenylethylenediamine, 2-amino-thiazole, 2-(aminomethyl)pyridine, 2-(2-aminoethyl)pyridine, 2-(diphenylphosphino)ethylamine, 3-(diphenylphosphino)propylamine, 2-(2-aminoethyl)furan, 2-(aminomethyl)furan, 2-(2-aminoethyl)-thiophene, 2-(aminomethyl)thiophene, 2-aminoethyl-(phenyl)sulfide, 2-phenoxyethylamine, 2-methoxy-ethylamine, 2-ethoxyethylamine, or 2-isopropoxyethylamine. In some embodiments, the amine having Structure A3 can be N,N-dimethylethylenediamine, N,N-diethylethylenediamine, N,N-diphenylethylene-diamine, 1-(2-aminoethyl)morpholine, 2-aminothiazole, 2-(aminomethyl)pyridine, 2-(2-aminoethyl)-pyridine, 2-(diphenylphosphino)ethylamine, 3-(diphenylphosphino)propylamine, 2-aminoethyl-(phenyl)-sulfide, 2-phenoxyethylamine, 2-methoxyethylamine, 2-ethoxyethylamine, or 2-isopropoxyethylamine In yet other embodiments, the amine having Structure A3 can be N,N-dimethylethylenediamine or N,N-diethylethylenediamine; alternatively, N,N-diphenylethylenediamine, 2-(diphenylphosphino)ethylamine, 3-(diphenylphosphino)propylamine; alternatively, 2-(aminomethyl)pyridine, 2-(2-aminoethyl)pyridine; or alternatively, 2-phenoxyethylamine, 2-methoxyethylamine, 2-ethoxyethylamine, or 2-isopropoxyethyl-amine. In further embodiments, the amine having Structure A3 can be N,N-dimethylethylenediamine; alternatively, N,N-diethylethylenediamine; alternatively, N,N-diphenylethylenediamine; alternatively, 2-(diphenylphosphino)ethylamine; alternatively, 3-(diphenylphosphino)propylamine; alternatively, 2-aminothiazole; alternatively, 2-(aminomethyl)pyridine; alternatively, 2-(2-aminoethyl)pyridine; or alternatively, 2-aminoethyl-(phenyl)sulfide.

In a non-limiting embodiment, the amine having Structure A3 can be 2-aminoethyl-(4-methyl-phenyl) sulfide, 2-aminoethyl-(4-ethylphenyl)sulfide, 2-aminoethyl-(4-isopropylphenyl)sulfide, 2-amin-oethyl-(4-tert-butylphenyl)sulfide. In some non-limiting embodiments, the amine having Structure A3 can be 2-aminoethyl-(4-chlorophenyl)sulfide; alternatively, 2-aminoethyl-(4-methylphenyl)sulfide; alternatively, a 2-aminoethyl-(4-ethylphenyl)sulfide; alternatively, 2-aminoethyl-(4-isopropylphenyl)-sulfide; or alternatively, 2-aminoethyl-(4-tert-butylphenyl)sulfide. In other non-limiting embodiments, the amine having Structure A3 can be 2-aminoethyl-(2,6-dimethylphenyl)sulfide; or alternatively, 2-aminoethyl-(3,5-dimethylphenyl)sulfide. In yet other non-limiting embodiments, the amine having Structure A3 can be 2-aminoethyl-(4-methoxyphenyl)sulfide, 2-aminoethyl-(4-ethoxyphenyl)sulfide, 2-aminoethyl-(4-isopropoxyphenyl)sulfide, or 2-aminoethyl-(4-tert-butoxyphenyl)sulfide. In further embodiments, the amine having Structure A3 can be 2-aminoethyl-(4-methoxyphenyl)sulfide; alternatively, 2-aminoethyl-(4-ethoxyphenyl)sulfide; alternatively, 2-aminoethyl-(4-isopropoxyphenyl)-sulfide; or alternatively, 2-aminoethyl-(4-tert-butoxyphenyl)sulfide.

In an aspect, $D^1$ of the amine having Structure A4 can be any $D^1$ described herein. $D^1$ is described herein as a feature of the $N^2$-phosphinyl amidine metal salt complexes utilized in various aspects of this disclosure. Since the amines having structure A3 can be utilized to prepare embodiments of the $N^2$-phosphinyl amidine compounds having Structure NP4, the aspects and embodiments of $D^1$ can utilized without limitation to further describe the amines having Structures A4.

Within this disclosure, nitriles can be used to ultimately prepare the $N^2$-phosphinyl amidine compounds and/or the $N^2$-phosphinyl amidine metal salt complexes utilized in various aspects of this disclosure. In various embodiments, nitriles which can be utilized can have Structure N1, N2, or N3; alternatively, N1; alternatively, N2; or alternatively, N3.

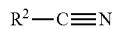

Structure N1

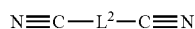

Structure N2

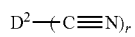

Structure N3 compounds having Structures NP1-NP5 and are described herein. Since nitriles N1-N3 are utilized to ultimately prepare embodiments of the $N^2$-phosphinyl amidine compounds having Structures NP1-NP5, $R^2$, $L^2$, $D^2$, and r within nitrile Structures N1-N3 are independently described as features of the $N^2$-phosphinyl amidine compounds Structures NP1-NP10, NP11, NP13, NP15, NP16, NP18, and/or NP20. Since nitrile having Structures N1-N3 are ultimately utilized to prepare embodiments of $N^2$-phospinyl amidine compounds having Structures NP1-NP10, NP11, NP13, NP15, NP16, NP18, and/or NP20, the $R^2$, $L^2$, $D^2$, and r descriptions for the $N^2$-phospinyl amidine compounds may be utilized without limitation to further describe the amine Structures N1-N3.

In an aspect, the nitrile having Structure N1 can be acetonitrile, propanenitrile, a butanenitrile, a pentanenitrile, a hexanenitrile, a heptanenitrile, an octanenitrile, a nonane nitrile, a decanenitrile, an undecanenitrile, a dodecanenitrile, a tridecanenitrile, a tetradecanenitrile, a pentadecanenitrile, a hexadecanenitrile, a heptadecane, an octadecanenitrile, a nonadecanenitrile, or an eicosane nitrile; or alternatively, acetonitrile, propanenitrile, a butanenitrile, a pentanenitrile, a hexanenitrile, a heptane nitrile, an octanenitrile, a nonane nitrile, a decanenitrile, or an undecanenitrile. In some embodiments, the nitrile having Structure N1 can be acetonitrile, propanenitrile, n-butanenitrile, 2-methylpropanenitrile, n-pentanenitrile, 3-methylbutanenitrile, 2-methyl-butanenitrile, 2,2-dimethylpropanenitrile, n-hexanenitrile, 3-methylbutanenitrile, or 3,3-dimethylbutanenitrile; alternatively, acetonitrile, propanenitrile, 2-methylpropanenitrile, 2,2-dimethylpropanenitrile, or 3,3-dimethylbutanenitrile; alternatively, acetonitrile; alternatively, propanenitrile; alternatively, n-butanenitrile; alternatively, n-pentanenitrile; alternatively, 2-methylpropanenitrile; alternatively, 2,2-dimethylpropanenitrile; or alternatively, 3,3-dimethylbutanenitrile.

In an aspect, the nitrile having Structure N1 can be cyclobutylcarbonitrile, a substituted cyclobutylcarbonitrile, cyclopentylcarbonitrile, a substituted cyclopentylcarbonitrile, cyclohexyl-carbonitrile, a substituted cyclohexylcarbonitrile, cycloheptylcarbonitrile, a substituted cycloheptylcarbonitrile, cyclooctylcarbonitrile, or a substituted cyclooctylcarbonitrile. In some embodiments, the nitrile can be cyclopentylcarbonitrile, a substituted cyclopentylcarbonitrile, cyclohexylcarbonitrile, a substituted cyclohexylcarbonitrile. In other embodiments, the nitrile can be cyclobutylcarbonitrile or a substituted cyclobutylcarbonitrile; alternatively, cyclopentylcarbonitrile or a substituted cyclopentyl-carbonitrile; alternatively, cyclohexylcarbonitrile or a substituted cyclohexylcarbonitrile; alternatively, cycloheptylcarbonitrile or a substituted cycloheptylcarbonitrile; or alternatively, cyclooctylcarbonitrile, or a substituted cyclooctylcarbonitrile. In further embodiments, the nitrile can be cyclopentylcarbonitrile; alternatively, a substituted cyclopentylcarbonitrile; cyclohexylcarbonitrile; or alternatively, a substituted cyclohexylcarbonitrile. Substituents and substituents patterns for the $R^2$ cycloalkyl groups are described herein and can be utilized without limitation to further describe the substituted cycloalkylcarbonitriles which can be utilized in aspects and/or embodiments described herein.

In an aspect, the nitrile having Structure N1 can have Structure N4. The $R^{21c}$, $R^{22c}$, $R^{23c}$, $R^{24c}$, and $R^{25c}$ substituents, substituent patterns, and n for the $R^2$ group having Structure N4 are described Structure N4

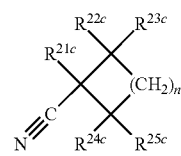

herein and can be utilized without limitation to describe the nitrile having Structure N4 which can be utilized in the various aspects and/or embodiments described herein.

In an embodiment, the nitrile having Structure N1 can be benzonitrile or a substituted benzonitrile. In some embodiments, the nitrile having Structure N1 can be benzonitrile; or alternatively, a substituted benzonitrile. In an embodiment, the substituted benzonitrile can be a 2-substituted benzonitrile, a 3-substituted benzonitrile, a 4-substituted benzonitrile, a 2,4-disubstituted benzonitrile, a 2,6-disubstituted benzonitrile, a 3,5-disubstituted benzonitrile, or a 2,4,6-trisubstituted benzonitrile. In other embodiments, the substituted benzonitrile can be a 2-substituted benzonitrile, a 4-substituted benzonitrile, a 2,4-disubstituted benzonitrile, or a 2,6-disubstituted benzonitrile; alternatively, a 3-substituted benzonitrile or a 3,5-disubstituted benzonitrile; alternatively, a 2-substituted benzonitrile or a 4-substituted benzonitrile; alternatively, a 2,4-disubstituted benzonitrile or a 2,6-disubstituted benzo-nitrile; alternatively, a 2-substituted benzonitrile; alternatively, a 3-substituted benzonitrile; alternatively, a 4-substituted benzonitrile; alternatively, a 2,4-disubstituted benzonitrile; alternatively, a 2,6-disubstituted benzonitrile; alternatively, a, 3,5-disubstituted benzonitrile; or alternatively, a 2,4,6-trisubstituted benzonitrile. Substituents for the $R^2$ phenyl groups are generally disclosed herein and can be utilized without limitation to further describe the substituted benzonitriles which can be utilized in the various aspects and/or embodiments described herein.

In an aspect, the nitrile having Structure N1 can have Structure N5. The $R^{22}$, $R^{23}$, $R^{24}$, $R^{25}$, and $R^{26}$ substituents and substituent patterns for the $R^2$ group having Structure G4 are described

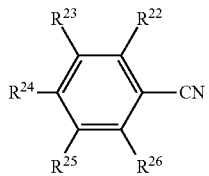

Structure N5 herein and can be utilized without limitation to describe the nitrile having Structure N5 which can be utilized in the various aspects and/or embodiments described herein.

In an embodiment, the nitrile having Structure N1 can be phenylacetonitrile, a substituted phenylacetonitrile, 2-phenylpropanenitrile, a substituted 2-phenylpropanenitrile, 3-phenylpropanenitrile, or a substituted 3-phenylpropanenitrile. In some embodiments, the nitrile having Structure N1 can be phenylacetonitrile or a substituted phenylacetonitrile; alternatively, 2-phenylpropanenitrile or a substituted 2-phenylpropanenitrile; alternatively, 3-phenylpropanenitrile or a substituted 3-phenyl-propanenitrile; or alternatively, phenylacetonitrile, 2-phenylpropanenitrile, or 3-phenylpropanenitrile. In other embodiments, the nitrile having Structure N1 can be phenylacetonitrile; alterantively, a substituted phenylacetonitrile; alterantively, 2-phenylpropanenitrile; alterantively, a substituted 2-phenylpropane-nitrile; alterantively, 3-phenylpropanenitrile; or alterantively, a substituted 3-phenylpropanenitrile. Substituents for $R^2$ benzyl group, 1-phenyleth-1-yl, and/or 2-phenyleth-1-yl groups are generally disclosed herein and can be utilized without limitation to further describe the substituted phenylaceto-nitriles, 2-phenylpropanenitriles, and/or 3-phenylpropanenitriles which can be utilized in the various aspects and/or embodiments described herein.

In an aspect, the nitrile having Structure N1 can be a pyridinecarbonitrile, a substituted pyridinecarbonitrile, a furancarbonitrile, a substituted furancarbonitrile, a thiophenecarbonitrile, or a substituted thiophenecarbonitrile. In an embodiment, the nitrile having Structure N1 can be a pyridine-carbonitrile or a substituted pyridinecarbonitrile; alternatively, a furancarbonitrile or a substituted furancarbonitrile; or alternatively, a thiophenecarbonitrile, or a substituted thiophenecarbonitrile. In some embodiments, the nitrile having Structure N1 can be a pyridinecarbonitrile, a furancarbonitrile, or a thiophenecarbonitrile. In other embodiments, the nitrile having Structure N1 can be a pyridine-carbonitrile; alternatively, a substituted pyridinecarbonitrile; alternatively, a furancarbonitrile; alternatively, a substituted furancarbonitrile; alternatively, a thiophenecarbonitrile; or alternatively, a substituted thiophenecarbonitrile.

In an embodiment, the pyridinecarbonitrile (or substituted pyridinecarbonitrile) can be 2-pyridinecarbonitrile, a substituted 2-pyridinecarbonitrile, 3-pyridinecarbonitrile, a substituted 3-pyridinecarbonitrile, 4-pyridinecarbonitrile, or a substituted 4-pyridinecarbonitrile; alternatively, 2-pyridinecarbonitrile, 3-pyridinecarbonitrile, or 4-pyridinecarbonitrile. In some embodiments, the pyridinecarbonitrile (or substituted pyridinecarbonitrile) can be 2-pyridinecarbonitrile or a substituted 2-pyridinecarbonitrile; alternatively, 3-pyridinecarbonitrile or a substituted 3-pyridinecarbonitrile; alternatively, 4-pyridinecarbonitrile, or a substituted 4-pyridinecarbonitrile; alternatively, 2-pyridine-carbonitrile; alternatively, a substituted 2-pyridinecarbonitrile; alternatively, 3-pyridinecarbonitrile; alternatively, a substituted 3-pyridinecarbonitrile; alternatively, 4-pyridinecarbonitrile; or alternatively, a substituted 4-pyridinecarbonitrile. In an embodiment, the pyridinecarbonitrile (or substituted pyridine-carbonitrile) can be a 2-substituted-3-pyridinecarbonitrile, a 4-substituted-3-pyridinecarbonitrile, a 5-substituted-3-pyridinecarbonitrile, a 6-substituted-3-pyridinecarbonitrile, a 2,4-disubstituted-3-pyridine-carbonitrile, a 2,6-disubstituted-3-pyridinecarbonitrile, or a 2,4,6-trisubstituted-3-pyridinecarbonitrile; alternatively, a 2-substituted-3-pyridinecarbonitrile, a 4-substituted-3-pyridinecarbonitrile, a 6-substituted-3-pyridinecarbonitrile; alternatively, a 2,4-disubstituted-3-pyridinecarbonitrile or a 2,6-disubstituted-3-pyridinecarbonitrile; alternatively, a 2-substituted-3-pyridinecarbonitrile; alternatively, a 4-substituted-3-pyridinecarbonitrile; alternatively, a 5-substituted-3-pyridinecarbonitrile; alternatively, a 6-substituted-3-pyridinecarbonitrile; alternatively, a 2,4-disubstituted-3-pyridinecarbonitrile; alternatively, a 2,6-disubstituted-3-pyridinecarbonitrile; or alternatively, a 2,4,6-trisubstituted-3-pyridine-carbonitrile. In an embodiment, the pyridinecarbonitrile (or substituted-pyridinecarbonitrile) can be a 2-substituted-4-pyridinecarbonitrile, a 3-substituted-4-pyridinecarbonitrile, a 5-substituted-4-pyridine-carbonitrile, a 6-substituted-4-pyridinecarbonitrile, a 2,6-disubstituted-4-pyridinecarbonitrile, or a 3,5-disubstituted-4-pyridinecarbonitrile; alternatively, 2-substituted-4-pyridinecarbonitrile, a 6-substituted-4-pyridinecarbonitrile; alternatively, a 3-substituted-4-pyridinecarbonitrile or a 5-substituted-4-pyridine-carbonitrile; alternatively, a 2-substituted-4-pyridinecarbonitrile; alternatively, a 3-substituted-4-pyridine-carbonitrile; alternatively, a 5-substituted-4-pyridinecarbonitrile; alternatively, a 6-substituted-4-pyridine-carbonitrile; alternatively, a 2,6-disubstituted-4-pyridinecarbonitrile; or alternatively, a 3,5-disubstituted-4-pyridinecarbonitrile. Substituents for the R² pyridinyl groups are generally disclosed herein and can be utilized without limitation to further describe the substituted pyridinecarbonitriles which can be utilized in the various aspects and/or embodiments described herein.

In an embodiment, the furancarbonitrile (or substituted furancarbonitrile) can be 2-furan-carbonitrile, a substituted 2-furancarbonitrile, a 3-furancarbonitrile, or a substituted 3-furancarbonitrile; alternatively, a 2-furancarbonitrile or a 3-furancarbonitrile. In some embodiments, the furancarbonitrile (or substituted furancarbonitrile) can be a 2-furancarbonitrile or a substituted 2-furancarbonitrile; alternatively, a 3-furancarbonitrile or a substituted 3-furancarbonitrile; alternatively, a 2-furancarbonitrile; alternatively, a substituted 2-furancarbonitrile; alternatively, a 3-furancarbonitrile; or alternatively, a substituted 3-furancarbonitrile. In an embodiment, the furancarbonitrile (or substituted furancarbonitrile) can be a 2-substituted-3-furancarbonitrile, a 4-substituted-3-furancarbonitrile, or a 2,4-disubstituted-3-furancarbonitrile; alternatively, a 2-substituted-3-furancarbonitrile; alternatively, a 4-substituted-3-furancarbonitrile; or alternatively, a 2,4-disubstituted-3-furancarbonitrile. Substituents for the R² furyl groups are generally disclosed herein and can be utilized without limitation to further describe the substituted furancarbonitriles which can be utilized in the various aspects and/or embodiments described herein.

In an embodiment, the thiophenenitrile (or substituted thiophenenitrile) can be a 2-thiophenecarbonitrile, a substituted 2-thiophenecarbonitrile, a 3-thiophenecarbonitrile, or a substituted 3-thiophenecarbonitrile; alternatively, a 2-thiophenecarbonitrile or a 3-thiophenecarbonitrile. In some embodiments, the thiophenenitrile (or substituted thiophenenitrile) group can be a 2-thiophenecarbonitrile or a substituted 2-thiophenecarbonitrile; alternatively, a 3-thiophenecarbonitrile or a substituted 3-thiophenecarbonitrile; alternatively, a 2-thiophenecarbonitrile; alternatively, a substituted 2-thiophene-carbonitrile; alternatively, a 3-thiophenecarbonitrile; or alternatively, a substituted 3-thiophene-carbonitrile. In an embodiment, the thiophenenitrile (or substituted thiophenenitrile) can be a 2-substituted-3-thiophenecarbonitrile, a 4-substituted-3-thiophenecarbonitrile, or a 2,4-disubstituted-3-thiophenecarbonitrile; alternatively, a 2-substituted-3-thiophenecarbonitrile; alternatively, a 4-substituted-3-thiophenecarbonitrile; or alternatively, a 2,4-disubstituted-3-thiophenecarbonitrile. Substituents for the R² thienyl groups are generally disclosed herein and can be utilized without limitation to further describe the substituted thiophenecarbonitriles which can be utilized in the various aspects and/or embodiments described herein.

In a non-limiting embodiment, the nitrile having Structure N1 can be benzonitrile, a 2-alkylbenzonitrile, a 3-alkylbenzonitrile, a 4-alkylbenzonitrile, a 2,4-dialkylbenzonitrile a 2,6-dialkyl-benzonitrile, a 3,5-dialkylbenzonitrile, or a 2,4,6-trialkylbenzonitrile; alternatively, a 2-alkylbenzonitrile, a 4-alkylbenzonitrile, a 2,4-dialkylbenzonitrile, a 2,6-dialkylbenzonitrile, or a 2,4,6-trialkylbenzonitrile; alternatively, a 2-alkylbenzonitrile or a 4-alkylbenzonitrile; alternatively, a 2,4-dialkylbenzonitrile or a 2,6-dialkylbenzonitrile; alternatively, a 3-alkylbenzonitrile or a 3,5-dialkylbenzonitrile; alternatively, a 2-alkylbenzonitrile or a 2,6-dialkylbenzonitrile; alternatively, a 2-alkylbenzonitrile; alternatively, a 3-alkyl-benzonitrile; alternatively, a 4-alkylbenzonitrile; alternatively, a 2,4-dialkylbenzonitrile; alternatively, a 2,6-dialkylbenzonitrile; alternatively, a 3,5-dialkylbenzonitrile; or alternatively, a 2,4,6-trialkylbenzo-nitrile. In another non-limiting embodiment, the nitrile having Structure N1 can be benzonitrile, a 2-alkoxybenzonitrile, a 3-alkoxybenzonitrile, a 4-alkoxybenzonitrile, or 3,5-dialkoxybenzonitrile; alternatively, a 2-alkoxybenzonitrile or a 4-alkoxybenzonitrile; alternatively, a 3-alkoxybenzonitrile or 3,5-dialkoxybenzonitrile; alternatively, a 2-alkoxybenzonitrile; alternatively, a 3-alkoxybenzonitrile; alternatively, a 4-alkoxybenzonitrile; or alternatively, a 3,5-dialkoxybenzonitrile. In other non-limiting embodiments, the nitrile having Structure N1 can be benzonitrile, a 2-halobenzonitrile, a 3-halobenzo-nitrile, a 4-halobenzonitrile, a 2,6-dihalobenzonitrile, or a 3,5-dialkylbenzonitrile; alternatively, a 2-halobenzonitrile, a 4-halobenzonitrile, or a 2,6-dihalobenzonitrile; alternatively, a 2-halobenzonitrile or a 4-halobenzonitrile; alternatively, a 3-halobenzonitrile or a 3,5-dihalobenzonitrile; alternatively, a 2-halo-benzonitrile; alternatively, a 3-halobenzonitrile; alternatively, a 4-halobenzonitrile; alternatively, a 2,6-dihalobenzonitrile; or alternatively, a 3,5-dialkylbenzonitrile.

Halides, alkyl group substituents, and alkoxy group substituents are independently described herein and can be utilized, without limitation, to further describe the alkylbenzonitriles, dialkyl-benzonitriles, trialkylbenzonitriles, alkoxybenzonitriles, dialkoxybenzonitriles, halobenzonitriles, or dihalobenzonitriles which can be utilized in the various aspects and/or embodiments described herein. Generally, the halides, alkyl substituents, or alkoxy substituents of the dialkylbenzonitriles, trialkyl-benzonitriles, dialkoxybenzonitriles, or dihalobenzonitriles can be the same; or alternatively, the halo, alkyl substituents, or alkoxy substituents of alkylbenzonitriles, dialkylbenzonitriles, trialkylbenzonitriles, dialkoxybenzonitriles, or dihalobenzonitriles can be different.

In a non-limiting embodiment, the nitrile having Structure N1 can be 2-methylbenzonitrile, 2-ethylbenzonitrile, 2-isopropylbenzonitrile, 2-tert-butylbenzonitrile, 4-methylbenzonitrile, 4-ethylbenzo-nitrile, 4-isopropylbenzonitrile, or 4-tert-butylbenzonitrile; alternatively, 2-methylbenzonitrile, 2-ethylbenzonitrile, 2-isopropylbenzonitrile, or 2-tert-butylbenzonitrile; alternatively, 4-methylbenzonitrile, 4-ethylbenzonitrile, 4-isopropylbenzonitrile, or 4-tert-butylbenzonitrile; alternatively, 2-methylbenzonitrile; alternatively, 2-ethylbenzonitrile; alternatively, 2-isopropylbenzonitrile; alternatively, 2-tert-butylbenzonitrile; alternatively, 4-methylbenzonitrile; alternatively, 4-ethylbenzonitrile; alternatively, 4-isopropylbenzonitrile; or alternatively, 4-tert-butylbenzonitrile. In another non-limiting embodiment, the nitrile having Structure N1 can be a 2-methoxybenzonitrile, 2-ethoxybenzonitrile, 2-isopropoxybenzonitrile, 2-tert-butoxybenzonitrile, 4-methoxybenzonitrile, 4-ethoxybenzonitrile, 4-isopropoxybenzonitrile, or 4-tert-butoxybenzonitrile; alternatively, 2-methoxybenzonitrile, 2-ethoxy-benzonitrile, 2-isopropoxybenzonitrile, or 2-tert-butoxybenzonitrile; alternatively, 4-methoxybenzonitrile, 4-ethoxybenzonitrile, 4-isopropoxybenzonitrile, or 4-tert-butoxybenzonitrile; alternatively, 2-methoxy-benzonitrile; alternatively, 2-ethoxybenzonitrile; alternatively, 2-isopropoxybenzonitrile; alternatively, 2-tert-butoxybenzonitrile; alternatively, 4-methoxybenzonitrile; alternatively, 4-ethoxybenzonitrile; alternatively, 4-isopropoxybenzonitrile; or alternatively, 4-tert-butoxybenzonitrile. In other non-limiting embodiments, the nitrile having Structure N1 can be 2-fluorobenzonitrile, 2-chlorobenzonitrile, 3-fluoro-benzonitrile, 3-chlorobenzonitrile, 4-fluorobenzonitrile, 4-chlorobenzonitrile, 3,5-difluorobenzonitrile, or 3,5-dichlorobenzonitrile; alternatively, 2-fluorobenzonitrile or 2-chlorobenzonitrile; alternatively, 3-fluorobenzonitrile or 3-chlorobenzonitrile; alternatively, 4-fluorobenzonitrile or 4-chlorobenzonitrile; alternatively, 3,5-difluorobenzonitrile or 3,5-dichlorobenzonitrile; alternatively, 3-fluorobenzonitrile, 3-chlorobenzonitrile, 3,5-difluorobenzonitrile or 3,5-dichlorobenzonitrile; alternatively, 3-fluorobenzo-nitrile or 3,5-difluorobenzonitrile; alternatively, 2-fluorobenzonitrile; alternatively, 2-chlorobenzonitrile; alternatively, 3-fluorobenzonitrile; alternatively, 3-chlorobenzonitrile; alternatively, 4-fluorobenzonitrile; alternatively, 4-chlorobenzonitrile; alternatively, 3,5-difluorobenzonitrile; or alternatively, 3,5-dichloro-benzonitrile.

In an aspect, $L^2$ of the nitrile having Structure N2 can be any $L^2$ described herein. $L^2$ is described herein as a feature of the $N^2$-phosphinyl amidine metal salt complexes utilized in various aspects and/or embodiments of this disclosure. Since the nitriles having structure N2 can be utilized to prepare embodiments of the $N^2$-phosinyl amidine compounds having Structure NP2, the aspects and/or embodiments of $L^2$ can utilized without limitation to further describe the nitriles having Structures N2.

In an embodiment, the nitrile having Structure N2 can be oxanitrile, propanedinitrile, a butanedinitrile, a pentanedinitrile, a hexanedinitrile, a heptanedinitrile, an octanedinitrile, a nonane-dinitrile, a decanedinitrile, an undecanedinitrile, a dodecanedinitrile, a tridecanedinitrile, a tetradecane-dinitrile, a pentadecanedinitrile, a hexadecanedinitrile, a heptadecanedinitrile, an octadecanedinitrile, a nonadecanedinitrile, an eicosanedinitrile, or a heneicosanedinitrile; or alternatively, propanedinitrile, a butanedinitrile, a pentanedinitrile, a hexanedinitrile, heptanedinitrile, an octanedinitrile, a nonaedinitrile, a decanedinitrile, an undecanedinitrile, a dodecanedinitrile. In some embodiments, the nitrile having Structure N2 can be propanedinitrile, a butanedinitrile, a pentanedinitrile, a hexanedinitrile, or a heptane-dinitrile. In other embodiments, the amine having Structure N2 can be oxanitrile; alternatively, propane-dinitrile; alternatively, a butane-dinitrile; alternatively, a pentanedinitrile; alternatively, a hexanedinitrile; alternatively, a heptanedinitrile; alternatively, an octanedinitrile; alternatively, a noanedinitrile; alternatively, a decanedinitrile; alternatively, an undecanedinitrile; alternatively, a dodecanedinitrile; alternatively, a tridecanedinitrile; alternatively, a tetradecanedinitrile; alternatively, a pentadecane-dinitrile; alternatively, a hexadecanedinitrile; alternatively, a heptadecanedinitrile; alternatively, an octadecanedinitrile; alternatively, a nonadecanedinitrile; alternatively, an eicosanedinitrile; or alternatively, a heneicosanedinitrile. In some embodiments, the nitrile having Structure N2 can be propanedinitrile, n-butanedinitrile, 2-methylpropanedinitrile, n-pentanedinitrile, 2-methylbutanedinitrile, n-hexanedinitrile, 2,3-dimethylbutanedinitrile, n-heptanedinitrile, 2,2-dimethylpentanedinitrile, n-octane-dinitrile, or 2,2,3,3-tetramethylbutanedinitrile; propanedinitrile, n-butanedinitrile, n-pentanedinitrile, n-hexanedinitrile, n-heptanedinitrile, or n-octanedinitrile; alternatively, propanedinitrile; alternatively, n-butanedinitrile; alternatively, 2-methylpropanedinitrile; alternatively, n-pentanedinitrile; alternatively, 2-methylbutanedinitrile; alternatively, n-hexanedinitrile; alternatively, 2,3-dimethylbutanedinitrile; alternatively, n-heptanedinitrile; alternatively, 2,2-dimethylpentanedinitrile; alternatively, n-octanedinitrile; or alternatively, 2,2,3,3-tetramethylbutanedinitrile.

In an aspect, the nitrile having Structure N2 can have the formula $N{\equiv}C{-}CR^{1a}R^{2a}(CH_2)_tCR^{3a}R^{4a}{-}C{\equiv}N$. $R^{1a}$, $R^{2a}$, $R^{3a}$, $R^{4a}$, and t are described herein as embodiments of an $L^2$ group having structure $-CR^{1a}R^{2a}(CH_2)_tCR^{3a}R^{4a}-$. The descriptions of $R^{1a}$, $R^{2a}$, $R^{3a}$, $R^{4a}$ and t can be utilized without limitation to further describe the nitriles having the formula $N{\equiv}C{-}CR^{1a}R^{2a}(CH_2)_tCR^{3a}R^{4a}{-}C{\equiv}N$ which can be utilized in the various aspects and/or embodiments described herein.

In an embodiment, the nitrile having Structure N2 can be a cyclobutanedicarbonitrile, a substituted cyclobutanedicarbonitrile, a cyclopentanedicarbonitrile, a substituted cyclopentanedicarbonitrile, a cyclohexanedicarbonitrile, a substituted cyclohexanedicarbonitrile, a cycloheptanedicarbonitrile, a substituted cycloheptanedicarbonitrile, a cyclooctanedicarbonitrile, or a substituted cyclooctanedicarbonitrile. In some embodiments, the nitrile having Structure N2 can be a cyclopentanedicarbonitrile, a substituted cyclopentanedicarbonitrile, a cyclohexanedicarbonitrile, a substituted cyclohexanedicarbonitrile. In other embodiments, the nitrile having Structure N2 can be a cyclobutanedicarbonitrile or a substituted cyclobutanedicarbonitrile; alternatively, a cyclopentane-dicarbonitrile or a substituted cyclopentanedicarbonitrile; alternatively, a cyclohexanedicarbonitrile or a substituted cyclohexanedicarbonitrile; alternatively, a cycloheptanedicarbonitrile or a substituted cycloheptanedicarbonitrile; or alternatively, a cyclooctanedicarbonitrile, or a substituted cyclooctane-dicarbonitrile. In further embodiments, the nitrile having Structure N2 can be a cyclopentane-dicarbonitrile; alternatively, a substituted cyclopentanedicarbonitrile; a cyclohexanedicarbonitrile; or alternatively, a substituted cyclohexanedicarbonitrile.

In an embodiment, the nitrile having Structure N2 can be 1,3-cyclopentanedicarbonitrile, a substituted 1,3-cyclopentanedicarbonitrile, 1,3-cyclohexanedicarbonitrile, a substituted 1,3-cyclohexane-dicarbonitrile, 1,4-cyclohexanedicarbonitrile, or a substituted 1,4-cyclohexanedicarbonitrile; alternatively, 1,3-cyclopentanedicarbonitrile, 1,3-cyclohexanedicarbonitrile, or 1,4-cyclohexanedicarbonitrile. In some embodiments, the nitrile having Structure N2 can be 1,3-cyclopentanedicarbonitrile or a substituted 1,3-cyclopentanedicarbonitrile; alternatively, 1,3-cyclohexanedicarbonitrile a substituted 1,3-cyclohexane-dicarbonitrile, 1,4-cyclohexanedicarbonitrile, or a substituted 1,4-cyclohexanedicarbonitrile; alternatively, 1,3-cyclohexanedicarbonitrile or a substituted 1,3-cyclohexanedicarbonitrile; alternatively, 1,4-cyclohexanedicarbonitrile or a substituted 1,4-cyclohexanedicarbonitrile; alternatively, 1,3-cyclopentanedicarbonitrile; alternatively, 1,3-cyclohexanedicarbonitrile; or alternatively, 1,4-cyclohexanedicarbonitrile.

$L^2$ substituents and substituent patterns for substituted $L^2$ cycloalkane groups are generally disclosed herein and can be utilized without limitation to further describe the substituted cycloalkanedicarbonitriles which can be utilized as the nitrile having Structure N2 in the various aspects and/or embodiments described herein.

In an aspect, the nitrile having Structure N2 can be a bi(cyclylcarbonitrile), a substituted bi(cyclylcarbonitrile), a bis(cyclylcarbonitrile)methane, a substituted bis(cyclylcarbonitrile)methane, a bis(cyclylcarbonitrile)ethane, or a substituted bis(cyclylcarbonitrile)ethane; or alternatively, a bis(cyclyl-carbonitrile), a bis(cyclylcarbonitrile)methane, or a bis(cyclylcarbonitrile)ethane. In an embodiment, the nitrile having Structure N2 can be a bi(cyclylcarbonitrile) or a substituted bi(cyclylcarbonitrile); alternatively, a bis(cyclylcarbonitrile)methane or a substituted bis(cyclylcarbonitrile)methane; or alternatively, a bis(cyclylcarbonitrile)ethane or a substituted bis(cyclylcarbonitrile)ethane. In some embodiments, the nitrile having Structure N2 can be a bi(cyclylcarbonitrile); alternatively, a substituted bi(cyclylcarbonitrile); alternatively, a bis(cyclylcarbonitrile)methane; alternatively, a substituted bis(cyclylcarbonitrile)methane; alternatively, a bis(cyclylcarbonitrile)ethane; or alternatively, a substituted bis(cyclylcarbonitrile)ethane. In an aspect, the nitrile having Structure N2 can be a bi(cyclohexylcarbonitrile), a substituted bi(cyclohexylcarbonitrile), a bis(cyclohexylcarbonitrile)methane, a substituted bis(cyclohexylcarbonitrile)methane, a bis(cyclohexylcarbonitrile)ethane, or a substituted bis(cyclohexylcarbonitrile)ethane; or alternatively, a bi(cyclohexylcarbonitrile), a bis(cyclohexylcarbonitrile)methane, or a bis(cyclohexylcarbonitrile)ethane. In an embodiment, the nitrile having Structure N2 can be a bi(cyclohexylcarbonitrile) or a substituted bi(cyclohexylcarbonitrile); alternatively, a bis(cyclohexylcarbonitrile)methane or a substituted bis(cyclohexylcarbonitrile)methane; or alternatively, a bis(cyclohexylcarbonitrile)ethane or a substituted bis(cyclohexylcarbonitrile)ethane. In some embodiments, the nitrile having Structure N2 can be a bi(cyclohexylcarbonitrile); alternatively, a substituted bi(cyclohexylcarbonitrile); alternatively, a bis(cyclohexylcarbonitrile)methane; alternatively, a substituted bis(cyclohexylcarbonitrile)methane; alternatively, a bis(cyclohexylcarbonitrile)ethane; or alternatively, a substituted bis(cyclohexylcarbonitrile)ethane. $L^2$ substituents and substituent patterns for substituted $L^2$ bicyclylene groups, bis(cyclylene)methane groups, and bis(cyclylene)ethane groups are generally disclosed herein and can be utilized without limitation to further describe the substituted bi(cyclylcarbonitrile)s, substituted bis(cyclylcarbonitrile)methanes, and substituted bis(cyclylcarbonitrile)ethanes which can be utilized as the nitrile having Structure N2 in the various aspects and/or embodiments described herein.

In an embodiment, the nitrile having Structure N2 can be 4,4'-bicyclohexyldicarbonitrile, 3,3'-disubstituted-4,4'-bicyclohexyldicarbonitrile, a 3,3',5,5'-tetrasubstituted-4,4'-bicyclohexyl-dicarbonitrile, bis(4-cyclohexylcarbonitrile)methane, a bis(3-substituted-4-cyclohexylcarbonitrile)-methane, a bis(3,5-disubstituted-4-cyclohexylcarbonitrile)methane, bis-1,2-(4-cyclohexylcarbonitrile)-ethane, a bis-1,2-(3-substituted-4-cyclohexylcarbonitrile)ethane, a bis-1,2-(3,5-disubstituted-4-cyclohexylcarbonitrile)ethane. In some embodiments, the nitrile having Structure N2 can be 4,4'-bicyclohexyldicarbonitrile, a 3,3'-disubstituted-4,4'-bicyclohexyldicarbonitrile, a 3,3',5,5'-tetra-substituted-4,4'-bicyclohexyldicarbonitrile; alternatively, a bis(4-cyclohexylcarbonitrile)methane, a bis(3-substituted-4-cyclohexylcarbonitrile)methane or a bis(3,5-disubstituted-4-cyclohexylcarbonitrile)-methane; alternatively, bis-1,2-(4-cyclohexylcarbonitrile)ethane, a bis-1,2-(3-substituted-4-cyclohexyl-carbonitrile)ethane or a bis-1,2-(3,5-disubstituted-4-cyclohexylcarbonitrile)ethane. In other embodiments, the nitrile having Structure N2 can be 4,4'-bicyclohexyldicarbonitrile; alternatively, 3,3'-disubstituted-4,4'-bicyclohexyldicarbonitrile; alternatively, a 3,3',5,5'-tetrasubstituted-4,4'-bicyclohexyl-dicarbonitrile; alternatively, bis(4-cyclohexylcarbonitrile)methane; alternatively, a bis(3-substituted-4-cyclohexylcarbonitrile)methane; alternatively, a bis(3,5-disubstituted-4-cyclohexylcarbonitrile)methane; alternatively, bis-1,2-(4-cyclohexylcarbonitrile)ethane; alternatively, a bis-1,2-(3-substituted-4-cyclohexylcarbonitrile)ethane; or alternatively, a bis-1,2-(3,5-disubstituted-4-cyclohexylcarbonitrile)-ethane. Generally, any bis(cyclohexylcarbonitrile)ethane disclosed herein (substituted or unsubstituted) can be a bis-1,1-(cyclohexylcarbonitrile)ethane or a bis-1,2-(cyclohexylcarbonitrile)ethane group; alternatively, a bis-1,1-(cyclohexylcarbonitrile)ethane; or alternatively, a bis-1,2-(cyclohexyl-carbonitrile)ethane. Substituents for the substituted $L^2$ bicyclohex-4,4'-ylene groups, bis(cyclohex-4-ylene)methane groups, and a bis-1,2-(cyclohex-4-ylene)ethane groups are generally disclosed herein and can be utilized without limitation to further describe the substituted 4,4'-bicyclohexyldicarbonitriles, substituted bis(4-cyclohexylcarbonitrile)methanes, and substituted bis-1,2-(4-cyclohexylcarbonitrile)ethanes which can be utilized as the nitrile having Structure N2 in the various aspects and/or embodiments described herein.

In an aspect, the nitrile having Structure N2 can be a benzenedicarbonitrile or a substituted benzenedicarbonitrile. In an embodiment, the nitrile having Structure N2 can be a benzenedicarbonitrile; or alternatively, a substituted benzenedicarbonitrile. In some embodiments, the nitrile having Structure N2 can be 1,2-benzenedicarbonitrile or a substituted 1,2-benzenedicarbonitrile; alternatively, 1,2-benzenedicarbonitrile; or alternatively, a substituted 1,2-benzenedicarbonitrile. In other embodiments, the nitrile having Structure N2 can be 1,3-benzenedicarbonitrile or a substituted 1,3-benzenedicarbonitrile; alternatively, 1,3-benzenedicarbonitrile; or alternatively, a substituted 1,3-benzenedicarbonitrile. In yet other embodiments, the nitrile having Structure N2 can be 1,4-benzenedicarbonitrile or a substituted 1,4-benzenedicarbonitrile; alternatively, a 1,4-benzenedicarbonitrile; or alternatively, a substituted 1,4-benzenedicarbonitrile. In further embodiments, the nitrile having Structure N2 can be 1,2-benzenedicarbonitrile, 1,3-benzenedicarbonitrile, or 1,4-benzenedicarbonitrile; alternatively, 1,3-benzenedicarbonitrile, or 1,4-benzenedicarbonitrile. In other embodiments, the nitrile having Structure N2 can be a substituted 1,2-benzenedicarbonitrile, a substituted 1,3-benzenedicarbonitrile, or a substituted 1,4-benzenedicarbonitrile; alternatively, a substituted 1,3-benzenedicarbonitrile, or a substituted 1,4-benzenedicarbonitrile. In a non-limiting embodiment, the nitrile having Structure N2 can be a 2,6-disubstituted 1,4-benzenedicarbonitrile, a 2,3-disubstituted 1,4-benzenedicarbonitrile, a 2,5-disubstituted 1,4-benzenedicarbonitrile, or a 2,3,5,6-tetrasubstituted 1,4-benzenedicarbonitrile. In some embodiments, the nitrile having Structure N2 can be a 2,6-disubstituted 1,4-benzenedicarbonitrile or a 2,5-disubstituted 1,4-benzenedicarbonitrile; alternatively, a 2,6-disubstituted 1,4-benzenedicarbonitrile; alternatively, a 2,3-disubstituted 1,4-benzenedicarbonitrile; alternatively, a 2,5-disubstituted 1,4-benzenedicarbonitrile; or alternatively, a 2,3,5,6-tetrasubstituted 1,4-benzenedicarbonitrile. $L^2$ substituents and substituent patterns for substituted $L^2$ phenylene groups are generally disclosed herein and can be utilized without limitation to further describe the substituted benzenedicarbonitriles which can be utilized as the nitrile having Structure N2 in the various aspects and/or embodiments described herein.

In an aspect, the nitrile having Structure N2 can be a naphthalenedicarbonitrile or a substituted naphthalenedicarbonitrile. In an embodiment, the nitrile having Structure N2 can be a naphthalene-dicarbonitrile; or alternatively, a substituted naphthalenedicarbonitrile. In some embodiments, the nitrile having Structure N2 can be 1,3-naphthalenedicarbonitrile, a substituted 1,3-naphthalenedicarbonitrile, 1,4-naphthalenedicarbonitrile, a substituted 1,4-naphthalenedicarbonitrile, 1,5-naphthalenedicarbonitrile, a substituted 1,5-naphthalenedicarbonitrile, 1,6-naphthalenedicarbonitrile, a substituted 1,6-naphthalene-dicarbonitrile, 1,7-naphthalenedicarbonitrile, a substituted 1,7-naphthalenedicarbonitrile, 1,8-naphthalenedicarbonitrile, or a substituted 1,8-naphthalenedicarbonitrile. In other embodiments, the nitrile having Structure N2 can be 1,3-naphthalenedicarbonitrile or a substituted 1,3-naphthalene-dicarbonitrile; alternatively, 1,4-naphthalenedicarbonitrile or a substituted 1,4-naphthalenedicarbonitrile; alternatively, 1,5-naphthalenedicarbonitrile or a substituted 1,5-naphthalenedicarbonitrile; alternatively, 1,6-naphthalenedicarbonitrile or a substituted 1,6- naphthalenedicarbonitrile; alternatively, 1,7-naphthalenedicarbonitrile or a substituted 1,7-naphthalenedicarbonitrile; or alternatively, 1,8-naphthalenedicarbonitrile or a substituted 1,8-naphthalenedicarbonitrile. In yet other embodiments, the nitrile having Structure N2 can be 1,3-naphthalenedicarbonitrile; alternatively, a substituted 1,3-naphthalene-dicarbonitrile; alternatively, 1,4-naphthalenedicarbonitrile; alternatively, a substituted 1,4-naphthalene-dicarbonitrile; alternatively, 1,5-naphthalenedicarbonitrile; alternatively, a substituted 1,5-naphthalene-dicarbonitrile; alternatively, 1,6-naphthalenedicarbonitrile; alternatively, a substituted 1,6-naphthalene-dicarbonitrile; alternatively, 1,7-naphthalenedicarbonitrile; alternatively, a substituted 1,7-naphthalene-dicarbonitrile; alternatively, 1,8-naphthalenedicarbonitrile; or alternatively, a substituted 1,8-naphthalene-dicarbonitrile. $L^2$ substituents and substituent patterns for substituted $L^2$ naphthylene groups are generally disclosed herein and can be utilized without limitation to further describe the substituted naphthalene-dicarbonitriles which can be utilized as the nitrile having Structure N2 in the various aspects and/or embodiments described herein.

In an aspect, the nitrile having Structure N2 can be a bi(phenylcarbonitrile), a substituted bi(phenylcarbonitrile), a bis(phenylcarbonitrile)methane group, a substituted bis(phenylcarbonitrile)-methane group, a bis(phenylcarbonitrile)ethane group, or a substituted bis(phenylcarbonitrile)ethane group; or alternatively, a bi(phenylcarbonitrile), a bis(phenylcarbonitrile)methane group, or a bis(phenyl-carbonitrile) ethane group. In an embodiment, the nitrile having Structure N2 can be a bi(phenyl-carbonitrile) or a substituted bi(phenylcarbonitrile); alternatively, bis(phenylcarbonitrile)methane group or a substituted bis(phenylcarbonitrile)methane group; or alternatively, a bis(phenylcarbonitrile)ethane group or a substituted bis(phenylcarbonitrile)ethane group. In some embodiments, the nitrile having Structure N2 can be a bi(phenylcarbonitrile); alternatively, a substituted bi(phenylcarbonitrile); alternatively, a bis(phenylcarbonitrile)methane group; alternatively, a substituted bis(phenylcarbonitrile)methane group; alternatively, a bis(phenylcarbonitrile)ethane group; or alternatively, a substituted bis(phenylcarbonitrile)ethane group.

In an embodiment, the nitrile having Structure N2 can be 2,2'-bi(phenylcarbonitrile), a substituted 2,2'-bi(phenylcarbonitrile), 3,3'-bi(phenylcarbonitrile), a substituted 3,3'-bi(phenyl-carbonitrile), 4,4'-bi(phenylcarbonitrile), or a substituted 4,4'-bi(phenylcarbonitrile); or alternatively, 3,3'-bi(phenylcarbonitrile), a substituted 3,3'-bi(phenylcarbonitrile), 4,4'-bi(phenylcarbonitrile), or a substituted 4,4'-bi(phenylcarbonitrile). In some embodiments, the nitrile having Structure N2 can be 2,2'-bi(phenyl-carbonitrile) or a substituted 2,2'-bi(phenylcarbonitrile); alternatively, 3,3'-bi(phenyl-carbonitrile) or a substituted 3,3'-bi(phenylcarbonitrile); or alternatively, 4,4'-bi(phenyl-carbonitrile) or a substituted 4,4'-bi(phenylcarbonitrile). In other embodiments, the nitrile having Structure N2 can be 2,2'-bi(phenylcarbonitrile); alternatively, a substituted 2,2'-bi(phenylcarbonitrile); alternatively, 3,3'-bi(phenylcarbonitrile); alternatively, a substituted 3,3'-bi(phenylcarbonitrile); alternatively, 4,4'-bi(phenylcarbonitrile); or alternatively, a substituted 4,4'-bi(phenylcarbonitrile).

In an embodiment, the nitrile having Structure N2 can be bis(2-phenylcarbonitrile)methane, a substituted bis(2-phenylcarbonitrile)methane, bis(3-phenylcarbonitrile)methane, a substituted bis(3-phenylcarbonitrile)methane, bis(4-phenylcarbonitrile)methane, or a substituted bis(4-phenylcarbonitrile)-methane; or alternatively, bis(3-phenylcarbonitrile) methane, a substituted bis(3-phenylcarbonitrile)-methane, bis(4-phenylcarbonitrile)methane, or a substituted bis(4-phenylcarbonitrile)methane. In some embodiments, the nitrile having Structure N2 can be bis(2-phenylcarbonitrile)methane or a substituted bis(2-phenylcarbonitrile)methane; alternatively, bis(3-phenylcarbonitrile)methane or a substituted bis(3-phenylcarbonitrile)methane; or alternatively, bis(4-phenylcarbonitrile)methane or a substituted bis(4-phenylcarbonitrile)methane. In other embodiments, the nitrile having Structure N2 can be bis(2-phenyl-carbonitrile)methane; alternatively, a substituted bis(2-phenylcarbonitrile)methane; alternatively, bis(3-phenylcarbonitrile)methane; alternatively, a substituted bis(3-phenylcarbonitrile)methane; alternatively, bis(4-phenylcarbonitrile)methane; or alternatively, a substituted bis(4-phenylcarbonitrile)methane.

In an embodiment, the nitrile having Structure N2 can be bis(2-phenylcarbonitrile)ethane, a substituted bis(2-phenylcarbonitrile)ethane, bis(3-phenylcarbonitrile)ethane, a substituted bis(3-phenyl-carbonitrile)ethane, bis(4-phenylcarbonitrile)ethane, or a substituted bis(4-phenylcarbonitrile) ethane; or alternatively, bis(3-phenylcarbonitrile)ethane, a substituted bis(3-phenylcarbonitrile)ethane, bis(4-phenylcarbonitrile)ethane, or a substituted bis(4-phenylcarbonitrile) ethane. In some embodiments, the nitrile having Structure N2 can be bis(2-phenylcarbonitrile)ethane or a substituted bis(2-phenylcarbonitrile)-ethane; alternatively, bis(3-phenylcarbonitrile)ethane or a substituted bis(3-phenylcarbonitrile) ethane; or alternatively, bis(4-phenylcarbonitrile)ethane or a substituted bis(4-phenylcarbonitrile)ethane. In other embodiments, the nitrile having Structure N2 can be bis(2-phenylcarbonitrile)ethane; alternatively, a substituted bis(2-phenylcarbonitrile)ethane; alternatively, bis(3-phenylcarbonitrile) ethane; alternatively, a substituted bis(3-phenylcarbonitrile) ethane; alternatively, bis(4-phenylcarbonitrile)ethane; or alternatively, a substituted bis(4-phenylcarbonitrile)ethane. Generally, any bis(phenylcarbonitrile)ethane disclosed herein (substituted or unsubstituted) can be a bis-1,1-(phenylcarbonitrile)ethane or a bis-1,2-(phenylcarbonitrile) ethane group; alternatively, a bis-1,1-(phenylcarbonitrile)ethane; or alternatively, a bis-1,2-(phenylcarbonitrile)ethane.

In an embodiment, the nitrile having Structure N2 can be a 3,3'-disubstituted-4,4'-bi(phenyl-carbonitrile), a 3,3',5,5'-tetrasubstituted-4,4'-bi(phenylcarbonitrile), a bis(3-substituted-4-phenyl-carbonitrile)methane, a bis(3,5-disubstituted-4-phenylcarbonitrile)methane, a bis-1,2-(3-substituted-4-phenylcarbonitrile)ethane, or a bis-1,2-(3,5-disubstituted-4-phenylcarbonitrile)ethane. In some embodiments, the nitrile having Structure N2 can be a 3,3'-disubstituted-4,4'-bi(phenylcarbonitrile) or a 3,3',5,5'-tetrasubstituted-4,4'-bi(phenylcarbonitrile); alternatively, a bis(3-substituted-4-phenyl-carbonitrile)methane or a bis(3,5-disubstituted-4-phenylcarbonitrile)methane; alternatively, a bis-1,2-(3-substituted-4-phenylcarbonitrile)ethane or a bis-1,2-(3,5-disubstituted-4-phenylcarbonitrile)ethane. In other embodiments, the nitrile having Structure N2 can be a 3,3'-disubstituted-4,4'-bi(phenylcarbonitrile); alternatively, 3,3',5,5'-tetrasubstituted-4,4'-bi(phenylcarbonitrile); alternatively, a bis(3-substituted-4-phenylcarbonitrile)methane; alternatively, a bis(3,5-disubstituted-4-phenylcarbonitrile) methane; alternatively, a bis-1,2-(3-substituted-4-phenylcarbonitrile)ethane; or alternatively, a bis-1,2-(3,5-disubstituted-4-phenylcarbonitrile)ethane.

$L^2$ substituents and substituent patterns for general and specific substituted $L^2$ biphenylene groups, bis(phenylene) methane groups, and bis(phenylene)ethane groups are generally disclosed herein and can be utilized without limitation to further describe the general and specific substituted bi(phenylcarbonitrile)s, substituted bis(phenylcarbonitrile)methanes, and substituted bis(phenylcarbonitrile)ethanes which can be utilized as the nitrile having Structure N2 in the various aspects and/or embodiments described herein.

In an embodiment, the nitrile having Structure N2 can be a di(methylcarbonitrile)cycloalkane or a substituted di(methylcarbonitrile)cycloalkane; alternatively, a di(methylcarbonitrile)cycloalkane. The cycloalkane group of the di(methylcarbonitrile)cycloalkanes (substituted or unsubstituted) can be cyclobutane group, a substituted cyclobutane group, a cyclopentane group, a substituted cyclopentane group, a cyclohexane group, a substituted cyclohexane group, a cycloheptane group, a substituted cycloheptane group, a cyclooctane group, or a substituted cyclooctane group; alternatively, a cyclopentane group, a substituted cyclopentane group, a cyclohexane group, or a substituted cyclohexane group; alternatively, a cyclobutane group or a substituted cyclobutane group; alternatively, a cyclopentane group or a substituted cyclopentane group; alternatively, a cyclohexane group or a substituted cyclohexane group; alternatively, a cycloheptane group or a substituted cycloheptane group; or alternatively, a cyclooctane group, or a substituted cyclooctane group. In some embodiments, the cycloalkane group of the di(methylcarbonitrile)cycloalkanes (substituted or unsubstituted) can be cyclobutane group, a cyclopentane group, a cyclohexane group, a cycloheptane group, or a cyclooctane group; or alternatively, a cyclopentane group or a cyclohexane group. In other embodiments, the cycloalkane group of the di(methylcarbonitrile)cycloalkanes (substituted or unsubstituted) can be cyclopentane group; alternatively, a substituted cyclopentane group; a cyclohexane group; or alternatively, a substituted cyclohexane group.

In an embodiment, the nitrile having Structure N2 can be 1,3-di(methylcarbonitrile)-cyclopentane, a substituted 1,3-di(methylcarbonitrile)cyclopentane, 1,3-di(methylcarbonitrile)-cyclohexane, a substituted 1,3-di(methylcarbonitrile)cyclohexane, 1,4-di(methylcarbonitrile)cyclohexane, or a substituted 1,4-di(methylcarbonitrile)cyclohexane; alternatively, 1,3-di(methylcarbonitrile)cyclo-pentane, 1,3-di(methylcarbonitrile)cyclohexane, or 1,4-di(methylcarbonitrile)cyclohexane. In some embodiments, the nitrile having Structure N2 can be 1,3-di(methylcarbonitrile)cyclopentane or a substituted 1,3-di(methylcarbonitrile)cyclopentane; alternatively, 1,3-di(methylcarbonitrile)cyclohexane or a substituted 1,3-di(methylcarbonitrile)cyclohexane; alternatively, 1,4-di(methylcarbonitrile)cyclo-hexane or a substituted 1,4-di(methylcarbonitrile)cyclohexane; alternatively, 1,3-di(methylcarbonitrile)-cyclohexane or a substituted 1,3-di(methylcarbonitrile)cyclohexane; alternatively, 1,4-di(methylcarbonitrile)cyclohexane or a substituted 1,4-di(methylcarbonitrile)cyclohexane; alternatively, 1,3-di(methyl-carbonitrile)cyclopentane; alternatively, a 1,3-di(methylcarbonitrile)cyclohexane; or alternatively, a 1,4-di(methylcarbonitrile)cyclohexane.

In an aspect, the nitrile having Structure N2 can be a di(methylcarbonitrile)benzene, or a substituted di(methylcarbonitrile)benzene; alternatively, a di(methylcarbonitrile) benzene. In an embodiment, nitrile having Structure N2 can be a 1,2-di(methylcarbonitrile)benzene, a substituted 1,2-di(methylcarbonitrile)benzene, a 1,3-di(methylcarbonitrile)benzene, a substituted 1,3-di(methylcarbonitrile)benzene, a 1,4-di(methylcarbonitrile)benzene, or a substituted 1,4-di(methylcarbonitrile)benzene; alternatively, a 1,2-di(methylcarbonitrile)benzene, a 1,3-di(methylcarbonitrile) benzene, or a 1,4-di(methylcarbonitrile)benzene. In some embodiments, nitrile having Structure N2 can be a 1,2-di(methylcarbonitrile)benzene or a substituted 1,2-di(methylcarbonitrile)benzene; alternatively, a 1,3-di(methylcarbonitrile)benzene or a substituted 1,3-di(methylcarbonitrile)benzene; alternatively, a 1,4-di(methylcarbonitrile)benzene or a substituted 1,4-di(methylcarbonitrile)benzene; alternatively, a 1,2-di(methylcarbonitrile)benzene; alternatively, a 1,3-di(methylcarbonitrile)benzene; or alternatively, a 1,4-di(methylcarbonitrile)benzene.

$L^2$ substituents for the general and specific substituted di(methylene)cycloalkane groups and di(methylene)benzene groups are generally disclosed herein and can be utilized without limitation to further describe the general and specific substituted di(methylcarbonitrile)cycloalkanes and substituted di(methylcarbonitrile)benzenes which can be utilized as the nitrile having Structure N2 in the various aspects and/or embodiments described herein.

In an aspect, the nitrile having Structure N2 can have Structure N6, N7, N8, N9, N10, N11, N12, N13, N14, N15, N16, N17, N18, or N19. In some embodiments, the nitrile having Structure N2 can have Structure N6, N7, or N8; alternatively, Structure N9, N10, N11, or N12; alternatively, Structure N13, N14, or N15; or alternatively, Structure N16, N17, N18, or N19. In other embodiments, the nitrile having Structure N2 can have Structure N7 or N8; alternatively, Structure N9 or N10; alternatively, N11 or N12; alternatively, Structure N14 or N15; alternatively, Structure N16 or N17; or alternatively, Structure N18 or N19. In further embodiments, the nitrile having Structure N2 can have Structure N6; alternatively, Structure N7; alternatively, Structure N8; alternatively, Structure N9; alternatively, Structure N10; alternatively, Structure N11; alternatively, Structure N12; alternatively, Structure N13; alternatively, Structure N14; alternatively, Structure N15; alternatively, Structure N16; alternatively, Structure N17; alternatively, Structure N18 or alternatively, Structure N19.

TABLE 5

Dinitriles which can be utilized as the nitrile having Structure N2.

| Structure | |
|---|---|
| Structure N6 | Cyclohexane with substituents $R^{1L}$, $R^{3L}$, $R^{4L}$, $R^{5L}$, $R^{6L}$, $R^{7L}$, $R^{8L}$, $R^{9L}$, $R^{10L}$, $R^{11L}$ and two CN groups |
| Structure N7 | Cyclohexane with substituents $R^{21L}$, $R^{22L}$, $R^{23L}$, $R^{25L}$, $R^{26L}$, $R^{27L}$, $R^{28L}$, $R^{29L}$, $R^{30L}$, $R^{31L}$ and two CN groups |
| Structure N8 | Cyclohexane with substituents $R^{41L}$, $R^{42L}$, $R^{43L}$, $R^{44L}$, $R^{45L}$, $R^{47L}$, $R^{48L}$, $R^{49L}$, $R^{50L}$, $R^{51L}$ and NC, CN groups |
| Structure N9 | Bis-cyclohexane with substituents $R^{21L}$, $R^{22L}$, $R^{23L}$, $R^{25L}$, $R^{26L}$, $R^{27L}$, $R^{28L}$, $R^{29L}$, $R^{30L}$, $R^{31L}$, $R^{21L'}$, $R^{22L'}$, $R^{23L'}$, $R^{25L'}$, $R^{26L'}$, $R^{27L'}$, $R^{28L'}$, $R^{29L'}$, $R^{30L'}$, $R^{31L'}$ and NC, CN groups |

TABLE 5-continued

Dinitriles which can be utilized as the nitrile having Structure N2.

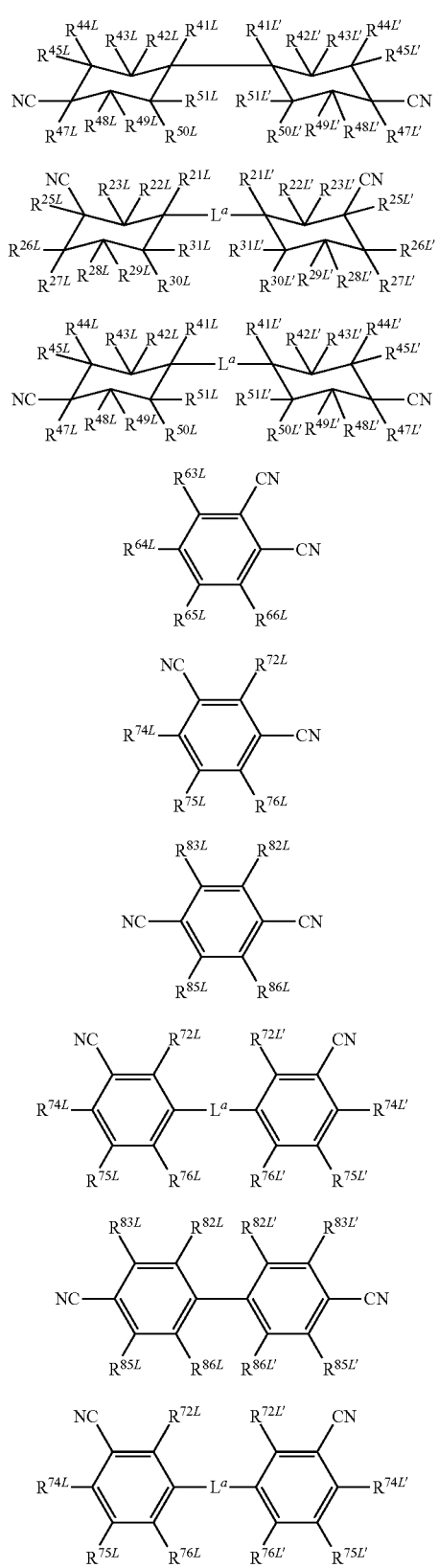

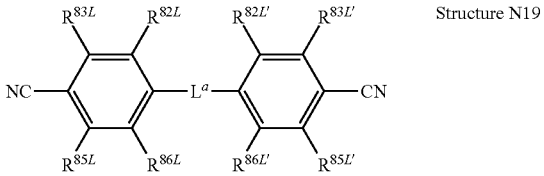

Aspects and embodiments for $R^{1L}$-$R^{11L}$, $R^{21L}$-$R^{31L}$, $R^{21L'}$-$R^{31L'}$, $R^{41L}$-$R^{51L}$, $R^{41L'}$-$R^{51'}$, $R^{62L}$-$R^{66L}$, $R^{72L}$-$R^{76L}$, $R^{72L'}$-$R^{76L'}$, $R^{82L}$-$R^{86L}$, $R^{82L'}$-$R^{86L'}$, and $L^a$, are herein described for L2 which can be utilized in N2-phospinyl amidine compounds have Structure NP3, NP8, NP13, or NP18. These aspects and embodiments can be utilized without limitation to describe the nitriles having Structures N6—N19 which can be utilized in the various aspects and/or embodiments described herein.

In a non-limiting embodiment, the nitrile having Structure N2 can be 1,4-benzenedicarbonitrile, 2,6-dimethyl-1,4-benzenedicarbonitrile, 2,6-diethyl-1,4-benzenedicarbonitrile, 2,6-diisopropyl 1,4-benzenedicarbonitrile, 2,6-di-tert-butyl-1,4-benzenedicarbonitrile, 2,5-dimethyl-1,4-benzenedicarbonitrile, 2,5-diethyl-1,4-benzenedicarbonitrile, 2,5-diisopropyl-1,4-benzenedicarbonitrile, 2,5-di-tert-butyl-1,4-benzenedicarbonitrile, or 2,3,5,6-tetramethyl-1,4-benzenedicarbonitrile. In other non-limiting embodiments, the nitrile having Structure N2 can be 1,4-benzenedicarbonitrile, 2,6-dimethyl-1,4-benzenedicarbonitrile, 2,6-diethyl-1,4-benzenedicarbonitrile, 2,6-diisopropyl 1,4-benzenedicarbonitrile, or 2,6-di-tert-butyl-1,4-benzenedicarbonitrile; alternatively, 2,5-dimethyl-1,4-benzenedicarbonitrile, 2,5-diethyl-1,4-benzenedicarbonitrile, 2,5-diisopropyl-1,4-benzenedicarbonitrile, or 2,5-di-tert-butyl-1,4-benzenedicarbonitrile. In yet further non-limiting embodiments, the nitrile having Structure N2 can be 1,4-benzenedicarbonitrile; alternatively, 2,6-dimethyl-1,4-benzenedicarbonitrile; alternatively, 2,6-diethyl-1,4-benzenedicarbonitrile; alternatively, 2,6-diisopropyl 1,4-benzenedicarbonitrile; alternatively, 2,6-di-tert-butyl-1,4-benzenedicarbonitrile; alternatively, 2,5-dimethyl-1,4-benzene-dicarbonitrile; alternatively, 2,5-diethyl-1,4-benzenedicarbonitrile; alternatively, 2,5-diisopropyl-1,4-benzenedicarbonitrile; alternatively, 2,5-di-tert-butyl-1,4-benzenedicarbonitrile; or alternatively, 2,3,5,6-tetramethyl-1,4-benzenedicarbonitrile.

In a non-limiting embodiment, the nitrile having Structure N2 can be 3,3'-dimethyl-4,4'-bi(phenylcarbonitrile), 3,3'-diethyl-4,4'-bi(phenylcarbonitrile), 3,3'-diisopropyl-4,4'-bi (phenyl-carbonitrile), 3,3'-di-tert-butyl-4,4'-bi(phenylcarbonitrile), 3,3',5,5'-tetramethyl-4,4'-bi(phenyl-carbonitrile), 3,3',5,5'-tetraethyl-4,4'-bi(phenylcarbonitrile), 3,3',5,5'-tetraisopropyl-4,4'-bi(phenylcarbonitrile), or 3,3',5,5'-tetra-tert-butyl-4,4'-bi(phenylcarbonitrile). In some embodiments, the nitrile having Structure N2 can be 3,3'-dimethyl-4,4'-bi(phenylcarbonitrile), 3,3'-diethyl-4,4'-bi(phenylcarbonitrile), 3,3'-diisopropyl-4,4'-bi(phenylcarbonitrile), or 3,3'-di-tert-butyl-4,4'-bi(phenylcarbonitrile); alternatively, 3,3',5,5'-tetramethyl-4,4'-bi(phenylcarbonitrile), 3,3',5,5'-tetraethyl-4,4'-bi(phenylcarbonitrile), 3,3',5,5'-tetraisopropyl-4,4'-bi(phenylcarbonitrile), or 3,3',5,5'-tetra-tert-butyl-4,4'-bi(phenyl-carbonitrile). In other embodiments, the nitrile having Structure N2 can be 3,3'-dimethyl-4,4'-bi(phenyl-carbonitrile); alternatively, 3,3'-diethyl-4,4'-bi(phenylcarbonitrile); alternatively, 3,3'-diisopropyl-4,4'-bi(phenylcarbonitrile); alternatively, 3,3'-di-tert-butyl-4,4'-bi(phenylcarbonitrile); alternatively, 3,3',5,5'-tetramethyl-4,4'-bi(phenylcarbonitrile); alternatively, 3,3',5,5'-tetraethyl-4,4'-bi(phenylcarbonitrile); alternatively, 3,3',5,5'-tetraisopropyl-4,4'-bi(phenylcarbonitrile); or alternatively, 3,3',5,5'-tetra-tert-butyl-4,4'-bi(phenylcarbonitrile).

In a non-limiting embodiment, the nitrile having Structure N2 can be bis(3-methyl-4-phenylcarbonitrile)methane, bis(3-ethyl-4-phenylcarbonitrile)methane, bis(3-isopropyl-4-phenyl-carbonitrile)methane, bis(3-tert-butyl-4-phenylcarbonitrile)methane bis(3,5-dimethyl-4-phenylcarbonitrile)methane, bis(3,5-diethyl-4-phenylcarbonitrile)methane, bis(3,5-diisopropyl-4-phenylcarbonitrile)-methane, or bis(3,5-di-tert-butyl-4-phenylcarbonitrile)methane. In some embodiments, the nitrile having Structure N2 can be bis(3-methyl-4-phenylcarbonitrile)methane, bis(3-ethyl-4-phenyl-carbonitrile)-methane, bis(3-isopropyl-4-phenylcarbonitrile)methane, or bis(3-tert-butyl-4-phenylcarbonitrile)methane; or alternatively, bis(3,5-dimethyl-4-phenylcarbonitrile)methane, bis(3,5-diethyl-4-phenylcarbonitrile)-methane, bis(3,5-diisopropyl-4-phenylcarbonitrile)methane, or bis(3,5-di-tert-butyl-4-phenylcarbonitrile)-methane. In other embodiments, the nitrile having Structure N2 can be bis(3-methyl-4-phenylcarbonitrile)methane; alternatively, bis(3-ethyl-4-phenylcarbonitrile)methane; alternatively, bis(3-isopropyl-4-phenylcarbonitrile)methane; alternatively, bis(3-tert-butyl-4-phenylcarbonitrile)methane; alternatively, bis(3,5-dimethyl-4-phenylcarbonitrile)methane; alternatively, bis(3,5-diethyl-4-phenylcarbonitrile)-methane; alternatively, bis(3,5-diisopropyl-4-phenylcarbonitrile)methane; or alternatively, bis(3,5-di-tert-butyl-4-phenylcarbonitrile)methane.

In a non-limiting embodiment, the nitrile having Structure N2 can be bis(3-methyl-4-phenyl-carbonitrile)ethane, bis(3-ethyl-4-phenylcarbonitrile)ethane, bis(3-isopropyl-4-phenylcarbonitrile)ethane, bis(3-tert-butyl-4-phenylcarbonitrile)ethane, bis(3,5-dimethyl-4-phenylcarbonitrile)ethane, bis(3,5-diethyl-4-phenylcarbonitrile)ethane, bis(3,5-diisopropyl-4-phenyl-carbonitrile)ethane, or bis(3,5-di-tert-butyl-4-phenylcarbonitrile)ethane. In some embodiments, the nitrile having Structure N2 can be bis(3-methyl-4-phenylcarbonitrile)ethane, bis(3-ethyl-4-phenylcarbonitrile)ethane, bis(3-isopropyl-4-phenyl-carbonitrile)ethane, or bis(3-tert-butyl-4-phenylcarbonitrile)ethane; alternatively, bis(3,5-dimethyl-4-phenylcarbonitrile)ethane, bis(3,5-diethyl-4-phenylcarbonitrile)ethane, bis(3,5-diisopropyl-4-phenyl-carbonitrile)ethane, or bis(3,5-di-tert-butyl-4-phenylcarbonitrile)ethane. In other embodiments, the nitrile having Structure N2 can be bis(3-methyl-4-phenylcarbonitrile)ethane; alternatively, bis(3-ethyl-4-phenyl-carbonitrile)ethane; alternatively, bis(3-isopropyl-4-phenylcarbonitrile)ethane; alternatively, bis(3-tert-butyl-4-phenylcarbonitrile)ethane; alternatively, bis(3,5-dimethyl-4-phenylcarbonitrile)ethane; alternatively, bis(3,5-diethyl-4-phenylcarbonitrile)ethane; alternatively, bis(3,5-diisopropyl-4-phenyl-carbonitrile)ethane; or alternatively, bis(3,5-di-tert-butyl-4-phenylcarbonitrile)ethane. Generally, these substituted bis(phenylcarbonitrile)ethanes can be bis-1,1-(phenylcarbonitrile)ethane or bis-1,2-(phenyl-carbonitrile)ethane group; alternatively, bis-1,1-(phenylcarbonitrile)ethane; or alternatively, bis-1,2-(phenylcarbonitrile)ethane.

In an aspect, $D^2$ of the nitrile having Structure N3 can be any $D^2$ described herein. $D^2$ is described herein as a feature of the $N^2$-phosphinyl amidine metal salt complexes having Structure NP5, NP10, NP15, or NP20 utilized in various aspects of this disclosure. Since the nitriles having Structure N3 can be utilized to prepare embodiments of the $N^2$-phospinyl amidine compounds having Structure NP5, NP10, NP15, or NP20, the aspects and embodiments of $D^2$ can utilized without limitation to further describe the nitriles having Structure N3.

Within this disclosure, acid halides can be used to ultimately prepare the $N^2$-phosphinyl amidine compounds and/or the $N^2$-phosphinyl amidine metal salt complexes utilized in various aspects of this disclosure. In various embodiments, acid halides which can be utilized can have Structure AC1, AC2, or AC3; alternatively, AC1; alternatively, AC2; or alternatively, AC3. $R^2$, $L^2$, and $D^2$ are described as

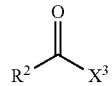

Structure AC1

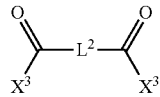

Structure AC2

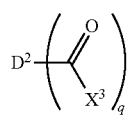

Structure AC3

$R^2$, $L^2$, $D^2$, and q within acid halide Structures A1-A3 are independently described as features of the $N^2$-phosphinyl amidine compounds having Structures NP1-NP10, NP11, NP13, NP15, NP16, NP18, and/or NP20. Since the acid halide having Structures A1-A3 are ultimately utilized to prepare embodiments of $N^2$-phosphinyl amidine compounds having Structures NP1-NP10, NP11, NP13, NP15, NP16, NP18, and/or NP20, the $R^2$, $L^2$, $D^2$, and q descriptions for the $N^2$-phosphinyl amidine compounds can be utilized without limitation to further describe the acid halide Structures A1-A3. Additionally, $X^3$ has been described within the methods of preparing $N^2$-phosphinyl amidine compounds having Structures NP1-NP10, NP11, NP13, NP15, NP16, NP18, and/or NP20 and this description can be utilized without limitation to further describe the acid halide Structures A1-A3.

In an aspect, the acid halide having Structure AC1 can be an acetyl halide, a propionyl halide, a butanoyl halide, a pentanoyl halide, a hexanoyl halide, a heptanoyl halide, an octanoyl halide, a nonanoyl halide, a decanoyl halide, an undecanoyl halide, a dodecanoyl halide, a tridecanoyl halide, a tetradecanoyl halide, a pentadecanoyl halide, a hexadecanoyl halide, a heptadecanoyl halide, an octadecanoyl halide, a nonadecanoyl halide, or an eicosanoyl halide; or alternatively, an acetyl halide, a propionyl halide, a butanoyl halide, a pentanoyl halide, a hexanoyl halide, a heptanoyl halide, an octanoyl halide, a nonanoyl halide, a decanoyl halide, or an undecanoyl halide. In some embodiments, the acid halide having Structure AC1 can be an acetyl halide, a propionyl halide, an n-butanoyl halide, a 2-methylpropanyl halide, an n-pentanoyl halide, a 3-methylbutanoyl halide, a 2-methylbutanol halide, a 2,2-dimethylpropanoyl halide, an n-hexanoyl halide, a 3-methylbutanoyl halide, a 2-methylbutanoyl halide, or a 3,3-dimethylbutanoyl halide; alternatively, an acetyl halide, a propanoyl halide, a 2-methylpropanoyl halide, a 2,2-dimethylpropanonyl halide, or a 3,3-dimethylbutanoyl halide; alternatively, an acetyl halide; alternatively, a propanoyl halide; alternatively, an n-butanoyl halide; alternatively, an n-pentanoyl halide; alternatively, a 2-methylpropanonyl halide; alternatively, a 2,2-dimethyl propanonyl halide; or alternatively, a 3,3-dimethylbutanoyl halide.

In an aspect, the acid halide having Structure AC1 can be acetyl chloride, propionyl chloride, a butanoyl chloride, a pentanoyl chloride, a hexanoyl chloride, a heptanoyl chloride, an octanoyl chloride, a nonanoyl chloride, a decanoyl chloride, an undecanoyl chloride, a dodecanoyl chloride, a tridecanoyl chloride, a tetradecanoyl chloride, a pentadecanoyl chloride, a hexadecanoyl chloride, a heptadecanoyl, an octadecanoyl chloride, a nonadecanoyl chloride, or an eicosanoyl chloride; or alternatively, acetyl chloride, propionyl chloride, a butanoyl chloride, a pentanoyl chloride, a hexanoyl chloride, a heptanoyl chloride, an octanoyl chloride, a nonanoyl chloride, a decanoyl chloride, or an undecanoyl chloride. In some embodiments, the acid halide having Structure AC1 can be acetyl chloride, propionyl chloride, n-butanoyl chloride, 2-methylpropanyl chloride, n-pentanoyl chloride, 3-methylbutanoyl chloride, 2-methylbutanol chloride, 2,2-dimethylpropanoyl chloride, n-hexanoyl chloride, 3-methylbutanoyl chloride, 2-methylbutanoyl chloride group, or 3,3-dimethylbutanoyl chloride; alternatively, acetyl chloride, propanoyl chloride, 2-methylpropanoyl chloride, 2,2-dimethylpropanonyl chloride, or 3,3-dimethylbutanoyl chloride; alternatively, acetyl chloride; alternatively, propanoyl chloride; alternatively, n-butanoyl chloride; alternatively, n-pentanoyl chloride; alternatively, 2-methylpropanonyl chloride; alternatively, 2,2-dimethyl propanonyl chloride; or alternatively, 3,3-dimethylbutanoyl chloride.

In an aspect, the acid halide having Structure AC1 can be a cyclobutylcarbonyl halide, a substituted cyclobutylcarbonyl halide, a cyclopentylcarbonyl halide, a substituted cyclopentylcarbonyl halide, a cyclohexylcarbonyl halide, a substituted cyclohexylcarbonyl halide, a cycloheptylcarbonyl halide, a substituted cycloheptylcarbonyl halide, a cyclooctylcarbonyl halide, or a substituted cyclooctylcarbonyl halide. In some embodiments, the acid halide can be a cyclopentylcarbonyl halide, a substituted cyclopentylcarbonyl halide, a cyclohexylcarbonyl halide, a substituted cyclohexylcarbonyl halide. In other embodiments, the acid halide can be a cyclobutylcarbonyl halide or a substituted cyclobutylcarbonyl halide; alternatively, a cyclopentylcarbonyl halide or a substituted cyclopentyl-carbonyl halide; alternatively, a cyclohexylcarbonyl halide or a substituted cyclohexylcarbonyl halide; alternatively, a cycloheptylcarbonyl halide or a substituted cycloheptylcarbonyl halide; or alternatively, a cyclooctylcarbonyl halide, or a substituted cyclooctylcarbonyl halide. In further embodiments, the acid halide can be a cyclopentylcarbonyl halide; alternatively, a substituted cyclopentylcarbonyl halide; alternatively, a cyclohexylcarbonyl halide; or alternatively, a substituted cyclohexylcarbonyl halide. In other embodiments, the acid halide having Structure AC1 can be cyclobutylcarbonyl chloride, a substituted cyclobutylcarbonyl chloride, cyclopentylcarbonyl chloride, a substituted cyclopentylcarbonyl chloride, cyclohexylcarbonyl chloride, a substituted cyclohexylcarbonyl chloride, cycloheptylcarbonyl chloride, a substituted cycloheptylcarbonyl chloride, cyclooctylcarbonyl chloride, or a substituted cyclooctylcarbonyl chloride. In some other embodiments, the acid halide can be cyclopentylcarbonyl chloride, a substituted cyclopentylcarbonyl chloride, cyclohexylcarbonyl chloride, or a substituted cyclohexylcarbonyl chloride. In further embodiments, the acid chloride can be cyclobutylcarbonyl chloride or a substituted cyclobutylcarbonyl chloride; alternatively, cyclopentylcarbonyl chloride or a substituted cyclopentylcarbonyl chloride; alternatively, cyclohexylcarbonyl chloride or a substituted cyclohexylcarbonyl chloride; alternatively, cycloheptylcarbonyl chloride or a substituted cycloheptyl-carbonyl chloride; or alternatively, cyclooctylcarbonyl chloride, or a substituted cyclooctylcarbonyl chloride. In yet further embodiments, the acid chloride can be cyclopentylcarbonyl chloride; alternatively, a substituted cyclopentylcarbonyl chloride; cyclohexylcarbonyl chloride; or alternatively, a substituted cyclohexylcarbonyl chloride. Substituents and substituents patterns for the $R^2$ cycloalkyl groups are described herein and can be utilized without limitation to further describe the substituted cycloalkylcarbonyl halides or cycloalkylcarbonyl chlorides which can be utilized in aspects and/or embodiments described herein.

In an aspect, the acid having Structure AC1 can have Structure AC4. The $R^{21c}$, $R^{22c}$, $R^{23c}$, $R^{24c}$, and $R^{25c}$ substituents, substituent patterns, and n for the $R^2$ group having Structure G3 are described

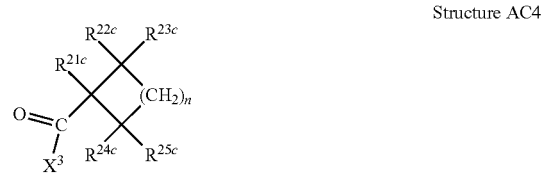

Structure AC4 herein and can be utilized without limitation to describe the acid halide having Structure AC4 which can be utilized in the various aspects and/or embodiments described herein. In an embodiment, the $X^3$ of the acid halide having Structure AC4 can be a chloride or a bromide; alternatively, a chloride; or alternatively, a bromide.

In an embodiment, the acid halide having Structure AC1 can be benzoyl halide or a substituted benzoyl halide. In some embodiments, the acid halide having Structure AC1 can be benzoyl halide; or alternatively, a substituted benzoyl halide. In an embodiment, the substituted benzoyl halide can be a 2-substituted benzoyl halide, a 3-substituted benzoyl halide, a 4-substituted benzoyl halide, a 2,4-disubstituted benzoyl halide, a 2,6-disubstituted benzoyl halide, a 3,5-disubstituted benzoyl halide, or a 2,4,6-trisubstituted benzoyl halide. In other embodiments, the substituted benzoyl halide can be a 2-substituted benzoyl halide, a 4-substituted benzoyl halide, a 2,4-disubstituted benzoyl halide, or a 2,6-disubstituted benzoyl halide; alternatively, a 3-substituted benzoyl halide or a 3,5-disubstituted benzoyl halide; alternatively, a 2-substituted benzoyl halide or a 4-substituted benzoyl halide; alternatively, a 2,4-disubstituted benzoyl halide or a 2,6-disubstituted benzoyl halide; alternatively, a 2-substituted benzoyl halide; alternatively, a 3-substituted benzoyl halide; alternatively, a 4-substituted benzoyl halide; alternatively, a 2,4-disubstituted benzoyl halide; alternatively, a 2,6-disubstituted benzoyl halide; alternatively, 3,5-disubstituted benzoyl halide; or alternatively, a 2,4,6-trisubstituted benzoyl halide. In other embodiments, the acid halide having Structure AC1 can be benzoyl chloride or a substituted benzoyl chloride. In some other embodiments, the acid halide having Structure AC1 can be benzoyl chloride; or alternatively, a substituted benzoyl chloride. In further embodiments, the substituted benzoyl chloride can be a 2-substituted benzoyl chloride, a 3-substituted benzoyl chloride, a 4-substituted benzoyl chloride, a 2,4-disubstituted benzoyl chloride, a 2,6-disubstituted benzoyl chloride, a 3,5-disubstituted benzoyl chloride, or a 2,4,6-trisubstituted benzoyl chloride. In yet further embodiments, the substituted benzoyl chloride can be a 2-substituted benzoyl chloride, a 4-substituted benzoyl chloride, a 2,4- disubstituted benzoyl chloride, or a 2,6-disubstituted benzoyl chloride; alternatively, a 3-substituted benzoyl chloride or a 3,5-disubstituted benzoyl chloride; alternatively, a 2-substituted benzoyl chloride or a 4-substituted benzoyl chloride; alternatively, a 2,4-disubstituted benzoyl chloride or a 2,6-disubstituted benzoyl chloride; alternatively, a 2-substituted benzoyl chloride; alternatively, a 3-substituted benzoyl chloride; alternatively, a 4-substituted benzoyl chloride; alternatively, a 2,4-disubstituted benzoyl chloride; alternatively, a 2,6-disubstituted benzoyl chloride; alternatively, a 3,5-disubstituted benzoyl chloride; or alternatively, a 2,4,6-trisubstituted benzoyl chloride. Substituents for the $R^2$ phenyl groups are generally disclosed herein and can be utilized without limitation to further describe the substituted benzoyl halides or benzoyl chlorides which can be utilized in the various aspects and/or embodiments described herein.

In an aspect, the acid halide having Structure AC1 can have Structure AC5. The $R^{22}$, $R^{23}$, $R^{24}$, $R^{25}$, and $R^{26}$ substituents and substituent patterns for the $R^2$ group having Structure G4 are described

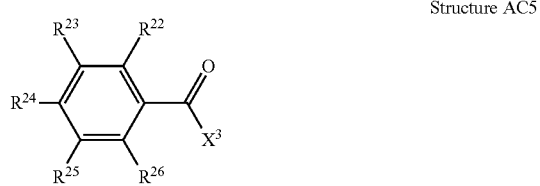

Structure AC5 herein and can be utilized without limitation to describe the acid halide having Structure AC5 which can be utilized in the various aspects and/or embodiments described herein. In an embodiment, the $X^3$ of the acid halide having Structure AC5 can be a chloride or a bromide; alternatively, a chloride; or alternatively, a bromide.

In an aspect, the acid halide having Structure AC1 can be a pyridinecarbonyl halide, a substituted pyridinecarbonyl halide, a furancarbonyl halide, a substituted furancarbonyl halide, a thiophenecarbonyl halide, or a substituted thiophenecarbonyl halide. In an embodiment, the acid halide having Structure AC1 can be a pyridinecarbonyl halide or a substituted pyridinecarbonyl halide; alternatively, a furancarbonyl halide or a substituted furancarbonyl halide; or alternatively, a thiophene-carbonyl halide, or a substituted thiophenecarbonyl halide. In some embodiments, the acid halide having Structure AC1 can be a pyridinecarbonyl halide, a furancarbonyl halide, or a thiophenecarbonyl halide. In other embodiments, the acid halide having Structure AC1 can be a pyridinecarbonyl halide; alternatively, a substituted pyridinecarbonyl halide; alternatively, a furancarbonyl halide; alternatively, a substituted furancarbonyl halide; alternatively, a thiophenecarbonyl halide; or alternatively, a substituted thiophenecarbonyl halide. In other embodiments, the acid halide having Structure AC1 can be a pyridine-carbonyl chloride, a substituted pyridinecarbonyl chloride, a furancarbonyl chloride, a substituted furancarbonyl chloride, a thiophenecarbonyl chloride, or a substituted thiophenecarbonyl chloride. In some other embodiments, the acid halide having Structure AC1 can be a pyridinecarbonyl chloride or a substituted pyridinecarbonyl chloride; alternatively, a furancarbonyl chloride or a substituted furan-carbonyl chloride; or alternatively, a thiophenecarbonyl chloride, or a substituted thiophenecarbonyl chloride. In yet other embodiments, the acid halide having Structure AC1 can be a pyridinecarbonyl chloride, a furancarbonyl chloride, or a thiophenecarbonyl chloride. In further embodiments, the acid halide having Structure AC1 can be a pyridinecarbonyl chloride; alternatively, a substituted pyridine-carbonyl chloride; alternatively, a furancarbonyl chloride; alternatively, a substituted furancarbonyl chloride; alternatively, a thiophenecarbonyl chloride; or alternatively, a substituted thiophenecarbonyl chloride.

In an embodiment, the pyridinecarbonyl halide (or substituted pyridinecarbonyl halide) can be 2-pyridinecarbonyl halide, a substituted 2-pyridinecarbonyl halide, a 3-pyridinecarbonyl halide, a substituted 3-pyridinecarbonyl halide, a 4-pyridinecarbonyl halide, or a substituted 4-pyridinecarbonyl halide; alternatively, 2-pyridinecarbonyl halide, 3-pyridinecarbonyl halide, or 4-pyridinecarbonyl halide. In some embodiments, the pyridinecarbonyl halide (or substituted pyridinecarbonyl halide) can be a 2-pyridinecarbonyl halide or a substituted 2-pyridinecarbonyl halide; alternatively, a 3-pyridinecarbonyl halide or a substituted 3-pyridinecarbonyl halide; alternatively, a 4-pyridinecarbonyl halide, or a substituted 4-pyridinecarbonyl halide; alternatively, a 2-pyridinecarbonyl halide; alternatively, a substituted 2-pyridinecarbonyl halide; alternatively, a 3-pyridinecarbonyl halide; alternatively, a substituted 3-pyridinecarbonyl halide; alternatively, a 4-pyridinecarbonyl halide; or alternatively, a substituted 4-pyridinecarbonyl halide. In an embodiment, the pyridinecarbonyl halide (or substituted pyridinecarbonyl halide) can be a 2-substituted-3-pyridinecarbonyl halide, a 4-substituted-3-pyridine-carbonyl halide, a 5-substituted-3-pyridinecarbonyl halide, a 6-substituted-3-pyridinecarbonyl halide, a 2,4-disubstituted-3-pyridinecarbonyl halide, a 2,6-disubstituted-3-pyridinecarbonyl halide, or a 2,4,6-trisubstituted-3-pyridinecarbonyl halide; alternatively, a 2-substituted-3-pyridinecarbonyl halide, a 4-substituted-3-pyridinecarbonyl halide, a 6-substituted-3-pyridinecarbonyl halide; alternatively, a 2,4-disubstituted-3-pyridinecarbonyl halide or a 2,6-disubstituted-3-pyridinecarbonyl halide; alternatively, a 2-substituted-3-pyridinecarbonyl halide; alternatively, a 4-substituted-3-pyridinecarbonyl halide; alternatively, a 5-substituted-3-pyridinecarbonyl halide; alternatively, a 6-substituted-3-pyridinecarbonyl halide; alternatively, a 2,4-disubstituted-3-pyridinecarbonyl halide; alternatively, a 2,6-disubstituted-3-pyridinecarbonyl halide; or alternatively, a 2,4,6-trisubstituted-3-pyridinecarbonyl halide. In an embodiment, the pyridinecarbonyl halide (or substituted-pyridinecarbonyl halide) can be a 2-substituted-4-pyridinecarbonyl halide, a 3-substituted-4-pyridinecarbonyl halide, a 5-substituted-4-pyridinecarbonyl halide, a 6-substituted-4-pyridinecarbonyl halide, a 2,6-disubstituted-4-pyridinecarbonyl halide, or a 3,5-disubstituted-4-pyridinecarbonyl halide; alternatively, a 2-substituted-4-pyridinecarbonyl halide, or a 6-substituted-4-pyridinecarbonyl halide; alternatively, a 3-substituted-4-pyridinecarbonyl halide or a 5-substituted-4-pyridinecarbonyl halide; alternatively, a 2-substituted-4-pyridinecarbonyl halide; alternatively, a 3-substituted-4-pyridinecarbonyl halide; alternatively, a 5-substituted-4-pyridinecarbonyl halide; alternatively, a 6-substituted-4-pyridinecarbonyl halide; alternatively, a 2,6-disubstituted-4-pyridinecarbonyl halide; or alternatively, a 3,5-disubstituted-4-pyridinecarbonyl halide. In other embodiments, the pyridinecarbonyl chloride (or substituted pyridinecarbonyl chloride) can be 2-pyridinecarbonyl chloride, a substituted 2-pyridinecarbonyl chloride, 3-pyridinecarbonyl chloride, a substituted 3-pyridinecarbonyl chloride, 4-pyridinecarbonyl chloride, or a substituted 4-pyridinecarbonyl chloride; or alternatively, 2-pyridinecarbonyl chloride, 3-pyridinecarbonyl chloride, or 4-pyridinecarbonyl chloride. In some embodiments, the pyridinecarbonyl chloride (or substituted pyridinecarbonyl chloride) can be 2-pyridinecarbonyl chloride or a substituted 2-pyridinecarbonyl chloride; alternatively, 3-pyridine-carbonyl chloride or a substituted 3-pyridinecarbonyl chloride; alternatively, 4-pyridinecarbonyl chloride, or a substituted 4-pyridinecarbonyl chloride; alternatively, 2-pyridinecarbonyl chloride; alternatively, a substituted 2-pyridinecarbonyl chloride; alternatively, 3-pyridinecarbonyl chloride; alternatively, a substituted 3-pyridinecarbonyl chloride; alternatively, 4-pyridinecarbonyl chloride; or alternatively, a substituted 4-pyridinecarbonyl chloride. In some other embodiments, the pyridinecarbonyl chloride (or substituted pyridinecarbonyl chloride) can be a 2-substituted-3-pyridinecarbonyl chloride, a 4-substituted-3-pyridinecarbonyl chloride, a 5-substituted-3-pyridinecarbonyl chloride, a 6-substituted-3-pyridine-carbonyl chloride, a 2,4-disubstituted-3-pyridinecarbonyl chloride, a 2,6-disubstituted-3-pyridinecarbonyl chloride, or a 2,4,6-trisubstituted-3-pyridinecarbonyl chloride; alternatively, a 2-substituted-3-pyridine-carbonyl chloride, a 4-substituted-3-pyridinecarbonyl chloride, or a 6-substituted-3-pyridinecarbonyl chloride; alternatively, a 2,4-disubstituted-3-pyridinecarbonyl chloride or a 2,6-disubstituted-3-pyridine-carbonyl chloride; alternatively, a 2-substituted-3-pyridinecarbonyl chloride; alternatively, a 4-substituted-3-pyridinecarbonyl chloride; alternatively, a 5-substituted-3-pyridinecarbonyl chloride; alternatively, a 6-substituted-3-pyridinecarbonyl chloride; alternatively, a 2,4-disubstituted-3-pyridine-carbonyl chloride; alternatively, a 2,6-disubstituted-3-pyridinecarbonyl chloride; or alternatively, a 2,4,6-trisubstituted-3-pyridinecarbonyl chloride. In yet other embodiments, the pyridinecarbonyl chloride (or substituted-pyridinecarbonyl chloride) can be a 2-substituted-4-pyridinecarbonyl chloride, a 3-substituted-4-pyridinecarbonyl chloride, a 5-substituted-4-pyridinecarbonyl chloride, a 6-substituted-4-pyridine-carbonyl chloride, a 2,6-disubstituted-4-pyridinecarbonyl chloride, or a 3,5-disubstituted-4-pyridine-carbonyl chloride; alternatively, a 2-substituted-4-pyridinecarbonyl chloride or a 6-substituted-4-pyridine-carbonyl chloride; alternatively, a 3-substituted-4-pyridinecarbonyl chloride or a 5-substituted-4-pyridine-carbonyl chloride; alternatively, a 2-substituted-4-pyridinecarbonyl chloride; alternatively, a 3-substituted-4-pyridinecarbonyl chloride; alternatively, a 5-substituted-4-pyridinecarbonyl chloride; alternatively, a 6-substituted-4-pyridinecarbonyl chloride; alternatively, a 2,6-disubstituted-4-pyridine-carbonyl chloride; or alternatively, a 3,5-disubstituted-4-pyridinecarbonyl chloride. Substituents for the $R^2$ pyridinyl groups are generally disclosed herein and can be utilized without limitation to further describe the substituted pyridinecarbonyl halides or substituted pyridinecarbonyl chlorides which can be utilized in the various aspects and/or embodiments described herein.

In an embodiment, the furancarbonyl halide (or substituted furancarbonyl halide) can be a 2-furancarbonyl halide, a substituted 2-furancarbonyl halide, a 3-furancarbonyl halide, or a substituted 3-furancarbonyl halide; alternatively, a 2-furancarbonyl halide or a 3-furancarbonyl halide. In some embodiments, the furancarbonyl halide (or substituted furancarbonyl halide) can be a 2-furancarbonyl halide or a substituted 2-furancarbonyl halide; alternatively, a 3-furancarbonyl halide or a substituted 3-furancarbonyl halide; alternatively, 2-furancarbonyl halide; alternatively, a substituted 2-furancarbonyl halide; alternatively, a 3-furancarbonyl halide; or alternatively, a substituted 3-furancarbonyl halide. In an embodiment, the furancarbonyl halide (or substituted furancarbonyl halide) can be a 2-substituted-3-furancarbonyl halide, a 4-substituted-3-furancarbonyl halide, or a 2,4-disubstituted-3-furancarbonyl halide; alternatively, a 2-substituted-3-furancarbonyl halide; alternatively, a 4-substituted-3-furancarbonyl halide; or alternatively, a 2,4-disubstituted-3-furancarbonyl halide. In other embodiments, the furancarbonyl chloride (or substituted furancarbonyl chloride) can be 2-furancarbonyl chloride, a substituted 2-furancarbonyl chloride, 3-furancarbonyl chloride, or a substituted 3-furancarbonyl chloride; alternatively, 2-furancarbonyl chloride or 3-furancarbonyl chloride. In some other embodiments, the furancarbonyl chloride (or substituted furancarbonyl chloride) can be a 2-furancarbonyl chloride or a substituted 2-furancarbonyl chloride; alternatively, 3-furancarbonyl chloride or a substituted 3-furancarbonyl chloride; alternatively, 2-furancarbonyl chloride; alternatively, a substituted 2-furan-carbonyl chloride; alternatively, 3-furancarbonyl chloride; or alternatively, a substituted 3-furancarbonyl chloride. In yet other embodiments, the furancarbonyl chloride (or substituted furancarbonyl chloride) can be a 2-substituted-3-furancarbonyl chloride, a 4-substituted-3-furancarbonyl chloride, or a 2,4-disubstituted-3-furancarbonyl chloride; alternatively, a 2-substituted-3-furancarbonyl chloride; alternatively, a 4-substituted-3-furancarbonyl chloride; or alternatively, a 2,4-disubstituted-3-furan-carbonyl chloride. Substituents for the $R^2$ furyl groups are generally disclosed herein and can be utilized without limitation to further describe the substituted furancarbonyl halides or substituted furancarbonyl chlorides which can be utilized in the various aspects and/or embodiments described herein.

In an embodiment, the thiophenecarbonyl halide (or substituted thiophenecarbonyl halide) can be a 2-thiophenecarbonyl halide, a substituted 2-thiophenecarbonyl halide, a 3-thiophenecarbonyl halide, or a substituted 3-thiophenecarbonyl halide; alternatively, a 2-thiophenecarbonyl halide or a 3-thiophenecarbonyl halide. In some embodiments, the thiophenecarbonyl halide (or substituted thiophenecarbonyl halide) group can be a 2-thiophenecarbonyl halide or a substituted 2-thiophene-carbonyl halide; alternatively, a 3-thiophenecarbonyl halide or a substituted 3-thiophenecarbonyl halide; alternatively, a 2-thiophenecarbonyl halide; alternatively, a substituted 2-thiophenecarbonyl halide; alternatively, a 3-thiophenecarbonyl halide; or alternatively, a substituted 3-thiophenecarbonyl halide. In an embodiment, the thiophenecarbonyl halide (or substituted thiophenecarbonyl halide) can be a 2-substituted-3-thiophenecarbonyl halide, a 4-substituted-3-thiophenecarbonyl halide, or a 2,4-disubstituted-3-thiophenecarbonyl halide; alternatively, a 2-substituted-3-thiophenecarbonyl halide; alternatively, a 4-substituted-3-thiophenecarbonyl halide; or alternatively, a 2,4-disubstituted-3-thiophenecarbonyl halide. In other embodiments, the thiophenecarbonyl chloride (or substituted thiophenecarbonyl chloride) can be 2-thiophenecarbonyl chloride, a substituted 2-thiophenecarbonyl chloride, 3-thiophenecarbonyl chloride, or a substituted 3-thiophenecarbonyl chloride; alternatively, 2-thiophenecarbonyl chloride or 3-thiophenecarbonyl chloride. In some other embodiments, the thiophenecarbonyl chloride (or substituted thiophenecarbonyl chloride) group can be 2-thiophenecarbonyl chloride or a substituted 2-thiophenecarbonyl chloride; alternatively, 3-thiophenecarbonyl chloride or a substituted 3-thiophenecarbonyl chloride; alternatively, 2-thiophenecarbonyl chloride; alternatively, a substituted 2-thiophenecarbonyl chloride; alternatively, 3-thiophenecarbonyl chloride; or alternatively, a substituted 3-thiophenecarbonyl chloride. In further embodiments, the thiophenecarbonyl chloride (or substituted thiophenecarbonyl chloride) can be a 2-substituted-3-thiophenecarbonyl chloride, a 4-substituted-3-thiophenecarbonyl chloride, or a 2,4-disubstituted-3-thiophenecarbonyl chloride; alternatively, a 2-substituted-3-thiophenecarbonyl chloride; alternatively, a 4-substituted-3-thiophene-carbonyl chloride; or alternatively, a 2,4-disubstituted-3-thiophenecarbonyl chloride. Substituents for the $R^2$ thienyl groups are generally disclosed herein and can be utilized without limitation to further describe the substituted thiophenecarbonyl halides or substituted thiophenecarbonyl chlorides which can be utilized in the various aspects and/or embodiments described herein.

In a non-limiting embodiment, the acid halide having Structure AC1 can be a benzoyl halide, a 2-alkylbenzoyl halide, a 3-alkylbenzoyl halide, a 4-alkylbenzoyl halide, a 2,4-dialkylbenzoyl halide a 2,6-dialkylbenzoyl halide, a 3,5-dialkylbenzoyl halide, or a 2,4,6-trialkylbenzoyl halide; alternatively, a 2-alkylbenzoyl halide, a 4-alkylbenzoyl halide, a 2,4-dialkylbenzoyl halide, a 2,6-dialkylbenzoyl halide, or a 2,4,6-trialkylbenzoyl halide; alternatively, a 2-alkylbenzoyl halide or a 4-alkylbenzoyl halide; alternatively, a 2,4-dialkylbenzoyl halide a 2,6-dialkylbenzoyl halide; alternatively, a 3-alkylbenzoyl halide or a 3,5-dialkylbenzoyl halide; alternatively, a 2-alkylbenzoyl halide or a 2,6-dialkylbenzoyl halide; alternatively, a benzoyl halide; alternatively, a 2-alkylbenzoyl halide; alternatively, a 3-alkyl-benzoyl halide; alternatively, a 4-alkylbenzoyl halide; alternatively, a 2,4-dialkylbenzoyl halide; alternatively, a 2,6-dialkylbenzoyl halide; alternatively, a 3,5-dialkylbenzoyl halide; or alternatively, a 2,4,6-trialkylbenzoyl halide. In another non-limiting embodiment, the acid halide having Structure AC1 can be a benzoyl halide, a 2-alkoxybenzoyl halide, a 3-alkoxybenzoyl halide, a 4-alkoxybenzoyl halide, or 3,5-dialkoxybenzoyl halide; alternatively, a 2-alkoxybenzoyl halide or a 4-alkoxybenzoyl halide; alternatively, a 3-alkoxybenzoyl halide or 3,5-dialkoxybenzoyl halide; alternatively, a 2-alkoxybenzoyl halide; alternatively, 3-alkoxybenzoyl halide; alternatively, a 4-alkoxybenzoyl halide; alternatively, 3,5-dialkoxybenzoyl halide. In other non-limiting embodiments, the acid halide having Structure AC1 can be a benzoyl halide, a 2-halobenzoyl halide, a 3-halobenzoyl halide, a 4-halobenzoyl halide, a 2,6-dihalo-benzoyl halide, or a 3,5-dialkylbenzoyl halide; alternatively, a 2-halobenzoyl halide, a 4-halobenzoyl halide, or a 2,6-dihalobenzoyl halide; alternatively, a 2-halobenzoyl halide or a 4-halobenzoyl halide; alternatively, a 3-halobenzoyl halide or a 3,5-dihalobenzoyl halide; alternatively, a 2-halobenzoyl halide; alternatively, a 3-halobenzoyl halide; alternatively, a 4-halobenzoyl halide; alternatively, a 2,6-dihalo-benzoyl halide; or alternatively, a 3,5-dialkylbenzoyl halide. In other embodiments, the acid halide having Structure AC1 can be benzoyl chloride, a 2-alkylbenzoyl chloride, a 3-alkylbenzoyl chloride, a 4-alkylbenzoyl chloride, a 2,4-dialkylbenzoyl chloride a 2,6-dialkylbenzoyl chloride, a 3,5-dialkylbenzoyl chloride, or a 2,4,6-trialkylbenzoyl chloride; alternatively, a 2-alkylbenzoyl chloride, a 4-alkylbenzoyl chloride, a 2,4-dialkylbenzoyl chloride, a 2,6-dialkylbenzoyl chloride, or a 2,4,6-trialkylbenzoyl chloride; alternatively, a 2-alkylbenzoyl chloride or a 4-alkylbenzoyl chloride; alternatively, a 2,4-dialkylbenzoyl chloride a 2,6-dialkylbenzoyl chloride; alternatively, a 3-alkylbenzoyl chloride or a 3,5-dialkylbenzoyl chloride; alternatively, a 2-alkylbenzoyl chloride or a 2,6-dialkylbenzoyl chloride; alternatively, a 2-alkylbenzoyl chloride; alternatively, a 3-alkylbenzoyl chloride; alternatively, a 4-alkylbenzoyl chloride; alternatively, a 2,4-dialkylbenzoyl chloride; alternatively, a 2,6-dialkylbenzoyl chloride; alternatively, a 3,5-dialkylbenzoyl chloride; or alternatively, a 2,4,6-trialkylbenzoyl chloride. In some other embodiments, the acid halide having Structure AC1 can be benzoyl chloride, a 2-alkoxybenzoyl chloride, a 3-alkoxybenzoyl chloride, a 4-alkoxybenzoyl chloride, or a 3,5-dialkoxybenzoyl chloride; alternatively, a 2-alkoxybenzoyl chloride or a 4-alkoxybenzoyl chloride; alternatively, a 3-alkoxybenzoyl chloride or 3,5-dialkoxybenzoyl chloride; alternatively, a 2-alkoxybenzoyl chloride; alternatively, a 3-alkoxybenzoyl chloride; alternatively, a 4-alkoxybenzoyl chloride; alternatively, a 3,5-dialkoxybenzoyl chloride. In yet other embodiments, the acid halide having Structure AC1 can be benzoyl chloride, a 2-halobenzoyl chloride, a 3-halobenzoyl chloride, a 4-halobenzoyl chloride, a 2,6-dihalobenzoyl chloride, or a 3,5-dialkylbenzoyl chloride; alternatively, a 2-halobenzoyl chloride, a 4-halobenzoyl chloride, or a 2,6-dihalobenzoyl chloride; alternatively, a 2-halobenzoyl chloride or a 4-halobenzoyl chloride; alternatively, a 3-halobenzoyl chloride or a 3,5-dihalobenzoyl chloride; alternatively, a 2-halobenzoyl chloride; alternatively, a 3-halobenzoyl chloride; alternatively, a 4-halobenzoyl chloride; alternatively, a 2,6-dihalobenzoyl chloride; or alternatively, a 3,5-dialkylbenzoyl chloride.

The halide substituents, alkyl group substituents, and alkoxy group substituents are independently described herein and can be utilized, without limitation, to further describe the alkyl-benzoyl halides or alkylbenzoyl chlorides, dialkylbenzoyl halides or dialkylbenzoyl chlorides, trialkyl-benzoyl halides or trialkylbenzoyl chlorides, alkoxybenzoyl halides or alkoxybenzoyl chlorides, dialkoxy-benzoyl halides or dialkoxybenzoyl chlorides, halobenzoyl halides or halobenzoyl chlorides, and dihalo-benzoyl halides or dihalobenzoyl chlorides. Generally, the halide substituents, alkyl substituents, or alkoxy substituents of the dialkylbenzoyl halides or dialkylbenzoyl chlorides, trialkylbenzoyl halides or trialkylbenzoyl chlorides, dialkoxybenzoyl halides or dialkoxybenzoyl chlorides, and dihalobenzoyl halides or dihalobenzoyl chlorides can be the same; or alternatively, the halo, alkyl substituents, or alkoxy substituents of the dialkylbenzoyl halides or dialkylbenzoyl chlorides, trialkylbenzoyl halides or trialkyl-benzoyl chlorides, dialkoxybenzoyl halides or dialkoxybenzoyl chlorides, and dihalobenzoyl halides or dihalobenzoyl chlorides can be different.

In a non-limiting embodiment, the acid halide having Structure AC1 can be a 2-methyl-benzoyl halide, a 2-ethylbenzoyl halide, a 2-isopropylbenzoyl halide, a 2-tert-butylbenzoyl halide, a 4-methylbenzoyl halide, a 4-ethylbenzoyl halide, a 4-isopropylbenzoyl halide, or a 4-tert-butylbenzoyl halide; alternatively, a 2-methylbenzoyl halide, a 2-ethylbenzoyl halide, a 2-isopropylbenzoyl halide, or a 2-tert-butylbenzoyl halide; alternatively, a 4-methylbenzoyl halide a 4-ethylbenzoyl halide, a 4-isopropylbenzoyl halide, or a 4-tert-butylbenzoyl halide; alternatively, a 2-methylbenzoyl halide; alternatively, a 2-ethylbenzoyl halide; alternatively, a 2-isopropylbenzoyl halide; alternatively, a 2-tert-butylbenzoyl halide; alternatively, a 4-methylbenzoyl halide; alternatively, a 4-ethylbenzoyl halide; alternatively, a 4-isopropylbenzoyl halide; or alternatively, a 4-tert-butylbenzoyl halide. In another non-limiting embodiment, the acid halide having Structure AC1 can be a 2-methoxybenzoyl halide, a 2-ethoxybenzoyl halide, a 2-isoprooxybenzoyl halide, a 2-tert-butoxybenzoyl halide, a 4-methoxybenzoyl halide, a 4-ethoxybenzoyl halide, a 4-isoprooxybenzoyl halide, or a 4-tert-butoxybenzoyl halide; alternatively, a 2-methoxybenzoyl halide, a 2-ethoxybenzoyl halide, a 2-isoprooxybenzoyl halide, or a 2-tert-butoxybenzoyl halide; alternatively, a 4-methoxybenzoyl halide, a 4-ethoxybenzoyl halide, a 4-isoprooxybenzoyl halide, or a 4-tert-butoxybenzoyl halide; alternatively, a 2-methoxybenzoyl halide; alternatively, a 2-ethoxybenzoyl halide; alternatively, a 2-isoprooxybenzoyl halide; alternatively, a 2-tert-butoxybenzoyl halide; alternatively, a 4-methoxybenzoyl halide; alternatively, a 4-ethoxybenzoyl halide; alternatively, a 4-isopropoxybenzoyl halide; or alternatively, a 4-tert-butoxybenzoyl halide. In other non-limiting embodiments, the acid halide having Structure AC1 can be a 2-fluorobenzoyl halide, a 2-chlorobenzoyl halide, a 3-fluorobenzoyl halide, a 3-chlorobenzoyl halide, a 4-fluorobenzoyl halide, a 4-chlorobenzoyl halide, a 3,5-difluorobenzoyl halide, or a 3,5-dichlorobenzoyl halide; alternatively, a 2-fluorobenzoyl halide or a 2-chlorobenzoyl halide; alternatively, a 3-fluorobenzoyl halide or a 3-chloro-benzoyl halide; alternatively, a 4-fluorobenzoyl halide or a 4-chlorobenzoyl halide; alternatively, a 3,5-difluorobenzoyl halide or a 3,5-dichlorobenzoyl halide; alternatively, a 3-fluorobenzoyl halide, a 3-chlorobenzoyl halide, a 3,5-difluorobenzoyl halide or a 3,5-dichlorobenzoyl halide; alternatively, a 3-fluorobenzoyl halide or a 3,5-difluorobenzoyl halide; alternatively, a 2-fluorobenzoyl halide; alternatively, a 2-chlorobenzoyl halide; alternatively, a 3-fluorobenzoyl halide; alternatively, a 3-chloro-benzoyl halide; alternatively, a 4-fluorobenzoyl halide; alternatively, a 4-chlorobenzoyl halide; alternatively, a 3,5-difluorobenzoyl halide; or alternatively, a 3,5-dichlorobenzoyl halide. In other embodiments, the acid halide having Structure AC1 can be 2-methylbenzoyl chloride, 2-ethylbenzoyl chloride, 2-isopropylbenzoyl chloride, 2-tert-butylbenzoyl chloride, 4-methylbenzoyl chloride, 4-ethyl-benzoyl chloride, 4-isopropylbenzoyl chloride, or 4-tert-butylbenzoyl chloride; alternatively, 2-methyl-benzoyl chloride, 2-ethylbenzoyl chloride, 2-isopropylbenzoyl chloride, or 2-tert-butylbenzoyl chloride; alternatively, 4-methyl-benzoyl chloride, 4-ethylbenzoyl chloride, 4-isopropylbenzoyl chloride, or 4-tert-butylbenzoyl chloride; alternatively, 2-methylbenzoyl chloride; alternatively, 2-ethylbenzoyl chloride; alternatively, 2-isopropylbenzoyl chloride; alternatively, 2-tert-butylbenzoyl chloride; alternatively, 4-methyl-benzoyl chloride; alternatively, 4-ethylbenzoyl chloride; alternatively, 4-isopropylbenzoyl chloride; or alternatively, 4-tert-butylbenzoyl chloride. In some other embodiments, the acid halide having Structure AC1 can be 2-methoxybenzoyl chloride, 2-ethoxybenzoyl chloride, 2-isopropoxy-benzoyl chloride, 2-tert-butoxybenzoyl chloride, 4-methoxybenzoyl chloride, 4-ethoxybenzoyl chloride, 4-isopropoxybenzoyl chloride, or 4-tert-butoxybenzoyl chloride; alternatively, 2-methoxybenzoyl chloride, 2-ethoxybenzoyl chloride, 2-isopropoxybenzoyl chloride, or 2-tert-butoxybenzoyl chloride; alternatively, 4-methoxybenzoyl chloride, 4-ethoxybenzoyl chloride, 4-isopropoxybenzoyl chloride, or 4-tert-butoxybenzoyl chloride; alternatively, 2-methoxybenzoyl chloride; alternatively, 2-ethoxybenzoyl chloride; alternatively, 2-isopropoxybenzoyl chloride; alternatively, 2-tert-butoxybenzoyl chloride; alternatively, 4-methoxybenzoyl chloride; alternatively, 4-ethoxybenzoyl chloride; alternatively, 4-isopropoxybenzoyl chloride; or alternatively, 4-tert-butoxybenzoyl chloride. In yet other embodiments, the acid halide having Structure AC1 can be 2-fluorobenzoyl chloride, 2-chlorobenzoyl chloride, 3-fluorobenzoyl chloride, 3-chlorobenzoyl chloride, 4-fluorobenzoyl chloride, 4-chlorobenzoyl chloride, 3,5-difluorobenzoyl chloride, or 3,5-dichlorobenzoyl chloride; alternatively, 2-fluorobenzoyl chloride or 2-chlorobenzoyl chloride; alternatively, 3-fluorobenzoyl chloride or 3-chlorobenzoyl chloride; alternatively, 4-fluorobenzoyl chloride or 4-chlorobenzoyl chloride; alternatively, 3,5-difluorobenzoyl chloride or 3,5-dichlorobenzoyl chloride; alternatively, 3-fluorobenzoyl chloride, 3-chlorobenzoyl chloride, 3,5-difluorobenzoyl chloride or 3,5-dichlorobenzoyl chloride; alternatively, 3-fluorobenzoyl chloride or 3,5-difluorobenzoyl chloride; alternatively, 2-fluorobenzoyl chloride; alternatively, 2-chlorobenzoyl chloride; alternatively, 3-fluorobenzoyl chloride; alternatively, 3-chlorobenzoyl chloride; alternatively, 4-fluorobenzoyl chloride; alternatively, 4-chlorobenzoyl chloride; alternatively, 3,5-difluorobenzoyl chloride; or alternatively, 3,5-dichlorobenzoyl chloride.

In an aspect, $L^2$ of the acid halide having Structure AC2 can be any $L^2$ described herein. $L^2$ is described herein as a feature of the $N^2$-phosphinyl amidine compounds and $N^2$-phosphinyl amidine metal salt complexes utilized in various aspects and/or embodiments of this disclosure. Since the acid halides having Structure AC2 can be utilized to prepare $N^2$-phospinyl amidine compounds having Structure NP3, NP8, NP13, and NP18, the aspects and/or embodiments of $L^2$ can utilized without limitation to further describe the acid halides having Structure AC2.

In an embodiment, the acid halide having Structure AC2 can be an ethanedioyl dihalide, a propanedioyl dihalide, a butanedioyl dihalide, a pentanedioyl dihalide, a hexanedioyl dihalide, a heptanedioyl dihalide, an octanedioyl dihalide, a nonanedioyl dihalide, a decanedioyl dihalide, an undecanedioyl dihalide, a dodecanedioyl dihalide, a tridecanedioyl dihalide, a tetradecanedioyl dihalide, a pentadecanedioyl dihalide, a hexadecanedioyl dihalide, a heptadecanedioyl dihalide, an octadecanedioyl dihalide, a nonadecanedioyl dihalide, an eicosanedioyl dihalide, or a heneicosanedioyl dihalide; or alternatively, a propanedioyl dihalide, a butanedioyl dihalide, a pentanedioyl dihalide, a hexanedioyl dihalide, a heptanedioyl dihalide, an octanedioyl dihalide, a noanedioyl dihalide, a decanedioyl dihalide, an undecanedioyl dihalide, a dodecanedioyl dihalide. In some embodiments, the acid halide having Structure AC2 can be a propanedioyl dihalide, a butanedioyl dihalide, a pentanedioyl dihalide, a hexane-dioyl dihalide, or a heptanedioyl dihalide. In other embodiments, the acid halide having Structure AC2 can be an ethanedioyl dihalide; alternatively, a propanedioyl dihalide; alternatively, a butanedioyl dihalide; alternatively, a pentanedioyl dihalide; alternatively, a hexanedioyl dihalide; alternatively, a heptanedioyl dihalide; alternatively, an octanedioyl dihalide; alternatively, a noanedioyl dihalide; alternatively, a decanedioyl dihalide; alternatively, an undecanedioyl dihalide; alternatively, a dodecane-dioyl dihalide; alternatively, a tridecanedioyl dihalide; alternatively, a tetradecanedioyl dihalide; alternatively, a pentadecanedioyl dihalide; alternatively, a hexadecanedioyl dihalide; alternatively, a heptadecanedioyl dihalide; alternatively, an octadecanedioyl dihalide; alternatively, a nonadecanedioyl dihalide; alternatively, an eicosanedioyl dihalide; or alternatively, a heneicosanedioyl dihalide. In some embodiments, the acid halide having Structure AC2 can be an ethanedioyl dihalide, a propanedioyl dihalide, an n-butanedioyl dihalide, a 2-methylpropanedioyl dihalide, an n-pentanedioyl dihalide, a 2-methylbutanedioyl dihalide, an n-hexanedioyl dihalide, a 2,3-dimethylbutanedioyl dihalide, an n-heptane-dioyl dihalide, a 2,2-dimethylpentanedioyl dihalide, an n-octanedioyl dihalide, or a 2,2,3,3-tetramethyl-butanedioyl dihalide; a propanedioyl dihalide, an n-butanedioyl dihalide, an n-pentanedioyl dihalide, an n-hexanedioyl dihalide, an n-heptanedioyl dihalide, or an n-octanedioyl dihalide; alternatively, an ethanedioyl dihalide; alternatively, a propanedioyl dihalide; alternatively, an n-butanedioyl dihalide; alternatively, a 2-methylpropanedioyl dihalide; alternatively, an n-pentanedioyl dihalide; alternatively, a 2-methylbutanedioyl dihalide; alternatively, an n-hexanedioyl dihalide; alternatively, a 2,3-dimethyl-butanedioyl dihalide; alternatively, an n-heptanedioyl dihalide; alternatively, a 2,2-dimethylpentanedioyl dihalide; alternatively, an n-octanedioyl dihalide; or alternatively, a 2,2,3,3-tetramethylbutanedioyl dihalide. In other embodiments, the acid halide having Structure AC2 can be ethanedioyl dichloride, propanedioyl dichloride, butanedioyl dichloride, pentanedioyl dichloride, hexanedioyl dichloride, heptanedioyl dichloride, octanedioyl dichloride, nonanedioyl dichloride, decanedioyl dichloride, undecanedioyl dichloride, dodecanedioyl dichloride, tridecanedioyl dichloride, tetradecanedioyl dichloride, pentadecanedioyl dichloride, hexadecanedioyl dichloride, heptadecanedioyl dichloride, octadecanedioyl dichloride, nonadecanedioyl dichloride, eicosanedioyl dichloride, or heneicosanedioyl dichloride; or alternatively, propanedioyl dichloride, butanedioyl dichloride, pentanedioyl dichloride, hexanedioyl dichloride, heptanedioyl dichloride, octanedioyl dichloride, noanedioyl dichloride, decanedioyl dichloride, undecanedioyl dichloride, dodecanedioyl dichloride. In some other embodiments, the acid halide having Structure AC2 propanedioyl dichloride, butanedioyl dichloride, pentanedioyl dichloride, hexanedioyl dichloride, or heptanedioyl dichloride. In yet other embodiments, the acid halide having Structure AC2 can be ethanedioyl dichloride; alternatively, propanedioyl dichloride; alternatively, butanedioyl dichloride; alternatively, pentanedioyl dichloride; alternatively, hexanedioyl dichloride; alternatively, heptanedioyl dichloride; alternatively, octanedioyl dichloride; alternatively, noanedioyl dichloride; alternatively, decanedioyl dichloride; alternatively, undecanedioyl dichloride; alternatively, dodecanedioyl dichloride; alternatively, tridecanedioyl dichloride; alternatively, tetradecanedioyl dichloride; alternatively, pentadecanedioyl dichloride; alternatively, hexadecanedioyl dichloride; alternatively, heptadecanedioyl dichloride; alternatively, octadecanedioyl dichloride; alternatively, nonadecanedioyl dichloride; alternatively, eicosanedioyl dichloride; or alternatively, heneicosanedioyl dichloride. In further embodiments, the acid halide having Structure AC2 can be ethanedioyl dichloride, propanedioyl dichloride, n-butanedioyl dichloride, 2-methylpropanedioyl dichloride, n-pentanedioyl dichloride, 2-methylbutanedioyl dichloride, n-hexanedioyl dichloride, 2,3-dimethylbutanedioyl dichloride, n-heptanedioyl dichloride, 2,2-dimethylpentanedioyl dichloride, n-octanedioyl dichloride, or 2,2,3,3-tetramethylbutanedioyl dichloride; alternatively, propanedioyl dichloride, n-butanedioyl dichloride, n-pentanedioyl dichloride, n-hexanedioyl dichloride, n-heptanedioyl dichloride, or n-octanedioyl dichloride; alternatively, ethanedioyl dichloride; alternatively, propanedioyl dichloride; alternatively, n-butanedioyl dichloride; alternatively, 2-methylpropanedioyl dichloride; alternatively, n-pentanedioyl dichloride; alternatively, 2-methylbutanedioyl dichloride; alternatively, n-hexanedioyl dichloride; alternatively, 2,3-dimethylbutanedioyl dichloride; alternatively, n-heptanedioyl dichloride; alternatively, 2,2-dimethylpentanedioyl dichloride; alternatively, n-octanedioyl dichloride; or alternatively, 2,2,3,3-tetramethylbutanedioyl dichloride.

In an aspect, the acid halide having Structure AC2 can have the formula ClC(O)—$CR^{1a}R^{2a}(CH_2)_tCR^{3a}R^{4a}$—C(O)Cl. $R^{1a}$, $R^{2a}$, $R^{3a}$, $R^{4a}$, and t are described herein as embodiments of an $L^2$ group having structure —$CR^{1a}$, $R^{2a}(CH_2)_t$ $CR^{3a}R^{4a}$—. The descriptions of $R^{1a}$, $R^{2a}$, $R^{3a}$, $R^{4a}$, and t can be utilized without limitation to further describe the acid halides having the formula ClC(O)—$CR^{1a}R^{2a}(CH_2)_t$ $CR^{3a}R^{4a}$—C(O)Cl. In an embodiment, the $X^3$ of the acid halide having the structure ClC(O)—$CR^{1a}R^{2a}(CH_2)_t$ $CR^{3a}R^{4a}$—C(O)Cl can be a chloride or a bromide; alternatively, a chloride; or alternatively, a bromide.

In an embodiment, the acid halide having Structure AC2 can be a cyclobutanedicarbonyl-halide, a substituted cyclobutanedicarbonylhalide, a cyclopentanedicarbonylhalide, a substituted cyclopentanedicarbonylhalide, a cyclohexanedicarbonylhalide, a substituted cyclohexanedicarbonyl-halide, a cycloheptanedicarbonylhalide, a substituted cycloheptanedicarbonylhalide, a cyclooctane-dicarbonylhalide, or a substituted cyclooctanedicarbonylhalide. In some embodiments, the acid halide having Structure AC2 can be a cyclopentanedicarbonylhalide, a substituted cyclopentanedicarbonyl-halide, a cyclohexanedicarbonylhalide, or a substituted cyclohexanedicarbonylhalide. In other embodiments, the acid halide having Structure AC2 can be a cyclobutanedicarbonylhalide or a substituted cyclobutanedicarbonylhalide; alternatively, a cyclopentanedicarbonylhalide or a substituted cyclopentane-dicarbonylhalide; alternatively, a cyclohexanedicarbonylhalide or a substituted cyclohexanedicarbonylhalide; alternatively, a cycloheptanedicarbonylhalide or a substituted cycloheptanedicarbonylhalide; or alternatively, a cyclooctanedicarbonylhalide or a substituted cyclooctanedicarbonylhalide. In further embodiments, the acid halide having Structure AC2 can be a cyclopentanedicarbonylhalide; alternatively, a substituted cyclopentanedicarbonylhalide; a cyclohexanedicarbonylhalide; or alternatively, a substituted cyclohexanedicarbonylhalide. In other embodiments, the acid halide having Structure AC2 can be cyclobutanedicarbonylchloride, a substituted cyclobutanedicarbonylchloride, cyclopentanedicarbonyl-chloride, a substituted cyclopentanedicarbonylchloride, cyclohexanedicarbonylchloride, a substituted cyclohexanedicarbonylchloride, cycloheptanedicarbonylchloride, a substituted cycloheptanedicarbonylchloride, cyclooctanedicarbonylchloride, or a substituted cyclooctanedicarbonylchloride. In some other embodiments, the acid halide having Structure AC2 can be cyclopentanedicarbonylchloride, a substituted cyclopentanedicarbonylchloride, cyclohexanedicarbonylchloride, a substituted cyclohexanedicarbonyl-chloride. In yet other embodiments, the acid halide having Structure AC2 can be cyclobutanedicarbonylchloride or a substituted cyclobutanedicarbonylchloride; alternatively, cyclopentanedicarbonylchloride or a substituted cyclopentanedicarbonylchloride; alternatively, cyclohexanedicarbonylchloride or a substituted cyclohexanedicarbonylchloride; alternatively, cycloheptanedicarbonylchloride or a substituted cycloheptanedicarbonylchloride; or alternatively, cyclooctanedicarbonylchloride, or a substituted cyclooctanedicarbonylchloride. In still further embodiments, the acid halide having Structure AC2 can be a cyclopentanedicarbonylchloride; alternatively, a substituted cyclopentanedicarbonylchloride; cyclohexanedicarbonylchloride; or alternatively, a substituted cyclohexanedicarbonylchloride.

In an embodiment, the acid halide having Structure AC2 can be a 1,3-cyclopentanedicarbonyl-halide, a substituted 1,3-cyclopentanedicarbonylhalide, a 1,3-cyclohexanedicarbonylhalide, a substituted 1,3-cyclohexanedicarbonylhalide, a 1,4-cyclohexanedicarbonylhalide, or a substituted 1,4-cyclohexane-dicarbonylhalide; alternatively, a 1,3-cyclopentanedicarbonylhalide, a 1,3-cyclohexanedicarbonylhalide, or a 1,4-cyclohexanedicarbonylhalide. In some embodiments, the acid halide having Structure AC2 can be a 1,3-cyclopentanedicarbonylhalide or a substituted 1,3-cyclopentanedicarbonylhalide; alternatively, a 1,3-cyclohexanedicarbonylhalide, a substituted 1,3-cyclohexanedicarbonylhalide, a 1,3-cyclohexane-dicarbonylhalide, or a substituted 1,4-cyclohexanedicarbonylhalide; alternatively, a 1,3-cyclohexane-dicarbonylhalide or a substituted 1,3-cyclohexanedicarbonylhalide; alternatively, a 1,4-cyclohexane-dicarbonylhalide or a substituted 1,4-cyclohexanedicarbonylhalide; alternatively, a 1,3-cyclopentane-dicarbonylhalide; alternatively, a 1,3- cyclohexanedicarbonylhalide; or alternatively, a 1,4-cyclohexane-dicarbonylhalide. In an embodiment, the acid halide having Structure AC2 can be 1,3-cyclopentane-dicarbonylchloride, a substituted 1,3-cyclopentanedicarbonylchloride, 1,3-cyclohexanedicarbonyl-chloride, a substituted 1,3-cyclohexanedicarbonylchloride, 1,4-cyclohexanedicarbonylchloride, or a substituted 1,4-cyclohexanedicarbonylchloride; alternatively, 1,3-cyclopentanedicarbonylchloride, 1,3-cyclohexanedicarbonylchloride, or 1,4-cyclohexanedicarbonylchloride. In some embodiments, the acid halide having Structure AC2 can be 1,3-cyclopentanedicarbonylchloride or a substituted 1,3-cyclopentanedicarbonylchloride; alternatively, 1,3-cyclohexanedicarbonylchloride or a substituted 1,3-cyclohexanedicarbonylchloride, 1,3-cyclohexanedicarbonylchloride, or a substituted 1,4-cyclohexane-dicarbonylchloride; alternatively, 1,3-cyclohexanedicarbonylchloride or a substituted 1,3-cyclohexane-dicarbonylchloride; alternatively, 1,4-cyclohexanedicarbonylchloride or a substituted 1,4-cyclohexane-dicarbonylchloride; alternatively, 1,3-cyclopentanedicarbonylchloride; alternatively, 1,3-cyclohexanedicarbonylchloride; or alternatively, 1,4-cyclohexanedicarbonylchloride. $L^2$ substituents and substituent patterns for substituted $L^2$ cycloalkane groups are generally disclosed herein and can be utilized without limitation to further describe the substituted cycloalkanedicarbonylhalides or substituted cycloalkane-dicarbonylchlorides which can be utilized as the acid halide having Structure AC2 in the various aspects and/or embodiments described herein.

In an aspect, the acid halide having Structure AC2 can be a bi(cyclylcarbonylhalide), a substituted bi(cyclylcarbonylhalide), a bis(cyclylcarbonylhalide)methane, a substituted bis(cyclylcarbonylhalide)methane, a bis(cyclylcarbonylhalide)ethane, or a substituted bis(cyclylcarbonyl-halide)ethane; or alternatively, a bis(cyclylcarbonylhalide), a bis(cyclylcarbonylhalide)methane, or a bis(cyclylcarbonylhalide)ethane. In an embodiment, the acid halide having Structure AC2 can be a bi(cyclylcarbonylhalide) or a substituted bi(cyclylcarbonylhalide); alternatively, bis(cyclylcarbonyl-halide)methane or a substituted bis(cyclylcarbonylhalide)methane; or alternatively, a bis(cyclylcarbonyl-halide)ethane or a substituted bis(cyclylcarbonylhalide)ethane. In some embodiments, the acid halide having Structure AC2 can be a bi(cyclylcarbonylhalide); alternatively, a substituted bi(cyclylcarbonyl-halide); alternatively, a bis(cyclylcarbonylhalide)methane; alternatively, a substituted bis(cyclylcarbonyl-halide)methane; alternatively, a bis(cyclylcarbonylhalide)ethane; or alternatively, a substituted bis(cyclyl-carbonylhalide)ethane. In an aspect, the acid halide having Structure AC2 can be a bi(cyclohexyl-carbonylhalide), a substituted bi(cyclohexyl-carbonylhalide), a bis(cyclohexylcarbonylhalide)methane, a substituted bis(cyclohexylcarbonylhalide)methane, a bis(cyclohexylcarbonylhalide)ethane, or a substituted bis(cyclohexylcarbonylhalide)ethane; or alternatively, a bi(cyclohexylcarbonylhalide), a bis(cyclohexylcarbonylhalide)methane, or a bis(cyclohexylcarbonylhalide)ethane. In an embodiment, the acid halide having Structure AC2 can be a bi(cyclohexylcarbonylhalide) or a substituted bi(cyclohexyl-carbonylhalide); alternatively, a bis(cyclohexylcarbonylhalide)methane or a substituted bis(cyclohexyl-carbonylhalide)methane; or alternatively, a bis(cyclohexylcarbonylhalide)ethane or a substituted bis(cyclohexylcarbonylhalide)ethane. In some embodiments, the acid halide having Structure AC2 can be a bi(cyclohexylcarbonylhalide); alternatively, a substituted bi(cyclohexylcarbonylhalide); alternatively, a bis(cyclohexylcarbonylhalide)methane; alternatively, a substituted bis(cyclohexyl-carbonylhalide)methane; alternatively, a bis(cyclohexylcarbonylhalide)ethane; or alternatively, a substituted bis(cyclohexylcarbonylhalide)ethane. In an aspect, the acid halide having Structure AC2 can be a bi(cyclylcarbonylchloride), a substituted bi(cyclylcarbonylchloride), a bis(cyclylcarbonyl-chloride)methane, a substituted bis(cyclylcarbonylchloride)methane, a bis(cyclylcarbonylchloride)ethane, or a substituted bis(cyclylcarbonylchloride)ethane; or alternatively, a bis(cyclylcarbonylchloride), a bis(cyclylcarbonylchloride)methane, or a bis(cyclylcarbonylchloride)ethane. In an embodiment, the acid halide having Structure AC2 can be a bi(cyclylcarbonylchloride) or a substituted bi(cyclylcarbonyl-chloride); alternatively, bis(cyclylcarbonylchloride)methane or a substituted bis(cyclylcarbonyl-chloride)methane; or alternatively, a bis(cyclylcarbonylchloride)ethane or a substituted bis(cyclyl-carbonylchloride)ethane. In some embodiments, the acid halide having Structure AC2 can be a bi(cyclylcarbonylchloride); alternatively, a substituted bi(cyclylcarbonylchloride); alternatively, a bis(cyclylcarbonylchloride)methane; alternatively, a substituted bis(cyclylcarbonylchloride)methane; alternatively, a bis(cyclylcarbonylchloride)ethane; or alternatively, a substituted bis(cyclylcarbonyl-chloride)ethane. In other embodiments, the acid halide having Structure AC2 can be bi(cyclohexyl-carbonylchloride), a substituted bi(cyclohexy-lcarbonylchloride), bis(cyclohexylcarbonylchloride)-methane, a substituted bis(cyclohexylcarbonylchloride)methane, bis(cyclohexylcarbonylchloride)ethane, or a substituted bis(cyclohexylcarbonylchloride)ethane; or alternatively, bi(cyclohexylcarbonylchloride), bis(cyclohexylcarbonylchloride)methane, or bis(cyclohexylcarbonylchloride)ethane. In some other embodiments, the acid halide having Structure AC2 can be bi(cyclohexylcarbonylchloride) or a substituted bi(cyclohexylcarbonylchloride); alternatively, bis(cyclohexylcarbonylchloride)methane or a substituted bis(cyclohexylcarbonyl-chloride)methane; or alternatively, bis(cyclohexylcarbonylchloride)-ethane or a substituted bis(cyclohexylcarbonylchloride)ethane. In yet other embodiments, the acid halide having Structure AC2 can be bi(cyclohexylcarbonylchloride); alternatively, a substituted bi(cyclohexyl-carbonylchloride); alternatively, bis(cyclohexylcarbonylchloride)methane; alternatively, a substituted bis(cyclohexylcarbonylchloride)methane; alternatively, bis(cyclohexylcarbonylchloride)ethane; or alternatively, a substituted bis(cyclohexylcarbonylchloride)ethane. $L^2$ substituents and substituent patterns for substituted $L^2$ bicyclylene groups, bis(cyclylene)methane groups, and bis(cyclylene)ethane groups are generally disclosed herein and can be utilized without limitation to further describe the substituted bi(cyclylcarbonylhalide)s, substituted bi(cyclylcarbonyl-chloride)s, substituted bis(cyclyl-carbonylhalide)methanes, substituted bis(cyclylcarbonylchloride)methanes, substituted bis(cyclyl-carbonylhalide)ethanes, and substituted bis(cyclylcarbonylchloride)ethanes which can be utilized as the acid halide having Structure AC2 in the various aspects and/or embodiments described herein.

In an embodiment, the acid halide having Structure AC2 can be a 4,4'-bicyclohexyl-dicarbonylhalide, a 3,3'-disubstituted-4,4'-bicyclohexyldicarbonylhalide, a 3,3',5,5'-tetrasubstituted-4,4'-bicyclohexyldicarbonylhalide, a bis(4-cyclohexylcarbonylhalide)methane, a bis(3-substituted-4-cyclohexylcarbonylhalide)methane, a bis(3,5-disubstituted-4-cyclohexylcarbonylhalide)methane, a bis-1,2-(4-cyclohexylcarbonylhalide)ethane, a bis-1,2-(3-substituted-4-cyclohexylcarbonylhalide)ethane, a bis-1,2-(3,5-disubstituted-4-cyclohexylcarbonylhalide)ethane. In some embodiments, the acid halide having Structure AC2 can be 4,4'-bicyclohexyldicarbonylhalide, a 3,3'-disubstituted-4,4'- bicyclohexyl-dicarbonylhalide, a 3,3',5,5'-tetrasubstituted-4,4'-bicyclohexyldicarbonylhalide; alternatively, a bis(4-cyclohexylcarbonylhalide)methane, a bis(3-substituted-4-cyclohexylcarbonylhalide)methane or a bis(3,5-disubstituted-4-cyclohexylcarbonylhalide)methane; alternatively, a bis-1,2-(4-cyclohexylcarbonyl-halide)ethane, a bis-1,2-(3-substituted-4-cyclohexylcarbonylhalide)ethane or a bis-1,2-(3,5-disubstituted-4-cyclohexylcarbonylhalide)ethane. In other embodiments, the acid halide having Structure AC2 can be a 4,4'-bicyclohexyldicarbonylhalide; alternatively, a 3,3'-disubstituted-4,4'-bicyclohexyldicarbonylhalide; alternatively, a 3,3',5,5'-tetrasubstituted-4,4'-bicyclohexyldicarbonylhalide; alternatively, a bis(4-cyclohexylcarbonylhalide)methane; alternatively, a bis(3-substituted-4-cyclohexylcarbonylhalide)-methane; alternatively, a bis(3,5-disubstituted-4-cyclohexylcarbonylhalide)methane; alternatively, a bis-1,2-(4-cyclohexylcarbonylhalide)ethane; alternatively, a bis-1,2-(3-substituted-4-cyclohexylcarbonyl-halide)ethane; or alternatively, a bis-1,2-(3,5-disubstituted-4-cyclohexylcarbonylhalide)ethane.

Generally, any bis(cyclohexylcarbonylhalide)ethane disclosed herein (substituted or unsubstituted) can be a bis-1,1-(cyclohexylcarbonylhalide)ethane or a bis-1,2-(cyclohexylcarbonylhalide)ethane group; alternatively, a bis-1,1-(cyclohexylcarbonylhalide)ethane; or alternatively, a bis-1,2-(cyclohexylcarbonyl-halide)ethane. In other embodiments, the acid halide having Structure AC2 can be 4,4'-bicyclohexyl-dicarbonylchloride, a 3,3'-disubstituted-4,4'-bicyclohexyldicarbonylchloride, a 3,3',5,5'-tetrasubstituted-4,4'-bicyclohexyldicarbonylchloride, bis(4-cyclohexylcarbonylchloride)methane, a bis(3-substituted-4-cyclohexylcarbonylchloride)methane, a bis(3,5-disubstituted-4-cyclohexylcarbonylchloride)methane, bis-1,2-(4-cyclohexylcarbonylchloride)ethane, a bis-1,2-(3-substituted-4-cyclohexylcarbonylchloride)ethane, or a bis-1,2-(3,5-disubstituted-4-cyclohexylcarbonylchloride)ethane.

In some other embodiments, the acid halide having Structure AC2 can be 4,4'-bicyclohexyldicarbonylchloride, a 3,3'-disubstituted-4,4'-bicyclohexyldicarbonylchloride, a 3,3',5,5'-tetrasubstituted-4,4'-bicyclohexyldicarbonylchloride; alternatively, bis(4-cyclohexylcarbonylchloride)methane, a bis(3-substituted-4-cyclohexylcarbonyl-chloride)methane or a bis(3,5-disubstituted-4-cyclohexylcarbonylchloride)methane; or alternatively, bis-1,2-(4-cyclohexylcarbonylchloride)ethane, a bis-1,2-(3-substituted-4-cyclohexylcarbonylchloride)ethane or a bis-1,2-(3,5-disubstituted-4-cyclohexylcarbonylchloride)ethane. In yet other embodiments, the acid halide having Structure AC2 can be 4,4'-bicyclohexyldicarbonylchloride; alternatively, a 3,3'-disubstituted-4,4'-bicyclohexyldicarbonylchloride; alternatively, a 3,3',5,5'-tetrasubstituted-4,4'-bicyclohexyldicarbonylchloride; alternatively, bis(4-cyclohexylcarbonylchloride)methane; alternatively, a bis(3-substituted-4-cyclohexylcarbonylchloride)methane; alternatively, a bis(3,5-disubstituted-4-cyclohexylcarbonylchloride)methane; alternatively, bis-1,2-(4-cyclohexylcarbonylchloride)ethane; alternatively, a bis-1,2-(3-substituted-4-cyclohexylcarbonylchloride)ethane; or alternatively, a bis-1,2-(3,5-disubstituted-4-cyclohexylcarbonylchloride)ethane. Generally, any bis(cyclohexylcarbonyl-chloride)ethane disclosed herein (substituted or unsubstituted) can be a bis-1,1-(cyclohexylcarbonyl-chloride)ethane or a bis-1,2-(cyclohexylcarbonylchloride)ethane group; alternatively, a bis-1,1-(cyclohexylcarbonylchloride)ethane; or alternatively, a bis-1,2-(cyclohexylcarbonylchloride)ethane. Substituents for the substituted $L^2$ bicyclohex-4,4'-ylene groups, bis(cyclohex-4-ylene)methane groups, and a bis-1,2-(cyclohex-4-ylene) ethane groups are generally disclosed herein and can be utilized without limitation to further describe the substituted 4,4'-bicyclohexyldicarbonylhalides, substituted 4,4'-bicyclohexyldicarbonychlorides, substituted bis(4-cyclohexylcarbonylhalide)methanes, substituted bis(4-cyclohexylcarbonylchloride)methanes, substituted bis-1,2-(4-cyclohexylcarbonylhalide)ethanes, and substituted bis-1,2-(4-cyclohexylcarbonylhalide)ethanes which can be utilized as the acid halide having Structure AC2 in the various aspects and/or embodiments described herein.

In an aspect, the acid halide having Structure AC2 can be a benzenedicarbonylhalide or a substituted benzenedicarbonylhalide. In an embodiment, the acid halide having Structure AC2 can be a benzenedicarbonylhalide; or alternatively, a substituted benzenedicarbonylhalide. In some embodiments, the acid halide having Structure AC2 can be a 1,2-benzenedicarbonylhalide or a substituted 1,2-benzene-dicarbonylhalide; alternatively, a 1,2-benzenedicarbonylhalide; or alternatively, a substituted 1,2-benzenedicarbonylhalide. In other embodiments, the acid halide having Structure AC2 can be a 1,3-benzenedicarbonylhalide or a substituted 1,3-benzenedicarbonylhalide; alternatively, a 1,3-benzene-dicarbonylhalide; or alternatively, a substituted 1,3-benzenedicarbonylhalide. In yet other embodiments, the acid halide having Structure AC2 can be a 1,4-benzenedicarbonylhalide or a substituted 1,4-benzene-dicarbonylhalide; alternatively, a 1,4-benzenedicarbonylhalide; or alternatively, a substituted 1,4-benzenedicarbonylhalide. In further embodiments, the acid halide having Structure AC2 can be a 1,2-benzenedicarbonylhalide, a 1,3-benzenedicarbonylhalide, or a 1,4-benzenedicarbonylhalide; alternatively, a 1,3-benzenedicarbonylhalide, or a 1,4-benzenedicarbonylhalide. In other embodiments, the acid halide having Structure AC2 can be a substituted 1,2-benzenedicarbonylhalide, a substituted 1,3-benzene-dicarbonylhalide, or a substituted 1,4-benzenedicarbonylhalide; alternatively, a substituted 1,3-benzene-dicarbonylhalide or a substituted 1,4-benzenedicarbonylhalide. In a non-limiting embodiment, the acid halide having Structure AC2 can be a 2,6-disubstituted 1,4-benzenedicarbonylhalide, a 2,3-disubstituted 1,4-benzenedicarbonylhalide, a 2,5-disubstituted 1,4-benzenedicarbonylhalide, or a 2,3,5,6-tetrasubstituted 1,4-benzenedicarbonylhalide. In some embodiments, the acid halide having Structure AC2 can be a 2,6-disubstituted 1,4-benzenedicarbonylhalide or a 2,5-disubstituted 1,4-benzenedicarbonyl-halide; alternatively, a 2,6-disubstituted 1,4-benzenedicarbonylhalide; alternatively, a 2,3-disubstituted 1,4-benzenedicarbonylhalide; alternatively, a 2,5-disubstituted 1,4-benzenedicarbonylhalide; or alternatively, a 2,3,5,6-tetrasubstituted 1,4-benzenedicarbonylhalide. In other embodiments, the acid halide having Structure AC2 can be a benzenedicarbonylchloride or a substituted benzenedicarbonyl-chloride. In an embodiment, the acid halide having Structure AC2 can be a benzenedicarbonylchloride; or alternatively, a substituted benzenedicarbonylchloride. In some other embodiments, the acid halide having Structure AC2 can be 1,2-benzenedicarbonylchloride or a substituted 1,2-benzenedicarbonyl-chloride; alternatively, 1,2-benzenedicarbonylchloride; or alternatively, a substituted 1,2-benzene-dicarbonylchloride. In yet other embodiments, the acid halide having Structure AC2 can be 1,3-benzenedicarbonylchloride or a substituted 1,3-benzenedicarbonylchloride; alternatively, 1,3-benzene-dicarbonylchloride; or alternatively, a substituted 1,3-benzenedicarbonylchloride. In further embodiments, the acid halide having Structure AC2 can be 1,4-benzenedicarbonylchloride or a substituted 1,4-benzenedicarbonylchloride; alternatively, 1,4-benzenedicarbonylchloride; or alternatively, a substituted 1,4-benzenedicarbonylchloride. In some further embodiments, the acid halide having Structure AC2 can be 1,2-benzenedicarbonylchloride, 1,3-benzenedicarbonylchloride, or 1,4-benzene-dicarbonylchloride; alternatively, 1,3-benzenedicarbonylchloride or 1,4-benzenedicarbonylchloride. In yet further embodiments, the acid halide having Structure AC2 can be a substituted 1,2-benzene-dicarbonylchloride, a substituted 1,3-benzenedicarbonylchloride, or a substituted 1,4-benzenedicarbonyl-chloride; alternatively, a substituted 1,3-benzenedicarbonylchloride or a substituted 1,4-benzene-dicarbonylchloride. In some non-limiting embodiments, the acid halide having Structure AC2 can be a 2,6-disubstituted 1,4-benzenedicarbonylchloride, a 2,3-disubstituted 1,4-benzenedicarbonylchloride, a 2,5-disubstituted 1,4-benzenedicarbonylchloride, or a 2,3,5,6-tetrasubstituted 1,4-benzenedicarbonyl-chloride. In some other embodiments, the acid halide having Structure AC2 can be a 2,6-disubstituted 1,4-benzenedicarbonylchloride or a 2,5-disubstituted 1,4-benzenedicarbonylchloride; alternatively, a 2,6-disubstituted 1,4-benzenedicarbonylchloride; alternatively, a 2,3-disubstituted 1,4-benzenedicarbonyl-chloride; alternatively, a 2,5-disubstituted 1,4-benzenedicarbonylchloride; or alternatively, a 2,3,5,6-tetrasubstituted 1,4-benzenedicarbonylchloride. $L^2$ substituents and substituent patterns for substituted $L^2$ phenylene groups are generally disclosed herein and can be utilized without limitation to further describe the substituted benzenedicarbonylhalides or substituted benzenedicarbonylchlorides which can be utilized as the acid halide having Structure AC2 in the various aspects and/or embodiments described herein.

In an aspect, the acid halide having Structure AC2 can be a naphthalenedicarbonylhalide or a substituted naphthalenedicarbonylhalide. In an embodiment, the acid halide having Structure AC2 can be a naphthalenedicarbonylhalide; or alternatively, a substituted naphthalenedicarbonylhalide. In some embodiments, the acid halide having Structure AC2 can be a 1,3-naphthalenedicarbonylhalide, a substituted 1,3-naphthalenedicarbonylhalide, a 1,4-naphthalenedicarbonylhalide, a substituted 1,4-naphthalenedicarbonylhalide, a 1,5-naphthalenedicarbonylhalide, a substituted 1,5-naphthalenedicarbonylhalide, a 1,6-naphthalenedicarbonylhalide, a substituted 1,6-naphthalenedicarbonylhalide, a 1,7-naphthalenedicarbonylhalide, a substituted 1,7-naphthalenedicarbonylhalide, a 1,8-naphthalenedicarbonylhalide, or a substituted 1,8-naphthalenedicarbonylhalide. In other embodiments, the acid halide having Structure AC2 can be a 1,3-naphthalenedicarbonylhalide or a substituted 1,3-naphthalenedicarbonylhalide; alternatively, a 1,4-naphthalenedicarbonylhalide or a substituted 1,4-naphthalenedicarbonylhalide; alternatively, a 1,5-naphthalenedicarbonylhalide or a substituted 1,5-naphthalenedicarbonylhalide; alternatively, a 1,6-naphthalenedicarbonylhalide or a substituted 1,6-naphthalenedicarbonylhalide; alternatively, a 1,7-naphthalenedicarbonylhalide or a substituted 1,7-naphthalenedicarbonylhalide; or alternatively, a 1,8-naphthalenedicarbonylhalide or a substituted 1,8-naphthalenedicarbonylhalide. In yet other embodiments, acid halide having Structure AC2 can be a 1,3-naphthalenedicarbonylhalide; alternatively, a substituted 1,3-naphthalenedicarbonylhalide; alternatively, a 1,4-naphthalenedicarbonylhalide; alternatively, a substituted 1,4-naphthalenedicarbonylhalide; alternatively, a 1,5-naphthalenedicarbonylhalide; alternatively, a substituted 1,5-naphthalenedicarbonyl-halide; alternatively, a 1,6-naphthalenedicarbonylhalide; alternatively, a substituted 1,6-naphthalenedicarbonylhalide; alternatively, a 1,7-naphthalenedicarbonylhalide; alternatively, a substituted 1,7-naphthalenedicarbonylhalide; alternatively, a 1,8-naphthalenedicarbonylhalide; or alternatively, a substituted 1,8-naphthalenedicarbonylhalide. In other embodiments, the acid halide having Structure AC2 can be a naphthalenedicarbonylchloride or a substituted naphthalenedicarbonylchloride. In some other embodiments, the acid halide having Structure AC2 can be a naphthalenedicarbonylchloride; or alternatively, a substituted naphthalenedicarbonylchloride. In yet other embodiments, the acid halide having Structure AC2 can be 1,3-naphthalenedicarbonylchloride, a substituted 1,3-naphthalene-dicarbonylchloride, 1,4-naphthalenedicarbonylchloride, a substituted 1,4-naphthalenedicarbonylchloride, 1,5-naphthalenedicarbonylchloride, a substituted 1,5-naphthalenedicarbonylchloride, 1,6-naphthalene-dicarbonylchloride, a substituted 1,6-naphthalenedicarbonylchloride, 1,7-naphthalenedicarbonylchloride, a substituted 1,7-naphthalenedicarbonylchloride, 1,8-naphthalenedicarbonylchloride, or a substituted 1,8-naphthalenedicarbonylchloride. In further embodiments, the acid halide having Structure AC2 can be 1,3-naphthalenedicarbonylchloride or a substituted 1,3-naphthalenedicarbonylchloride; alternatively, 1,4-naphthalenedicarbonylchloride or a substituted 1,4-naphthalenedicarbonylchloride; alternatively, 1,5-naphthalenedicarbonylchloride or a substituted 1,5-naphthalenedicarbonylchloride; alternatively, 1,6-naphthalenedicarbonylchloride or a substituted 1,6-naphthalenedicarbonylchloride; alternatively, 1,7-naphthalenedicarbonylchloride or a substituted 1,7-naphthalenedicarbonylchloride; or alternatively, 1,8-naphthalenedicarbonylchloride or a substituted 1,8-naphthalenedicarbonylchloride. In yet further embodiments, acid halide having Structure AC2 can be 1,3-naphthalenedicarbonylchloride; alternatively, a substituted 1,3-naphthalenedicarbonylchloride; alternatively, 1,4-naphthalenedicarbonylchloride; alternatively, a substituted 1,4-naphthalenedicarbonylchloride; alternatively, 1,5-naphthalenedicarbonyl-chloride; alternatively, a substituted 1,5-naphthalenedicarbonylchloride; alternatively, 1,6-naphthalene-dicarbonylchloride; alternatively, a substituted 1,6-naphthalenedicarbonylchloride; alternatively, 1,7-naphthalenedicarbonylchloride; alternatively, a substituted 1,7-naphthalenedicarbonylchloride; alternatively, 1,8-naphthalenedicarbonylchloride; or alternatively, a substituted 1,8-naphthalene-dicarbonylchloride. $L^2$ substituents and substituent patterns for substituted $L^2$ naphthylene groups are generally disclosed herein and can be utilized without limitation to further describe the substituted naphthalenedicarbonylhalides or substituted naphthalenedicarbonylchlorides which can be utilized as the acid halide having Structure AC2 in the various aspects and/or embodiments described herein.

In an aspect, the acid halide having Structure AC2 can be a bi(phenylcarbonylhalide), a substituted bi(phenylcarbonylhalide), a bis(phenylcarbonylhalide)methane group, a substituted bis(phenylcarbonylhalide)methane group, a bis(phenylcarbonylhalide)ethane group, or a substituted bis (phenylcarbonylhalide)ethane group; or alternatively, a bi(phenylcarbonylhalide), a bis(phenyl-carbonylhalide) methane group, or a bis(phenylcarbonylhalide)ethane group. In an embodiment, the acid halide having Structure AC2 can be a bi(phenylcarbonylhalide) or a substituted bi(phenylcarbonylhalide); alternatively, bis(phenylcarbonylhalide)methane group or a substituted bis(phenylcarbonylhalide)methane group; or alternatively, a bis(phenylcarbonylhalide)ethane group or a substituted bis(phenylcarbonyl-halide)ethane group. In some embodiments, the acid halide having Structure AC2 can be a bi(phenyl-carbonylhalide); alternatively, a substituted bi(phenylcarbonylhalide); alternatively, a bis (phenylcarbonyl-halide)methane group; alternatively, a substituted bis(phenylcarbonylhalide)methane group; alternatively, a bis(phenylcarbonylhalide)ethane group; or alternatively, a substituted bis(phenylcarbonylhalide)ethane group.

In other embodiments, the acid halide having Structure AC2 can be a bi(phenylcarbonyl-halide), a substituted bi(phenylcarbonylhalide), a bis(phenylcarbonylhalide)methane group, a substituted bis(phenylcarbonylhalide)methane group, a bis(phenylcarbonylhalide)ethane group, or a substituted bis(phenylcarbonylhalide)ethane group; or alternatively, a bi(phenylcarbonylhalide), a bis(phenyl-carbonylhalide)methane group, or a bis(phenylcarbonylhalide)ethane group. In some other embodiments, the acid halide having Structure AC2 can be a bi(phenylcarbonylhalide) or a substituted bi(phenyl-carbonylhalide); alternatively, a bis(phenyl-carbonylhalide)methane group or a substituted bis(phenyl-carbonylhalide)methane group; or alternatively, a bis(phenylcarbonylhalide)ethane group or a substituted bis(phenylcarbonylhalide)ethane group. In yet other embodiments, the acid halide having Structure AC2 can be a bi(phenylcarbonylhalide); alternatively, a substituted bi(phenylcarbonylhalide); alternatively, a bis(phenylcarbonylhalide)methane group; alternatively, a substituted bis(phenylcarbonylhalide)methane group; alternatively, a bis(phenylcarbonylhalide)ethane group; or alternatively, a substituted bis(phenylcarbonylhalide)ethane group. In other embodiments, the acid halide having Structure AC2 can be a bi(phenylcarbonylchloride), a substituted bi(phenylcarbonylchloride), a bis(phenylcarbonylchloride)-methane, a substituted bis(phenylcarbonylchloride)methane, a bis(phenyl-carbonylchloride)ethane, or a substituted bis(phenylcarbonylchloride)ethane; or alternatively, a bi(phenylcarbonylchloride), a bis(phenylcarbonylchloride)methane, or a bis(phenylcarbonylchloride)ethane group. In some other embodiments, the acid halide having Structure AC2 can be a bi(phenylcarbonylchloride) or a substituted bi(phenylcarbonylchloride); alternatively, bis(phenylcarbonylchloride)methane group or a substituted bis(phenylcarbonylchloride)methane group; or alternatively, a bis(phenylcarbonylchloride)ethane group or a substituted bis(phenylcarbonylchloride)ethane group. In yet other embodiments, the acid halide having Structure AC2 can be a bi(phenylcarbonylchloride); alternatively, a substituted bi(phenylcarbonyl-chloride); alternatively, a bis(phenylcarbonylchloride)methane group; alternatively, a substituted bis(phenylcarbonylchloride)methane group; alternatively, a bis(phenylcarbonylchloride)ethane group; or alternatively, a substituted bis(phenylcarbonylchloride)ethane group.

In an embodiment, the acid halide having Structure AC2 can be a 2,2'-bi(phenylcarbonyl-halide), a substituted 2,2'-bi(phenylcarbonylhalide), a 3,3'-bi(phenylcarbonylhalide), a substituted 3,3'-bi(phenylcarbonylhalide), a 4,4'-bi(phenylcarbonylhalide), or a substituted 4,4'-bi(phenylcarbonylhalide); or alternatively, a 3,3'-bi(phenylcarbonylhalide), a substituted 3,3'-bi(phenylcarbonylhalide), a 4,4'-bi(phenylcarbonylhalide), or a substituted 4,4'-bi(phenylcarbonylhalide). In some embodiments, the acid halide having Structure AC2 can be a 2,2'-bi(phenylcarbonylhalide) or a substituted 2,2'-bi(phenylcarbonylhalide); alternatively, a 3,3'-bi(phenylcarbonylhalide) or a substituted 3,3'-bi(phenylcarbonylhalide); or alternatively, a 4,4'-bi(phenylcarbonylhalide) or a substituted 4,4'-bi(phenylcarbonylhalide). In other embodiments, the acid halide having Structure AC2 can be a 2,2'-bi(phenylcarbonylhalide); alternatively, a substituted 2,2'-bi(phenylcarbonylhalide); alternatively, a 3,3'-bi(phenylcarbonylhalide); alternatively, a substituted 3,3'-bi(phenylcarbonylhalide); alternatively, a 4,4'-bi(phenylcarbonylhalide); or alternatively, a substituted 4,4'-bi(phenylcarbonylhalide). In other embodiments, the acid halide having Structure AC2 can be 2,2'-bi(phenylcarbonylchloride), a substituted 2,2'-bi(phenylcarbonylchloride), 3,3'-bi(phenylcarbonylchloride), a substituted 3,3'-bi(phenylcarbonyl-chloride), 4,4'-bi(phenylcarbonylchloride), or a substituted 4,4'-bi(phenylcarbonylchloride); or alternatively, 3,3'-bi(phenylcarbonylchloride), a substituted 3,3'-bi(phenylcarbonylchloride), 4,4'-bi(phenylcarbonylchloride), or a substituted 4,4'-bi(phenylcarbonylchloride). In some other embodiments, the acid halide having Structure AC2 can be 2,2'-bi(phenylcarbonylchloride) or a substituted 2,2'-bi(phenylcarbonylchloride); alternatively, 3,3'-bi(phenylcarbonylchloride) or a substituted 3,3'-bi(phenylcarbonylchloride); or alternatively, 4,4'-bi(phenylcarbonylchloride) or a substituted 4,4'-bi(phenylcarbonylchloride). In yet other embodiments, the acid halide having Structure AC2 can be 2,2'-bi(phenylcarbonylchloride); alternatively, a substituted 2,2'-bi(phenylcarbonylchloride); alternatively, 3,3'-bi(phenylcarbonylchloride); alternatively, a substituted 3,3'-bi(phenylcarbonyl-chloride); alternatively, 4,4'-bi(phenylcarbonylchloride); or alternatively, a substituted 4,4'-bi(phenyl-carbonylchloride).

In an embodiment, the acid halide having Structure AC2 can be bis(2-phenylcarbonylhalide)-methane, a substituted bis(2-phenylcarbonylhalide)methane, a bis(3-phenylcarbonylhalide)methane, a substituted bis(3-phenylcarbonylhalide)methane, a bis(4-phenylcarbonylhalide)methane, or a substituted bis(4-phenylcarbonylhalide)methane; or alternatively, a bis(3-phenylcarbonylhalide)methane, a substituted bis(3-phenylcarbonylhalide)methane, a bis(4-phenylcarbonylhalide)methane, or a substituted bis(4-phenylcarbonylhalide)methane. In some embodiments, the acid halide having Structure AC2 can be a bis(2-phenylcarbonylhalide)methane or a substituted bis(2-phenylcarbonylhalide)methane; alternatively, a bis(3-phenylcarbonylhalide)methane or a substituted bis(3-phenylcarbonylhalide)methane; or alternatively, a bis(4-phenylcarbonylhalide)methane or a substituted bis(4-phenylcarbonylhalide)methane. In other embodiments, the acid halide having Structure AC2 can be a bis(2-phenylcarbonylhalide)-methane; alternatively, a substituted bis(2-phenylcarbonylhalide)methane; alternatively, a bis(3-phenylcarbonylhalide)methane; alternatively, a substituted bis(3-phenylcarbonylhalide)methane; alternatively, a bis(4-phenylcarbonylhalide)methane; or alternatively, a substituted bis(4-phenylcarbonylhalide)methane. In some embodiments, the acid halide having Structure AC2 can be bis(2-phenylcarbonylchloride)-methane, a substituted bis(2-phenylcarbonylchloride)methane, bis(3-phenylcarbonylchloride)methane, a substituted bis(3-phenylcarbonylchloride)methane, bis(4-phenylcarbonylchloride)methane, or a substituted bis(4-phenylcarbonylchloride)methane; or alternatively, bis(3-phenylcarbonylchloride)-methane, a substituted bis(3-phenylcarbonylchloride)methane, bis(4-phenylcarbonylchloride)methane, or a substituted bis(4-phenylcarbonylchloride)methane. In some other embodiments, the acid halide having Structure AC2 can be bis(2-phenylcarbonylchloride)methane or a substituted bis(2-phenylcarbonyl-chloride)methane; alternatively, bis(3-phenylcarbonylchloride)methane or a substituted bis(3-phenyl-carbonylchloride)methane; or alternatively, bis(4-phenylcarbonylchloride)methane or a substituted bis(4-phenylcarbonylchloride)methane. In yet other embodiments, the acid halide having Structure AC2 can be bis(2-phenylcarbonylchloride)methane; alternatively, a substituted bis(2-phenylcarbonylchloride)-methane; alternatively, bis(3-phenylcarbonylchloride)methane; alternatively, a substituted bis (3-phenyl-carbonylchloride)methane; alternatively, bis(4-phenylcarbonylchloride)methane; or alternatively, a substituted bis(4-phenylcarbonylchloride)methane.

In an embodiment, the acid halide having Structure AC2 can be bis(2-phenylcarbonyl-halide)ethane, a substituted bis(2-phenylcarbonylhalide)ethane, a bis(3-phenylcarbonylhalide)ethane, a substituted bis(3-phenylcarbonylhalide)ethane, a bis(4-phenylcarbonylhalide)ethane, or a substituted bis(4-phenylcarbonylhalide)ethane; or alternatively, a bis(3-phenylcarbonylhalide)ethane, a substituted bis(3-phenylcarbonylhalide)ethane, a bis(4-phenylcarbonylhalide)ethane, or a substituted bis(4-phenylcarbonylhalide)ethane. In some embodiments, the acid halide having Structure AC2 can be a bis(2-phenylcarbonylhalide)ethane or a substituted bis(2-phenylcarbonylhalide)ethane; alternatively, a bis(3-phenylcarbonylhalide)ethane or a substituted bis(3-phenylcarbonylhalide)ethane; or alternatively, a bis(4-phenylcarbonylhalide)ethane or a substituted bis(4-phenylcarbonylhalide)ethane. In other embodiments, the acid halide having Structure AC2 can be a bis(2-phenylcarbonylhalide)ethane; alternatively, a substituted bis(2-phenylcarbonylhalide)ethane; alternatively, a bis(3-phenylcarbonyl-halide)ethane; alternatively, a substituted bis(3-phenylcarbonylhalide)ethane; alternatively, a bis(4-phenylcarbonylhalide)ethane; or alternatively, a substituted bis(4-phenylcarbonylhalide)ethane. In other embodiments, the acid halide having Structure AC2 can be bis(2-phenylcarbonylchloride)ethane, a substituted bis(2-phenylcarbonylchloride)ethane, bis(3-phenylcarbonylchloride)ethane, a substituted bis(3-phenylcarbonylchloride)ethane, bis(4-phenylcarbonylchloride)ethane, or a substituted bis(4-phenylcarbonylchloride)ethane; or alternatively, bis(3-phenylcarbonylchloride)ethane, a substituted bis(3-phenylcarbonylchloride)ethane, bis(4-phenylcarbonylchloride)ethane, or a substituted bis(4-phenylcarbonylchloride)ethane. In some other embodiments, the acid halide having Structure AC2 can be bis(2-phenylcarbonylchloride)ethane or a substituted bis(2-phenylcarbonylchloride)ethane; alternatively, bis(3-phenylcarbonylchloride)ethane or a substituted bis(3-phenylcarbonylchloride)ethane; or alternatively, bis(4-phenylcarbonylchloride)ethane or a substituted bis(4-phenylcarbonylchloride)ethane. In yet other embodiments, the acid halide having Structure AC2 can be bis(2-phenylcarbonylchloride)ethane; alternatively, a substituted bis(2-phenylcarbonylchloride)ethane; alternatively, bis(3-phenylcarbonyl-chloride)ethane; alternatively, a substituted bis(3-phenylcarbonylchloride)ethane; alternatively, bis(4-phenylcarbonylchloride)ethane; or alternatively, a substituted bis(4-phenylcarbonylchloride)ethane. Generally, any bis(phenylcarbonylhalide)ethane bis(phenylcarbonylchloride)ethane disclosed herein (substituted or unsubstituted) can be a bis-1,1-(phenylcarbonylhalide)ethane or a bis-1,2-(phenyl-carbonylhalide)ethane group (bis-1,1-(phenylcarbonylchloride)ethane or a bis-1,2-(phenylcarbonyl-chloride)ethane group); alternatively, a bis-1,1-(phenylcarbonylhalide)ethane (bis-1,1-(phenylcarbonyl-chloride)ethane); or alternatively, a bis-1,2-(phenylcarbonylhalide)ethane (or bis-1,2-(phenylcarbonyl-chloride)ethane).

In an embodiment, the acid halide having Structure AC2 can be a 3,3'-disubstituted-4,4'-bi(phenylcarbonylhalide), a 3,3',5,5'-tetrasubstituted-4,4'-bi(phenylcarbonylhalide), a bis(3-substituted-4-phenylcarbonylhalide)methane, a bis(3,5-disubstituted-4-phenylcarbonylhalide)methane, a bis-1,2-(3-substituted-4-phenylcarbonylhalide)ethane, a bis-1,2-(3,5-disubstituted-4-phenylcarbonylhalide)ethane. In some embodiments, the acid halide having Structure AC2 can be a 3,3'-disubstituted 4,4'-bi(phenylcarbonylhalide) or a 3,3',5, 5'-tetrasubstituted-4,4'-bi(phenylcarbonylhalide); alternatively, a bis(3-substituted-4-phenylcarbonylhalide)methane or a bis(3,5-disubstituted-4-phenylcarbonyl-halide)methane; alternatively, a bis-1,2-(3-substituted-4-phenylcarbonylhalide)ethane or a bis-1,2-(3,5-disubstituted-4-phenylcarbonylhalide)ethane. In other embodiments, the acid halide having Structure AC2 can be a 3,3'-disubstituted-4,4'-bi(phenylcarbonylhalide); alternatively, a 3,3',5,5'-tetra-substituted-4,4'-bi(phenylcarbonylhalide); alternatively, a bis(3-substituted-4-phenylcarbonylhalide)-methane; alternatively, a bis(3,5-disubstituted-4-phenylcarbonylhalide)methane; alternatively, a bis-1,2-(3-substituted-4-phenylcarbonylhalide)ethane; or alternatively, a bis-1,2-(3,5-disubstituted-4-phenyl-carbonylhalide)ethane. In some other embodiments, the acid halide having Structure AC2 can be a 3,3'-disubstituted-4,4'-bi(phenylcarbonylchloride), a 3,3',5,5'-tetrasubstituted-4,4'-bi(phenylcarbonyl-chloride), a bis(3-substituted-4-phenylcarbonylchloride)methane, a bis(3,5-disubstituted-4-phenyl-carbonylchloride)methane, a bis-1,2-(3-substituted-4-phenylcarbonylchloride)ethane, a bis-1,2-(3,5-disubstituted-4-phenylcarbonylchloride)ethane. In yet other embodiments, the acid halide having Structure AC2 can be a 3,3'-disubstituted 4,4'-bi(phenylcarbonylchloride) or a 3,3',5, 5'-tetrasubstituted-4,4'-bi(phenylcarbonylchloride); alternatively, a bis(3-substituted-4-phenylcarbonylchloride)methane or a bis(3,5-disubstituted-4-phenylcarbonylchloride)methane; alternatively, a bis-1,2-(3-substituted-4-phenylcarbonylchloride)ethane or a bis-1,2-(3,5-disubstituted-4-phenylcarbonylchloride)ethane. In further embodiments, the acid halide having Structure AC2 can be a 3,3'-disubstituted-4,4'-bi(phenylcarbonyl-chloride); alternatively, a 3,3',5,5'-tetrasubstituted-4,4'-bi(phenylcarbonylchloride); alternatively, a bis(3-substituted-4-phenylcarbonylchloride)methane; alternatively, a bis(3,5-disubstituted-4-phenylcarbonyl-chloride)methane; alternatively, a bis-1,2-(3-substituted-4-phenylcarbonylchloride)ethane; or alternatively, a bis-1,2-(3,5-disubstituted-4-phenylcarbonyl-chloride)ethane.

$L^2$ substituents and substituent patterns for general and specific substituted $L^2$ biphenylene groups, bis(phenylene)methane groups, and bis(phenylene)ethane groups are generally disclosed herein and can be utilized without limitation to further describe the general and specific substituted bi(phenyl-carbonylhalide)s, substituted bi(phenylcarbonylchloride)s, substituted bis(phenylcarbonylhalide)-methanes, substituted bis(phenylcarbonylchloride)methanes, substituted bis(phenylcarbonylhalide)-ethanes, and substituted bis(phenylcarbonylchloride)ethanes which can be utilized as the nitrile having Structure N2 in the various aspects and/or embodiments described herein.

In an embodiment, the acid halide having Structure AC2 can be a di(methylcarbonyl-halide)cycloalkane or a substituted di(methylcarbonylhalide)cycloalkane; alternatively, a di(methyl-carbonylhalide)cycloalkane; di(methylcarbonyl-halide)cycloalkane or a substituted di(methyl-carbonylhalide)cycloalkane; alternatively, a di(methylcarbonylhalide)cycloalkane. The cycloalkane group of the di(methylcarbonylhalide)cycloalkanes or di(methylcarbonylchloride)cycloalkanes (substituted or unsubstituted) can be cyclobutane group, a substituted cyclobutane group, a cyclopentane group, a substituted cyclopentane group, a cyclohexane group, a substituted cyclohexane group, a cycloheptane group, a substituted cycloheptane group, a cyclooctane group, or a substituted cyclooctane group; alternatively, a cyclopentane group, a substituted cyclopentane group, a cyclohexane group, or a substituted cyclohexane group; alternatively, a cyclobutane group or a substituted cyclobutane group; alternatively, a cyclopentane group or a substituted cyclopentane group; alternatively, a cyclohexane group or a substituted cyclohexane group; alternatively, a cycloheptane group or a substituted cyclo-heptane group; or alternatively, a cyclooctane group, or a substituted cyclooctane group. In some embodiments, the cycloalkane group of the di(methylcarbonylhalide)cycloalkanes or di(methylcarbonyl-chloride)cycloalkanes (substituted or unsubstituted) can be cyclobutane group, a cyclopentane group, a cyclohexane group, a cycloheptane group, or a cyclooctane group; or alternatively, a cyclopentane group or a cyclohexane group. In other embodiments, the cycloalkane group of the di(methylcarbonylhalide)-cycloalkanes or di(methylcarbonylchloride)cycloalkanes (substituted or unsubstituted) can be cyclo-pentane group; alternatively, a substituted cyclopentane group; a cyclohexane group; or alternatively, a substituted cyclohexane group.

In an embodiment, the acid halide having Structure AC2 can be a 1,3-di(methylcarbonyl-halide)cyclopentane, a substituted 1,3-di(methylcarbonylhalide)cyclopentane, a 1,3-di(methylcarbonyl-halide)cyclohexane, a substituted 1,3-di(methylcarbonylhalide)cyclohexane, a 1,4-di(methylcarbonyl-halide)cyclohexane, or a substituted 1,4-di(methylcarbonylhalide)cyclohexane; alternatively, a 1,3-di(methylcarbonylhalide)cyclopentane, a 1,3-di(methylcarbonylhalide)cyclohexane, or 1,4-di(methylcarbonylhalide)cyclohexane. In some embodiments, the acid halide having Structure AC2 can be a 1,3-di(methylcarbonylhalide)cyclopentane or a substituted 1,3-di(methylcarbonylhalide)cyclopentane; alternatively, a 1,3-di(methylcarbonylhalide)cyclohexane or a substituted 1,3-di(methylcarbonylhalide)-cyclohexane, a 1,4-di(methylcarbonylhalide)cyclohexane or a substituted 1,4-di(methylcarbonylhalide)-cyclohexane; alternatively, a 1,3-di(methylcarbonylhalide)cyclohexane or a substituted 1,3-di(methyl-carbonylhalide)cyclohexane; alternatively, a 1,4-di(methylcarbonylhalide)cyclohexane or a substituted 1,4-di(methylcarbonylhalide)cyclohexane; alternatively, a 1,3-di(methylcarbonylhalide)cyclopentane; alternatively, a 1,3-di(methylcarbonylhalide)cyclohexane; or alternatively, a 1,4-di(methylcarbonyl-halide)cyclohexane. In other embodiments, the acid halide having Structure AC2 can be 1,3-di(methyl-carbonylchloride)cyclopentane, a substituted 1,3-di(methylcarbonylchloride)cyclopentane, 1,3-di(methyl-carbonylchloride)cyclohexane, a substituted 1,3-di(methylcarbonylchloride)cyclohexane, 1,4-di(methyl-carbonylchloride)cyclohexane, or a substituted 1,4-di(methylcarbonylchloride)cyclohexane; alternatively, 1,3-di(methylcarbonylchloride)cyclopentane, 1,3-di(methylcarbonylchloride)cyclohexane, or 1,4-di(methylcarbonylchloride)cyclohexane. In some other embodiments, the acid halide having Structure AC2 can be 1,3-di(methylcarbonylchloride)cyclopentane or a substituted 1,3-di(methyl-carbonylchloride)cyclopentane; alternatively, 1,3-di(methylcarbonylchloride)cyclohexane, a substituted 1,3-di(methylcarbonylchloride)cyclohexane, 1,4-di(methyl-carbonylchloride)cyclohexane or a substituted 1,4-di(methylcarbonylchloride)cyclohexane; alternatively, 1,3-di(methylcarbonylchloride)cyclohexane or a substituted 1,3-di(methylcarbonylchloride)cyclohexane; alternatively, 1,4-di(methylcarbonylchloride)-cyclohexane or a substituted 1,4-di(methylcarbonylchloride)cyclohexane; alternatively, 1,3-di(methyl-carbonylchloride)cyclopentane; alternatively, a 1,3-di(methylcarbonylchloride)cyclohexane; or alternatively, a 1,4-di(methylcarbonylchloride)cyclohexane.

In other embodiments, the acid halide having Structure AC2 can be a di(methylcarbonyl-halide)benzene, or a substituted di(methylcarbonylhalide)benzene; alternatively, a di(methylcarbonyl-halide) benzene. In some other embodiments, the acid halide having Structure AC2 can be a 1,2-di(methylcarbonylhalide)benzene, a substituted 1,2-di(methylcarbonylhalide)benzene, a 1,3-di(methylcarbonylhalide)benzene, a substituted 1,3-di(methylcarbonylhalide)benzene, a 1,4-di(methylcarbonylhalide)benzene, or a substituted 1,4-di(methylcarbonylhalide)benzene; alternatively, a 1,2-di(methylcarbonylhalide)benzene, a 1,3-di(methylcarbonylhalide)benzene, or a 1,4-di(methylcarbonylhalide)benzene. In yet other embodiments, the acid halide having Structure AC2 can be a 1,2-di(methylcarbonylhalide)benzene or a substituted 1,2-di(methylcarbonylhalide)benzene; alternatively, a 1,3-di(methylcarbonylhalide)benzene or a substituted 1,3-di(methylcarbonylhalide)-benzene; alternatively, a 1,4-di(methylcarbonylhalide)benzene or a substituted 1,4-di(methylcarbonyl-halide)benzene; alternatively, a 1,2-di(methylcarbonylhalide)benzene; alternatively, a 1,3-di(methyl-carbonylhalide)benzene; or alternatively, a 1,4-di(methylcarbonylhalide)benzene. In further embodiments, the acid halide having Structure AC2 can be a di(methylcarbonylchloride)benzene or a substituted di(methylcarbonylchloride)benzene; or alternatively, a di(methylcarbonylchloride)benzene. In yet further embodiments, the acid halide having Structure AC2 can be 1,2-di(methylcarbonylchloride)-benzene, a substituted 1,2-di(methylcarbonylchloride)benzene, 1,3-di(methylcarbonylchloride)benzene, a substituted 1,3-di(methylcarbonylchloride)benzene, 1,4-di(methylcarbonylchloride)benzene, or a substituted 1,4-di(methylcarbonylchloride)benzene; alternatively, 1,2-di(methylcarbonylchloride)-benzene, 1,3-di(methylcarbonylchloride)benzene, or 1,4-di(methylcarbonylchloride)benzene. In other embodiments, the acid halide having Structure AC2 can be 1,2-di(methylcarbonylchloride)benzene or a substituted 1,2-di(methylcarbonylchloride)benzene; alternatively, 1,3-di(methylcarbonylchloride)benzene or a substituted 1,3-di(methylcarbonylchloride)benzene; alternatively, 1,4-di(methylcarbonylchloride)-benzene or a substituted 1,4-di(methylcarbonylchloride)benzene; alternatively, 1,2-di(methylcarbonyl-chloride)benzene; alternatively, 1,3-di(methylcarbonylchloride)benzene; or alternatively, 1,4-di(methyl-carbonylchloride)benzene.

$L^2$ substituents for the general and specific substituted di(methylene)cycloalkane groups and di(methylene)benzene groups are generally disclosed herein and can be utilized without limitation to further describe the general and specific substituted di(methylcarbonylhalide)cycloalkanes, substituted di(methylcarbonylhalide)benzenes, specific substituted di(methylcarbonylchloride)cycloalkanes, and substituted di(methylcarbonylchloride)benzenes which can be utilized as the acid halide having Structure AC2 in the various aspects and/or embodiments described herein.

In an aspect, the acid halide having Structure AC2 can have Structure AC6, AC7, AC8, AC9, AC10, AC11, AC12, AC13, AC14, AC15, AC16, AC17, AC18, or AC19. In some embodiments, the acid halide having Structure AC2 can have Structure AC6, AC7, or AC8; alternatively, AC9, AC10, AC11, or AC12; alternatively, AC13, AC14, or AC15; or alternatively, AC16, AC17, AC18, or AC19. In other embodiments, the acid halide having Structure AC2 can have Structure AC7 or AC8; alternatively, AC9 or AC10; alternatively, AC11 or AC12; alternatively, AC14 or AC15; alternatively, AC16 or AC17; or alternatively, AC18 or AC19. In further embodiments, the acid halide having Structure AC2 can have Structure AC6; alternatively, Structure AC7; alternatively, Structure AC8; alternatively, Structure AC9; alternatively, Structure AC10;

alternatively, Structure AC11; alternatively, Structure AC12; alternatively, Structure AC13; alternatively, Structure AC14; alternatively, Structure AC15; alternatively, Structure AC16; alternatively, Structure AC17; alternatively, Structure AC18; or alternatively, Structure AC19.

TABLE 4

Dicarbonylhalides which can be utilized as the acid halide having Structure AC2.

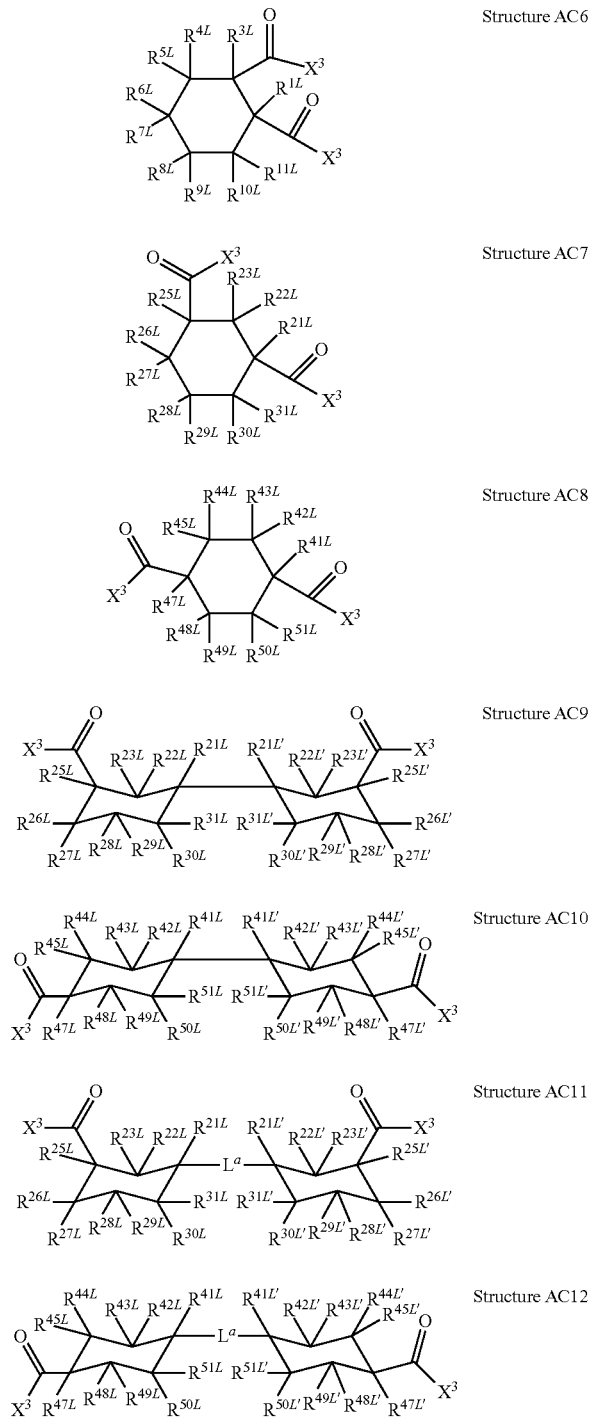

TABLE 4-continued

Dicarbonylhalides which can be utilized as the acid halide having Structure AC2.

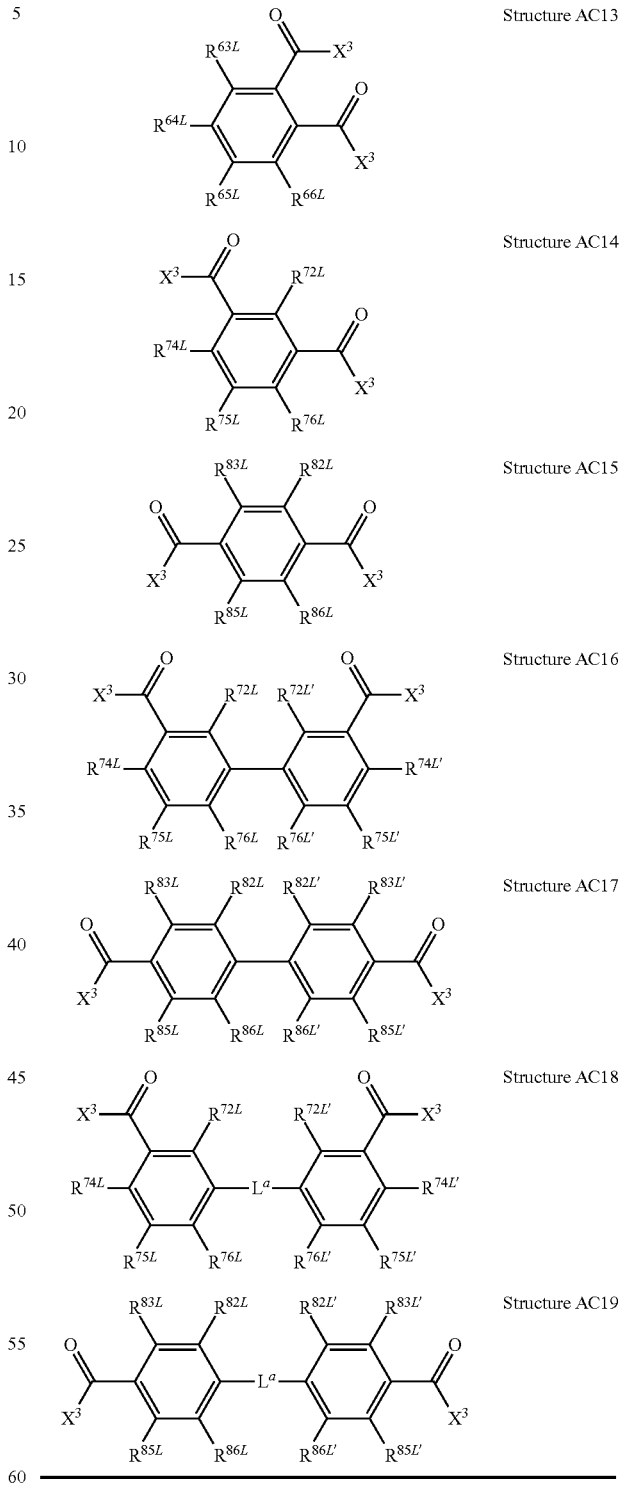

Aspects and embodiments for $R^{1L}$-$R^{11L}$, $R^{21L}$-$R^{31L}$, $R^{21L'}$-$R^{31L'}$, $R^{41L}$-$R^{51L}$, $R^{41L'}$-$R^{51'}$, $R^{62L}$-$R^{66L}$, $R^{72L}$-$R^{76L}$, $R^{72L'}$-$R^{76L'}$, $R^{82L}$-$R^{86L}$, $R^{82L'}$-$R^{86L'}$, and $L^a$, are herein described for $L^2$ which can be utilized in $N^2$-phospinyl amidine compounds have Structure NP3, NP8, NP13, or NP18. These aspects and embodiments can be utilized without limitation to describe the acid halides having Structures AC6-AC19 which can be utilized in the various aspects and/or embodiments described herein. In an embodiment, the $X^3$ of the acid halide having the Structures AC6-AC19 can be a chloride or a bromide; alternatively, a chloride; or alternatively, a bromide.

In a non-limiting embodiment, the acid halide having Structure AC2 can be a 1,4-benzene-dicarbonylhalide, a 2,6-dimethyl-1,4-benzenedicarbonylhalide, a 2,6-diethyl-1,4-benzenedicarbonyl-halide, a 2,6-diisopropyl 1,4-benzenedicarbonylhalide, a 2,6-di-tert-butyl-1,4-benzenedicarbonylhalide, a 2,5-dimethyl-1,4-benzenedicarbonylhalide, a 2,5-diethyl-1,4-benzenedicarbonylhalide, a 2,5-diisopropyl-1,4-benzenedicarbonylhalide, a 2,5-di-tert-butyl-1,4-benzenedicarbonylhalide, or a 2,3,5,6-tetramethyl-1,4-benzenedicarbonylhalide. In other non-limiting embodiments, the acid halide having Structure AC2 can be a 1,4-benzenedicarbonylhalide, a 2,6-dimethyl-1,4-benzenedicarbonylhalide, a 2,6-diethyl-1,4-benzenedicarbonylhalide, a 2,6-diisopropyl-1,4-benzenedicarbonylhalide, or a 2,6-di-tert-butyl-1,4-benzenedicarbonylhalide; alternatively, a 2,5-dimethyl-1,4-benzenedicarbonylhalide, a 2,5-diethyl-1,4-benzenedicarbonylhalide, a 2,5-diisopropyl-1,4-benzenedicarbonylhalide, or a 2,5-di-tert-butyl-1,4-benzenedicarbonylhalide. In yet further non-limiting embodiments, the acid halide having Structure AC2 can be a 1,4-benzenedicarbonylhalide; alternatively, a 2,6-dimethyl-1,4-benzenedicarbonylhalide; alternatively, a 2,6-diethyl-1,4-benzenedicarbonylhalide; alternatively, a 2,6-diisopropyl-1,4-benzene-dicarbonylhalide; alternatively, a 2,6-di-tert-butyl-1,4-benzenedicarbonylhalide; alternatively, a 2,5-dimethyl-1,4-benzenedicarbonylhalide; alternatively, a 2,5-diethyl-1,4-benzenedicarbonylhalide; alternatively, a 2,5-diisopropyl-1,4-benzenedicarbonylhalide; alternatively, a 2,5-di-tert-butyl-1,4-benzenedicarbonylhalide; or alternatively, a 2,3,5,6-tetramethyl-1,4-benzenedicarbonylhalide. In other embodiments, the acid halide having Structure AC2 can be 1,4-benzenedicarbonylchloride, 2,6-dimethyl-1,4-benzenedicarbonylchloride, 2,6-diethyl-1,4-benzenedicarbonylchloride, 2,6-diisopropyl 1,4-benzenedicarbonylchloride, 2,6-di-tert-butyl-1,4-benzenedicarbonylchloride, 2,5-dimethyl-1,4-benzenedicarbonylchloride, 2,5-diethyl-1,4-benzenedicarbonylchloride, 2,5-diisopropyl-1,4-benzenedicarbonylchloride, 2,5-di-tert-butyl-1,4-benzenedicarbonylchloride, or 2,3,5,6-tetramethyl-1,4-benzenedicarbonylchloride. In some other embodiments, the acid halide having Structure AC2 can be 1,4-benzenedicarbonylchloride, 2,6-dimethyl-1,4-benzenedicarbonylchloride, 2,6-diethyl-1,4-benzene-dicarbonylchloride, 2,6-diisopropyl-1,4-benzenedicarbonylchloride, or 2,6-di-tert-butyl-1,4-benzene-dicarbonylchloride; alternatively, 2,5-dimethyl-1,4-benzenedicarbonylchloride, 2,5-diethyl-1,4-benzene-dicarbonylchloride, 2,5-diisopropyl-1,4-benzenedicarbonylchloride, or 2,5-di-tert-butyl-1,4-benzene-dicarbonylchloride. In yet other embodiments, the acid halide having Structure AC2 can be 1,4-benzene-dicarbonylchloride; alternatively, 2,6-dimethyl-1,4-benzenedicarbonylchloride; alternatively, 2,6-diethyl-1,4-benzenedicarbonylchloride; alternatively, 2,6-diisopropyl-1,4-benzenedicarbonylchloride; alternatively, 2,6-di-tert-butyl-1,4-benzenedicarbonylchloride; alternatively, 2,5-dimethyl-1,4-benzenedicarbonylchloride; alternatively, 2,5-diethyl-1,4-benzenedicarbonylchloride; alternatively, 2,5-diisopropyl-1,4-benzenedicarbonylchloride; alternatively, 2,5-di-tert-butyl-1,4-benzenedicarbonyl-chloride; or alternatively, 2,3,5,6-tetramethyl-1,4-benzenedicarbonylchloride.

In a non-limiting embodiment, the acid halide having Structure AC2 can be a 3,3'-dimethyl-4,4'-bi(phenylcarbonylhalide), a 3,3'-diethyl-4,4'-bi(phenylcarbonylhalide), a 3,3'-diisopropyl-4,4'-bi(phenylcarbonylhalide), a 3,3'-di-tert-butyl-4,4'-bi(phenylcarbonylhalide), a 3,3',5,5'-tetramethyl-4,4'-bi(phenylcarbonylhalide), a 3,3',5,5'-tetraethyl-4,4'-bi(phenylcarbonylhalide), a 3,3',5,5'-tetraisopropyl-4,4'-bi(phenylcarbonylhalide), or a 3,3',5,5'-tetra-tert-butyl-4,4'-bi(phenylcarbonylhalide). In some embodiments, the acid halide having Structure AC2 can be a 3,3'-dimethyl-4,4'-bi(phenylcarbonyl-halide), a 3,3'-diethyl-4,4'-bi(phenylcarbonylhalide), a 3,3'-diisopropyl-4,4'-bi(phenylcarbonylhalide), or a 3,3'-di-tert-butyl-4,4'-bi(phenylcarbonylhalide); alternatively, a 3,3',5,5'-tetramethyl-4,4'-bi(phenyl-carbonylhalide), a 3,3',5,5'-tetraethyl-4,4'-bi(phenylcarbonylhalide), a 3,3',5,5'-tetraisopropyl-4,4'-bi(phenylcarbonylhalide), or a 3,3',5,5'-tetra-tert-butyl-4,4'-bi(phenylcarbonylhalide). In other embodiments, the acid halide having Structure AC2 can be a 3,3'-dimethyl-4,4'-bi(phenylcarbonyl-halide); alternatively, a 3,3'-diethyl-4,4'-bi(phenylcarbonylhalide); alternatively, a 3,3'-diisopropyl-4,4'-bi(phenylcarbonylhalide); alternatively, a 3,3'-di-tert-butyl-4,4'-bi(phenylcarbonylhalide); alternatively, a 3,3',5,5'-tetramethyl-4,4'-bi(phenylcarbonylhalide); alternatively, a 3,3',5,5'-tetraethyl-4,4'-bi(phenylcarbonylhalide); alternatively, a 3,3',5,5'-tetraisopropyl-4,4'-bi(phenylcarbonylhalide); or alternatively, a 3,3',5,5'-tetra-tert-butyl-4,4'-bi(phenylcarbonylhalide). In other embodiments, the acid halide having Structure AC2 can be 3,3'-dimethyl-4,4'-bi(phenylcarbonylchloride), 3,3'-diethyl-4,4'-bi(phenyl-carbonylchloride), 3,3'-diisopropyl-4,4'-bi(phenylcarbonylchloride), 3,3'-di-tert-butyl-4,4'-bi(phenylcarbonylchloride), 3,3',5,5'-tetramethyl-4,4'-bi(phenylcarbonylchloride), 3,3',5,5'-tetraethyl-4,4'-bi(phenylcarbonylchloride), 3,3',5,5'-tetraisopropyl-4,4'-bi(phenylcarbonylchloride), or 3,3',5,5'-tetra-tert-butyl-4,4'-bi(phenylcarbonylchloride). In some other embodiments, the acid halide having Structure AC2 can be 3,3'-dimethyl-4,4'-bi(phenylcarbonylchloride), 3,3'-diethyl-4,4'-bi(phenylcarbonylchloride), 3,3'-diisopropyl-4,4'-bi(phenylcarbonylchloride), or 3,3'-di-tert-butyl-4,4'-bi(phenylcarbonylchloride); or alternatively, 3,3',5,5'-tetramethyl-4,4'-bi(phenylcarbonylchloride), 3,3',5,5'-tetraethyl-4,4'-bi(phenyl-carbonylchloride), 3,3',5,5'-tetraisopropyl-4,4'-bi(phenylcarbonylchloride), or 3,3',5,5'-tetra-tert-butyl-4,4'-bi(phenylcarbonylchloride). In yet other embodiments, the acid halide having Structure AC2 can be 3,3'-dimethyl-4,4'-bi(phenylcarbonylchloride); alternatively, 3,3'-diethyl-4,4'-bi(phenylcarbonyl-chloride); alternatively, 3,3'-diisopropyl-4,4'-bi(phenylcarbonylchloride); alternatively, 3,3'-di-tert-butyl-4,4'-bi(phenylcarbonylchloride); alternatively, 3,3',5,5'-tetramethyl-4,4'-bi(phenylcarbonylchloride); alternatively, 3,3',5,5'-tetraethyl-4,4'-bi(phenylcarbonylchloride); alternatively, 3,3',5,5'-tetraisopropyl-4,4'-bi(phenylcarbonylchloride); or alternatively, 3,3',5,5'-tetra-tert-butyl-4,4'-bi(phenylcarbonyl-chloride).

In a non-limiting embodiment, the acid halide having Structure AC2 can be a bis(3-methyl-4-phenylcarbonylhalide)methane, a bis(3-ethyl-4-phenylcarbonylhalide)methane, a bis(3-isopropy-4-phenylcarbonylhalide)methane, a bis (3-tert-butyl-4-phenylcarbonylhalide)methane, a bis(3,5-dimethyl-4-phenylcarbonylhalide)methane, a bis(3,5-diethyl-4-phenylcarbonylhalide)methane, a bis(3,5-diisopropy-4-phenylcarbonylhalide)methane, or a bis(3,5-di-tert-butyl-4-phenylcarbonylhalide)methane. In some embodiments, the acid halide having Structure AC2 can be a bis(3-methyl-4-phenylcarbonyl-halide)methane, a bis(3-ethyl-4-phenylcarbonylhalide)methane, a bis(3-isopropy-4- phenylcarbonyl-halide)methane, or a bis(3-tert-butyl-4-phenylcarbonylhalide)methane; or alternatively, a bis(3,5-dimethyl-4-phenylcarbonylhalide)methane, a bis(3,5-diethyl-4-phenylcarbonylhalide)methane, a bis(3,5-diisopropy-4-phenylcarbonylhalide)methane, or a bis(3,5-di-tert-butyl-4-phenylcarbonylhalide)methane. In other embodiments, the acid halide having Structure AC2 can be a bis(3-methyl-4-phenylcarbonyl-halide)methane; alternatively, a bis(3-ethyl-4-phenylcarbonylhalide)methane; alternatively, a bis(3-isopropy-4-phenylcarbonylhalide)methane; alternatively, a bis(3-tert-butyl-4-phenylcarbonylhalide)methane; alternatively, a bis(3,5-dimethyl-4-phenylcarbonylhalide)methane; alternatively, a bis(3,5-diethyl-4-phenylcarbonylhalide)methane; alternatively, a bis(3,5-diisopropy-4-phenylcarbonylhalide)-methane; or alternatively, a bis(3,5-di-tert-butyl-4-phenylcarbonylhalide)methane. In other embodiments, the acid halide having Structure AC2 can be bis(3-methyl-4-phenylcarbonylchloride)methane, bis(3-ethyl-4-phenylcarbonylchloride)methane, bis(3-isopropy-4-phenylcarbonylchloride)methane, bis(3-tert-butyl-4-phenyl-carbonylchloride)methane, bis(3,5-dimethyl-4-phenylcarbonylchloride)methane, bis(3,5-diethyl-4-phenylcarbonylchloride)methane, bis(3,5-diisopropy-4-phenylcarbonylchloride)methane, or bis(3,5-di-tert-butyl-4-phenylcarbonylchloride)methane. In some other embodiments, the acid halide having Structure AC2 can be bis(3-methyl-4-phenylcarbonylchloride)methane, bis(3-ethyl-4-phenyl-carbonylchloride)methane, bis(3-isopropy-4-phenylcarbonylchloride)methane, bis(3-tert-butyl-4-phenyl-carbonylchloride)methane; or alternatively, bis(3,5-dimethyl-4-phenylcarbonylchloride)methane, bis(3,5-diethyl-4-phenylcarbonylchloride)methane, bis(3,5-diisopropy-4-phenylcarbonylchloride)methane, or bis(3,5-di-tert-butyl-4-phenylcarbonylchloride)methane. In yet other embodiments, the acid halide having Structure AC2 can be bis(3-methyl-4-phenylcarbonylchloride)methane; alternatively, bis(3-ethyl-4-phenylcarbonylchloride)methane; alternatively, bis(3-isopropy-4-phenylcarbonylchloride)methane; alternatively, bis(3-tert-butyl-4-phenylcarbonylchloride)methane; alternatively, bis(3,5-dimethyl-4-phenylcarbonylchloride)methane; alternatively, bis(3,5-diethyl-4-phenylcarbonylchloride)methane; alternatively, bis(3,5-diisopropy-4-phenylcarbonylchloride)methane; or alternatively, bis(3,5-di-tert-butyl-4-phenylcarbonylchloride)methane.

In a non-limiting embodiment, the acid halide having Structure AC2 can be a bis(3-methyl-4-phenylcarbonylhalide)ethane, a bis(3-ethyl-4-phenylcarbonylhalide)ethane, a bis(3-isopropy-4-phenylcarbonylhalide)ethane, a bis(3-tert-butyl-4-phenylcarbonylhalide)ethane a bis(3,5-dimethyl-4-phenylcarbonylhalide)ethane, a bis(3,5-diethyl-4-phenylcarbonylhalide)ethane, a bis(3,5-diisopropy-4-phenylcarbonylhalide)ethane, or a bis(3,5-di-tert-butyl-4-phenylcarbonylhalide)ethane. In some embodiments, the acid halide having Structure AC2 can be a bis(3-methyl-4-phenylcarbonylhalide)ethane, a bis(3-ethyl-4-phenylcarbonylhalide)ethane, a bis(3-isopropy-4-phenylcarbonylhalide)ethane, a bis(3-tert-butyl-4-phenylcarbonylhalide)ethane; alternatively, a bis(3,5-dimethyl-4-phenylcarbonylhalide)-ethane, a bis(3,5-diethyl-4-phenylcarbonylhalide)ethane, a bis(3,5-diisopropy-4-phenylcarbonyl-halide)ethane, or a bis(3,5-di-tert-butyl-4-phenylcarbonylhalide)ethane. In other embodiments, the acid halide having Structure AC2 can be a bis(3-methyl-4-phenylcarbonylhalide)ethane; alternatively, a bis(3-ethyl-4-phenylcarbonylhalide)ethane; alternatively, a bis(3-isopropyl-4-phenylcarbonylhalide)ethane; alternatively, a bis(3-tert-butyl-4-phenylcarbonylhalide)ethane; alternatively, a bis(3,5-dimethyl-4-phenylcarbonylhalide)ethane; alternatively, a bis(3,5-diethyl-4-phenylcarbonylhalide)ethane; alternatively, a bis(3,5-diisopropyl-4-phenylcarbonylhalide)ethane; or alternatively, a bis(3,5-di-tert-butyl-4-phenylcarbonylhalide)ethane. Generally, these substituted bis(phenylcarbonylhalide)ethanes can be a bis-1,1-(phenylcarbonylhalide)ethane or a bis-1,2-(phenylcarbonylhalide)ethane group; alternatively, a bis-1,1-(phenylcarbonylhalide)ethane; or alternatively, a bis-1,2-(phenylcarbonylhalide)ethane.

In other embodiments, the acid halide having Structure AC2 can be bis(3-methyl-4-phenylcarbonylchloride)ethane, bis(3-ethyl-4-phenylcarbonylchloride)ethane, bis(3-isopropyl-4-phenyl-carbonylchloride)ethane, bis(3-tert-butyl-4-phenylcarbonylchloride)ethane bis(3,5-dimethyl-4-phenylcarbonylchloride)ethane, bis(3,5-diethyl-4-phenylcarbonylchloride)ethane, bis(3,5-diisopropyl-4-phenyl-carbonylchloride)ethane, or bis(3,5-di-tert-butyl-4-phenylcarbonylchloride)ethane. In some other embodiments, the acid halide having Structure AC2 can be bis(3-methyl-4-phenylcarbonylchloride)-ethane, bis(3-ethyl-4-phenylcarbonylchloride)ethane, bis(3-isopropyl-4-phenylcarbonylchloride)ethane, bis(3-tert-butyl-4-phenylcarbonylchloride)ethane; or alternatively, bis(3,5-dimethyl-4-phenylcarbonylchloride)ethane, bis(3,5-diethyl-4-phenylcarbonylchloride)ethane, bis(3,5-diisopropyl-4-phenylcarbonyl-chloride)ethane, or bis(3,5-di-tert-butyl-4-phenylcarbonylchloride)ethane. In yet other embodiments, the acid halide having Structure AC2 can be bis(3-methyl-4-phenylcarbonylchloride)ethane; alternatively, bis(3-ethyl-4-phenylcarbonylchloride)ethane; alternatively, bis(3-isopropyl-4-phenylcarbonylchloride)-ethane; alternatively, bis(3-tert-butyl-4-phenylcarbonylchloride)ethane; alternatively, bis(3,5-dimethyl-4-phenylcarbonylchloride)ethane; alternatively, bis(3,5-diethyl-4-phenylcarbonylchloride)ethane; alternatively, bis(3,5-diisopropyl-4-phenylcarbonylchloride)ethane; or alternatively, bis(3,5-di-tert-butyl-4-phenylcarbonylchloride)ethane. Generally, these substituted bis(phenylcarbonylchloride)ethanes can be bis-1,1-(phenylcarbonylchloride)ethane or bis-1,2-(phenylcarbonylchloride)ethane group; alternatively, bis-1,1-(phenylcarbonylchloride)ethane; or alternatively, bis-1,2-(phenylcarbonyl-chloride)ethane.

In an aspect, $D^2$ of the acid halide having Structure AC3 can be any $D^2$ described herein. $D^2$ is described herein as a feature of the $N^2$-phosphinyl amidine compounds having Structure NP5, NP10, NP15, or NP20 utilized in various aspects and/or embodiments of this disclosure. Since the acid halide having Structure AC3 can be utilized to prepare embodiments of the $N^2$-phospinyl amidine compounds having Structure having Structure NP5, NP10, NP15, or NP20, the aspects and/or embodiments of $D^2$ can utilized without limitation to further describe the acid halides having Structure AC3. In an embodiment, any acid halide having Structure AC3 described herein can be an acid chloride or an acid bromide, unless explicitly recited otherwise. In some embodiments, the acid halide having Structure AC3 can be an acid chloride; or alternatively, an acid bromide.

Within this disclosure, phosphine halides can be used to ultimately prepare the $N^2$-phosphinyl amidine compounds and/or the $N^2$-phosphinyl amidine metal salt complexes utilized in various aspects of this disclosure. In various embodiments, phosphine halides which can be utilized have Structure PH1.

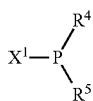

Structure PH1

$R^4$ and $R^5$ are described as features of $N^2$-phosphinyl amidine compounds having Structures NP1-NP10, NP11, NP13, NP15, NP16, NP18, and/or NP20 and are described herein. Additionally, $X^1$ is described herein as a feature of the phosphine halides. Since the phosphine halides are utilized to ultimately prepare embodiments of the $N^2$-phospinyl amidine compounds having Structures NP1-NP10, NP11, NP13, NP15, NP16, NP18, and/or NP20, $X^1$, $R^4$, and $R^5$ can utilized without limitation to further describe the phosphine halides having Structure PH1.

In an aspect, the phosphine halide can be a diphenylphosphine halide, a dialkylphosphine halide, a bis(mono-halo substituted phenyl)phosphine halide, a bis(mono-alkyl substituted phenyl)phosphine halide, or a bis(mono-alkoxy substituted phenyl)phosphine halide; alternatively, a diphenylphosphine halide; alternatively, a dialkylphosphine halide; alternatively, a bis(mono-halo substituted phenyl) phosphine halide; alternatively, a bis(mono-alkyl substituted phenyl)phosphine halide; or alternatively, a bis(mono-alkoxy substituted phenyl)phosphine halide. In another aspect, phosphine halide can be an (alkyl)(phenyl)phosphine halide, a (mono-halo substituted phenyl)(phenyl)phosphine halide, a (mono-alkyl substituted phenyl)(phenyl)phosphine halide, a (mono-alkoxy substituted phenyl)(phenyl)phosphine halide, a (mono-alkyl substituted phenyl)(mono-halo substituted phenyl) phosphine halide, or a (mono-alkyl substituted phenyl)(mono-alkoxy substituted phenyl) phosphine halide; alternatively, (alkyl)(phenyl)phosphine halide; alternatively, a (mono-halo substituted phenyl)(phenyl)phosphine halide; alternatively, a (mono-alkyl substituted phenyl)(phenyl) phosphine halide; alternatively, a (mono-alkoxy substituted phenyl)(phenyl)phosphine halide; alternatively, a (mono-alkyl substituted phenyl)(mono-halo substituted phenyl) phosphine halide; or alternatively, a (mono-alkyl substituted phenyl)(mono-alkoxy substituted phenyl) phosphine halide. In another aspect, phosphine halide can be a bis(dihalo substituted phenyl)phosphine halide, a bis(dialkyl substituted phenyl)phosphine halide, a bis(dialkoxy substituted phenyl) phosphine halide, a bis(trialkylphenyl)-phosphine halide, or a bis(trialkoxyphenyl)phosphine halide; alternatively, a bis(dihalo substituted phenyl)phosphine halide; alternatively, a bis (dialkyl substituted phenyl)phosphine halide; alternatively, a bis(dialkoxy substituted phenyl)phosphine halide; alternatively, a bis(trialkylphenyl)phosphine halide; or alternatively, a bis(trialkoxyphenyl)phosphine halide. Halo, alkyl, and alkoxy substituents for the substituted phenyl group embodiments of the phosphine halides have been disclosed herein and can be utilized, without limitation to further describe the phosphine halides which can be utilized in aspects and embodiments described herein.

In a non-limiting aspect, the phosphine halide can be dimethylphosphine chloride, diethylphosphine chloride, diisopropylphosphine chloride, di-tert-butylphosphine chloride, or di-neo-pentylphosphine chloride. In an embodiment, the phosphine halide can be dimethylphosphine chloride; alternatively, diethylphosphine chloride; alternatively, diisopropylphosphine chloride; alternatively, di-tert-butylphosphine chloride; or alternatively, di-neo-pentylphosphine chloride.

In a non-limiting aspect, the phosphine halide can be (methyl)(phenyl)phosphine chloride, (ethyl)(phenyl)phosphine chloride, (isopropyl)(phenyl)phosphine chloride, (tert-butyl) (phenyl)phosphine chloride, or (neo-pentyl)(phenyl)phosphine chloride. In an embodiment, the phosphine halide can be (methyl)(phenyl)phosphine chloride; alternatively, (ethyl) (phenyl)phosphine chloride; alternatively, (isopropyl)(phenyl)phosphine chloride; alternatively, (tert-butyl)(phenyl) phosphine chloride; or alternatively, (neo-pentyl)(phenyl) phosphine chloride.

In some non-limiting embodiments, the phosphine halide can be dicyclopentylphosphine chloride, dicyclohexylphosphine chloride; alternatively, dicyclopentylphosphine chloride; or alternatively, dicyclohexylphosphine chloride.

In yet another non non-limiting aspect, the phosphine halide can be bis(2-fluorophenyl)-phosphine chloride, bis(2-chlorophenyl)phosphine chloride, bis(3-fluorophenyl)phosphine chloride, bis(3-chlorophenyl)phosphine chloride, bis (4-fluorophenyl)phosphine chloride, or bis(4-chloro-phenyl) phosphine chloride. In some embodiments, the phosphine halide can be bis(2-fluorophenyl)-phosphine chloride, bis(3-fluorophenyl)phosphine chloride, or bis(4-fluorophenyl) phosphine chloride; or alternatively, bis(2-chlorophenyl) phosphine chloride, bis(3-chlorophenyl)phosphine chloride, or bis(4-chlorophenyl)phosphine chloride. In other embodiments, the phosphine halide can be bis(2-fluoro-phenyl) phosphine chloride; alternatively, bis(2-chlorophenyl)phosphine chloride; alternatively, bis(3-fluorophenyl)phosphine chloride; alternatively, bis(3-chlorophenyl)phosphine chloride; alternatively, bis(4-fluorophenyl)phosphine chloride; or alternatively, bis(4-chlorophenyl)phosphine chloride.

In yet another non non-limiting aspect, the phosphine halide can be (2-fluorophenyl)(phenyl)-phosphine chloride, (2-chlorophenyl)(phenyl)phosphine chloride, (3-fluorophenyl)(phenyl)phosphine chloride, (3-chlorophenyl)(phenyl) phosphine chloride, (4-fluorophenyl)(phenyl)phosphine chloride, or (4-chlorophenyl)(phenyl)phosphine chloride. In some embodiments, the phosphine halide can be (2-fluorophenyl)(phenyl)phosphine chloride, (3-fluorophenyl)(phenyl)phosphine chloride, or (4-fluoro-phenyl)(phenyl)phosphine chloride; or alternatively, (2-chlorophenyl)(phenyl) phosphine chloride, (3-chlorophenyl)(phenyl)phosphine chloride, or (4-chlorophenyl)(phenyl)phosphine chloride. In other embodiments, the phosphine halide can be (2-fluorophenyl)(phenyl)phosphine chloride; alternatively, (2-chlorophenyl)(phenyl)phosphine chloride; alternatively, (3-fluorophenyl)(phenyl)phosphine chloride; alternatively, (3-chlorophenyl)(phenyl)phosphine chloride; alternatively, (4-fluorophenyl)(phenyl)-phosphine chloride; or alternatively, (4-chlorophenyl)(phenyl)phosphine chloride.

In yet another non non-limiting aspect, the phosphine halide can be diphenylphosphine chloride, bis(2-methylphenyl)phosphine chloride, bis(2-ethylphenyl)phosphine chloride, bis(2-isopropyl-phenyl)phosphine chloride, bis(2-tert-butylphenyl)phosphine chloride, bis(3-methylphenyl) phosphine chloride, bis(3-ethylphenyl)phosphine chloride, bis(3-isopropylphenyl)phosphine chloride, bis(3-tert-butylphenyl)phosphine chloride, diphenylphosphine chloride, bis(4-methylphenyl)phosphine chloride, bis(4-ethylphenyl) phosphine chloride, bis(4-isopropylphenyl)phosphine chloride, or bis(4-tert-butylphenyl)phosphine chloride. In an embodiment, the phosphine halide can be bis(2-methyl-phenyl)phosphine chloride, bis(2-ethylphenyl)phosphine chloride, bis(2-isopropylphenyl)phosphine chloride, or bis(2-tert-butylphenyl)phosphine chloride; alternatively, diphenylphosphine chloride, bis(3-methylphenyl)phosphine chloride, bis(3-ethylphenyl)phosphine chloride, bis(3-isopropylphenyl)-phosphine chloride, or bis(3-tert-butylphenyl) phosphine chloride; or alternatively, diphenylphosphine chloride, bis(4-methylphenyl)phosphine chloride, bis(4-ethylphenyl)phosphine chloride, bis(4-isopropyl-phenyl)phosphine chloride, or bis(4-tert-butylphenyl)phosphine chloride. In other embodiments, the phosphine halide can be diphenylphosphine chloride; alternatively, bis(2-methylphenyl) phosphine chloride; alternatively, bis(2-ethylphenyl)phosphine chloride; alternatively, bis(2-isopropylphenyl)phosphine chloride; alternatively, bis(2-tert-butylphenyl) phosphine chloride; alternatively, bis(3-methyl-phenyl) phosphine chloride; alternatively, bis(3-ethylphenyl) phosphine chloride; alternatively, bis(3-isopropylphenyl) phosphine chloride; alternatively, bis(3-tert-butylphenyl) phosphine chloride; alternatively, diphenylphosphine chloride; alternatively, bis(4-methylphenyl)phosphine chloride; alternatively, bis(4-ethylphenyl)phosphine chloride, bis (4-isopropylphenyl)phosphine chloride; or alternatively, bis (4-tert-butylphenyl)phosphine chloride.

In yet another non non-limiting aspect, the phosphine halide can be diphenylphosphine chloride, (2-methylphenyl) (phenyl)phosphine chloride, (2-ethylphenyl)(phenyl)phosphine chloride, (2-isopropylphenyl)(phenyl)phosphine chloride, (2-tert-butylphenyl)(phenyl)phosphine chloride, (3-methylphenyl)(phenyl)phosphine chloride, (3-ethylphenyl)(phenyl)phosphine chloride, (3-isopropyl-phenyl)(phenyl)phosphine chloride, (3-tert-butylphenyl)(phenyl)phosphine chloride, diphenylphosphine chloride, (4-methylphenyl)(phenyl)phosphine chloride, (4-ethylphenyl)(phenyl)phosphine chloride, (4-isopropylphenyl)(phenyl)phosphine chloride, or (4-tert-butylphenyl)(phenyl) phosphine chloride. In an embodiment, the phosphine halide can be (2-methylphenyl)(phenyl)phosphine chloride, (2-ethylphenyl)-(phenyl)phosphine chloride, (2-isopropylphenyl) (phenyl)phosphine chloride, or (2-tert-butylphenyl)-(phenyl) phosphine chloride; alternatively, diphenylphosphine chloride, (3-methylphenyl)(phenyl)-phosphine chloride, (3-ethylphenyl)(phenyl)phosphine chloride, (3-isopropylphenyl)(phenyl)phosphine chloride, or (3-tert-butylphenyl) (phenyl)phosphine chloride; or alternatively, diphenylphosphine chloride, (4-methylphenyl)(phenyl)phosphine chloride, (4-ethylphenyl)(phenyl)phosphine chloride, (4-isopropyl-phenyl)(phenyl)phosphine chloride, or (4-tert-butylphenyl)(phenyl)phosphine chloride. In other embodiments, the phosphine halide can be diphenylphosphine chloride; alternatively, (2-methylphenyl)-(phenyl)phosphine chloride; alternatively, (2-ethylphenyl)(phenyl)phosphine chloride; alternatively, (2-isopropylphenyl)(phenyl)phosphine chloride; alternatively, (2-tert-butylphenyl)(phenyl) phosphine chloride; alternatively, (3-methylphenyl)(phenyl) phosphine chloride; alternatively, (3-ethylphenyl)-(phenyl) phosphine chloride; alternatively, (3-isopropylphenyl) (phenyl)phosphine chloride; alternatively, (3-tert-butylphenyl)(phenyl)phosphine chloride; alternatively, diphenylphosphine chloride; alternatively, (4-methylphenyl) (phenyl)phosphine chloride; alternatively, (4-ethylphenyl) (phenyl)phosphine chloride, (4-isopropylphenyl)(phenyl) phosphine chloride; or alternatively, (4-tert-butylphenyl) (phenyl)phosphine chloride.

In yet another non-limiting aspect, the phosphine halide can be diphenylphosphine chloride, bis(2-methoxyphenyl) phosphine chloride, bis(2-ethoxyphenyl)phosphine chloride, bis(2-isopropoxy-phenyl)phosphine chloride, bis(2-tert-butoxyphenyl)phosphine chloride, bis(3-methoxyphenyl)phosphine chloride, bis(3-ethoxyphenyl)phosphine chloride, bis(3-isopropoxyphenyl)phosphine chloride, bis(3-tert-butoxyphenyl)phosphine chloride, diphenoxyphosphine chloride, bis(4-methoxyphenyl)-phosphine chloride, bis(4-ethoxyphenyl)phosphine chloride, bis(4-isopropoxyphenyl) phosphine chloride, or bis(4-tert-butoxyphenyl)phosphine chloride. In an embodiment, the phosphine halide can be bis(2-methoxyphenyl)phosphine chloride, bis(2-ethoxyphenyl)phosphine chloride, bis(2-isopropoxy-phenyl)phosphine chloride, or bis(2-tert-butoxyphenyl)phosphine chloride; alternatively, diphenoxy-phosphine chloride, bis(3-methoxyphenyl)phosphine chloride, bis(3-ethoxyphenyl)phosphine chloride, bis(3-isopropoxyphenyl)phosphine chloride, or bis (3-tert-butoxyphenyl)phosphine chloride; or alternatively, diphenoxyphosphine chloride, bis(4-methoxyphenyl)phosphine chloride, bis(4-ethoxy-phenyl)phosphine chloride, bis (4-isopropoxyphenyl)phosphine chloride, or bis(4-tert-butoxyphenyl)-phosphine chloride. In other embodiments, the phosphine halide can be diphenylphosphine chloride; alternatively, bis(2-methoxyphenyl)phosphine chloride; alternatively, bis(2-ethoxyphenyl)phosphine chloride; alternatively, bis(2-isopropoxyphenyl)phosphine chloride; alternatively, bis(2-tert-butoxy-phenyl)phosphine chloride; alternatively, bis(3-methoxyphenyl)phosphine chloride; alternatively, bis (3-ethoxyphenyl)phosphine chloride; alternatively, bis(3-isopropoxyphenyl)phosphine chloride; alternatively, bis(3-tert-butoxyphenyl)phosphine chloride; alternatively, diphenoxyphosphine chloride; alternatively, bis(4-methoxyphenyl)phosphine chloride; alternatively, bis(4-ethoxyphenyl)phosphine chloride, bis(4-isopropoxyphenyl)phosphine chloride; or alternatively, bis(4-tert-butoxyphenyl)phosphine chloride.

In yet another non non-limiting aspect, the phosphine halide can be diphenylphosphine chloride, (2-methoxyphenyl)(phenyl)phosphine chloride, (2-ethoxyphenyl)(phenyl) phosphine chloride, (2-isopropoxyphenyl)(phenyl)phosphine chloride, (2-tert-butoxyphenyl)(phenyl)phosphine chloride, (3-methoxyphenyl)(phenyl)phosphine chloride, (3-ethoxyphenyl)(phenyl)phosphine chloride, (3-isopropoxyphenyl)(phenyl)phosphine chloride, (3-tert-butoxyphenyl)(phenyl)phosphine chloride, diphenoxyphosphine chloride, (4-methoxyphenyl)(phenyl)phosphine chloride, (4-ethoxyphenyl)-(phenyl)phosphine chloride, (4-isopropoxyphenyl)(phenyl)phosphine chloride, or (4-tert-butoxyphenyl)-(phenyl)phosphine chloride. In an embodiment, the phosphine halide can be (2-methoxyphenyl)(phenyl)-phosphine chloride, (2-ethoxyphenyl)(phenyl)phosphine chloride, (2-isopropoxyphenyl)(phenyl)-phosphine chloride, or (2-tert-butoxyphenyl)(phenyl)phosphine chloride; alternatively, diphenoxy-phosphine chloride, (3-methoxyphenyl) (phenyl)phosphine chloride, (3-ethoxyphenyl)(phenyl)phosphine chloride, (3-isopropoxyphenyl)(phenyl)phosphine chloride, or (3-tert-butoxyphenyl)(phenyl)phosphine chloride; or alternatively, diphenoxyphosphine chloride, (4-methoxyphenyl)(phenyl)phosphine chloride, (4-ethoxyphenyl) (phenyl)phosphine chloride, (4-isopropoxyphenyl)(phenyl) phosphine chloride, or (4-tert-butoxyphenyl)(phenyl) phosphine chloride. In other embodiments, the phosphine halide can be diphenylphosphine chloride; alternatively, (2-methoxyphenyl)(phenyl)phosphine chloride; alternatively, (2-ethoxyphenyl)(phenyl)phosphine chloride; alternatively, (2-isopropoxyphenyl)(phenyl)phosphine chloride; alternatively, (2-tert-butoxyphenyl)(phenyl)phosphine chloride; alternatively, (3-methoxy-phenyl)(phenyl)phosphine chloride; alternatively, (3-ethoxyphenyl)(phenyl)phosphine chloride; alternatively, (3-isopropoxyphenyl)(phenyl)phosphine chloride; alternatively, (3-tert-butoxyphenyl)-(phenyl) phosphine chloride; alternatively, diphenoxyphosphine chloride; alternatively, (4-methoxy-phenyl)(phenyl)phosphine chloride; alternatively, (4-ethoxyphenyl)(phenyl)phosphine chloride, (4-isopropoxyphenyl)(phenyl)phosphine chloride; or alternatively, (4-tert-butoxyphenyl)(phenyl)-phosphine chloride.

Within this disclosure, halogenated compounds can be used to prepare the $N^2$-phosphinyl amidine compounds and/or the $N^2$-phosphinyl amidine metal salt complexes utilized in various aspects of this disclosure. In various embodiments, the halogenated compounds which can be utilized can have Structure HC1. $R^3$ is described as a feature of $N^2$-phosphinyl amidine having Structures NP1-NP10, NP11, NP13, NP15, NP16, NP18, and/or NP20.

$X^2R^3$                    Structure HC1

Since the halogenated HC1 is utilized to ultimately prepare embodiments of the $N^2$-phospinyl amidine compounds having Structures NP1-NP10, NP11, NP13, NP15, NP16, NP18, and/or NP20, the $R^3$ description can be utilized without limitation to further describe the halogenated compound having Structure HC1. Generally, $X^2$ of Structure HC1 represents a halide. In an embodiment, $X^2$ of the halogenated compound can be fluoride, chloride, bromide, or iodide; alternatively, fluoride; alternatively, chloride; alternatively, bromide; or alternatively, iodide.

In an aspect, the halogenated compound having Structure HC1 can be a methylhalide, an ethylhalide, a propylhalide, a butylhalide, a pentylhalide, a hexylhalide, a heptylhalide, an octylhalide, a nonylhalide, a decylhalide, a undecylhalide, a dodecylhalide, a tridecylhalide, a tetradecylhalide, a pentadecylhalide, a hexadecylhalide, a heptadecylhalide, an octadecylhalide, or a nonadecylhalide; or alternatively, a methylhalide, an ethylhalide, a propylhalide, a butylhalide, a pentylhalide, a hexylhalide, a heptylhalide, an octylhalide, a nonylhalide, or a decylhalide. In some embodiments, the halogenated compound having Structure HC1 can be a methylhalide, an ethylhalide, an n-propylhalide, an iso-propylhalide, butylhalide, an iso-butylhalide, a sec-butylhalide, a tert-butylhalide, an n-pentylhalide, an iso-pentylhalide, a sec-pentylhalide, or an neopentylhalide; alternatively, a methylhalide, an ethyl-halide, an iso-propylhalide, a tert-butylhalide, or a neopentylhalide; alternatively, a methylhalide; alternatively, an ethylhalide; alternatively, an n-propylhalide; alternatively, an iso-propylhalide; alternatively, a tert-butylhalide; or alternatively, a neopentylhalide.

In an aspect, the halogenated compound having Structure HC1 can be a cyclobutylhalide, a substituted cyclobutylhalide, a cyclopentylhalide, a substituted cyclopentylhalide, a cyclohexylhalide, a substituted cyclohexylhalide, a cycloheptylhalide, a substituted cycloheptylhalide, a cyclooctylhalide, or a substituted cyclooctylhalide. In an embodiment the halide having Structure HC1 can be a cyclopentylhalide, a substituted cyclopentylhalide, a cyclohexylhalide, or a substituted cyclohexylhalide. In other embodiments, the halogenated compound having Structure HC1 can be a cyclobutylhalide or a substituted cyclobutylhalide; alternatively, a cyclopentylhalide or a substituted cyclopentylhalide; alternatively, a cyclohexylhalide or a substituted cyclohexylhalide; alternatively, a cycloheptylhalide or a substituted cycloheptylhalide; or alternatively, a cyclooctylhalide, or a substituted cyclooctylhalide. In further embodiments, the halogenated compound having Structure HC1 can be a cyclopentylhalide; alternatively, a substituted cyclopentylhalide; a cyclohexylhalide; or alternatively, a substituted cyclohexylhalide. Substituents and substituents patterns for the $R^1$ cycloalkyl groups are described herein and can be utilized without limitation to further describe the substituted cycloalkylhalides which can be utilized in aspects and embodiments described herein.

In various embodiments, the halogenated compounds which can be utilized can have Structure HC2. $R^{11c}$, $R^{12c}$, $R^{13c}$, $R^{14c}$, and R

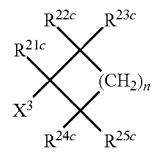

Structure HC2

$R^{15c}$ substituents, substituent patterns, and n for the $R^3$ group having Structure G5 are described herein and can be utilized without limitation to describe halogenated compound having Structure HC2 which can be utilized in the various aspects and/or embodiments described herein. In an embodiment, $X^2$ of the halogenated compound having Structure HC2 can be fluoride, chloride, bromide, or iodide; alternatively, fluoride; alternatively, chloride; alternatively, bromide; or alternatively, iodide.

In an aspect, the halogenated compound can be a benzylhalide or a substituted benzylhalide. In an embodiment, the halogenated compound can be a benzylhalide; or alternatively, a substituted benzyl halide.

Various aspect and embodiments described herein refer non-hydrogen substituents such as halogen (or halo, halide), hydrocarbyl, hydrocarboxy, alkyl, and/or alkoxy substituents. The non-hydrogen substituents of any aspect or embodiment calling for a substituent can be a halide, a $C_1$ to $C_{10}$ hydrocarbyl group, or a $C_1$ to $C_{10}$ hydrocarboxy group; alternatively, a halide or a $C_1$ to $C_{10}$ hydrocarbyl group; alternatively, a halide or a $C_1$ to $C_{10}$ hydrocarboxy group; alternatively, a $C_1$ to $C_{10}$ hydrocarbyl group or a $C_1$ to $C_{10}$ hydrocarboxy group; alternatively, a halide; alternatively, a $C_1$ to $C_{10}$ hydrocarbyl group; or alternatively, a $C_1$ to $C_{10}$ hydrocarboxy group. In other embodiments, the non-hydrogen substituents of any aspect or embodiment calling for a substituent can be a halide, a $C_1$ to $C_5$ hydrocarbyl group, or a $C_1$ to $C_5$ hydrocarboxy group; alternatively, a halide or a $C_1$ to $C_5$ hydrocarbyl group; alternatively, a halide or a $C_1$ to $C_5$ hydrocarboxy group; alternatively, a $C_1$ to $C_5$ hydrocarbyl group or a $C_1$ to $C_5$ hydrocarboxy group; alternatively, a halide; alternatively, a $C_1$ to $C_5$ hydrocarbyl group; or alternatively, a $C_1$ to $C_5$ hydrocarboxy group.

In an embodiment, any halide substituent of any aspect or embodiment calling for a substituent can be a fluoride, chloride, bromide, or iodide; alternatively, a fluoride or chloride. In some embodiments, any halide substituent of any aspect or embodiment calling for a substituent can be a fluoride; alternatively, a chloride; alternatively, a bromide; or alternatively, an iodide.

In an embodiment, any hydrocarbyl substituent can be an alkyl group, an aryl group, or an aralkyl group; alternatively, an alkyl group; alternatively, an aryl group; or alternatively, an aralkyl group. In an embodiment, any alkyl substituent of any aspect or embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of any aspect or embodiment calling for a substituent can be phenyl group, a tolyl group, a xylyl group, or a 2,4,6-trimethylphenyl group; alternatively, a phenyl group; alternatively, a tolyl group; alternatively, a xylyl group; or alternatively, a 2,4,6-trimethylphenyl group. In an embodiment, any aralkyl substituent of any aspect or embodiment calling for a substituent can be benzyl group or an ethylphenyl group (2-phenyleth-1-yl or 1-phenyleth-1-yl); alternatively, a benzyl group; alternatively, an ethylphenyl group; alternatively, a 2-phenyleth-1-yl group; or alternatively, a 1-phenyleth-1-yl group.

In an embodiment, any hydrocarboxy substituent of any aspect or embodiment calling for a substituent can be an alkoxy group, an aryloxy group, or an aralkoxy group; alternatively, an alkoxy group; alternatively, an aryloxy group, or an aralkoxy group. In an embodiment, any alkoxy substituent of any aspect or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy substituent of any aspect or embodiment calling for a substituent can be phenoxy group, a toloxy group, a xyloxy group, or a 2,4,6-trimethylphenoxy group; alternatively, a phenoxy group; alternatively, a toloxy group; alternatively, a xyloxy group; or alternatively, a 2,4,6-trimethylphenoxy group. In an embodiment, any aralkoxy substituent of any aspect or embodiment calling for a substituent can be benzoxy group.

The methods described herein can utilize one or more solvents. Solvent which can be utilized in aspects of the present disclosure include without limitation water, hydrocarbons, halogenated hydrocarbons, ethers, carbonates, esters, ketones, aldehydes, alcohols, nitriles and combinations thereof. In some embodiments, an aspect of the invention may call for a polar solvent. Polar solvents which can be utilized include without limitation water ethers, carbonates, esters, ketones, aldehydes, alcohols, nitriles, and mixtures thereof; alternatively, ethers, carbonates, esters, ketones, aldehydes, alcohols, nitriles, and mixtures thereof; alternatively, ethers, esters, ketones, alcohols, nitriles, and mixtures thereof; alternatively, ethers; alternatively, carbonates; alternatively, esters; alternatively, ketones; alternatively, aldehydes; alternatively, alcohols; or alternatively, nitriles. In some embodiments, an aspect of the invention may call for an aprotic polar solvent. Aprotic polar solvents which can be utilized include without limitation ethers, esters, ketones, aldehydes, nitriles, and mixtures thereof; alternatively, ethers, nitriles and mixtures thereof; alternatively, esters, ketones, aldehydes and mixtures thereof; alternatively, ethers; alternatively, esters; alternatively, ketones; alternatively, aldehydes; or alternatively, nitriles. In other embodiments, an aspect of the disclosure may call for a non-polar solvent. Non-polar solvents include without limitation hydrocarbons, halogenated hydrocarbons, or mixtures thereof; alternatively, a hydrocarbon; or alternatively, a halogenated hydrocarbon. In another embodiment, an aspect of the present disclosure may call for a solvent that is substantially unreactive with a metal alkyl. Solvents which are unreactive with a metal alkyl include without limitation ethers, hydrocarbons, and mixtures thereof; alternatively, ethers; or alternatively, hydrocarbons.

Hydrocarbons and halogenated hydrocarbon can include, for example, aliphatic hydrocarbons, aromatic hydrocarbons, petroleum distillates, halogenated aliphatic hydrocarbons, halogenated aromatic hydrocarbons, or combinations thereof; alternatively, aliphatic hydrocarbons, aromatic hydrocarbons, halogenated aliphatic hydrocarbons, halogenated aromatic hydrocarbons, and combinations thereof; alternatively, aliphatic hydrocarbons; alternatively, aromatic hydrocarbons; alternatively, halogenated aliphatic hydrocarbons; or alternatively, halogenated aromatic hydrocarbons. Aliphatic hydrocarbons which can be useful as a solvent include $C_3$ to $C_{20}$ aliphatic hydrocarbons; alternatively, $C_4$ to $C_{15}$ aliphatic hydrocarbons; or alternatively, $C_5$ to $C_{10}$ aliphatic hydrocarbons. The aliphatic hydrocarbons can be cyclic or acyclic and/or can be linear or branched, unless otherwise specified. Non-limiting examples of suitable acyclic aliphatic hydrocarbon solvents that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, isobutane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, propane; alternatively, iso-butane; alternatively, n-butane; alternatively, butane (n-butane or a mixture of linear and branched $C_4$ acyclic aliphatic hydrocarbons); alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons). Non-limiting examples of suitable cyclic aliphatic hydrocarbon solvents include cyclohexane, methyl cyclohexane; alternatively, cyclohexane; or alternatively, methylcyclohexane. Aromatic hydrocarbons which can be useful as a solvent include $C_6$ to $C_{20}$ aromatic hydrocarbons; or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene.

Halogenated aliphatic hydrocarbons which can be useful as a solvent include $C_1$ to $C_{15}$ halogenated aliphatic hydrocarbons; alternatively, $C_1$ to $C_{10}$ halogenated aliphatic hydrocarbons; or alternatively, $C_1$ to $C_5$ halogenated aliphatic hydrocarbons. The halogenated aliphatic hydrocarbons can be cyclic or acyclic and/or can be linear or branched, unless otherwise specified. Non-limiting examples of suitable halogenated aliphatic hydrocarbons which can be utilized include methylene chloride, chloroform, carbon tetrachloride, dichloroethane, trichloroethane, and combinations thereof; alternatively, methylene chloride, chloroform, dichloroethane, trichloroethane, and combinations thereof; alternatively, methylene chloride; alternatively, chloroform; alternatively, carbon tetrachloride; alternatively, dichloroethane; or alternatively, trichloroethane. Halogenated aromatic hydrocarbons which can be useful as a solvent include $C_6$ to $C_{20}$ halogenated aromatic hydrocarbons; or alternatively, $C_6$ to $C_{10}$ halogenated aromatic hydrocarbons. Non-limiting examples of suitable halogenated aromatic hydrocarbons include chlorobenzene, dichlorobenzene, and combinations thereof; alternatively, chlorobenzene and dichlorobenzene.

Ethers, carbonates, esters, ketones, aldehydes, or alcohols which can be useful as a solvent include $C_2$ to $C_{20}$ ethers, carbonates, esters, ketones, aldehydes, or alcohols; alternatively, $C_2$ to $C_{10}$ ethers, carbonates, esters, ketones, aldehydes, or alcohols; or alternatively, $C_2$ to $C_5$ ethers, carbonates, esters, ketones, aldehydes, or alcohols. Suitable ether solvents can be cyclic or acyclic. Non-limiting examples of suitable ethers which can be useful as a solvent include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group. $C_1$ to $C_5$ alkyl substituent group are disclosed herein and can be utilized without limitation of further describe the substituted tetrahydrofuran, dihydrofuran, furan, 1,3-dioxane, or 1,4 dioxane solvents. Non-limiting examples of suitable carbonates which can be utilized as a solvent include ethylene carbonate, propylene carbonate, diethyl carbonate, diethyl carbonate, glycerol carbonate, and combinations thereof. Non-limiting examples of suitable esters which can be utilized as a solvent include ethyl acetate, propyl acetate, butyl acetate, isobutyl isobutyrate, methyl lactate, ethyl lactate, and combinations thereof. Non-limiting examples of suitable ketones which can be utilized as a solvent include acetone, ethyl methyl ketone, methyl isobutyl ketone, and combinations thereof. Non-limiting examples of suitable alcohols which can be utilized as a solvent include methanol, ethanol, propanol, isopropanol, n-butanol, isobutanol, pentanol, hexanol, heptanol, octanol, benzyl alcohol, phenol, cyclohexanol, and the like, or combinations thereof.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

Unless indicated otherwise, when a range of any type is disclosed or claimed, for example a range of the number of carbon atoms, molar ratios, temperatures, and the like, it is intended to disclose or claim individually each possible number that such a range could reasonably encompass, including any sub-ranges encompassed therein. For example, when describing a range of the number of carbon atoms, each possible individual integral number and ranges between integral numbers of atoms that the range includes are encompassed therein. Thus, by disclosing a $C_1$ to $C_{10}$ alkyl group or an alkyl group having from 1 to 10 carbon atoms or "up to" 10 carbon atoms, Applicants' intent is to recite that the alkyl group can have 1, 2, 3, 4, 5, 6, 7, 8, 9, or 10 carbon atoms, and these methods of describing such a group are interchangeable. When describing a range of measurements such as molar ratios, every possible number that such a range could reasonably encompass can, for example, refer to values within the range with one significant digit more than is present in the end points of a range. In this example, a molar ratio between 1.03:1 and 1.12:1 includes individually molar ratios of 1.03:1, 1.04:1, 1.05:1, 1.06:1, 1.07:1, 1.08:1, 1.09:1, 1.10:1, 1.11:1, and 1.12:1. Applicants' intent is that these two methods of describing the range are interchangeable. Moreover, when a range of values is disclosed or claimed, which Applicants intent to reflect individually each possible number that such a range could reasonably encompass, Applicants also intend for the disclosure of a range to reflect, and be interchangeable with, disclosing any and all sub-ranges and combinations of sub-ranges encompassed therein. In this aspect, Applicants' disclosure of a $C_1$ to $C_{10}$ alkyl group is intended to literally encompass a $C_1$ to $C_6$ alkyl, a $C_4$ to $C_8$ alkyl, a $C_2$ to $C_7$ alkyl, a combination of a $C_1$ to $C_3$ and a $C_5$ to $C_7$ alkyl, and so forth. When describing a range in which the end points of the range have different numbers of significant digits, for example, a molar ratio from 1:1 to 1.2:1, every possible number that such a range could reasonably encompass can, for example, refer to values within the range with one significant digit more than is present in the end point of a range having the greatest number of significant digits, in this case 1.2:1. In this example, a molar ratio from 1:1 to 1.2:1 includes individually molar ratios of 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, and 1.20, all relative to 1, and any and all sub-ranges and combinations of sub-ranges encompassed therein. Accordingly, Applicants reserve the right to proviso out or exclude any individual members of any such group, including any sub-ranges or combinations of sub-ranges within the group, if for any reason Applicants choose to claim less than the full measure of the disclosure, for example, to account for a reference that Applicants are unaware of at the time of the filing of the application.

In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can suggest themselves to one of ordinary skill in the art without departing from the spirit of the present invention or the scope of the appended claims.

The data and descriptions provided in the following examples are given to show particular aspects and embodiments of the compounds, catalyst systems, and olefin oligomerization and/or olefin polymerization methods disclosed, and to demonstrate a number of the practices and advantages thereof. The examples are given as a more detailed demonstration of some of the aspects and embodiments described herein and are not intended to limit the disclosure or claims in any manner.

EXAMPLES

Synthesis of Amidine Compounds

Amines, nitriles, and n-butyl lithium were utilized as obtained from the chemical supplier. The solvents were dried and/or purified using conventional methods and stored under conditions to limit their ability to pick-up water. The syntheses of the amidine compounds were performed using standard air-free procedures and techniques.

Table 7 provides the amines and nitriles utilized in amidine syntheses 1-9 along with the produced amidine compounds.

Amidine Synthesis 1—$N^1$-(2,6-dimethylphenyl)benzamidine (Amidine I)

2,6-dimethylaniline (6.15 mL, 50.0 mmol) was added to 100 mL of diethylether and cooled to 0° C. Butyllithium (26.0 mL of 2.0 M solution in diethylether, 52.0 mmol) was added dropwise to the cooled aniline solution, affording an off-white solid after complete addition. The slurry was warmed to room temperature and stirred for 2 hours. Benzonitrile (5.2 mL, 51.0 mmol) was added slowly resulting in the formation of a suspended yellow-orange solid after complete addition. Stirring was continued for 1 hour and the solvent was removed in vacuo. Tetrahydrofuran (150 mL) was added and the mixture was refluxed overnight under argon, yielding a dark orange-red solution. Distilled water (2.0 mL, 112 mmol) was added and the mixture became a milky yellow solution after stirring for 30 minutes at room temperature. Solid, presumably lithium hydroxide, was removed via aerobic filtration and the remaining solvent was removed in vacuo, to produce a light yellow solid. The solid was slurried in 80 mL of pentane and stirred for 2 hours. Filtration of the slurry yielded 10.28 g (92%) of white solid. $^1$H NMR (400 MHz, CDCl$_3$): 7.93 (d, 2H), 7.48 (m, 3H), 7.06 (d, 2H), 6.90 (t, 1H), 4.58 (s, 2H), 2.17 (s, 6H).

Amidine Synthesis 2—$N^1$-(2,6-diisopropylphenyl)benzamidine (Amidine II)

Procedure as described for Amidine I using the following amounts: 8.50 mL of 2,6-diisopropylaniline (45.0 mmol); 23.5 mL of 2.0 M butyllithium (47.0 mmol); 4.70 mL of benzonitrile (46.0 mmol). Filtration of the final pentane solution yielded 6.31 g (50%) of white solid. $^1$H NMR (400 MHz, CDCl$_3$): 7.92 (d, 2H), 7.48 (m, 3H), 7.17 (d, 2H), 7.09 (t, 1H), 4.59 (s, 2H), 3.06 (septet, 2H), 1.20 (d, 12H).

Amidine Synthesis 3—4-methyl-$N^1$-(2,6-dimethylphenyl)benzamidine (Amidine III)

Procedure as described for Amidine I using the following amounts: 6.15 mL of 2,6-dimethylaniline (50.0 mmol); 25.0 mL of 2.0 M butyllithium (50.0 mmol), 5.86 g of 4-methylbenzonitrile (50.0 mmol). After refluxing overnight, the solution was deep red. Addition of water yielded a yellow solution with suspended solid. Solution was filtered, taken to dryness, resuspended in 100 mL of pentane and stirred vigorously for 1 hour. The resulting white solid was filtered, washed with 10 mL of pentane and dried in vacuo yielding 11.19 g (90%) of white powder. $^1$H NMR (400 MHz, CDCl$_3$): 7.83 (d, 2H), 7.26 (d, 2H), 7.05 (d, 2H), 6.89 (t, 1H), 4.54 (s, 2H), 2.42 (s, 3H), 2.15 (s, 6H).

Amidine Synthesis 4—4-tert-butyl-$N^1$-(2,6-dimethylphenyl)benzamidine (Amidine IV)

Procedure as described for Amidine I using the following amounts: 6.15 mL of 2,6-dimethylaniline (50.0 mmol); 26.0 mL of 2.0 M butyllithium (52.0 mmol), 8.50 mL of 4-t-butylbenzonitrile (50.0 mmol). After refluxing overnight, the solution was red-orange. Addition of water yielded a yellow solution with suspended solid. Solution was filtered, taken to dryness, resuspended in 100 mL of pentane and stirred vigorously for 1 hour. The resulting white solid was filtered and dried in vacuo yielding 11.19 g of white powder. The filtrate was concentrated to approximately 50 mL and cooled to −10° C. An additional 1.47 g of solid was isolated. Total yield 10.60 g (76%). $^1$H NMR (400 MHz, CDCl$_3$): 7.87 (d, 2H), 7.50 (d, 2H), 7.04 (d, 2H), 6.90 (t, 1H), 4.56 (s, 2H), 2.15 (s, 6H), 1.36 (s, 9H). $^{13}$C {$^1$H} NMR (100 MHz, CDCl$_3$): 154.27, 153.01, 146.97, 133.12, 129.16, 128.53, 126.83, 125.88, 123.05, 35.21, 31.59, 18.17.

Amidine Synthesis 5—$N^1$-(2-isopropyl-6-methylphenyl)-4-methylbenzamidine (Amidine V)

Procedure as described for Amidine I using the following amounts: 7.80 mL of 2-isopropyl-6-methylaniline (50.0 mmol); 25.0 mL of 2.0 M butyllithium (50.0 mmol), 5.86 g of 4-methylbenzonitrile (50.0 mmol). After refluxing overnight, the solution was dark brown. Addition of water yielded an orange-brown solution with suspended solid. Solution was filtered and taken to dryness. The residue was treated with 100 mL of pentane stirred overnight and filtered yielding 10.98 g (83%) of beige material. $^1$H NMR (400 MHz, CDCl$_3$): 7.82 (d, 2H), 7.26 (d, 2H), 7.15 (d, 1H), 7.05 (d, 1H), 6.98 (t, 1H), 4.56 (s, 2H), 3.09 (septet, 1H), 2.42 (s, 3H), 2.15 (s, 3H), 1.21 (d, 3H), 1.16 (d, 3H).

Amidine Synthesis 6—$N^1$-(2-tert-butylphenyl)-4-methylbenzamidine (Amidine VI)

Procedure as described for Amidine I using the following amounts: 7.80 mL of 2-t-butylaniline (50.0 mmol); 25.0 mL of 2.0 M butyllithium (50.0 mmol), 5.86 g of 4-methylbenzonitrile (50.0 mmol). After refluxing overnight, the solution was dark brown. Addition of water yielded an orange solution with suspended solid. Solution was filtered and taken to dryness. The residue was treated with 75 mL of pentane, stirred overnight, and filtered yielding 11.14 g (84%) of off-white material. $^1$H NMR (400 MHz, CDCl$_3$): 7.82 (d, 2H), 7.41 (d, 1H), 7.27 (d, 2H), 7.17 (t, 1H), 7.00 (t, 1H), 6.82 (d, 1H), 4.75 (s, 2H), 2.42 (s, 3H), 1.40 (s, 9H).

Amidine Synthesis 7—4-tert-butyl-N$^1$-(2-tert-butylphenyl)benzamidine (Amidine VII)

Procedure as described for Amidine I using the following amounts: 7.80 mL of 2-t-butylaniline (50.0 mmol); 25.0 mL of 2.0 M butyllithium (50.0 mmol), 8.50 ml of 4-t-butylbenzonitrile (50.0 mmol). After refluxing overnight, the solution was dark brown. Addition of water yielded an orange solution with suspended solid. Solution was filtered and taken to dryness. The residue was treated with 75 mL of pentane, stirred for 30 minutes, and filtered yielding 13.43 g (87%) of light orange solid. $^1$H NMR (400 MHz, CDCl$_3$): 7.87 (d, 2H), 7.49 (d, 2H), 7.41 (d, 1H), 7.17 (t, 1H), 7.00 (t, 1H), 6.81 (d, 1H), 4.75 (s, 2H), 1.41 (s, 9H), 1.36 (s, 9H).

Amidine Synthesis 8—N$^1$-(2-ethylphenyl)-4-methylbenzamidine (Amidine VIII)

Procedure as described for Amidine I using the following amounts: 6.18 mL of 2-ethylaniline (50.0 mmol); 25.0 mL of 2.0 M butyllithium (50.0 mmol), 5.86 g of 4-methylbenzonitrile (50.0 mmol). After refluxing overnight, the solution was dark brown. Addition of water yielded a yellow solution with suspended solid. Solution was filtered and taken to dryness. The residue was treated with 75 mL of pentane, stirred overnight, and filtered yielding 10.51 g (88%) of light yellow solid. $^1$H NMR (400 MHz, CDCl$_3$): 7.79 (d, 2H), 7.25 (d, 3H), 7.17 (t, 1H), 7.02 (t, 1H), 6.86 (d, 1H), 4.68 (s, 2H), 2.57 (q, 2H), 2.41 (s, 3H), 1.17 (t, 3H).

Amidine Synthesis 9—4-methyl-N$^1$-phenylbenzamidine (Amidine IX)

Procedure as described for Amidine I using the following amounts: 4.60 mL of aniline (50.0 mmol); 25.0 mL of 2.0 M butyllithium (50.0 mmol), 5.86 g of 4-methylbenzonitrile (50.0 mmol). After refluxing overnight, the solution was orange. Addition of water yielded a yellow solution with suspended solid. Solution was filtered and taken to dryness. The residue was treated with 50 mL of pentane, stirred for 30 minutes, and filtered yielding 8.23 g (78%) of light yellow solid. $^1$H NMR (400 MHz, CDCl$_3$): 7.76 (d, 2H), 7.36 (t, 2H), 7.25 (d, 2H), 7.06 (t, 1H), 6.98 (d, 2H), 4.79 (s, 2H), 2.40 (s, 3H).

Amidine Synthesis 10—N$^1$-(2-isopropylphenyl)-4-methylbenzamidine (Amidine X)

2-isopropylaniline (5.0 mL, 36.1 mmol) was added to 100 mL of diethylether and cooled to 0° C. Butyllithium (18.0 mL of 2.0 M solution in pentane, 36.1 mmol) was added dropwise to the cooled aniline solution, affording a light yellow suspension after complete addition. The slurry was warmed to room temperature and stirred for 2 hours. Toluonitrile (4.23 g, 36.1 mmol) was added slowly resulting in the formation of a bright yellow solution after complete addition. Stirring was continued for 1 hour and the solvent was removed in vacuo. Tetrahydrofuran (150 mL) was added and the mixture was refluxed overnight under argon, yielding a dark orange-brown solution. Distilled water (2.0 mL, 112 mmol) was added and the mixture became a milky yellow solution after stirring for 30 minutes at room temperature. Solid, presumably lithium hydroxide, was removed via aerobic filtration and the remaining solvent was removed in vacuo, to produce a light yellow solid. The solid was slurried in 50 mL of pentane and stirred for 2 hours. Filtration of the slurry yielded 7.56 g (83%) of light yellow solid. $^1$H NMR (400 MHz, CDCl$_3$): 7.77 (d, 2H), 7.30 (d, 1H), 7.22 (d, 2H), 7.15 (t, 1H), 7.04 (t, 1H), 6.83 (d, 1H), 4.70 (s, 2H), 3.16 (septet, 1H), 2.40 (s, 3H), 1.19 (d, 6H).

Amidine Synthesis 11—N$^1$-(2-n-propylphenyl)-4-methylbenzamidine (Amidine XI)

Procedure as described for Amidine X using the following amounts: 6.00 mL of 2-n-propylaniline (42.6 mmol); 21.3 mL of 2.0 M butyllithium (42.6 mmol); 5.00 g of toluonitrile (42.6 mmol). Filtration of the final pentane solution yielded 9.53 g (89%) of light yellow solid. $^1$H NMR (400 MHz, CDCl$_3$): 7.76 (d, 2H), 7.22 (m, 3H), 7.15 (t, 1H), 6.99 (t, 1H), 6.84 (d, 1H), 4.69 (s, 2H), 2.51 (t, 2H), 2.39 (s, 3H), 1.58 (m, 2H), 0.90 (t, 3H).

Amidine Synthesis 12—N$^1$-(2-(dimethylamino)ethyl)benzamidine (Amidine XI)

Procedure as described for Amidine I using the following amounts: 6.00 mL of 2-n-propylaniline (42.6 mmol); 21.3 mL of 2.0 M butyllithium (42.6 mmol); 5.00 g of toluonitrile (42.6 mmol). Filtration of the final pentane solution yielded 9.53 g (89%) of light yellow solid. $^1$H NMR (400 MHz, CDCl$_3$): 7.76 (d, 2H), 7.22 (m, 3H), 7.15 (t, 1H), 6.99 (t, 1H), 6.84 (d, 1H), 4.69 (s, 2H), 2.51 (t, 2H), 2.39 (s, 3H), 1.58 (m, 2H), 0.90 (t, 3H).

Amidine Synthesis 13—N$^1$-(2-(phenylthio)phenyl)benzamidine (Amidine XIII)

Procedure as described for Amidine I using the following amounts and modifications: 10.06 g of 2-phenylthioaniline (50.0 mmol); 25.0 mL of 2.0 M butyllithium (50.0 mmol), 5.20 mL of benzonitrile (51.0 mmol). After refluxing overnight, the solution was green-brown. Addition of water yielded a light brown solution with suspended solid. Solution was taken to dryness, resuspended in 75 mL of pentane, filtered, washed with 10 mL of pentane and dried in vacuo yielding 10.56 g (69%) of beige powder. $^1$H NMR (400 MHz, C$_6$D$_6$): 7.76 (d, 2H), 7.42 (d, 2H), 7.31 (d, 1H), 7.1-6.8 (m, 8H), 6.78 (t, 1H), 4.08 (s, 2H).

Amidine Synthesis 14—N$^1$-(2-morpholinoethyl)benzamidine (Amidine XIV)

Procedure as described for Amidine I using the following amounts and modifications: 6.6 mL of 4-(2-aminoethyl)morpholine (50.0 mmol); 25.0 mL of 2.0 M butyllithium (50.0 mmol), 5.20 mL of benzonitrile (51.0 mmol). After refluxing overnight, the solution was green-brown. Addition of water yielded a light brown solution with suspended solid. Solution was filtered, taken to dryness, resuspended in 100 mL of pentane and stirred vigorously for 1 hour. A white solid deposited, which was filtered, washed with 10 mL of pentane and dried in vacuo yielding 8.17 g (70%) of white powder. $^1$H NMR (400 MHz, CDCl$_3$): 7.57 (br, 2H), 7.43 (m, 3H), 6.4 (br, 1H), 5.3 (br, 1H), 3.71 (m, 4H), 3.47 (br, 2H), 2.65 (m, 2H), 2.51 (br, 4H).

Amidine Synthesis 15—N¹
(thiazol-2-vbbenzamidine (Amidine XV)

Procedure as described for Amidine I using the following amounts and modifications: 5.01 g of 2-aminothiazole (50.0 mmol), 26.0 mL of 2.0 M butyllithium (52.0 mmol), 5.20 mL of benzonitrile (51.0 mmol). After refluxing overnight, the solution was green-brown. Addition of water yielded a red-brown solution with suspended solid. Solution was taken to dryness yielding 6.66 g (66%) of yellow-orange material. $^1$H NMR (400 MHz, $C_6D_6$): 10.1 (br, 1H), 7.68 (d, 2H), 7.34 (d, 1H), 7.04 (m, 3H), 6.40 (d, 1H), 5.35 (br, 1H), 2.26 (s, 6H).

TABLE 7

Amines, Nitriles, and Product Amidine Compounds of Amidine Syntheses 1-15

| Synthesis Designation | Amine | Nitrile | Amidine |
|---|---|---|---|
| Amidine Synthesis 1 | 2,6-dimethylaniline | benzonitrile | Amidine I |
| Amidine Synthesis 2 | 2,6-diisopropylaniline | benzonitrile | Amidine II |
| Amidine Synthesis 3 | 2,6-dimethylaniline | 4-methylbenzonitrile | Amidine III |
| Amidine Synthesis 4 | 2,6-dimethylaniline | 4-tert-butylbenzonitrile | Amidine IV |

TABLE 7-continued

Amines, Nitriles, and Product Amidine Compounds of Amidine Syntheses 1-15

| Synthesis Designation | Amine | Nitrile | Amidine |
|---|---|---|---|
| Amidine Synthesis 5 | 2-isopropyl-6-methylaniline | 4-methylbenzonitrile | Amidine V |
| Amidine Synthesis 6 | 2-tert-butylaniline | 4-methylbenzonitrile | Amidine VI |
| Amidine Synthesis 7 | 2-tert-butylaniline | 4-tert-butylbenzonitrile | Amidine VII |
| Amidine Synthesis 8 | 2-ethylaniline | 4-methylbenzonitrile | Amidine VIII |

TABLE 7-continued

Amines, Nitriles, and Product Amidine Compounds of Amidine Syntheses 1-15

| Synthesis Designation | Amine | Nitrile | Amidine |
|---|---|---|---|
| Amidine Synthesis 9 | aniline (Ph-NH₂) | 4-methylbenzonitrile | Amidine IX |
| Amidine Synthesis 10 | 2-isopropylaniline | 4-methylbenzonitrile | Amidine X |
| Amidine Synthesis 11 | 2-propylaniline | 4-methylbenzonitrile | Amidine XI |
| Amidine Synthesis 12 | N,N-dimethylethylenediamine | 4-methylbenzonitrile | Amidine XII |
| Amidine Synthesis 13 | 2-(phenylthio)aniline | 4-methylbenzonitrile | Amidine XIII |

TABLE 7-continued

Amines, Nitriles, and Product Amidine Compounds of Amidine Syntheses 1-15

| Synthesis Designation | Amine | Nitrile | Amidine |
|---|---|---|---|
| Amidine Synthesis 14 | morpholine-N-CH2CH2-NH2 | 4-methylphenyl-C≡N | Amidine XIV |
| Amidine Synthesis 15 | 2-aminothiazole | 4-methylphenyl-C≡N | Amidine XV |

Synthesis of N²-Substituted Amidine Compounds

Acid halides, amines, and phosphorus pentachloride were utilized as obtained from the chemical supplier. The solvents were dried and/or purified using conventional methods and stored under conditions to limit their ability to pick-up water. The syntheses of the N²-substituted amidine compounds were performed using standard air-free procedures and techniques.

Table 8 provides the acid halides and amines utilized in amide syntheses 1 and 2 along with the product amide. Table 8 provides the amides and product α-halo-substituted imines of α-halo-substituted imines syntheses 1 and 2. Table 9 provides the α-halo-substituted imines and the product N²-substituted amidines of N²-Substituted Amidine Synthesis 1 and 2.

Amide Synthesis 1—N-(2-ethylphenyl)acetamide (Amide I)

2-ethylaniline (12.4 mL, 100 mmol) and NEt$_3$ (15.4 mL, 110 mmol) were added to 100 mL of dichloromethane and cooled to 0° C. Acetyl chloride (7.10 mL 100 mmol) was added dropwise to the cooled aniline solution, affording a peach colored suspension after complete addition. The slurry was warmed to room temperature and heated to reflux overnight. The suspension was taken to dryness and the solid was treated with 200 mL of water. The solid was collected by filtration, washed with 200 mL of diethylether and dried in vacuo, yielding 9.45 g (58%) of white solid. $^1$H NMR (400 MHz, CDCl$_3$): 7.68 (d, 1H), 7.26-7.11 (m, 4H), 2.59 (q, 2H), 2.18 (s, 3H), 1.22 (t, 3H).

Amide Synthesis 2—N-(2-tert-butylphenyl)-4-methylbenzamide (Amide II)

2-tert-butylaniline (14.0 mL, 90 mmol) and NEt$_3$ (14.0 mL, 100 mmol) were added to 100 mL of dichloromethane and cooled to 0° C. P-toluoylchloride (12.0 mL, 90 mmol) was added dropwise to the cooled aniline solution, affording a suspension after complete addition. The slurry was warmed to room temperature and heated to reflux overnight. The suspension was taken to dryness and the solid was treated with 150 mL of water. The solid was collected by filtration, washed with 150 mL of diethylether and dried in vacuo, yielding 23.14 g (96%) of white solid. $^1$H NMR (400 MHz, CDCl$_3$): 7.86 (s, 1H), 7.80 (d, 2H), 7.74 (d, 1H), 7.43 (d, 1H), 7.31 (d, 2H), 7.26 (d, 1H), 7.17 (t, 1H), 2.44 (s, 3H), 1.45 (s, 9H).

TABLE 8

Acid Halides, Amines, and Product Amide Compounds of Amide Syntheses 1 and 2.

| Synthesis Designation | Acid Halide | Amine | Amide |
|---|---|---|---|
| Amide Synthesis 1 | acetyl chloride | 2-ethylaniline | Amide I |

TABLE 8-continued

Acid Halides, Amines, and Product Amide Compounds of Amide Syntheses 1 and 2.

| Synthesis Designation | Acid Halide | Amine | Amide |
|---|---|---|---|
| Amide Synthesis 2 | (4-methylbenzoyl chloride) | (2-tert-butylaniline) | Amide II |

α-Halo-Substituted Imine Synthesis 1—N-(1-chloroethylidene)-2-ethylbenzenamine (HS Imine I)

Phosphorus pentachloride (8.97 g, 43 mmol) was dissolved in 100 mL of benzene. Under a gentle argon purge, N-(2-ethylphenyl)acetamide (Amide I) (6.52 g, 40 mmol) was added slowly with stirring at room temperature. The yellow solution was refluxed for 2 hours. Benzene was removed in vacuo, yielding a brown oil. The oil was distilled under reduced pressure (45-50° C., 0.10 Torr) affording 6.08 g (84%) of a clear oil. $^1$H NMR (400 MHz, $C_6D_6$): 7.07 (t, 2H), 6.99 (t, 1H), 6.80 (d, 1H), 2.50 (q, 2H), 2.08 (s, 3H), 1.11 (t, 3H).

α-Halo-Substituted Imine Synthesis 2—2-tert-butyl-N-(chloro(p-tolyl)methylene)benzenamine (HS Imine II)

Phosphorus pentachloride (6.88 g, 33 mmol) was dissolved in 50 mL of benzene. Under a gentle argon purge, N-(2-tert-butylphenyl)-4-methylbenzamide (Amide II) (8.02 g, 30 mmol) was added slowly with stirring at room temperature. The yellow solution was refluxed for 2 hours. Benzene was removed in vacuo, yielding a yellow solid (8.22 g, 96%). $^1$H NMR (400 MHz, $C_6D_6$): 8.17 (d, 2H), 7.38 (d, 1H), 7.11 (t, 1H), 7.06 (t, 1H), 6.90 (d, 2H), 6.85 (d, 1H), 1.98 (s, 3H), 1.42 (s, 9H).

TABLE 9

Amides and Product α-Halo-Substituted Imines of α-Halo-Substituted Imine Syntheses 1-2.

| Synthesis Designation | Amide | α-Halo-Substituted Imine |
|---|---|---|
| α-Halo-Substituted Imine Synthesis 1 | Amide I | HS Imine I |
| α-Halo-Substituted Imine Synthesis 2 | Amide II | HS Imine II |

$N^2$-Substituted Amidine Synthesis 1—N-(2-ethylphenyl)-$N^2$-(2-ethylphenyl)acetamidine (NS Amidine I)

N-(1-chloroethylidene)-2-ethylbenzenamine (HS Imine I) (1.82 g, 10 mmol) was dissolved in 50 mL of toluene. 2-ethylaniline (1.24 mL, 10 mmol) was added dropwise at room temperature, resulting in a light pink solution, which was refluxed overnight. Toluene was removed under vacuum. Sodium hydroxide (100 mL of 0.10 M solution, 10 mmol) was added and the solution was stirred for 1 hour. The solid that deposited was extracted into 150 mL of diethylether. The ether layer was dried with MgSO$_4$, filtered and taken to dryness, leaving 2.20 g of pink solid. The pink solid was dissolved in 60 mL of pentane and cooled to −30° C. A white crystalline solid was collected and dried (2.11 g, 79%). The $^1$H NMR spectrum is complex and is consistent with a mixture of E/Z isomers.

$N^2$-Substituted Amidine Synthesis 2—N-(2-tert-butylphenyl)-$N^2$-(2-tert-butylphenyl)-4-methylbenzamidine (NS Amidine II)

2-tert-butyl-N-(chloro(p-tolyl)methylene)benzenamine (HS Imine II) (2.86 g, 10 mmol) was dissolved in 50 mL of toluene. 2-tert-butylaniline (1.56 mL, 10 mmol) was added dropwise at room temperature, resulting in a yellow solution, which was refluxed overnight. Toluene was removed under vacuum. Sodium hydroxide (100 mL of 0.10 M solution, 10 mmol) was added and the solution was stirred for 1 hour. The solid that deposited was extracted into 150 mL of diethylether. The ether layer was dried with MgSO$_4$, filtered, and taken to dryness, leaving 3.72 g (93%) of white solid. The $^1$H NMR spectrum is complex and is consistent with a mixture of E/Z isomers.

100 mL of diethylether, cooled to 0° C., and treated with 10.5 mL of 2.0 M butyllithium (21.0 mmol). A sticky yellow solid formed upon complete addition. The diethylether was decanted and replaced with 100 mL of pentane. Vigorous stirring eventually yielded a free-flowing, off-white solid which was collected and dried (7.08 g).

Synthesis of $N^2$-Phosphinylamidine Compounds

The amidine compounds were utilized as prepared using the methods described herein. The phosphine halides, metal salts, and n-butyl lithium were utilized as obtained from the chemical supplier. The solvents were dried and/or purified using conventional methods and stored under conditions to limit their ability to pick-up water. The syntheses of the

TABLE 10

α-Halo-Substituted Imines and Product $N^2$-Substituted Amidine of $N^2$-Substituted Amidine Syntheses 1-2.

| Synthesis Designation | α-Halo-Substituted Imine | Amine | $N^2$-Substituted Amidine |
|---|---|---|---|
| $N^2$-Substituted Amidine Synthesis 1 | HS Imine I | | NS Amidine I |
| $N^2$-Substituted Amidine Synthesis 2 | HS Imine II | | NS Amidine II |

Synthesis of Metal Amidinate Compounds

The metal amidinate compound was prepared using the methods described herein Amines, nitriles, and n-butyl lithium were utilized as obtained from the chemical supplier. The solvents were dried and/or purified using conventional methods and stored under conditions to limit their ability to pick-up water. The syntheses of the amidine compounds were performed using standard air-free procedures and techniques.

Metal Amidinate Synthesis 1—Lithium $N^1$-(2-(diphenylphosphino)ethyl)benzamidinate (NP Amidinate I)

Procedure as described for Amidine I was used with the modification that the resultant amidinate was not neutralized. The following amounts were used with the additional noted modifications: 6.23 g of 2-diphenylphosphinoethylamine (27.2 mmol), 13.6 mL of 2.0 M butyllithium (27.2 mmol), 2.80 mL of benzonitrile (27.2 mmol). Normal workup yielded a thick oil that failed to solidify. The thick oil was dissolved in $N^2$-phosphinylamidine compounds were performed using standard air-free procedures and techniques.

Table 11 provides the amidines and phosphine halides utilized in $N^2$-phosphinylamidine syntheses 1-20 in addition to the product $N^2$-phosphinylamidine compounds.

$N^2$-phosphinylamidine Synthesis 1—$N^1$-(2,6-dimethylphenyl)-$N^2$-(diphenylphosphino)benzamidine (NP Amidine I)

$N^1$-(2,6-dimethylphenyl)benzamidine (3.36 g, 15.0 mmol) was dissolved in 50 mL of diethylether and cooled to 0° C. Butyllithium (7.50 mL of 2.0 M solution in diethylether, 15.0 mmol) was added dropwise, producing a fluffy white suspended solid. The slurry was warmed to room temperature and stirred for 2 hours. Chlorodiphenylphosphine (2.69 mL, 15.0 mmol) was added slowly at room temperature. The suspended solid became finer and denser and the solution became slightly yellow upon complete addition of the phosphine. Stirring was continued for 1 hour. The solution was filtered to remove a small amount of white solid, presumably lithium chloride, and the solvent was removed in vacuo. The yellow foamy residue was suspended in 50 mL of pentane and stirred for 3 hours. Filtration and drying afforded 3.46 g (56%) of off-white solid.

$N^2$-phosphinylamidine Synthesis 2—$N^1$-(2,6-diisopropylphenyl)-$N^2$-(diphenylphosphino)benzamidine (NP Amidine II)

Procedure as described for NP Amidine I using the following amounts: 4.20 g $N^1$-(2,6-diisopropylphenyl)benzamidine (15.0 mmol), 7.50 mL of 2.0 M butyllithium (15.0 mmol), 2.70 mL of chlorodiphenylphosphine (15.0 mmol). Following removal of lithium chloride via filtration and removal of solvent in vacuo, the sticky residue was dissolved in 20 mL of pentane, reduced in volume to 5 mL (cold), producing a while solid that was filtered and dried (5.33 g, 76%).

$N^2$-phosphinylamidine Synthesis 3—$N^2$-(diisopropylphosphino)-4-methyl-$N^1$-(2,6-dimethylphenyl)-benzamidine (NP Amidine III)

Procedure as described for NP Amidine I using the following amounts: 1.19 g of 4-methyl-$N^1$-(2,6-dimethylphenyl)benzamidine (Amidine III, 5.0 mmol), 2.50 mL of 2.0 M butyllithium (5.0 mmol), 0.80 mL chlorodiisopropylphosphine (5.0 mmol). After filtration to remove lithium chloride and removal of solvent, a yellow oil was isolated (1.76 g).

$N^2$-phosphinylamidine Synthesis 4—4-methyl-$N^1$-(2,6-dimethylphenyl)-$N^2$-(diphenylphosphino)-benzamidine (NP Amidine IV)

Procedure as described for NP Amidine I using the following amounts: 1.19 g of 4-methyl-$N^1$-(2,6-dimethylphenyl)benzamidine (Amidine III, 5.0 mmol), 2.50 mL of 2.0 M butyllithium (5.0 mmol), 0.93 mL chlorodiphenylphosphine (5.0 mmol). After filtration to remove lithium chloride and removal of solvent, the oily product was treated with 20 mL of pentane. After 1 hour stirring at room temperature, a white solid formed. The solution was concentrated to approximately 10 mL and filtered while cold, yielding 1.64 g (78%) after drying.

$N^2$-phosphinylamidine Synthesis 5—4-tert-butyl-$N^1$-(2,6-dimethylphenyl)-$N^2$-(diphenylphosphino)-benzamidine (NP Amidine V)

Procedure as described for NP Amidine I using the following amounts: 1.40 g of 4-t-butyl-$N^1$-(2,6-dimethylphenyl)benzamidine (Amidine IV, 5.0 mmol), 2.50 mL of 2.0 M butyllithium (5.0 mmol), 0.93 mL chlorodiphenylphosphine (5.0 mmol). After filtration to remove lithium chloride and removal of solvent, the sticky residue was treated with 20 mL of pentane. After 1 hour stirring at room temperature, the pentane was removed in vacuo yielding 2.16 g (93%) of off-white solid.

$N^2$-phosphinylamidine Synthesis 6—4-tert-butyl-$N^2$-(diisopropylphosphino)-$N^1$-(2,6-dimethylphenyl)-benzamidine (NP Amidine VI)

Procedure as described for NP Amidine I using the following amounts: 1.40 g of 4-t-butyl-$N^1$-(2,6-dimethylphenyl)benzamidine (Amidine IV, 5.0 mmol), 2.50 mL of 2.0 M butyllithium (5.0 mmol), 0.80 mL chlorodiisopropylphosphine (5.0 mmol). After filtration to remove lithium chloride and removal of solvent, a slightly cloudy yellow oil was isolated (2.04 g, 100%).

$N^2$-phosphinylamidine Synthesis 7—$N^1$-(2-isopropyl-6-methylphenyl)-4-methyl-$N^2$-(diphenyl-phosphino)benzamidine (NP Amidine VII)

Procedure as described for NP Amidine I using the following amounts: 1.33 g of $N^1$-(2-isopropyl-6-methylphenyl)-4-methylbenzamidine (Amidine V, 5.0 mmol), 2.50 mL of 2.0 M butyllithium (5.0 mmol), 0.93 mL chlorodiphenylphosphine (5.0 mmol). After filtration to remove lithium chloride and removal of solvent, the residue was treated with 20 mL of pentane. Prolonged stirring deposited a beige solid which was collected and dried (1.62 g, 72%).

$N^2$-phosphinylamidine Synthesis 8—4-tert-butyl-$N^1$-(2-tert-butylphenyl)-$N^2$-(diphenylphosphino)-benzamidine (NP Amidine VIII)

Procedure as described for NP Amidine I using the following amounts: 1.33 g of $N^1$-(2-tert-butylphenyl)-4-methylbenzamidine (Amidine VI, 5.0 mmol), 2.50 mL of 2.0 M butyllithium (5.0 mmol), 0.93 mL chlorodiphenylphosphine (5.0 mmol). After filtration to remove lithium chloride and removal of solvent, the residue was treated with 20 mL of pentane. Removal of pentane deposited a yellow solid which was collected and dried (2.05 g, 91%).

$N^2$-phosphinylamidine Synthesis 9—$N^1$-(2-isopropyl-6-methylphenyl)-$N^2$-(diisopropyl-phosphino)-4-methylbenzamidine (NP Amidine IX)

Procedure as described for NP Amidine I using the following amounts: 1.33 g of $N^1$-(2-isopropyl-6-methylphenyl)-4-methylbenzamidine (Amidine V, 5.0 mmol), 2.50 mL of 2.0 M butyllithium (5.0 mmol), 0.80 mL chlorodiisopropylphosphine (5.0 mmol). After filtration to remove lithium chloride and removal of solvent, a yellow semi-solid was isolated (1.86 g, 97%).

$N^2$-phosphinylamidine Synthesis 10—$N^1$-(2-tert-butylphenyl)-$N^2$-(diisopropylphosphino)-4-methyl-benzamidine (NP Amidine X)

Procedure as described for NP Amidine I using the following amounts: 1.33 g of $N^1$-(2-tert-butylphenyl)-4-methylbenzamidine (Amidine VI, 5.0 mmol), 2.50 mL of 2.0 M butyllithium (5.0 mmol), 0.80 mL chlorodiisopropylphosphine (5.0 mmol). After filtration to remove lithium chloride and removal of solvent, a yellow semi-solid was isolated (1.9 g, 100%).

$N^2$-phosphinylamidine Synthesis 11—4-tert-butyl-$N^1$-(2-tert-butylphenyl)-$N^2$-(diphenylphosphino)-benzamidine (NP Amidine XI)

Procedure as described for NP Amidine I using the following amounts: 1.54 g of 4-tert-butyl-$N^1$-(2-tert-butylphenyl)benzamidine (Amidine VII, 5.0 mmol), 2.50 mL of 2.0 M butyllithium (5.0 mmol), 0.93 mL chlorodiphenylphosphine (5.0 mmol). After filtration to remove lithium chloride and removal of solvent, a yellow solid was collected and dried (2.31 g, 94%).

$N^2$-phosphinylamidine Synthesis 12—4-tert-butyl-$N^1$-(2-tert-butylphenyl)-$N^2$-(diisopropylphosphino)-benzamidine (NP Amidine XII)

Procedure as described for NP Amidine I using the following amounts: 1.54 g of 4-tert-butyl-$N^1$-(2-tert-butylphenyl) benzamidine (Amidine VII, 5.0 mmol), 2.50 mL of 2.0 M butyllithium (5.0 mmol), 0.80 mL chlorodiisopropylphosphine (5.0 mmol). After filtration to remove lithium chloride and removal of solvent, a yellow semi-solid was isolated (1.9 g, 100%).

$N^2$-phosphinylamidine Synthesis 13—$N^1$-(2-ethylphenyl)-4-methyl-$N^2$-(diphenylphosphino)benzamidine (NP Amidine XIII)

Procedure as described for NP Amidine I using the following amounts: 1.19 g of $N^1$-(2-ethylphenyl)-4-methylbenzamidine (Amidine VIII, 5.0 mmol), 2.50 mL of 2.0 M butyllithium (5.0 mmol), 0.93 mL chlorodiphenylphosphine (5.0 mmol). After filtration to remove lithium chloride and removal of solvent, the residue was treated with 20 mL of pentane. The light yellow solid was collected and dried (1.45 g, 69%).

$N^2$-phosphinylamidine Synthesis 14—$N^1$-(2-ethylphenyl)-$N^2$-(diisopropylphosphino)-4-methyl-benzamidine (NP Amidine XIV)

Procedure as described for NP Amidine I using the following amounts: 1.19 g of $N^1$-(2-ethylphenyl)-4-methylbenzamidine (Amidine VIII, 5.0 mmol), 2.50 mL of 2.0 M butyllithium (5.0 mmol), 0.80 mL chlorodiisopropylphosphine (5.0 mmol). After filtration to remove lithium chloride and removal of solvent, a yellow oil was isolated (1.77 g, 100%).

$N^2$-phosphinylamidine Synthesis 15—4-methyl-$N^1$-phenyl-$N^2$-diphenylphosphino benzamidine (NP Amidine XV)

Procedure as described for NP Amidine I using the following amounts: 1.05 g of 4-methyl-$N^1$-phenylbenzamidine (Amidine IX, 5.0 mmol), 2.50 mL of 2.0 M butyllithium (5.0 mmol), 0.93 mL chlorodiphenylphosphine (5.0 mmol). After filtration to remove lithium chloride and removal of solvent, the residue was treated with 20 mL of pentane. The yellow solid was collected and dried (1.85 g, 94%).

$N^2$-phosphinylamidine Synthesis 16—$N^2$-(diisopropylphosphino)-4-methyl-N'-phenylbenzamidine (NP Amidine XVI)

Procedure as described for NP Amidine I using the following amounts: 1.05 g of 4-methyl-$N^1$-phenylbenzamidine (Amidine IX, 5.0 mmol), 2.50 mL of 2.0 M butyllithium (5.0 mmol), 0.80 mL chlorodiisopropylphosphine (5.0 mmol). After filtration to remove lithium chloride and removal of solvent, a yellow oil was isolated (1.62 g, 99%).

$N^2$-phosphinylamidine Synthesis 17—$N^1$-(2-isopropylphenyl)-$N^2$-(diisopropylphosphino)-4-methylbenzamidine (NP Amidine XVII)

$N^1$-(2-isopropylphenyl)-4-methylbenzamidine (1.26 g, 5.0 mmol) was dissolved in 25 mL of diethylether and cooled to 0° C. Butyllithium (2.50 mL of 2.0 M solution in pentane, 5.0 mmol) was added dropwise, producing a fluffy white suspended solid. The slurry was warmed to room temperature and stirred for 2 hours. Chlorodiisopropylphosphine (0.80 mL, 5.0 mmol) was added slowly at room temperature. The suspended solid became finer and denser and the solution became slightly yellow upon complete addition of the phosphine. Stirring was continued for 1 hour. The solution was filtered to remove a small amount of white solid, presumably lithium chloride, and the solvent was removed in vacuo. The yellow foamy residue was suspended in 25 mL of pentane, stirred for 2 hours and taken to dryness under vacuum, affording 1.64 g (70%) of yellow solid.

$N^2$-phosphinylamidine Synthesis 18—$N^1$-(2-n-propylphenyl)-$N^2$-(diphenylphosphino)-4-methylbenzamidine (NP Amidine XVIII)

Procedure as described for NP Amidine XVII using the following amounts: 1.26 g of $N^1$-(2-n-propylphenyl)-4-methylbenzamidine (5.0 mmol), 2.50 mL of 2.0 M butyllithium (5.0 mmol), 0.90 mL of chlorodiphenylphosphine (5.0 mmol). 1.76 g (74%) of light yellow solid was collected.

$N^2$-phosphinylamidine Synthesis 19—$N^1$-(2-(dimethylamino)ethyl)-$N^2$-(diisopropylphosphino)-benzamidine (NP Amidine XIX)

Procedure as described for NP Amidine I using the following amounts and modifications: 0.956 g of $N^1$-(2-(dimethylamino)ethyl)benzamidine (Amidine XII, 5.0 mmol), 2.50 mL of 2.0 M butyllithium (5.0 mmol), 0.80 mL chlorodiisopropylphosphine (5.0 mmol). After filtration to remove lithium chloride and removal of solvent, a yellow oil was isolated (1.52 g, 99%).

$N^2$-phosphinylamidine Synthesis 20—$N^1$-(2-(dimethylamino)ethyl)-$N^2$-(diphenylphosphino)-benzamidine (NP Amidine XX)

Procedure as described for NP Amidine I using the following amounts and modifications: 0.956 g of $N^1$-(2-(dimethylamino)ethyl)benzamidine (Amidine XII, 5.0 mmol), 2.50 mL of 2.0 M butyllithium (5.0 mmol), 0.93 mL chlorodiphenylphosphine (5.0 mmol). After filtration to remove lithium chloride and removal of solvent, the oily product was treated with 20 mL of pentane. After 1 hour stirring at room temperature, a white solid formed. The solution was concentrated to approximately 10 mL and filtered while cold, yielding 0.891 g (47%) after drying.

$N^2$-phosphinylamidine Synthesis 21—$N^2$-(diisopropylphosphino)-$N^1$-(2-(diphenylphosphino)ethyl)-benzamidine (NP Amidine XXI)

Procedure as described for NP Amidine XVII with the following modification: the metal amidinate was not prepared from the amidine compound but was utilized as isolated in Amidinate Synthesis 1. The amount of reagents utilized: 1.69 g of lithium $N^1$-(2-(diphenylphosphino)ethyl)-benzamidinate (Amidinate 1, 5.0 mmol), 0.80 mL chlorodiisopropylphosphine (5.0 mmol). After filtration to remove lithium chloride and removal of solvent, a yellow oil was isolated (1.72 g, 77%).

$N^2$-phosphinylamidine Synthesis 22—$N^2$-(diphenylphosphino)-$N^1$-(2-(diphenylphosphino)ethyl)-benzamidine (NP Amidine XXII)

Procedure as described for NP Amidine XVII with the following modification: the metal amidinate was not prepared from the amidine compound but was utilized as isolated in Amidinate Synthesis 1. The amount of reagents utilized: 1.69 g of lithium $N^1$-(2-(diphenylphosphino)ethyl)-benzamidinate (Amidinate 1, 5.0 mmol), 0.93 mL chlorodiphenylphosphine (5.0 mmol). After filtration to remove lithium chloride and removal of solvent, the yellow foamy residue was treated with 40 mL of pentane. Scraping the walls of the flask yielded a yellow solid that was collected and dried (2.04 g, 79%).

$N^2$-phosphinylamidine Synthesis 23—$N^2$-(diisopropylphosphino)-$N^1$-(2-(phenylthio)phenyl)-benzamidine (NP Amidine XXIII)

Procedure as described for NP Amidine I using the following amounts and modifications: 1.52 g of $N^1$-(2-(phenylthio)phenyl)benzamidine (Amidine XIV, 5.0 mmol), 2.50 mL of 2.0 M butyllithium (5.0 mmol), 0.80 mL chlorodiisopropylphosphine (5.0 mmol). After filtration to remove lithium chloride and removal of solvent, a yellow oil was isolated (2.07 g, 98%).

$N^2$-phosphinylamidine Synthesis 24—$N^2$-(diphenylphosphino)-$N^1$-(2-(phenylthio)phenyl)benzamidine (NP Amidine XXIV)

Procedure as described for NP Amidine I using the following amounts and modifications: 1.34 g of $N^1$-(2-(phenylthio)phenyl)benzamidine (Amidine XIV, 4.4 mmol), 2.20 mL of 2.0 M butyllithium (4.4 mmol), 0.78 mL chlorodiphenylphosphine (4.4 mmol). After filtration to remove lithium chloride and removal of solvent, a sticky solid was isolated (2.01 g, 93%).

$N^2$-phosphinylamidine Synthesis 25—$N^2$-(diisopropylphosphino)-$N^1$-(2-morpholinoethyl)benzamidine (NP Amidine XXV)

Procedure as described for NP Amidine XVII using the following amounts: 0.956 g of $N^1$-(2-morpholinoethyl)benzamidine (Amidine XV, 5.0 mmol), 2.50 mL of 2.0 M butyllithium (5.0 mmol), 0.80 mL chlorodiisopropylphosphine (5.0 mmol). After filtration to remove lithium chloride and removal of solvent, a yellow oil was isolated (1.71 g, 98%).

$N^2$-phosphinylamidine Synthesis 26—$N^1$-(2-morpholinoethyl)-$N^2$-(diphenylphosphino)benzamidine (NP Amidine XXVI)

Procedure as described for NP Amidine XVII using the following amounts: 1.17 g of $N^1$-(2-morpholinoethyl)benzamidine (Amidine XV, 5.0 mmol), 2.50 mL of 2.0 M butyllithium (5.0 mmol), 0.93 mL chlorodiphenylphosphine (5.0 mmol). After filtration to remove lithium chloride and removal of solvent, the oily product was treated with 20 mL of pentane. Removal of the pentane yielded 1.33 g of off-white solid (64%).

$N^2$-phosphinylamidine Synthesis 27—$N^2$-(diphenylphosphino)-$N^1$-(thiazol-2-yl)benzamidine (NP Amidine XXVII)

Procedure as described for NP Amidine XVII using the following amounts: 3.06 g of $N^1$-(thiazol-2-yl)benzamidine (Amidine XVI, 15.0 mmol), 7.50 mL of 2.0 M butyllithium (15.0 mmol), 0.93 mL of chlorodiphenylphosphine (15.0 mmol). Following removal of lithium chloride, the solvent was removed from the filtrate to give a sticky residue. The sticky residue was suspended in 100 mL of pentane. Vigorous stirring and scraping eventually yielded an off-white solid after 2 hours. The solid was collected and dried (2.59 g). The lithium chloride solid separated from reaction solution was extracted with 100 mL of diethylether, filtered, taken to dryness, and treated with 100 mL of pentane. Stirring and scraping produced white solid that was collected and dried yielding an additional 1.56 g of solid. Combined yield 4.15 g (71%).

$N^2$-phosphinylamidine Synthesis 28—$N^1$-(2-ethylphenyl)-N-(2-ethylphenyl)-N-(diisopropylphosphino)acetamidine (NSP Amidine I)

$N^1$-(2-ethylphenyl)-N-(2-ethylphenyl)acetamidine (NS Amidine I) (0.798 g, 3.0 mmol) was dissolved in 50 mL of diethylether and cooled to 0° C. Butyllithium (1.50 mL of 2.0 M solution in pentane, 3.0 mmol) was added dropwise, producing a light yellow solution. The solution was warmed to room temperature and stirred for 2 hours. Chlorodiisopropylphosphine (0.48 mL, 3.0 mmol) was added slowly at room temperature. A white suspension formed, which was stirred overnight at room temperature. The slurry was filtered to remove a small amount of white solid, presumably lithium chloride, and the solvent was removed in vacuo to produce 1.14 g (99%) of yellow oil.

$N^2$-phosphinylamidine Synthesis 29—$N^1$-(2-tert-butylphenyl)-N-(2-tert-butylphenyl)-N-(diisopropylphosphino)-4-methylbenzamidine (NSP Amidine II)

$N^1$-(2-tert-butylphenyl)-N-(2-tert-butylphenyl)-4-methylbenzamidine (NS Amidine II) (1.20 g, 3.0 mmol) was dissolved in 50 mL of diethylether and cooled to 0° C. Butyllithium (1.50 mL of 2.0 M solution in pentane, 3.0 mmol) was added dropwise, producing a light yellow solution. The solution was warmed to room temperature and stirred for 2 hours. Chlorodiisopropylphosphine (0.48 mL, 3.0 mmol) was added slowly at room temperature. A white suspension formed, which was stirred overnight at room temperature. The slurry was filtered to remove a small amount of white solid, presumably lithium chloride, and the solvent was removed in vacuo to produce 1.35 g (87%) of yellow solid.

TABLE 11

Amidines, Phosphine Halides, and Product N²-Phosphinyl Amidine Compounds of
N²-Phosphinyl Amine Syntheses 1-29.

| Run # | Amidine | Phosphine Halide Compound | N²-Phosphinyl Amidine |
|---|---|---|---|
| N²-Phosphinyl-amidine Synthesis 1 | Amidine I | Cl–P(Ph)₂ | NP Amidine I |
| N²-Phosphinyl-amidine Synthesis 2 | Amidine II | Cl–P(Ph)₂ | NP Amidine II |
| N²-Phosphinyl-amidine Synthesis 3 | Amidine III | Cl–P(iPr)₂ | NP Amidine III |
| N²-Phosphinyl-amidine Synthesis 4 | Amidine III | Cl–P(Ph)₂ | NP Amidine IV |

TABLE 11-continued
Amidines, Phosphine Halides, and Product N²-Phosphinyl Amidine Compounds of
N²-Phosphinyl Amine Syntheses 1-29.
| Run # | Amidine | Phosphine Halide Compound | N²-Phosphinyl Amidine |
|---|---|---|---|
| N²-Phosphinyl-amidine Synthesis 5 | 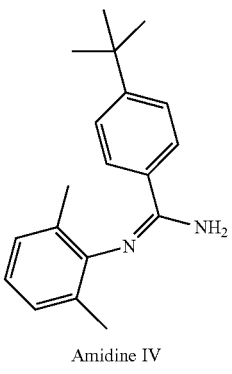  Amidine IV | 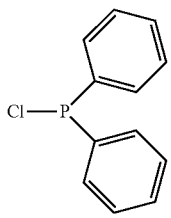 | 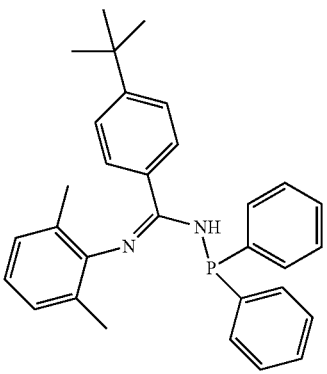  NP Amidine V |
| N²-Phosphinyl-amidine Synthesis 6 | 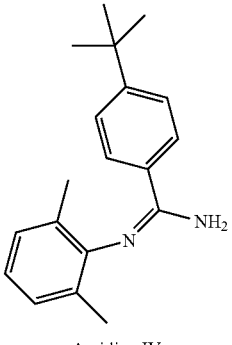  Amidine IV | 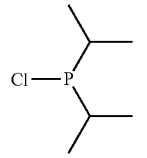 | 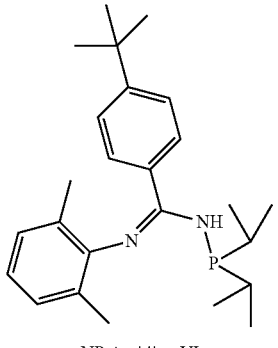  NP Amidine VI |
| N²-Phosphinyl-amidine Synthesis 7 | 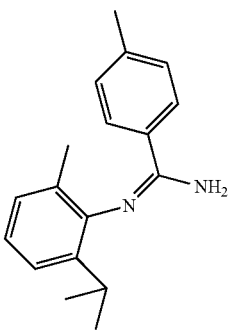 [SMILES: Cc1ccc(/C(N)=N\c2c(C)cccc2C(C)C)cc1]  Amidine V | 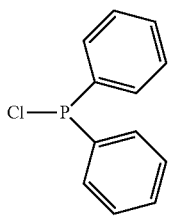 | 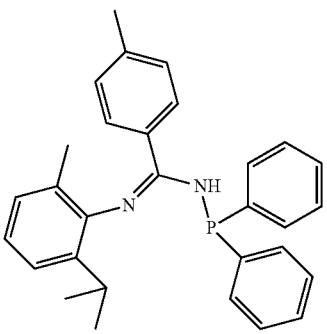  NP Amidine VII |

TABLE 11-continued

Amidines, Phosphine Halides, and Product N²-Phosphinyl Amidine Compounds of
N²-Phosphinyl Amine Syntheses 1-29.

| Run # | Amidine | Phosphine Halide Compound | N²-Phosphinyl Amidine |
|---|---|---|---|
| N²-Phosphinyl-amidine Synthesis 8 | 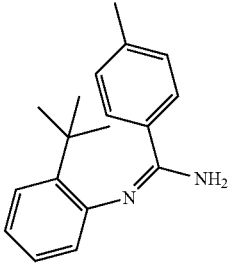<br>Amidine VI | 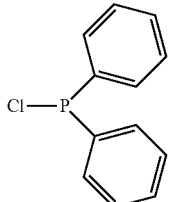 | 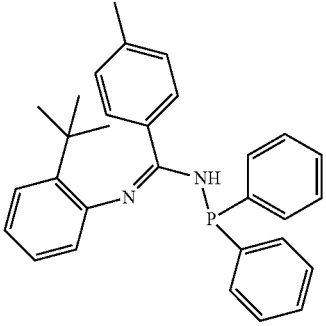<br>NP Amidine VIII |
| N²-Phosphinyl-amidine Synthesis 9 | 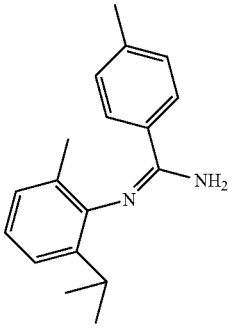<br>Amidine V | 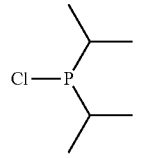 | 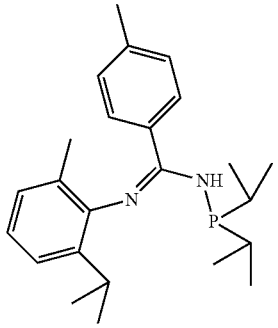<br>NP Amidine IX |
| N²-Phosphinyl-amidine Synthesis 10 | 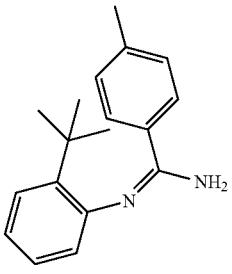 [SMILES: Cc1ccc(/C(N)=N\c2ccccc2C(C)(C)C)cc1]<br>Amidine VI | 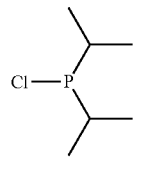 | 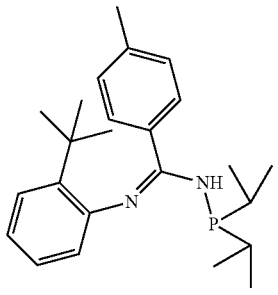<br>NP Amidine X |
| N²-Phosphinyl-amidine Synthesis 11 | 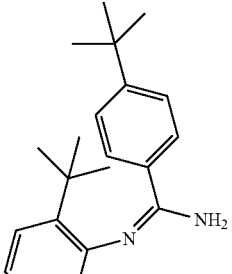<br>Amidine VIII | 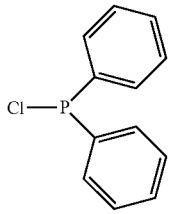 | 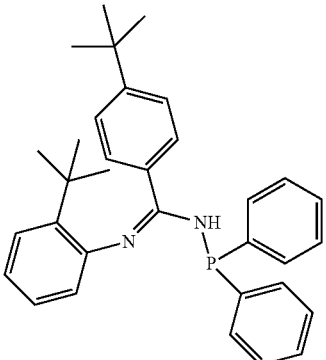<br>NP Amidine XI |

TABLE 11-continued

Amidines, Phosphine Halides, and Product N²-Phosphinyl Amidine Compounds of
N²-Phosphinyl Amine Syntheses 1-29.

| Run # | Amidine | Phosphine Halide Compound | N²-Phosphinyl Amidine |
|---|---|---|---|
| N²-Phosphinyl-amidine Synthesis 12 | Amidine VIII | Cl—P(iPr)₂ | NP Amidine XII |
| N²-Phosphinyl-amidine Synthesis 13 | Amidine VIII | Cl—PPh₂ | NP Amidine XIII |
| N²-Phosphinyl-amidine Synthesis 14 | Amidine VIII | Cl—P(iPr)₂ | NP Amidine XIV |
| N²-Phosphinyl-amidine Synthesis 15 | Amidine IX | Cl—PPh₂ | NP Amidine XV |

US 8,680,003 B2

TABLE 11-continued

Amidines, Phosphine Halides, and Product N²-Phosphinyl Amidine Compounds of
N²-Phosphinyl Amine Syntheses 1-29.

| Run # | Amidine | Phosphine Halide Compound | N²-Phosphinyl Amidine |
|---|---|---|---|
| N²-Phosphinyl-amidine Synthesis 16 | 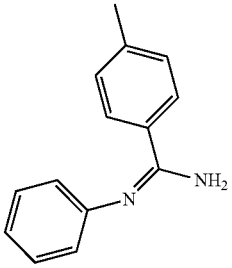 [SMILES: Cc1ccc(/C(N)=N\c2ccccc2)cc1]<br>Amidine IX | 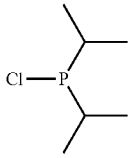 | 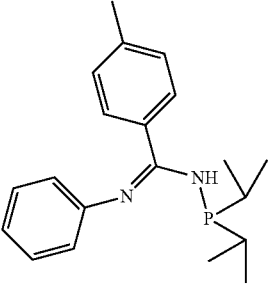<br>NP Amidine XVI |
| N²-Phosphinyl-amidine Synthesis 17 | 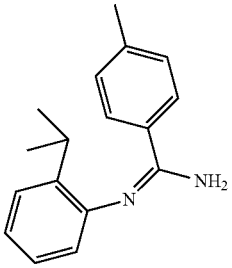 [SMILES: Cc1ccc(/C(N)=N\c2ccccc2C(C)C)cc1]<br>Amidine X | 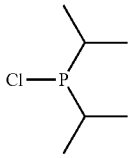 | 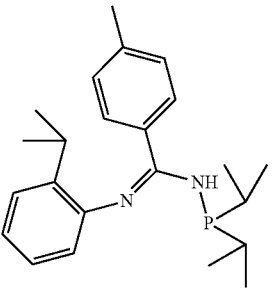<br>NP Amidine XVII |
| N²-Phosphinyl-amidine Synthesis 18 | 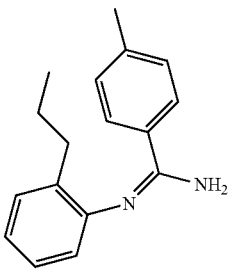 [SMILES: CCCc1ccccc1/N=C(/N)c1ccc(C)cc1]<br>Amidine XI | 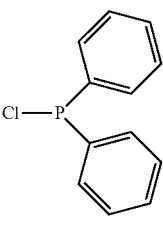 | 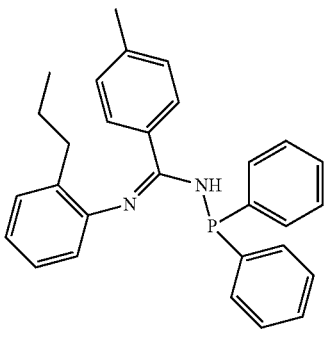<br>NP Amidine XVIII |
| N²-Phosphinyl-amidine Synthesis 19 | 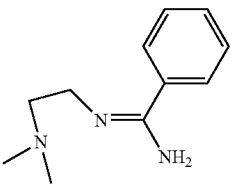<br>Amidine XII | 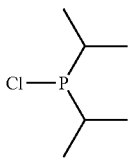 | 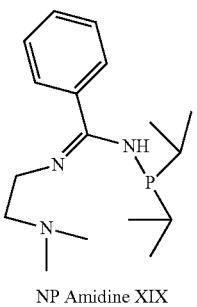<br>NP Amidine XIX |

TABLE 11-continued

Amidines, Phosphine Halides, and Product N²-Phosphinyl Amidine Compounds of
N²-Phosphinyl Amine Syntheses 1-29.

| Run # | Amidine | Phosphine Halide Compound | N²-Phosphinyl Amidine |
|---|---|---|---|
| N²-Phosphinyl-amidine Synthesis 20 | 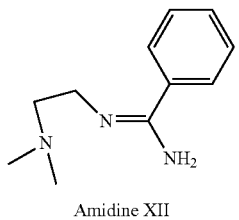<br>Amidine XII | 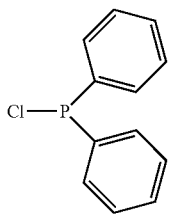 [SMILES: ClP(c1ccccc1)c1ccccc1] | 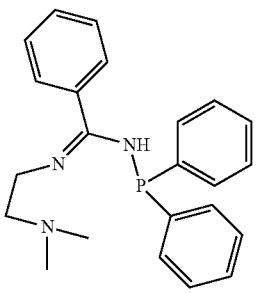<br>NP Amidine XX |
| N²-Phosphinyl-amidine Synthesis 21 | 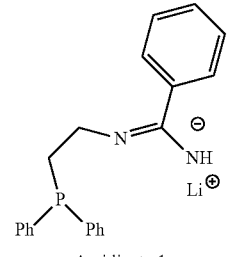<br>Amidinate 1 | 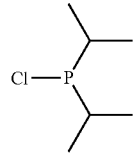 | 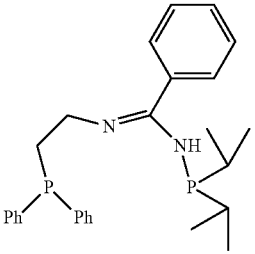<br>NP Amidine XXI |
| N²-Phosphinyl-amidine Synthesis 22 | 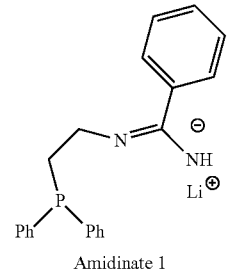 [SMILES: N/C(=N/CCP(c1ccccc1)c1ccccc1)c1ccccc1 ; [Li+]]<br>Amidinate 1 | 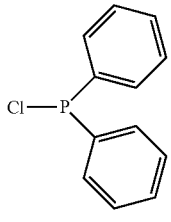 [SMILES: ClP(c1ccccc1)c1ccccc1] | 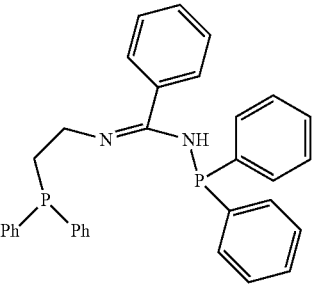<br>NP Amidine XXII |
| N²-Phosphinyl-amidine Synthesis 23 | 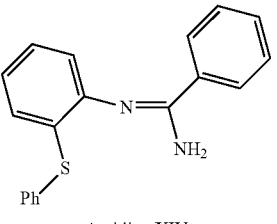<br>Amidine XIV | 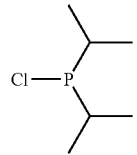 | 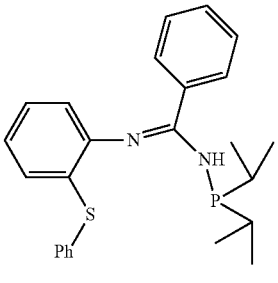<br>NP Amidine XXIII |

TABLE 11-continued

Amidines, Phosphine Halides, and Product N²-Phosphinyl Amidine Compounds of
N²-Phosphinyl Amine Syntheses 1-29.

| Run # | Amidine | Phosphine Halide Compound | N²-Phosphinyl Amidine |
|---|---|---|---|
| N²-Phosphinyl-amidine Synthesis 24 | 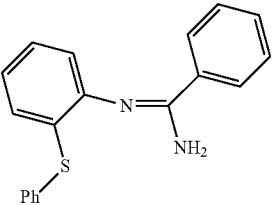<br>Amidine XIV | 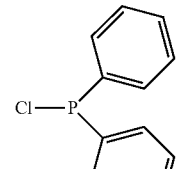 | 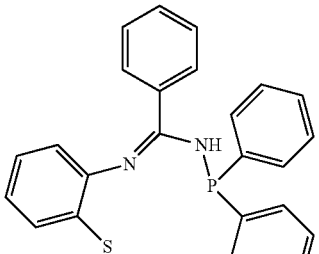<br>NP Amidine XXIV |
| N²-Phosphinyl-amidine Synthesis 25 | 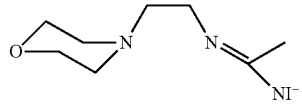<br>Amidine XV | 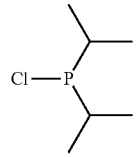 | 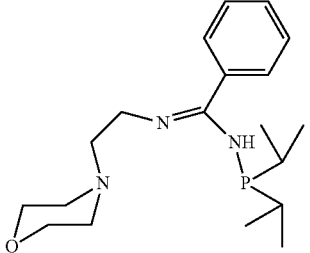<br>NP Amidine XXV |
| N²-Phosphinyl-amidine Synthesis 26 | 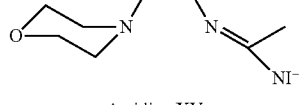<br>Amidine XV | 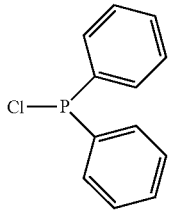 [SMILES: ClP(c1ccccc1)c1ccccc1] | 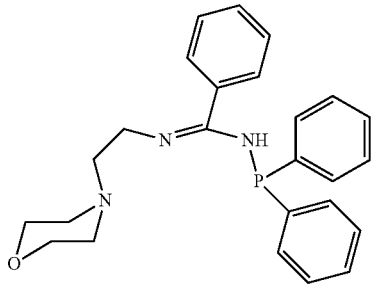<br>NP Amidine XXVI |
| N²-Phosphinyl-amidine Synthesis 27 | 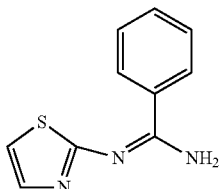<br>Amidine XVI | 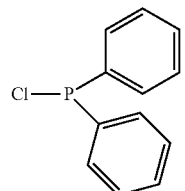 | 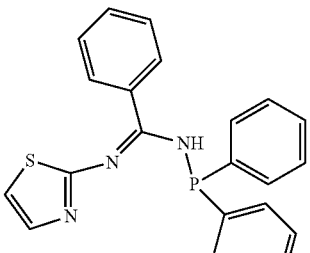<br>NP Amidine XXVII |

TABLE 11-continued

Amidines, Phosphine Halides, and Product N²-Phosphinyl Amidine Compounds of
N²-Phosphinyl Amine Syntheses 1-29.

| Run # | Amidine | Phosphine Halide Compound | N²-Phosphinyl Amidine |
|---|---|---|---|
| N²-Phosphinyl-amidine Synthesis 28 | 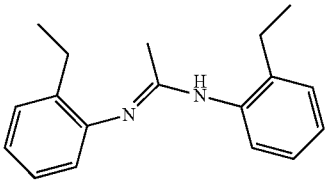<br>NS Amidine I | 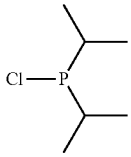 | 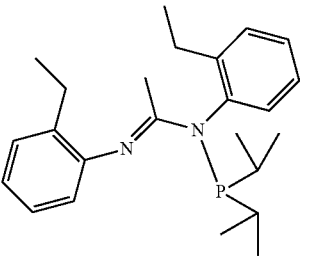<br>NSP Amidine I |
| N²-Phosphinyl-amidine Synthesis 29 | 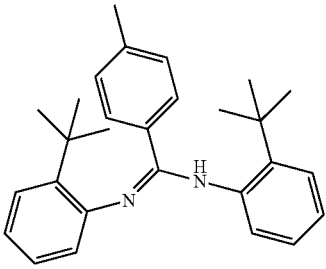<br>NS Amidine II | 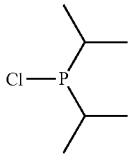 | 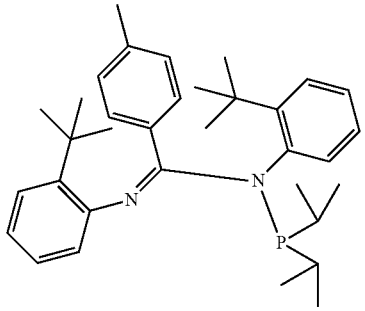<br>NSP Amidine II |

Synthesis of N²-Phosphinylamidine Compounds

The N²-phosphinylamidine compounds were utilized as prepared using the methods described herein. The halogenated compounds and butyllithium were utilized as obtained from the chemical supplier. The solvents were dried and/or purified using conventional methods and stored under conditions to limit their ability to pick-up water. The syntheses of the alkylated N²-phosphinylamidine compounds were performed using standard air-free procedures and techniques.

Table 12 provides the amidine compounds and halogenated compounds utilized in the N²-phosphinylamidine alkylations 1 and 2 in addition to the product alkylated N²-phosphinylamidine compounds.

N²-phosphinylamidine Alkylation 1—N¹-(2-isopropylphenyl)-N-(diisopropylphosphino)-N-methyl-4-methylbenzamidine (NSP Amidine III)

N¹-(2-isopropylphenyl)-N-(diisopropylphosphino)-4-methylbenzamidine (1.40 g, 3.0 mmol) was dissolved in 25 mL of diethylether and cooled to 0° C. Butyllithium (1.50 mL of 2.0 M solution in pentane, 3.0 mmol) was added dropwise, producing a cloudy yellow suspension. The slurry was warmed to room temperature and stirred for 2 hours. Methyliodide (1.5 mL of 2.0 M solution in THF) was added dropwise at room temperature and stirred continued for 1 hour. The solution became clear yellow. The solvent was removed under vacuum and replaced with 20 mL of diethylether. A small amount of solid (presumably LiI) was removed by filtration and the filtrate was taken to dryness, yielding 0.94 g (65%) of sticky yellow solid.

N²-phosphinylamidine Alkylation 2—N¹-(2-n-propylphenyl)-N-(diphenylphosphino)-N-methyl-4-methylbenzamidine (NSP Amidine IV)

Procedure as described for NSP Amidine III using the following amounts: 1.42 g of N¹-(2-n-propylphenyl)-N-(diphenylphosphino)-4-methylbenzamidine (3.0 mmol), 1.50 mL of 2.0 M butyllithium (15.0 mmol), 1.50 mL of 2.0 M methyliodide (3.0 mmol). Following removal of lithium iodide via filtration and removal of solvent in vacuo, a yellow sticky residue was recovered (1.63 g, 67%).

TABLE 12

Amidine Compounds, Halogenated Compounds, and Product $N^2$-Phosphinylamidine Compounds of $N^2$-Phosphinylamidine Alkylations 1 and 2.

| Run | $N^2$-Phosphinyl Amidine | Halogenated Compound | Alkylated $N^2$-Phosphinyl Amidine |
|---|---|---|---|
| $N^2$-phosphinyl-amidine Alkylation 1 | 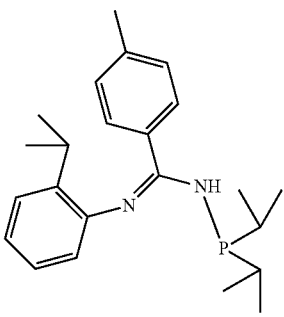<br>NP Amidine XVII | $CH_3I$ | 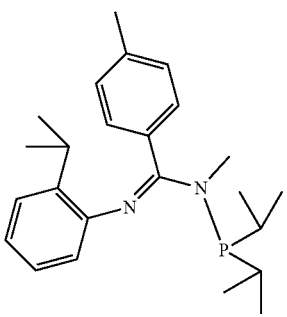<br>NSP Amidine III |
| $N^2$-phosphinyl-amidine Alkylation 2 | 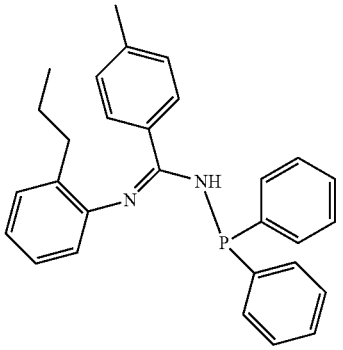<br>NP Amidine XVIII | $CH_3I$ | 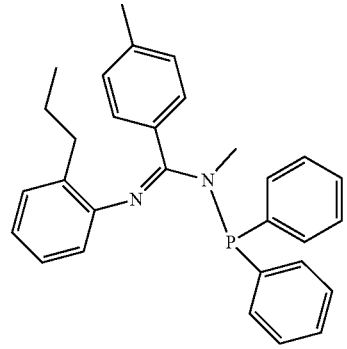<br>NSP Amidine IV |

Synthesis of $N^2$-Phosphinylamidinate Metal Salts

The $N^2$-phosphinylamidinecompounds were utilized as prepared using the methods described herein. The metal salts and butyllithium were utilized as obtained from the chemical supplier. The solvents were dried and/or purified using conventional methods and stored under conditions to limit their ability to pick-up water. The syntheses of the $N^2$-phosphinylamidinate metal salt complexes were performed using standard Schlenk and/or inert atmosphere glove box techniques. It should be noted that the Tables in this section provide what is believed to be the structure of a freshly prepared $N^2$-phosphinylamidinate metal salt complex based upon the structure of an $N^2$-phosphinylamidine metal complex subjected to X-ray crystallography. However, the $N^2$-phosphinylamidinate metal salt complex can contain more or or less neutral ligand than is shown in the structure without departing from the present disclosure. As will be come apparent, and without being limited to theory, it is believed that the structure of the $N^2$-phosphinylamidinate metal salt complex can change with time and that this change can be due to the loss of the neutral ligand from the $N^2$-phosphinylamidinate metal complex or $N^2$-phosphinylamidinate metal complex crystal lattice. Additionally, the $N^2$-phosphinylamidinate metal complex structures formally show a monomeric form of a metal compound complexed to $N^2$-phosphinylamidinate. However, it should be noted that these structures do not necessarily imply that dimeric and/or oligomeric forms of structures having bridging $X_p$ groups (e.g. Cl) which connect metal atoms complexed to the $N^2$-phosphinylamidinate are not formed. The monomeric structures provided herein can encompass the dimeric and/or oligomeric forms of structures having bridging $X_p$ groups which can connect metal atoms complexed to the $N^2$-phosphinylamidinate.

Table 13 provides the $N^2$-phosphinylamidine compounds and metal salts compounds utilized in the $N^2$-phosphinylamidinate metal salt synthesis 1-3 in addition to the product $N^2$-phosphinylamidinate metal salt complexes.

$N^2$-Phosphinylamidinate Metal Salt Synthesis 1—[$N^1$-(2,6-dimethylphenyl)-$N^2$-(diphenylphosphino)benzamidinate](THF)$CrCl_2$ (NP Amidine Metal Salt Complex A1)

$N^1$-(2,6-dimethylphenyl)-N-(diphenylphosphino)benzamidine (NP Amidine I) (0.204 g, 0.500 mmol) was dissolved in 20 mL of THF and cooled to $-100°$ C. Butyllithium (0.25 mL of 2.0 M solution in diethyl ether, 0.50 mmol) was added dropwise, resulting in a yellow solution upon warming to room temperature. Stirring continued for 2 hours. $CrCl_3$ (THF)$_3$ (0.187 g, 0.500 mmol) was dissolved in 10 mL of THF and was added dropwise to the amidinate solution. The solution was dark green after complete addition. Stirring was continued for 1 hour at room temperature after which the solvent was removed in vacuo. Diethyl ether (30 mL) was added and the solution was filtered to remove a white precipitate, presumably LiCl. The green filtrate was taken to dryness yielding 0.250 g of green solid. Anal. Calc. (Found) for C$_{31}$H$_{32}$ON$_2$PCrCl$_2$: C, 61.80 (56.91); H, 5.35 (5.37); N, 4.65 (4.79).

N$^2$-Phosphinylamidinate Metal Salt Synthesis 2—[N$^1$-(2,6-diisopropylphenyl)-N$^2$-(diphenylphosphino)benzamidinate] (THF)CrCl, (NP Amidine Metal Salt Complex A2)

N$^1$-(2,6-diisopropylphenyl)-N-(diphenylphosphino)benzamidine (NP Amidine II, 0.464 g, 1.00 mmol) was dissolved in 50 mL of diethyl ether and cooled to 0° C. Butyllithium (0.50 mL of 2.0 M solution in diethyl ether, 1.00 mmol) was added dropwise, resulting in a yellow solution after complete addition. The mixture was warmed to room temperature and stirred for 1 hour. CrCl$_3$(THF)$_3$ (0.374 g, 1.00 mmol) was dissolved in 20 mL of THF and treated with small portions of the benzamidinate solution via pipet. The resulting green solution was stirred for 2 hours at room temperature. The mixture was taken to dryness, extracted into 50 mL of diethyl ether, filtered to remove LiCl, and taken to dryness to yield a green powder (0.627 g, 95.2%). Anal. Calc. (Found) for C$_{35}$H$_{40}$ON2PCrC12: C, 63.83 ( ); H, 6.12 ( ); N, 4.25 ( ).

N$^2$-Phosphinylamidinate Metal Salt Synthesis 3—[4-methyl-N$^1$-(2,6-dimethylphenyl)-N$^2$-(diphenylphosphino)benzamidinate] (THF)CrCl, (NP Amidine Metal Salt Complex A3)

4-methyl-N$^1$-(2,6-dimethylphenyl)-N-(diphenylphosphino)benzamidine (NP Amidine IV, 0.211 g, 0.500 mmol) was dissolved in 50 mL of diethyl ether and cooled to 0° C. Butyllithium (0.25 mL of 2.0 M solution in diethyl ether, 0.50 mmol) was added dropwise, resulting in a yellow solution after complete addition. The mixture was warmed to room temperature and stirred for 1 hour. CrCl$_3$(THF)$_3$ (0.187 g, 0.500 mmol) was dissolved in 20 mL of THF and treated with small portions of the benzamidinate solution via pipet. The resulting green solution was stirred for 2 hours at room temperature. The mixture was taken to dryness, extracted into 15 mL of diethyl ether, filtered to remove LiCl, and taken to dryness, affording 0.155 g of solid (54.5%). Anal. Calc. (Found) for C$_{32}$H$_{34}$ON$_2$PCrCl$_2$: C, 67.61 ( ); H, 6.03 ( ); N, 4.93 ( ).

TABLE 13

N$^2$-Phosphinylamidine Compounds, Metal Salts, and Product N$^2$-Phosphinylamidinate Metal Salt Complexes of N2-Phosphinylamidinate Metal Salt Syntheses 1-3.

| Run # | N$^2$-Phosphinyl Amidine | Metal Salt | Metal Salt N$^2$-Phosphinyl Amidinate |
|---|---|---|---|
| N$^2$-Phosphinyl-amidinate Metal Salt Synthesis 3 | NP Amidine I | CrCl$_3$(THF)$_3$ | NP Amidine Metal Salt Complex A1 |
| N$^2$-Phosphinyl-amidinate Metal Salt Synthesis 3 | NP Amidine II | CrCl$_3$(THF)$_3$ | NP Amidine Metal Salt Complex A2 |

TABLE 13-continued

N²-Phosphinylamidine Compounds, Metal Salts, and Product N²-Phosphinylamidinate
Metal Salt Complexes of N2-Phosphinylamidinate Metal Salt Syntheses 1-3.

| Run # | N²-Phosphinyl Amidine | Metal Salt | Metal Salt N²-Phosphinyl Amidinate |
|---|---|---|---|
| N²-Phosphinyl- amidinate Metal Salt Synthesis 3 | 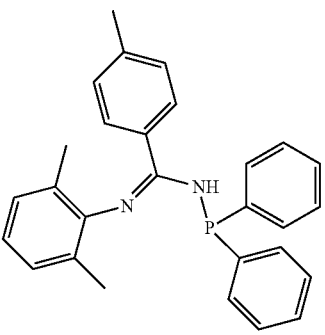<br>NP Amidine IV | CrCl₃(THF)₃ | 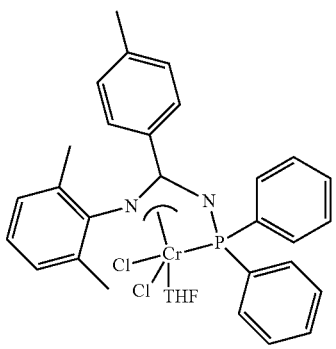<br>NP Amidine Metal Salt Complex A3 |

Synthesis of N²-Substituted Amidine Compounds

Amines, nitriles, n-butyl lithium, phosphine halides were utilized as obtained from the chemical supplier. The solvents were dried and/or purified using conventional methods and stored under conditions to limit their ability to pick-up water. The syntheses of the amidine compounds were performed using standard air-free procedures and techniques. Several N²-phosphinylamidine compounds were prepared from amines, nitriles, n-butyl lithium, phosphine halides without isolating the intermediate metal amidinate of amidine compound. The procedure utilized is provided below.

A glass 500 mL three-necked round bottomed flask fitted with a) an adapter that can connect to two glass addition funnels, b) a nitrogen purge line, and c) vacuum source. The flask also contained a magnetic stir bar to enable stirring with a magnetic stirrer. The round bottomed flask apparatus was then purged with dry nitrogen for 30 minutes before use while the round bottomed flask was cooled in an ice water bath.

In a dry box, seven addition funnels were prepared. The first addition funnel (125 mL) was charged with 110 mL anhydrous diethyl ether. The second addition funnel (125 mL) was charged with 90 mL anhydrous diethyl ether and the amine. The third addition funnel (50 mL) was charged with 2.0 M n-butyl lithium in pentane. The fourth addition funnel (125 ml) was charged with a nitrile. A fifth addition funnel (500 mL) was charged with about 210 mL of anhydrous THF. A sixth addition funnel (125 mL) was charged with a chlorophosphine. The seventh addition funnel (250 mL) was charged with 225 mL of anhydrous n-pentane. The addition funnels prepared, sealed, and removed from the dry box as needed.

The amine solution and diethyl ether addition funnels were mounted to the round bottomed flask adapter. Once the apparatus had been purged and the round bottomed flask cooled, all of the amine solution was charged to the round bottomed flask. Then 45 mL of diethyl ether from the diethyl ether addition funnel was sent through the round bottomed flask adapter to flush the amine into the round bottomed flask. The amine solution addition funnel was replaced with the n-butyl lithium addition funnel. When the contents of the round bottomed flask attained a temperature between 0° C. and 5° C., all of the n-butyl lithium solution was added dropwise to the round bottomed flask over about 20 minutes. The ice water bath was removed from around the round bottomed flask and the contents of the round bottomed flask mixture were allowed to slowly warm to room temperature. The third addition funnel was replaced with the nitrile addition funnel while the contents of the round bottomed flask were stirred for two hours at room temperature. The nitrile was then added dropwise to the round bottomed flask over about 20 minutes. The contents of the round bottomed flask were then stirred at room temperature for one hour.

Using reduced pressure, the ether was removed from the round bottomed flask leaving a yellow-brown solid. The round bottomed flask was purged with dry nitrogen. The fourth addition funnel was replaced with the THF addition funnel Once the round bottomed flask had been purged with nitrogen, all of the THF was added to the round bottomed flask. The contents of the round bottomed flask were heated to 60° C. and stirred for about 16 hours. The contents of the round bottomed flask were cooled to room temperature. While the contents of the round bottomed flask were cooling to room temperature the fifth addition funnel was replaced with the addition funnel containing the chlorophosphine. Once the contents of the round bottomed flask attained room temperature, all of the chlorophosphine was added dropwise to the round bottomed flask over about 20 minutes and then stirred for one hour at room temperature. The THF was then evaporated the THF from the round bottomed flask under reduced pressure while applying heat with a heating mantle to main a temperature around 50° C. to 60° C. The sixth addition funnel was replaced with the addition funnel containing n-pentane. The round bottomed flask was allowed to cool to room temperature and about 100 ml of n-pentane was added to the round bottomed flask to disperse the solid residue to give a brown solution which was stirred for about three hours at room temperature to dissolve the organic product. The finely divided LiCl salt was then removed from the solution by suction filtration. The N²-phosphinylamidine compound was then collected by crystallization from the clear brown filtrate solution. Typical yield range from 60% to 80%.

Five different syntheses were performed using this procedure. The materials utilized and the quantity of the reagent is provided in Table 14.

TABLE 14

Regents utilized to prepare $N^2$-phosphinylamidine compounds using amines, nitriles, n-butyl lithium, phosphine halides without isolating the intermediate metal amidinate of amidine compound.

| Run | Amine | n-Butyl Lithiium | Nitrile | Chlorophosphine |
|---|---|---|---|---|
| 1 | 2,4,6-Trimethyl-aniline (9.2 g - 68 mmol) | 35.5 mL - 71 mmol | 4-t-Butyl-benzonitrile (11 g - 69 mmol) | Diisopropyl-phosphorus Chloride (27.9 g - 68 mmol) |
| 2 | 2,4,6-Trimethyl-aniline (9.2 g - 68 mmol) | 35.5 mL - 71 mmol | 3,5-dimethyl-4-methoxy-benzonitrile (11.2 g - 69 mmol) | Diisopropyl-phosphorus Chloride (27 g - 68 mmol) |
| 3 | 2,4,6-Trimethyl-aniline (9.2 g - 68 mmol) | 35.5 mL - 71 mmol | 4-t-Butyl-benzonitrile (11 g - 69 mmol) | Diphenyl-phosphorus Chloride (32.5 g - 68 mmol) |
| 4 | 2,4,6-Trimethyl-aniline (9.2 g - 68 mmol) | 35.5 mL - 71 mmol | Benzonitrile (11.2 g - 69 mmol) | Diisopropyl-phosphorus Chloride (32.6 g - 68 mmol) |
| 5 | 2,4,6-Trimethyl-aniline (9.2 g - 68 mmol) | 35.5 mL - 71 mmol | 4-t-Butyl-benzonitrile (11 g - 69 mmol) | Diisobutyl-phosphorus Chloride (32.5 g - 68 mmol) |

Synthesis of $N^2$-Phosphinylamidine Metal Salt Complexes

The $N^2$-phosphinylamidine compounds were utilized as prepared using the methods described herein. The metal salts and butyllithium were utilized as obtained from the chemical supplier. The solvents were dried and/or purified using conventional methods and stored under conditions to limit their ability to pick-up water. The syntheses of the $N^2$-phosphinylamidine metal salt complexes were performed using standard Schlenk and/or inert atmosphere glove box techniques. It should be noted that the Tables in this section provide what is believed to be the structure of a freshly prepared $N^2$-phosphinylamidine metal salt complex based upon the structure of an $N^2$-phosphinylamidine metal complex subjected to X-ray crystallography. However, the $N^2$-phosphinylamidine metal salt complex can contain more or or less neutral ligand than is shown in the structure without departing from the present disclosure. As will be come apparent, and without being limited to theory, it is believed that the structure of the $N^2$-phosphinylamidine metal salt complex can change with time and that this change can be due to the loss of the neutral ligand from the $N^2$-phosphinylamidine metal complex or $N^2$-phosphinylamidine metal complex crystal lattice. It should also be noted that the structure of the $N^2$-phosphinylamidine metal salt complexes utilizing an $N^2$-phosphinylamidine compound including a metal salt complexing group shows that the metal complexing group is not ligated to the metal salt. It is not known whether or not the metal complex is ligated to the metal salt and the present disclosure encompasses the possibility that the metal salt complexing group is ligated or not ligated to the metal salt any particular $N^2$-phosphinylamidine metal salt complex. Additionally, the $N^2$-phosphinylamidine metal complex structures formally show a monomeric form of a metal compound complexed to a $N^2$-phosphinylamidine compound. However, it should be noted that these structures do not necessarily imply that dimeric and/or oligomeric forms of structures having bridging $X_p$ groups (e.g. Cl) which connect metal atoms complexed to the $N^2$-phosphinylamidine compound are not formed. The monomeric structures provided herein can encompass the dimeric and/or oligomeric forms of structures having bridging $X_p$ groups which can connect metal atoms complexed to the $N^2$-phosphinylamidine compound.

Table 15 provides the $N^2$-phosphinylamidine compounds and metal salts compounds utilized in the $N^2$-phosphinylamidine metal salt synthesis 1-19 in addition to the product $N^2$-phosphinylamidine metal salt complexes.

$N^2$-Phosphinylamidine Metal Salt Complex Synthesis 1—[$N^1$-(2,6-dimethylphenyl)-$N^2$-(diphenylphosphino)benzamidine](THF)$CrCl_3$ (NP Amidine Metal Salt Complex B1)

$CrCl_3(THF)_3$ (0.200 g, 0.534 mmol) was dissolved in 15 mL of THF. $N^1$-(2,6-dimethylphenyl)-$N^2$-(diphenylphosphino)benzamidine (NP Amidine I) (0.220 g, 0.534 mmol) was added as a solid in small portions. The resulting blue-green solution was stirred overnight at room temperature and taken to dryness. The residue was washed with 10 mL of diethyl ether and 20 mL of pentane, collected and dried affording 0.317 g (83.5%) of blue solid, which analyzed satisfactorily as a THF solvate. Anal. Calc. (Found) for $C_{35}H_{41}O_2N_2PCrCl_3$: C, 59.12 (58.57); H, 5.81 (5.84); N, 3.94 (3.92)

$N^2$-Phosphinylamidine Metal Salt Complex Synthesis 2—[4-methyl-$N^1$-(2,6-dimethylphenyl)-$N^2$-(diphenylphosphino)benzamidine](THF)$CrCl_3$ (NP Amidine Metal Salt Complex B2)

Procedure as described for NP Amidine Metal Salt Complex B1 using the following amounts: 4-methyl-$N^1$-(2,6-dimethylphenyl)-$N^2$-(diphenylphosphino)benzamidine (NP Amidine IV, 0.211 g, 0.500 mmol), $CrCl_3(THF)_3$ (0.187 g, 0.500 mmol). The resulting blue-green solution was stirred overnight at room temperature, taken to dryness, washed with 10 mL of pentane and dried to yield 0.313 g of green product (95.7%). Anal. Calc. (Found) for $C_{32}H_{35}ON_2PCrCl_3$: C, 58.86 ( ); H, 5.40 ( ); N, 4.29 ( ).

$N^2$-Phosphinylamidine Metal Salt Complex Synthesis 3—[$N^2$-(diisopropylphosphino)-4-methyl-$N^1$-(2,6-dimethylphenyl)benzamidine](THF)$CrCl_3$ (NP Amidine Metal Salt Complex B3)

Procedure as described for NP Amidine Metal Salt Complex B1 using the following amounts: $N^2$-(diisopropylphosphino)-4-methyl-$N^1$-(2,6-dimethylphenyl)benzamidine (NP Amidine III, 0.158 g, 0.464 mmol), $CrCl_3(THF)_3$ (0.174 g, 0.464 mmol). The resulting blue-green solution was stirred overnight at room temperature and taken to dryness. The residue was dissolved in 3 mL of THF and recrystallized via pentane diffusion to yield 0.186 g (68.5%) of crystalline blue solid. Anal. Calc. (Found) for $C_{26}H_{39}ON_2PCrCl_3$: C, 53.39 ( ); H, 6.72 ( ); N, 4.79 ( ).

$N^2$-Phosphinylamidine Metal Salt Complex Synthesis 4—[4-tert-butyl-$N^1$-(2,6-dimethylphenyl)-$N^2$-(diphenylphosphino)benzamidine](THF)CrCl$_3$ (NP Amidine Metal Salt Complex B4)

Procedure as described for NP Amidine Metal Salt Complex B1 using the following amounts: 4-tert-butyl-$N^1$-(2,6-dimethylphenyl)-$N^2$-(diphenylphosphino)benzamidine (NP Amidine V, 0.232 g, 0.500 mmol), $CrCl_3(THF)_3$ (0.187 g, 0.500 mmol). The resulting blue solution was stirred for 2 hours at room temperature, depositing a light blue solid. The volatiles were removed in vacuo, the residue was washed with pentane and dried affording 0.348 g (99%) of blue solid. Anal. Calc. (Found) for $C_{35}H_{41}ON_2PCrCl_3$: C, 60.48 ( ); H, 5.95 ( ); N, 4.03 ( ).

$N^2$-Phosphinylamidine Metal Salt Complex Synthesis 5—[4-tert-butyl-$N^2$-(diisopropylphosphino)-$N^1$-(2,6-dimethylphenyl)benzamidine](THF)CrCl$_3$ (NP Amidine Metal Salt Complex B5)

Procedure as described for NP Amidine Metal Salt Complex B1 using the following amounts, with the following modifications: 4-tert-butyl-$N^2$-(diisopropylphosphino)-$N^1$-(2,6-dimethylphenyl)benzamidine (NP Amidine VI, 0.256 g, 0.644 mmol), $CrCl_3(THF)_3$ (0.241 g, 0.644 mmol). The ligand was preweighed in a disposable pipet and washed into a vial with 10 mL of diethyl ether. The ligand solution was added dropwise to $CrCl_3(THF)_3$ dissolved in 15 mL of THF. The resulting blue solution was stirred for 1 hour at room temperature, depositing a light blue solid. After the volatiles were removed in vacuo, the residue was washed with pentane and dried affording 0.403 g (99%) of blue solid. Anal. Calc. (Found) for $C_{29}H_{45}ON_2PCrCl_3$: C, 55.55 ( ); H, 7.23 ( ); N, 4.47 ( ).

$N^2$-Phosphinylamidine Metal Salt Complex Synthesis 6—[$N^1$-(2-isopropyl-6-methylphenyl)-$N^2$-(diisopropylphosphino)-4-methylbenzamidine](THF)CrCl$_3$ (NP Amidine Metal Salt Complex B6)

Procedure as described for NP Amidine Metal Salt Complex B5 using the following amounts: $N^1$-(2-isopropyl-6-methylphenyl)-$N^2$-(diisopropylphosphino)-4-methylbenzamidine (NP Amidine IX, 0.192 g, 0.500 mmol), $CrCl_3(THF)_3$ (0.187 g, 0.500 mmol). The resulting blue solution was stirred for 1 hour at room temperature. After the volatiles were removed in vacuo, the residue was washed with pentane and dried affording 0.303 g (99%) of blue solid. Anal. Calc. (Found) for $C_{28}H_{43}ON_2PCrCl_3$: C, 54.86 ( ); H, 7.07 ( ); N, 4.57 ( ).

$N^2$-Phosphinylamidine Metal Salt Complex Synthesis 7—$N^1$-(2-tert-butylphenyl)-$N^2$-(diisopropylphosphino)-4-methylbenzamidine](THF)CrCl$_3$ (NP Amidine Metal Salt Complex B7)

Procedure as described for NP Amidine Metal Salt Complex B5 using the following amounts: $N^1$-(2-tert-butylphenyl)-$N^2$-(diisopropylphosphino)-4-methylbenzamidine (NP Amidine X, 0.192 g, 0.500 mmol), $CrCl_3(THF)_3$ (0.187 g, 0.500 mmol). The resulting green solution was stirred for 1 hour at room temperature. After the volatiles were removed in vacuo, the residue was washed with pentane and dried affording 0.305 g (99%) of blue solid. Anal. Calc. (Found) for $C_{28}H_{43}ON_2PCrCl_3$: C, 54.86 ( ); H, 7.07 ( ); N, 4.57 ( ).

$N^2$-Phosphinylamidine Metal Salt Complex Synthesis 8—[4-tert-butyl-$N^1$-(2-tert-butylphenyl)-$N^2$-(diphenylphosphino)benzamidine](THF)CrCl, (NP Amidine Metal Salt Complex B8)

4-tert-butyl-$N^1$-(2-tert-butylphenyl)-$N^2$-(diphenylphosphino)benzamidine (NP Amidine XI) (0.212 g, 0.430 mmol) was dissolved in 20 mL of THF. Solid $CrCl_2$ (0.0615 g, 0.500 mmol) was added to the amidine solution. The solution slowly became lime green. Stirring was continued overnight at room temperature, after which the solvent was removed in vacuo. The green residue was washed with pentane and taken to dryness yielding 0.160 g of green solid.

$N^2$-Phosphinylamidine Metal Salt Complex Synthesis 9—[4-tert-butyl-$N^1$-(2-tert-butylphenyl)-$N^2$-(diisopropylphosphino)benzamidine](THF)CrCl$_3$ (NP Amidine Metal Salt Complex B9)

Procedure as described for NP Amidine Metal Salt Complex B5 using the following amounts: 4-tert-butyl$N^1$-(2-tert-butylphenyl)-$N^2$-(diisopropylphosphino)benzamidine (NP Amidine XII, 0.212 g, 0.500 mmol), $CrCl_3(THF)_3$ (0.187 g, 0.500 mmol). The resulting green solution was stirred overnight at room temperature. After the volatiles were removed in vacuo, the residue was washed with pentane and dried affording 0.253 g (77.2%) of green solid. Anal. Calc. (Found) for $C_{31}H_{49}ON_2PCrCl_3$: C, 56.84 ( ); H, 7.54 ( ); N, 4.28 ( ).

$N^2$-Phosphinylamidine Metal Salt Complex Synthesis 10—[$N^1$-(2-ethylphenyl)-4-methyl-$N^2$-(diphenylphosphino)benzamidine](THF)CrCl$_3$ (NP Amidine Metal Salt Complex B10)

Procedure as described for NP Amidine Metal Salt Complex B5 using the following amounts: $N^1$-(2-ethylphenyl)-4-methyl-$N^2$-(diphenylphosphino)benzamidine (NP Amidine XIII, 0.211 g, 0.500 mmol), $CrCl_3(THF)_3$ (0.187 g, 0.500 mmol). The resulting blue solution was stirred overnight at room temperature. After the volatiles were removed in vacuo, the residue was washed with pentane and dried affording 0.357 g (%) of blue solid. Anal. Calc. (Found) for $C_{32}H_{35}ON_2PCrCl_3$: C, 58.86 ( ); H, 5.40 ( ); N, 4.29 ( ).

$N^2$-Phosphinylamidine Metal Salt Complex Synthesis 11—[$N^1$-(2-ethylphenyl)-$N^2$-(diisopropylphosphino)-4-methylbenzamidine](THF)CrCl$_3$ (NP Amidine Metal Salt Complex B11)

Procedure as described for NP Amidine Metal Salt Complex B5 using the following amounts: $N^1$-(2-ethylphenyl)-$N^2$-(diisopropylphosphino)-4-methylbenzamidine (NP Amidine XIV, 0.177 g, 0.500 mmol), $CrCl_3(THF)_3$ (0.187 g, 0.500 mmol). The resulting blue solution was stirred overnight at room temperature. After the volatiles were removed in vacuo, the residue was washed with pentane and dried affording 0.281 g (96%) of blue solid. Anal. Calc. (Found) for $C_{26}H_{39}ON_2PCrCl_3$: C, 53.38 ( ); H, 6.72 ( ); N, 4.79 ( ).

N²-Phosphinylamidine Metal Salt Complex Synthesis 12—[4-methyl-N¹-phenyl-N²-(diphenylphosphino)benzamidine](THF)CrCl₃ (NP Amidine Metal Salt Complex B12)

Procedure as described for NP Amidine Metal Salt Complex B5 using the following amounts: 4-methyl-N¹-phenyl-N²-(diphenylphosphino)benzamidine (NP Amidine XV, 0.197 g, 0.500 mmol), CrCl₃(THF)₃ (0.187 g, 0.500 mmol). The resulting blue solution was stirred overnight at room temperature. After the volatiles were removed in vacuo, the residue was washed with pentane and dried affording 0.327 g (%) of turquoise solid. Anal. Calc. (Found) for $C_{30}H_{31}ON_2PCrCl_3$: C, 57.66 ( ); H, 5.00 ( ); N, 4.48 ( ).

N²-Phosphinylamidine Metal Salt Complex Synthesis 13—[N²-(diisopropylphosphino)-4-methyl-N¹-phenylbenzamidine](THF)CrCl₃ (NP Amidine Metal Salt Complex B13)

Procedure as described for NP Amidine Metal Salt Complex B5 using the following amounts: N²-(diisopropylphosphino)-4-methyl-N¹-phenylbenzamidine (NP Amidine XVI, 0.163 g, 0.500 mmol), CrCl₃(THF)₃ (0.187 g, 0.500 mmol). The resulting blue solution was stirred overnight at room temperature. After the volatiles were removed in vacuo, the residue was washed with pentane and dried affording 0.278 g (99%) of blue solid. Anal. Calc. (Found) for $C_{24}H_{35}ON_2PCrCl_3$: C, 51.76 ( ); H, 6.34 ( ); N, 5.03 ( ).

N²-Phosphinylamidine Metal Salt Complex Synthesis 14—[N¹-(2-isopropylphenyl)-N²-(diisopropylphosphino)-4-methylbenzamidine](THF)CrCl₃ (NP Amidine Metal Salt Complex B14)

N¹-(2-isopropylphenyl)-N²-(diisopropylphosphino)-4-methylbenzamidine (NP Amidine XVII, 0.234 g, 0.637 mmol) was dissolved in 10 mL of THF and added dropwise to a solution of CrCl₃(THF)₃ (0.193 g, 0.515 mmol) dissolved in 15 mL of THF. The resulting dark blue solution was stirred overnight at room temperature and taken to dryness. The residue was washed with 20 mL of pentane, collected and dried affording 0.336 g of blue solid.

N²-Phosphinylamidine Metal Salt Complex Synthesis 15—[N¹-(2-n-propylphenyl)-N²-(diphenylphosphino)-4-methylbenzamidine](THF)CrCl₃ (NP Amidine Metal Salt Complex B15)

N¹-(2-n-propylphenyl)-N²-(diphenylphosphino)-4-methylbenzamidine (NP Amidine XVIII, 0.236 g, 0.541 mmol) was dissolved in 10 mL of THF and added dropwise to a solution of CrCl₃(THF)₃ (0.190 g, 0.507 mmol) dissolved in 15 mL of THF. The resulting dark blue solution was stirred overnight at room temperature and taken to dryness. The residue was washed with 20 mL of pentane, collected and dried affording 0.379 g of blue solid.

N²-Phosphinylamidine Metal Salt Complex Synthesis 16—[N¹-(2-ethylphenyl)-N²-(2-ethylphenyl)-N²-(diisopropylphosphino)acetamidine](THF)CrCl₃ (NP Amidine Metal Salt Complex C1)

N¹-(2-ethylphenyl)-N²-(2-ethylphenyl)-N²-(diisopropylphosphino)acetamidine (NPS Amidine I, 0.191 g, 0.500 mmol) was dissolved in 15 mL of THF. CrCl₃(THF)₃ (0.187 g, 0.500 mmol) was added as a solid in small portions. The resulting blue solution was stirred overnight at room temperature and taken to dryness. The residue was washed with 20 mL of pentane, collected and dried affording 0.256 g (81%) of blue solid.

N²-Phosphinylamidine Metal Salt Complex Synthesis 17—[N¹-(2-tert-butylphenyl)-N²-(2-tert-butylphenyl)-N²-(diisopropylphosphino)-4-methylbenzamidine] (THF)CrCl₃ (NP Amidine Metal Salt Complex C2)

N¹-(2-tert-butylphenyl)-N²-(2-tert-butylphenyl)-N²-(diisopropylphosphino)-4-methylbenzamidine (NPS Amidine II, 0.261 g, 0.50 mmol) was added to CrCl₃ (0.064 g, 0.50 mmol) suspended in 15 mL of THF. The solution, which slowly became green, was stirred overnight at room temperature and taken to dryness. The residue was washed with 20 mL of pentane, collected and dried affording 0.120 g of green solid.

N²-Phosphinylamidine Metal Salt Complex Synthesis 18—[N¹-(2-isopropylphenyl)-N¹-(diisopropylphosphino)-N²-methyl-4-methylbenzamidine](THF)CrCl₃ (NP Amidine Metal Salt Complex C3)

CrCl₃(THF)₃ (0.187 g, 0.500 mmol) was dissolved in 15 mL of THF. N¹-(2-isopropylphenyl)-N²-(diisopropylphosphino)-N²-methyl-4-methylbenzamidine (NSP Amidine III, 0.241 g, 0.500 mmol) was added as a solid in small portions. The resulting blue-green solution was stirred overnight at room temperature and taken to dryness. The residue was washed with 20 mL of pentane, collected and dried affording 0.279 g (76.7%) of blue solid.

N²-Phosphinylamidine Metal Salt Complex Synthesis 19—[N¹-(2-n-propylphenyl)-N²-(diphenylphosphino)-N²-methyl-4-methylbenzamidine](THF)CrCl₃ (NP Amidine Metal Salt Complex C4)

Procedure as described for NP Amidine Metal Salt Complex C3 using the following amounts: N¹-(2-n-propylphenyl)-N²-(diphenylphosphino)-N²-methyl-4-methylbenzamidine (NSP Amidine IV, 0.243 g, 0.500 mmol), CrCl₃(THF)₃ (0.187 g, 0.500 mmol). The resulting green solution was stirred overnight at room temperature and taken to dryness, yielding 0.344 g of green product (94.0%).

N²-Phosphinylamidine Metal Salt Complex Synthesis 20—[N¹-(2-(dimethylamino)ethyl)-N²-(diisopropylphosphino)benzamidine]CrCl₃ (NP Amidine Metal Salt Complex D1)

Procedure as described for NP Amidine Metal Salt Complex B1 using the following amounts and modifications: N¹-(2-(dimethylamino)ethyl)-N¹-(diisopropylphosphino)benzamidine (NP Amidine XIX, 0.207 g, 0.673 mmol), $CrCl_3$(THF)$_3$ (0.252 g, 0.673 mmol). The ligand was preweighed in a disposable pipet and washed into a vial with 10 mL of diethyl ether. The ligand solution was added dropwise to $CrCl_3$(THF)$_3$ dissolved in 15 mL of THF. The resulting blue-green solution was stirred for 30 minutes at room temperature and taken to dryness. The residue was dissolved in 3 mL of THF and recrystallized via pentane diffusion to yield 0.271 g (86.4%) of crystalline blue solid. Anal. Calc. (Found) for $C_{17}H_{30}N_3PCrCl_3$: C, 43.84 ( ); H, 6.49 ( ); N, 9.02 ( ).

$N^2$-Phosphinylamidine Metal Salt Complex Synthesis 21—[$N^1$-(2-(dimethylamino)ethyl)-$N^2$-(diphenylphosphino)benzamidine]CrCl$_3$ (NP Amidine Metal Salt Complex D2)

Procedure as described for NP Amidine Metal Salt Complex B1 using the following amounts and modifications: $N^1$-(2-(dimethylamino)ethyl)-$N^2$-(diphenylphosphino)benzamidine (NP Amidine XX, 0.200 g, 0.534 mmol), $CrCl_3$(THF)$_3$ (0.200 g, 0.534 mmol). The resulting blue-green solution was stirred overnight at room temperature and taken to dryness. The residue was dissolved in 3 mL of THF and recrystallized via pentane diffusion to yield 0.254 g (89.1%) of dark crystalline solid. Anal. Calc. (Found) for $C_{23}H_{26}N_3PCrCl_3$: C, 51.75 ( ); H, 4.91 ( ); N, 7.87 ( ).

$N^2$-Phosphinylamidine Metal Salt Complex Synthesis 22—[$N^2$-(diphenylphosphino)-$N^1$-(2-(diphenylphosphino)ethyl)benzamidine]CrCl$_3$ (NP Amidine Metal Salt Complex D3)

Procedure as described for NP Amidine Metal Salt Complex B1 using the following amounts and modifications: $N^2$-(diphenylphosphino)-$N^1$-(2-(diphenylphosphino)ethyl)benzamidine (NP Amidine XXII, 0.276 g, 0.534 mmol), $CrCl_3$(THF)$_3$ (0.200 g, 0.534 mmol). The resulting blue-green solution was stirred for 3 hours at room temperature, taken to dryness, washed with 10 mL of n-pentane and dried to yield 0.364 g of green product (91.2%), which analyzed as a THF solvate. Anal. Calc. (Found) for $C_{37}H_{38}ON_2P_2CrCl_3$: C, 59.49 (58.24); H, 5.13 (5.12); N, 3.75 (3.85).

$N^2$-Phosphinylamidine Metal Salt Complex Synthesis 23—[$N^2$-(diisopropylphosphino)-$N^1$-(2-(phenylthio)phenyl)benzamidine](THF)CrCl$_3$ (NP Amidine Metal Salt Complex D4)

Procedure as described for NP Amidine Metal Salt Complex B1 using the following amounts and modifications: $N^2$-(diisopropylphosphino)-$N^1$-(2-(phenylthio)phenyl)benzamidine (NP Amidine XXIII, 0.136 g, 0.323 mmol), $CrCl_3$(THF)$_3$ (0.121 g, 0.323 mmol). The resulting blue solution was stirred for 1 hour at room temperature. After the volatiles were removed in vacuo, the residue was washed with n-pentane and dried affording 0.202 g (96%) of blue solid. Anal. Calc. (Found) for $C_{29}H_{37}ON_2PSCrCl_3$: C, 53.50 ( ); H, 5.73 ( ); N, 4.30 ( ); S, 4.93 ( ).

$N^2$-Phosphinylamidine Metal Salt Complex Synthesis 24—[$N^2$-(diphenylphosphino)-$N^1$-(2-(phenylthio)phenyl)benzamidine](THF)CrCl$_3$ (NP Amidine Metal Salt Complex D5)

Procedure as described for NP Amidine Metal Salt Complex B1 using the following amounts and modifications: $N^2$-(diphenylphosphino)-$N^1$-(2-(phenylthio)phenyl)benzamidine (NP Amidine XXIV, 0.395 g, 0.809 mmol), $CrCl_3$(THF)$_3$ (0.303 g, 0.809 mmol). The resulting blue-green solution was stirred overnight at room temperature and taken to dryness, yielding 0.608 g of blue product (99.5%), which analyzed as a THF hemisolvate. Anal. Calc. (Found) for $C_{37}H_{37}O_{1.5}N_2PSCrCl_3$: C, 58.85 (57.63); H, 4.94 (5.20); N, 3.71 (3.61); S, 4.25 (3.87).

$N^2$-Phosphinylamidine Metal Salt Complex Synthesis 25—[$N^2$-(diisopropylphosphino)-$N^1$-(2-morpholinoethyl)benzamidine]CrCl$_3$ (NP Amidine Metal Salt Complex D6)

Procedure as described for NP Amidine Metal Salt Complex B1 using the following amounts and modifications: $N^2$-(diisopropylphosphino)-$N^1$-(2-morpholinoethyl)benzamidine (NP Amidine XXV, 0.187 g, 0.535 mmol), $CrCl_3$(THF)$_3$ (0.252 g, 0.673 mmol). The resulting blue-green solution was stirred for 30 minutes at room temperature and taken to dryness. The residue was washed with 3 mL of MeCN and dried to yield 0.231 g (85.1%) of blue solid. Anal. Calc. (Found) for $C_{19}H_{32}ON_3PCrCl_3$: C, 44.94 ( ); H, 6.35 ( ); N, 8.27 ( ).

$N^2$-Phosphinylamidine Metal Salt Complex Synthesis 26—[$N^1$-(2-morpholinoethyl)-$N^2$-(diphenylphosphino)benzamidine]CrCl$_3$ (NP Amidine Metal Salt Complex D7)

Procedure as described for NP Amidine Metal Salt Complex B1 using the following amounts and modifications: $N^1$-(2-morpholinoethyl)-$N^2$-(diphenylphosphino)benzamidine (NP Amidine XXVI, 0.222 g, 0.534 mmol), $CrCl_3$(THF)$_3$ (0.200 g, 0.534 mmol). The resulting blue-green solution was stirred overnight at room temperature and taken to dryness. The residue was dissolved in 3 mL of THF and recrystallized via pentane diffusion to yield 0.222 g (72.2%) of blue solid. Anal. Calc. (Found) for $C_{23}H_{28}ON_3PCrCl_3$: C, 52.14 ( ); H, 4.90 ( ); N, 7.30 ( ).

$N^2$-Phosphinylamidine Metal Salt Complex Synthesis 27—[4-methyl-$N^2$-(diphenylphosphino)-$N^1$-(thiazol-2-yl)benzamidine](THF)CrCl$_3$ (NP Amidine Metal Salt Complex D8)

Procedure as described for NP Amidine Metal Salt Complex B1 using the following amounts and modifications: 4-methyl-$N^2$-(diphenylphosphino)-$N^1$'-(thiazol-2-yl)benzamidine (NP Amidine XXVII, 0.194 g, 0.500 mmol), $CrCl_3$(THF)$_3$ (0.187 g, 0.500 mmol). The resulting green solution was stirred overnight at room temperature, depositing a green solid. The solid was collected and dried affording 0.176 g (55.7%). Anal. Calc. (Found) for $C_{27}H_{28}ON_3PSCrCl_3$: C, 51.32 ( ); H, 4.47 ( ); N, 6.65 ( ); S, 5.07 ( ).

TABLE 15

N²-Phosphinylamidine Compounds, Metal Salts, and Product N²-Phosphinylamidine Metal Salt Complexes of N²-Phosphinylamidine Metal Salt Syntheses 1-27.

| Run # | N²-Phosphinyl Amidine | Metal Salt | N²-Phosphinyl Amidine Metal Salt Complex |
|---|---|---|---|
| N²-Phosphinyl-amidine Metal Salt Synthesis 1 | 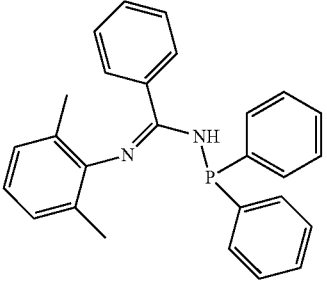<br>NP Amidine I | CrCl₃(THF)₃ | 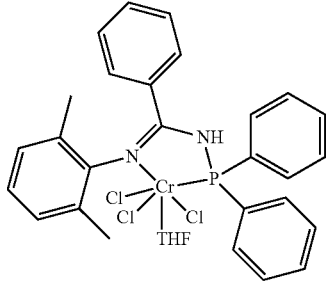<br>NP Amidine Metal Salt Complex B1 |
| N²-Phosphinyl-amidine Metal Salt Synthesis 2 | 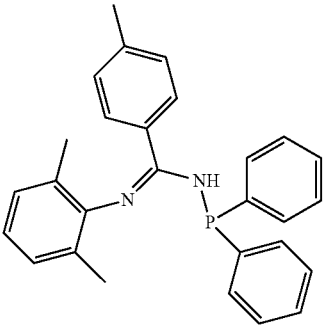<br>NP Amidine IV | CrCl₃(THF)₃ | 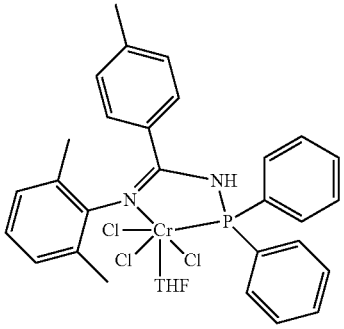<br>NP Amidine Metal Salt Complex B2 |
| N²-Phosphinyl-amidine Metal Salt Synthesis 3 | 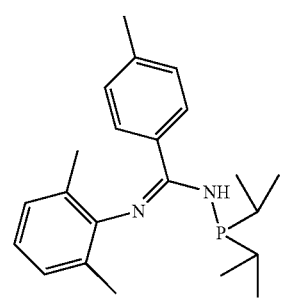<br>NP Amidine III | CrCl₃(THF)₃ | 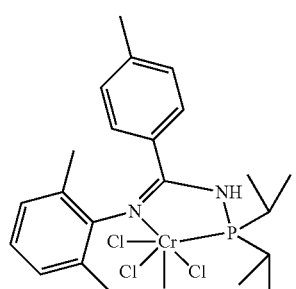<br>NP Amidine Metal Salt Complex B3 |

TABLE 15-continued

N²-Phosphinylamidine Compounds, Metal Salts, and Product N²-Phosphinylamidine
Metal Salt Complexes of N²-Phosphinylamidine Metal Salt Syntheses 1-27.

| Run # | N²-Phosphinyl Amidine | Metal Salt | N²-Phosphinyl Amidine Metal Salt Complex |
|---|---|---|---|
| N²-Phosphinyl-amidine Metal Salt Synthesis 4 | NP Amidine V | $CrCl_3(THF)_3$ | NP Amidine Metal Salt Complex B4 |
| N²-Phosphinyl-amidine Metal Salt Synthesis 5 | NP Amidine VI | $CrCl_3(THF)_3$ | NP Amidine Metal Salt Complex B5 |
| N²-Phosphinyl-amidine Metal Salt Synthesis 6 | NP Amidine IX | $CrCl_3(THF)_3$ | NP Amidine Metal Salt Complex B6 |

TABLE 15-continued

N²-Phosphinylamidine Compounds, Metal Salts, and Product N²-Phosphinylamidine
Metal Salt Complexes of N²-Phosphinylamidine Metal Salt Syntheses 1-27.

| Run # | N²-Phosphinyl Amidine | Metal Salt | N²-Phosphinyl Amidine Metal Salt Complex |
|---|---|---|---|
| N²-Phosphinyl-amidine Metal Salt Synthesis 7 | 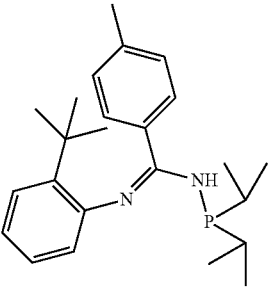<br>NP Amidine X | CrCl₃(THF)₃ | 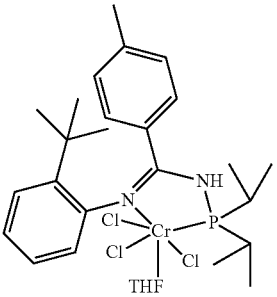<br>NP Amidine Metal Salt Complex B7 |
| N²-Phosphinyl-amidine Metal Salt Synthesis 8 | 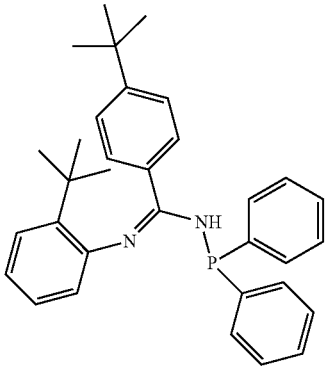<br>NP Amidine XI | | 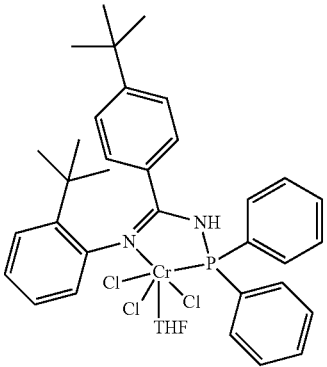<br>NP Amidine Metal Salt Complex B8 |
| N²-Phosphinyl-amidine Metal Salt Synthesis 9 | 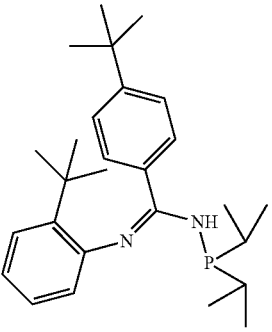<br>NP Amidine XII | CrCl₃(THF)₃ | 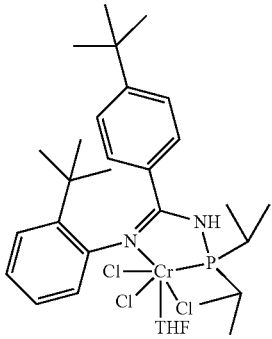<br>NP Amidine Metal Salt Complex B9 |

TABLE 15-continued

N²-Phosphinylamidine Compounds, Metal Salts, and Product N²-Phosphinylamidine
Metal Salt Complexes of N²-Phosphinylamidine Metal Salt Syntheses 1-27.

| Run # | N²-Phosphinyl Amidine | Metal Salt | N²-Phosphinyl Amidine Metal Salt Complex |
|---|---|---|---|
| N²-Phosphinyl-amidine Metal Salt Synthesis 10 | NP Amidine XIII | CrCl₃(THF)₃ | NP Amidine Metal Salt Complex B10 |
| N²-Phosphinyl-amidine Metal Salt Synthesis 11 | NP Amidine XIV | CrCl₃(THF)₃ | NP Amidine Metal Salt Complex B11 |
| N²-Phosphinyl-amidine Metal Salt Synthesis 12 | NP Amidine XV | CrCl₃(THF)₃ | NP Amidine Metal Salt Complex B12 |
| N²-Phosphinyl-amidine Metal Salt Synthesis 13 | NP Amidine XVI | CrCl₃(THF)₃ | NP Amidine Metal Salt Complex B13 |

TABLE 15-continued

N²-Phosphinylamidine Compounds, Metal Salts, and Product N²-Phosphinylamidine
Metal Salt Complexes of N²-Phosphinylamidine Metal Salt Syntheses 1-27.

| Run # | N²-Phosphinyl Amidine | Metal Salt | N²-Phosphinyl Amidine Metal Salt Complex |
|---|---|---|---|
| N²-Phosphinyl-amidine Metal Salt Synthesis 14 | NP Amidine XVII | CrCl₃(THF)₃ | NP Amidine Metal Salt Complex B14 |
| N²-Phosphinyl-amidine Metal Salt Synthesis 15 | NP Amidine XVIII | CrCl₃(THF)₃ | NP Amidine Metal Salt Complex B15 |
| N²-Phosphinyl-amidine Metal Salt Synthesis 16 | NPS Amidine I | CrCl₃(THF)₃ | NP Amidine Metal Salt Complex C1 |
| N²-Phosphinyl-amidine Metal Salt Synthesis 17 | NPS Amidine II | CrCl₃(THF)₃ | NP Amidine Metal Salt Complex C2 |

TABLE 15-continued

N²-Phosphinylamidine Compounds, Metal Salts, and Product N²-Phosphinylamidine Metal Salt Complexes of N²-Phosphinylamidine Metal Salt Syntheses 1-27.

| Run # | N²-Phosphinyl Amidine | Metal Salt | N²-Phosphinyl Amidine Metal Salt Complex |
|---|---|---|---|
| N²-Phosphinyl-amidine Metal Salt Synthesis 18 | 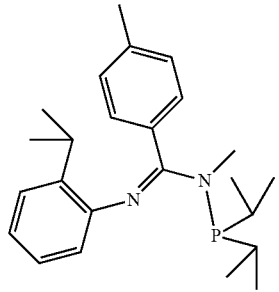<br>NPS Amidine III | CrCl₃(THF)₃ | 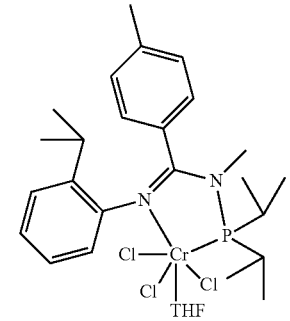<br>NP Amidine Metal Salt Complex C3 |
| N²-Phosphinyl-amidine Metal Salt Synthesis 19 | 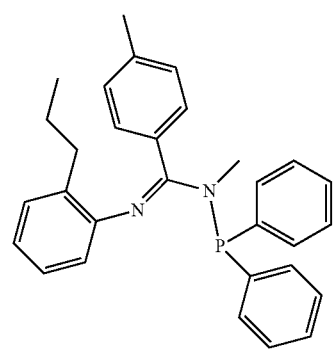<br>NPS Amidine IV | CrCl₃(THF)₃ | 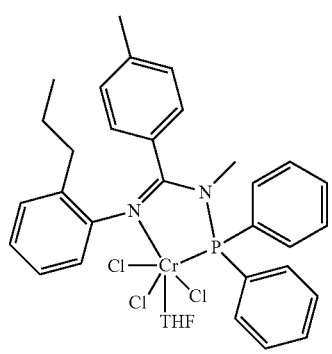<br>NP Amidine Metal Salt Complex C4 |
| N²-Phosphinyl-amidine Metal Salt Synthesis 20 | 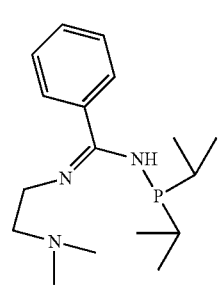<br>NP Amidine XIX | | 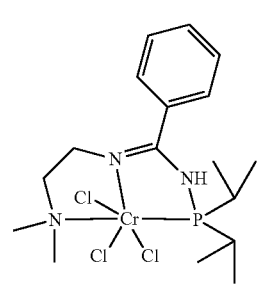<br>NP Amidine Metal Salt Complex D1 |

325 326

TABLE 15-continued

N²-Phosphinylamidine Compounds, Metal Salts, and Product N²-Phosphinylamidine
Metal Salt Complexes of N²-Phosphinylamidine Metal Salt Syntheses 1-27.

| Run # | N²-Phosphinyl Amidine | Metal Salt | N²-Phosphinyl Amidine Metal Salt Complex |
|---|---|---|---|
| N²-Phosphinyl-amidine Metal Salt Synthesis 21 | 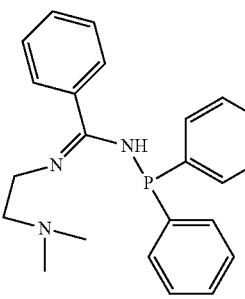<br>NP Amidine XX | | 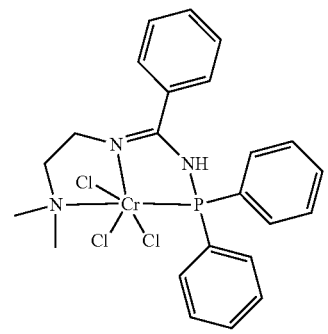<br>NP Amidine Metal Salt Complex D2 |
| N²-Phosphinyl-amidine Metal Salt Synthesis 22 | 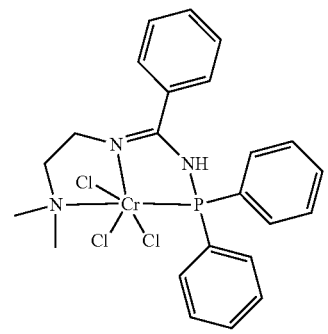<br>NP Amidine XXII | | 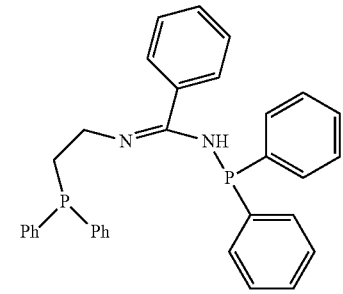<br>NP Amidine Metal Salt Complex D3 |
| N²-Phosphinyl-amidine Metal Salt Synthesis 23 | 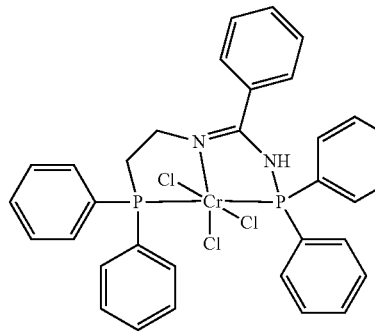<br>NP Amidine XXIII | | 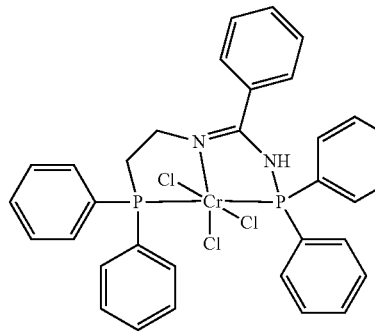<br>NP Amidine Metal Salt Complex D4 |
| N²-Phosphinyl-amidine Metal Salt Synthesis 24 | 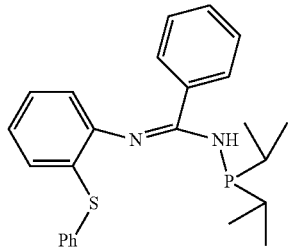<br>NP Amidine XXIV | | 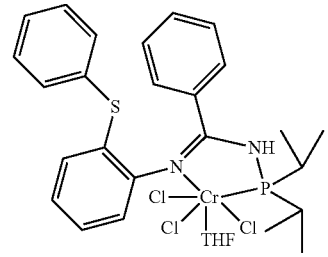<br>NP Amidine Metal Salt Complex D5 |

TABLE 15-continued

N²-Phosphinylamidine Compounds, Metal Salts, and Product N²-Phosphinylamidine
Metal Salt Complexes of N²-Phosphinylamidine Metal Salt Syntheses 1-27.

| Run # | N²-Phosphinyl Amidine | Metal Salt | N²-Phosphinyl Amidine Metal Salt Complex |
|---|---|---|---|
| N²-Phosphinyl-amidine Metal Salt Synthesis 25 | NP Amidine XXV | | NP Amidine Metal Salt Complex D6 |
| N²-Phosphinyl-amidine Metal Salt Synthesis 26 | NP Amidine XXVI | | NP Amidine Metal Salt Complex D7 |
| N²-Phosphinyl-amidine Metal Salt Synthesis 27 | NP Amidine XXVII | | NP Amidine Metal Salt Complex D8 |

$N^2$-Phosphinyl-Amidine Metal Salt Complexes

Table 16 provides additional $N^2$-phosphinylamidine metal salt complexes prepared utilizing the methods described herein.

TABLE 16

Additional $N^2$-Phosphinyl-Amidine Metal Salt Complexes (NP Amidine Metal Salt Complexes)

B16
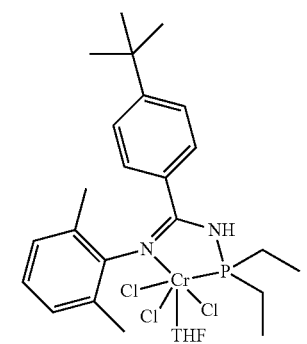

B17
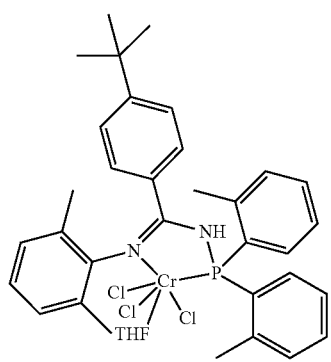

B18
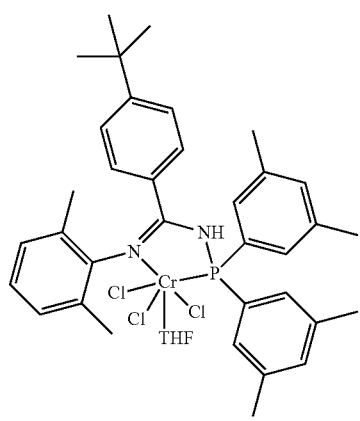

TABLE 16-continued

Additional $N^2$-Phosphinyl-Amidine Metal Salt Complexes (NP Amidine Metal Salt Complexes)

B19
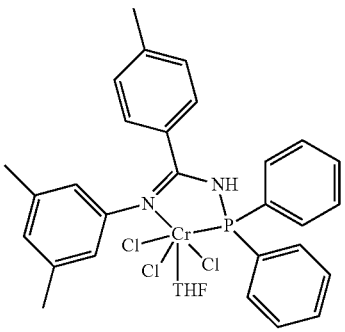

B20
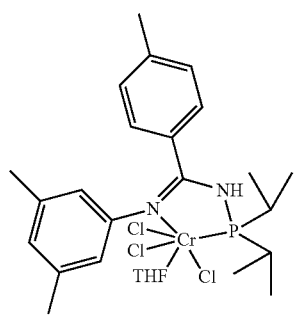

B21
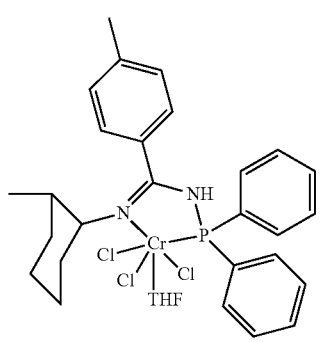

B22
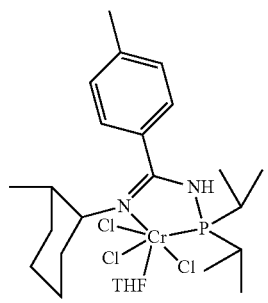

TABLE 16-continued
Additional N²-Phosphinyl-Amidine Metal Salt Complexes (NP Amidine Metal Salt Complexes)
B23
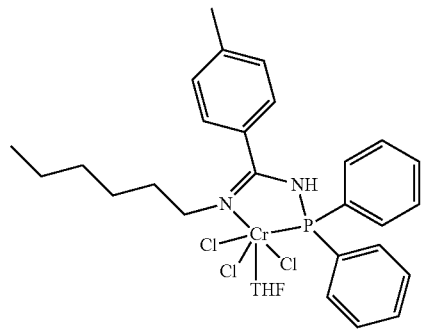
B24
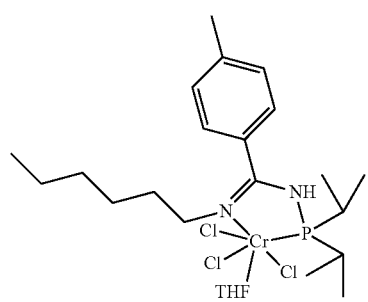
B25
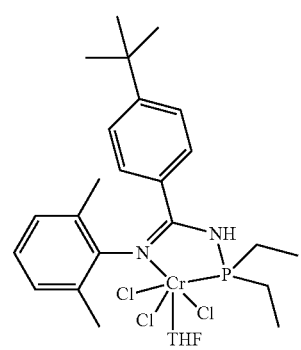
B26
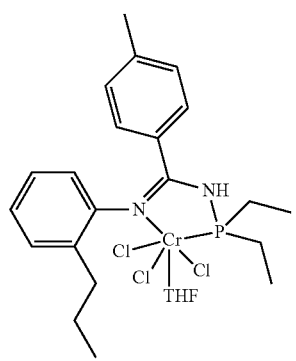
TABLE 16-continued
Additional N²-Phosphinyl-Amidine Metal Salt Complexes (NP Amidine Metal Salt Complexes)
B27
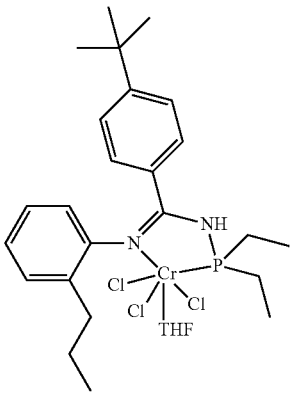
B28
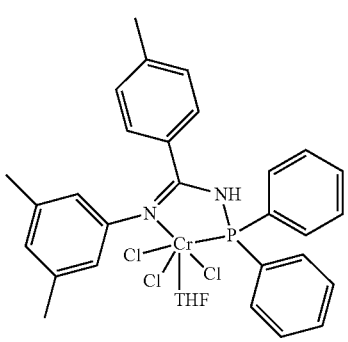
B29
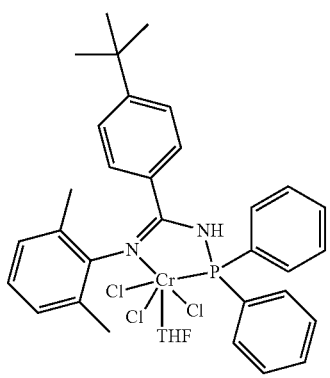
B30
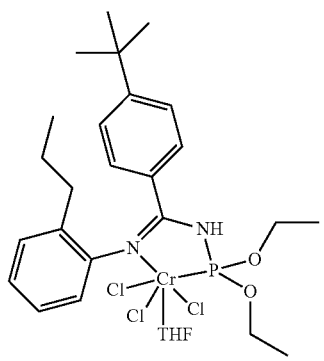

TABLE 16-continued
Additional N²-Phosphinyl-Amidine Metal Salt Complexes (NP Amidine Metal Salt Complexes)
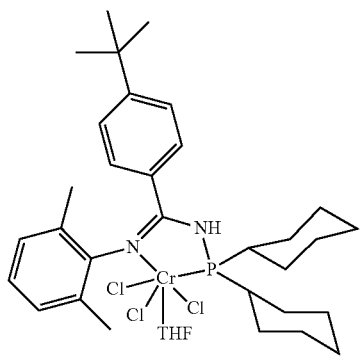
B31
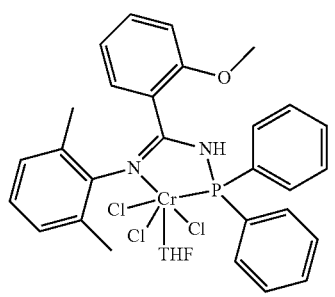
B32
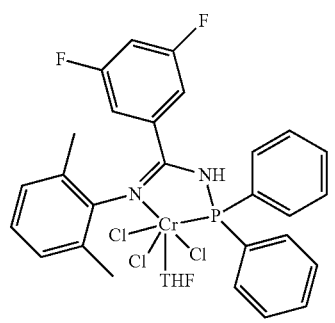
B33
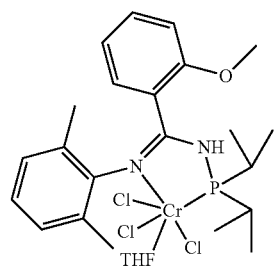
B34
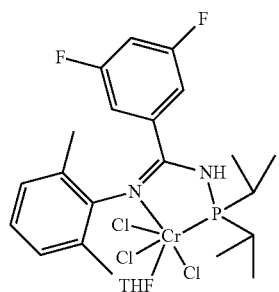
B35
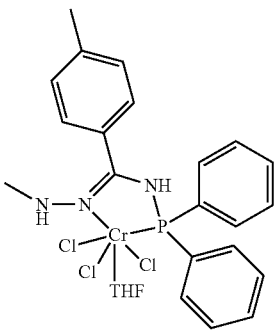
B36
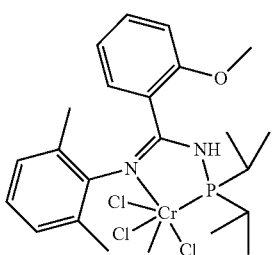
B37
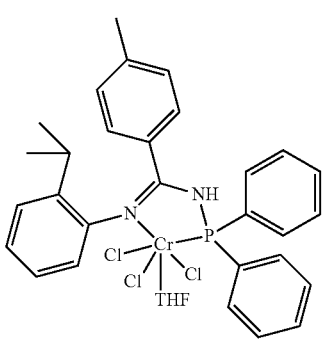
B38
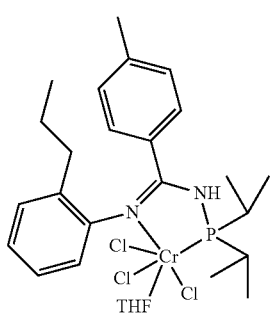
B39
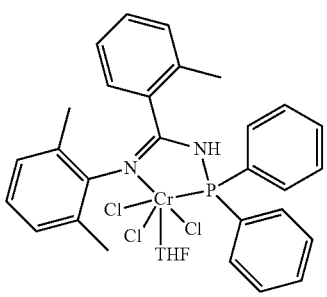
B40

TABLE 16-continued
Additional N²-Phosphinyl-Amidine Metal Salt Complexes (NP Amidine Metal Salt Complexes)
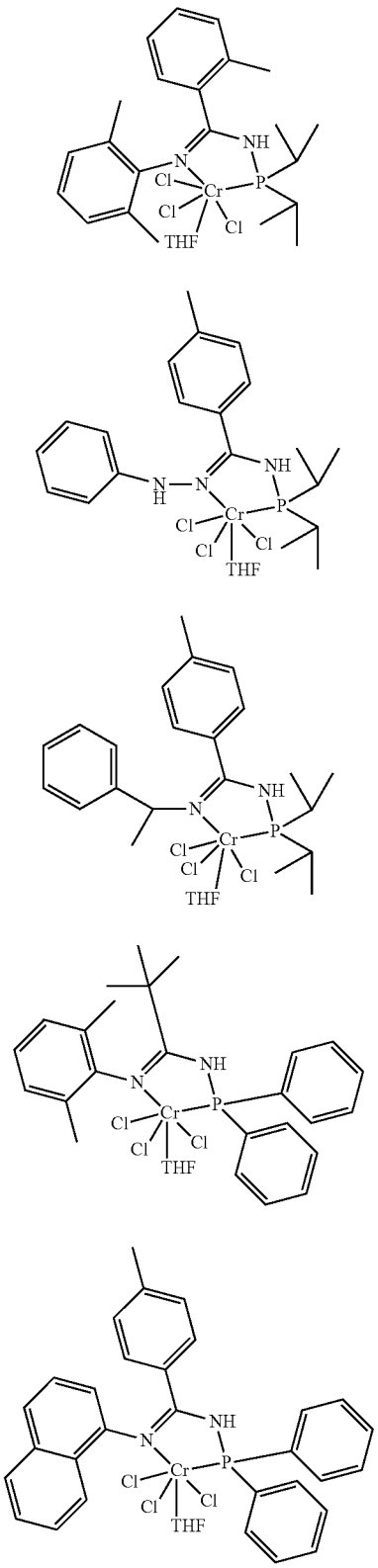
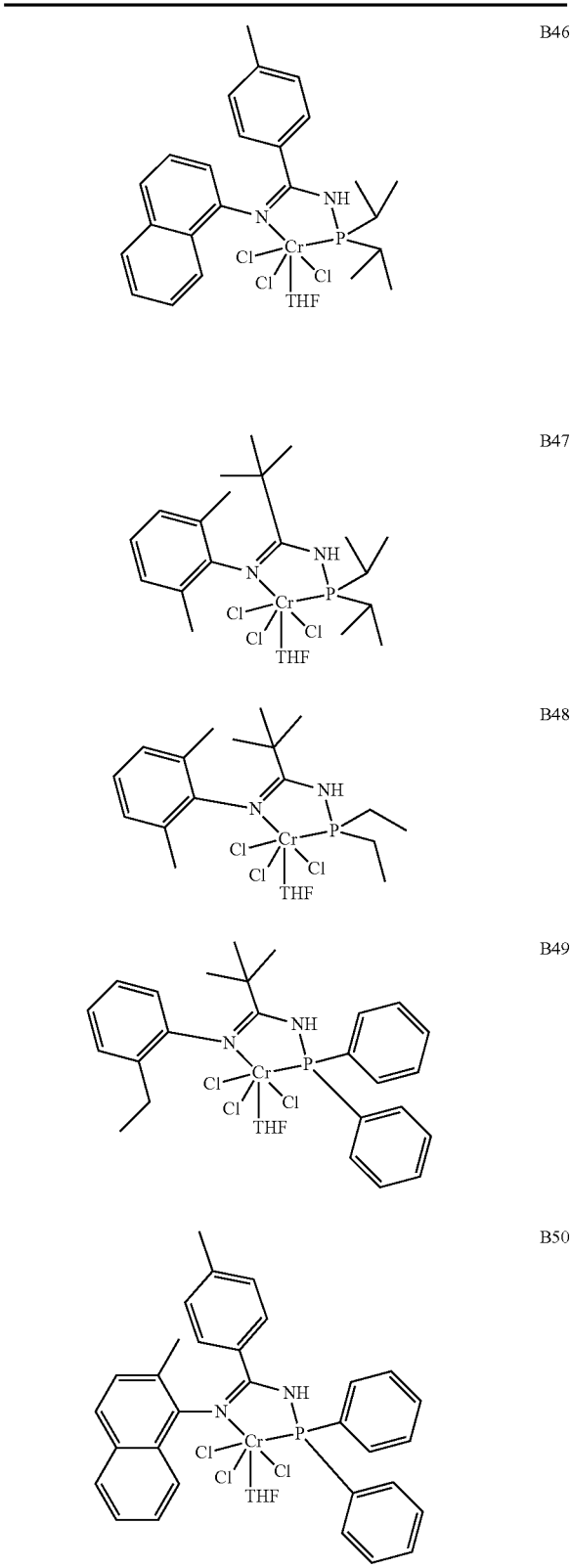

TABLE 16-continued
Additional N²-Phosphinyl-Amidine Metal Salt Complexes (NP Amidine Metal Salt Complexes)
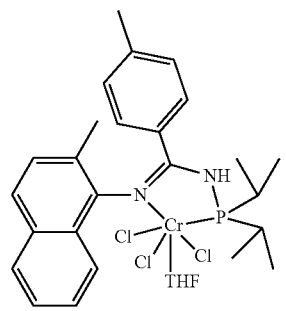
B51
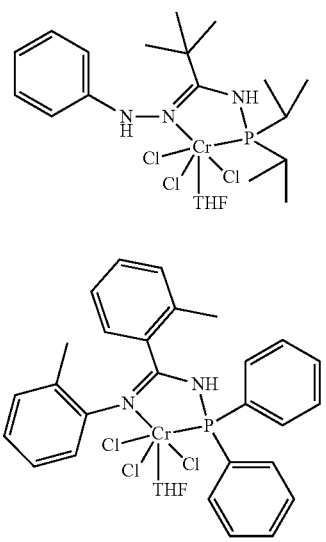
B52
B53
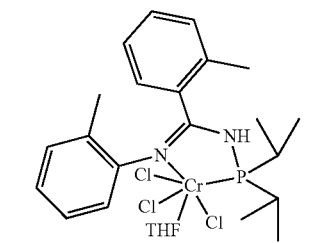
B54
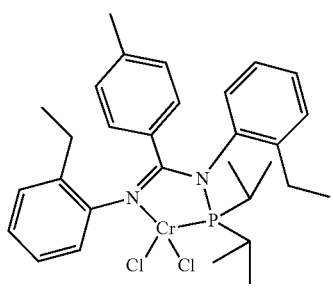
B55
TABLE 16-continued
Additional N²-Phosphinyl-Amidine Metal Salt Complexes (NP Amidine Metal Salt Complexes)
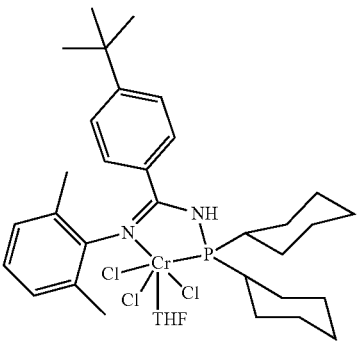
B56
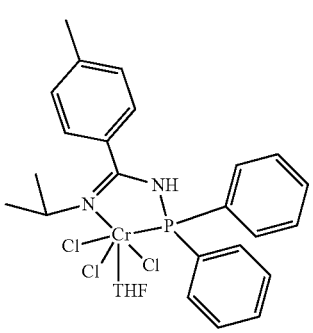
B57
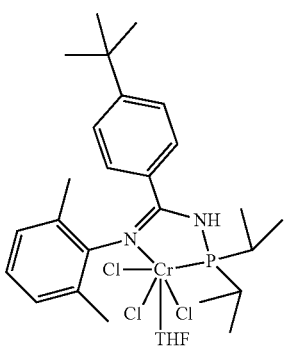
B58
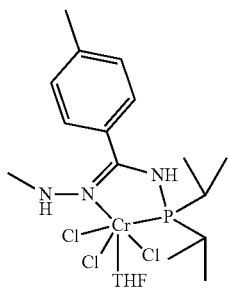
B59

TABLE 16-continued
Additional N²-Phosphinyl-Amidine Metal Salt Complexes (NP Amidine Metal Salt Complexes)
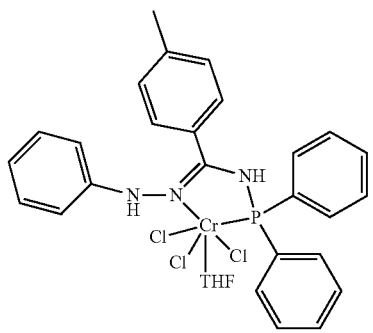
B60
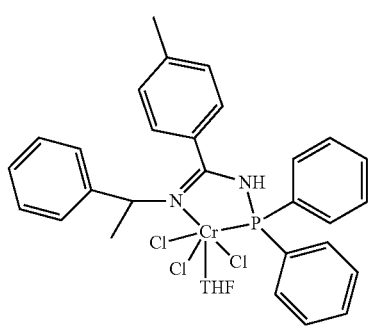
B61
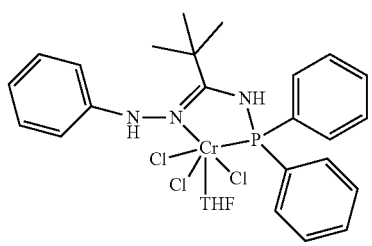
B62
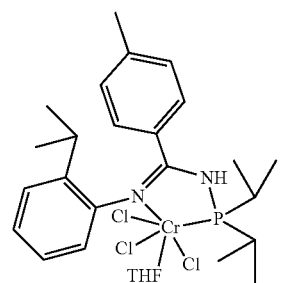
B63
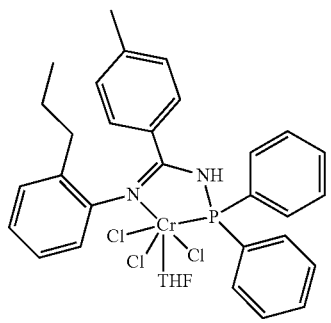
B64
TABLE 16-continued
Additional N²-Phosphinyl-Amidine Metal Salt Complexes (NP Amidine Metal Salt Complexes)
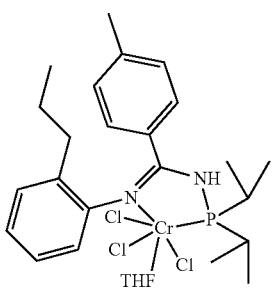
B65
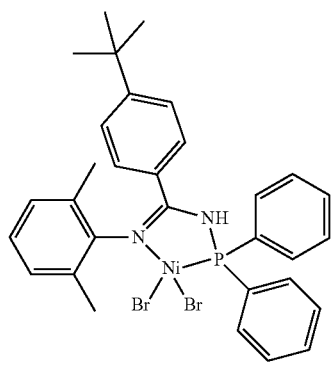
B66
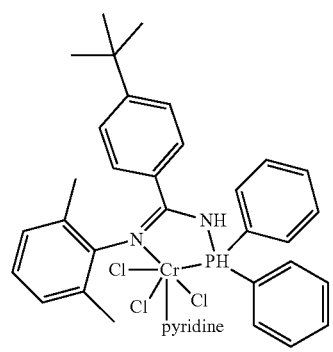
B67
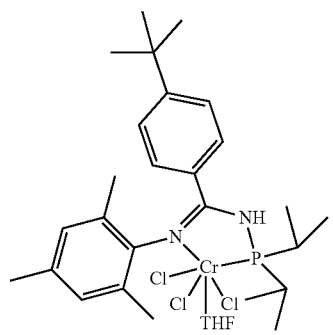
B68

TABLE 16-continued
Additional N²-Phosphinyl-Amidine Metal Salt Complexes (NP Amidine Metal Salt Complexes)
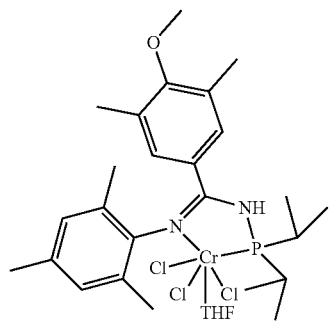
B69
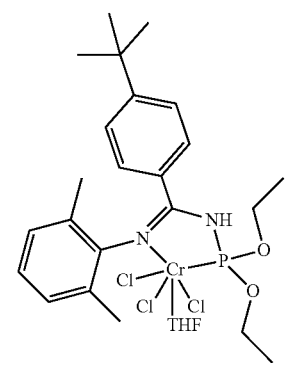
B70
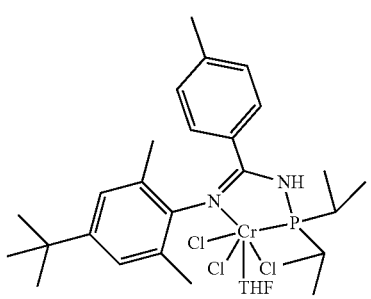
B71
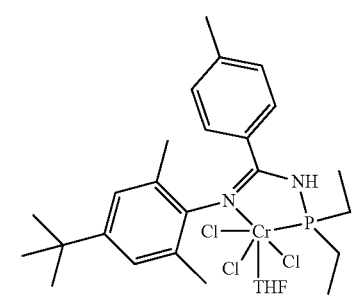
B72
TABLE 16-continued
Additional N²-Phosphinyl-Amidine Metal Salt Complexes (NP Amidine Metal Salt Complexes)
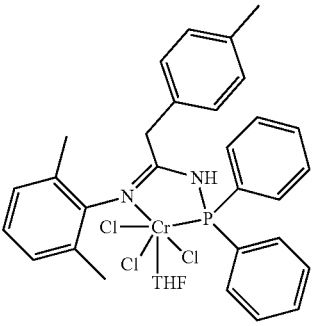
B73
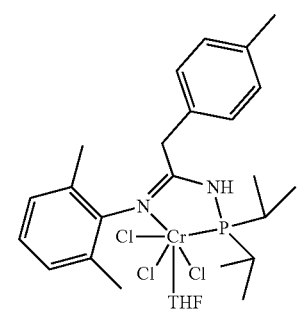
B74
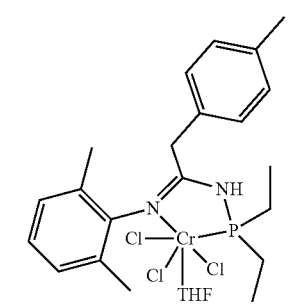
B75
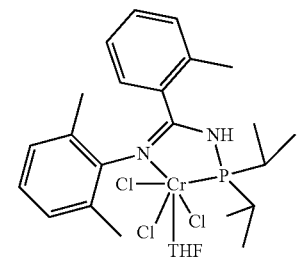
B76
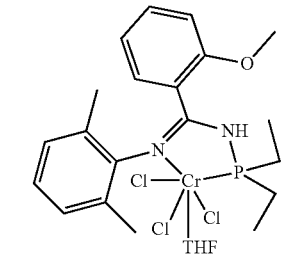
B77

TABLE 16-continued
Additional N²-Phosphinyl-Amidine Metal Salt Complexes (NP Amidine Metal Salt Complexes)
B78
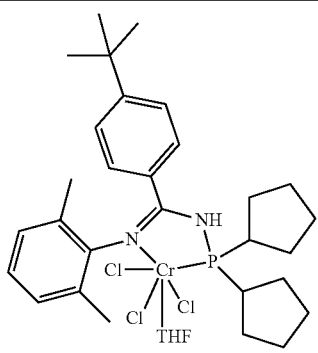
B79
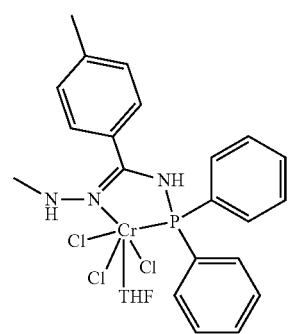
B80
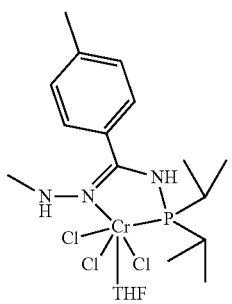
B81
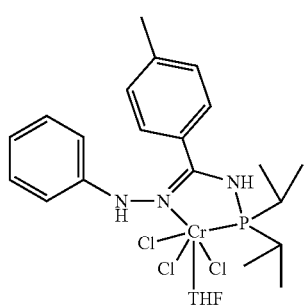
C5
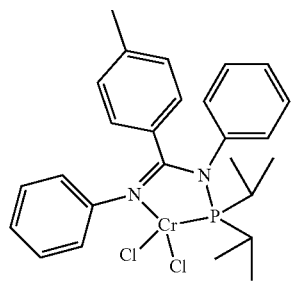
TABLE 16-continued
Additional N²-Phosphinyl-Amidine Metal Salt Complexes (NP Amidine Metal Salt Complexes)
C6
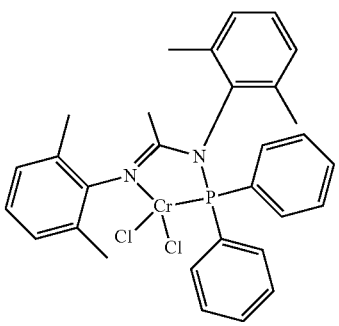
C7
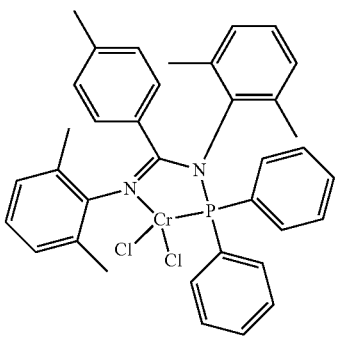
C8
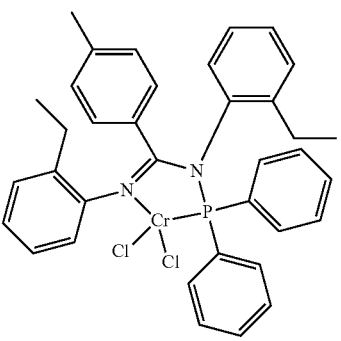
C9
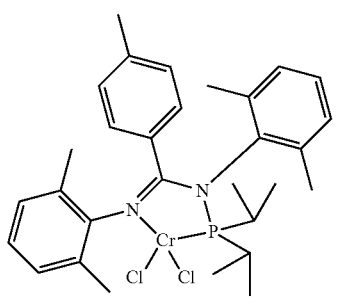

TABLE 16-continued

Additional N²-Phosphinyl-Amidine Metal Salt Complexes (NP Amidine Metal Salt Complexes)

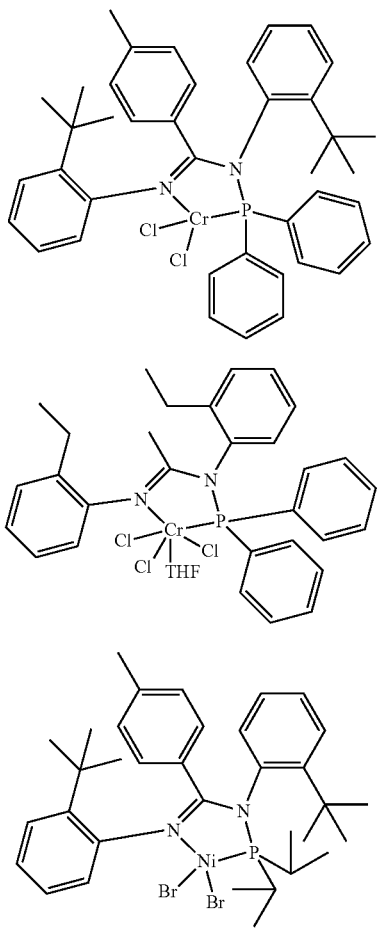

Olefin Oligomerization

The N²-phosphinylamidinecompounds and N²-phosphinylamidine metal salt complexes were utilized as prepared using the methods described herein. The MMAO-3A was utilized as obtained from the chemical supplier. The solvents were dried and/or purified using conventional methods and stored under conditions to limit their ability to pick-up water. In the product analyses, reference to an amount of $C_6$ or $C_8$ products refer to all oligomerization products having 6 or 8 carbon atoms, respectively. References to weight percent of 1-hexene or 1-octene refer to the weight percent of 1-hexene or 1-octene in the $C_6$ or $C_8$ product portion, respectively (e.g product purities).

Example 1

Ethylene Oligomerization Run 1

A 1L stainless steel reactor was dried under vacuum at 110° C. for at least 8 hours prior to use. The reactor was then cooled to room temperature and opened to the atmosphere. A flame-sealed glass NMR tube (Wilmad 505-PS) containing NP Amidine Metal Salt Complex B1 (10 mg complex, 0.014 mmol, 0.7 mg Cr) and ethylbenzene (1.5 g) was attached to the cooling coil near the pneumatic stirrer such that the tube would break upon stirring initiation. The reactor was closed, evacuated and warmed to 40° C. A solution of cyclohexane (400 mL) and MMAO-3A (1.1 g, 6.7 wt % Al solution in heptanes) was then charged into the reactor along with ethylene (~400 psi). The stirrer was activated to break the NMR tube, after which the ethylene pressure was increased to 850 psig and fed on-demand. The reaction was allowed to proceed for 30 minutes (starting from the introduction of ethylene) at 40° C. After 30 minutes, water cooling was applied to the reactor system. Once the temperature reached 35° C., the unreacted ethylene and hydrogen gas was vented to the atmosphere. A liquid sample was collected and analyzed by GC-FID; for this run ethylbenzene was used as the internal standard. Solids (~1.0 g) were collected by filtering the solution and cleaning the reactor walls and cooling coil.

Ethylene Oligomerization Run 2

A 0.5 L stainless steel reactor was dried under vacuum at 110° C. for at least 8 hours prior to use. The reactor was then cooled to room temperature and opened to the atmosphere. A flame-sealed glass NMR tube (Wilmad 505-PS) containing NP Amidine I (5 mg, 0.012 mmol), Cr(acac)$_3$ (2 mg, 0.006 mmol, 0.3 mg Cr), ethylbenzene (0.8 g) and C9 (0.5 g, internal standard) was attached to the cooling coil near the pneumatic stirrer such that the tube would break upon stirring initiation. The reactor was closed, evacuated and warmed to 50° C. A solution of cyclohexane (150 mL) and MMAO-3A (1.5 g, 6.7 wt % Al solution in heptanes) was then charged into the reactor along with ethylene (~400 psi) and hydrogen (50 psig). The stirrer was activated to break the NMR tube, after which the ethylene pressure was increased to 850 psig and fed on-demand The reaction was allowed to proceed for 30 minutes (starting from the introduction of ethylene) at 50° C. After 30 minutes, water cooling was applied to the reactor system. Once the temperature reached 35° C., the unreacted ethylene gas was vented to the atmosphere. A liquid sample was collected and analyzed by GC-FID. Solids (<1.0 g) were collected by filtering the solution and cleaning the reactor walls and cooling coil.

Ethylene Oligomerization Run 3—Standard Method

A 1L stainless steel reactor was dried under vacuum at 110° C. for at least 8 hour prior to use. The reactor was then cooled to 50° C. In the drybox, a 20 mL glass vial was charged with NP Amidine Metal Salt Complex B2 (10 mg complex, 0.014 mmol, 0.7 mg Cr) and ethylbenzene (1.5 g). MMAO-3A (3.3 g, 6.7 wt % Al solution in heptanes) was added to the blue heterogeneous solution resulting in formation of a yellow solution. The yellow solution was then added to 0.5 L glass charger containing 400 ml cyclohexane. This solution was removed from the drybox and charged into the reactor. Hydrogen (50 psig) was added followed by ethylene (850 psig, fed on-demand) The reaction was allowed to proceed for 30 minutes (starting from the introduction of ethylene) at 50° C. After 30 minutes, water cooling was applied to the reactor system. Once the temperature reached 35° C., the unreacted ethylene and hydrogen gas was vented to the atmosphere. A liquid sample was collected and analyzed by GC-FID; for this run ethylbenzene was used as the internal standard. Solids (1.5 g) were collected by filtering the solution and cleaning the reactor walls and cooling coil.

Ethylene Oligomerization Run 4

A 1L stainless steel reactor was dried under vacuum at 110° C. for at least 8 h prior to use. The reactor was then cooled to 50° C. In the drybox, a 20 mL glass vial was charged with NP Amidine IV (15 mg, 0.037 mmol), Cr(acac)$_3$ (6.0 mg, 0.017 mmol, 0.9 mg Cr) and ethylbenzene (2.0 g). MMAO-3A (2.9 g, 6.7 wt % Al solution in heptanes) and none (0.50 g, internal standard) were added resulting in formation of a yellow homogeneous solution. The yellow solution was then added to glass charger containing 400 ml cyclohexane. This solution was removed from the drybox and charged into the reactor.

Hydrogen (50 psig) was added followed by ethylene (850 psig, fed on-demand). The reaction was allowed to proceed for 30 minutes (starting from the introduction of ethylene) at 50° C. After 30 minutes, water cooling was applied to the reactor system. Once the temperature reached 35° C., the unreacted ethylene and hydrogen gas was vented to the atmosphere. A liquid sample was collected and analyzed by GC-FID. Solids (4.5 g) were collected by filtering the solution and cleaning the reactor walls and cooling coil.

TABLE 17

Results of Olefin Oligomerization Runs 1-4

| Run # | Solids (wt. %) | $C_6 + C_8$ Activity (g/g Cr) | $C_6$ (wt. %) | 1-hexene (wt. %) | $C_8$ (wt. %) | 1-octene (wt. %) |
|---|---|---|---|---|---|---|
| 1 | 12 | 9,500 | 68.1 | 93.2 | 30.2 | 97.6 |
| 2 | 100 | trace | — | — | — | — |
| 3 | 3 | 62,000 | 79.3 | 96.9 | 18.7 | 98.5 |
| 4 | 58 | 3,200 | 64.2 | 94.9 | 24.5 | 98.3 |

Oligomerization Procedure—Oligomerization Runs 5-106

A 1L stainless steel reactor was dried under vacuum at 110° C. for at least 8 hour prior to use. The reactor was then cooled to 50° C. In a drybox, a 20 mL glass vial was charged with an $N^2$-phosphinyl amidine metal complex (NP Amidine Metal Salt Complex), catalyst system solvent, and MMAO-3A (6.7 wt % Al solution in heptanes). This solution was then added to 0.5 L glass charger containing the bulk oligomerization solvent. The combined solution was removed from the drybox and charged into the 1 L stainless steel reactor. The reactor was then charged with hydrogen and ethylene charged to the reactor on-demand. The identity of the $N^2$-phosphinyl amidine metal salt complex, the amount of the complex, the catalyst solvent, the oligomerization solvent, the amount of the oligomerization solvent, the hydrogen pressure, the ethylene pressure, the oligomerization time and oligomerization pressure for ethylene oligomerization runs 5-26 and 27-106 are provided in Table 18 and Table 20, respectively. The reaction was allowed to proceed at the temperatures and for the times indicated in Table 18 and Table 20, respectively.

At reaction completion, water cooling was applied to the 1L stainless steel reactor. When the reactor temperature reached 35° C., the unreacted ethylene and hydrogen gas was vented to the atmosphere. A liquid sample was then collected and analyzed by GC-FID. The reactor solids were collected by filtering the reaction and cleaning the reactor walls and cooling coil. The product analysis of the products of the ethylene oligomerization runs 5-26 and 27-106 are provided in Table 19 and Table 21, respectively.

TABLE 18

$N^2$-Phosphinyl Amidine Complex, Catalyst System Ratios, and Reaction Condition for Ethylene Oligomerization Runs 5-26.

| Run # | NP Amidine Metal Salt Complex | Catalyst System Solvent[†] | Complex (mg) | Complex (mmol) | Cr (g) | Al:Cr ratio | Bulk Solvent[‡] | Reaction Time (min) | Ethylene Pressure (psi) | Hydrogen Pressure | Reaction Temp. (° C.) |
|---|---|---|---|---|---|---|---|---|---|---|---|
| 5 | B2 | EB | 10 | 0.014 | 0.7 | 600 | 0.4 L, cyH | 30 | 850 | 50 | 50 |
| 6 | B4 | EB | 10 | 0.013 | 0.7 | 600 | 0.4 L, cyH | 30 | 850 | 50 | 50 |
| 7 | B4 | EB | 10 | 0.013 | 0.7 | 600 | 0.4 L, cyH | 90 | 850 | 50 | 50 |
| 8 | B4 | DCM | 15 | 0.020 | 1.0 | 600 | 0.4 L, cyH | 30 | 850 | 50 | 50 |
| 9 | B4 | DCM | 15 | 0.020 | 1.0 | 600 | 0.4 L, cyH | 60 | 850 | 50 | 50 |
| 10 | B4 | DCM | 15 | 0.020 | 1.0 | 600 | 0.4 L, cyH | 120 | 850 | 50 | 50 |
| 11 | B2 | DCM | 35 | 0.048 | 2.5 | 450 | 0.4 L, cyH | 30 | 850 | 50 | 50 |
| 12 | B2 | DCM | 11 | 0.015 | 0.8 | 550 | 0.4 L, cyH | 30 | 850 | 50 | 50 |
| 13 | B2 | DCM | 6 | 0.008 | 0.4 | 1000 | 0.4 L, cyH | 90 | 850 | 50 | 50 |
| 14 | B2 | DCM | 6 | 0.008 | 0.4 | 1000 | 0.4 L, cyH | 30 | 850 | 50 | 40 |
| 15 | B2 | DCM | 5 | 0.007 | 0.4 | 1200 | 0.4 L, cyH | 30 | 850 | 50 | 50 |
| 16 | B2 | DCM | 5 | 0.007 | 0.4 | 1200 | 0.4 L, cyH | 30 | 850 | 50 | 70 |
| 17 | B2 | DCM | 5 | 0.007 | 0.4 | 1200 | 0.4 L, cyH | 30 | 850 | 50 | 90 |
| 18 | B2 | DCM | 4 | 0.006 | 0.3 | 1500 | 0.4 L, cyH | 180 | 850 | 50 | 50 |
| 19 | A1 | EB | 10 | 0.017 | 0.9 | 500 | 0.4 L, cyH | 30 | 850 | 50 | 75 |
| 20 | A3 | DCM | 6 | 0.010 | 0.5 | 700 | 0.4 L, cyH | 60 | 850 | 50 | 50 |
| 21 | B3 | DCM | 10 | 0.015 | 0.8 | 500 | 0.4 L, cyH | 30 | 850 | 50 | 60 |
| 22 | B5 | DCM | 12 | 0.017 | 0.9 | 400 | 0.4 L, cyH | 30 | 850 | 50 | 50 |
| 23 | B5 | EB | 12 | 0.017 | 0.9 | 400 | 0.4 L, cyH | 30 | 850 | 50 | 50 |
| 24 | B5 | EB | 12 | 0.017 | 0.9 | 400 | 0.4 L, cyH | 30 | 850 | 50 | 90 |
| 25 | B5 | EB | 12 | 0.017 | 0.9 | 400 | 0.25 L, cyH | 30 | 850 | 50 | 120 |
| 26 | B5 | EB | 7 | 0.010 | 0.5 | 200 | 0.4 L, cyH | 30 | 850 | 50 | 50 |

[†]EB = ethylbenzene, DCM = Dichloromethane
[‡]cyH = cyclohexane

TABLE 19

Product of Ethylene Oligomerization Runs 5-26.

| Run # | NP Amidine Metal Salt Complex | Product Type Solid (g) | Product Type Liquid (g) | Product Type Solid (wt. %) | Carbon Number Distribution (Wt. %) $C_6$ | $C_8$ | $C_{10}$ | $C_{12}$ | $C_{14+}$ | Productivities and Activities $C_6 + C_8$ (%) | $C_6 + C_8$ (g/g Cr) | Product Purities (Wt. %) 1-hexene (wt. %) | MeCp (wt. %) | 1-octene (wt. %) |
|---|---|---|---|---|---|---|---|---|---|---|---|---|---|---|
| 5 | B2 | 1.5 | 45.4 | 3 | 79.3 | 18.7 | 0.9 | 0.4 | 0.7 | 98.0 | 62,038 | 96.92 | 1.17 | 98.49 |
| 6 | B4 | 1.1 | 52.9 | 2 | 76.1 | 20.1 | 1.0 | 0.4 | 2.4 | 96.2 | 75,077 | 96.15 | 1.43 | 98.51 |
| 7 | B4 | 4.4 | 80.8 | 5 | 78.1 | 20.1 | 0.9 | 0.4 | 0.5 | 98.2 | 117,058 | 96.48 | 1.29 | 98.55 |

TABLE 19-continued

Product of Ethylene Oligomerization Runs 5-26.

| Run # | NP Amidine Metal Salt Complex | Product Type Solid (g) | Liquid (g) | Solid (wt. %) | Carbon Number Distribution (Wt. %) $C_6$ | $C_8$ | $C_{10}$ | $C_{12}$ | $C_{14+}$ | Productivities and Activities $C_6 + C_8$ (%) | $C_6 + C_8$ (g/g Cr) | Product Purities (Wt. %) 1-hexene (wt. %) | MeCp (wt. %) | 1-octene (wt. %) |
|---|---|---|---|---|---|---|---|---|---|---|---|---|---|---|
| 8 | B4 | NA | 7.4 | NA | 74.5 | 22.5 | 1.3 | 0.8 | 0.9 | 97.0 | 7,060 | 95.30 | 1.61 | 97.07 |
| 9 | B4 | NA | 18.1 | NA | 74.5 | 21.9 | 1.1 | 0.7 | 1.8 | 96.4 | 17,161 | 95.66 | 1.54 | 98.23 |
| 10 | B4 | 14.5 | 31.6 | 31 | 75.3 | 21.8 | 0.8 | 0.5 | 1.6 | 97.1 | 30,178 | 95.96 | 1.47 | 98.35 |
| 11 | B2 | 3.7 | 30.0 | 11 | 77.4 | 20.5 | 1.0 | 0.6 | 0.5 | 97.9 | 11,701 | 96.26 | 1.36 | 97.86 |
| 12 | B2 | 5.4 | 18.6 | 23 | 77.4 | 20.3 | 0.8 | 0.4 | 1.1 | 97.7 | 23,035 | 96.21 | 1.35 | 98.37 |
| 13 | B2 | 2.9 | 41.2 | 7 | 77.2 | 21.2 | 0.8 | 0.3 | 0.5 | 98.4 | 94,214 | 96.14 | 1.44 | 98.47 |
| 14 | B2 | 5.4 | 13.0 | 29 | 72.3 | 25.3 | 0.8 | 0.4 | 1.2 | 97.6 | 29,486 | 94.62 | 1.98 | 98.19 |
| 15 | B2 | 6.0 | 13.0 | 32 | 76.3 | 20.5 | 1.4 | 0.7 | 1.1 | 96.8 | 35,093 | 95.93 | 1.42 | 97.26 |
| 16 | B2 | 9.6 | 14.3 | 40 | 83.8 | 13.4 | 0.6 | 0.6 | 1.6 | 97.2 | 38,762 | 98.06 | 0.65 | 98.73 |
| 17 | B2 | 11.4 | 12.0 | 49 | 88.2 | 8.0 | 0.9 | 0.6 | 2.3 | 96.2 | 32,193 | 98.74 | 0.32 | 98.47 |
| 18 | B2 | 32.2 | 29.6 | 52 | 75.2 | 21.3 | 0.9 | 0.7 | 1.9 | 96.5 | 99,572 | 96.16 | 1.43 | 98.44 |
| 19 | A1 | 1.5 | 12.5 | 11 | 83.6 | 12.5 | 0.7 | 0.5 | 2.7 | 96.1 | 13,918 | 97.97 | 0.68 | 98.53 |
| 20 | A3 | 7.5 | 3.1 | 71 | 71.2 | 22.0 | 2.5 | 1.4 | 2.9 | 93.2 | 5,709 | 94.06 | 1.43 | 96.10 |
| 21 | B3 | 1.8 | 5.0 | 26 | 93.8 | 2.6 | 1.4 | 0.5 | 1.7 | 96.4 | 6,090 | 98.55 | 0.07 | 88.76 |
| 22 | B5 | 1.6 | 3.4 | 32 | 91.5 | 2.9 | 1.3 | 0.4 | 3.9 | 94.4 | 3,586 | 98.28 | 0.09 | 91.25 |
| 23 | B5 | 0.5 | 98.9 | 0.5 | 95.9 | 2.2 | 1.6 | 0.1 | 0.1 | 98.1 | 108,407 | 99.57 | 0.04 | 99.32 |
| 24 | B5 | 1.1 | 292 | 0 | 91.8 | 0.5 | 7.2 | 0.1 | 0.4 | 92.3 | 301,145 | 99.39 | 0.01 | 97.32 |
| 25 | B5 | 46.0 | 149 | 24 | 92.5 | 1.6 | 5.3 | 0.2 | 0.3 | 94.1 | 156,663 | 99.17 | 0.04 | 96.36 |
| 26 | B5 | 1.2 | 18.1 | 6 | 96.4 | 2.2 | 1.1 | 0.1 | 0.1 | 98.6 | 34,185 | 99.43 | 0.04 | 98.03 |

TABLE 20

$N^2$-Phosphinyl Amidine Complex, Catalyst System Ratios, and Reaction Condition for Ethylene Oligomerization Runs 27-106

| Run # | Complex | Catalyst System Solvent† | Complex (mg) | Complex (mmol) | Cr (g) | Al:Cr ratio | Bulk Solvent‡ | Reaction Time (min) | Ethylene Pressure (psi) | Hydrogen Pressure | Reaction Temp. (° C.) |
|---|---|---|---|---|---|---|---|---|---|---|---|
| 27 | B12 | EB | 10 | 0.0143 | 0.7 | 500 | 0.4 L, cyH | 30 | 850 | 50 | 50 |
| 28 | B13 | EB | 12 | 0.0191 | 1.0 | 500 | 0.4 L, cyH | 30 | 850 | 50 | 55 |
| 29 | B10 | EB | 7 | 0.0097 | 0.5 | 500 | 0.4 L, cyH | 30 | 850 | 50 | 50 |
| 30 | B10 | EB | 10 | 0.0138 | 0.7 | 600 | 0.4 L, cyH | 30 | 850 | 50 | 55 |
| 31 | B6 | EB | 10 | 0.0146 | 0.8 | 500 | 0.4 L, cyH | 30 | 850 | 50 | 60 |
| 32 | B7 | EB | 10 | 0.0146 | 0.8 | 600 | 0.4 L, cyH | 30 | 850 | 50 | 50 |
| 33 | B8 | EB | 10 | 0.0126 | 0.7 | 500 | 0.4 L, cyH | 30 | 850 | 50 | 50 |
| 34 | B11 | EB | 9 | 0.0121 | 0.6 | 700 | 0.4 L, cyH | 30 | 850 | 50 | 60 |
| 35 | B11 | EB | 10 | 0.0135 | 0.7 | 500 | 0.4 L, cyH | 30 | 850 | 50 | 50 |
| 36 | B11 | EB | 7 | 0.0094 | 0.5 | 500 | 0.4 L, cyH | 30 | 850 | 50 | 50 |
| 37 | B4 | EB | 10 | 0.0130 | 0.7 | 600 | 0.4 L, cyH | 30 | 850 | 50 | 90 |
| 38 | B11 | EB | 13 | 0.0175 | 0.9 | 400 | 0.4 L, cyH | 30 | 850 | 50 | 90 |
| 39 | B10 | EB | 12 | 0.0166 | 0.9 | 400 | 0.4 L, cyH | 30 | 850 | 50 | 90 |
| 40 | B4 | EB | 10 | 0.0130 | 0.7 | 600 | 0.4 L, cyH | 30 | 850 | 50 | 50 |
| 41 | B16 | EB | 10 | 0.0149 | 0.8 | 400 | 0.4 L, cyH | 30 | 850 | 50 | 50 |
| 42 | B31 | EB | 12 | 0.0170 | 0.9 | 400 | 0.4 L, cyH | 30 | 850 | 50 | 50 |
| 43 | B19 | EB | 12 | 0.0166 | 0.9 | 400 | 0.4 L, cyH | 30 | 850 | 50 | 50 |
| 44 | B34 | EB | 6 | 0.0089 | 0.5 | 500 | 0.4 L, cyH | 30 | 850 | 50 | 50 |
| 45 | B34 | EB | 6 | 0.0089 | 0.5 | 500 | 0.4 L, cyH | 30 | 850 | 50 | 60 |
| 46 | B19 | EB | 12 | 0.0166 | 0.9 | 400 | 0.4 L, cyH | 30 | 850 | 50 | 90 |
| 47 | B21 | EB | 12 | 0.0167 | 0.9 | 400 | 0.4 L, cyH | 30 | 850 | 50 | 50 |
| 48 | B39 | EB | 6 | 0.0089 | 0.5 | 500 | 0.4 L, cyH | 30 | 850 | 50 | 60 |
| 49 | B40 | EB | 10 | 0.0135 | 0.7 | 600 | 0.4 L, cyH | 30 | 850 | 50 | 50 |
| 50 | B17 | EB | 13 | 0.0163 | 0.9 | 400 | 0.4 L, cyH | 30 | 850 | 50 | 50 |
| 51 | B41 | EB | 11 | 0.0167 | 0.9 | 400 | 0.4 L, cyH | 30 | 850 | 50 | 50 |
| 52 | B35 | EB | 6 | 0.0088 | 0.5 | 500 | 0.4 L, cyH | 30 | 850 | 50 | 60 |
| 53 | B32 | EB | 13 | 0.0175 | 0.9 | 400 | 0.4 L, cyH | 30 | 850 | 50 | 50 |
| 54 | B39 | EB | 6 | 0.0089 | 0.5 | 500 | 0.4 L, cyH | 30 | 850 | 50 | 60 |
| 55 | B15 | EB | 6 | 0.0081 | 0.4 | 500 | 0.4 L, cyH | 30 | 850 | 50 | 60 |
| 56 | B18 | EB | 14 | 0.0170 | 0.9 | 400 | 0.4 L, cyH | 30 | 850 | 50 | 50 |
| 57 | B20 | EB | 11 | 0.0167 | 0.9 | 400 | 0.4 L, cyH | 30 | 850 | 50 | 50 |
| 58 | B24 | EB | 11 | 0.0173 | 0.9 | 400 | 0.4 L, cyH | 30 | 850 | 50 | 50 |
| 59 | B14 | EB | 11 | 0.0164 | 0.9 | 400 | 0.4 L, cyH | 20 | 850 | 50 | 55 |
| 60 | B22 | EB | 6 | 0.0092 | 0.5 | 500 | 0.4 L, cyH | 30 | 850 | 50 | 60 |
| 61 | B42 | EB | 11 | 0.0171 | 0.9 | 400 | 0.4 L, cyH | 30 | 850 | 50 | 50 |
| 62 | B43 | EB | 11 | 0.0167 | 0.9 | 400 | 0.4 L, cyH | 30 | 850 | 50 | 50 |
| 63 | B23 | EB | 12 | 0.0170 | 0.9 | 400 | 0.4 L, cyH | 30 | 850 | 50 | 50 |
| 64 | B36 | EB | 6 | 0.0092 | 0.5 | 400 | 0.4 L, cyH | 30 | 850 | 50 | 60 |
| 65 | C3 | EB | 12 | 0.0175 | 0.9 | 400 | 0.4 L, cyH | 30 | 850 | 50 | 50 |

TABLE 20-continued

N²-Phosphinyl Amidine Complex, Catalyst System Ratios, and Reaction Condition for Ethylene Oligomerization Runs 27-106

| Run # | Complex | Catalyst System Solvent† | Complex (mg) | Complex (mmol) | Cr (g) | Al:Cr ratio | Bulk Solvent‡ | Reaction Time (min) | Ethylene Pressure (psi) | Hydrogen Pressure | Reaction Temp. (°C.) |
|---|---|---|---|---|---|---|---|---|---|---|---|
| 66 | B46 | EB | 12 | 0.0177 | 0.9 | 400 | 0.4 L, cyH | 30 | 850 | 50 | 50 |
| 67 | B25 | EB | 10 | 0.0149 | 0.8 | 400 | 0.4 L, cyH | 30 | 850 | 50 | 50 |
| 68 | B44 | EB | 12 | 0.0174 | 0.9 | 400 | 0.4 L, cyH | 30 | 850 | 50 | 50 |
| 69 | C1 | EB | 6 | 0.0088 | 0.5 | 500 | 0.4 L, cyH | 30 | 850 | 50 | 60 |
| 70 | B45 | EB | 6 | 0.0080 | 0.4 | 500 | 0.4 L, cyH | 30 | 850 | 50 | 60 |
| 71 | B38 | EB | 6 | 0.0081 | 0.4 | 500 | 0.4 L, cyH | 30 | 850 | 50 | 60 |
| 72 | B56 | EB | 6 | 0.0085 | 0.4 | 500 | 0.4 L, cyH | 30 | 850 | 50 | 60 |
| 73 | B31 | EB | 6 | 0.0085 | 0.4 | 500 | 0.4 L, cyH | 30 | 850 | 50 | 60 |
| 74 | B5 | EB | 6 | 0.0086 | 0.4 | 500 | 0.4 L, cyH | 30 | 850 | 50 | 60 |
| 75 | B55 | EB | 6 | 0.0096 | 0.5 | 500 | 0.4 L, cyH | 30 | 850 | 50 | 60 |
| 76 | B26 | EB | 12 | 0.0187 | 1.0 | 400 | 0.4 L, cyH | 30 | 850 | 50 | 50 |
| 77 | B47 | EB | 6 | 0.0096 | 0.5 | 500 | 0.4 L, cyH | 30 | 850 | 50 | 60 |
| 78 | B50 | EB | 12 | 0.0158 | 0.8 | 400 | 0.4 L, cyH | 30 | 850 | 50 | 50 |
| 79 | B49 | EB | 6 | 0.0087 | 0.5 | 500 | 0.4 L, cyH | 30 | 850 | 50 | 60 |
| 80 | B27 | EB | 6 | 0.0088 | 0.5 | 500 | 0.4 L, cyH | 30 | 850 | 50 | 60 |
| 81 | B33 | EB | 6 | 0.0080 | 0.4 | 500 | 0.4 L, cyH | 30 | 850 | 50 | 60 |
| 82 | B37 | EB | 6 | 0.0089 | 0.5 | 500 | 0.4 L, cyH | 30 | 850 | 50 | 60 |
| 83 | B37 | EB | 6 | 0.0089 | 0.5 | 500 | 0.4 L, cyH | 30 | 850 | 50 | 90 |
| 84 | B37 | EB | 6 | 0.0089 | 0.5 | 500 | 0.4 L, cyH | 30 | 850 | 50 | 90 |
| 85 | B5 | EB | 7 | 0.0100 | 0.5 | 400 | 0.4 L, cyH | 30 | 50 | 50 | 90 |
| 86 | B48 | EB | 6 | 0.0101 | 0.5 | 500 | 0.4 L, cyH | 30 | 850 | 50 | 60 |
| 87 | B51 | EB | 6 | 0.0087 | 0.5 | 500 | 0.4 L, cyH | 30 | 850 | 50 | 60 |
| 88 | B41 | EB | 6 | 0.0091 | 0.5 | 500 | 0.4 L, cyH | 30 | 850 | 50 | 90 |
| 89 | B29 | EB | 10 | 0.0130 | 0.7 | 400 | 0.4 L, cyH | 30 | 850 | 10 | 50 |
| 90 | B53 | EB | 10 | 0.0143 | 0.7 | 400 | 0.4 L, cyH | 30 | 850 | 50 | 50 |
| 91 | B30 | EB | 12 | 0.0171 | 0.9 | 400 | 0.4 L, cyH | 30 | 850 | 50 | 50 |
| 92 | B54 | EB | 12 | 0.0187 | 1.0 | 400 | 0.4 L, cyH | 20 | 850 | 50 | 60 |
| 93 | B52 | EB | 10 | 0.0164 | 0.9 | 400 | 0.4 L, cyH | 30 | 850 | 50 | 50 |
| 94 | B28 | EB | 12 | 0.0166 | 0.9 | 400 | 0.4 L, cyH | 30 | 850 | 50 | 70 |
| 95 | B54 | EB | 6 | 0.0093 | 0.5 | 400 | 0.4 L, cyH | 30 | 850 | 50 | 50 |
| 96 | B37 | EB | 6 | 0.0089 | 0.5 | 400 | 0.4 L, cyH | 30 | 875 | 25 | 70 |
| 97 | B41 | EB | 6 | 0.0091 | 0.5 | 400 | 0.4 L, cyH | 30 | 875 | 25 | 70 |
| 98 | B25 | EB | 6.4 | 0.0096 | 0.5 | 400 | 0.4 L, cyH | 30 | 850 | 50 | 70 |
| 99 | B25 | EB | 6.8 | 0.0102 | 0.5 | 400 | 0.4 L, cyH | 30 | 850 | 50 | 60 |
| 100 | B25 | EB | 6.4 | 0.0096 | 0.5 | 400 | 0.4 L, cyH | 30 | 850 | 50 | 80 |
| 101 | B5 | EB | 7 | 0.0100 | 0.5 | 400 | 0.4 L, cyH | 30 | 50 | 50 | 60 |
| 102 | D5 | DCM | 5 | 0.007 | 0.3 | 1000 | 0.4 L, cyH | 30 | 850 | 50 | 50 |
| 103 | D5 | DCM | 6 | 0.008 | 0.4 | 850 | 0.4 L, cyH | 60 | 850 | 50 | 90 |
| 104 | D5⁻** | DCM | 5 | 0.007 | 0.4 | 1000 | 0.4 L, cyH | 60 | 850 | 50 | 90 |
| 105 | D4 | DCM | 4 | 0.006 | 0.3 | 1000 | 0.4 L, cyH | 30 | 850 | 50 | 50 |
| 106 | D4 | EB | 11 | 0.017 | 0.9 | 400 | 0.4 L, cyH | 30 | 850 | 50 | 50 |

†EB = ethylbenzene.
‡cyH = cyclohexane.
**Complex was the negatively charged Amidinate complex.

TABLE 21

Product of Ethylene Oligomerization Runs 27-106

| | NP Amidine | Product Type | | | Carbon Number Distribution (Wt. %) | | | | | Productivities and Activities | | Product Purities (Wt. %) | | |
|---|---|---|---|---|---|---|---|---|---|---|---|---|---|---|
| Run # | Metal Salt Complex | Solid (g) | Liquid (g) | Solid (wt. %) | $C_6$ | $C_8$ | $C_{10}$ | $C_{12}$ | $C_{14+}$ | $C_6+C_8$ (%) | $C_6+C_8$ (g/g Cr) | 1-hexene (wt. %) | MeCp (wt. %) | 1-octene (wt. %) |
| 27 | B12 | 0.8 | 2.1 | 27.6 | 38.2 | 13.6 | 19.1 | 10.2 | 18.9 | 51.8 | 1,458 | 72.47 | 9.29 | 71.65 |
| 28 | B13 | 1.8 | 5.5 | 24.7 | 45.2 | 28.4 | 9.6 | 7.4 | 9.4 | 73.6 | 4,080 | 28.15 | 29.51 | 75.37 |
| 29 | B10 | 0.8 | 0.4 | 66.7 | 52.7 | 19.2 | 10.7 | 7.2 | 10.2 | 71.9 | 571 | 38.81 | 74.30 | 74.30 |
| 30 | B10 | 1.2 | 5.6 | 17.6 | 51.0 | 21.1 | 8.8 | 7.8 | 11.3 | 72.1 | 5,615 | 37.34 | 24.36 | 70.50 |
| 31 | B6 | 0.4 | 6.4 | 5.9 | 98.9 | 0.7 | 0.5 | 0.0 | 0.0 | 99.6 | 8,398 | 99.25 | 0.08 | NA |
| 32 | B7 | 1.6 | 9.3 | 14.7 | 96.8 | 1.1 | 1.0 | 0.4 | 0.7 | 97.9 | 11,995 | 99.19 | 0.06 | NA |
| 33 | B8 | 0.7 | 1.7 | 29.2 | 86.3 | 9.0 | 3.0 | 1.0 | 0.7 | 95.3 | 2,478 | 90.40 | 2.23 | 83.11 |
| 34 | B11 | 1.1 | 98.3 | 1.1 | 93.2 | 5.4 | 1.1 | 0.2 | 0.1 | 98.6 | 153,485 | 96.09 | 1.71 | 94.38 |
| 35 | B11 | 0.5 | 40.6 | 1.2 | 90.2 | 8.7 | 0.8 | 0.2 | 0.1 | 98.9 | 57,227 | 92.89 | 3.17 | 92.64 |
| 36 | B11 | 0.2 | 44.7 | 0.4 | 91.8 | 7.4 | 0.6 | 0.1 | 0.1 | 99.2 | 90,282 | 94.14 | 2.74 | 94.01 |
| 37 | B4 | 1.5 | 8.8 | 14.6 | 92.4 | 5.8 | 0.8 | 0.6 | 0.4 | 98.2 | 12,749 | 98.61 | 0.22 | 94.77 |
| 38 | B11 | 1.0 | 26.7 | 3.6 | 93.9 | 4.8 | 0.8 | 0.2 | 0.3 | 98.7 | 28,891 | 98.15 | 0.76 | 97.64 |
| 39 | B10 | 0.5 | 0.7 | 41.7 | 74.0 | 14.0 | 5.6 | 2.9 | 3.5 | 88.0 | 714 | 80.78 | 4.77 | 78.53 |
| 40 | B4 | 2.1 | 21.9 | 8.8 | 79.1 | 19.8 | 0.5 | 0.3 | 0.3 | 98.9 | 31,953 | 96.21 | 1.31 | 98.34 |

TABLE 21-continued

Product of Ethylene Oligomerization Runs 27-106

| Run # | NP Amidine Metal Salt Complex | Product Type Solid (g) | Liquid (g) | Solid (wt. %) | Carbon Number Distribution (Wt. %) | | | | | Productivities and Activities $C_6 + C_8$ (%) | $C_6 + C_8$ (g/g Cr) | Product Purities (Wt. %) | | |
|---|---|---|---|---|---|---|---|---|---|---|---|---|---|---|
| | | | | | $C_6$ | $C_8$ | $C_{10}$ | $C_{12}$ | $C_{14+}$ | | | 1-hexene (wt. %) | MeCp (wt. %) | 1-octene (wt. %) |
| 41 | B16 | 1.1 | 5.6 | 16.4 | 69.2 | 26.5 | 1.4 | 0.8 | 2.1 | 95.7 | 6,897 | 96.02 | 1.26 | 97.94 |
| 42 | B31 | 0.9 | 34.5 | 2.5 | 96.9 | 1.9 | 1.0 | 0.1 | 0.1 | 98.8 | 38,628 | 99.60 | 0.03 | 98.05 |
| 43 | B19 | 12.1 | 117.2 | 9.4 | 45.9 | 32.2 | 8.2 | 6.2 | 7.5 | 78.1 | 106,359 | 31.46 | 29.94 | 78.44 |
| 44 | B34 | 0.4 | 11.2 | 3.4 | 95.7 | 1.5 | 2.1 | 0.3 | 0.4 | 97.2 | 23,484 | 99.50 | 0.03 | 98.04 |
| 45 | B34 | 0.5 | 12.3 | 3.9 | 97.7 | 0.4 | 1.7 | 0.1 | 0.1 | 98.1 | 26,029 | 99.74 | 0.00 | 93.54 |
| 46 | B19 | 125.0 | 13.8 | 90.1 | 60.3 | 23.9 | 7.5 | 3.2 | 5.1 | 84.2 | 13,502 | 83.84 | 8.06 | 94.58 |
| 47 | B21 | 0.7 | 0.0 | 100.0 | 0.0 | 0.0 | 0.0 | 0.0 | 0.0 | 0.0 | 0 | NA | NA | NA |
| 48 | B39 | 0.5 | 67.7 | 0.7 | 92.8 | 6.0 | 1.0 | 0.2 | 0.0 | 98.8 | 143,864 | 95.87 | 2.02 | 95.62 |
| 49 | B40 | 0.7 | 4.4 | 13.7 | 86.4 | 11.1 | 1.5 | 0.9 | 0.1 | 97.5 | 6,097 | 98.30 | 0.46 | 95.49 |
| 50 | B17 | 0.8 | 0.0 | 100.0 | 0.0 | 0.0 | 0.0 | 0.0 | 0.0 | 0.0 | 0 | 0.00 | 0.00 | 0.00 |
| 51 | B41 | 0.6 | 126.6 | 0.5 | 97.4 | 0.7 | 1.8 | 0.1 | 0.0 | 98.1 | 142,657 | 99.79 | 0.01 | 98.01 |
| 52 | B35 | 0.8 | | | 0.0 | 0.0 | 0.0 | 0.0 | 0.0 | 0.0 | | 0.00 | 0.00 | 0.00 |
| 53 | B32 | 0.7 | 3.9 | 15.2 | 88.3 | 10.9 | 0.4 | 0.1 | 0.3 | 99.2 | 4,241 | 98.55 | 0.19 | 97.84 |
| 54 | B39 | 0.8 | 109.4 | 0.7 | 94.5 | 4.1 | 1.3 | 0.1 | 0.0 | 98.6 | 232,007 | 97.49 | 1.13 | 95.77 |
| 55 | B15 | 0.8 | 1.8 | 30.8 | 59.3 | 21.5 | 6.5 | 5.3 | 7.4 | 80.8 | 3,436 | 46.97 | 21.80 | 76.66 |
| 56 | B18 | 0.9 | 1.9 | 32.1 | 76.5 | 21.9 | 0.6 | 0.3 | 0.7 | 98.4 | 2,114 | 94.18 | 1.16 | 97.12 |
| 57 | B20 | 2.2 | 1.9 | 53.7 | 30.8 | 23.1 | 12.2 | 11.6 | 22.3 | 53.9 | 1,176 | 52.75 | 16.66 | 80.66 |
| 58 | B24 | 0.7 | 8.2 | 7.9 | 81.8 | 16.6 | 0.9 | 0.5 | 0.2 | 98.4 | 8,986 | 90.61 | 4.58 | 96.20 |
| 59 | B14 | 0.9 | 117.5 | 0.8 | 93.6 | 5.0 | 1.2 | 0.1 | 0.1 | 98.6 | 135,919 | 95.88 | 1.78 | 94.52 |
| 60 | B22 | 0.3 | 0.4 | 42.9 | 75.4 | 20.0 | 2.2 | 1.3 | 1.1 | 95.4 | 794 | 90.44 | 1.23 | NA |
| 61 | B42 | 4.7 | 1.6 | 74.6 | 50.7 | 41.2 | 3.6 | 2.6 | 1.9 | 91.9 | 1,655 | 89.24 | 3.30 | 96.81 |
| 62 | B43 | 0.7 | 0.4 | 63.6 | 0.0 | 0.0 | 0.0 | 0.0 | 0.0 | 0.0 | 0 | 0.00 | 0.00 | 0.00 |
| 63 | B23 | 1.1 | 0.7 | 61.1 | 52.6 | 31.1 | 4.2 | 4.6 | 7.5 | 83.7 | 662 | 69.05 | 10.95 | 90.36 |
| 64 | B36 | 0.1 | 21.4 | 0.5 | 92.8 | 6.4 | 0.6 | 0.1 | 0.1 | 99.2 | 44,224 | 99.42 | 0.08 | 99.13 |
| 65 | C3 | 0.5 | 1.9 | 20.8 | 88.0 | 8.8 | 1.7 | 1.0 | 0.5 | 96.8 | 2,019 | 90.71 | 3.23 | 84.02 |
| 66 | B46 | 0.4 | 61.5 | 0.6 | 88.7 | 9.3 | 1.2 | 0.5 | 0.3 | 98.0 | 65,586 | 92.96 | 3.46 | 88.34 |
| 67 | B25 | 0.9 | 6.1 | 12.9 | 65.7 | 31.1 | 1.2 | 1.3 | 0.7 | 96.8 | 7,599 | 96.29 | 1.21 | 97.91 |
| 68 | B44 | 2.4 | 1.5 | 61.5 | 54.7 | 35.2 | 3.1 | 2.0 | 5.0 | 89.9 | 1,493 | 88.42 | 2.99 | 94.34 |
| 69 | C1 | 0.1 | 6.2 | 1.6 | 85.8 | 12.7 | 0.8 | 0.2 | 0.5 | 98.5 | 13,408 | 93.34 | 3.68 | 92.52 |
| 70 | B45 | 0.2 | 4.3 | 4.4 | 92.5 | 5.3 | 0.4 | 1.8 | 0.0 | 97.8 | 10,070 | 93.06 | 3.93 | 92.53 |
| 71 | B38 | 0.8 | 0.4 | 66.7 | 56.4 | 11.2 | 2.3 | 30.2 | 0.0 | 67.6 | 641 | 69.58 | 14.60 | 66.12 |
| 72 | B56 | 0.3 | 127.4 | 0.2 | 95.5 | 0.9 | 2.0 | 0.5 | 1.1 | 96.4 | 278,354 | 99.75 | 0.03 | 97.90 |
| 73 | B31 | 0.1 | 9.3 | 1.1 | 96.4 | 1.3 | 1.0 | 0.5 | 0.8 | 97.7 | 20,593 | 99.18 | 0.01 | 88.16 |
| 74 | B5 | 21.0 | 221.8 | 8.6 | 96.1 | 1.0 | 2.8 | 0.1 | 0.0 | 97.1 | 481,285 | 99.49 | 0.01 | 98.76 |
| 75 | B55 | 0.1 | 5.3 | 1.9 | 92.2 | 6.1 | 0.2 | 1.5 | 0.0 | 98.3 | 10,403 | 96.29 | 1.65 | 89.28 |
| 76 | B26 | 0.8 | 1.8 | 30.8 | 58.6 | 30.5 | 2.2 | 5.3 | 3.4 | 89.1 | 1,653 | 66.28 | 15.52 | 84.17 |
| 77 | B47 | | 39.5 | | 96.2 | 2.8 | 0.6 | 0.1 | 0.3 | 99.0 | 78,087 | 99.57 | 0.06 | 98.94 |
| 78 | B50 | 0.8 | 16.6 | 4.6 | 87.8 | 10.7 | 0.8 | 0.2 | 0.0 | 98.5 | 19,944 | 96.26 | 1.51 | 95.89 |
| 79 | B49 | | 0.4 | | 35.0 | 22.4 | 20.6 | 11.5 | 10.5 | 57.4 | 509 | 54.79 | 12.71 | 76.12 |
| 80 | B27 | | 1.6 | | 73.7 | 17.3 | 4.6 | 1.8 | 2.6 | 91.0 | 3,197 | 78.15 | 10.15 | 84.77 |
| 81 | B33 | 0.2 | 0.3 | 40.0 | 66.8 | 17.8 | 8.8 | 3.7 | 2.9 | 84.6 | 608 | 83.19 | 0.00 | 70.35 |
| 82 | B37 | 0.2 | 270.2 | 0.1 | 94.6 | 0.1 | 5.0 | 0.2 | 0.1 | 94.7 | 551,970 | 99.69 | 0.00 | 93.27 |
| 83 | B37 | | 29.1 | | 98.0 | 0.2 | 1.4 | 0.2 | 0.2 | 98.2 | 61,643 | 99.59 | 0.01 | 45.43? |
| 84 | B37 | | 28.7 | | 96.7 | 0.6 | 1.6 | 0.4 | 0.7 | 97.3 | 60,239 | 99.35 | 0.02 | 45.87 |
| 85 | B5 | 21.6 | 189.3 | 10.2 | 95.7 | 1.2 | 3.0 | 0.1 | 0.0 | 96.9 | 351,357 | 99.68 | 0.02 | 98.15 |
| 86 | B48 | | 3.3 | | 67.6 | 28.2 | 1.8 | 1.0 | 1.4 | 95.8 | 6,025 | 94.80 | 1.37 | 96.14 |
| 87 | B51 | | 68.1 | | 94.7 | 3.8 | 1.3 | 0.1 | 0.1 | 98.5 | 149,007 | 99.49 | 0.11 | 99.08 |
| 88 | B41 | | 11.3 | | 91.2 | 5.3 | 1.5 | 0.7 | 1.3 | 96.5 | 22,963 | 98.99 | 0.11 | 94.72 |
| 89 | B29 | 1.5 | 11.2 | 11.8 | 78.3 | 20.5 | 0.5 | 0.3 | 0.4 | 98.8 | 16,325 | 96.32 | 1.36 | 98.37 |
| 90 | B53 | 1.9 | 5.1 | 27.1 | 74.9 | 15.9 | 2.8 | 3.9 | 2.5 | 90.8 | 6,234 | 81.61 | 6.86 | 80.43 |
| 91 | B30 | 3.0 | 1.7 | 63.8 | 44.2 | 32.9 | 6.1 | 5.9 | 10.9 | 77.1 | 1,477 | 74.92 | 9.03 | 87.56 |
| 92 | B54 | 2.3 | 135.5 | 1.7 | 94.7 | 3.8 | 1.3 | 0.1 | 0.1 | 98.5 | 137,534 | 98.13 | 0.87 | 95.13 |
| 93 | B52 | 4.3 | 1.8 | 70.5 | 54.4 | 30.7 | 9.3 | 4.3 | 1.3 | 85.1 | 1,794 | 94.69 | 0.42 | 97.69 |
| 94 | B28 | 1.2 | 2.0 | 37.5 | 39.2 | 23.8 | 8.8 | 7.5 | 20.7 | 63.0 | 1,464 | 46.58 | 20.73 | 77.74 |
| 95 | B54 | 8.3 | 71.7 | 10.4 | 94.4 | 4.5 | 0.7 | 0.1 | 0.3 | 98.9 | 146,143 | 97.54 | 1.14 | 93.28 |
| 96 | B37 | 5.2 | 68.6 | 7.0 | 97.6 | 1.1 | 1.3 | 0.0 | 0.0 | 98.7 | 146,057 | 99.87 | 0.02 | 98.23 |
| 97 | B41 | 13.3 | 110.3 | 10.8 | 97.6 | 1.0 | 1.3 | 0.0 | 0.1 | 98.6 | 229,025 | 99.89 | 0.01 | 98.68 |
| 98 | B25 | 5.1 | 29.9 | 14.6 | 82.8 | 15.6 | 1.0 | 0.4 | 0.2 | 98.4 | 59,161 | 98.83 | 0.41 | 98.98 |
| 99 | B25 | 3.4 | 25.7 | 11.7 | 77.2 | 19.8 | 2.2 | 0.3 | 0.5 | 97.0 | 47,179 | 98.15 | 0.70 | 98.54 |
| 100 | B25 | 35.1 | 37.0 | 48.7 | 85.0 | 13.2 | 1.0 | 0.3 | 0.5 | 98.2 | 73,061 | 98.99 | 0.33 | 98.94 |
| 101 | B5 | 0.7 | 86.9 | 0.8 | 96.6 | 1.7 | 1.5 | 0.1 | 0.1 | 98.3 | 163,624 | 99.49 | 0.03 | 98.90 |
| 102 | D5 | 1.1 | 2.7 | 29 | 94.4 | 1.9 | 1.4 | 0.5 | 1.8 | 96.3 | 7,551 | 97.75 | 0.14 | 71.66 |
| 103 | D5 | 5.5 | 4.8 | 53 | 86.9 | 2.5 | 2.3 | .8 | 6.5 | 89.4 | 10,386 | 98.01 | 0.21 | 83.43 |
| 104 | D5-** | 32.6 | 2.2 | 94 | 39.3 | 10.6 | 10.8 | 8.9 | 30.4 | | 2,882 | 92.31 | 0.8 | 89.56 |
| 105 | D4 | 0.7 | 1.5 | 32 | 94.5 | 1.5 | 0.8 | 1.3 | 1.9 | | 4,507 | 5.77 | 0.27 | NA |
| 106 | D4 | .3 | .7 | 15 | 89.1 | 0.6 | 1.7 | 0.0 | 8.6 | 89.7 | 1,736 | 96.9 | 0 | NA |

Example 2

The effects of aging the $N^2$-phosphinyl amidine metal salt complex, treating the $N^2$-phosphinyl amidine metal salt complex with a neutral ligand, treating the $N^2$-phosphinyl amidine metal salt complex with a neutral ligand, and aging the treated $N^2$-phosphinyl amidine metal salt complex with a neutral ligand were investigated. Specifically, referring to Table 21, Run 74 was carried out using a $N^2$-phosphinyl amidine metal salt complex B55 that had been stored for about 5 months. Run 201 was carried out using approximately 50 mg of a $N^2$-phosphinyl amidine metal salt complex B5 that had been stored for about 5 months dissolved in a mixture of 0.5 g ethylbenzene and 0.5 g THF. to provide the $N^2$-phosphinyl amidine metal salt complex B58 in a 50/50 mixture of THF and ethylbenzene. B5 Run 101 was carried out using approximately 50 mg of an $N^2$-phosphinyl amidine metal salt complex B5 that had been stored for about 5 months and then dissolved in 1 g anhydrous tetrahydrofuran (THF). The THF was allowed to evaporate to dryness over 18 hours in a dry box, and the resulting blue solid was used immediately. Hereinafter this is referred to as "THF-treated B5."

Run 40 was carried out with $N^2$-phosphinyl amidine metal salt complex B4 which had been stored for 6 months after preparation. Run 203 was carried out using B67 which was produced as follows: a 20 mL glass vial was charged with 7 mg anhydrous pyridine (dried over 4 Å molecular sieves), 31 mg B4, and 2 g methylene chloride. The resulting turquoise blue solution was allowed to stand for 3 hours, followed by slow solvent evaporation forming blue crystals. The crystals were captured prior to total solvent evaporation and were dried under vacuum.

For ethylene oligomerization runs 201, 202, and 204-214, a 1 L stainless steel reactor was dried under vacuum at 110° C. for at least 8 hour prior to use. The reactor was then cooled to 50° C. In a dry box, a 20 mL glass vial was charged with an $N^2$-phosphinyl amidine metal salt complex, 1 g catalyst system solvent, and MMAO-3A (7.6 wt % Al solution in heptanes) to provide the desired Al:Cr molar ratio. This solution was then added to 0.5 L glass charger containing 400 mL of the oligomerization solvent, cyclohexane. The combined solution was removed from the dry box and charged into the 1 L stainless steel reactor. Hydrogen was added to the reactor followed by ethylene (fed on-demand). The identity of the $N^2$-phosphinyl amidine metal salt complex, the amount of the complex, the catalyst solvent, the oligomerization solvent, the amount of the oligomerization solvent, the hydrogen pressure, the ethylene pressure, the oligomerization time and oligomerization pressure for ethylene oligomerization Runs 74, 40, 101, and 201-202 are provided in Table 22. The reaction was allowed to proceed at the temperatures and for the times indicated in Table 22.

At reaction completion, water cooling was applied to the 1 L stainless steel reactor system. Once the temperature reached 35° C., the unreacted ethylene and hydrogen gas were vented to the atmosphere. A liquid sample was collected and analyzed by GC-FID. The reactor solids were collected by filtering the solution and cleaning the reactor walls and cooling coils. Table 22 also provides an analysis of the products of ethylene oligomerization Runs 74, 40, 201-202. The amount of polymer production (g polymer), amount of liquid product (g liquid product), wt % polymer, product distribution (as wt % of liquid product), amount of $C_6+C_8$ product as a wt % of liquid product, catalyst activity (g $C_6+C_8$/g Cr), wt % 1-hexene in the $C_6$ product, and wt % 1-octene in the $C_8$ product, and the weight percent of methylcyclopentane produced.

TABLE 22

| Run # | 74 | 201 | 101 | 40 | 202 |
|---|---|---|---|---|---|
| Catalyst System and Oligomerization Conditions | | | | | |
| Amidine Metal Salt Complex | B5 | B5 | B5 | B4 | B67 |
| Catalyst System Solvent | EB | EB/THF | EB | EB | EB |
| Complex (mg) | 6 | 7 | 7 | 10 | 10 |
| Complex (mmol) | 0.0086 | 0.0100 | 0.0100 | 0.0130 | 0.0130 |
| Cr (mg) | 0.45 | 0.52 | 0.52 | 0.68 | 0.68 |
| Al:Cr molar ratio | 500 | 400 | 400 | 600 | 400 |
| Bulk Solvent, cyclohexane (mL) | 400 | 400 | 400 | 400 | 400 |
| Reaction Time (min) | 30 | 30 | 30 | 30 | 30 |
| Ethylene Pressure (psi) | 850 | 850 | 850 | 850 | 850 |
| Hydrogen Pressure (psi) | 50 | 50 | 50 | 50 | 50 |
| Reaction Temperature (° C.) | 60 | 60 | 60 | 50 | 50 |
| Oligomerization Product Product Type | | | | | |
| Solid/Polymer (g) | 21 | 0 | 0.7 | 2.1 | 0.1 |
| Liquid (g) | 221.8 | 0 | 86.9 | 21.9 | 15.7 |
| Solid/Polymer (wt %) | 8.6 | N/A | 0.8 | 8.8 | 0.6 |
| Carbon Number Distribution | | | | | |
| $C_6$ | 96.1 | 0 | 96.6 | 79.1 | 78.6 |
| $C_8$ | 1 | 0 | 1.7 | 19.8 | 20.1 |
| $C_{10}$ | 2.8 | 0 | 1.5 | 0.5 | 0.5 |
| $C_{12}$ | 0.1 | 0 | 0.1 | 0.3 | 0.4 |
| $C_{14+}$ | 0 | 0 | 0.1 | 0.3 | 0.4 |
| Productivities and Activities | | | | | |
| $C_6+C_8$ (wt %) | 97.1 | NA | 98.3 | 98.9 | 98.7 |
| $C_6+C_8$ (g/g Cr) | 481,285 | NA | 163,624 | 31,953 | 22,861 |
| Product Purities | | | | | |
| 1-Hexene (wt %) | 99.49 | NA | 99.49 | 96.21 | 96.47 |
| Methylcyclopentane | 0.1 | NA | 0.3 | 1.31 | 1.34 |
| 1-Octene (wt %) | 98.76 | NA | 98.9 | 98.34 | 98.29 |

Referring to Table 22, the oligomerization runs show the impact that the $N^2$-phosphinyl amidine metal salt metal complex age and the treatment of the $N^2$-phosphinyl amidine metal salt with a neutral ligand had on ethylene oligomerization.

As can be seen in Table 22, $N^2$-phosphinyl amidine metal salt complexes which had been stored for significant periods of time (Run 74, complex B5 stored for 5 months and Run 40, Complex B4, stored for 6 months) prior to preparing the catalyst system produced significant amounts of polymer (8.6 wt % and 8.8 wt %, respectively). Table 22 data also show that $N^2$-phosphinyl amidine metal salt complexes can be treated with a neutral ligand such that the $N^2$-phosphinyl amidine metal salt complex can then be utilized in a catalyst system which can produce less polymer. In Run 101, the $N^2$-phosphinyl amidine metal salt complex that was treated with the same neutral ligand as was originally present in the $N^2$-phosphinyl amidine metal salt complex (i.e., THF), resulted in a catalyst system producing 0.6 wt % polymer. In run 202, the $N^2$-phosphinyl amidine metal salt complex that was treated with a different neutral ligand (i.e., pyridine) than was originally present in the $N^2$-phosphinyl amidine metal salt complex (THF), resulted in a catalyst system producing 0.6 wt % polymer.

Referring to Run 74, the $N^2$-phosphinyl amidine metal salt complex B5, which had been stored for 5 months, produced a catalyst system having a productivity of 481,285 g($C_6$+$C_8$)/g (Cr). Run 201 shows use of this $N^2$-phosphinyl amidine metal salt complex in a catalyst system wherein one-half of the normal amount of catalyst solvent, ethylbenzene, was replaced with neutral ligand, THF, (as described previously). The replacement of one half of the ethylbenzene with THF resulted in an inactive catalyst system. This indicates that a large excess of neutral ligand can act as a catalyst system poison. However, isolation of $N^2$-phosphinyl amidine metal salt complex B5 from a solution containing a neutral ligand (THF), in Run 101, produced an active catalyst system having a reduced productivity (163,624 g ($C_6$+$C_8$)/g (Cr)) while producing less polymer (0.8 wt %). Reviewing the effects of aging an $N^2$-phosphinyl amidine metal salt complex and treatment of an aged $N^2$-phosphinyl amidine metal salt complex have on catalyst system productivity and polymer production, it can be seen that there are both positive and negative effects to aging an $N^2$-phosphinyl amidine metal salt complex and that these effects can be balanced to provide an optimum catalyst system using an $N^2$-phosphinyl amidine metal salt complex. Further, this experiment shows that the effects related to the aging of the $N^2$-phosphinyl amidine metal salt complex can be reversed by treatment with a neutral ligand.

Additional $N^2$-phosphinyl amidine metal salt complexes were used in catalyst systems for olefin oligomerizations using the methods described in this example. The oligomerization conditions and product analyses for oligomerization Runs 204-214 are provided in Table 23.

TABLE 23

| Run No. | 204 | 205 | 206 | 207 | 208 | 209 |
|---|---|---|---|---|---|---|
| Catalyst System and Oligomerization Conditions | | | | | | |
| Amidine Metal Salt Complex | B69 | B72 | B70 | B74 | B75 | B76 |
| Complex (mg) | 7 | 5 | 4 | 6 | 6 | 7 |
| Complex mmol | 0.0098 | 0.0073 | 0.0057 | 0.0091 | 0.0093 | 0.0107 |
| Cr (mg) | 0.51 | 0.38 | 0.30 | 0.47 | 0.49 | 0.55 |
| Al:Cr molar ratio | 400 | 800 | 1000 | 800 | 600 | 400 |
| Catalyst System Solvent, Ethylbenzene (g) | 1 | 1 | 1 | 1 | 1 | 1 |
| Catalyst System Aging Time (hours) | 3.5 | 2 | 2 | 2 | 18 | >1 |
| Reaction Time (min) | 30 | 30 | 30 | 30 | 30 | 30 |
| Ethylene Pressure (psi) | 850 | 850 | 850 | 875 | 875 | 850 |
| Hydrogen Pressure (psi) | 50 | 50 | 50 | 25 | 25 | 50 |
| Reaction Temperature (° C.) | 80 | 70 | 70 | 70 | 70 | 60 |
| Oligomerization Product Product Type | | | | | | |
| Solid/Polymer (g) | 3.4 | 0.05 | 0.4 | 27.3 | 1.9 | 1.7 |
| Liquid (g) | 228.9 | 43.1 | 2.4 | 212.1 | 25.3 | 263 |
| Solid/Polymer (wt %) | 1.5 | 0.1 | 14.3 | 11.4 | 6.99 | 0.6 |
| Carbon Number Distribution | | | | | | |
| $C_6$ | 95.2 | 81.5 | 63.0 | 93.9 | 81.8 | 96.2 |
| $C_8$ | 1.2 | 17.1 | 32.5 | 3.2 | 16.4 | 0.3 |
| $C_{10}$ | 3.4 | 1.0 | 1.6 | 2.7 | 1.3 | 3.4 |
| $C_{12}$ | 0.1 | 0.3 | 1.5 | 0.1 | 0.3 | 0.1 |
| $C_{14+}$ | 0.1 | 0.1 | 1.4 | 0.1 | 0.2 | 0.0 |
| Productivities and Activities | | | | | | |
| $C_6$ + $C_8$ (wt %) | 96.4 | 98.6 | 95.5 | 97.1 | 98.2 | 96.5 |
| $C_6$ + $C_8$ (g/g Cr) | 433,511 | 111,979 | 7,747 | 434,368 | 51,203 | 458,107 |
| Product Purities | | | | | | |
| 1-Hexene (wt %) | 99.72 | 98.72 | 95.20 | 99.68 | 99.01 | 99.85 |
| Methylcyclopentane | 0.02 | 0.46 | 1.43 | 0.06 | 0.27 | 0.00 |
| 1-Octene (wt %) | 98.64 | 98.89 | 97.09 | 99.34 | 99.06 | 96.33 |

| Run No. | 210 | 211 | 212 | 213 | 214 |
|---|---|---|---|---|---|
| Catalyst System and Oligomerization Conditions | | | | | |
| Amidine Metal Salt Complex | B77 | B78 | B73 | B73 | B73 |
| Complex (mg) | 8 | 7 | 7 | 7 | 7 |

TABLE 23-continued

|  | | | | | |
|---|---|---|---|---|---|
| Complex mmol | 0.0124 | 0.0099 | 0.0097 | 0.0097 | 0.0097 |
| Cr (mg) | 0.64 | 0.51 | 0.50 | 0.50 | 0.50 |
| Al:Cr molar ratio | 800 | 400 | 800 | 800 | 800 |
| Catalyst System Solvent, Ethylbenzene (g) | 1 | 1 | 1 | 1 | 1 |
| Catalyst System Aging Time (hours) | 1 | 20 | 4 | 2‡ | 20 |
| Reaction Time (min) | 30 | 15 | 30 | 30 | 15 |
| Ethylene Pressure (psi) | 875 | 875 | 875 | 875 | 875 |
| Hydrogen Pressure (psi) | 25 | 25 | 25 | 25 | 25 |
| Reaction Temperature (° C.) | 70 | 70 | 70 | 60 | 70 |
| Oligomerization Product Product Type | | | | | |
| Solid/Polymer (g) | 0.04 | 0.2 | 2.3 | 2 | 0.03 |
| Liquid (g) | 230.6 | 274.7 | 115.8 | 107.7 | 47.1 |
| Solid/Polymer (wt %) | 0.0 | 0.07 | 1.9 | 1.8 | 0.1 |
| Carbon Number Distribution | | | | | |
| $C_6$ | 96.1 | 94.6 | 66.5 | 61.6 | 68.3 |
| $C_8$ | 0.9 | 1.0 | 31.1 | 36.0 | 29.6 |
| $C_{10}$ | 2.9 | 4.2 | 1.2 | 1.1 | 0.9 |
| $C_{12}$ | 0.1 | 0.1 | 0.7 | 0.7 | 0.6 |
| $C_{14+}$ | 0.0 | 0.1 | 0.5 | 0.6 | 0.6 |
| Productivities and Activities | | | | | |
| $C_6 + C_8$ (wt %) | 97.0 | 95.6 | 97.6 | 97.6 | 97.9 |
| $C_6 + C_8$ (g/g Cr) | 346,804 | 511,598 | 225,132 | 209,384 | 91,851 |
| Product Purities | | | | | |
| 1-Hexene (wt %) | 99.83 | 99.75 | 97.26 | 96.54 | 97.47 |
| Methylcyclopentane | 0.02 | 0.02 | 1.07 | 1.34 | 0.94 |
| 1-Octene (wt %) | 96.49 | 98.64 | 99.22 | 99.05 | 98.80 |

‡Catalyst system was aged at 50° C.

Example 3

The effect of aging a catalyst system comprising a metal alkyl and an $N^2$-phosphinyl amidine metal salt complex before contacting the catalyst system with an olefin, the effect of aging the metal alkyl before contacting the metal alkyl with an $N^2$-phosphinyl amidine metal salt complex, and the effect that the catalyst system solvent has on various olefin oligomerization parameters was investigated. The $N^2$-phosphinyl amidine metal salt complexes were contacted with a metal alkyl in ethyl benzene at room temperature under the conditions indicated in Table 24. The catalyst system mixture of $N^2$-phosphinyl amidine metal salt complex and metal alkyl was subsequently contacted with ethylene and hydrogen under the oligomerization process conditions indicated in Table 24 using the method described in Example 2. The results demonstrate that varying the time in which the metal alkyl and $N^2$-phosphinyl amidine metal salt complexes are contacted prior to exposure to a monomer affects both the catalyst activity and the amount of polymer formation.

TABLE 24

| Run No. | 301 | 302 | 303 | 304 | 305 |
|---|---|---|---|---|---|
| Catalyst System and Oligomerization Conditions | | | | | |
| Amidine Metal Salt Complex | B68 | B68 | B68 | B68 | B71 |
| Complex (mg) | 7 | 7 | 7 | 7 | 7 |
| Complex mmol | 0.0098 | 0.0098 | 0.0098 | 0.0098 | 0.0098 |
| Cr (mg) | 0.51 | 0.51 | 0.51 | 0.51 | 0.51 |
| Al:Cr molar ratio | 400 | 400 | 400 | 400 | 400 |
| Catalyst System Solvent, Ethylbenzene (g) | 1.0 | 1.0 | 1.0 | 1.0 | 1.0 |
| Metal Alkyl Thermal Aging Time (days) | — | — | — | — | — |
| Catalyst System Aging Time (hours) | 0.17 | 2 | 18 | 72 | 16 |
| Reaction Time (min) | 30 | 30 | 30 | 30 | 30 |
| Ethylene Pressure (psi) | 850 | 850 | 850 | 850 | 850 |
| Hydrogen Pressure (psi) | 50 | 50 | 50 | 50 | 50 |
| Reaction Temperature (° C.) | 60 | 60 | 60 | 60 | 70 |
| Oligomerization Product Product Type | | | | | |
| Solid/Polymer (g) | 5.8 | 4.1 | 0.9 | 1.9 | 0.1 |
| Liquid (g) | 69.5 | 169.7 | 139.6 | 154.7 | 316.9 |
| Solid/Polymer (wt %) | 7.7 | 2.4 | 0.6 | 1.2 | 0.03 |
| Carbon Number Distribution | | | | | |
| $C_6$ | 96.4 | 95.9 | 96.5 | 96.5 | 92.7 |
| $C_8$ | 2.1 | 1.7 | 1.6 | 1.3 | 0.6 |
| $C_{10}$ | 1.2 | 2.3 | 1.8 | 2.0 | 6.3 |
| $C_{12}$ | 0.1 | 0.1 | 0.1 | 0.1 | 0.1 |

TABLE 24-continued

| | | | | | |
|---|---|---|---|---|---|
| $C_{14+}$ | 0.2 | 0.0 | 0.0 | 0.1 | 0.3 |
| Productivities and Activities | | | | | |
| $C_6 + C_8$ (wt %) | 98.5 | 97.6 | 98.1 | 97.8 | 93.3 |
| $C_6 + C_8$ (g/g Cr) | 134,126 | 324,506 | 268,316 | 296,429 | 578,445 |
| Product Purities | | | | | |
| 1-Hexene (wt %) | 99.69 | 99.67 | 99.71 | 99.57 | 99.67 |
| Methylcyclopentane | 0.03 | 0.03 | 0.02 | 0.04 | 0.01 |
| 1-Octene (wt %) | 98.83 | 98.86 | 98.49 | 98.32 | 97.95 |

| | | | | |
|---|---|---|---|---|
| Run No. | 306 | 307 | 308 | 309 |
| Catalyst System and Oligomerization Conditions | | | | |
| Amidine Metal Salt Complex | B71 | B72 | B72 | B72 |
| Complex (mg) | 7 | 4 | 4 | 4 |
| Complex mmol | 0.0098 | 0.0058 | 0.0058 | 0.0058 |
| Cr (mg) | 0.51 | 0.30 | 0.30 | 0.30 |
| Al:Cr molar ratio | 400 | 500 | 500 | 500 |
| Catalyst System Solvent, Ethylbenzene (g) | 1.0 | 0.5 | 1.5 | 0.5 |
| Metal Alkyl Thermal Aging Time (days) | 6 | — | — | — |
| Catalyst System Aging Time (hours) | 16 | 48 | 48 | 3 |
| Reaction Time (min) | 30 | 30 | 30 | 30 |
| Ethylene Pressure (psi) | 850 | 850 | 850 | 850 |
| Hydrogen Pressure (psi) | 50 | 50 | 50 | 50 |
| Reaction Temperature (° C.) | 70 | 70 | 70 | 70 |
| Oligomerization Product | | | | |
| Product Type | | | | |
| Solid/Polymer (g) | 0.8 | 2.1 | 2.5 | 2.6 |
| Liquid (g) | 312.9 | 119.2 | 86.7 | 21.9 |
| Solid/Polymer (wt %) | 0.3 | 1.7 | 2.8 | 10.6 |
| Carbon Number Distribution | | | | |
| $C_6$ | 93.7 | 83.6 | 83.7 | 85.3 |
| $C_8$ | 0.9 | 14.2 | 14.5 | 13.2 |
| $C_{10}$ | 5.2 | 1.7 | 1.4 | 1.0 |
| $C_{12}$ | 0.1 | 0.5 | 0.3 | 0.3 |
| $C_{14+}$ | 0.1 | 0.0 | 0.1 | 0.2 |
| Productivities and Activities | | | | |
| $C_6 + C_8$ (wt %) | 94.6 | 97.8 | 98.2 | 98.5 |
| $C_6 + C_8$ (g/g Cr) | 579,101 | 383,977 | 280,428 | 71,051 |
| Product Purities | | | | |
| 1-Hexene (wt %) | 99.70 | 98.97 | 98.97 | 98.89 |
| Methylcyclopentane | 0.01 | 0.33 | 0.33 | 0.31 |
| 1-Octene (wt %) | 98.55 | 98.91 | 98.90 | 98.44 |

Runs 301-304, 307, and 309 show the effect that aging the catalyst system containing MMAO and the $N^2$-phosphinyl amidine metal salt complex B68 at room temperature had on an ethylene oligomerization. Aging the catalyst system increases the productivity of the catalyst system and decreases the weight percentage of polymer formed.

Runs 305 and 306 show the effect that thermal aging of the metal alkyl (MMAO) has on an ethylene oligomerization. In these two runs, an ethylene oligomerization was performed using a first catalyst system which was prepared using MMAO as it was supplied (Run 305) and was compared to an ethylene oligomerization that was performed using a second catalyst system using MMAO which had been "thermally aged" at 55° C. for 6 days in a sealed vial under a dry nitrogen atmosphere (Run 306). In each instance, the catalyst system was prepared using the $N^2$-phosphinyl amidine metal salt complex B71 and the catalyst system was aged at room temperature in ethylbenzene for 16 hours before being contacted with ethylene and hydrogen under the conditions indicated in Table 24. Surprisingly, it was observed that the oligomerization catalyst system using the thermally-aged MMAO produced less polymer product than the oligomerization catalyst system comprising the non-thermally aged MMAO. In both instances the catalyst systems displayed comparable catalyst system productivities.

Runs 307-308 show the effects that the amount of catalyst system solvent can have on a catalyst system containing a metal alkyl and an $N^2$-phosphinyl amidine metal salt complex mixture. Specifically, increasing the quantity of the catalyst system solvent (ethylbenzene) reduces the catalyst system productivity and increases the weight percentage of polymer formed during ethylene oligomerization.

The results demonstrate that the catalyst system activity and polymer formation can be altered by thermally aging the metal alkyl, aging the catalyst system containing a metal alkyl and an $N^2$-phosphinyl metal salt complex, and/or adjusting the amount of solvent in which the catalyst system is prepared.

Example 4

The solubility of several $N^2$-phosphinyl amidine metal salt complexes in ethylbenzene was investigated. $N^2$-phosphinyl amidine metal salt complexes B25, B5, B72, and B68 were prepared using the methodologies described herein. The structures of these complexes are presented in Table 25. The solubility of each complex was determined by charging a 20 mL glass vial with 10 mg of the $N^2$-phosphinyl amidine metal salt complex (blue) and 1.0 g of ethylbenzene. The solutions were then mixed and allowed to stand. If the ethylbenzene remained colorless, the $N^2$-phosphinyl amidine metal salt complex was considered insoluble. If the ethylbenzene turned light blue but observable solids remained in the vial, the $N^2$-phosphinyl amidine metal salt complex was considered slightly soluble. If all the solids dissolved and the solution turned blue, the $N^2$-phosphinyl amidine metal salt complex was considered soluble. The results of this solubility testing are shown below.

TABLE 25

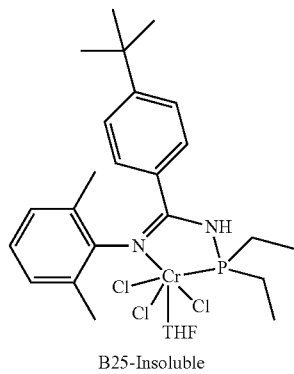

B25-Insoluble

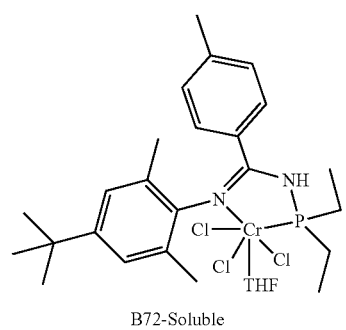

B72-Soluble

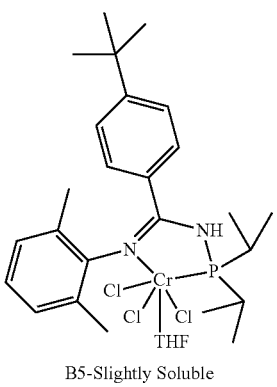

B5-Slightly Soluble

TABLE 25-continued

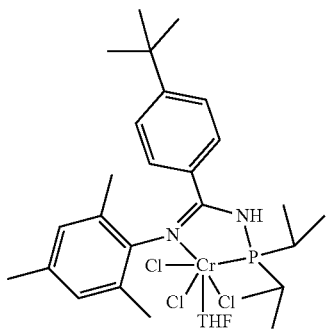

B68-Soluble

Comparing the solubility of $N^2$-phosphinyl amidine metal salt complex B25 to the solubility of $N^2$-phosphinyl amidine metal salt complex B72, and the solubility of $N^2$-phosphinyl amidine metal salt complex B5 to the solubility of $N^2$-phosphinyl amidine metal salt complex B78, it can be seen that having a substituent group in the 4-position of an aromatic group attached to the $N^1$ nitrogen atom of an $N^2$-phosphinyl amidine metal salt complex increases the solubility of the $N^2$-phosphinyl amidine metal salt complex in an aromatic solvent.

While preferred embodiments of the invention have been shown and described, modifications thereof can be made by one skilled in the art without departing from the spirit and teachings of the disclosure. The embodiments described herein are exemplary only, and are not intended to be limiting. Many variations and modifications of the disclosure are possible and are within the scope of the invention. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Background is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed:

1. An $N^2$-phosphinyl amidine compound characterized by having the formula:

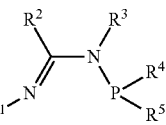

wherein:
$R^1$ is a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group, $R^2$ is a $C_1$ to $C_{30}$ organyl group consisting essentially of inert functional groups wherein the inert functional groups are selected from the group consisting of halo groups, nitro groups, hydrocarboxy groups, sulfidyl groups, hydrocarbyl groups, or combinations thereof, $R^3$ is hydrogen, and $R^4$ and $R^5$ are each independently a $C_1$ to $C_{30}$ organyl group consisting essentially of inert functional groups wherein the inert functional groups are selected from the group consisting of halo groups, nitro groups, hydrocarboxy groups, sulfidyl groups, hydrocarbyl groups, or combinations thereof.

2. A method of preparing the $N^2$-phosphinyl amidine compound according to claim 1, characterized by having the formula:

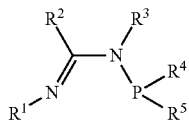

wherein:
$R^1$ is a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group, $R^2$ is a $C_1$ to $C_{30}$ organyl group consisting essentially of inert functional groups wherein the inert functional groups are selected from the group consisting of halo groups, nitro groups, hydrocarboxy groups, sulfidyl groups, hydrocarbyl groups, or combinations thereof, $R^3$ is hydrogen, and $R^4$ and $R^5$ are each independently a $C_1$ to $C_{30}$ organyl group consisting essentially of inert functional groups wherein the inert functional groups are selected from the group consisting of halo groups, nitro groups, hydrocarboxy groups, sulfidyl groups, hydrocarbyl groups, or combinations thereof, comprising:

a) contacting a metal amide with a nitrile under conditions capable of forming a metal amidinate; and b) contacting a phosphine halide with the metal amidinate under conditions capable of forming a compound comprising an $N^2$-phosphinyl amidine group.

3. A metal salt complex of the $N^2$-phosphinyl amidine compound according to claim 1, characterized by having the formula:

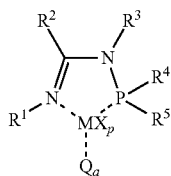

wherein:
$R^1$ is a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group, $R^2$ is a $C_1$ to $C_{30}$ organyl group consisting essentially of inert functional groups wherein the inert functional groups are selected from the group consisting of halo groups, nitro groups, hydrocarboxy groups, sulfidyl groups, hydrocarbyl groups, or combinations thereof, $R^3$ is hydrogen, $R^4$ and $R^5$ are each independently a $C_1$ to $C_{30}$ organyl group consisting essentially of inert functional groups wherein the inert functional groups are selected from the group consisting of halo groups, nitro groups, hydrocarboxy groups, sulfidyl groups, hydrocarbyl groups, or combinations thereof, $MX_p$ represents the metal salt where M is a transition metal, X is a monoanion, and p ranges from 2 to 6, Q is a neutral ligand, and a ranges from 0 to 6.

4. A method of preparing the $N^2$-phosphinyl amidine metal salt complex according to claim 3, characterized by having the formula:

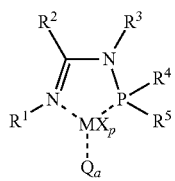

wherein:
$R^1$ is a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group, $R^2$ is a $C_1$ to $C_{30}$ organyl group consisting essentially of inert functional groups wherein the inert functional groups are selected from the group consisting of halo groups, nitro groups, hydrocarboxy groups, sulfidyl groups, hydrocarbyl groups, or combinations thereof, $R^3$ is hydrogen, $R^4$ and $R^5$ are each independently a $C_1$ to $C_{30}$ organyl group consisting essentially of inert functional groups wherein the inert functional groups are selected from the group consisting of halo groups, nitro groups, hydrocarboxy groups, sulfidyl groups, hydrocarbyl groups, or combinations thereof, $MX_p$ represents the metal salt where M is a transition metal, X is a monoanion, and p ranges from 2 to 6, Q is a neutral ligand, and a ranges from 0 to 6, comprising:

a) contacting a transition metal salt with an $N^2$-phosphinyl amidine compound, characterized by having the formula:

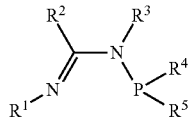

wherein:
$R^1$ is a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group, $R^2$ is a $C_1$ to $C_{30}$ organyl group consisting essentially of inert functional groups wherein the inert functional groups are selected from the group consisting of halo groups, nitro groups, hydrocarboxy groups, sulfidyl groups, hydrocarbyl groups, or combinations thereof, $R^3$ is hydrogen, and $R^4$ and $R^5$ are each independently a $C_1$ to $C_{30}$ organyl group consisting essentially of inert functional groups wherein the inert functional groups are selected from the group consisting of halo groups, nitro groups, hydrocarboxy groups, sulfidyl groups, hydrocarbyl groups, or combinations thereof; and b) forming the $N^2$-phosphinyl amidine metal salt complex.

5. The $N^2$-phosphinyl amidine compound of claim 1, wherein $R^1$ is a phenyl group or a substituted phenyl group.

6. The $N^2$-phosphinyl amidine compound of claim 1, wherein $R^1$ is a phenyl group, a 2-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group.

7. The $N^2$-phosphinyl amidine compound of claim 1, wherein each substituent of the substituted phenyl group of $R^1$ is independently a halide, a $C_1$ to $C_5$ alkyl group, or a $C_1$ to $C_5$ alkoxy group.

8. The $N^2$-phosphinyl amidine compound of claim 1, wherein $R^1$ is a phenyl group, a 2-methylphenyl group, a 2-ethylphenyl group, a 2-isopropylphenyl group, a 2-tert-butylphenyl group, a 4-methylphenyl group, a 4-ethylphenyl group, a 4-isopropylphenyl group, a 4-tert-butylphenyl group, a 2,6-dimethylphenyl group, a 2,6-diethylphenyl group, a 2,6-diisopropylphenyl group, a 2-methyl-6-isopropylphenyl group, a 3,5-dimethylphenyl group, a 2,4,6-trimethylphenyl group, or a 2,6-dimethyl-4-tert-butylphenyl group.

9. The $N^2$-phosphinyl amidine compound of claim 1, wherein $R^2$ is a $C_1$ to $C_{15}$ alkyl group, a $C_4$ to $C_{20}$ cycloalkyl group, a $C_4$ to $C_{20}$ substituted cycloalkyl group, a $C_3$ to $C_{15}$ aliphatic heterocyclic group, a $C_3$ to $C_{51}$ substituted aliphatic heterocyclic group, a $C_6$ to $C_{20}$ aryl group, a $C_6$ to $C_{20}$ substituted aryl group, a $C_7$ to $C_{20}$ aralkyl group, a $C_7$ to $C_{20}$ substituted aralkyl group, a $C_3$ to $C_{20}$ heteroaryl group, or a $C_3$ to $C_{20}$ substituted heteroaryl group.

10. The $N^2$-phosphinyl amidine compound of claim 1, wherein $R^2$ is a phenyl group or a $C_6$ to $C_{20}$ substituted phenyl group.

11. The $N^2$-phosphinyl amidine compound of claim 1, wherein $R^2$ is a benzyl group, a $C_6$ to $C_{20}$ substituted benzyl group, an ethylphenyl group, or a $C_6$ to $C_{20}$ substituted ethylphenyl group.

12. The $N^2$-phosphinyl amidine compound of claim 1, wherein $R^4$ and $R^5$ are independently a $C_1$ to $C_{15}$ alkyl group, a $C_4$ to $C_{20}$ cycloalkyl group, a $C_4$ to $C_{20}$ substituted cycloalkyl group, a $C_3$ to $C_{15}$ aliphatic heterocyclic group, a $C_3$ to $C_{15}$ substituted aliphatic heterocyclic group, a $C_6$ to $C_{20}$ aryl group, a $C_6$ to $C_{20}$ substituted aryl group, a $C_3$ to $C_{20}$ heteroaryl group, or a $C_3$ to $C_{20}$ substituted heteroaryl group.

13. The $N^2$-phosphinyl amidine compound of claim 1, wherein $R^4$ and $R^5$ are independently a methyl group, an ethyl group, an isopropyl group, a tert-butyl group, or a neopentyl group.

14. The $N^2$-phosphinyl amidine compound of claim 1, wherein $R^4$ and $R^5$ are each independently a cyclopentyl group, a substituted cyclopentyl group, a cyclohexyl group, or a substituted cyclohexyl group.

15. The $N^2$-phosphinyl amidine compound of claim 1, wherein $R^4$ and $R^5$ are independently a phenyl group or a substituted phenyl group.

16. The $N^2$-phosphinyl amidine compound of claim 1, wherein $R^4$ and $R^5$ are independently a phenyl group, a 2-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group.

17. The $N^2$-phosphinyl amidine compound of claim 1, wherein
$R^1$ is a phenyl group or a substituted phenyl group,
$R^2$ is a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, a $C_6$ to $C_{20}$ substituted aryl group, a $C_7$ to $C_{20}$ aralkyl group, or a $C_7$ to $C_{20}$ substituted aralkyl group,
$R^3$ is hydrogen, and
$R^4$ and $R^5$ are independently a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group.

18. The method of claim 2, wherein the metal amidinate of step a) is neutralized with a protic compound to form a non-metal amidine compound prior to step b).

19. The method of claim 18, wherein the non-metal amidine compound is isolated and optionally purified and then contacted with a metal alkyl compound to form the metal amidinate.

20. The method of claim 2, wherein the metal amidinate of step a) is contacted with the phosphine halide without forming a non-metal amidine compound.

21. The method of claim 2, wherein the compound comprising the $N^2$-phosphinyl amidine group is isolated and optionally purified.

22. The method of claim 2, wherein the metal amide is formed by contacting an amine and a Group 1 or Group 2 metal alkyl.

23. The method of claim 2, wherein the metal amide has Structure MA1, the nitrile has Structure N1, the phosphine halide has the Structure PH1,

Structure MA1
Structure N1
Structure PH1 and the compound comprising a $N^2$-phosphinyl amidine group is characterized by having the formula:

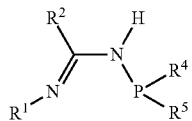

wherein
$X^1$ is selected from fluoro, chloro, bromo, and iodo,
$M^A$ is a Group 1 or Group 2 metal,
$R^1$ is a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group,
$R^2$ is a $C_1$ to $C_{30}$ organyl group consisting essentially of inert functional groups wherein the inert functional groups are selected from the group consisting of halo groups, nitro groups, hydrocarboxy groups, sulfidyl groups, hydrocarbyl groups, or combinations thereof, and
$R^4$ and $R^5$ are each independently a $C_1$ to $C_{30}$ organyl group consisting essentially of inert functional groups wherein the inert functional groups are selected from the group consisting of halo groups, nitro groups, hydrocarboxy groups, sulfidyl groups, hydrocarbyl groups, or combinations thereof.

24. The method of claim 2, wherein the metal amide has Structure MA1, the nitrile has Structure N1, the phosphine halide has the Structure PH1,

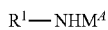
Structure MA1

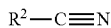
Structure N1

Structure PH1 and the compound comprising a $N^2$-phosphinyl amidine group is characterized by having the formula:

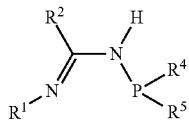

wherein
$X^1$ is selected from fluoro, chloro, bromo, and iodo,
$M^4$ is a Group 1 or Group 2 metal,
$R^1$ is a phenyl group or a substituted phenyl group,
$R^2$ is a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, a $C_7$ to $C_{20}$ substituted aryl group, a $C_7$ to $C_{20}$ aralkyl group, or a $C_7$ to $C_{20}$ substituted aralkyl group; and
$R^4$ and $R^5$ are each independently a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group.

25. The metal salt complex of claim 3, wherein the metal salt comprises a Group 3-10 transition metal.

26. The metal salt complex of claim 3, wherein the metal of the metal salt is in a +2 or +3 oxidation state.

27. The metal salt complex of claim 3, wherein the metal salt comprises chromium.

28. The metal salt complex of claim 3, wherein the metal salt is a chromium(III) carboxylate, a chromium(III) β-diketonate, or a chromium(III) halide.

29. The metal salt complex of claim 3, wherein the metal salt is chromium(III) chloride.

30. The method of claim 4, wherein the transition metal salt and the $N^2$-phosphinyl amidine compound are contacted at a transition metal salt to $N^2$-phosphinyl amidine compound equivalent ratio of at least 0.9:1.

31. The method of claim 4, wherein the transition metal salt and the $N^2$-phosphinyl amidine compound are contacted in a solvent.

* * * * *

UNITED STATES PATENT AND TRADEMARK OFFICE
CERTIFICATE OF CORRECTION

PATENT NO. : 8,680,003 B2  
APPLICATION NO. : 13/519825  
DATED : March 25, 2014  
INVENTOR(S) : Orson L. Sydora et al.

Page 1 of 1

It is certified that error appears in the above-identified patent and that said Letters Patent is hereby corrected as shown below:

In the Claims

Column 367, Claim 9, line 31, replace "a $C_3$ to $C_{51}$" with --a $C_3$ to $C_{15}$--
Column 370, Claim 24, line 7, replace "a C; to $C_2$" with --a $C_6$ to $C_{20}$--

Signed and Sealed this  
Sixth Day of October, 2015

Michelle K. Lee  
*Director of the United States Patent and Trademark Office*